US010086042B2

(12) United States Patent
Schreiber et al.

(10) Patent No.: US 10,086,042 B2
(45) Date of Patent: Oct. 2, 2018

(54) COMPOSITIONS AND METHODS FOR ADJOINING TYPE I AND TYPE II EXTRACELLULAR DOMAINS AS HETEROLOGOUS CHIMERIC PROTEINS

(71) Applicant: Heat Biologics, Inc., Durham, NC (US)

(72) Inventors: Taylor Schreiber, Durham, NC (US); George Fromm, Durham, NC (US); Suresh De Silva, Durham, NC (US); Neal Schilling, Durham, NC (US)

(73) Assignee: Heat Biologics, Inc., Durham, NC (US)

( * ) Notice: Subject to any disclaimer, the term of this patent is extended or adjusted under 35 U.S.C. 154(b) by 0 days.

(21) Appl. No.: 15/804,533

(22) Filed: Nov. 6, 2017

(65) Prior Publication Data

US 2018/0064787 A1  Mar. 8, 2018

Related U.S. Application Data

(63) Continuation of application No. 15/281,196, filed on Sep. 30, 2016.

(60) Provisional application No. 62/372,574, filed on Aug. 9, 2016, provisional application No. 62/263,313, filed on Dec. 4, 2015, provisional application No. 62/235,727, filed on Oct. 1, 2015.

(51) Int. Cl.
*A61K 38/17* (2006.01)
*C07K 14/00* (2006.01)
*C07K 19/00* (2006.01)
*A61K 38/00* (2006.01)

(52) U.S. Cl.
CPC ........ *A61K 38/1774* (2013.01); *A61K 38/177* (2013.01); *C07K 14/00* (2013.01); *C07K 19/00* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,844,095 A | 12/1998 | Linsley et al. | |
| 7,569,663 B2 | 8/2009 | Tykocinski et al. | |
| 8,039,437 B2 | 10/2011 | Tykocinski et al. | |
| 8,080,246 B2 | 12/2011 | Lin et al. | |
| 8,329,657 B2 | 12/2012 | Tykocinski et al. | |
| 8,735,553 B1 * | 5/2014 | Li | C07K 16/2803 424/144.1 |
| 9,029,315 B2 | 5/2015 | Chen et al. | |
| 9,221,895 B2 | 12/2015 | Tykocinski | |
| 9,388,230 B2 | 7/2016 | Elhalel | |
| 9,657,082 B2 | 5/2017 | Tykocinski | |
| 2003/0232323 A1 * | 12/2003 | Freeman | A61K 38/1709 435/4 |
| 2007/0036783 A1 | 2/2007 | Humeau et al. | |
| 2009/0226435 A1 | 9/2009 | Khare | |
| 2011/0041190 A1 | 2/2011 | Tykocinski et al. | |
| 2013/0039911 A1 | 2/2013 | Bedi et al. | |
| 2013/0065815 A1 | 3/2013 | Tykocinski et al. | |
| 2013/0243697 A1 | 9/2013 | Tykocinski et al. | |
| 2014/0113370 A1 * | 4/2014 | Camphausen | C07K 14/78 435/328 |
| 2014/0154252 A1 | 6/2014 | Thompson et al. | |
| 2014/0227315 A1 | 8/2014 | Tykocinski et al. | |
| 2014/0242077 A1 | 8/2014 | Choi et al. | |
| 2014/0286858 A1 | 9/2014 | Zimmerman et al. | |
| 2015/0098942 A1 | 4/2015 | Curti et al. | |
| 2015/0174268 A1 | 6/2015 | Li | |
| 2015/0183881 A1 | 7/2015 | Bedi et al. | |
| 2015/0190506 A1 | 7/2015 | Cheung et al. | |
| 2015/0191525 A1 | 7/2015 | Epstein et al. | |
| 2015/0353642 A1 | 12/2015 | Tykocinski | |
| 2015/0368350 A1 | 12/2015 | Tykocinski et al. | |
| 2015/0376260 A1 | 12/2015 | Elhalel et al. | |
| 2016/0024176 A1 | 1/2016 | Damschroder et al. | |
| 2016/0166685 A1 | 6/2016 | Cheung et al. | |
| 2016/0177276 A1 | 6/2016 | Lo et al. | |
| 2016/0340409 A1 | 11/2016 | Dranitzki-Elhalel | |
| 2016/0347846 A1 | 12/2016 | Tykocinski | |

FOREIGN PATENT DOCUMENTS

| | | | | |
|---|---|---|---|---|
| WO | 2001049318 A1 | 12/2001 | | |
| WO | WO 2005/047334 | * 5/2005 | ............. | C07K 19/00 |
| WO | WO 2007/149880 | * 12/2007 | ............. | C07K 14/43 |
| WO | 2010003118 A1 | 1/2010 | | |
| WO | 2010005519 A1 | 1/2010 | | |
| WO | 2010105068 A1 | 9/2010 | | |
| WO | 2012042480 A1 | 4/2012 | | |
| WO | 2013019615 A2 | 2/2013 | | |
| WO | 2013164694 A1 | 11/2013 | | |
| WO | 2013173820 A2 | 11/2013 | | |

(Continued)

OTHER PUBLICATIONS

Ali et al. (Vaccine, 22: 3585-3594, 2004).*
Zhang et al. (Immunity, 20: 337-347, 2004).*
Compaan et al. (Structure, 14: 1321-1330, 2006).*
Anderson et al., "Lag-3, Tim-3, and TIGIT: Co-Inhibitory Receptors with Specialized Functions in Immune Regulation", Immunity vol. 44, 2016, pp. 989-1004.
Bartkowiak et al., "4-1BB agonists: Multi-Potent Potentiators of Tumor Immunity", Frontiers in Oncology, 2015, vol. 5, Article 117, pp. 1-16.
Batlevi et al., "Novel Immunotherapies in Lymphoid Malignancies", Nature Reviews, Clinical Oncology, vol. 13, 2016, pp. 25-40.
Callahan, et al., "Targeting T Cell Co-receptors for Cancer Therapy", Immunity, vol. 44, 2016, pp. 1069-1078.

(Continued)

*Primary Examiner* — Nelson B Moseley, II
(74) *Attorney, Agent, or Firm* — Morgan, Lewis & Bockius LLP

(57) ABSTRACT

The present invention relates to, inter alia, compositions and methods, including chimeric proteins that find use in the treatment of disease, such as immunotherapies for cancer and autoimmunity. In part, the invention provides, in various embodiments, fusions of extracellular domains of transmembrane proteins that can have stimulatory or inhibitory effects.

23 Claims, 41 Drawing Sheets

Specification includes a Sequence Listing.

(56) References Cited

FOREIGN PATENT DOCUMENTS

| | | | |
|---|---|---|---|
| WO | 2014094122 A1 | 6/2014 | |
| WO | 2014106839 A1 | 6/2014 | |
| WO | 2014121085 A1 | 8/2014 | |
| WO | 2014121093 A1 | 8/2014 | |
| WO | 2014121099 A1 | 8/2014 | |
| WO | 2014134165 A1 | 9/2014 | |
| WO | 2014164427 A1 | 10/2014 | |
| WO | 2015095423 A2 | 6/2015 | |
| WO | 2015104406 A2 | 7/2015 | |
| WO | 2015112534 A2 | 7/2015 | |
| WO | 2015116178 A1 | 8/2015 | |
| WO | 2015183902 A1 | 12/2015 | |
| WO | 2015200828 A1 | 12/2015 | |
| WO | 2016025385 A1 | 2/2016 | |

OTHER PUBLICATIONS

Curran et al., Editorial: Advances in Combination Tumor Immunotherapy, Frontiers in Oncology, 2015, vol. 5, Article 198, pp. 1-2.
de Visser et al., Paradoxical Roles of the Immune System During Cancer Development, Nature Reviews Cancer, (2006) 6:24-37.
Guo et al., PD-1 Blockade and OX40 Triggering Synergistically Protects Against Tumor Growth in a Murine Model of Ovarian Cancer, PLOS One, 2014, vol. 9, issue 2, pp. 1-10.
Huang et al., "CTLA-4-FAS ligand functions as a trans signal converter protein in bridging antigen-presenting cells and T cells," International Immunology, vol. 13, No. 4, 2001, pp. 529-539.
International Search Report and Written Opinion, International Application No. PCT/US2016/054598, dated Jan. 9, 2017, 17 pages.
Karman, et al., "Ligation of Cytotoxic T Lymphocyte Antigen-4 to T Cell Receptor Inhibits T Cell Activation and Directs Differentiation into Foxp3+ Regulatory T Cells," The Journal of Biological Chemistry, vol. 287, No. 14, 2012, pp. 11098-11107.
Kermer, et al., An Antibody Fusion Protein for Cancer Immunotherapy Mimicking IL-15 trans-Presentation at the Tumor Site, Molecular Cancer Therapeutics, vol. 11, No. 6, 2012, pp. 1279-1288.
Khalil, et al., "The Future of Cancer Treatment: Immunomodulation, CARs and Combination Immunotherapy", Nature Reviews Clinical Oncology, 2016, pp. 1-18.
Ledford, "The Perfect Blend", Nature, vol. 532, 2016, pp. 162-164.
Linch, et al., "OX40 Agonists and Combination Immunotherapy: Putting the Pedal to the Metal", Frontiers in Oncology, vol. 5, article 34, 2015, pp. 1-14.
Mahoney, Combination Cancer Immunotherapy and New Immunomodulatory Targets Nature Reviews Drug Discovery (2015)14; 561-585.
Orbach, et al. "CD40•FasL and CTLA-4•FasL Fusion Proteins Induce Apoptosis in Malignant Cell Lines by Dual Signaling," The American Journal of Pathology, vol. 177, No. 6, 2010, pp. 3159-3168.
Pardoll, "The Blockade of Immune Checkpoints in Cancer Immunotherapy", Nature Reviews Cancer, vol. 12, 2012, pp. 252-264.
Schildberg, et al., "Coinhibitory Pathways in the B7-CD28 Ligand-Receptor Family", Immunity vol. 44, 2016, pp. 955-972.
Scott, et al., "Antibody Therapy of Cancer", Nature Reviews Cancer, vol. 12, 2012, pp. 278-287.
Spiess, et al., "Alternative Molecular Formats and Therapeutic Applications for Bispecific Antibodies", Molecular Immunology vol. 67, 2015, pp. 95-106.
Ward-Kavanagh, et al., "The TNF Receptor Superfamily in Co-stimulating and Co-inhibitory Responses", Immunity, vol. 44, 2016, pp. 1005-1019.
Zhang, et al., "Targeted and Untargeted CD137L Fusion Proteins for the Immunotherapy of Experimental Solid Tumors", Clin Cancer Res 2007, vol. 13 No. 9, pp. 2758-2767.
Zhao, et al. "A Bispecific Protein Capable of Engaging CTLA-4 and MHCII Protects Non-Obese Diabetic Mice from Autoimmune Diabetes," PLOS One, vol. 8, Issue 5, 2013, pp. 1-11.

* cited by examiner

A.

B.

A.

B.

Predicted Structure and Immunogenicity of SL-279252

A.

B.

C.

D.

E. Example Purification of SL-279252

Coomassie-Gel:

Quantification: BGG standard curve

Elution Profile :

| Sample | Abs at 280 nm | Stdev | Protein [µg/ml] | Stdev |
|---|---|---|---|---|
| h279-1-252 | 0,386 | 0,002 | 1016,4 | 5,5 |

F. Example Purification of Human CD172a-Fc-OX40L

G. Example Purification Run of CD172a-Fc-CD40L

H. Example Purification Run of Human TIGIT-Fc-OX40L

N. Example Purification Run of Canine PD1-Fc-OX40L

O. Example Purification Run of Mouse PD1-Fc-OX40L

Coomassie-Gel:

Elution Profile:

| Sample | Abs at 280 nm | Stdev | Protein [µg/ml] | Stdev |
|---|---|---|---|---|
| mPD1-Fc-OX40L | 0,134 | 0,001 | 284,2 | 2,4 |

P. Example Purification Run of Mouse PD1-Fc-GITRL

| Sample | Abs at 280 nm | Stdev | Protein [µg/ml] | Stdev |
|---|---|---|---|---|
| Mouse_PD1-Fc-GITRL | 0,383 | 0,003 | 971,8 | 6,6 |

Q. Example Purification Run of Mouse PD1-Fc-41BBL

| Sample | Abs at 280 nm | Stdev | Protein [µg/ml] | Stdev |
|---|---|---|---|---|
| Mouse_PD1-Fc-41BBL | 0,374 | 0,002 | 945,5 | 5,7 |

R. Example Purification Run of Mouse PD1-Fc-TL1A

Coomassie-Gel:

| Sample | Abs at 280 nm | Stdev | Protein [µg/ml] | Stdev |
|---|---|---|---|---|
| Mouse_PD1-Fc-TL1A | 0,403 | 0,005 | 1033,8 | 13,9 |

S. Example Purification Run of CD115-Fc-CD40L

| Sample | Abs at 280 nm | Stdev | Protein [µg/ml] | Stdev |
|---|---|---|---|---|
| m115154 (1:1 dilution) | 0.139 | 0.001 | 222.2 | 2.2 |

T. Example Purification Run of PD1-Fc-GITRL

Coomassie-Gel:

Quantification: BGG standard curve

Elution Profile:

| Sample | Abs at 280 nm | Stdev | Protein [µg/ml] | Stdev |
|---|---|---|---|---|
| h279TNFSF18 (1:1 dilution) | 0,332 | 0,004 | 807,8 | 10,3 |

SEQUENCE LISTING

```
<160> NUMBER OF SEQ ID NOS: 78

<210> SEQ ID NO 1
<211> LENGTH: 1605
<212> TYPE: DNA
<213> ORGANISM: Artificial sequence
<220> FEATURE:
<223> OTHER INFORMATION: Synthetic sequence

<400> SEQUENCE: 1
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccaccccag cccctcaccc     480
aggccagccg gccagttcca atctaagtac ggccctccct gcctagctg tcccgcccct     540 gaatttctgg gcggaccctc cgtgtttctg ttcccccaa agcccaagga caccctgatg     600
atcagccgga cccccgaagt gacctgtgtg gtggtggatg tgtcccagga agatcccgag     660
gtgcagttca attggtacgt ggacggggtg gaagtgcaca cgccaagac caagcccaga     720 gaggaacagt tcaacagcac ctaccgggtg gtgtctgtgc tgaccgtgct gcaccaggat     780
tggctgagcg gcaaagagta caagtgcaag gtgtccagca gggcctgcc cagcagcatc     840 gaaaagacca tcagcaacgc caccggccag cccagggaac cccaggtgta cactgccc      900 cctagccagg aagagatgac caagaaccag gtgtccctga catgcctcgt gaagggcttc     960
tacccctccg atatcgccgt ggaatgggag agcaacggcc agccagagaa caactacaag    1020
accacccccc cagtgctgga cagcgacggc tcattcttcc tgtactcccg gctgacagtg    1080
```

```
gacaagagca gctggcagga aggcaacgtg ttcagctgca gcgtgatgca cgaagccctg    1140
cacaaccact acacccagaa gtccctgagc ctgtccctgg gcaaaataga gggacgaatg    1200
gaccaggtat cacatcggta tcctcgaatt caaagtatca agtacaatt taccgaatat     1260 aagaaggaga aaggtttcat cctcacttcc caaaaggagg atgaaatcat gaaggtgcag    1320
aacaactcag tcatcatcaa ctgtgatggg ttttatctca tctccctgaa gggctacttc    1380
tcccaggaag tcaacattag ccttcattac cagaaggatg aggagcccct cttccaactg    1440
aagaaggtca ggtctgtcaa ctccttgatg gtggcctctc tgacttacaa agacaaagtc    1500
tacttgaatg tgaccactga caatacctcc ctggatgact ccatgtgaa tggcggagaa     1560 ctgattctta tccatcaaaa tcctggtgaa ttctgtgtcc tttga                    1605
```

<210> SEQ ID NO 2
<211> LENGTH: 534
<212> TYPE: PRT
<213> ORGANISM: Artificial sequence
<220> FEATURE:
<223> OTHER INFORMATION: Synthetic sequence

<400> SEQUENCE: 2

```
Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
           100                 105                 110

Ala Arg Arg Asn Asp Ser Gly Thr Tyr Leu Cys Gly Ala Ile Ser Leu
       115                 120                 125

Ala Pro Lys Ala Gln Ile Lys Glu Ser Leu Arg Ala Glu Leu Arg Val
   130                 135                 140

Thr Glu Arg Arg Ala Glu Val Pro Thr Ala His Pro Ser Pro Ser Pro
145                 150                 155                 160

Arg Pro Ala Gly Gln Phe Gln Ser Lys Tyr Gly Pro Pro Cys Pro Ser
                165                 170                 175

Cys Pro Ala Pro Glu Phe Leu Gly Gly Pro Ser Val Phe Leu Phe Pro
           180                 185                 190

Pro Lys Pro Lys Asp Thr Leu Met Ile Ser Arg Thr Pro Glu Val Thr
       195                 200                 205

Cys Val Val Val Asp Val Ser Gln Glu Asp Pro Glu Val Gln Phe Asn
   210                 215                 220

Trp Tyr Val Asp Gly Val Glu Val His Asn Ala Lys Thr Lys Pro Arg
225                 230                 235                 240

Glu Glu Gln Phe Asn Ser Thr Tyr Arg Val Val Ser Val Leu Thr Val
                245                 250                 255

Leu His Gln Asp Trp Leu Ser Gly Lys Glu Tyr Lys Cys Lys Val Ser
           260                 265                 270
```

```
Ser Lys Gly Leu Pro Ser Ser Ile Glu Lys Thr Ile Ser Asn Ala Thr
            275                 280                 285
Gly Gln Pro Arg Glu Pro Gln Val Tyr Thr Leu Pro Pro Ser Gln Glu
        290                 295                 300
Glu Met Thr Lys Asn Gln Val Ser Leu Thr Cys Leu Val Lys Gly Phe
305                 310                 315                 320
Tyr Pro Ser Asp Ile Ala Val Glu Trp Glu Ser Asn Gly Gln Pro Glu
                325                 330                 335
Asn Asn Tyr Lys Thr Thr Pro Pro Val Leu Asp Ser Asp Gly Ser Phe
            340                 345                 350
Phe Leu Tyr Ser Arg Leu Thr Val Asp Lys Ser Ser Trp Gln Glu Gly
        355                 360                 365
Asn Val Phe Ser Cys Ser Val Met His Glu Ala Leu His Asn His Tyr
    370                 375                 380
Thr Gln Lys Ser Leu Ser Leu Ser Leu Gly Lys Ile Glu Gly Arg Met
385                 390                 395                 400
Asp Gln Val Ser His Arg Tyr Pro Arg Ile Gln Ser Ile Lys Val Gln
                405                 410                 415
Phe Thr Glu Tyr Lys Lys Glu Lys Gly Phe Ile Leu Thr Ser Gln Lys
            420                 425                 430
Glu Asp Glu Ile Met Lys Val Gln Asn Asn Ser Val Ile Ile Asn Cys
        435                 440                 445
Asp Gly Phe Tyr Leu Ile Ser Leu Lys Gly Tyr Phe Ser Gln Glu Val
    450                 455                 460
Asn Ile Ser Leu His Tyr Gln Lys Asp Glu Glu Pro Leu Phe Gln Leu
465                 470                 475                 480
Lys Lys Val Arg Ser Val Asn Ser Leu Met Val Ala Ser Leu Thr Tyr
                485                 490                 495
Lys Asp Lys Val Tyr Leu Asn Val Thr Thr Asp Asn Thr Ser Leu Asp
            500                 505                 510
Asp Phe His Val Asn Gly Gly Glu Leu Ile Leu Ile His Gln Asn Pro
        515                 520                 525
Gly Glu Phe Cys Val Leu
    530

<210> SEQ ID NO 3
<211> LENGTH: 1782
<212> TYPE: DNA
<213> ORGANISM: Artificial sequence
<220> FEATURE:
<223> OTHER INFORMATION: Synthetic sequence

<400> SEQUENCE: 3
atgcagattc ctcaggcccc ttggcctgtc gtgtgggctg tgctgcagct gggatggcgg      60
cctggctggt ttctggacag ccccgacaga ccctggaacc ccctacatt ttcccctgcc     120 ctgctggtcg tgaccgaggg cgacaatgcc accttcacct gtagcttcag caacaccagc     180
gagagcttcg tgctgaactg gtacagaatg agccccagca accagaccga caagctggcc     240
gccttccccg aggatagatc tcagcccggc caggactgcc ggttcagagt gacccagctg     300
cccaacggcc gggacttcca catgtctgtc gtgcgggcca cggaacga cagcggcaca     360 tatctgtgcg gcgccatcag cctggccccc aaggcccaga tcaaagagag cctgagagcc     420
gagctgagag tgaccgagag aagggccgaa tgcctaccg cccacccta cccatctcca     480 agacctgccg gccagttcca gtctaagtac ggccctcctt gccccagctg tcccgcccct     540
```

```
gaatttctgg gcggacccag cgtgttcctg ttccccccaa agcccaagga cacccctgatg    600 atcagccgga cccccgaagt gacctgcgtg gtggtggatg tgtcccagga agatcccgag    660
gtgcagttca attggtacgt ggacggcgtg gaagtgcaca acgccaagac caagcccaga    720
gaggaacagt tcaacagcac ctaccgggtg tgtccgtgc tgaccgtgct gcaccaggat     780
tggctgagcg gcaaagagta caagtgcaag gtgtccagca agggcctgcc cagcagcatc    840
gagaaaacca tcagcaacgc caccggccag cccagggaac cccaggtgta cactctgccc   900
cctagccagg aagagatgac caagaaccag gtgtccctga cctgtctcgt gaagggcttc    960 taccctccg atatcgccgt ggaatggag agcaacggcc agcctgagaa caactacaag     1020
accacccccc cagtgctgga cagcgacggc tcattttcc tgtactccag actgaccgtg    1080
gacaagagca gctggcagga aggcaacgtg ttcagctgct ccgtgatgca cgaggccctg    1140
cacaaccact acacccagaa gtccctgtct ctgagcctgg gcaagatcga gggccggatg    1200
gatagagccc agggcgaagc ctgcgtgcag ttccaggctc tgaagggcca ggaattcgcc    1260
cccagccacc agcaggtgta cgcccctctg agagctgacg gcgacaagcc tagagcccac    1320
ctgacagtcg tgcggcagac ccctaccagc cacttcaaga atcagttccc agccctgcac    1380
tgggagcacg agctgggcct ggccttcacc aagaacagaa tgaactacac caacaagttt   1440
ctgctgatcc ccgagagcgg cgactacttc atctacagcc aagtgacctt ccggggcatg    1500
accagcgagt gcagcgagat cagacaggcc ggcagaccta acaagcccga cagcatcacc    1560
gtcgtgatca ccaaagtgac cgacagctac cccgagccca cacagctgct gatgggcacc    1620
aagagcgtgt gcgaagtggg cagcaactgg ttccagccca tctacctggg cgccatgttc    1680
agtctgcaag agggcgataa gctgatggtc aacgtgtccg acatctcccct ggtggattac   1740 accaaagagg acaagacctt cttcggcgcc tttctgctct ga                       1782
```

<210> SEQ ID NO 4
<211> LENGTH: 1782
<212> TYPE: DNA
<213> ORGANISM: Artificial sequence
<220> FEATURE:
<223> OTHER INFORMATION: Synthetic sequence

<400> SEQUENCE: 4

```
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccacccag cccctcaccc    480 aggccagccg gccagttcca atctaagtac ggccctccct gccctagctg tcccgcccct   540
gaatttctgg gcggaccctc cgtgtttctg ttccccccaa agcccaagga cacccctgatg   600 atcagccgga cccccgaagt gacctgtgtg gtggtggatg tgtcccagga agatcccgag    660
gtgcagttca attggtacgt ggacggggtg gaagtgcaca acgccaagac caagcccaga    720
gaggaacagt tcaacagcac ctaccgggtg tgtctgtgc tgaccgtgct gcaccaggat     780
tggctgagcg gcaaagagta caagtgcaag gtgtccagca agggcctgcc cagcagcatc    840
```

```
gaaaagacca tcagcaacgc caccggccag cccagggaac cccaggtgta cacactgccc    900
cctagccagg aagagatgac caagaaccag gtgtccctga catgcctcgt gaagggcttc    960 taccccctccg atatcgccgt ggaatgggag agcaacggcc agccagagaa caactacaag   1020
accacccccc cagtgctgga cagcgacggc tcattcttcc tgtactcccg gctgacagtg   1080
gacaagagca gctggcagga aggcaacgtg ttcagctgca gcgtgatgca cgaagccctg   1140
cacaaccact acacccagaa gtccctgagc ctgtccctgg gcaaaataga gggacgaatg   1200
gaccgggccc agggagaggc ctgtgtgcag ttccaggctc taaaaggaca ggagtttgca   1260
ccttcacatc agcaagttta tgcacctctt agagcagacg gagataagcc aagggcacac   1320
ctgacagttg tgagacaaac tcccacacag cactttaaaa atcagttccc agctctgcac   1380
tgggaacatg aactaggcct ggccttcacc aagaaccgaa tgaactatac caacaaattc   1440
ctgctgatcc cagagtcggg agactacttc atttactccc aggtcacatt ccgtgggatg   1500
acctctgagt gcagtgaaat cagacaagca ggccgaccaa caagccaga ctccatcact    1560 gtggtcatca ccaaggtaac agacagctac cctgagccaa cccagctcct catggggacc   1620
aagtctgtat gcgaagtagg tagcaactgg ttccagccca tctacctcgg agccatgttc   1680
tccttgcaag aaggggacaa gctaatggtg aacgtcagtg acatctcttt ggtggattac   1740 acaaagaag ataaaacctt ctttggagcc ttcttactat ag                       1782
```

<210> SEQ ID NO 5
<211> LENGTH: 593
<212> TYPE: PRT
<213> ORGANISM: Artificial sequence
<220> FEATURE:
<223> OTHER INFORMATION: Synthetic sequence

<400> SEQUENCE: 5

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ser Lys Tyr Gly Pro Pro Cys Pro Ser
                165                 170                 175

Cys Pro Ala Pro Glu Phe Leu Gly Gly Pro Ser Val Phe Leu Phe Pro
            180                 185                 190
```

Pro Lys Pro Lys Asp Thr Leu Met Ile Ser Arg Thr Pro Glu Val Thr
            195                 200                 205
Cys Val Val Asp Val Ser Gln Glu Asp Pro Glu Val Gln Phe Asn
210                 215                 220
Trp Tyr Val Asp Gly Val Glu Val His Asn Ala Lys Thr Lys Pro Arg
225                 230                 235                 240
Glu Glu Gln Phe Asn Ser Thr Tyr Arg Val Val Ser Val Leu Thr Val
                245                 250                 255
Leu His Gln Asp Trp Leu Ser Gly Lys Glu Tyr Lys Cys Lys Val Ser
            260                 265                 270
Ser Lys Gly Leu Pro Ser Ser Ile Glu Lys Thr Ile Ser Asn Ala Thr
        275                 280                 285
Gly Gln Pro Arg Glu Pro Gln Val Tyr Thr Leu Pro Pro Ser Gln Glu
290                 295                 300
Glu Met Thr Lys Asn Gln Val Ser Leu Thr Cys Leu Val Lys Gly Phe
305                 310                 315                 320
Tyr Pro Ser Asp Ile Ala Val Glu Trp Glu Ser Asn Gly Gln Pro Glu
                325                 330                 335
Asn Asn Tyr Lys Thr Thr Pro Pro Val Leu Asp Ser Asp Gly Ser Phe
            340                 345                 350
Phe Leu Tyr Ser Arg Leu Thr Val Asp Lys Ser Ser Trp Gln Glu Gly
        355                 360                 365
Asn Val Phe Ser Cys Ser Val Met His Glu Ala Leu His Asn His Tyr
370                 375                 380
Thr Gln Lys Ser Leu Ser Leu Ser Leu Gly Lys Ile Glu Gly Arg Met
385                 390                 395                 400
Asp Arg Ala Gln Gly Glu Ala Cys Val Gln Phe Gln Ala Leu Lys Gly
                405                 410                 415
Gln Glu Phe Ala Pro Ser His Gln Gln Val Tyr Ala Pro Leu Arg Ala
            420                 425                 430
Asp Gly Asp Lys Pro Arg Ala His Leu Thr Val Val Arg Gln Thr Pro
        435                 440                 445
Thr Gln His Phe Lys Asn Gln Phe Pro Ala Leu His Trp Glu His Glu
450                 455                 460
Leu Gly Leu Ala Phe Thr Lys Asn Arg Met Asn Tyr Thr Asn Lys Phe
465                 470                 475                 480
Leu Leu Ile Pro Glu Ser Gly Asp Tyr Phe Ile Tyr Ser Gln Val Thr
                485                 490                 495
Phe Arg Gly Met Thr Ser Glu Cys Ser Glu Ile Arg Gln Ala Gly Arg
            500                 505                 510
Pro Asn Lys Pro Asp Ser Ile Thr Val Val Ile Thr Lys Val Thr Asp
        515                 520                 525
Ser Tyr Pro Glu Pro Thr Gln Leu Leu Met Gly Thr Lys Ser Val Cys
530                 535                 540
Glu Val Gly Ser Asn Trp Phe Gln Pro Ile Tyr Leu Gly Ala Met Phe
545                 550                 555                 560
Ser Leu Gln Glu Gly Asp Lys Leu Met Val Asn Val Ser Asp Ile Ser
                565                 570                 575
Leu Val Asp Tyr Thr Lys Glu Asp Lys Thr Phe Phe Gly Ala Phe Leu
            580                 585                 590
Leu

<210> SEQ ID NO 6

<211> LENGTH: 1554
<212> TYPE: DNA
<213> ORGANISM: Artificial sequence
<220> FEATURE:
<223> OTHER INFORMATION: Synthetic sequence

<400> SEQUENCE: 6

```
atgaagacat tgcctgccat gcttggaact gggaaattat tttgggtctt cttcttaatc      60
ccatatctgg acatctggaa catccatggg aaagaatcat gtgatgtaca gctttatata     120
aagagacaat ctgaacactc catcttagca ggagatccct tgaactaga atgccctgtg      180
aaatactgtg ctaacaggcc tcatgtgact tggtgcaagc tcaatggaac aacatgtgta     240
aaacttgaag atagacaaac aagttggaag gaagagaaga acatttcatt tttcattcta     300
cattttgaac cagtgcttcc taatgacaat gggtcatacc gctgttctgc aaattttcag     360
tctaatctca ttgaaagcca ctcaacaact ctttatgtga cagatgtaaa aagtgcctca     420
gaacgaccct ccaaggacga atggcaagc tctaagtacg cccctccctg ccctagctgt      480
cccgcccctg aatttctggg cggacccctcc gtgtttctgt tccccccaaa gcccaaggac     540
accctgatga tcagccggac ccccgaagtg acctgtgtgg tggtggatgt gtcccaggaa     600
gatcccgagg tgcagttcaa ttggtacgtg acggggtgg aagtgcacaa cgccaagacc      660
aagcccagag aggaacagtt caacagcacc taccgggtgg tgtctgtgct gaccgtgctg     720
caccaggatt ggctgagcgg caaagagtac aagtgcaagg tgtccagcaa gggcctgccc     780
agcagcatcg aaaagaccat cagcaacgcc accggccagc caggaacc ccaggtgtac       840
acactgcccc ctagccagga agagatgacc aagaaccagg tgccctgac atgcctcgtg      900
aagggcttct acccctccga tatcgccgtg gaatgggaga gcaacggcca gccagagaac     960
aactacaaga ccacccccc agtgctggac agcgacggct cattcttcct gtactcccgg    1020
ctgacagtgg acaagagcag ctggcaggaa ggcaacgtgt cagctgcag cgtgatgcac    1080
gaagccctgc acaaccacta cacccagaag tccctgagcc tgtccctggg caaaatagag    1140
ggacgaatgg accaggtatc acatcggtat cctcgaattc aaagtatcaa agtacaattt    1200
accgaatata gaaggagaa aggtttcatc ctcacttccc aaaaggagga tgaaatcatg    1260
aaggtgcaga caaactcagt catcatcaac tgtgatgggt tttatctcat ctccctgaag    1320
ggctacttct cccaggaagt caacattagc cttcattacc agaaggatga ggagcccctc    1380
ttccaactga agaaggtcag gtctgtcaac tccttgatgg tggcctctct gacttacaaa    1440
gacaaagtct acttgaatgt gaccactgac aatacctccc tggatgactt ccatgtgaat    1500
ggcggagaac tgattcttat ccatcaaaat cctggtgaat tctgtgtcct ttga          1554
```

<210> SEQ ID NO 7
<211> LENGTH: 517
<212> TYPE: PRT
<213> ORGANISM: Artificial sequence
<220> FEATURE:
<223> OTHER INFORMATION: Synthetic sequence

<400> SEQUENCE: 7

```
Met Lys Thr Leu Pro Ala Met Leu Gly Thr Gly Lys Leu Phe Trp Val
1               5                  10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45
```

```
Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
    130                 135                 140

Lys Asp Glu Met Ala Ser Ser Lys Tyr Gly Pro Pro Cys Pro Ser Cys
145                 150                 155                 160

Pro Ala Pro Glu Phe Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser Gln Glu Asp Pro Glu Val Gln Phe Asn Trp
            195                 200                 205

Tyr Val Asp Gly Val Glu Val His Asn Ala Lys Thr Lys Pro Arg Glu
    210                 215                 220

Glu Gln Phe Asn Ser Thr Tyr Arg Val Val Ser Val Leu Thr Val Leu
225                 230                 235                 240

His Gln Asp Trp Leu Ser Gly Lys Glu Tyr Lys Cys Lys Val Ser Ser
                245                 250                 255

Lys Gly Leu Pro Ser Ser Ile Glu Lys Thr Ile Ser Asn Ala Thr Gly
            260                 265                 270

Gln Pro Arg Glu Pro Gln Val Tyr Thr Leu Pro Pro Ser Gln Glu Glu
            275                 280                 285

Met Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Arg Leu Thr Val Asp Lys Ser Ser Trp Gln Glu Gly Asn
            340                 345                 350

Val Phe Ser Cys Ser Val Met His Glu Ala Leu His Asn His Tyr Thr
            355                 360                 365

Gln Lys Ser Leu Ser Leu Ser Leu Gly Lys Ile Glu Gly Arg Met Asp
    370                 375                 380

Gln Val Ser His Arg Tyr Pro Arg Ile Gln Ser Ile Lys Val Gln Phe
385                 390                 395                 400

Thr Glu Tyr Lys Lys Glu Lys Gly Phe Ile Leu Thr Ser Gln Lys Glu
                405                 410                 415

Asp Glu Ile Met Lys Val Gln Asn Asn Ser Val Ile Ile Asn Cys Asp
            420                 425                 430

Gly Phe Tyr Leu Ile Ser Leu Lys Gly Tyr Phe Ser Gln Glu Val Asn
            435                 440                 445

Ile Ser Leu His Tyr Gln Lys Asp Glu Glu Pro Leu Phe Gln Leu Lys
    450                 455                 460

Lys Val Arg Ser Val Asn Ser Leu Met Val Ala Ser Leu Thr Tyr Lys
```

```
                465                 470                 475                 480
            Asp Lys Val Tyr Leu Asn Val Thr Thr Asp Asn Thr Ser Leu Asp Asp
                                485                 490                 495

Phe His Val Asn Gly Gly Glu Leu Ile Leu Ile His Gln Asn Pro Gly
                            500                 505                 510

Glu Phe Cys Val Leu
                            515
```

```
<210> SEQ ID NO 8
<211> LENGTH: 1527
<212> TYPE: DNA
<213> ORGANISM: Artificial sequence
<220> FEATURE:
<223> OTHER INFORMATION: Synthetic sequence

<400> SEQUENCE: 8
```

| | | | | | |
|---|---|---|---|---|---|
| atgcgctggt | gtctcctcct | gatctgggcc | caggggctga | ggcaggctcc | cctcgcctca | 60 |
| ggaatgatga | caggcacaat | agaaacaacg | gggaacattt | ctgcagagaa | aggtggctct | 120 |
| atcatcttac | aatgtcacct | ctcctccacc | acggcacaag | tgacccaggt | caactgggag | 180 |
| cagcaggacc | agcttctggc | catttgtaat | gctgacttgg | ggtggcacat | ctccccatcc | 240 |
| ttcaaggatc | gagtggcccc | aggtcccggc | ctgggcctca | ccctccagtc | gctgaccgtg | 300 |
| aacgatacag | gggagtactt | ctgcatctat | cacacctacc | tgatgggac | gtacactggg | 360 |
| agaatcttcc | tggaggtcct | agaaagctca | gtggctgagc | acggtgccag | gttccagatt | 420 |
| ccatctaagt | acggccctcc | ctgccctagc | tgtcccgccc | ctgaatttct | gggcggaccc | 480 |
| tccgtgtttc | tgttcccccc | aaagcccaag | gacaccctga | tgatcagccg | gacccccgaa | 540 |
| gtgacctgtg | tggtggtgga | tgtgtcccag | gaagatcccg | aggtgcagtt | caattggtac | 600 |
| gtggacgggg | tggaagtgca | caacgccaag | accaagccca | gagaggaaca | gttcaacagc | 660 |
| acctaccggg | tggtgtctgt | gctgaccgtg | ctgcaccagg | attggctgag | cggcaaagag | 720 |
| tacaagtgca | aggtgtccag | caagggcctg | cccagcagca | tcgaaaagac | catcagcaac | 780 |
| gccaccggcc | agcccaggga | accccaggtg | tacacactgc | ccctagcca | ggaagagatg | 840 |
| accaagaacc | aggtgtccct | gacatgcctc | gtgaagggct | ctacccctc | cgatatcgcc | 900 |
| gtggaatggg | agagcaacgg | ccagccagag | aacaactaca | agaccacccc | ccagtgctg | 960 |
| gacagcgacg | gctcattctt | cctgtactcc | cggctgacag | tggacaagag | cagctggcag | 1020 |
| gaaggcaacg | tgttcagctg | cagcgtgatg | cacgaagccc | tgcacaacca | ctacacccag | 1080 |
| aagtccctga | gcctgtccct | gggcaaaata | gagggacgaa | tggaccaggt | atcacatcgg | 1140 |
| tatcctcgaa | ttcaaagtat | caaagtacaa | tttaccgaat | ataagaagga | gaaaggtttc | 1200 |
| atcctcactt | cccaaaagga | ggatgaaatc | atgaaggtgc | agaacaactc | agtcatcatc | 1260 |
| aactgtgatg | ggttttatct | catctccctg | aagggctact | tctcccagga | agtcaacatt | 1320 |
| agccttcatt | accagaagga | tgaggagccc | ctcttccaac | tgaagaaggt | caggtctgtc | 1380 |
| aactccttga | tggtggcctc | tctgacttac | aaagacaaag | tctacttgaa | tgtgaccact | 1440 |
| gacaataccc | ccctggatga | cttccatgtg | aatggcggag | aactgattct | tatccatcaa | 1500 |
| aatcctggtg | aattctgtgt | cctttga | | | | 1527 |

```
<210> SEQ ID NO 9
<211> LENGTH: 508
<212> TYPE: PRT
<213> ORGANISM: Artificial sequence
<220> FEATURE:
```

<223> OTHER INFORMATION: Synthetic sequence

<400> SEQUENCE: 9

Met Arg Trp Cys Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65              70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Ser Lys Tyr
    130                 135                 140

Gly Pro Pro Cys Pro Ser Cys Pro Ala Pro Glu Phe Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser Gln Glu Asp
            180                 185                 190

Pro Glu Val Gln Phe Asn Trp Tyr Val Asp Gly Val Glu Val His Asn
        195                 200                 205

Ala Lys Thr Lys Pro Arg Glu Glu Gln Phe Asn Ser Thr Tyr Arg Val
    210                 215                 220

Val Ser Val Leu Thr Val Leu His Gln Asp Trp Leu Ser Gly Lys Glu
225                 230                 235                 240

Tyr Lys Cys Lys Val Ser Ser Lys Gly Leu Pro Ser Ser Ile Glu Lys
                245                 250                 255

Thr Ile Ser Asn Ala Thr Gly Gln Pro Arg Glu Pro Gln Val Tyr Thr
            260                 265                 270

Leu Pro Pro Ser Gln Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Arg Leu Thr Val Asp Lys
                325                 330                 335

Ser Ser Trp Gln Glu Gly Asn Val Phe Ser Cys Ser Val Met His Glu
            340                 345                 350

Ala Leu His Asn His Tyr Thr Gln Lys Ser Leu Ser Leu Ser Leu Gly
        355                 360                 365

Lys Ile Glu Gly Arg Met Asp Gln Val Ser His Arg Tyr Pro Arg Ile
    370                 375                 380

Gln Ser Ile Lys Val Gln Phe Thr Glu Tyr Lys Lys Glu Lys Gly Phe
385                 390                 395                 400

```
Ile Leu Thr Ser Gln Lys Glu Asp Glu Ile Met Lys Val Gln Asn Asn
                405                 410                 415

Ser Val Ile Ile Asn Cys Asp Gly Phe Tyr Leu Ile Ser Leu Lys Gly
            420                 425                 430

Tyr Phe Ser Gln Glu Val Asn Ile Ser Leu His Tyr Gln Lys Asp Glu
        435                 440                 445

Glu Pro Leu Phe Gln Leu Lys Lys Val Arg Ser Val Asn Ser Leu Met
    450                 455                 460

Val Ala Ser Leu Thr Tyr Lys Asp Lys Val Tyr Leu Asn Val Thr Thr
465                 470                 475                 480

Asp Asn Thr Ser Leu Asp Asp Phe His Val Asn Gly Gly Glu Leu Ile
                485                 490                 495

Leu Ile His Gln Asn Pro Gly Glu Phe Cys Val Leu
                500                 505

<210> SEQ ID NO 10
<211> LENGTH: 1710
<212> TYPE: DNA
<213> ORGANISM: Artificial sequence
<220> FEATURE:
<223> OTHER INFORMATION: Synthetic sequence

<400> SEQUENCE: 10
atgttttcac atcttcccctt tgactgtgtc ctgctgctgc tgctgctact acttacaagg      60
tcctcagaag tggaatacag agcggaggtc ggtcagaatg cctatctgcc ctgcttctac     120
accccagccg ccccagggaa cctcgtgccc gtctgctggg gcaaaggagc ctgtcctgtg     180
tttgaatgtg gcaacgtggt gctcaggact gatgaaaggg atgtgaatta ttggacatcc     240
agatactggc taaatgggga tttccgcaaa ggagatgtgt ccctgaccat agagaatgtg     300
actctagcag acagtgggat ctactgctgc cggatccaaa tcccaggcat aatgaatgat     360
gaaaaattta acctgaagtt ggtcatcaaa ccagccaagg tcacccctgc accgactcgg     420
cagagagact tcactgcagc cttttccaagg atgcttacca ccaggggaca tggcccagca     480
gagacacaga cactggggag cctccctgat ataaatctaa cacaaatatc cacattggcc     540
aatgagttac gggactctag attggccaat gacttacggg actctggagc aaccatcaga     600
ataggctcta gtacggcccc tccctgccct agctgtcccg ccctgaattt ctgggcgga     660 ccctccgtgt ttctgttccc cccaaagccc aaggacaccc tgatgatcag ccggaccccc     720
gaagtgacct gtgtggtggt ggatgtgtcc caggaagatc ccgaggtgca gttcaattgg     780
tacgtggacg gggtggaagt gcacaacgcc aagaccaagc cagagagga acagttcaac     840 agcacctacc gggtggtgtc tgtgctgacc gtgctgcacc aggattggct gagcggcaaa     900
gagtacaagt gcaaggtgtc cagcaagggc ctgcccagca gcatcgaaaa gaccatcagc     960
aacgccaccg gccagcccag ggaaccccag gtgtacacac tgcccctag ccaggaagag     1020 atgaccaaga accaggtgtc cctgacatgc ctcgtgaagg gcttctaccc ctccgatatc     1080
gccgtggaat gggagagcaa cggccagcca gagaacaact acaagaccac ccccccagtg     1140
ctggacagcg acggctcatt cttcctgtac tccggctga cagtggacaa gagcagctgg     1200
caggaaggca acgtgttcag ctgcagcgtg atgcacgaag ccctgcacaa ccactacacc     1260
cagaagtccc tgagcctgtc cctgggcaaa atagagggac gaatggacca ggtatcacat     1320
cggtatcctc gaattcaaag tatcaaagta caatttaccg aatataagaa ggagaaaggt     1380
ttcatcctca cttcccaaaa ggaggatgaa atcatgaagg tgcagaacaa ctcagtcatc     1440
```

-continued

```
atcaactgtg atgggtttta tctcatctcc ctgaagggct acttctccca ggaagtcaac    1500
attagccttc attaccagaa ggatgaggag cccctcttcc aactgaagaa ggtcaggtct    1560
gtcaactcct tgatggtggc ctctctgact tacaaagaca aagtctactt gaatgtgacc    1620
actgacaata cctccctgga tgacttccat gtgaatggcg agaactgat tcttatccat     1680 caaaatcctg gtgaattctg tgtcctttga                                      1710
```

<210> SEQ ID NO 11
<211> LENGTH: 569
<212> TYPE: PRT
<213> ORGANISM: Artificial sequence
<220> FEATURE:
<223> OTHER INFORMATION: Synthetic sequence

<400> SEQUENCE: 11

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ser Lys Tyr Gly Pro Pro
        195                 200                 205

Cys Pro Ser Cys Pro Ala Pro Glu Phe Leu Gly Gly Pro Ser Val Phe
    210                 215                 220

Leu Phe Pro Pro Lys Pro Lys Asp Thr Leu Met Ile Ser Arg Thr Pro
225                 230                 235                 240

Glu Val Thr Cys Val Val Val Asp Val Ser Gln Glu Asp Pro Glu Val
                245                 250                 255

Gln Phe Asn Trp Tyr Val Asp Gly Val Glu Val His Asn Ala Lys Thr
            260                 265                 270

Lys Pro Arg Glu Glu Gln Phe Asn Ser Thr Tyr Arg Val Val Ser Val
        275                 280                 285

Leu Thr Val Leu His Gln Asp Trp Leu Ser Gly Lys Glu Tyr Lys Cys
    290                 295                 300

Lys Val Ser Ser Lys Gly Leu Pro Ser Ser Ile Glu Lys Thr Ile Ser
305                 310                 315                 320
```

Asn Ala Thr Gly Gln Pro Arg Glu Pro Gln Val Tyr Thr Leu Pro Pro
            325                 330                 335

Ser Gln Glu Glu Met Thr Lys Asn Gln Val Ser Leu Thr Cys Leu Val
            340                 345                 350

Lys Gly Phe Tyr Pro Ser Asp Ile Ala Val Glu Trp Glu Ser Asn Gly
            355                 360                 365

Gln Pro Glu Asn Asn Tyr Lys Thr Thr Pro Pro Val Leu Asp Ser Asp
        370                 375                 380

Gly Ser Phe Phe Leu Tyr Ser Arg Leu Thr Val Asp Lys Ser Ser Trp
385                 390                 395                 400

Gln Glu Gly Asn Val Phe Ser Cys Ser Val Met His Glu Ala Leu His
                405                 410                 415

Asn His Tyr Thr Gln Lys Ser Leu Ser Leu Ser Leu Gly Lys Ile Glu
            420                 425                 430

Gly Arg Met Asp Gln Val Ser His Arg Tyr Pro Arg Ile Gln Ser Ile
            435                 440                 445

Lys Val Gln Phe Thr Glu Tyr Lys Lys Glu Lys Gly Phe Ile Leu Thr
        450                 455                 460

Ser Gln Lys Glu Asp Glu Ile Met Lys Val Gln Asn Asn Ser Val Ile
465                 470                 475                 480

Ile Asn Cys Asp Gly Phe Tyr Leu Ile Ser Leu Lys Gly Tyr Phe Ser
                485                 490                 495

Gln Glu Val Asn Ile Ser Leu His Tyr Gln Lys Asp Glu Glu Pro Leu
            500                 505                 510

Phe Gln Leu Lys Lys Val Arg Ser Val Asn Ser Leu Met Val Ala Ser
            515                 520                 525

Leu Thr Tyr Lys Asp Lys Val Tyr Leu Asn Val Thr Thr Asp Asn Thr
        530                 535                 540

Ser Leu Asp Asp Phe His Val Asn Gly Gly Glu Leu Ile Leu Ile His
545                 550                 555                 560

Gln Asn Pro Gly Glu Phe Cys Val Leu
            565

<210> SEQ ID NO 12
<211> LENGTH: 2223
<212> TYPE: DNA
<213> ORGANISM: Artificial sequence
<220> FEATURE:
<223> OTHER INFORMATION: Synthetic sequence

<400> SEQUENCE: 12
atggagcccg ccggcccggc ccccggccgc ctcgggccgc tgctctgcct gctgctcgcc        60
gcgtcctgcg cctggtcagg agtggcgggt gaggaggagc tgcaggtgat tcagcctgac       120
aagtccgtgt tggttgcagc tggagagaca gccactctgc gctgcactgc gacctctctg       180
atccctgtgg ggcccatcca gtggttcaga ggagctggac caggccggga attaatctac       240
aatcaaaaag aaggccactt ccccgggta caactgtttt cagacctcac aaagagaaac       300
aacatggact tttccatccg catcggtaac atcacccag cagatgccgg cacctactac       360
tgtgtgaagt tccggaaagg agcccccgat gacgtggagt taagtctgg agcaggcact       420 gagctgtctg tgcgcgccaa acctctgcc ccgtgggtat cgggccctgc ggcgagggcc       480
acacctcagc acacagtgag cttcacctgc gagtcccacg gcttctcacc cagagacatc       540
accctgaaat ggttcaaaaa tgggaatgag ctctcagact ccagaccaa cgtggacccc       600

```
gtaggagaga gcgtgtccta cagcatccac agcacagcca aggtggtgct gacccgcgag    660
gacgttcact ctcaagtcat ctgcgaggtg gcccacgtca ccttgcaggg ggaccctctt    720
cgtgggactg ccaacttgtc tgagaccatc cgagttccac ccaccttgga ggttactcaa    780
cagcccgtga gggcagagaa ccaggtgaat gtcacctgcc aggtgaggaa gttctacccc    840
cagagactac agctgacctg gttggagaat ggaaacgtgt cccggacaga aacggcctca    900
accgttacag agaacaagga tggtacctac aactggatga gctggctcct ggtgaatgta    960
tctgcccaca gggatgatgt gaagctcacc tgccaggtgg agcatgacgg cagccagcg    1020
gtcagcaaaa gccatgacct gaaggtctca gcccacccga aggagcaggg ctcaaatacc    1080
gccgctgaga cactggatc taatgaacgg aacatctatt ctaagtacgg ccctccctgc    1140
cctagctgtc ccgcccctga atttctgggc ggaccctccg tgtttctgtt cccccccaaag   1200
cccaaggaca ccctgatgat cagccggacc cccgaagtga cctgtgtggt ggtggatgtg    1260
tcccaggaag atcccgaggt gcagttcaat tggtacgtgg acggggtgga agtgcacaac    1320
gccaagacca gcccagaga ggaacagttc aacagcacct accgggtggt gtctgtgctg    1380
accgtgctgc accaggattg gctgagcggc aaagagtaca agtgcaaggt gtccagcaag    1440
ggcctgccca gcagcatcga aaagaccatc agcaacgcca ccggccagcc cagggaaccc    1500
caggtgtaca cactgccccc tagccaggaa gagatgacca gaaccaggt gtccctgaca    1560
tgcctcgtga agggcttcta ccccctccgat atcgccgtgg aatgggagag caacggccag   1620
ccagagaaca actacaagac cacccccca gtgctggaca gcgacggctc attcttcctg    1680
tactcccggc tgacagtgga caagagcagc tggcaggaag caacgtgtt cagctgcagc    1740
gtgatgcacg aagccctgca caaccactac acccagaagt ccctgagcct gtccctgggc   1800
aaaatagagg gacgaatgga ccaggtatca catcggtatc ctcgaattca agtatcaaa    1860
gtacaattta ccgaatataa gaaggagaaa ggtttcatcc tcacttccca aaaggaggat    1920
gaaatcatga aggtgcagaa caactcagtc atcatcaact gtgatgggtt ttatctcatc    1980
tccctgaagg gctacttctc ccaggaagtc aacattagcc ttcattacca gaaggatgag    2040
gagccccctct tccaactgaa gaaggtcagg tctgtcaact ccttgatggt ggcctctctg    2100
acttacaaag acaaagtcta cttgaatgtg accactgaca atacctccct ggatgacttc    2160
catgtgaatg gcggagaact gattcttatc catcaaaatc ctggtgaatt ctgtgtcctt    2220
tga                                                                  2223
```

<210> SEQ ID NO 13
<211> LENGTH: 740
<212> TYPE: PRT
<213> ORGANISM: Artificial sequence
<220> FEATURE:
<223> OTHER INFORMATION: Synthetic sequence

<400> SEQUENCE: 13

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr

```
                65                  70                  75                  80
Asn Gln Lys Glu Gly His Phe Pro Arg Val Thr Thr Val Ser Asp Leu
                    85                  90                  95
Thr Lys Arg Asn Asn Met Asp Phe Ser Ile Arg Ile Gly Asn Ile Thr
                100                 105                 110
Pro Ala Asp Ala Gly Thr Tyr Tyr Cys Val Lys Phe Arg Lys Gly Ser
                115                 120                 125
Pro Asp Asp Val Glu Phe Lys Ser Gly Ala Gly Thr Glu Leu Ser Val
                130                 135                 140
Arg Ala Lys Pro Ser Ala Pro Val Val Ser Gly Pro Ala Ala Arg Ala
145                 150                 155                 160
Thr Pro Gln His Thr Val Ser Phe Thr Cys Glu Ser His Gly Phe Ser
                165                 170                 175
Pro Arg Asp Ile Thr Leu Lys Trp Phe Lys Asn Gly Asn Glu Leu Ser
                180                 185                 190
Asp Phe Gln Thr Asn Val Asp Pro Val Gly Glu Ser Val Ser Tyr Ser
                195                 200                 205
Ile His Ser Thr Ala Lys Val Val Leu Thr Arg Glu Asp Val His Ser
                210                 215                 220
Gln Val Ile Cys Glu Val Ala His Val Thr Leu Gln Gly Asp Pro Leu
225                 230                 235                 240
Arg Gly Thr Ala Asn Leu Ser Glu Thr Ile Arg Val Pro Pro Thr Leu
                245                 250                 255
Glu Val Thr Gln Gln Pro Val Arg Ala Glu Asn Gln Val Asn Val Thr
                260                 265                 270
Cys Gln Val Arg Lys Phe Tyr Pro Gln Arg Leu Gln Leu Thr Trp Leu
                275                 280                 285
Glu Asn Gly Asn Val Ser Arg Thr Glu Thr Ala Ser Thr Val Thr Glu
                290                 295                 300
Asn Lys Asp Gly Thr Tyr Asn Trp Met Ser Trp Leu Leu Val Asn Val
305                 310                 315                 320
Ser Ala His Arg Asp Asp Val Lys Leu Thr Cys Gln Val Glu His Asp
                325                 330                 335
Gly Gln Pro Ala Val Ser Lys Ser His Asp Leu Lys Val Ser Ala His
                340                 345                 350
Pro Lys Glu Gln Gly Ser Asn Thr Ala Ala Glu Asn Thr Gly Ser Asn
                355                 360                 365
Glu Arg Asn Ile Tyr Ser Lys Tyr Gly Pro Pro Cys Pro Ser Cys Pro
                370                 375                 380
Ala Pro Glu Phe Leu Gly Gly Pro Ser Val Phe Leu Phe Pro Pro Lys
385                 390                 395                 400
Pro Lys Asp Thr Leu Met Ile Ser Arg Thr Pro Glu Val Thr Cys Val
                405                 410                 415
Val Val Asp Val Ser Gln Glu Asp Pro Glu Val Gln Phe Asn Trp Tyr
                420                 425                 430
Val Asp Gly Val Glu Val His Asn Ala Lys Thr Lys Pro Arg Glu Glu
                435                 440                 445
Gln Phe Asn Ser Thr Tyr Arg Val Val Ser Val Leu Thr Val Leu His
                450                 455                 460
Gln Asp Trp Leu Ser Gly Lys Glu Tyr Lys Cys Lys Val Ser Ser Lys
465                 470                 475                 480
Gly Leu Pro Ser Ser Ile Glu Lys Thr Ile Ser Asn Ala Thr Gly Gln
                485                 490                 495
```

```
Pro Arg Glu Pro Gln Val Tyr Thr Leu Pro Pro Ser Gln Glu Glu Met
            500                 505                 510
Thr Lys Asn Gln Val Ser Leu Thr Cys Leu Val Lys Gly Phe Tyr Pro
            515                 520                 525
Ser Asp Ile Ala Val Glu Trp Glu Ser Asn Gly Gln Pro Glu Asn Asn
530                 535                 540
Tyr Lys Thr Thr Pro Pro Val Leu Asp Ser Asp Gly Ser Phe Phe Leu
545                 550                 555                 560
Tyr Ser Arg Leu Thr Val Asp Lys Ser Arg Trp Gln Glu Gly Asn Val
                565                 570                 575
Phe Ser Cys Ser Val Met His Glu Ala Leu His Asn His Tyr Thr Gln
            580                 585                 590
Lys Ser Leu Ser Leu Ser Leu Gly Lys Ile Glu Gly Arg Met Asp Gln
            595                 600                 605
Val Ser His Arg Tyr Pro Arg Ile Gln Ser Ile Lys Val Gln Phe Thr
            610                 615                 620
Glu Tyr Lys Lys Glu Lys Gly Phe Ile Leu Thr Ser Gln Lys Glu Asp
625                 630                 635                 640
Glu Ile Met Lys Val Gln Asn Asn Ser Val Ile Ile Asn Cys Asp Gly
                645                 650                 655
Phe Tyr Leu Ile Ser Leu Lys Gly Tyr Phe Ser Gln Glu Val Asn Ile
            660                 665                 670
Ser Leu His Tyr Gln Lys Asp Glu Glu Pro Leu Phe Gln Leu Lys Lys
            675                 680                 685
Val Arg Ser Val Asn Ser Leu Met Val Ala Ser Leu Thr Tyr Lys Asp
690                 695                 700
Lys Val Tyr Leu Asn Val Thr Thr Asp Asn Thr Ser Leu Asp Asp Phe
705                 710                 715                 720
His Val Asn Gly Gly Glu Leu Ile Leu Ile His Gln Asn Pro Gly Glu
                725                 730                 735
Phe Cys Val Leu
            740

<210> SEQ ID NO 14
<211> LENGTH: 1554
<212> TYPE: DNA
<213> ORGANISM: Artificial sequence
<220> FEATURE:
<223> OTHER INFORMATION: Synthetic sequence

<400> SEQUENCE: 14 atgggtccc cgggcatggt gctgggcctc ctggtgcaga tctgggccct gcaagaagcc      60
tcaagcctga gcgtgcagca ggggcccaac ttgctgcagg tgaggcaggg cagtcaggcg    120
accctggtct gccaggtgga ccaggccaca gcctgggaac ggctccgtgt taagtggaca    180
aaggatgggg ccatcctgtg tcaaccgtac atcaccaacg cagcctcag cctgggggtc     240 tgcgggcccc agggacggct ctcctggcag gcacccagcc atctcaccct gcagctggac    300
cctgtgagcc tcaaccacag cggggcgtac gtgtgctggg cggccgtaga gattcctgag    360
ttggaggagg ctgagggcaa cataacaagg ctctttgtgg acccagatga ccccacacag    420
aacagaaacc ggatcgcaag cttcccagga tctaagtacg ccctccctg ccctagctgt     480 cccgcccctg aatttctggg cggacccctcc gtgtttctgt tccccccaaa gcccaaggac    540 acccctgatga tcagccggac ccccgaagtg acctgtgtgg tggtggatgt gtcccaggaa   600
```

```
gatcccgagg tgcagttcaa ttggtacgtg gacggggtgg aagtgcacaa cgccaagacc    660
aagcccagag aggaacagtt caacagcacc taccgggtgg tgtctgtgct gaccgtgctg    720
caccaggatt ggctgagcgg caaagagtac aagtgcaagg tgtccagcaa gggcctgccc    780
agcagcatcg aaaagaccat cagcaacgcc accggccagc ccagggaacc ccaggtgtac    840
acactgcccc ctagccagga agagatgacc aagaaccagg tgtccctgac atgcctcgtg    900
aagggcttct acccctccga tatcgccgtg aatgggaga gcaacggcca gccagagaac    960
aactacaaga ccaccccccc agtgctggac agcgacggct cattcttcct gtactcccgg   1020
ctgacagtgg acaagagcag ctggcaggaa ggcaacgtgt tcagctgcag cgtgatgcac   1080
gaagccctgc acaaccacta cacccagaag tccctgagcc tgtccctggg caaaatagag   1140
ggacgaatgg accaggtatc acatcggtat cctcgaattc aaagtatcaa agtacaattt   1200
accgaatata agaaggagaa aggtttcatc ctcacttccc aaaaggagga tgaaatcatg   1260
aaggtgcaga caactcagt catcatcaac tgtgatgggt tttatctcat ctccctgaag   1320
ggctacttct cccaggaagt caacattagc cttcattacc agaaggatga ggagcccctc   1380
ttccaactga gaaggtcag gtctgtcaac tccttgatgg tggcctctct gacttacaaa   1440
gacaaagtct acttgaatgt gaccactgac aatacctccc tggatgactt ccatgtgaat   1500
ggcggagaac tgattcttat ccatcaaaat cctggtgaat tctgtgtcct ttga         1554
```

<210> SEQ ID NO 15
<211> LENGTH: 517
<212> TYPE: PRT
<213> ORGANISM: Artificial sequence
<220> FEATURE:
<223> OTHER INFORMATION: Synthetic sequence

<400> SEQUENCE: 15

```
Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Pro Thr Gln Asn Arg Asn Arg
    130                 135                 140

Ile Ala Ser Phe Pro Gly Ser Lys Tyr Gly Pro Pro Cys Pro Ser Cys
145                 150                 155                 160

Pro Ala Pro Glu Phe Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser Gln Glu Asp Pro Glu Val Gln Phe Asn Trp
```

```
              195                 200                 205
    Tyr Val Asp Gly Val Glu Val His Asn Ala Lys Thr Lys Pro Arg Glu
    210                 215                 220

Glu Gln Phe Asn Ser Thr Tyr Arg Val Val Ser Val Leu Thr Val Leu
225                 230                 235                 240

His Gln Asp Trp Leu Ser Gly Lys Glu Tyr Lys Cys Lys Val Ser Ser
                245                 250                 255

Lys Gly Leu Pro Ser Ser Ile Glu Lys Thr Ile Ser Asn Ala Thr Gly
            260                 265                 270

Gln Pro Arg Glu Pro Gln Val Tyr Thr Leu Pro Pro Ser Gln Glu Glu
        275                 280                 285

Met Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Arg Leu Thr Val Asp Lys Ser Ser Trp Gln Glu Gly Asn
            340                 345                 350

Val Phe Ser Cys Ser Val Met His Glu Ala Leu His Asn His Tyr Thr
        355                 360                 365

Gln Lys Ser Leu Ser Leu Ser Leu Gly Lys Ile Glu Gly Arg Met Asp
    370                 375                 380

Gln Val Ser His Arg Tyr Pro Arg Ile Gln Ser Ile Lys Val Gln Phe
385                 390                 395                 400

Thr Glu Tyr Lys Lys Glu Lys Gly Phe Ile Leu Thr Ser Gln Lys Glu
                405                 410                 415

Asp Glu Ile Met Lys Val Gln Asn Asn Ser Val Ile Ile Asn Cys Asp
            420                 425                 430

Gly Phe Tyr Leu Ile Ser Leu Lys Gly Tyr Phe Ser Gln Glu Val Asn
        435                 440                 445

Ile Ser Leu His Tyr Gln Lys Asp Glu Glu Pro Leu Phe Gln Leu Lys
    450                 455                 460

Lys Val Arg Ser Val Asn Ser Leu Met Val Ala Ser Leu Thr Tyr Lys
465                 470                 475                 480

Asp Lys Val Tyr Leu Asn Val Thr Thr Asp Asn Thr Ser Leu Asp Asp
                485                 490                 495

Phe His Val Asn Gly Gly Glu Leu Ile Leu Ile His Gln Asn Pro Gly
            500                 505                 510

Glu Phe Cys Val Leu
        515

<210> SEQ ID NO 16
<211> LENGTH: 3493
<212> TYPE: DNA
<213> ORGANISM: Homo sapiens

<400> SEQUENCE: 16
tcaatcgcct ttatctctg  gccctgggac ctttgcctat tttctgattg ataggctttg       60
ttttgtcttt acctccttct ttctggggaa aacttcagtt ttatcgcacg ttcccctttt     120
ccatatcttc atcttccctc tacccagatt gtgaagatgg aaagggtcca acccctggaa     180
gagaatgtgg gaaatgcagc caggccaaga ttcgagagga caagctatt  gctggtggcc     240 tctgtaattc agggactggg gctgctcctg tgcttcacct acatctgcct gcacttctct     300
```

| | |
|---|---|
| gctcttcagg tatcacatcg gtatcctcga attcaaagta tcaaagtaca atttaccgaa | 360 |
| tataagaagg agaaaggttt catcctcact tcccaaaagg aggatgaaat catgaaggtg | 420 |
| cagaacaact cagtcatcat caactgtgat gggttttatc tcatctccct gaagggctac | 480 |
| ttctcccagg aagtcaacat tagccttcat taccagaagg atgaggagcc cctcttccaa | 540 |
| ctgaagaagg tcaggtctgt caactccttg atggtggcct ctctgactta caaagacaaa | 600 |
| gtctacttga atgtgaccac tgacaatacc tccctggatg acttccatgt gaatggcgga | 660 |
| gaactgattc ttatccatca aaatcctggt gaattctgtg tcctttgagg ggctgatggc | 720 |
| aatatctaaa accaggcacc agcatgaaca ccaagctggg ggtggacagg gcatggattc | 780 |
| ttcattgcaa gtgaaggagc ctcccagctc agccacgtgg gatgtgacaa gaagcagatc | 840 |
| ctggccctcc cgcccccacc cctcaggat atttaaaact tatttatat accagttaat | 900 |
| cttatttatc cttatatttt ctaaattgcc tagccgtcac accccaagat tgccttgagc | 960 |
| ctactaggca cctttgtgag aaagaaaaaa tagatgcctc ttcttcaaga tgcattgttt | 1020 |
| ctattggtca ggcaattgtc ataataaact tatgtcattg aaaacggtac ctgactacca | 1080 |
| tttgctggaa atttgacatg tgtgtggcat tatcaaaatg aagaggagca aggagtgaag | 1140 |
| gagtggggtt atgaatctgc caaaggtggt atgaaccaac ccctggaagc caaagcggcc | 1200 |
| tctccaaggt taaattgatt gcagtttgca tattgcctaa atttaaactt tctcatttgg | 1260 |
| tgggggttca aagaagaat cagcttgtga aaaatcagga cttgaagaga gccgtctaag | 1320 |
| aaataccacg tgcttttttt ctttaccatt ttgctttccc agcctccaaa catagttaat | 1380 |
| agaaatttcc cttcaaagaa ctgtctgggg atgtgatgct ttgaaaaatc taatcagtga | 1440 |
| cttaagagag attttcttgt atacaggag agtgagataa cttattgtga agggttagct | 1500 |
| ttactgtaca ggatagcagg gaactggaca tctcagggta aaagtcagta cggattttaa | 1560 |
| tagcctgggg aggaaaacac attctttgcc acagacaggc aaagcaacac atgctcatcc | 1620 |
| tcctgcctat gctgagatac gcactcagct ccatgtcttg tacacacaga aacattgctg | 1680 |
| gtttcaagaa atgaggtgat cctattatca aattcaatct gatgtcaaat agcactaaga | 1740 |
| agttattgtg ccttatgaaa aataatgatc tctgtctaga ataccatag accatatata | 1800 |
| gtctcacatt gataattgaa actagaaggg tctataatca gcctatgcca gggcttcaat | 1860 |
| ggaatagtat cccttatgt ttagttgaaa tgtcccctta acttgatata atgtgttatg | 1920 |
| cttatggcgc tgtggacaat ctgatttttc atgtcaactt ccagatgat ttgtaacttc | 1980 |
| tctgtgccaa acctttata aacataaatt tttgagatat gtattttaaa attgtagcac | 2040 |
| atgtttccct gacattttca atagaggata caacatcaca gaatctttct ggatgattct | 2100 |
| gtgttatcaa ggaattgtac tgtgctacaa ttatctctag aatctccaga aaggtggagg | 2160 |
| gctgttcgcc cttacactaa atggtctcag ttggattttt ttttcctgtt ttctatttcc | 2220 |
| tcttaagtac accttcaact atattcccat ccctctattt taatctgtta tgaaggaagg | 2280 |
| taaataaaaa tgctaaatag aagaaattgt aggtaaggta agaggaatca agttctgagt | 2340 |
| ggctgccaag gcactcacag aatcataatc atggctaaat atttatggag gcctactgt | 2400 |
| ggaccaggca ctgggctaaa tacttacatt tacaagaatc attctgagac agatattcaa | 2460 |
| tgatatctgg cttcactact cagaagattg tgtgtgtgtt tgtgtgtgtg tgtgtgtgtg | 2520 |
| tatttcactt tttgttattg accatgttct gcaaaattgc agttactcag tgagtgatat | 2580 |
| ccgaaaagt aaacgtttat gactataggt aatatttaag aaaatgcatg gttcatttt | 2640 |

-continued

```
aagtttggaa ttttttatcta tatttctcac agatgtgcag tgcacatgca ggcctaagta   2700
tatgttgtgt gtgttgtttg tctttgatgt catggtcccc tctcttaggt gctcactcgc   2760
tttgggtgca cctggcctgc tcttcccatg ttggcctctg caaccacaca gggatatttc   2820
tgctatgcac cagcctcact ccaccttcct tccatcaaaa atatgtgtgt gtgtctcagt   2880
ccctgtaagt catgtccttc acagggagaa ttaacccttc gatatacatg gcagagtttt   2940
gtgggaaaag aattgaatga aaagtcagga gatcagaatt ttaaatttga cttagccact   3000
aactagccat gtaaccttgg gaaagtcatt tcccatttct gggtcttgct tttctttctg   3060
ttaaatgaga ggaatgttaa atatctaaca gtttagaatc ttatgcttac agtgttatct   3120
gtgaatgcac atattaaatg tctatgttct tgttgctatg agtcaaggag tgtaaccttc   3180
tcctttacta tgttgaatgt attttttct ggacaagctt acatcttcct cagccatctt   3240
tgtgagtcct tcaagagcag ttatcaattg ttagttagat attttctatt tagagaatgc   3300
ttaagggatt ccaatcccga tccaaatcat aatttgttct taagtatact gggcaggtcc   3360
cctattttaa gtcataattt tgtatttagt gctttcctgg ctctcagaga gtattaatat   3420
tgatattaat aatatagtta atagtaatat tgctatttac atggaaacaa ataaaagatc   3480
tcagaattca cta                                                       3493
```

<210> SEQ ID NO 17
<211> LENGTH: 183
<212> TYPE: PRT
<213> ORGANISM: Homo sapiens

<400> SEQUENCE: 17

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
        50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

<210> SEQ ID NO 18
<211> LENGTH: 684
<212> TYPE: DNA
<213> ORGANISM: Artificial sequence
<220> FEATURE:
<223> OTHER INFORMATION: Synthetic sequence

<400> SEQUENCE: 18

```
tctaagtacg gccctccctg ccctagctgt cccgcccctg aatttctggg cggaccctcc      60
gtgtttctgt tcccccaaa gcccaaggac accctgatga tcagccggac ccccgaagtg     120
acctgtgtgg tggtggatgt gtcccaggaa gatcccgagg tgcagttcaa ttggtacgtg     180
gacggggtgg aagtgcacaa cgccaagacc aagcccagag aggaacagtt caacagcacc     240
taccgggtgg tgtctgtgct gaccgtgctg caccaggatt ggctgagcgg caaagagtac     300
aagtgcaagg tgtccagcaa gggcctgccc agcagcatcg aaaagaccat cagcaacgcc     360
accggccagc ccagggaacc ccaggtgtac acactgcccc ctagccagga agagatgacc     420
aagaaccagg tgtccctgac atgcctcgtg aagggcttct acccctccga tatcgccgtg     480
gaatgggaga gcaacggcca gccagagaac aactacaaga ccaccccccc agtgctggac     540
agcgacggct cattcttcct gtactcccgg ctgacagtgg acaagagcag ctggcaggaa     600
ggcaacgtgt tcagctgcag cgtgatgcac gaagccctgc acaaccacta cacccagaag     660
tccctgagcc tgtccctggg caaa                                           684
```

<210> SEQ ID NO 19
<211> LENGTH: 867
<212> TYPE: DNA
<213> ORGANISM: Homo sapiens

<400> SEQUENCE: 19

```
atgcagatcc acaggcgcc ctggccagtc gtctgggcgg tgctacaact gggctggcgg      60
ccaggatggt tcttagactc cccagacagg ccctggaacc ccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccaccccag ccctcacccc     480
aggccagccg ccagttccaa accctggtg gttggtgtcg tgggcggcct gctgggcagc     540
ctggtgctgc tagtctgggt cctggccgtc atctgctccc gggccgcacg agggacaata     600
ggagccaggc gcaccggcca gcccctgaag gaggacccct cagccgtgcc tgtgttctct     660
gtggactatg gggagctgga tttccagtgg cgagagaaga cccccggagcc ccccgtgccc     720
tgtgtccctg agcagacgga gtatgccacc attgtctttc ctagcggaat gggcacctca     780
tcccccgccc cagggggctc agctgacggc cctcggagtg cccagccact gaggcctgag     840
gatggacact gctcttggcc cctctga                                        867
```

<210> SEQ ID NO 20
<211> LENGTH: 1623
<212> TYPE: DNA
<213> ORGANISM: Artificial sequence
<220> FEATURE:
<223> OTHER INFORMATION: Synthetic sequence

<400> SEQUENCE: 20

```
gtcgacgcca ccatgcagat cccacaggcg ccctggccag tcgtctgggc ggtgctacaa      60
```

| | | |
|---|---|---|
| ctgggctggc ggccaggatg gttcttagac tccccagaca ggccctggaa cccccccacc | 120 | |
| ttctccccag ccctgctcgt ggtgaccgaa ggggacaacg ccaccttcac ctgcagcttc | 180 | |
| tccaacacat cggagagctt cgtgctaaac tggtaccgca tgagcccag caaccagacg | 240 | |
| gacaagctgg ccgccttccc cgaggaccgc agccagcccg ccaggactg ccgcttccgt | 300 | |
| gtcacacaac tgcccaacgg gcgtgacttc cacatgagcg tggtcagggc ccggcgcaat | 360 | |
| gacagcggca cctacctctg tggggccatc tccctggccc ccaaggcgca gatcaaagag | 420 | |
| agcctgcggg cagagctcag ggtgacagag agaagggcag aagtgcccac agcccacccc | 480 | |
| agccctcac ccaggccagc cggccagttc aatctaagt acggccctcc ctgccctagc | 540 | |
| tgtcccgccc ctgaatttct gggcggaccc tccgtgtttc gttccccc aaagcccaag | 600 | |
| gacaccctga tgatcagccg gaccccgaa gtgacctgtg tggtggtgga tgtgtcccag | 660 | |
| gaagatcccg aggtgcagtt caattggtac gtggacgggg tggaagtgca aacgccaag | 720 | |
| accaagccca gagaggaaca gttcaacagc acctaccggg tggtgtctgt gctgaccgtg | 780 | |
| ctgcaccagg attggctgag cggcaaagag tacaagtgca aggtgtccag caagggcctg | 840 | |
| cccagcagca tcgaaaagac catcagcaac gccaccggcc agcccaggga accccaggtg | 900 | |
| tacacactgc cccctagcca ggaagagatg accaagaacc aggtgtccct gacatgcctc | 960 | |
| gtgaagggct tctacccctc cgatatcgcc gtggaatggg agagcaacgg ccagccagag | 1020 | |
| aacaactaca gaccacccc cccagtgctg gacagcgacg gctcattctt cctgtactcc | 1080 | |
| cggctgacag tggacaagag cagctggcag gaaggcaacg tgttcagctg cagcgtgatg | 1140 | |
| cacgaagccc tgcacaacca ctacacccag aagtccctga cctgtccct gggcaaaata | 1200 | |
| gagggacgaa tggaccaggt atcacatcgg tatcctcgaa ttcaaagtat caaagtacaa | 1260 | |
| tttaccgaat ataagaagga gaaggtttc atcctcactt cccaaaagga ggatgaaatc | 1320 | |
| atgaaggtgc agaacaactc agtcatcatc aactgtgatg gttttatct catctccctg | 1380 | |
| aagggctact ctcccagga agtcaacatt agccttcatt accagaagga tgaggagccc | 1440 | |
| ctcttccaac tgaagaaggt caggtctgtc aactccttga tggtggcctc tctgacttac | 1500 | |
| aaagacaaag tctacttgaa tgtgaccact gacaatacct ccctggatga cttccatgtg | 1560 | |
| aatggcggag aactgattct tatccatcaa aatcctggtg aattctgtgt cctttgagtc | 1620 | |
| gac | 1623 | |

<210> SEQ ID NO 21
<211> LENGTH: 1637
<212> TYPE: DNA
<213> ORGANISM: Homo sapiens

<400> SEQUENCE: 21

| | | |
|---|---|---|
| caccggcgag atctgccacc atgcagatcc tcaggcccc ctggcctgtc gtgtgggctg | 60 | |
| tgctgcagct gggatggcgg cctggctggt tcctggactc tcctgacaga ccctggaacc | 120 | |
| cccccacctt tagccctgct ctgctggtcg tgaccgaggg cgacaacgcc accttcacct | 180 | |
| gttccttcag caacaccctc cgagtccttcg tgctgaactg gtacagaatg tcccccagca | 240 | |
| accagaccga caagctggcc gccttccccg aggatagatc ccagcctgga caggactgcc | 300 | |
| ggttcagagt gacccagctg cccaacggcc gggacttcca catgtctgtc gtgcgggcca | 360 | |
| gacggaacga ctccggcaca tatctgtgcg gcgccatctc cctggccccc aaggctcaga | 420 | |
| tcaaagagtc tctgcgggcc gagctgagag tgaccgagag aagggctgag gtgccaaccg | 480 | |
| cccacccctag cccatctcca agacctgccg gccagttcca gtctaagtac ggccctcctt | 540 | |

```
gccctagctg ccctgcccct gaatttctgg gcggaccctc cgtgttcctg ttccccccaa    600
agcccaagga caccctgatg atctcccgga ccccgaagt gacctgcgtg gtggtggatg     660
tgtcccagga agatcccgag gtgcagttca attggtacgt ggacggcgtg aagtgcaca     720 acgccaagac caagcccaga gaggaacagt tcaactccac ctaccgggtg gtgtccgtgc    780
tgaccgtgct gcaccaggat tggctgtccg gcaaagagta caagtgcaag gtgtcctcca    840
agggcctgcc ctccagcatc gaaaagacca tctctaacgc caccggccag ccccgggaac    900
cccaggtgta cacactgcct ccaagccagg aagagatgac caagaaccag gtgtccctga    960
cctgtctcgt gaagggcttc taccccctcc gatatcgccg tggaatggga gtccaacggcc   1020 agcctgagaa caactacaag accaccccc ctgtgctgga ctccgacggc tccttcttcc     1080
tgtactcccg cctgaccgtg gacaagtcct cctggcagga aggcaacgtg ttctcctgct    1140
ccgtgatgca cgaggccctg cacaaccact acacccagaa gtccctgtcc ctgtctctgg    1200
gcaagatcga gggccggatg gatcaggtgt cacacagata ccccggatc cagtccatca     1260 aagtgcagtt taccgagtac aagaaagaga agggattcat cctgacctcc cagaaagagg    1320
acgagatcat gaaggtgcag aacaactccg tgatcatcaa ctgcgacggg ttctacctga    1380 tctcccctgaa gggctacttc agtcaggaag tgaacatcag cctgcactac cagaaggacg    1440 aggaaccct gttccagctg aagaaagtgc ggagcgtgaa ctccctgatg gtggcctctc    1500
tgacctacaa ggacaaggtg tacctgaacg tgaccaccga caatacctcc ctggacgact    1560 ccacgtgaa cggcggcgag ctgatcctga tccaccagaa ccctggcgag ttctgcgtgc     1620
tgtgactcga ggctagc                                                     1637
```

<210> SEQ ID NO 22
<211> LENGTH: 534
<212> TYPE: PRT
<213> ORGANISM: Artificial sequence
<220> FEATURE:
<223> OTHER INFORMATION: Synthetic sequence

<400> SEQUENCE: 22

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160
```

-continued

```
Arg Pro Ala Gly Gln Phe Gln Ser Lys Tyr Gly Pro Cys Pro Ser
            165                 170                 175

Cys Pro Ala Pro Glu Phe Leu Gly Gly Pro Ser Val Phe Leu Phe Pro
        180                 185                 190

Pro Lys Pro Lys Asp Thr Leu Met Ile Ser Arg Thr Pro Glu Val Thr
    195                 200                 205

Cys Val Val Val Asp Val Ser Gln Glu Asp Pro Glu Val Gln Phe Asn
210                 215                 220

Trp Tyr Val Asp Gly Val Glu Val His Asn Ala Lys Thr Lys Pro Arg
225                 230                 235                 240

Glu Glu Gln Phe Asn Ser Thr Tyr Arg Val Val Ser Val Leu Thr Val
                245                 250                 255

Leu His Gln Asp Trp Leu Ser Gly Lys Glu Tyr Lys Cys Lys Val Ser
            260                 265                 270

Ser Lys Gly Leu Pro Ser Ser Ile Glu Lys Thr Ile Ser Asn Ala Thr
        275                 280                 285

Gly Gln Pro Arg Glu Pro Gln Val Tyr Thr Leu Pro Pro Ser Gln Glu
    290                 295                 300

Glu Met Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Arg Leu Thr Val Asp Lys Ser Ser Trp Gln Glu Gly
        355                 360                 365

Asn Val Phe Ser Cys Ser Val Met His Glu Ala Leu His Asn His Tyr
    370                 375                 380

Thr Gln Lys Ser Leu Ser Leu Ser Leu Gly Lys Ile Glu Gly Arg Met
385                 390                 395                 400

Asp Gln Val Ser His Arg Tyr Pro Arg Ile Gln Ser Ile Lys Val Gln
                405                 410                 415

Phe Thr Glu Tyr Lys Lys Glu Lys Gly Phe Ile Leu Thr Ser Gln Lys
            420                 425                 430

Glu Asp Glu Ile Met Lys Val Gln Asn Asn Ser Val Ile Ile Asn Cys
        435                 440                 445

Asp Gly Phe Tyr Leu Ile Ser Leu Lys Gly Tyr Phe Ser Gln Glu Val
    450                 455                 460

Asn Ile Ser Leu His Tyr Gln Lys Asp Glu Glu Pro Leu Phe Gln Leu
465                 470                 475                 480

Lys Lys Val Arg Ser Val Asn Ser Leu Met Val Ala Ser Leu Thr Tyr
                485                 490                 495

Lys Asp Lys Val Tyr Leu Asn Val Thr Thr Asp Asn Thr Ser Leu Asp
            500                 505                 510

Asp Phe His Val Asn Gly Gly Glu Leu Ile Leu Ile His Gln Asn Pro
        515                 520                 525

Gly Glu Phe Cys Val Leu
    530
```

<210> SEQ ID NO 23
<211> LENGTH: 5
<212> TYPE: PRT
<213> ORGANISM: Artificial sequence
<220> FEATURE:
<223> OTHER INFORMATION: Synthetic sequence

```
<400> SEQUENCE: 23

Gly Gly Gly Gly Ser
1               5

<210> SEQ ID NO 24
<211> LENGTH: 5
<212> TYPE: PRT
<213> ORGANISM: Artificial sequence
<220> FEATURE:
<223> OTHER INFORMATION: Synthetic sequence

<400> SEQUENCE: 24

Glu Ala Ala Ala Lys
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic sequence

<400> SEQUENCE: 25

Ala Glu Ala Ala Ala Lys Ala
1               5

<210> SEQ ID NO 26
<211> LENGTH: 12
<212> TYPE: PRT
<213> ORGANISM: Artificial sequence
<220> FEATURE:
<223> OTHER INFORMATION: Synthetic sequence

<400> SEQUENCE: 26

Ala Glu Ala Ala Ala Lys Glu Ala Ala Ala Lys Ala
1               5                   10

<210> SEQ ID NO 27
<211> LENGTH: 46
<212> TYPE: PRT
<213> ORGANISM: Artificial sequence
<220> FEATURE:
<223> OTHER INFORMATION: Synthetic sequence

<400> SEQUENCE: 27

Ala Glu Ala Ala Ala Lys Glu Ala Ala Ala Lys Glu Ala Ala Ala Lys
1               5                   10                  15

Glu Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 28
<211> LENGTH: 5
<212> TYPE: PRT
<213> ORGANISM: Artificial sequence
<220> FEATURE:
<223> OTHER INFORMATION: Synthetic sequence

<400> SEQUENCE: 28

Pro Ala Pro Ala Pro
1               5

<210> SEQ ID NO 29
```

```
<211> LENGTH: 18
<212> TYPE: PRT
<213> ORGANISM: Artificial sequence
<220> FEATURE:
<223> OTHER INFORMATION: Synthetic sequence

<400> SEQUENCE: 29

Lys Glu Ser Gly Ser Val Ser Glu Gln Leu Ala Gln Phe Arg Ser
1               5                   10                  15

Leu Asp

<210> SEQ ID NO 30
<211> LENGTH: 14
<212> TYPE: PRT
<213> ORGANISM: Artificial sequence
<220> FEATURE:
<223> OTHER INFORMATION: Synthetic sequence

<400> SEQUENCE: 30

Glu Gly Lys Ser Ser Gly Ser Gly Ser Glu Ser Lys Ser Thr
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic sequence

<400> SEQUENCE: 31

Gly Ser Ala Gly Ser Ala Ala Gly Ser Gly Glu Phe
1               5                   10

<210> SEQ ID NO 32
<211> LENGTH: 143
<212> TYPE: PRT
<213> ORGANISM: Homo sapiens

<400> SEQUENCE: 32

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
                20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
        50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140

<210> SEQ ID NO 33
<211> LENGTH: 343
<212> TYPE: PRT
<213> ORGANISM: Homo sapiens
```

<400> SEQUENCE: 33

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr
            340
```

<210> SEQ ID NO 34
<211> LENGTH: 127
<212> TYPE: PRT
<213> ORGANISM: Homo sapiens

<400> SEQUENCE: 34

```
Lys Glu Ser Cys Asp Val Gln Leu Tyr Ile Lys Arg Gln Ser Glu His
1               5                   10                  15
```

```
Ser Ile Leu Ala Gly Asp Pro Phe Glu Leu Glu Cys Pro Val Lys Tyr
         20                  25                  30

Cys Ala Asn Arg Pro His Val Thr Trp Cys Lys Leu Asn Gly Thr Thr
             35                  40                  45

Cys Val Lys Leu Glu Asp Arg Gln Thr Ser Trp Lys Glu Glu Lys Asn
 50                  55                  60

Ile Ser Phe Phe Ile Leu His Phe Glu Pro Val Leu Pro Asn Asp Asn
 65                  70                  75                  80

Gly Ser Tyr Arg Cys Ser Ala Asn Phe Gln Ser Asn Leu Ile Glu Ser
                 85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg
        115                 120                 125

<210> SEQ ID NO 35
<211> LENGTH: 120
<212> TYPE: PRT
<213> ORGANISM: Homo sapiens

<400> SEQUENCE: 35

Met Met Thr Gly Thr Ile Glu Thr Thr Gly Asn Ile Ser Ala Glu Lys
1               5                  10                  15

Gly Gly Ser Ile Ile Leu Gln Cys His Leu Ser Ser Thr Thr Ala Gln
             20                  25                  30

Val Thr Gln Val Asn Trp Glu Gln Gln Asp Gln Leu Leu Ala Ile Cys
         35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120

<210> SEQ ID NO 36
<211> LENGTH: 181
<212> TYPE: PRT
<213> ORGANISM: Homo sapiens

<400> SEQUENCE: 36

Ser Glu Val Glu Tyr Arg Ala Glu Val Gly Gln Asn Ala Tyr Leu Pro
1               5                  10                  15

Cys Phe Tyr Thr Pro Ala Ala Pro Gly Asn Leu Val Pro Val Cys Trp
             20                  25                  30

Gly Lys Gly Ala Cys Pro Val Phe Glu Cys Gly Asn Val Val Leu Arg
         35                  40                  45

Thr Asp Glu Arg Asp Val Asn Tyr Trp Thr Ser Arg Tyr Trp Leu Asn
 50                  55                  60

Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                 85                  90                  95
```

```
Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180

<210> SEQ ID NO 37
<211> LENGTH: 202
<212> TYPE: PRT
<213> ORGANISM: Homo sapiens

<400> SEQUENCE: 37

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
                20                  25                  30

Thr Trp Gln Lys Lys Lys Ala Val Ser Pro Glu Asn Met Val Thr Phe
            35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly
        195                 200

<210> SEQ ID NO 38
<211> LENGTH: 128
<212> TYPE: PRT
<213> ORGANISM: Homo sapiens

<400> SEQUENCE: 38

Leu Ser Val Gln Gln Gly Pro Asn Leu Leu Gln Val Arg Gln Gly Ser
1               5                   10                  15

Gln Ala Thr Leu Val Cys Gln Val Asp Gln Ala Thr Ala Trp Glu Arg
                20                  25                  30
```

```
Leu Arg Val Lys Trp Thr Lys Asp Gly Ala Ile Leu Cys Gln Pro Tyr
            35                  40                  45

Ile Thr Asn Gly Ser Leu Ser Leu Gly Val Cys Gly Pro Gln Gly Arg
 50                  55                  60

Leu Ser Trp Gln Ala Pro Ser His Leu Thr Leu Gln Leu Asp Pro Val
 65                  70                  75                  80

Ser Leu Asn His Ser Gly Ala Tyr Val Cys Trp Ala Ala Val Glu Ile
                 85                  90                  95

Pro Glu Leu Glu Glu Ala Glu Gly Asn Ile Thr Arg Leu Phe Val Asp
                100                 105                 110

Pro Asp Asp Pro Thr Gln Asn Arg Asn Arg Ile Ala Ser Phe Pro Gly
            115                 120                 125

<210> SEQ ID NO 39
<211> LENGTH: 162
<212> TYPE: PRT
<213> ORGANISM: Homo sapiens

<400> SEQUENCE: 39

Phe Lys Val Ala Thr Pro Tyr Ser Leu Tyr Val Cys Pro Glu Gly Gln
 1               5                  10                  15

Asn Val Thr Leu Thr Cys Arg Leu Leu Gly Pro Val Asp Lys Gly His
                 20                  25                  30

Asp Val Thr Phe Tyr Lys Thr Trp Tyr Arg Ser Ser Arg Gly Glu Val
             35                  40                  45

Gln Thr Cys Ser Glu Arg Arg Pro Ile Arg Asn Leu Thr Phe Gln Asp
 50                  55                  60

Leu His Leu His His Gly Gly His Gln Ala Ala Asn Thr Ser His Asp
 65                  70                  75                  80

Leu Ala Gln Arg His Gly Leu Glu Ser Ala Ser Asp His His Gly Asn
                 85                  90                  95

Phe Ser Ile Thr Met Arg Asn Leu Thr Leu Leu Asp Ser Gly Leu Tyr
                100                 105                 110

Cys Cys Leu Val Val Glu Ile Arg His His His Ser Glu His Arg Val
            115                 120                 125

His Gly Ala Met Glu Leu Gln Val Gln Thr Gly Lys Asp Ala Pro Ser
130                 135                 140

Asn Cys Val Val Tyr Pro Ser Ser Ser Gln Asp Ser Glu Asn Ile Thr
145                 150                 155                 160

Ala Ala

<210> SEQ ID NO 40
<211> LENGTH: 242
<212> TYPE: PRT
<213> ORGANISM: Homo sapiens

<400> SEQUENCE: 40

Val Arg Ile Asn Gly Asp Gly Gln Glu Val Leu Tyr Leu Ala Glu Gly
 1               5                  10                  15

Asp Asn Val Arg Leu Gly Cys Pro Tyr Val Leu Asp Pro Glu Asp Tyr
                 20                  25                  30

Gly Pro Asn Gly Leu Asp Ile Glu Trp Met Gln Val Asn Ser Asp Pro
             35                  40                  45

Ala His His Arg Glu Asn Val Phe Leu Ser Tyr Gln Asp Lys Arg Ile
 50                  55                  60
```

Asn His Gly Ser Leu Pro His Leu Gln Gln Arg Val Arg Phe Ala Ala
65                  70                  75                  80

Ser Asp Pro Ser Gln Tyr Asp Ala Ser Ile Asn Leu Met Asn Leu Gln
                85                  90                  95

Val Ser Asp Thr Ala Thr Tyr Glu Cys Arg Val Lys Lys Thr Thr Met
            100                 105                 110

Ala Thr Arg Lys Val Ile Val Thr Val Gln Ala Arg Pro Ala Val Pro
        115                 120                 125

Met Cys Trp Thr Glu Gly His Met Thr Tyr Gly Asn Asp Val Val Leu
    130                 135                 140

Lys Cys Tyr Ala Ser Gly Gly Ser Gln Pro Leu Ser Tyr Lys Trp Ala
145                 150                 155                 160

Lys Ile Ser Gly His His Tyr Pro Tyr Arg Ala Gly Ser Tyr Thr Ser
                165                 170                 175

Gln His Ser Tyr His Ser Glu Leu Ser Tyr Gln Glu Ser Phe His Ser
            180                 185                 190

Ser Ile Asn Gln Gly Leu Asn Asn Gly Asp Leu Val Leu Lys Asp Ile
        195                 200                 205

Ser Arg Ala Asp Asp Gly Leu Tyr Gln Cys Thr Val Ala Asn Asn Val
    210                 215                 220

Gly Tyr Ser Val Cys Val Val Glu Val Lys Val Ser Asp Ser Arg Arg
225                 230                 235                 240

Ile Gly

<210> SEQ ID NO 41
<211> LENGTH: 427
<212> TYPE: PRT
<213> ORGANISM: Homo sapiens

<400> SEQUENCE: 41

Glu Asp Phe Arg Val Ile Gly Pro Ala His Pro Ile Leu Ala Gly Val
1               5                   10                  15

Gly Glu Asp Ala Leu Leu Thr Cys Gln Leu Leu Pro Lys Arg Thr Thr
            20                  25                  30

Met His Val Glu Val Arg Trp Tyr Arg Ser Glu Pro Ser Thr Pro Val
        35                  40                  45

Phe Val His Arg Asp Gly Val Glu Val Thr Glu Met Gln Met Glu Glu
    50                  55                  60

Tyr Arg Gly Trp Val Glu Trp Ile Glu Asn Gly Ile Ala Lys Gly Asn
65                  70                  75                  80

Val Ala Leu Lys Ile His Asn Ile Gln Pro Ser Asp Asn Gly Gln Tyr
                85                  90                  95

Trp Cys His Phe Gln Asp Gly Asn Tyr Cys Gly Glu Thr Ser Leu Leu
            100                 105                 110

Leu Lys Val Ala Gly Leu Gly Ser Ala Pro Ser Ile His Met Glu Gly
        115                 120                 125

Pro Gly Glu Ser Gly Val Gln Leu Val Cys Thr Ala Arg Gly Trp Phe
    130                 135                 140

Pro Glu Pro Gln Val Tyr Trp Glu Asp Ile Arg Gly Glu Lys Leu Leu
145                 150                 155                 160

Ala Val Ser Glu His Arg Ile Gln Asp Lys Asp Gly Leu Phe Tyr Ala
                165                 170                 175

Glu Ala Thr Leu Val Val Arg Asn Ala Ser Ala Glu Ser Val Ser Cys
            180                 185                 190

```
Leu Val His Asn Pro Val Leu Thr Glu Glu Lys Gly Ser Val Ile Ser
            195                 200                 205

Leu Pro Glu Lys Leu Gln Thr Glu Leu Ala Ser Leu Lys Val Asn Gly
210                 215                 220

Pro Ser Gln Pro Ile Leu Val Arg Val Gly Glu Asp Ile Gln Leu Thr
225                 230                 235                 240

Cys Tyr Leu Ser Pro Lys Ala Asn Ala Gln Ser Met Glu Val Arg Trp
                245                 250                 255

Asp Arg Ser His Arg Tyr Pro Ala Val His Val Tyr Met Asp Gly Asp
            260                 265                 270

His Val Ala Gly Glu Gln Met Ala Glu Tyr Arg Gly Arg Thr Val Leu
        275                 280                 285

Val Ser Asp Ala Ile Asp Glu Gly Arg Leu Thr Leu Gln Ile Leu Ser
290                 295                 300

Ala Arg Pro Ser Asp Asp Gly Gln Tyr Arg Cys Leu Phe Glu Lys Asp
305                 310                 315                 320

Asp Val Tyr Gln Glu Ala Ser Leu Asp Leu Lys Val Val Ser Leu Gly
                325                 330                 335

Ser Ser Pro Leu Ile Thr Val Glu Gly Gln Glu Asp Gly Glu Met Gln
            340                 345                 350

Pro Met Cys Ser Ser Asp Gly Trp Phe Pro Gln Pro His Val Pro Trp
        355                 360                 365

Arg Asp Met Glu Gly Lys Thr Ile Pro Ser Ser Gln Ala Leu Thr
370                 375                 380

Gln Gly Ser His Gly Leu Phe His Val Gln Thr Leu Leu Arg Val Thr
385                 390                 395                 400

Asn Ile Ser Ala Val Asp Val Thr Cys Ser Ile Ser Ile Pro Phe Leu
                405                 410                 415

Gly Glu Glu Lys Ile Ala Thr Phe Ser Leu Ser
            420                 425

<210> SEQ ID NO 42
<211> LENGTH: 235
<212> TYPE: PRT
<213> ORGANISM: Homo sapiens

<400> SEQUENCE: 42

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140
```

```
Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
        210                 215                 220

Pro Ser Pro Pro Ala Glu Gly Ser Thr Gly Asp
225                 230                 235
```

<210> SEQ ID NO 43
<211> LENGTH: 438
<212> TYPE: PRT
<213> ORGANISM: Homo sapiens

<400> SEQUENCE: 43

```
Leu Glu Val Gln Val Pro Glu Asp Pro Val Ala Leu Val Gly Thr
1               5                   10                  15

Asp Ala Thr Leu Cys Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
            35                  40                  45

His Ser Phe Ala Glu Gly Gln Asp Gln Gly Ser Ala Tyr Ala Asn Arg
        50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
                100                 105                 110

Pro Tyr Ser Lys Pro Ser Met Thr Leu Glu Pro Asn Lys Asp Leu Arg
            115                 120                 125

Pro Gly Asp Thr Val Thr Ile Thr Cys Ser Ser Tyr Gln Gly Tyr Pro
        130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
    210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
```

```
                275                 280                 285
Leu Leu Ala Gln Gly Asn Ala Ser Leu Arg Leu Gln Arg Val Arg Val
290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335

Met Thr Leu Glu Pro Asn Lys Asp Leu Arg Pro Gly Asp Thr Val Thr
                340                 345                 350

Ile Thr Cys Ser Ser Tyr Arg Gly Tyr Pro Glu Ala Glu Val Phe Trp
                355                 360                 365

Gln Asp Gly Gln Gly Val Pro Leu Thr Gly Asn Val Thr Thr Ser Gln
370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
                420                 425                 430

Thr Phe Pro Pro Glu Ala
                435

<210> SEQ ID NO 44
<211> LENGTH: 208
<212> TYPE: PRT
<213> ORGANISM: Homo sapiens

<400> SEQUENCE: 44

Cys Gln Gly Ser Ala Asp His Val Val Ser Ile Ser Gly Val Pro Leu
1               5                   10                  15

Gln Leu Gln Pro Asn Ser Ile Gln Thr Lys Val Asp Ser Ile Ala Trp
                20                  25                  30

Lys Lys Leu Leu Pro Ser Gln Asn Gly Phe His His Ile Leu Lys Trp
                35                  40                  45

Glu Asn Gly Ser Leu Pro Ser Asn Thr Ser Asn Asp Arg Phe Ser Phe
50                  55                  60

Ile Val Lys Asn Leu Ser Leu Leu Ile Lys Ala Ala Gln Gln Gln Asp
65                  70                  75                  80

Ser Gly Leu Tyr Cys Leu Glu Val Thr Ser Ile Ser Gly Lys Val Gln
                85                  90                  95

Thr Ala Thr Phe Gln Val Phe Val Phe Glu Ser Leu Leu Pro Asp Lys
                100                 105                 110

Val Glu Lys Pro Arg Leu Gln Gly Gln Gly Lys Ile Leu Asp Arg Gly
                115                 120                 125

Arg Cys Gln Val Ala Leu Ser Cys Leu Val Ser Arg Asp Gly Asn Val
130                 135                 140

Ser Tyr Ala Trp Tyr Arg Gly Ser Lys Leu Ile Gln Thr Ala Gly Asn
145                 150                 155                 160

Leu Thr Tyr Leu Asp Glu Glu Val Asp Ile Asn Gly Thr His Thr Tyr
                165                 170                 175

Thr Cys Asn Val Ser Asn Pro Val Ser Trp Glu Ser His Thr Leu Asn
                180                 185                 190

Leu Thr Gln Asp Cys Gln Asn Ala His Gln Glu Phe Arg Phe Trp Pro
                195                 200                 205
```

```
<210> SEQ ID NO 45
<211> LENGTH: 422
<212> TYPE: PRT
<213> ORGANISM: Homo sapiens

<400> SEQUENCE: 45

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380
```

```
Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
            405                 410                 415

Leu Pro Ala Gly His Leu
            420

<210> SEQ ID NO 46
<211> LENGTH: 498
<212> TYPE: PRT
<213> ORGANISM: Homo sapiens

<400> SEQUENCE: 46

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
```

```
                        325                 330                 335
Thr Lys Asp Thr Tyr Arg His Thr Phe Thr Leu Ser Leu Pro Arg Leu
                340                 345                 350
Lys Pro Ser Glu Ala Gly Arg Tyr Ser Phe Leu Ala Arg Asn Pro Gly
            355                 360                 365
Gly Trp Arg Ala Leu Thr Phe Glu Leu Thr Leu Arg Tyr Pro Pro Glu
        370                 375                 380
Val Ser Val Ile Trp Thr Phe Ile Asn Gly Ser Gly Thr Leu Leu Cys
385                 390                 395                 400
Ala Ala Ser Gly Tyr Pro Gln Pro Asn Val Thr Trp Leu Gln Cys Ser
                405                 410                 415
Gly His Thr Asp Arg Cys Asp Glu Ala Gln Val Leu Gln Val Trp Asp
                420                 425                 430
Asp Pro Tyr Pro Glu Val Leu Ser Gln Glu Pro Phe His Lys Val Thr
                435                 440                 445
Val Gln Ser Leu Leu Thr Val Glu Thr Leu Glu His Asn Gln Thr Tyr
                450                 455                 460
Glu Cys Arg Ala His Asn Ser Val Gly Ser Gly Ser Trp Ala Phe Ile
465                 470                 475                 480
Pro Ile Ser Ala Gly Ala His Thr His Pro Pro Asp Glu Phe Leu Phe
                485                 490                 495
Thr Pro

<210> SEQ ID NO 47
<211> LENGTH: 93
<212> TYPE: PRT
<213> ORGANISM: Homo sapiens

<400> SEQUENCE: 47

Leu Gln Cys Phe Cys His Leu Cys Thr Lys Asp Asn Phe Thr Cys Val
1               5                   10                  15
Thr Asp Gly Leu Cys Phe Val Ser Val Thr Glu Thr Thr Asp Lys Val
                20                  25                  30
Ile His Asn Ser Met Cys Ile Ala Glu Ile Asp Leu Ile Pro Arg Asp
            35                  40                  45
Arg Pro Phe Val Cys Ala Pro Ser Ser Lys Thr Gly Ser Val Thr Thr
        50                  55                  60
Thr Tyr Cys Cys Asn Gln Asp His Cys Asn Lys Ile Glu Leu Pro Thr
65                  70                  75                  80
Thr Val Lys Ser Ser Pro Gly Leu Gly Pro Val Glu Leu
                85                  90

<210> SEQ ID NO 48
<211> LENGTH: 214
<212> TYPE: PRT
<213> ORGANISM: Homo sapiens

<400> SEQUENCE: 48

His Gly Thr Glu Leu Pro Ser Pro Pro Ser Val Trp Phe Glu Ala Glu
1               5                   10                  15
Phe Phe His His Ile Leu His Trp Thr Pro Ile Pro Asn Gln Ser Glu
                20                  25                  30
Ser Thr Cys Tyr Glu Val Ala Leu Leu Arg Tyr Gly Ile Glu Ser Trp
            35                  40                  45
Asn Ser Ile Ser Asn Cys Ser Gln Thr Leu Ser Tyr Asp Leu Thr Ala
        50                  55                  60
```

Val Thr Leu Asp Leu Tyr His Ser Asn Gly Tyr Arg Ala Arg Val Arg
65                  70                  75                  80

Ala Val Asp Gly Ser Arg His Ser Asn Trp Thr Val Thr Asn Thr Arg
            85                  90                  95

Phe Ser Val Asp Glu Val Thr Leu Thr Val Gly Ser Val Asn Leu Glu
        100                 105                 110

Ile His Asn Gly Phe Ile Leu Gly Lys Ile Gln Leu Pro Arg Pro Lys
        115                 120                 125

Met Ala Pro Ala Asn Asp Thr Tyr Glu Ser Ile Phe Ser His Phe Arg
    130                 135                 140

Glu Tyr Glu Ile Ala Ile Arg Lys Val Pro Gly Asn Phe Thr Phe Thr
145                 150                 155                 160

His Lys Lys Val Lys His Glu Asn Phe Ser Leu Leu Thr Ser Gly Glu
                165                 170                 175

Val Gly Glu Phe Cys Val Gln Val Lys Pro Ser Val Ala Ser Arg Ser
            180                 185                 190

Asn Lys Gly Met Trp Ser Lys Glu Glu Cys Ile Ser Leu Thr Arg Gln
            195                 200                 205

Tyr Phe Thr Val Thr Asn
    210

<210> SEQ ID NO 49
<211> LENGTH: 173
<212> TYPE: PRT
<213> ORGANISM: Homo sapiens

<400> SEQUENCE: 49

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
            85                  90                  95

Glu Ser Cys Val Leu His Arg Ser Cys Ser Pro Gly Phe Gly Val Lys
        100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170

<210> SEQ ID NO 50
<211> LENGTH: 186
<212> TYPE: PRT
<213> ORGANISM: Homo sapiens

<400> SEQUENCE: 50

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
                20                  25                  30

Asn Thr Val Cys Arg Pro Cys Gly Pro Gly Phe Tyr Asn Asp Val Val
            35                  40                  45

Ser Ser Lys Pro Cys Lys Pro Cys Thr Trp Cys Asn Leu Arg Ser Gly
50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala
            180                 185

<210> SEQ ID NO 51
<211> LENGTH: 163
<212> TYPE: PRT
<213> ORGANISM: Homo sapiens

<400> SEQUENCE: 51

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
                20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln

<210> SEQ ID NO 52
```

```
<211> LENGTH: 126
<212> TYPE: PRT
<213> ORGANISM: Homo sapiens

<400> SEQUENCE: 52

Lys Ala Met His Val Ala Gln Pro Ala Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp
        115                 120                 125

<210> SEQ ID NO 53
<211> LENGTH: 220
<212> TYPE: PRT
<213> ORGANISM: Homo sapiens

<400> SEQUENCE: 53

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
210                 215                 220
```

<210> SEQ ID NO 54
<211> LENGTH: 201
<212> TYPE: PRT
<213> ORGANISM: Homo sapiens

<400> SEQUENCE: 54

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr
        195                 200

<210> SEQ ID NO 55
<211> LENGTH: 235
<212> TYPE: PRT
<213> ORGANISM: Homo sapiens

<400> SEQUENCE: 55

Leu Ile Ile Gly Phe Gly Ile Ser Gly Arg His Ser Ile Thr Val Thr
1               5                   10                  15

Thr Val Ala Ser Ala Gly Asn Ile Gly Glu Asp Gly Ile Leu Ser Cys
            20                  25                  30

Thr Phe Glu Pro Asp Ile Lys Leu Ser Asp Ile Val Ile Gln Trp Leu
        35                  40                  45

Lys Glu Gly Val Leu Gly Leu Val His Glu Phe Lys Glu Gly Lys Asp
    50                  55                  60

Glu Leu Ser Glu Gln Asp Glu Met Phe Arg Gly Arg Thr Ala Val Phe
65                  70                  75                  80

Ala Asp Gln Val Ile Val Gly Asn Ala Ser Leu Arg Leu Lys Asn Val
                85                  90                  95

Gln Leu Thr Asp Ala Gly Thr Tyr Lys Cys Tyr Ile Ile Thr Ser Lys
            100                 105                 110

Gly Lys Gly Asn Ala Asn Leu Glu Tyr Lys Thr Gly Ala Phe Ser Met
        115                 120                 125

Pro Glu Val Asn Val Asp Tyr Asn Ala Ser Ser Glu Thr Leu Arg Cys
            130                 135                 140

Glu Ala Pro Arg Trp Phe Pro Gln Pro Thr Val Val Trp Ala Ser Gln
145                 150                 155                 160

Val Asp Gln Gly Ala Asn Phe Ser Glu Val Ser Asn Thr Ser Phe Glu
                165                 170                 175

Leu Asn Ser Glu Asn Val Thr Met Lys Val Ser Val Leu Tyr Asn
            180                 185                 190

Val Thr Ile Asn Asn Thr Tyr Ser Cys Met Ile Glu Asn Asp Ile Ala
            195                 200                 205

Lys Ala Thr Gly Asp Ile Lys Val Thr Glu Ser Glu Ile Lys Arg Arg
            210                 215                 220

Ser His Leu Gln Leu Leu Asn Ser Lys Ala Ser
225                 230                 235

<210> SEQ ID NO 56
<211> LENGTH: 133
<212> TYPE: PRT
<213> ORGANISM: Homo sapiens

<400> SEQUENCE: 56

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
            35                  40                  45

Gly Phe Tyr Leu Ile Ser Leu Lys Gly Tyr Phe Ser Gln Glu Val Asn
        50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
            115                 120                 125

Glu Phe Cys Val Leu
        130

<210> SEQ ID NO 57
<211> LENGTH: 132
<212> TYPE: PRT
<213> ORGANISM: Homo sapiens

<400> SEQUENCE: 57

Thr Ser Leu Lys Pro Thr Ala Ile Glu Ser Cys Met Val Lys Phe Glu
1               5                   10                  15

Leu Ser Ser Ser Lys Trp His Met Thr Ser Pro Lys Pro His Cys Val
            20                  25                  30

Asn Thr Thr Ser Asp Gly Lys Leu Lys Ile Leu Gln Ser Gly Thr Tyr
            35                  40                  45

Leu Ile Tyr Gly Gln Val Ile Pro Val Asp Lys Lys Tyr Ile Lys Asp
        50                  55                  60

Asn Ala Pro Phe Val Val Gln Ile Tyr Lys Lys Asn Asp Val Leu Gln
65                  70                  75                  80

```
Thr Leu Met Asn Asp Phe Gln Ile Leu Pro Ile Gly Gly Val Tyr Glu
                 85                  90                  95

Leu His Ala Gly Asp Asn Ile Tyr Leu Lys Phe Asn Ser Lys Asp His
            100                 105                 110

Ile Gln Lys Thr Asn Thr Tyr Trp Gly Ile Ile Leu Met Pro Asp Leu
        115                 120                 125

Pro Phe Ile Ser
        130

<210> SEQ ID NO 58
<211> LENGTH: 205
<212> TYPE: PRT
<213> ORGANISM: Homo sapiens

<400> SEQUENCE: 58

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 59
<211> LENGTH: 195
<212> TYPE: PRT
<213> ORGANISM: Homo sapiens

<400> SEQUENCE: 59

Ser Gln Leu Arg Ala Gln Gly Glu Ala Cys Val Gln Phe Gln Ala Leu
1               5                   10                  15

Lys Gly Gln Glu Phe Ala Pro Ser His Gln Gln Val Tyr Ala Pro Leu
            20                  25                  30

Arg Ala Asp Gly Asp Lys Pro Arg Ala His Leu Thr Val Val Arg Gln
        35                  40                  45

Thr Pro Thr Gln His Phe Lys Asn Gln Phe Pro Ala Leu His Trp Glu
    50                  55                  60
```

```
His Glu Leu Gly Leu Ala Phe Thr Lys Asn Arg Met Asn Tyr Thr Asn
 65                  70                  75                  80

Lys Phe Leu Leu Ile Pro Glu Ser Gly Asp Tyr Phe Ile Tyr Ser Gln
                 85                  90                  95

Val Thr Phe Arg Gly Met Thr Ser Glu Cys Ser Glu Ile Arg Gln Ala
            100                 105                 110

Gly Arg Pro Asn Lys Pro Asp Ser Ile Thr Val Val Ile Thr Lys Val
            115                 120                 125

Thr Asp Ser Tyr Pro Glu Pro Thr Gln Leu Leu Met Gly Thr Lys Ser
130                 135                 140

Val Cys Glu Val Gly Ser Asn Trp Phe Gln Pro Ile Tyr Leu Gly Ala
145                 150                 155                 160

Met Phe Ser Leu Gln Glu Gly Asp Lys Leu Met Val Asn Val Ser Asp
                165                 170                 175

Ile Ser Leu Val Asp Tyr Thr Lys Glu Asp Lys Thr Phe Phe Gly Ala
                180                 185                 190

Phe Leu Leu
        195

<210> SEQ ID NO 60
<211> LENGTH: 215
<212> TYPE: PRT
<213> ORGANISM: Homo sapiens

<400> SEQUENCE: 60

His Arg Arg Leu Asp Lys Ile Glu Asp Glu Arg Asn Leu His Glu Asp
 1               5                  10                  15

Phe Val Phe Met Lys Thr Ile Gln Arg Cys Asn Thr Gly Glu Arg Ser
                20                  25                  30

Leu Ser Leu Leu Asn Cys Glu Glu Ile Lys Ser Gln Phe Glu Gly Phe
            35                  40                  45

Val Lys Asp Ile Met Leu Asn Lys Glu Glu Thr Lys Lys Glu Asn Ser
 50                  55                  60

Phe Glu Met Gln Lys Gly Asp Gln Asn Pro Gln Ile Ala Ala His Val
 65                  70                  75                  80

Ile Ser Glu Ala Ser Ser Lys Thr Thr Ser Val Leu Gln Trp Ala Glu
                 85                 90                  95

Lys Gly Tyr Tyr Thr Met Ser Asn Asn Leu Val Thr Leu Glu Asn Gly
            100                 105                 110

Lys Gln Leu Thr Val Lys Arg Gln Gly Leu Tyr Tyr Ile Tyr Ala Gln
            115                 120                 125

Val Thr Phe Cys Ser Asn Arg Glu Ala Ser Ser Gln Ala Pro Phe Ile
130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
                180                 185                 190

Val Asn Val Thr Asp Pro Ser Gln Val Ser His Gly Thr Gly Phe Thr
            195                 200                 205

Ser Phe Gly Leu Leu Lys Leu
210                 215
```

<210> SEQ ID NO 61
<211> LENGTH: 172
<212> TYPE: PRT
<213> ORGANISM: Homo sapiens

<400> SEQUENCE: 61

Gln Arg Thr Asp Ser Ile Pro Asn Ser Pro Asp Asn Val Pro Leu Lys
1               5                   10                  15

Gly Gly Asn Cys Ser Glu Asp Leu Leu Cys Ile Leu Lys Arg Ala Pro
            20                  25                  30

Phe Lys Lys Ser Trp Ala Tyr Leu Gln Val Ala Lys His Leu Asn Lys
        35                  40                  45

Thr Lys Leu Ser Trp Asn Lys Asp Gly Ile Leu His Gly Val Arg Tyr
    50                  55                  60

Gln Asp Gly Asn Leu Val Ile Gln Phe Pro Gly Leu Tyr Phe Ile Ile
65                  70                  75                  80

Cys Gln Leu Gln Phe Leu Val Gln Cys Pro Asn Asn Ser Val Asp Leu
                85                  90                  95

Lys Leu Glu Leu Leu Ile Asn Lys His Ile Lys Lys Gln Ala Leu Val
            100                 105                 110

Thr Val Cys Glu Ser Gly Met Gln Thr Lys His Val Tyr Gln Asn Leu
        115                 120                 125

Ser Gln Phe Leu Leu Asp Tyr Leu Gln Val Asn Thr Thr Ile Ser Val
    130                 135                 140

Asn Val Asp Thr Phe Gln Tyr Ile Asp Thr Ser Thr Phe Pro Leu Glu
145                 150                 155                 160

Asn Val Leu Ser Ile Phe Leu Tyr Ser Asn Ser Asp
                165                 170

<210> SEQ ID NO 62
<211> LENGTH: 243
<212> TYPE: PRT
<213> ORGANISM: Homo sapiens

<400> SEQUENCE: 62

Thr Asn Glu Leu Lys Gln Met Gln Asp Lys Tyr Ser Lys Ser Gly Ile
1               5                   10                  15

Ala Cys Phe Leu Lys Glu Asp Asp Ser Tyr Trp Asp Pro Asn Asp Glu
            20                  25                  30

Glu Ser Met Asn Ser Pro Cys Trp Gln Val Lys Trp Gln Leu Arg Gln
        35                  40                  45

Leu Val Arg Lys Met Ile Leu Arg Thr Ser Glu Glu Thr Ile Ser Thr
    50                  55                  60

Val Gln Glu Lys Gln Gln Asn Ile Ser Pro Leu Val Arg Glu Arg Gly
65                  70                  75                  80

Pro Gln Arg Val Ala Ala His Ile Thr Gly Thr Arg Gly Arg Ser Asn
                85                  90                  95

Thr Leu Ser Ser Pro Asn Ser Lys Asn Glu Lys Ala Leu Gly Arg Lys
            100                 105                 110

Ile Asn Ser Trp Glu Ser Ser Arg Ser Gly His Ser Phe Leu Ser Asn
        115                 120                 125

Leu His Leu Arg Asn Gly Glu Leu Val Ile His Glu Lys Gly Phe Tyr
    130                 135                 140

Tyr Ile Tyr Ser Gln Thr Tyr Phe Arg Phe Gln Glu Glu Ile Lys Glu
145                 150                 155                 160

Asn Thr Lys Asn Asp Lys Gln Met Val Gln Tyr Ile Tyr Lys Tyr Thr

```
                165                 170                 175
Ser Tyr Pro Asp Pro Ile Leu Leu Met Lys Ser Ala Arg Asn Ser Cys
            180                 185                 190

Trp Ser Lys Asp Ala Glu Tyr Gly Leu Tyr Ser Ile Tyr Gln Gly Gly
        195                 200                 205

Ile Phe Glu Leu Lys Glu Asn Asp Arg Ile Phe Val Ser Val Thr Asn
    210                 215                 220

Glu His Leu Ile Asp Met Asp His Glu Ala Ser Phe Phe Gly Ala Phe
225                 230                 235                 240

Leu Val Gly

<210> SEQ ID NO 63
<211> LENGTH: 155
<212> TYPE: PRT
<213> ORGANISM: Homo sapiens

<400> SEQUENCE: 63

Gln Arg Phe Ala Gln Ala Gln Gln Leu Pro Leu Glu Ser Leu Gly
1               5                   10                  15

Trp Asp Val Ala Glu Leu Gln Leu Asn His Thr Gly Pro Gln Gln Asp
            20                  25                  30

Pro Arg Leu Tyr Trp Gln Gly Gly Pro Ala Leu Gly Arg Ser Phe Leu
        35                  40                  45

His Gly Pro Glu Leu Asp Lys Gly Gln Leu Arg Ile His Arg Asp Gly
    50                  55                  60

Ile Tyr Met Val His Ile Gln Val Thr Leu Ala Ile Cys Ser Ser Thr
65                  70                  75                  80

Thr Ala Ser Arg His His Pro Thr Thr Leu Ala Val Gly Ile Cys Ser
                85                  90                  95

Pro Ala Ser Arg Ser Ile Ser Leu Leu Arg Leu Ser Phe His Gln Gly
            100                 105                 110

Cys Thr Ile Ala Ser Gln Arg Leu Thr Pro Leu Ala Arg Gly Asp Thr
        115                 120                 125

Leu Cys Thr Asn Leu Thr Gly Thr Leu Leu Pro Ser Arg Asn Thr Asp
    130                 135                 140

Glu Thr Phe Phe Gly Val Gln Trp Val Arg Pro
145                 150                 155

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67
```

<210> SEQ ID NO 68

<400> SEQUENCE: 68

000

<210> SEQ ID NO 69

<400> SEQUENCE: 69

000

<210> SEQ ID NO 70
<211> LENGTH: 217
<212> TYPE: PRT
<213> ORGANISM: Artificial sequence
<220> FEATURE:
<223> OTHER INFORMATION: Synthetic sequence

<400> SEQUENCE: 70

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

<210> SEQ ID NO 71
<211> LENGTH: 217
<212> TYPE: PRT
<213> ORGANISM: Artificial sequence
<220> FEATURE:
<223> OTHER INFORMATION: Synthetic sequence

<400> SEQUENCE: 71

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 72
<211> LENGTH: 217
<212> TYPE: PRT
<213> ORGANISM: Artificial sequence
<220> FEATURE:
<223> OTHER INFORMATION: Synthetic sequence

<400> SEQUENCE: 72

Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Thr Pro His
65                  70                  75                  80

Ser Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly Lys
    210                 215

<210> SEQ ID NO 73
<211> LENGTH: 11
<212> TYPE: PRT
<213> ORGANISM: Artificial sequence
<220> FEATURE:
<223> OTHER INFORMATION: Synthetic sequence

<400> SEQUENCE: 73

Ser Lys Tyr Gly Pro Pro Cys Pro Ser Cys Pro
1               5                   10

<210> SEQ ID NO 74
<211> LENGTH: 11
<212> TYPE: PRT
<213> ORGANISM: Artificial sequence
<220> FEATURE:
<223> OTHER INFORMATION: Synthetic sequence

<400> SEQUENCE: 74

Ser Lys Tyr Gly Pro Pro Cys Pro Pro Cys Pro
1               5                   10

<210> SEQ ID NO 75
<211> LENGTH: 6
<212> TYPE: PRT
<213> ORGANISM: Artificial sequence
<220> FEATURE:
<223> OTHER INFORMATION: Synthetic sequence

<400> SEQUENCE: 75

Ser Lys Tyr Gly Pro Pro
1               5

<210> SEQ ID NO 76
<211> LENGTH: 6
<212> TYPE: PRT
<213> ORGANISM: Artificial sequence
<220> FEATURE:
<223> OTHER INFORMATION: Synthetic sequence

<400> SEQUENCE: 76

Ile Glu Gly Arg Met Asp
1               5

<210> SEQ ID NO 77
<211> LENGTH: 9
<212> TYPE: PRT
<213> ORGANISM: Artificial sequence
<220> FEATURE:
<223> OTHER INFORMATION: Synthetic sequence

<400> SEQUENCE: 77

Gly Gly Gly Val Pro Arg Asp Cys Gly
1               5
```

```
<210> SEQ ID NO 78
<211> LENGTH: 15
<212> TYPE: PRT
<213> ORGANISM: Artificial sequence
<220> FEATURE:
<223> OTHER INFORMATION: Synthetic sequence

<400> SEQUENCE: 78

Ile Glu Gly Arg Met Asp Gly Gly Gly Ala Gly Gly Gly Gly
1               5                   10                  15
```

COMPOSITIONS AND METHODS FOR ADJOINING TYPE I AND TYPE II EXTRACELLULAR DOMAINS AS HETEROLOGOUS CHIMERIC PROTEINS

PRIORITY

This application is a continuation of U.S. application Ser. No. 15/281,196, filed Sep. 30, 2016. U.S. Ser. No. 15/281,196 claims the benefit of, and priority to, U.S. Provisional Application No. 62/235,727, filed Oct. 1, 2015, U.S. Provisional Application No. 62/263,313, filed Dec. 4, 2015, and U.S. Provisional Application No. 62/372,574, filed Aug. 9, 2016. The contents of each above-mentioned application are hereby incorporated by reference in their entireties.

TECHNICAL FIELD

The present invention relates to, inter alia, compositions and methods, including chimeric proteins that find use in the treatment of disease, such as immunotherapies for cancer and autoimmunity.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SHK-HTB-023C1_SequenceListing_ST25; date recorded: Nov. 6, 2017; file size: 139 KB).

BACKGROUND

The interaction between cancer and the immune system is complex and multifaceted. See de Visser et al., *Nat. Rev. Cancer* (2006) 6:24-37. While many cancer patients appear to develop an anti-tumor immune response, cancers also develop strategies to evade immune detection and destruction. Recently, immunotherapies have been developed for the treatment and prevention of cancer and other disorders. Immunotherapy provides the advantage of cell specificity that other treatment modalities lack. As such, methods for enhancing the efficacy of immune based therapies can be clinically beneficial. Advances in defining the mechanisms and molecules that regulate immune responses have provided novel therapeutic targets for treating cancer. For example, costimulatory and coinhibitory molecules play a central role in the regulation of T cell immune responses. However, despite impressive patient responses to antibody agents targeting these costimulatory and coinhibitory molecules, including for example anti-PD-1/PD-L1, checkpoint inhibition therapy still fails in many patients. Therefore, as with most cancer therapies, there remains a need for new compositions and methods that can improve the effectiveness of these agents.

SUMMARY

Accordingly, in various aspects, the present invention provides for compositions and methods that are useful for cancer immunotherapy, e.g. to manipulate or modify immune signals for therapeutic benefit. In various embodiments, the invention reverses or suppresses immune inhibitory signals while providing immune activating or co-stimulatory signals in a beneficial context. For instance, in one aspect, the present invention provides chimeric protein comprising: (a) a first extracellular domain of a type I transmembrane protein at or near the N-terminus, (b) a second extracellular domain of a type II transmembrane protein at or near the C-terminus, and (c) a linker, wherein one of the first and second extracellular domains is an immune inhibitory signal and one of the first and second extracellular domains is an immune stimulatory signal. By linking these two molecules in a functional orientation, coordination between the positive and negative signals can be achieved. For example, the present invention provides, in various embodiments, masking of negative immune signals and stimulation of positive immune signals in a single construct. In various embodiments, provides for compositions that are not antibodies, or based upon antibody-derived antigen binding domains (e.g. complementarity determining regions, CDRs), but rather provide direct receptor/ligand interaction.

In cancer patients, an immune response can be stimulated against tumor antigens to activate a patient's own immune system to kill tumor cells. However, some cancer cells devise strategies to evade an immune response in a process known as immuno-editing. This can include down-regulation of specific antigens, down-regulation of MHC I, up-regulation of immune regulatory surface molecules (PD-L1, PD-L2, CEACAM1, galectin-9, B7-H3, B7-H4, VISTA, CD47, etc.) or up-regulation of soluble immune inhibitory molecules (IDO, TGF-β, MICA, etc). In general, these strategies are co-opted by tumor cells so that when tumor-infiltrating immune killer cells encounter a tumor cell, those cells become directly inhibited by immunosuppressive factors and therefore cannot kill the tumor cell. Many of the immunosuppressive ligands co-opted by tumor cells to suppress an immune response interact with receptors that are type I membrane proteins. In some embodiments, the chimeric protein of the present invention comprises an extracellular domain of an immune inhibitory agent, including without limitation, one or more of TIM-3, BTLA, PD-1, CTLA-4, B7-H4, PD-L1, PD-L2, B7-H3, CD244, TIGIT, CD172a/SIRPα, VISTA/VSIG8, CD115, CD200, CD223, and TMIGD2. In some embodiments, the chimeric protein of the present invention comprises an extracellular domain of a type I membrane protein which has immune inhibitory properties. In various embodiments, the chimeric protein is engineered to disrupt, block, reduce, and/or inhibit the transmission of an immune inhibitory signal, by way of non-limiting example, the binding of PD-1 with PD-L1 or PD-L2 and/or the binding of CD172a with CD47 and/or the binding of TIM-3 with one or more of galectin-9 and/or phosphatidylserine.

Further, in addition to suppression of immune inhibitory signaling, it is often desirable to enhance immune stimulatory signal transmission to boost an immune response, for instance to enhance a patient's anti-tumor immune response. In some embodiments, the chimeric protein of the present invention comprises an extracellular domain of an immune stimulatory signal, which, without limitation, is one or more of OX-40 ligand, LIGHT (CD258), GITR ligand, CD70, CD30 ligand, CD40 ligand, CD137 ligand, TRAIL and TL1A. In some embodiments, the chimeric protein of the present invention comprises an extracellular domain of a type II membrane protein which has immune stimulatory properties. In various embodiments, the chimeric protein is engineered to enhance, increase, and/or stimulate the transmission of an immune stimulatory signal, by way of non-limiting example, the binding of GITR with one or more of GITR ligand and/or the binding of OX40 with OX40L and/or CD40 with CD40 ligand.

In various embodiments, the chimeric protein comprises an immune inhibitory receptor extracellular domain and an immune stimulatory ligand extracellular domain which can, without limitation, deliver an immune stimulation to a T cell while masking a tumor cell's immune inhibitory signals. In various embodiments, the present chimeric proteins provide improved immunotherapeutic benefits by effectively causing the substitution of an immune inhibitory signal for an immune stimulatory signal. For example, a chimeric protein construct comprising (i) the extracellular domain of PD-1 and (ii) extracellular domain of OX40L, allows for the disruption of an inhibitory PD-L1/L2 signal and its replacement with a stimulating OX40L. Accordingly, the present chimeric proteins, in some embodiments are capable of, or find use in methods involving, reducing or eliminating an inhibitory immune signal and/or increasing or activating an immune stimulatory signal. Such beneficial properties are enhanced by the single construct approach of the present chimeric proteins. For instance, the signal replacement can be effected nearly simultaneously and the signal replacement is tailored to be local at a site of clinical importance (e.g. the tumor microenvironment). Further embodiments apply the same principle to other chimeric protein constructs, such as, for example, (i) the extracellular domain of PD-1 and (ii) extracellular domain of GITRL; (i) the extracellular domain of BTLA and (ii) extracellular domain of OX40L; (i) the extracellular domain of TIGIT and (ii) extracellular domain of OX40L; (i) the extracellular domain of TMIGD2 and (ii) extracellular domain of OX40L; (i) the extracellular domain of TIM3 and (ii) extracellular domain of OX40L; and (i) the extracellular domain of CD172a or CD115 and (ii) extracellular domain of CD40L; among others.

Further still, in some embodiments, the present chimeric proteins are capable of, or find use in methods involving, shifting the balance of immune cells in favor of immune attack of a tumor. For instance, the present chimeric proteins can shift the ratio of immune cells at a site of clinical importance in favor of cells that can kill a tumor (e.g. T cells, cytotoxic T lymphocytes, T helper cells, natural killer (NK) cells, natural killer T (NKT) cells, anti-tumor macrophages (e.g. M1 macrophages), B cells, and dendritic cells and in opposition to cells that protect tumors (e.g. myeloid-derived suppressor cells (MDSCs), regulatory T cells (Tregs); tumor associated neutrophils (TANs), M2 macrophages, and tumor associated macrophages (TAMs)). In some embodiments, the present chimeric protein is capable of increasing a ratio of effector T cells to regulatory T cells.

In various embodiments, the present chimeric protein unexpectedly provides binding of the extracellular domain components to their respective binding partners with longer off rates (Kd or $K_{off}$) and therefore, inter alia, accords longer occupancy of the receptor to ligand and vice versa. For instance, in some embodiments, this provides a sustained negative signal masking effect. Further, in some embodiments, this delivers a longer positive signal effect, e.g. to allow an effector cell to be adequately stimulated (e.g. for proliferation and/or release of stimulatory signals like cytokines). Also, this stable synapse of cells (e.g. a tumor cell bearing negative signals and a T cell which could attack the tumor) provides spatial orientation to favor tumor reduction—such as positioning the T cells to attack tumor cells and/or sterically preventing the tumor cell from delivering negative signals, including negative signals beyond those masked by the chimeric protein of the invention. In still further embodiments, this provides longer on-target (e.g.

intra-tumoral) half-life ($t_{1/2}$) as compared to serum $t_{1/2}$ of the chimeric proteins. Such properties could have the combined advantage of reducing off-target toxicities associated with systemic distribution of the chimeric proteins.

Also in various aspects, the present chimeric protein is used in a method for treating cancer comprising administering an effective amount of a pharmaceutical composition comprising the chimeric protein to a patient in need thereof. In further aspects, the present chimeric protein is used in a method for treating infections, including without limitation, viral infections or other intracellular pathogens. In still further aspects, the present chimeric protein is used in a method for treating autoimmune diseases.

Fc-CD40L, αOX40, αPD-L1, and α GITR). Panel I shows a schematic for how each animal was treated in each experiment using the CT26 colon tumor model. Panel J provides representative flow cytometry plots used to calculate the serum concentration of each indicated serum cytokine using the Legend Plex bead array kit from BioLegend. Each indicated cytokine included in the panel is indicated, and the mean-fluorescence intensity of each bead cluster is used to calculate the relative concentration of each cytokine in the serum. Panel K provides an example for how the Legend Plex assay can be used as a pharmacodynamic biomarker of dose response for the PD1-Fc-OX40L fusion protein. Using the concentration of IFNγ as an example, increasing concentrations of this cytokine are shown to correspond with increasing treatment amounts of PD1-Fc-OX40L (panel K shows, left to right, untreated, 40 ug×1, 40 ug×2, 100 ug×1, and 100 ug×2). Panel L shows CT26 tumor growth kinetics for each treatment group.

Figure 12:
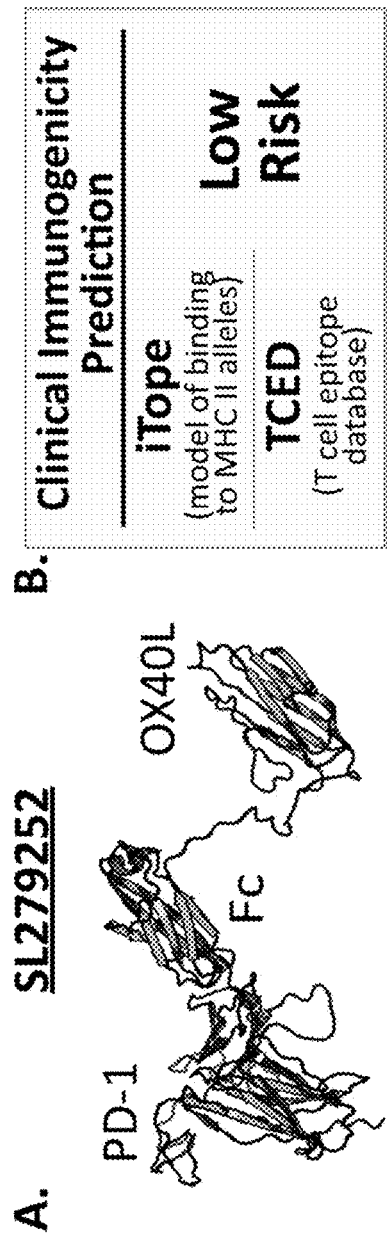

FIG. 12, panel A shows the predicted tertiary structure of human PD-1-Fc-OX40L as determined by RaptorX. Panel B shows immunogenicity assessment of human PD-1-Fc-OX40 using iTope, an in silico modeling algorithm (ANTITOPE/ABZENA), cross referenced to a proprietary T cell epitope database.

Figure 13:
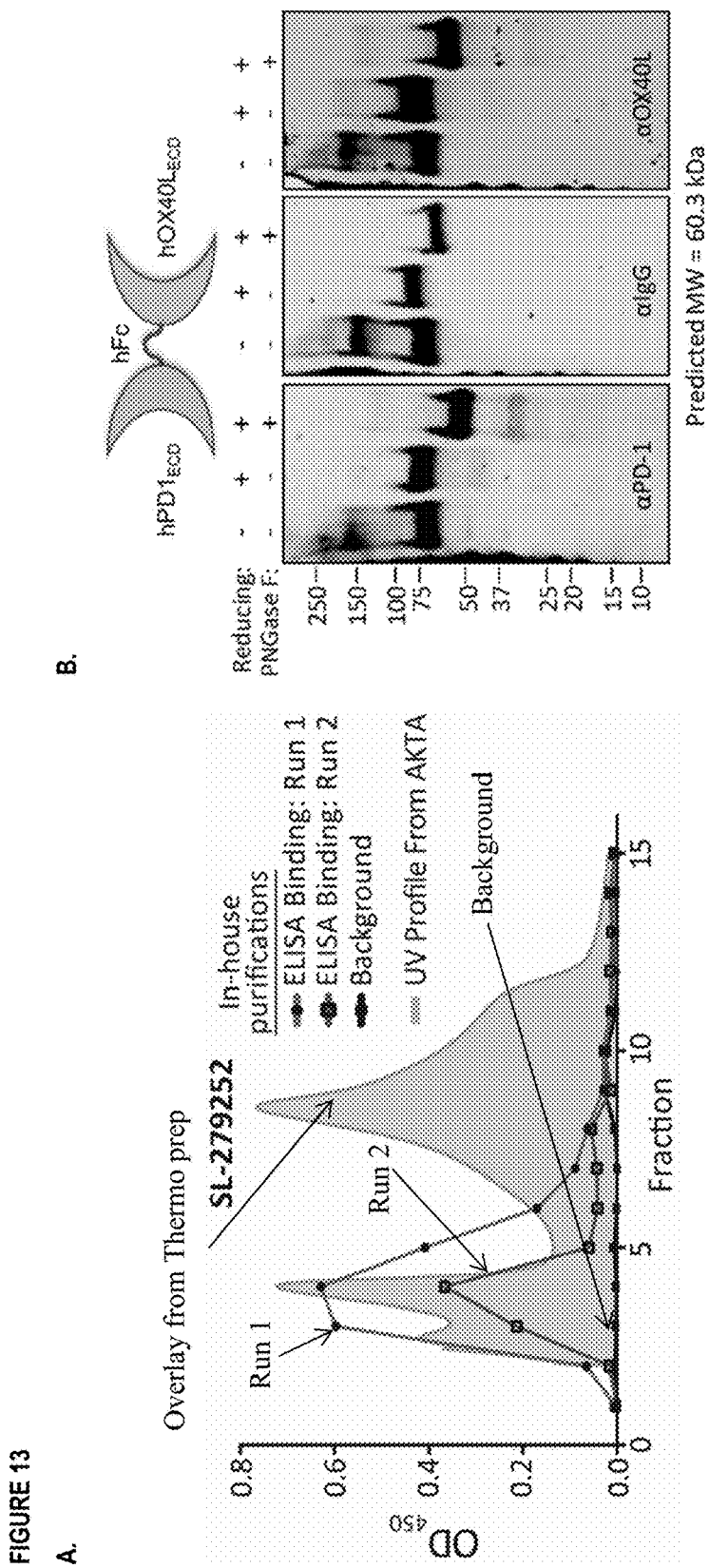
Figure 13:
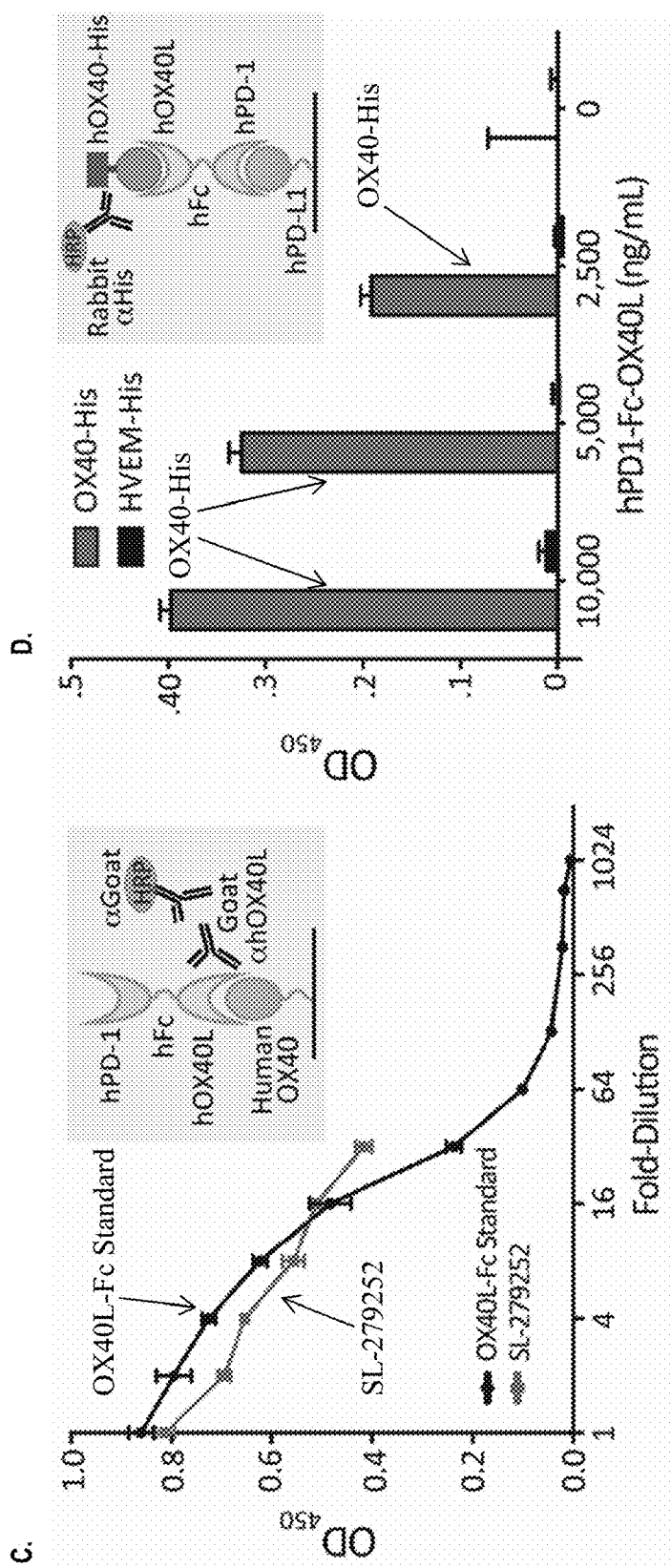

FIG. 13 shows characterization of human PD-1-Fc-OX40L (also referred to as SL-279252). Panel A shows protein A elution peaks ($OD_{450}$) from SL-279252 purified from stable (in-house) and or transient transfection (Thermo) preparations. ELISA results from each elution peak are overlayed on the absorbance readings to indicate that the SL279252 protein is contained within the first elution peak from the column. Panel B shows Western blot analysis of SL-279252, performed by probing purified protein with human anti-PD-1 (left gel), anti-Fc (middle gel), and anti-OX40L (right gel) antibodies, under non-reducing and reducing conditions, and with or without the deglycosylase PNGase F. The predicted molecular weight of monomeric SL-279252 is 60.3 kDa. Panel C shows results from functional ELISAs using capturing with recombinant hOX40 and detection with Gt-hOX40L/Gt-HRP as compared to a recombinant human OX40L-Fc standard. Panel D shows results from functional ELISAs designed to test functional binding for each side of SL-279252 simultaneously. Specifically, recombinant human PD-L1 was absorbed to a plate and used to capture SL-279252. Captured protein was then detected using recombinant hOX40-his/HRP rabbit anti-his versus HVEM-his as a negative control for specificity.

Figure 14:
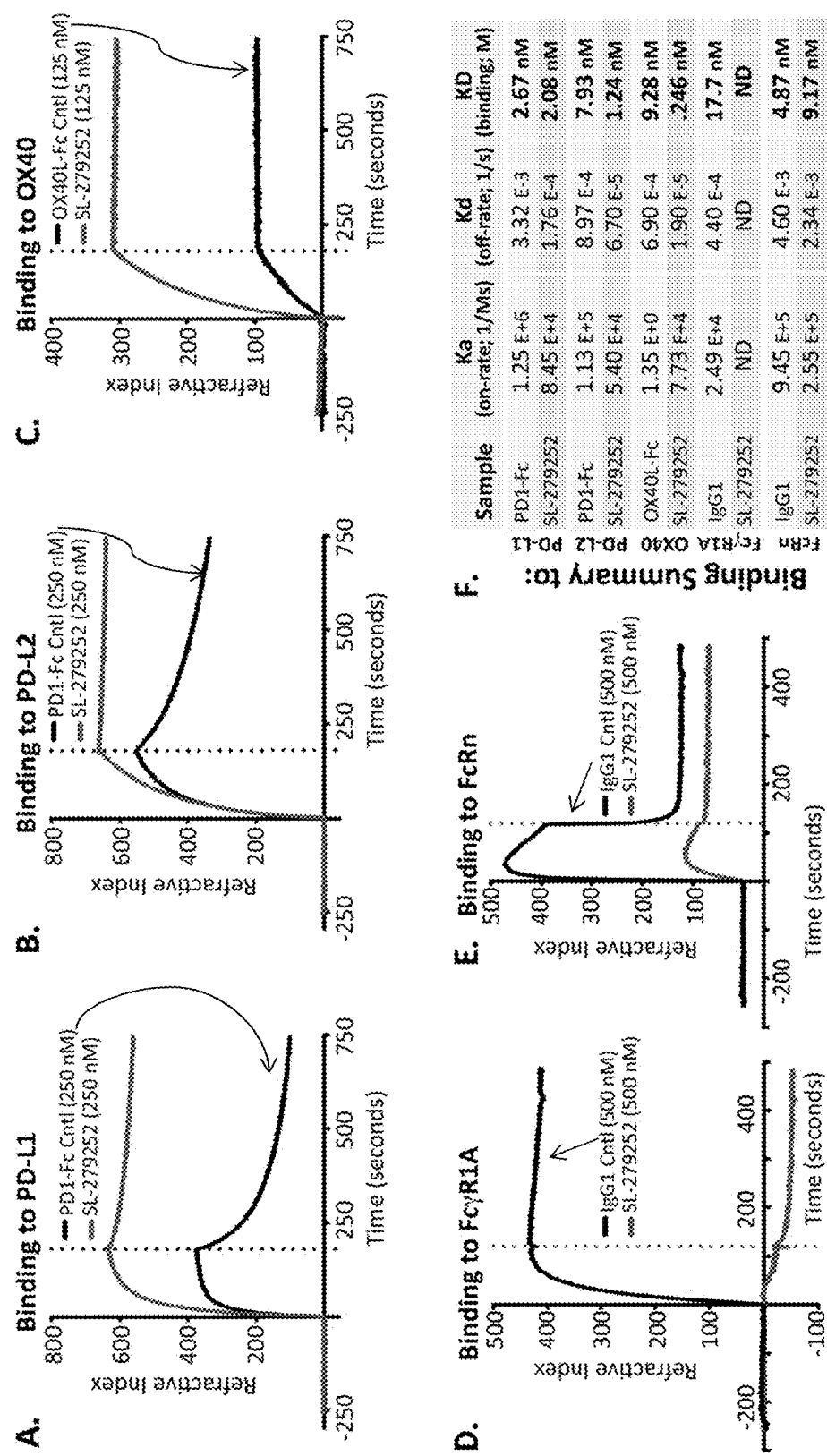
Figure 14:
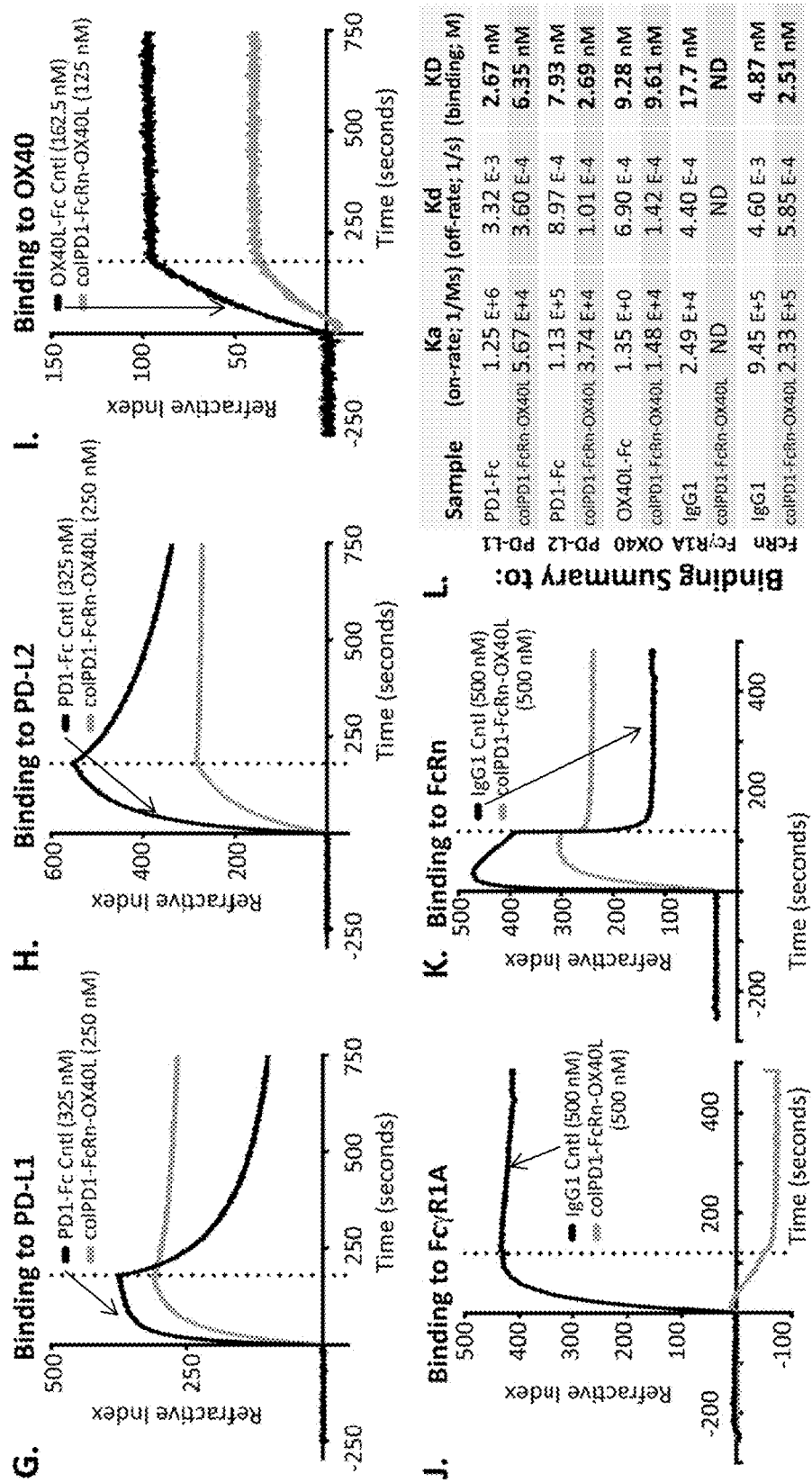
Figure 14:
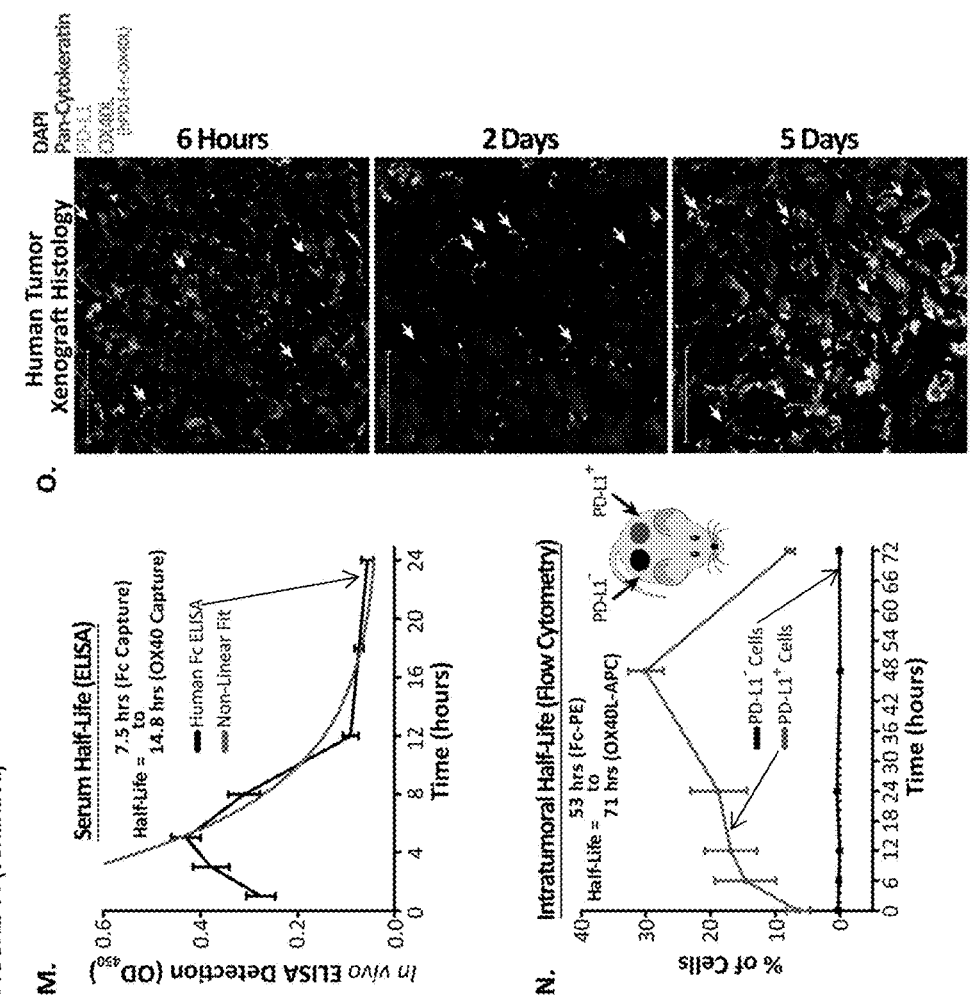

FIG. 14 shows surface plasmon resonance (SPR) and half-life analysis of SL-279252. The 'on-rate (Ka)', 'off-rate (Kd)', and binding affinity ($K_D$) were determined for SL-279252, when binding to human PD-L1 (panel A), human PD-L2 (panel B), human OX40 (panel C), human FcγR1A (panel D), and FcRn (panel E), compared with the appropriate controls. Panel F summarizes the on-rate (Ka), off rate (Kd), and binding affinity (KD) for each condition tested. The binding of a modified SL-279252 construct containing a distinct leader peptide as well as mutations in the Fc region to increase binding to FcRn was also tested when binding to human PD-L1 (panel G), human PD-L2 (panel H), human OX40 (panel I), human FcγR1A (panel J), and FcRn (panel K), compared with the appropriate controls. Panel L summarizes the on-rate (Ka), off rate (Kd), and binding affinity (KD) for each condition tested. Panel M shows the in vivo serum half-life of SL-279252 in C57BL/6 mice. Panel N shows the in vivo intra-tumoral half-life of SL-279252 in immunocompromised (NSG) mice that were implanted with human PD-L1 positive tumor on flank (HeLa-PD-L1) and PD-L1 negative tumor on the opposite flank (HeLa). On the indicated days, the two tumors were excised and bi-sected. Half of the bisected tumor was disaggregated and tested for SL-279252 binding by flow cytometry using antibodies against human OX40L. Panel O shows frozen sections from the other half of the bisected tumors 6 hours, 2 days and 5 days after treatment with a single injection of SL-279252. The figure indicates persistence of SL-279252 at least 5 days following administration.

Figure 15:
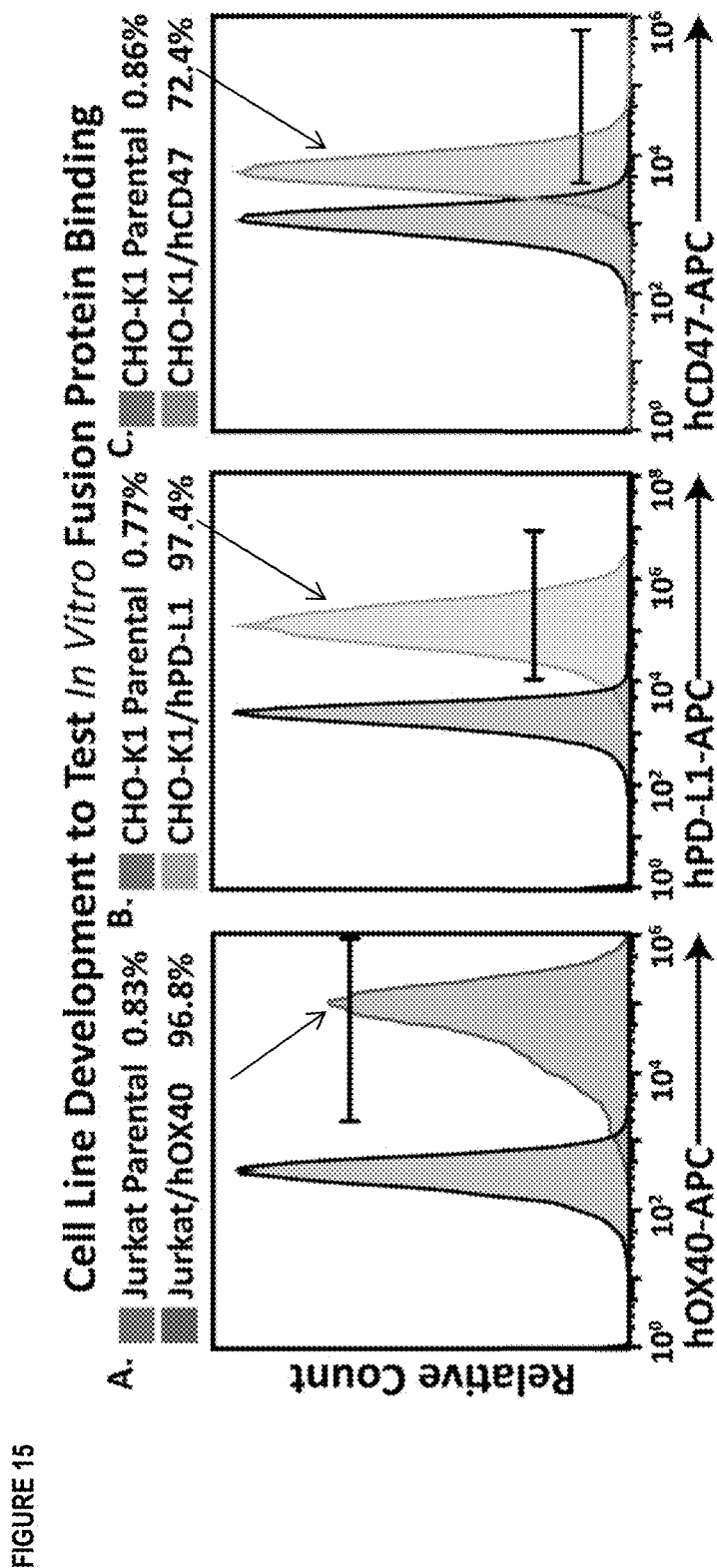
Figure 15:
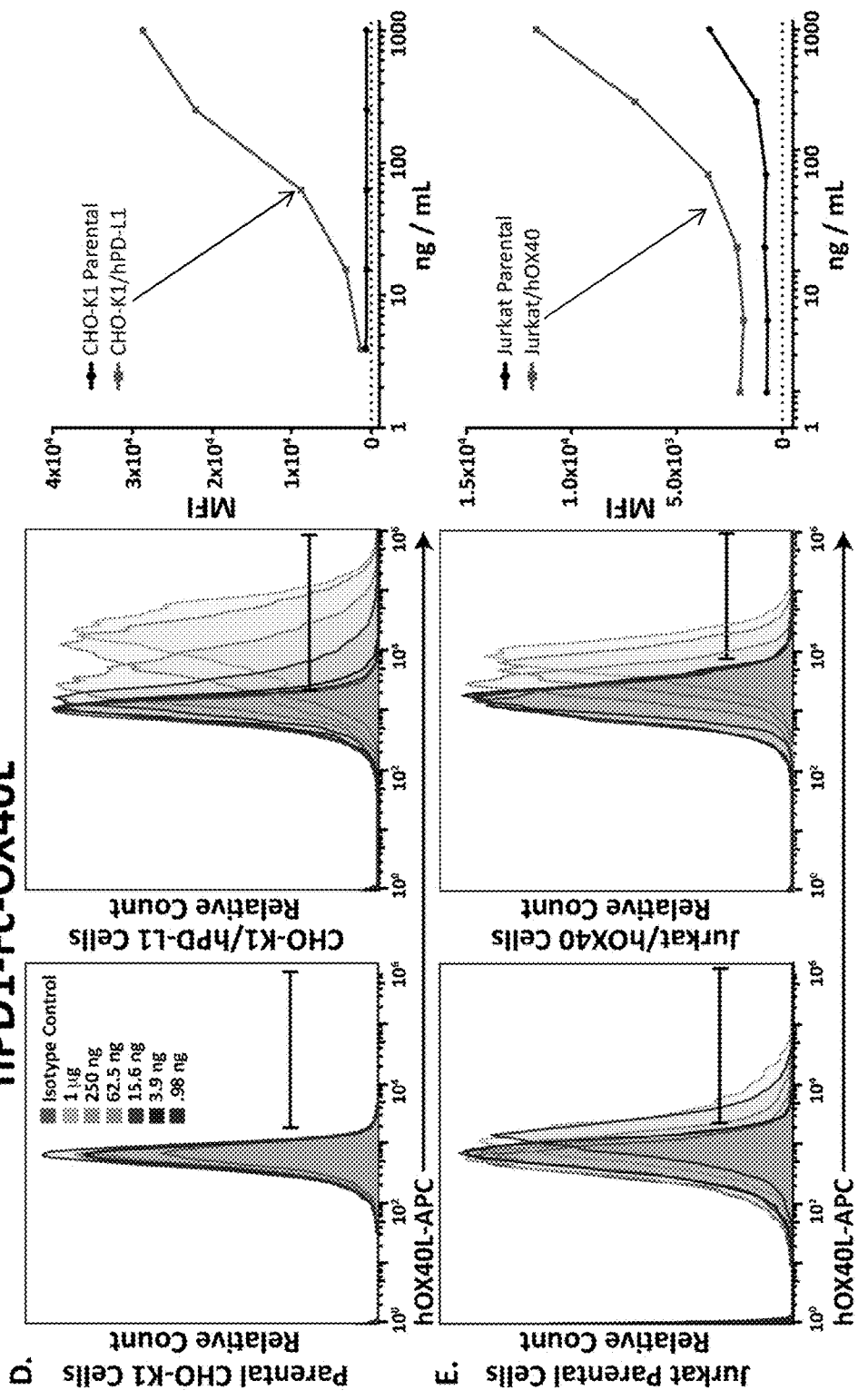
Figure 15:
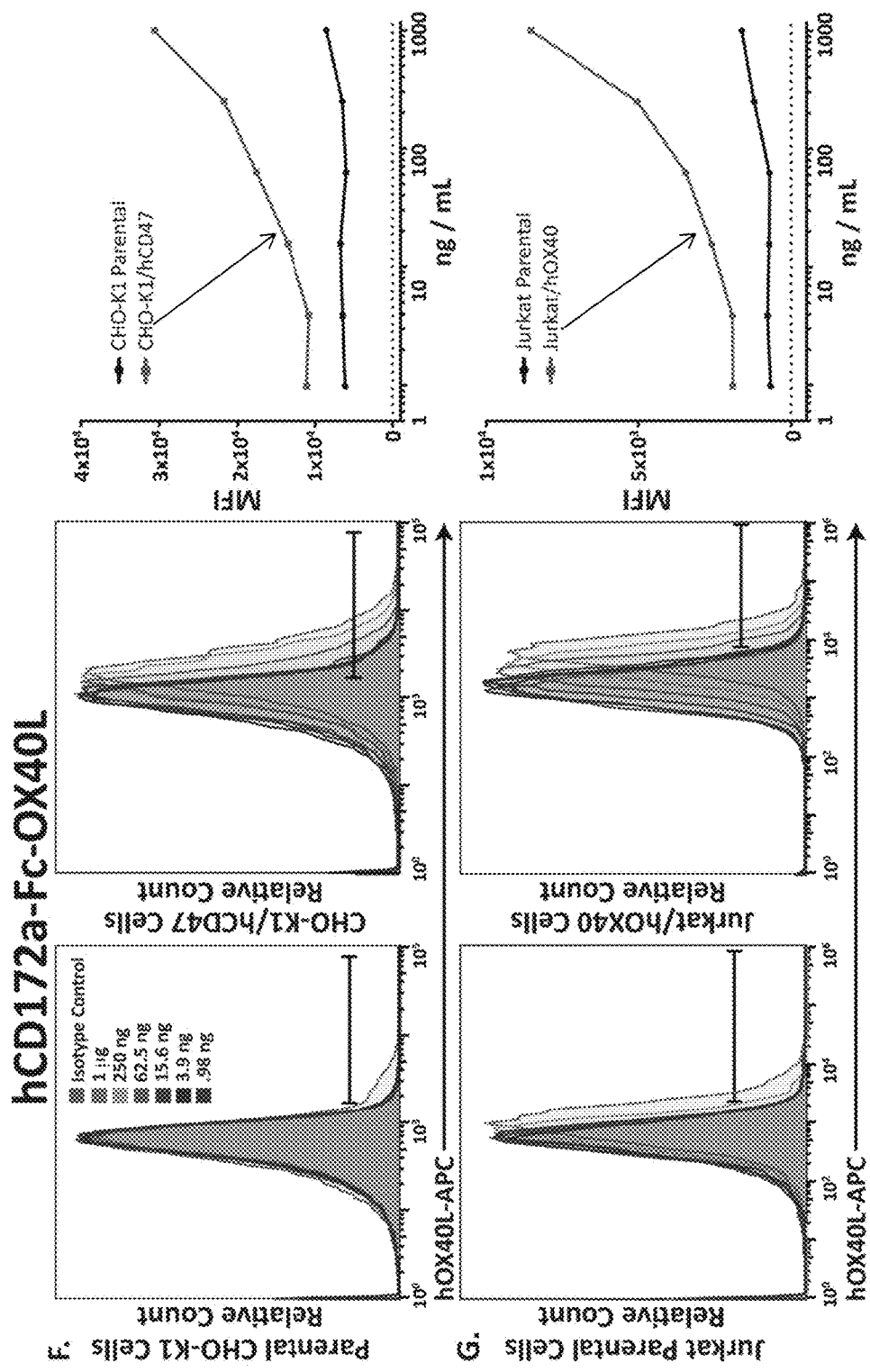
Figure 15:
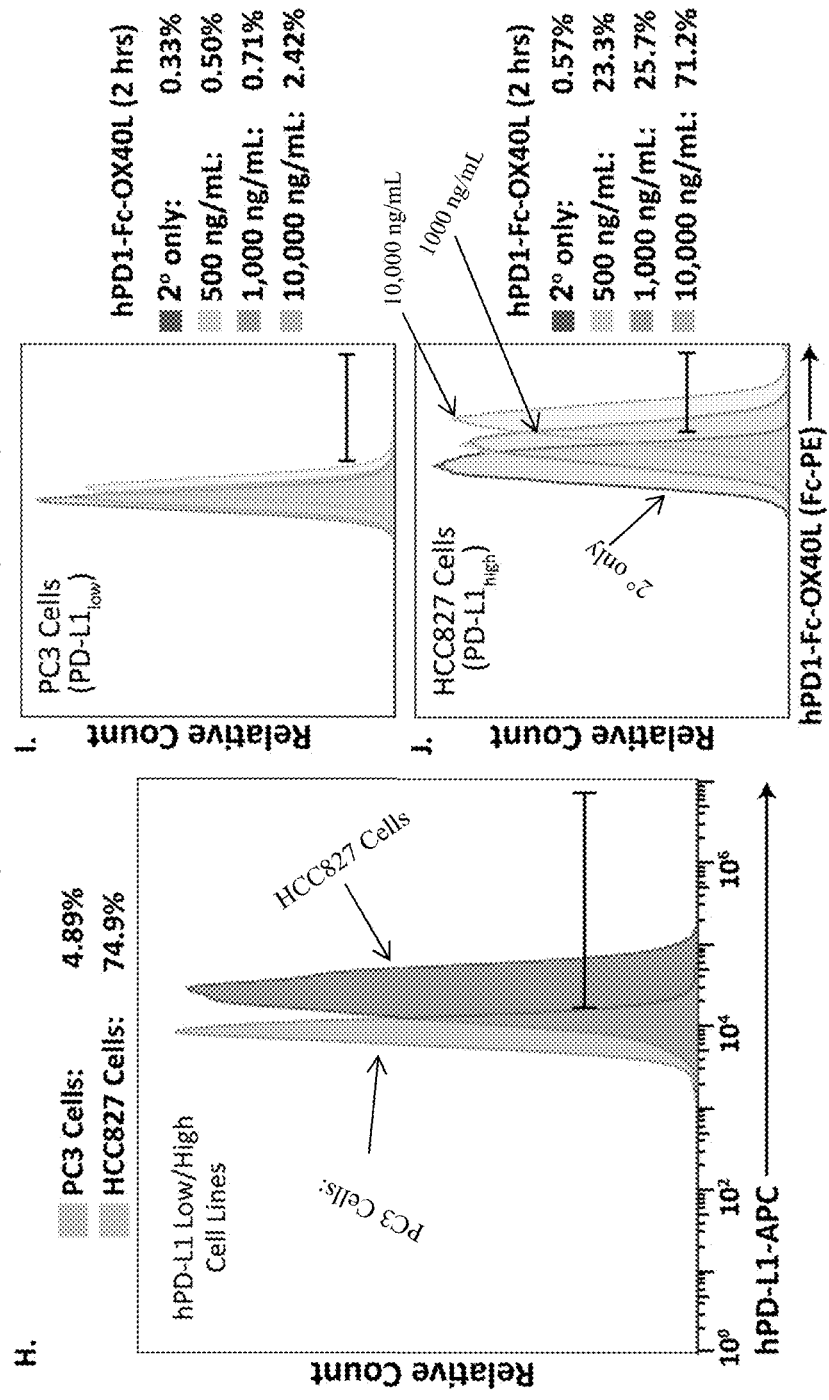

FIG. 15 shows binding of SL-279252 to cells in vitro. In panel A, parental Jurkat (cell population to the left) and Jurkat/hOX40 (cell population to the right) cells were assessed by flow cytometry using a hOX40-APC antibody. In panel B, parental CHO-K1 cells (cell population to the left) and CHO-K1/hPD-L1 (cell population to the right) were assessed by flow cytometry using a hPD-L1-APC antibody. In panel C, parental CHO-K1 cells (cell population to the left) and CHO-K1/hCD47 (cell population to the right) were assessed by flow cytometry using a hCD47-APC antibody. In panel D, increasing concentrations of SL-279252 were incubated with parental CHO-K1 cells (left panel) and CHO-K1/hPD-L1 (middle panel) and detected with anti-human OX40L-APC antibody. The right panel shows the titration curve for increasing concentrations of SL-279252. In panel E, increasing concentrations of SL-279252 were incubated with parental Jurkat cells (left panel) or Jurkat/hOX40 cells (middle panel) and detected with anti-human OX40L-APC antibody. The right panel shows the titration curve for increasing concentrations of SL-279252. In panel F, increasing concentrations of hCD172a-Fc-OX40L were incubated with parental CHO-K1 cells (left panel) or CHO-K1-CD47 cells (middle panel) and detected with an anti-human OX40L-APC antibody. The right panel shows the titration curve for increasing concentrations of hCD172a-Fc-OX40L. Panel G shows binding of increasing concentrations of hCD172a-Fc-OX40L to parental Jurkat cells (left panel) or Jurkat-hOX40 cells (middle panel). The right panel shows the titration curve for increasing concentrations of hCD172a-Fc-OX40L. In panel H, human PD-L1$_{low}$ (PC3 cells; cell population to the left) and PD-L1$_{high}$ (HCC827; cell population to the right) were identified by flow cytometry. In panel I, increasing concentrations of SL-279252 were incubated with PC3 cells. In panel J, increasing concentrations of SL-279252 were incubated with HCC827 cells for 2 hours. Cells were washed and analyzed by flow cytometry for SL-279252 binding (Fc-PE antibody).

Figure 16:
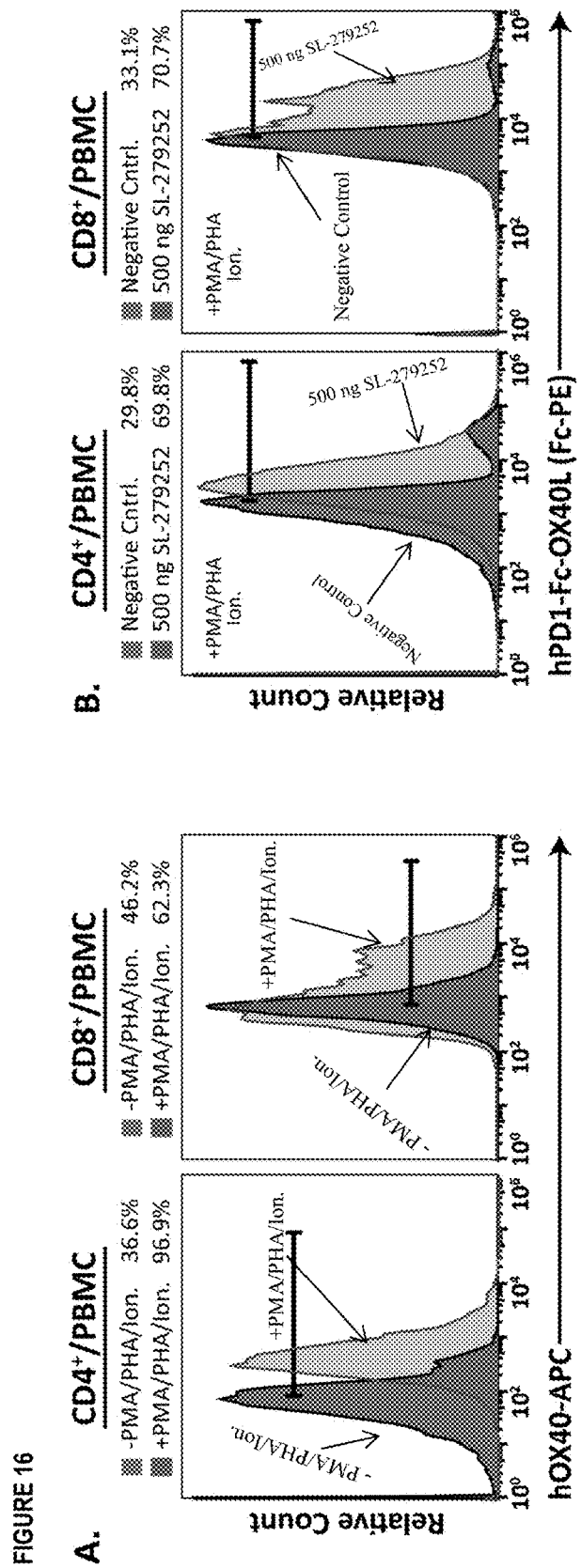
Figure 16:
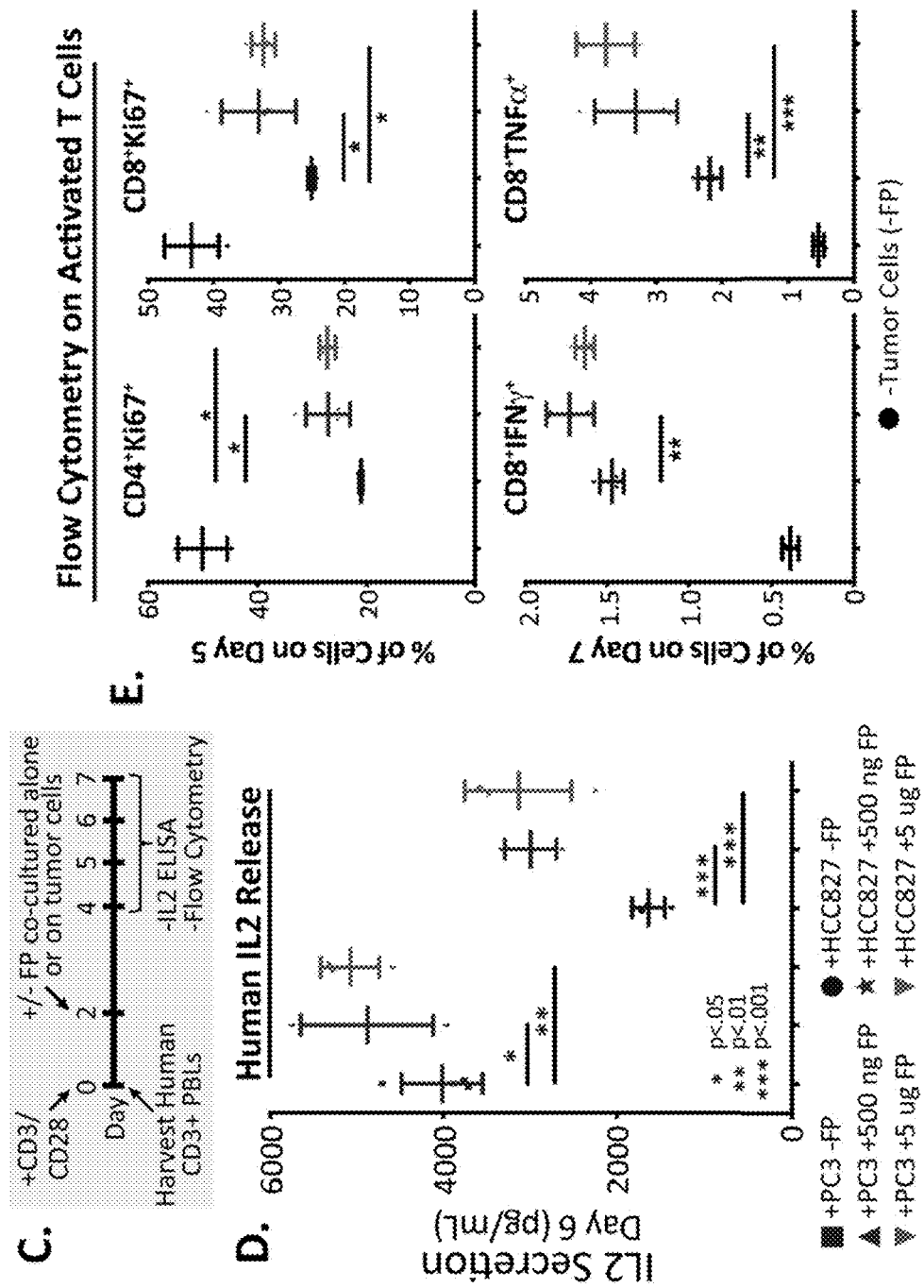

FIG. 16 shows the ex vivo functional characterization of SL-279252. In panel A, OX40 expression was detected in human T cells isolated from PBMCs treated for 2 days with PMA/PHA/Ionomycin (Ion.). In panel B, binding of SL-279252 was assessed in activated CD4+ and CD8+ cells (Fc-PE secondary). Panel C provides a schematic representation of a T cell/tumor co-culture assay to detect T cell activation as well as a time-line for the experiment. In panel D, co-culture media was assessed by IL2 ELISA 6 days after initial T cell isolation. The line graphs, from left to right, represent +PC3 (−FP), +PC3 (+500 ng FP), +PC3 (+5 ug FP), +HCC827 (−FP), +HCC827 (+500 ng FP), and +HCC827 (+5 ug FP). In panel E, co-cultured T cells were analyzed by flow cytometry 5 days after initial isolation for proliferation of CD4+ and CD8+ cells (Ki67) and 7 days after isolation for cytokine expression in CD8+ cells. The line graphs, from left to right, represent +HCC827 (−FP), +HCC827 (+500 ng FP), and +HCC827 (+5 ug FP).

Figure 17:
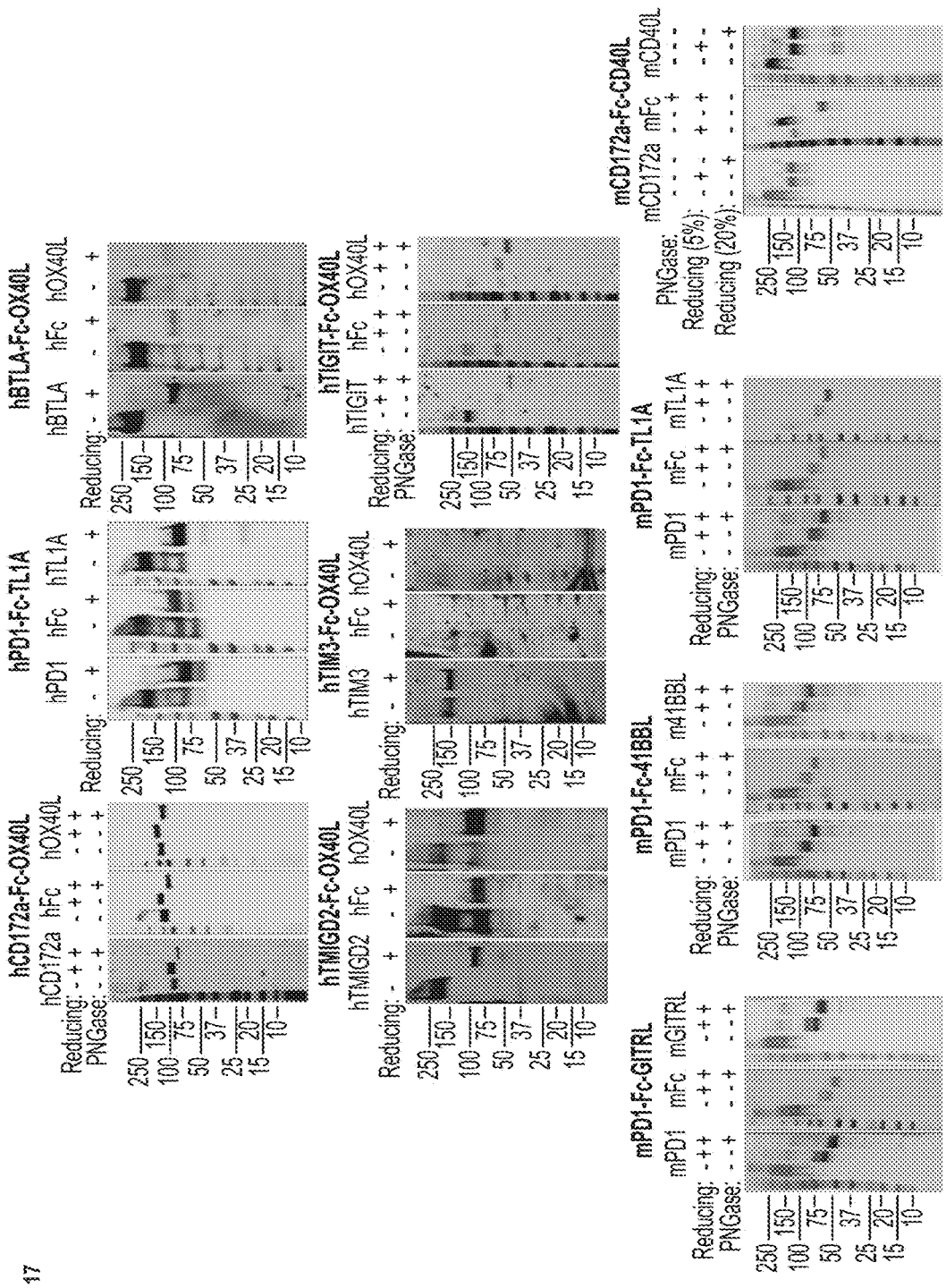
Figure 17:
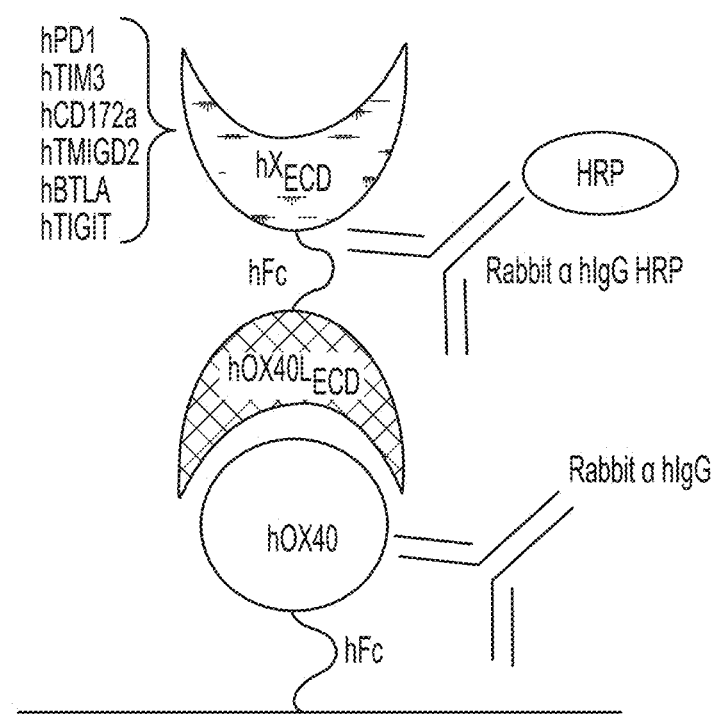
Figure 17:
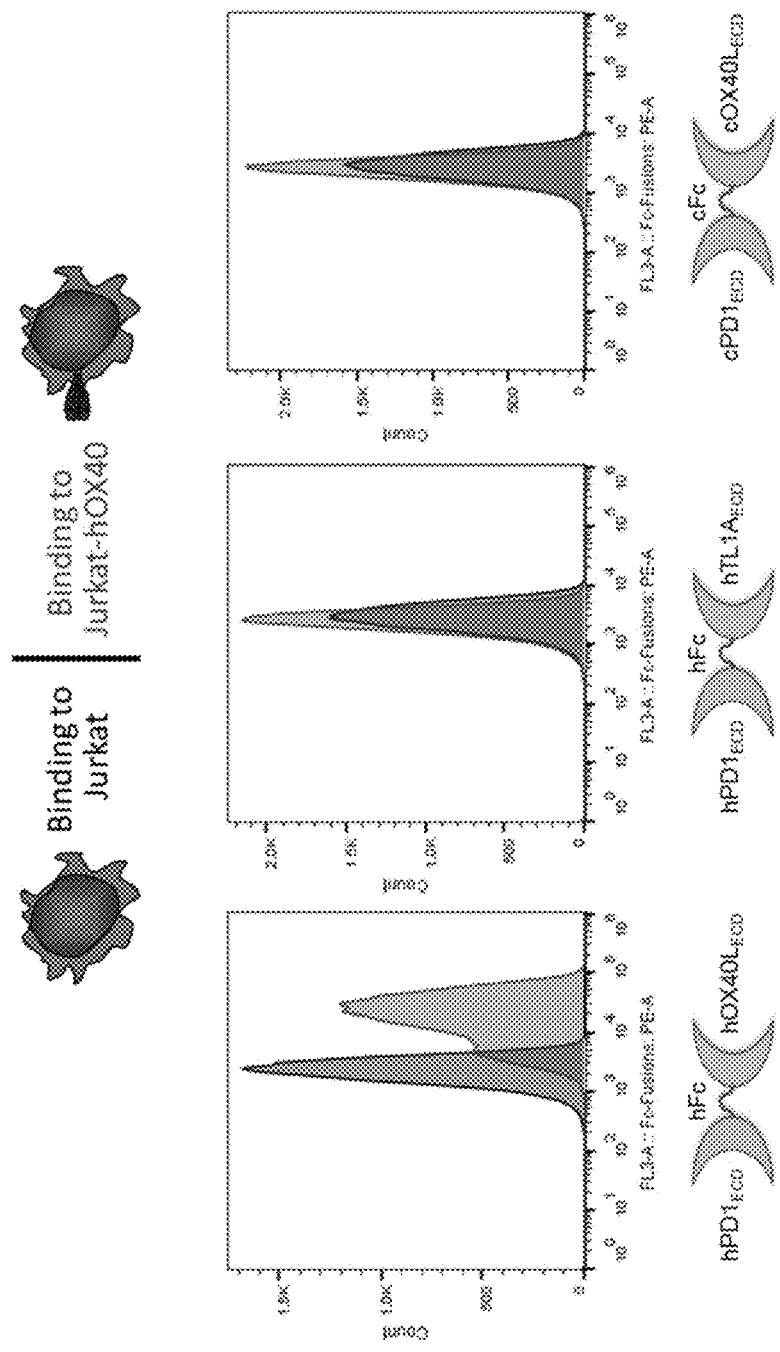
Figure 17:
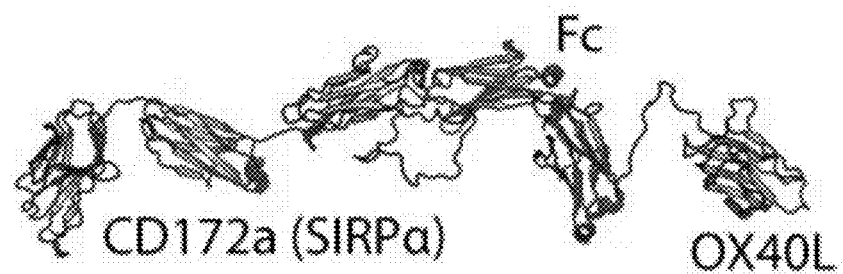
Figure 17:
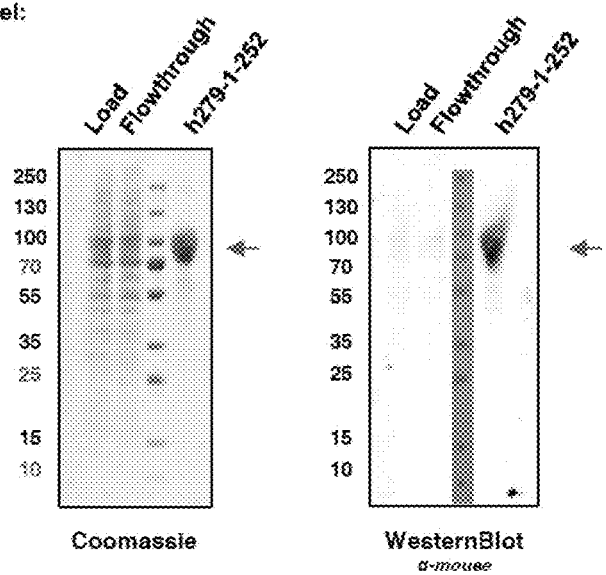
Figure 17:
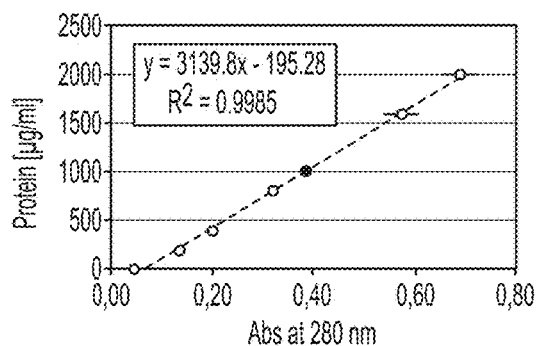
Figure 17:
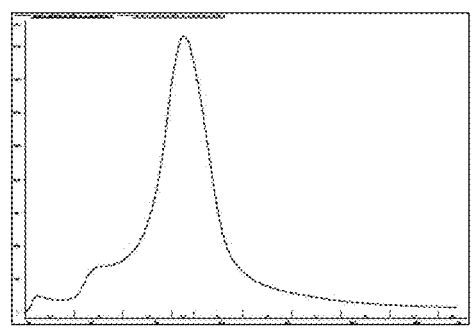
Figure 17:
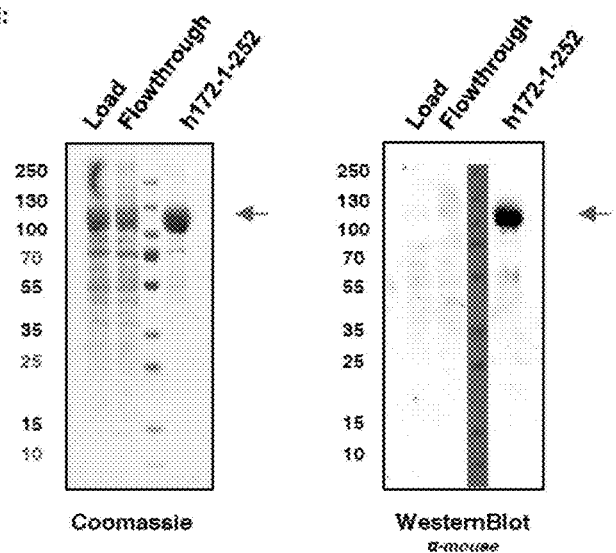
Figure 17:
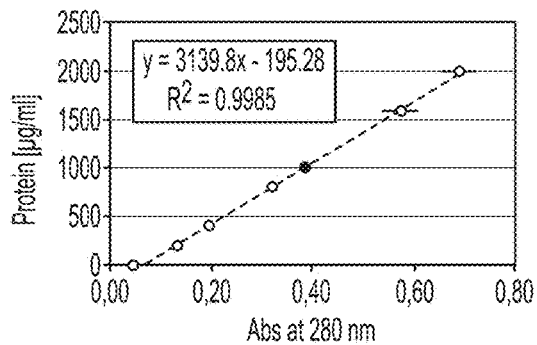
Figure 17:
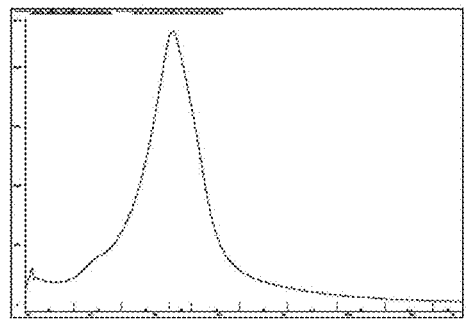
Figure 17:
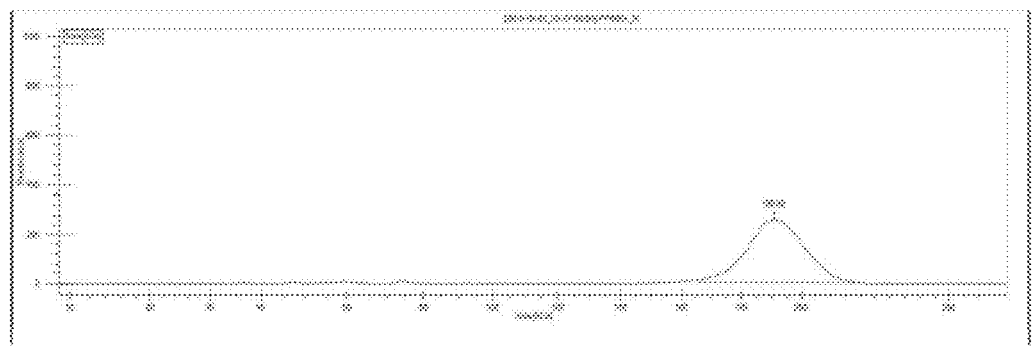
Figure 17:
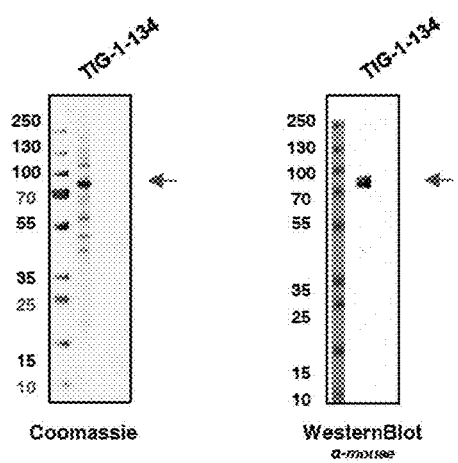
Figure 17:
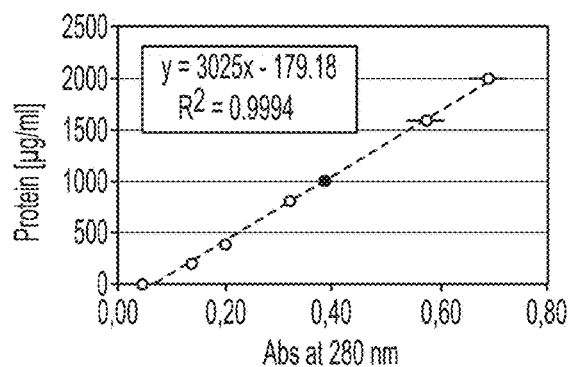
Figure 17:
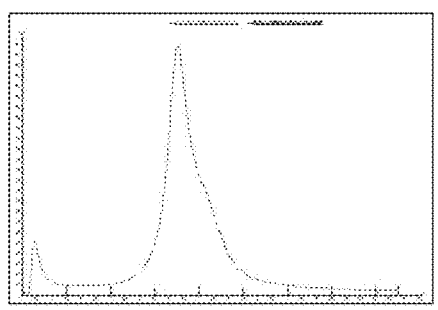
Figure 17:
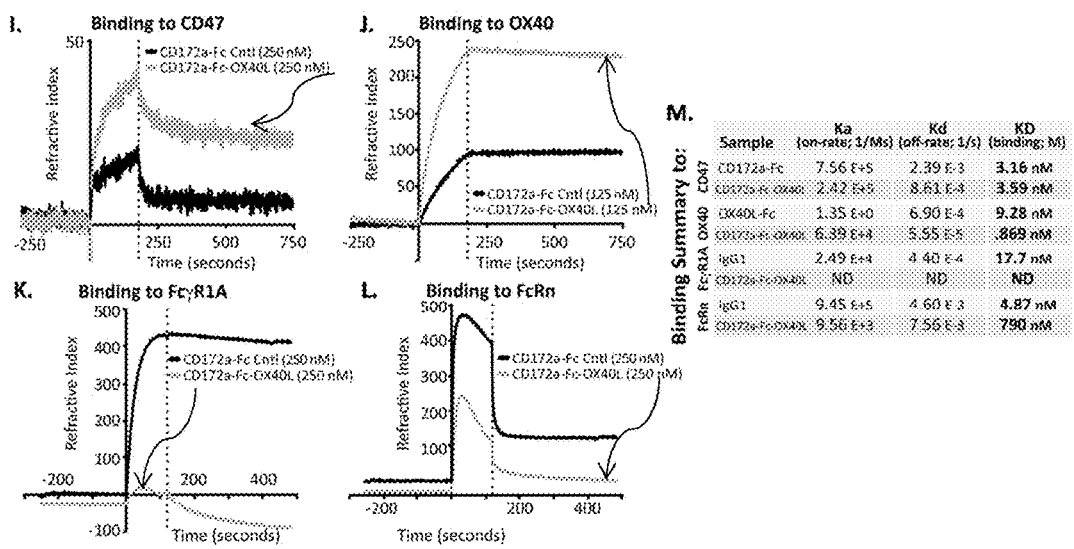
Figure 17:
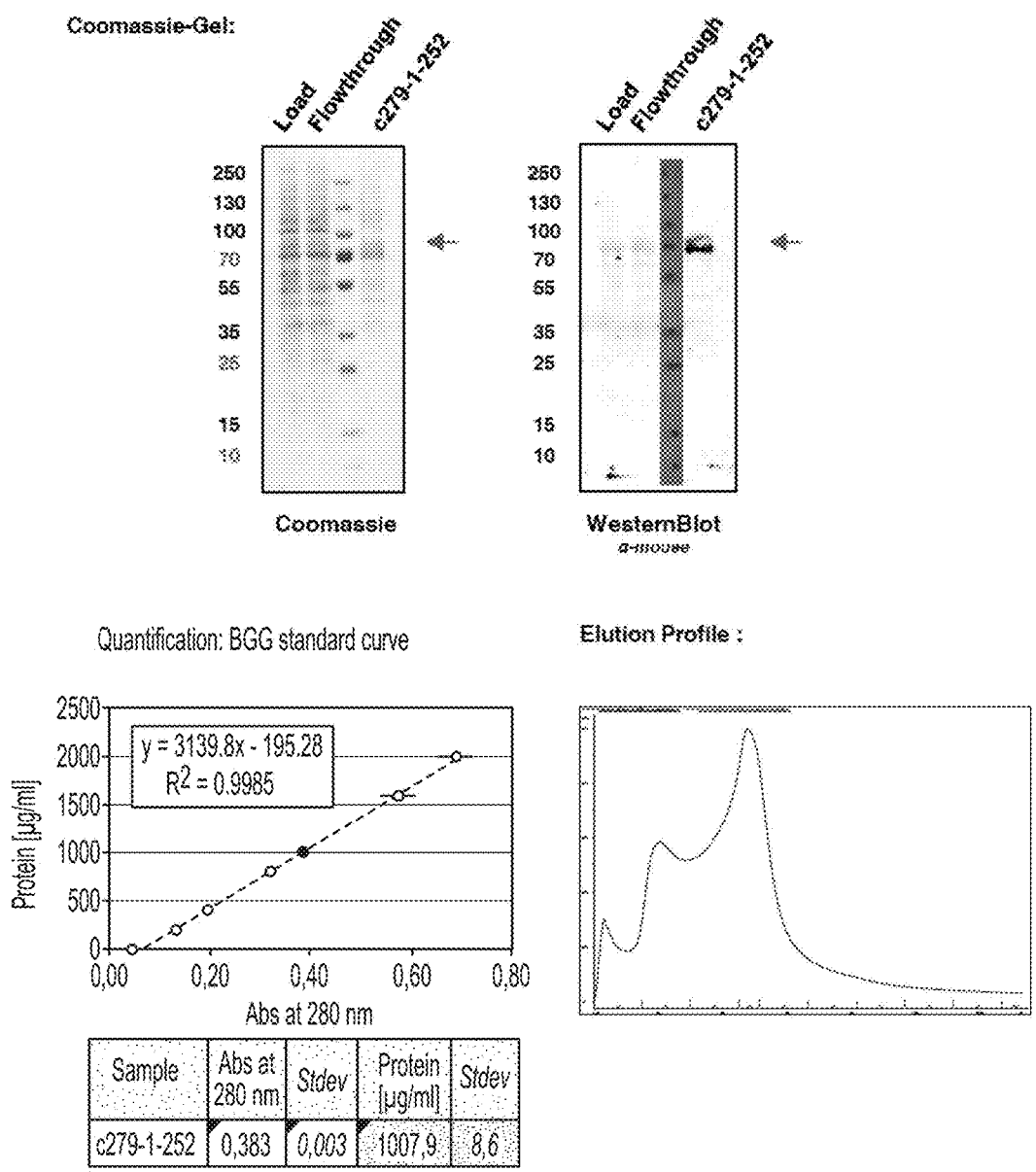
Figure 17:
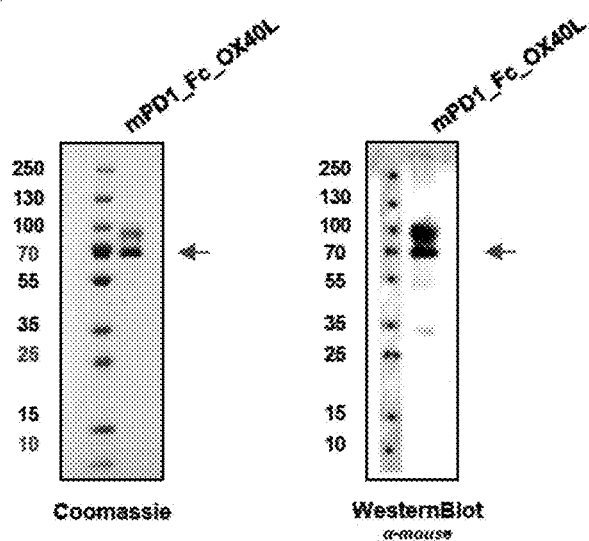
Figure 17:
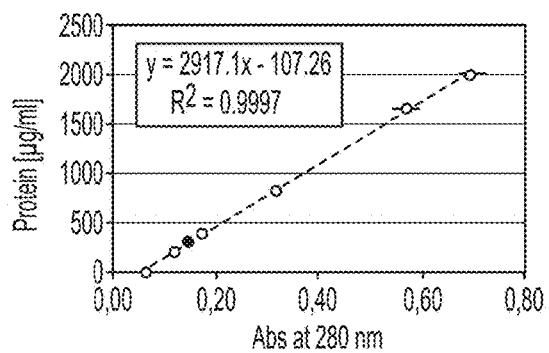
Figure 17:
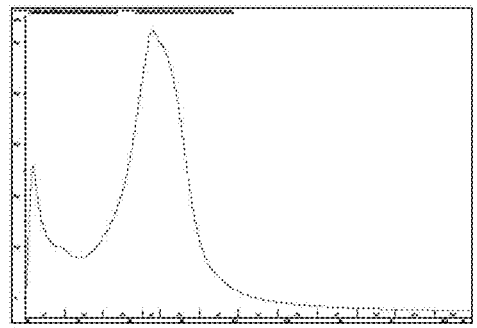
Figure 17:
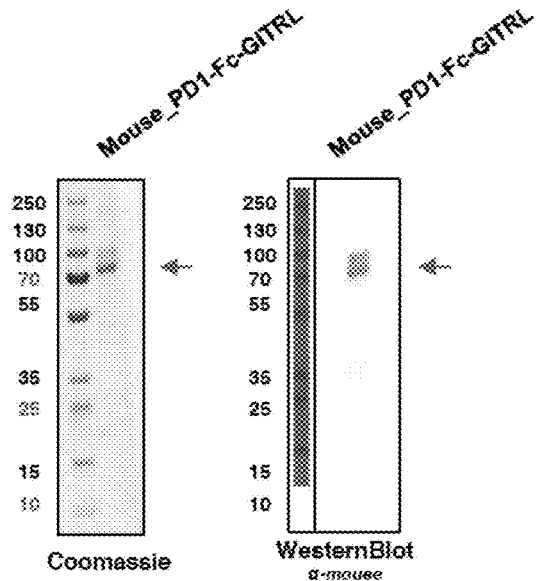
Figure 17:
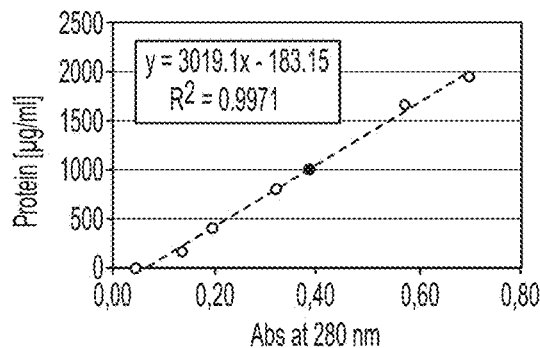
Figure 17:
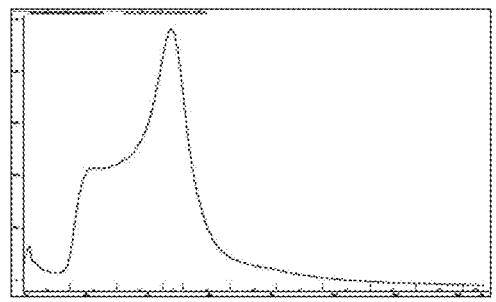
Figure 17:
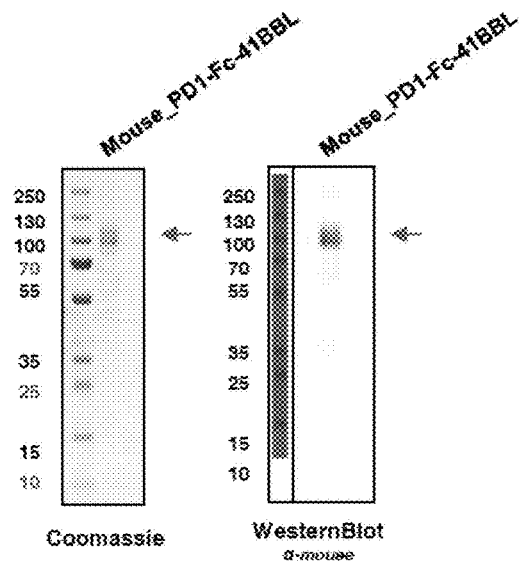
Figure 17:
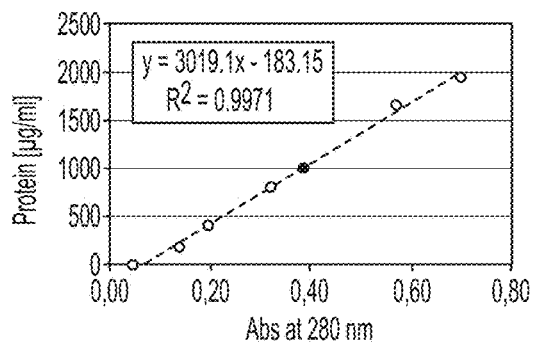
Figure 17:
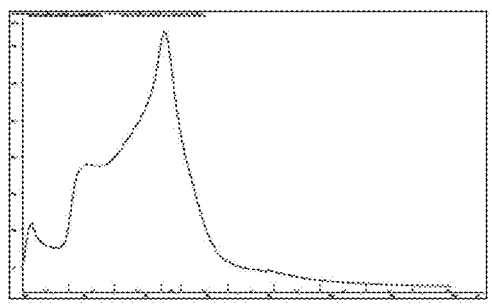
Figure 17:
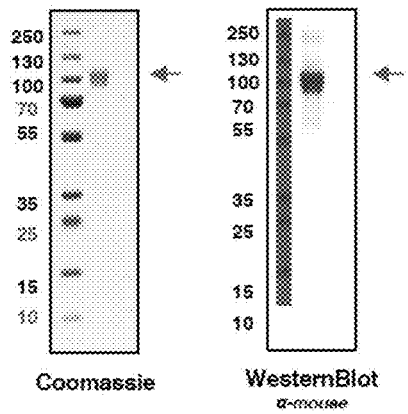
Figure 17:
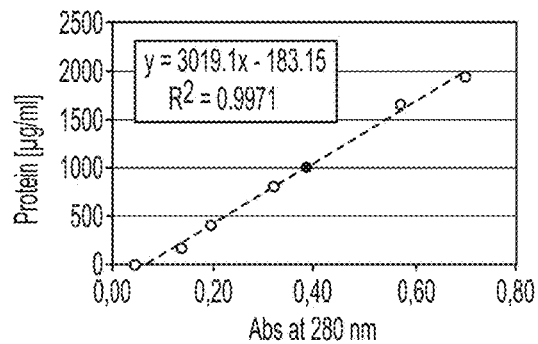
Figure 17:
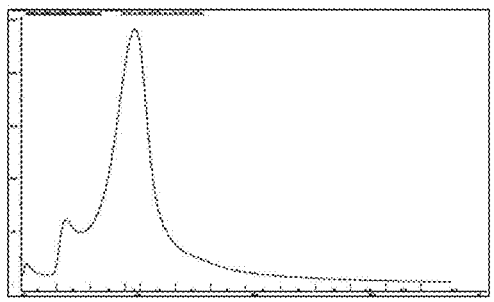
Figure 17:
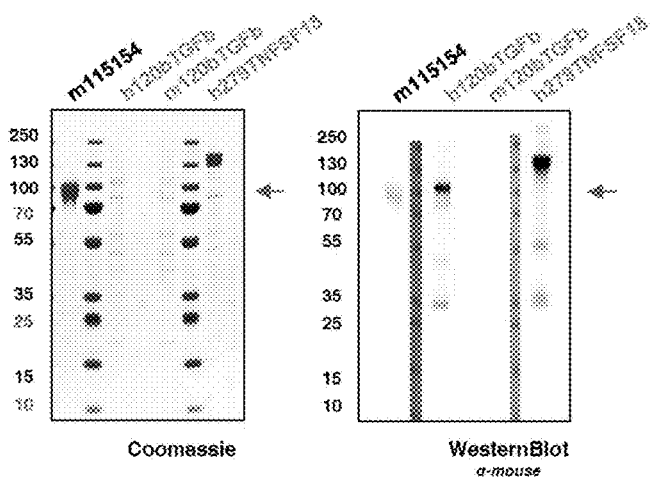
Figure 17:
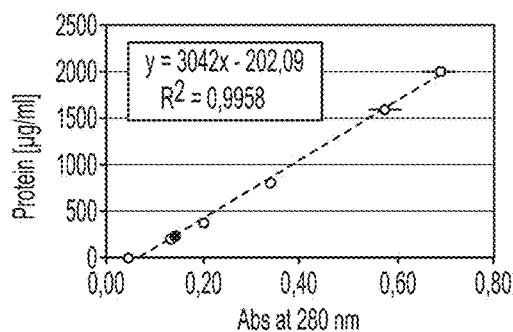
Figure 17:
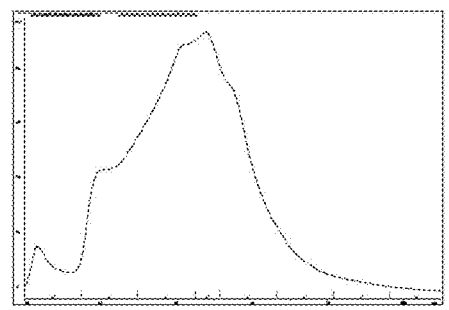
Figure 17:
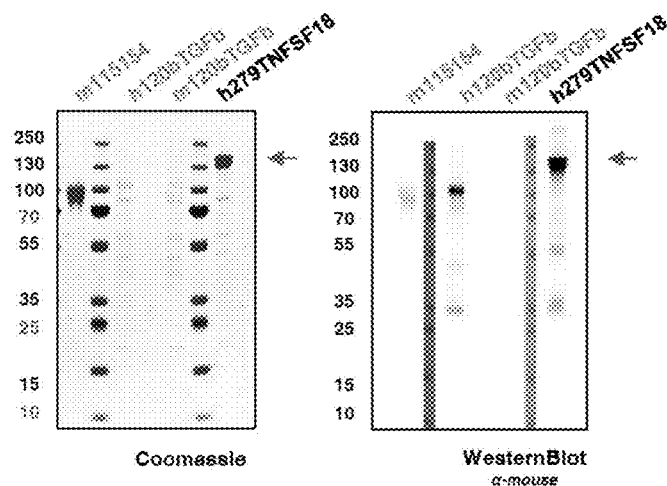
Figure 17:
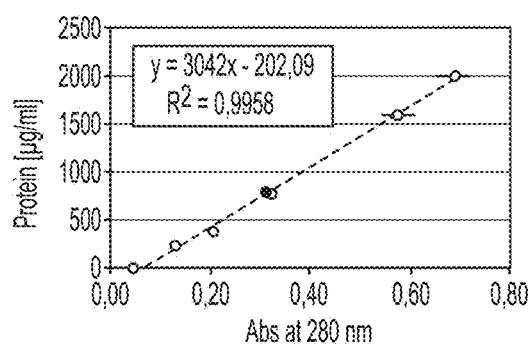
Figure 17:
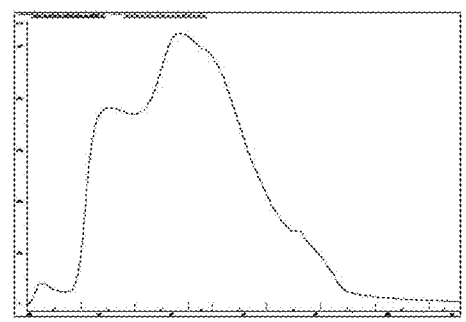

FIG. 17, panel A shows Western blot analysis of various chimeric proteins including hCD172a-Fc-OX40L, hPD1-Fc-TL1A, hBTLA-Fc-OX40L, hTMIGD2-Fc-OX40L, hTIM3-Fc-OX40L, mPD1-Fc-GITRL, mPD1-Fc-4-1BBL, mPD1-Fc-TL1A, mCD172a-Fc-CD40L. Each chimeric protein was probed with antibodies specific for each binding end and the central Fc domain. ELISA assays were performed to confirm binding of various chimeric proteins to human OX40. Panel B shows a schematic representation of the ELISA method used to detect binding of chimeric proteins to human OX40. Panel C shows results of human PD1-Fc-OX40L binding to parental Jurkat cells (left panel, left curve) or to Jurkat/OX40 cells (left panel, right curve). Two negative controls were used to demonstrate specificity: human PD1-Fc-TL1A (middle panel) and canine PD1-Fc-OX40L (right panel). Panel D shows the predicted tertiary structure of a human CD172a-Fc-OX40L as determined by RaptorX. Panel E shows an example production and purification of human PD1-Fc-OX40L (SL-279252) including the Coomassie-Gel (upper left), anti-IgG Western blot (upper right), eluted protein concentration (lower left) and elution profile from affinity chromatography (lower right). Panel F shows an example production and purification of human CD172a-Fc-OX40L including the Coomassie-Gel (upper left), anti-IgG Western blot (upper right), eluted protein concentration (lower left) and elution profile from affinity chromatography (lower right). Panel G shows an example production and purification of mouse CD172a-Fc-CD40L including the purification parameters (upper table) and the LabChip purified protein analysis (lower panel). Panel H shows an example production and purification of human TIGIT-Fc-OX40L including the Coomassie-Gel (upper left), anti-IgG Western blot (upper right), eluted protein concentration (lower left) and elution profile from affinity chromatography (lower right). Panel I shows the binding affinity of human CD172a-Fc-OX40L to immobilized recombinant CD47. Panel J shows the binding affinity of human CD172a-Fc-OX40L to immobilized recombinant human OX40. Panel K shows the binding affinity of human CD172a-Fc-OX40L to immobilized recombinant human FcγR1A. Panel L shows the binding affinity of human CD172a-Fc-OX40L to immobilized recombinant human FcRn. Panel M shows a summary of the on-rate (Ka), off-rate (Kd), and binding affinity (KD) for each condition tested. Panel N shows an example production and purification of canine PD1-Fc-OX40L including the Coomassie-Gel (upper left), anti-IgG Western blot (upper right), eluted protein concentration (lower left) and elution profile from affinity chromatography (lower right). Panel O shows an example production and purification of mouse PD1-Fc-OX40L including the Coomassie-Gel (upper left), anti-IgG Western blot (upper right), eluted protein concentration (lower left) and elution profile from affinity chromatography (lower right). Panel P shows an example production and purification of mouse PD1-Fc-GITRL including the Coomassie-Gel (upper left), anti-IgG Western blot (upper right), eluted protein concentration (lower left) and elution profile from affinity chromatography (lower right). Panel Q shows an example production and purification of mouse PD1-Fc-41BBL including the Coomassie-Gel (upper left), anti-IgG Western blot (upper right), eluted protein concentration (lower left) and elution profile from affinity chromatography (lower right). Panel R shows an example production and purification of mouse PD1-Fc-TL1A including the Coomassie-Gel (upper left), anti-IgG Western blot (upper right), eluted protein concentration (lower left) and elution profile from affinity chromatography (lower right). Panel S shows an example production and purification of mouse CD115-Fc-CD40L including the Coomassie-Gel (upper left), anti-IgG Western blot (upper right), eluted protein concentration (lower left) and elution profile from affinity chromatography (lower right). Panel T shows an example production and purification of human PD1-Fc-GITRL including the Coomassie-Gel (upper left), anti-IgG Western blot (upper right), eluted protein concentration (lower left) and elution profile from affinity chromatography (lower right).

DETAILED DESCRIPTION

The present invention is based, in part, on the discovery that chimeric proteins can be engineered from the extracellular, or effector, regions of immune-modulating transmembrane proteins in a manner that exploits the orientations of these proteins (e.g. type I versus type II) and therefore allows the delivery of immune stimulatory and/or immune inhibitory signals, including, for example, masking an immune inhibitory signal and replacing it with an immune stimulatory signal in the treatment of cancer.

Chimeric Proteins

In one aspect, the present invention relates to a chimeric protein comprising: (a) a first extracellular domain of a type I transmembrane protein at or near the N-terminus, (b) a second extracellular domain of a type II transmembrane protein at or near the C-terminus, and (c) a linker, wherein one of the first and second extracellular domains is an immune inhibitory signal and one of the first and second extracellular domains is an immune stimulatory signal.

In some embodiments, chimeric protein refers to a recombinant fusion protein, e.g. a single polypeptide having the extracellular domains described herein (and, optionally a linker). For example, in various embodiments, the chimeric protein is translated as a single unit in a cell. In some embodiments, chimeric protein refers to a recombinant protein of multiple polypeptides, e.g. multiple extracellular domains described herein, that are linked to yield a single unit, e.g. in vitro (e.g. with one or more synthetic linkers described herein).

In some embodiments, an extracellular domain refers to a portion of a transmembrane protein which is capable of interacting with the extracellular environment. In various embodiments, an extracellular domain refers to a portion of a transmembrane protein which is sufficient to bind to a ligand or receptor and effective transmit a signal to a cell. In various embodiments, an extracellular domain is the entire amino acid sequence of a transmembrane protein which is external of a cell or the cell membrane. In various embodiments, an extracellular domain is the that portion of an amino acid sequence of a transmembrane protein which is external of a cell or the cell membrane and is needed for signal transduction and/or ligand binding as may be assayed using methods know in the art (e.g. in vitro ligand binding and/or cellular activation assays).

In some embodiments, an immune inhibitory signal refers to a signal that diminishes or eliminates an immune response. For example, in the context of oncology, such signals may diminish or eliminate antitumor immunity. Under normal physiological conditions, inhibitory signal are useful in the maintenance of self-tolerance (e.g. prevention of autoimmunity) and also to protect tissues from damage when the immune system is responding to pathogenic infection. For instance, without limitation, immune inhibitory signal may be identified by detecting an increase in cellular proliferation, cytokine production, cell killing activity or phagocytic activity when such an inhibitory signal is blocked. Specific examples such inhibitory signals include blockade of PD-1 of PD-L1/L2 using antibody mediated blockade or through competitive inhibition of PD-L1/L2 using PD-1 containing fusion proteins. When such an inhibitory signal is blocked through inhibition of PD-L1/L2, it leads to enhance tumor killing activity by T cells because they are no longer being inhibited by PD-L1 or PD-L2. In another example, and inhibitory signal may be provided by CD47 to macrophages expressing CD172a. Binding of CD47 to CD172a typically inhibits the ability of a macrophage to phagocytose a target cell, which can be restored through blockade of CD47 with blocking antibodies or through competitive inhibition of CD47 using CD172a containing fusion proteins.

In some embodiments, an immune stimulatory signal refers to a signal that enhances an immune response. For example, in the context of oncology, such signals may enhance antitumor immunity. For instance, without limitation, immune stimulatory signal may be identified by directly stimulating proliferation, cytokine production, killing activity or phagocytic activity of leukocytes. Specific examples include direct stimulation of TNF superfamily receptors such as OX40, 4-1BB or TNFRSF25 using either receptor agonist antibodies or using fusion proteins encoding the ligands for such receptors (OX40L, 4-1BBL, TL1A, respectively). Stimulation from any one of these receptors may directly stimulate the proliferation and cytokine production of individual T cell subsets. Another example includes direct stimulation of an immune inhibitory cell with through a receptor that inhibits the activity of such an immune suppressor cell. This would include, for example, stimulation of CD4+FoxP3+ regulatory T cells with a GITR agonist antibody or GITRL containing fusion protein, which would reduce the ability of those regulatory T cells to suppress the proliferation of conventional CD4+ or CD8+ T cells. In another example, this would include stimulation of CD40 on the surface of an antigen presenting cell using a CD40 agonist antibody or a fusion protein containing CD40L, causing activation of antigen presenting cells including enhanced ability of those cells to present antigen in the context of appropriate native costimulatory molecules, including those in the B7 or TNF superfamily.

Figure 1:
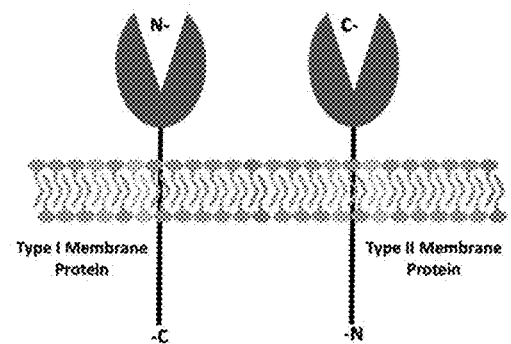
FIG. 1 shows illustrations of orientations of type I (left) and type II (right) membrane proteins in a cell membrane. In the type I membrane protein of the left panel, the amino terminus (denoted "N") faces the extracellular environment and the carboxy terminus (denoted "C") is localized to the intracellular environment. In contrast, the type II membrane protein of the right panel is characterized by an extracellular facing carboxy terminus and an amino terminus in the intracellular space.

Membrane proteins typically consist of an extracellular domain, one or a series of trans-membrane domains, and an intracellular domain. Without wishing to be bound by theory, the extracellular domain of a membrane protein is responsible for interacting with a soluble or membrane bound receptor or ligand. Without wishing to be bound by theory, the trans-membrane domain(s) are responsible for localizing a protein to the plasma membrane. Without wishing to be bound by theory, the intracellular domain of a membrane protein is responsible for coordinating interactions with cellular signaling molecules to coordinate intracellular responses with the extracellular environment (or visa-versa). There are two types of single-pass membrane proteins, those with an extracellular amino terminus and intracellular carboxy terminus (type I) and those with an extracellular carboxy terminus and intracellular amino terminus (type II). Both type I and type II membrane proteins can be either receptors or ligands. For type I membrane proteins, the amino terminus of the protein faces outside the cell, and therefore contains the functional domains that are responsible for interacting with other binding partners (either ligands or receptors) in the extracellular environment (FIG. 1, left image). For type II membrane proteins, the carboxy terminus of the protein faces outside the cell, and therefore contains the functional domains that are responsible for interacting with other binding partners (either ligands or receptors) in the extracellular environment (FIG. 1, right image). Thus, these two types of proteins have opposite orientations to each other.

Figure 3:
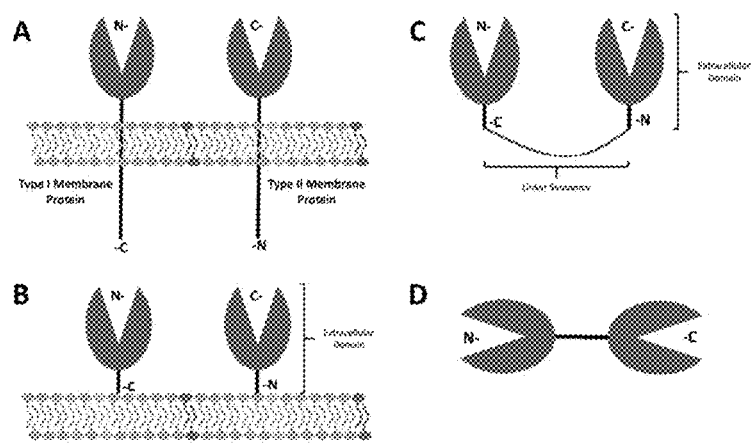
FIG. 3 shows a schematic illustration of how a type I and type II membrane protein (panel A) may be engineered with transmembrane and intracellular domains removed (panel B) and adjoined using a linker sequence (panel C) to generate a single fusion protein wherein the extracellular domains of the type I and type II membrane proteins each face outward in a single fusion protein (panel D). Panel C depicts the linkage of a type I and type II membrane protein by removal of the transmembrane and intracellular domains of each protein, and where the liberated extracellular domains (ECD) from each protein have been adjoined by a linker sequence. The ECD in this depiction may include the entire amino acid sequence of a candidate type I or type II protein which is typically localized outside the cell membrane, or any portion thereof which retains binding to the intended receptor or ligand. Panel D depicts adjoined extracellular domains in a linear construct wherein the extracellular domain of the type I membrane protein faces the 'left' side of the construct and the extracellular domain of the type II membrane protein faces the "right" side of the construct.

Because the outward facing domains of type I and type II membrane proteins are opposite (FIG. 1), it is possible to link the extracellular domains of a type I and type II membrane protein such that the 'outward facing' domains of the molecules are also in opposing orientation to each other (FIG. 3). The resulting construct would therefore consist of the extracellular domain of a type I membrane protein on the 'left' side of the molecule, connected to the extracellular domain of a type II membrane protein on the 'right' side of the molecule using a linker sequence. This construct could be produced by cloning of these three fragments (the extracellular domain of a type I protein, followed by a linker sequence, followed by the extracellular domain of a type II protein) into a vector (plasmid, viral or other) wherein the amino terminus of the complete sequence corresponded to the 'left' side of the molecule containing the type I protein and the carboxy terminus of the complete sequence corresponded to the 'right' side of the molecule containing the type II protein. Accordingly, in various embodiments, the present chimeric proteins are engineered as such.

In some embodiments, the extracellular domain may be used to produce a soluble protein to competitively inhibit signaling by that receptor's ligand. In some embodiments, the extracellular domain may be used to provide artificial signaling.

In some embodiments, the extracellular domain of a type I transmembrane protein is an immune inhibitory signal. In some embodiments, the extracellular domain of a type II transmembrane protein is an immune stimulatory signal.

In some embodiments, the present chimeric proteins comprise an extracellular domain of a type I transmembrane protein, or a functional fragment thereof. In some embodiments, the present chimeric proteins comprise an extracellular domain of a type II transmembrane protein, or a functional fragment thereof. In some embodiments, the present chimeric proteins comprise an extracellular domain of a type I transmembrane protein, or a functional fragment thereof, and an extracellular domain of a type II transmembrane protein, or a functional fragment thereof.

In various embodiments, the present chimeric proteins comprise an extracellular domain of a human type I transmembrane protein as recited in TABLE 1, or a functional fragment thereof. In various embodiments, the present chimeric proteins comprise an extracellular domain of a human type II transmembrane protein as recited in TABLE 2, or a functional fragment thereof. In some embodiments, the present chimeric proteins comprise an extracellular domain of a type I transmembrane protein as recited in TABLE 1, or a functional fragment thereof, and an extracellular domain of a type II transmembrane protein as recited in TABLE 2, or a functional fragment thereof. TABLEs 1 and 2 are provided elsewhere herein.

In various embodiments, the present chimeric proteins may be engineered to target one or more molecules that reside on human leukocytes including, without limitation, the extracellular domains (where applicable) of SLAMF4, IL-2 R α, 4-1BB/TNFRSF9, IL-2 R β, ALCAM, B7-1, IL-4 R, B7-H3, BLAME/SLAMF8, CEACAM1, IL-6 R, IL-7 Rα, IL-10R α, IL-I 0 R β, IL-12 R β1, IL-12 R β 2, CD2, IL-13 R α 1, IL-13, CD3, CD4, ILT2/CDS5j, ILT3/CDS5k, ILT4/CDS5d, ILT5/CDS5a, Integrin α 4/CD49d, CDS, Integrin α E/CD103, CD6, Integrin α M/CD 11 b, CDS, Integrin α X/CD11c, Integrin β 2/CDIS, KIR/CD15S, CD27/

TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, RANK/TNFRSF11A, CX3CR1, CX3CL1, L-Selectin, SIRP β 1, SLAM, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1 and TSLP R.

The activation of regulatory T cells is critically influenced by costimulatory and coinhibitory signals. Two major families of costimulatory molecules include the B7 and the tumor necrosis factor (TNF) families. These molecules bind to receptors on T cells belonging to the CD28 or TNF receptor families, respectively. Many well-defined coinhibitors and their receptors belong to the B7 and CD28 families.

In various embodiments, the present chimeric proteins may be engineered to target one or more molecules involved in immune inhibition, including for example: CTLA-4, PD-L1, PD-L2, PD-1, BTLA, HVEM, TIM3, GAL9, LAG3, VISTA/VSIG8, KIR, 2B4, TIGIT, CD160 (also referred to as BY55), CHK 1 and CHK2 kinases, A2aR, CEACAM (e.g., CEACAM-1, CEACAM-3 and/or CEACAM-5), and various B-7 family ligands (including, but are not limited to, B7-1, B7-2, B7-DC, B7-H1, B7-H2, B7-H3, B7-H4, B7-H5, B7-H6 and B7-H7).

In various embodiments, the chimeric protein of the present invention comprises an extracellular domain of an immune inhibitory agent, including without limitation, one or more of TIM-3, BTLA, PD-1, CTLA-4, CD244, CD160, TIGIT, SIRPα/CD172a, 2B4, VISTA, VSIG8, LAG3, CD200 and TMIGD2.

In some embodiments, the chimeric protein of the present invention comprises an extracellular domain of a type I membrane protein which has immune inhibitory properties. In various embodiments, the chimeric protein is engineered to disrupt, block, reduce, and/or inhibit the transmission of an immune inhibitory signal, by way of non-limiting example, the binding of PD-1 with PD-L1 or PD-L2 and/or the binding of CD172a with CD47 and/or the binding of TIM-3 with galectin-9 and/or phosphatidyserine.

In some embodiments, the chimeric protein of the present invention comprises an extracellular domain of an immune stimulatory signal is one or more of OX-40 ligand (OX-40L), LIGHT (CD258), GITR ligand (GITRL), CD70, CD30 ligand, CD40 ligand (CD40L), CD137 ligand, TRAIL, and TL1A.

In various embodiments, the chimeric protein simulates binding of an inhibitory signal ligand to its cognate receptor (e.g. PD-1 to PD-L1 or PD-L2; e.g. CD172a to CD47; e.g. CD115 to CSF1; e.g. TIM-3 to galectin-9 or phosphatidylserine) but inhibits the inhibitory signal transmission to an immune cell (e.g. a T cell, macrophage or other leukocyte).

In various embodiments, the chimeric protein comprises an immune inhibitory receptor extracellular domain and an immune stimulatory ligand extracellular domain which can, without limitation, deliver an immune stimulation to a T cell while masking a tumor cell's immune inhibitory signals. In various embodiments, the chimeric protein delivers a signal that has the net result of T cell activation.

In some embodiments, the chimeric protein comprises an immune inhibitory signal which is an ECD of a receptor of an immune inhibitory signal and this acts on a tumor cell that bears a cognate ligand of the immune inhibitory signal. In some embodiments, the chimeric protein comprises an immune stimulatory signal which is an ECD of a ligand of an immune stimulatory signal and this acts on a T cell that bears a cognate receptor of the immune stimulatory signal. In some embodiments, the chimeric protein comprises both (i) an immune inhibitory signal which is a receptor of an immune inhibitory signal and this acts on a tumor cell that bears a cognate ligand of the immune inhibitory signal and (ii) an immune stimulatory signal which is a ligand of an immune stimulatory signal and this acts on a T cell that bears a cognate receptor of the immune stimulatory signal.

Figure 2:
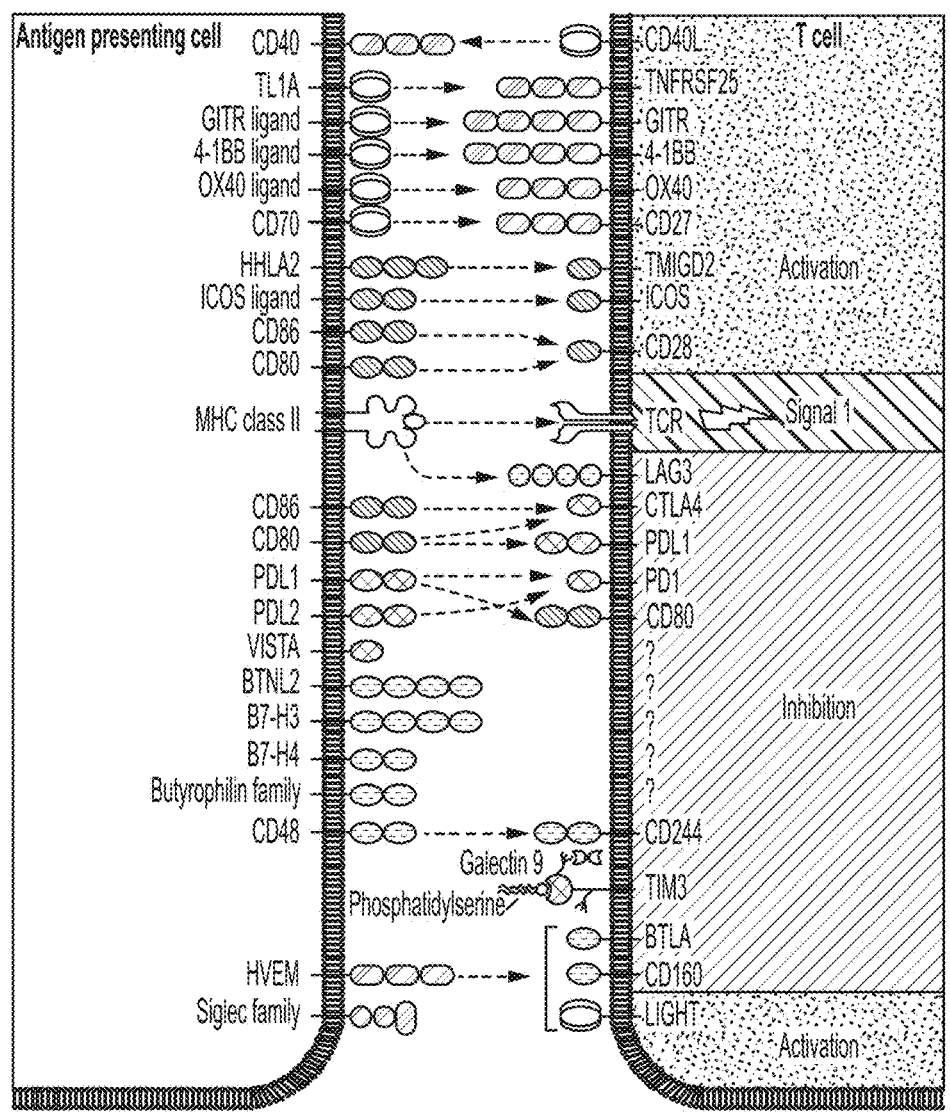
FIG. 2 shows immune inhibitory and immune stimulatory signaling that is relevant to the present invention (from Mahoney, *Nature Reviews Drug Discovery* 2015:14; 561-585).

In some embodiments, the chimeric protein of the present invention comprises an extracellular domain of one or more of the immune-modulating agents described in Mahoney, *Nature Reviews Drug Discovery* 2015:14; 561-585, the entire contents of which are hereby incorporated by reference. For example, with reference to present FIG. 2, the chimeric protein bears an immune inhibitory signal (denoted by "−") which is a receptor of the pair (i.e. right side of the figure) and the tumor cell bears a ligand selected from the left side of the figure. By way of further example, with reference to present FIG. 2, the chimeric protein bears an immune stimulatory signal (denoted by "+") which is a ligand of the pair (i.e. left side of the figure) and the tumor cell bears a receptor selected from the right side of the figure.

In some embodiments, the chimeric protein of the present invention comprises an extracellular domain of a type II membrane protein which has immune stimulatory properties. In various embodiments, the chimeric protein is engineered to enhance, increase, and/or stimulate the transmission of an immune stimulatory signal, by way of non-limiting example, the binding of GITR with one or more of GITR ligand and/or the binding of OX40 with OX40L and/or the binding of CD40 with CD40 ligand.

In some embodiments, the chimeric protein comprises the extracellular domain of the immune inhibitory agent PD-1 and is paired with an immune stimulatory agent as follows: PD-1/4-1BBL; PD-1/OX-40L; PD-1/LIGHT; PD-1/GITRL; PD-1/CD70; PD-1/CD30L; PD-1/CD40L; and PD-1/TL1A.

In an embodiment, the chimeric protein comprises the extracellular domain of the immune inhibitory agent PD-1 and is paired with the immune stimulatory agent OX-40L. In an embodiment, the chimeric protein comprises the amino acid sequence of SEQ ID NO: 22. In various embodiments, the chimeric protein binds to human PD-L1 or PD-L2 with a $K_D$ of about 1 nM to about 5 nM, for example, about 1 nM, about 1.5 nM, about 2 nM, about 2.5 nM, about 3 nM, about 3.5 nM, about 4 nM, about 4.5 nM, or about 5 nM. In various embodiments, the chimeric protein binds to human PD-L1 with a $K_D$ of about 5 nM to about 15 nM, for example, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 10.5 nM, about 11 nM, about 11.5 nM, about 12 nM, about 12.5 nM, about 13 nM, about 13.5 nM, about 14 nM, about 14.5 nM, or about 15 nM.

In various embodiments, the chimeric protein exhibits enhanced stability and protein half-life. In some embodiments, the chimeric protein binds to FcRn with high affinity. In various embodiments, the chimeric protein may bind to FcRn with a $K_D$ of about 70 nM to about 80 nM. For example, the chimeric protein may bind to FcRn with a $K_D$ of about 70 nM, about 71 nM, about 72 nM, about 73 nM, about 74 nM, about 75 nM, about 76 nM, about 77 nM, about 78 nM, about 79 nM, or about 80 nM. In some embodiments, the chimeric protein does not substantially bind to other Fc receptors (i.e. other than FcRn) with effector function.

In some embodiments, the chimeric protein comprises the extracellular domain of the immune inhibitory agent PD-L1 or PD-L2 and is paired with an immune stimulatory receptor as follows: PD-L1/4-1BB; PD-L1/OX-40; PD-L1/HVEM; PD-L1/GITR; PD-L1/CD27; PD-L1/CD28; PD-L1/CD30; PD-L1/CD40 and PD-L1/CD137.

In some embodiments, the chimeric protein comprises the extracellular domain of the immune inhibitory agent PD-L2 and is paired with an immune stimulatory receptor as follows: PD-L2/4-1BB; PD-L2/OX-40; PD-L2/HVEM; PD-L2/GITR; PD-L2/CD27; PD-L2/CD28; PD-L2/CD30; PD-L2/CD40 and PD-L2/CD137.

In some embodiments, the chimeric protein comprises the extracellular domain of the immune inhibitory agent TIM-3 and is paired with an immune stimulatory agent as follows: TIM-3/OX-40L; TIM-3/LIGHT; TIM-3/GITRL; TIM-3/CD70; TIM-3/CD30L; TIM-3/CD40L; TIM-3/CD137L; TIM-3/TL1A; and TIM-3/OX40L.

In some embodiments, the chimeric protein comprises the extracellular domain of the immune inhibitory agent BTLA and is paired with an immune stimulatory agent as follows: BTLA/OX-40L; BTLA/LIGHT; BTLA/GITRL; BTLA/CD70; BTLA/CD30L; BTLA/CD40L; BTLA/CD137L; BTLA/TL1A; and BTLA/OX40L.

In some embodiments, the chimeric protein comprises the extracellular domain of the immune inhibitory agent CD172a/SIRPα and is paired with an immune stimulatory agent as follows: CD172a/OX-40L; CD172a/LIGHT; CD172a/CD70; CD172a/CD30L; CD172a/CD40L; CD172a/CD137L; CD172a/TL1A; and CD172a/OX40L.

In some embodiments, the chimeric protein comprises the extracellular domain of the immune inhibitory agent CD115 and is paired with an immune stimulatory agent as follows: CD115/OX-40L; CD115/LIGHT; CD115/CD70; CD115/CD30L; CD115/CD40L; CD115/CD137L; CD115/TL1A; and CD115/OX40L.

In some embodiments, the chimeric protein comprises the extracellular domain of the immune inhibitory agent TIGIT and is paired with an immune stimulatory agent as follows: TIGIT/OX-40L; TIGIT/LIGHT; TIGIT/GITRL; TIGIT/CD70; TIGIT/CD30L; TIGIT/CD40L; TIGIT/CD137L; TIGIT/TL1A; and TIGIT/OX40L.

In some embodiments, the chimeric protein comprises the extracellular domain of the immune inhibitory agent TMIGD2 and is paired with an immune stimulatory agent as follows: TMIGD2/OX-40L; TMIGD2/LIGHT; TMIGD2/GITRL; TMIGD2/CD70; TMIGD2/CD30L; TMIGD2/CD40L; TMIGD2/CD137L; TMIGD2/TL1A; and TMIGD2/OX40L.

In some embodiments, the chimeric protein comprises the extracellular domain of the immune inhibitory agent LAG3 and is paired with an immune stimulatory agent as follows: LAG3/OX-40L; LAG3/LIGHT; LAG3/GITRL; LAG3/CD70; LAG3/CD30L; LAG3/CD40L; LAG3/CD137L; LAG3/TL1A; and LAG3/OX40L.

In some embodiments, the chimeric protein comprises the extracellular domain of the immune inhibitory agent VSIG8 and is paired with an immune stimulatory agent as follows: VSIG8/OX-40L; VSIG8/LIGHT; VSIG8/GITRL; VSIG8/CD70; VSIG8/CD30L; VSIG8/CD40L; VSIG8/CD137L; VSIG8/TL1A; and VSIG8/OX40L.

In some embodiments, the chimeric protein comprises the extracellular domain of the immune inhibitory agent CD200 and is paired with an immune stimulatory agent as follows: CD200/OX-40L; CD200/LIGHT; CD200/GITRL; CD200/CD70; CD200/CD30L; CD200/CD40L; CD200/CD137L; CD200/TL1A; and CD200/OX40L.

In various embodiments, the present chimeric proteins may comprises variants of the extracellular domains described herein, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequence of the extracellular domains, e.g. human extracellular domains, e.g. one or more of SEQ IDs NOs: 1-15 as a whole or relative to indicated domains therein. Included herein are various illustrative sequences, as SEQ IDs NOs: 1-15, which show extracellular domains as underlined or in bold and a linker in normal text. In various embodiments, the linker can be swapped for another described herein.

In an illustrative embodiment, the chimeric protein of the present invention comprises an extracellular domain of PD-1 and the extracellular domain of OX40L using the hinge-CH2-CH3 domain from a human IgG4 antibody sequence. In this embodiment, the extracellular domain of PD-1 is underlined, followed by the hinge-CH2-CH3 domain of human IgG4 and short linker (normal text), followed by the extracellular domain of OX40L (bold text):

```
                                          (SEQ ID NO: 1)
ATGCAGATCCCACAGGCGCCCTGGCCAGTCGTCTGGGCGGTGCT

ACAACTGGGCTGGCGGCCAGGATGGTTCTTAGACTCCCCAGACAG

GCCCTGGAACCCCCCCACCTTCTCCCCAGCCCTGCTCGTGGTGAC

CGAAGGGGACAACGCCACCTTCACCTGCAGCTTCTCCAACACATC

GGAGAGCTTCGTGCTAAACTGGTACCGCATGAGCCCCAGCAACCA

GACGGACAAGCTGGCCGCCTTCCCCGAGGACCGCAGCCAGCCCG

GCCAGGACTGCCGCTTCCGTGTCACACAACTGCCCAACGGGCGT

GACTTCCACATGAGCGTGGTCAGGGCCCGGCGCAATGACAGCGG

CACCTACCTCTGTGGGGCCATCTCCCTGGCCCCCAAGGCGCAGAT

CAAAGAGAGCCTGCGGGCAGAGCTCAGGGTGACAGAGAGAAGGG

CAGAAGTGCCCACAGCCCACCCCAGCCCCTCACCCAGGCCAGCC

GGCCAGTTCCAATCTAAGTACGGCCCTCCCTGCCCTAGCTGTCCC

GCCCCTGAATTTCTGGGCGGACCCTCCGTGTTTCTGTTCCCCCCA

AAGCCCAAGGACACCCTGATGATCAGCCGGACCCCCGAAGTGAC

CTGTGTGGTGGTGGATGTGTCCCAGGAAGATCCCGAGGTGCAGTT
```

-continued

```
CAATTGGTACGTGGACGGGGTGGAAGTGCACAACGCCAAGACCAA

GCCCAGAGAGGAACAGTTCAACAGCACCTACCGGTGGTGTCTGT

GCTGACCGTGCTGCACCAGGATTGGCTGAGCGGCAAAGAGTACAA

GTGCAAGGTGTCCAGCAAGGGCCTGCCCAGCAGCATCGAAAAGA

CCATCAGCAACGCCACCGGCCAGCCCAGGGAACCCCAGGTGTAC

ACACTGCCCCCTAGCCAGGAAGAGATGACCAAGAACCAGGTGTCC

CTGACATGCCTCGTGAAGGGCTTCTACCCCTCCGATATCGCCGTG

GAATGGGAGAGCAACGGCCAGCCAGAGAACAACTACAAGACCAC

CCCCCCAGTGCTGGACAGCGACGGCTCATTCTTCCTGTACTCCCG

GCTGACAGTGGACAAGAGCAGCTGGCAGGAAGGCAACGTGTTCA

GCTGCAGCGTGATGCACGAAGCCCTGCACAACCACTACACCCAGA

AGTCCCTGAGCCTGTCCCTGGGCAAAATAGAGGGACGAATGGACC

AGGTATCACATCGGTATCCTCGAATTCAAAGTATCAAAGTACAAT

TTACCGAATATAAGAAGGAGAAAGGTTTCATCCTCACTTCCCAAA

AGGAGGATGAAATCATGAAGGTGCAGAACAACTCAGTCATCATC

AACTGTGATGGGTTTTATCTCATCTCCCTGAAGGGCTACTTCTCC

CAGGAAGTCAACATTAGCCTTCATTACCAGAAGGATGAGGAGCC

CCTCTTCCAACTGAAGAAGGTCAGGTCTGTCAACTCCTTGATGGT

GGCCTCTCTGACTTACAAAGACAAAGTCTACTTGAATGTGACCAC

TGACAATACCTCCCTGGATGACTTCCATGTGAATGGCGGAGAACT

GATTCTTATCCATCAAAATCCTGGTGAATTCTGTGTCCTTTGA.
```

This sequence encodes a protein with an amino acid sequence:

```
                                    (SEQ ID NO: 2)
M Q I P Q A P W P V V W A V L Q L G W R P G W F L
D S P D R P W N P P T F S P A L L V V T E G D N A
T F T C S F S N T S E S F V L N W Y R M S P S N Q
T D K L A A F P E D R S Q P G Q D C R F R V T Q L
P N G R D F H M S V V R A R R N D S G T Y L C G A
I S L A P K A Q I K E S L R A E L R V T E R R A E
V P T A H P S P S P R P A G Q F Q S K Y G P P C P
S C P A P E F L G G P S V F L P P K P K D T L M
I S R T P E V T C V V V D V S Q E D P E V Q F N W
Y V D G V E V H N A K T K P R E E Q F N S T Y R V
V S V L T V L H Q D W L S G K E Y K C K V S S K G
L P S S I E K T I S N A T G Q P R E P Q V Y T L P
P S Q E E M T K N Q V S L T C L V K G F Y P S D I
A V E W E S N G Q P E N N Y K T T P P V L D S D G
S F F L Y S R L T V D K S S W Q E G N V F S C S V
M H E A L H N H Y T Q K S L S L S L G K I E G R M
D Q V S H R Y P R I Q S I K V Q F T E Y K K E K G
F I L T S Q K E D E I M K V Q N N S V I I N C D G
F Y L I S L K G Y F S Q E V N I S L H Y Q K D E E
P L F Q L K K V R S V N S L M V A S L T Y K D K V
Y L N V T T D N T S L D D F H V N G G E L I L I H
Q N P G E F C V L Stop
```

Further, this amino acid sequence, as well as the amino acid sequences of any of the extracellular domains described herein (whether or not explicitly listed) could also be achieved with codon-optimized nucleic acid sequences, such as the following sequence which is optimized for expression by Chinese Hamster (CHO) cells:

```
                                    (SEQ ID NO: 3)
ATGCAGATTCCTCAGGCCCCTTGGCCTGTCGTGTGGGCTGTGCTG

CAGCTGGGATGGCGGCCTGGCTGGTTTCTGGACAGCCCCGACAG

ACCCTGGAACCCCCCTACATTTTCCCCTGCCCTGCTGGTCGTGAC

CGAGGGCGACAATGCCACCTTCACCTGTAGCTTCAGCAACACCAG

CGAGAGCTTCGTGCTGAACTGGTACAGAATGAGCCCCAGCAACCA

GACCGACAAGCTGGCCGCCTTCCCCGAGGATAGATCTCAGCCCG

GCCAGGACTGCCGGTTCAGAGTGACCCAGCTGCCCAACGGCCGG

GACTTCCACATGTCTGTCGTGCGGGCCAGACGGAACGACAGCGG

CACATATCTGTGCGGCGCCATCAGCCTGGCCCCCAAGGCCCAGAT

CAAAGAGAGCCTGAGAGCCGAGCTGAGAGTGACCGAGAGAAGGG

CCGAAGTGCCTACCGCCCACCCTAGCCCATCTCCAAGACCTGCCG

GCCAGTTCCAGTCTAAGTACGGCCCTCCTTGCCCCAGCTGTCCCG

CCCCTGAATTTCTGGGCGGACCCAGCGTGTTCCTGTTCCCCCCAA

AGCCCAAGGACACCCTGATGATCAGCCGGACCCCCGAAGTGACCT

GCGTGGTGGTGGATGTGTCCCAGGAAGATCCCGAGGTGCAGTTC

AATTGGTACGTGGACGGCGTGGAAGTGCACAACGCCAAGACCAAG

CCCAGAGAGGAACAGTTCAACAGCACCTACCGGGTGGTGTCCGTG

CTGACCGTGCTGCACCAGGATTGGCTGAGCGGCAAAGAGTACAAG

TGCAAGGTGTCCAGCAAGGGCCTGCCCAGCAGCATCGAGAAAAC

CATCAGCAACGCCACCGGCCAGCCCAGGGAACCCCAGGTGTACA

CACTGCCCCCTAGCCAGGAAGAGATGACCAAGAACCAGGTGTCCC

TGACCTGTCTCGTGAAGGGCTTCTACCCCTCCGATATCGCCGTGG

AATGGGAGAGCAACGGCCAGCCTGAGAACAACTACAAGACCACCC

CCCCAGTGCTGGACAGCGACGGCTCATTTTTCCTGTACTCCAGAC

TGACCGTGGACAAGAGCAGCTGGCAGGAAGGCAACGTGTTCAGC

TGCTCCGTGATGCACGAGGCCCTGCACAACCACTACACCCAGAAG

TCCCTGTCTCTGAGCCTGGGCAAGATCGAGGGCCGGATGGATAG

AGCCCAGGGCGAAGCCTGCGTGCAGTTCCAGGCTCTGAAGGGC

CAGGAATTCGCCCCCAGCCACCAGCAGGTGTACGCCCCTCTGAG

AGCTGACGGCGACAAGCCTAGAGCCCACCTGACAGTCGTGCGG

CAGACCCCTACCCAGCACTTCAAGAATCAGTTCCCAGCCCTGCA

CTGGGAGCACGAGCTGGGCCTGGCCTTCACCAAGAACAGAATGA

ACTACACCAACAAGTTTCTGCTGATCCCCGAGAGCGGCGACTAC

TTCATCTACAGCCAAGTGACCTTCCGGGGCATGACCAGCGAGTG

CAGCGAGATCAGACAGGCCGGCAGACCTAACAAGCCCGACAGC

ATCACCGTCGTGATCACCAAAGTGACCGACAGCTACCCCGAGCC

CACACAGCTGCTGATGGGCACCAAGAGCGTGTGCGAAGTGGGC

AGCAACTGGTTCCAGCCCATCTACCTGGGCGCCATGTTCAGTCTG

CAAGAGGGCGATAAGCTGATGGTCAACGTGTCCGACATCTCCCT
```

Another embodiment of the present chimeric protein comprises the extracellular domain of PD-1 and the extracellular domain of costimulatory ligand, such as TL1A, 4-1BBL, ICOSL, GITRL, CD27 or CD40L. An example sequence encoding the extracellular domain of PD-1 (underlined)—Fc (normal text)—the extracellular domain of TL1A (bold text) is:

(SEQ ID NO: 4)
<u>ATGCAGATCCCACAGGCGCCCTGGCCAGTCGTCTGGGCGGTGCT</u>

<u>ACAACTGGGCTGGCGGCCAGGATGGTTCTTAGACTCCCCAGACAG</u>

<u>GCCCTGGAACCCCCCCACCTTCTCCCAGCCCTGCTCGTGGTGAC</u>

<u>CGAAGGGGACAACGCCACCTTCACCTGCAGCTTCTCCAACACATC</u>

<u>GGAGAGCTTCGTGCTAAACTGGTACCGCATGAGCCCCAGCAACCA</u>

<u>GACGGACAAGCTGGCCGCCTTCCCCGAGGACCGCAGCCAGCCCG</u>

<u>GCCAGGACTGCCGCTTCCGTGTCACACAACTGCCCAACGGGCGT</u>

<u>GACTTCCACATGAGCGTGGTCAGGGCCCGGCGCAATGACAGCGG</u>

<u>CACCTACCTCTGTGGGGCCATCTCCCTGGCCCCCAAGGCGCAGAT</u>

<u>CAAAGAGAGCCTGCGGGCAGAGCTCAGGGTGACAGAGAGAAGGG</u>

<u>CAGAAGTGCCCACAGCCCACCCCAGCCCCTCACCCAGGCCAGCC</u>

<u>GGCCAGTTCCAATC</u>TAAGTACGGCCCTCCCTGCCCTAGCTGTCCC

GCCCCTGAATTTCTGGGCGGACCCTCCGTGTTTCTGTTCCCCCCA

AAGCCCAAGGACACCCTGATGATCAGCCGGACCCCCGAAGTGAC

CTGTGTGGTGGTGGATGTGTCCCAGGAAGATCCCGAGGTGCAGTT

CAATTGGTACGTGGACGGGGTGGAAGTGCACAACGCCAAGACCAA

GCCCAGAGAGGAACAGTTCAACAGCACCTACCGGGTGGTGTCTGT

GCTGACCGTGCTGCACCAGGATTGGCTGAGCGGCAAAGAGTACAA

GTGCAAGGTGTCCAGCAAGGGCCTGCCCAGCAGCATCGAAAAGA

CCATCAGCAACGCCACCGGCCAGCCCAGGGAACCCCAGGTGTAC

ACACTGCCCCCTAGCCAGGAAGAGATGACCAAGAACCAGGTGTCC

CTGACATGCCTCGTGAAGGGCTTCTACCCCTCCGATATCGCCGTG

GAATGGGAGAGCAACGGCCAGCCAGAGAACAACTACAAGACCAC

CCCCCCAGTGCTGGACAGCGACGGCTCATTCTTCCTGTACTCCCG

GCTGACAGTGGACAAGAGCAGCTGGCAGGAAGGCAACGTGTTCA

GCTGCAGCGTGATGCACGAAGCCCTGCACAACCACTACACCCAGA

AGTCCCTGAGCCTGTCCCTGGGCAAAATAGAGGGACGAATGGACC

GGGCCCAGGGAGAGGCCTGTGTGCAGTTCCAGGCTCTAAAAGG

ACAGGAGTTTGCACCTTCACATCAGCAAGTTTATGCACCTCTTAG

AGCAGACGGAGATAAGCCAAGGGCACACCTGACAGTTGTGAGA

CAAACTCCCACACAGCACTTTAAAAATCAGTTCCCAGCTCTGCAC

TGGGAACATGAACTAGGCCTGGCCTTCACCAAGAACCGAATGAA

CTATACCAACAAATTCCTGCTGATCCCAGAGTCGGGAGACTACTT

CATTTACTCCCAGGTCACATTCCGTGGGATGACCTCTGAGTGCAG

TGAAATCAGACAAGCAGGCCGACCAAACAAGCCAGACTCCATCA

CTGTGGTCATCACCAAGGTAACAGACAGCTACCCTGAGCCAACC

CAGCTCCTCATGGGGACCAAGTCTGTATGCGAAGTAGGGTAGCAA

CTGGTTCCAGCCCATCTACCTCGGAGCCATGTTCTCCTTGCAAGA

AGGGGACAAGCTAATGGTGAACGTCAGTGACATCTCTTTGGTGG

ATTACACAAAAGAAGATAAAACCTTCTTTGGAGCCTTCTTACTAT

AG

This nucleotide sequence of SEQ ID NO: 4 may be codon optimized, to encode a protein with an amino acid sequence:

(SEQ ID NO: 5)
<u>M Q I P Q A P W P V V W A V L Q L G W R P G W F L</u>

<u>D S P D R P W N P P T F S P A L L V V T E G D N A</u>

<u>T F T C S F S N T S E S F V L N W Y R M S P S N Q</u>

<u>T D K L A A F P E D R S Q P G Q D C R F R V T Q L</u>

<u>P N G R D F H M S V V R A R R N D S G T Y L C G A</u>

<u>I S L A P K A Q I K E S L R A E L R V T E R R A E</u>

<u>V P T A H P S P S P R P A G Q F Q</u> S K Y G P P C P

S C P A P E F L G G P S V F L F P P K P K D T L M

I S R T P E V T C V V V D V S Q E D P E V Q F N W

Y V D G V E V H N A K T K P R E E Q F N S T Y R V

V S V L T V L H Q D W L S G K E Y K C K V S S K G

L P S S I E K T I S N A T G Q P R E P Q V Y T L P

P S Q E E M T K N Q V S L T C L V K G F Y P S D I

A V E W E S N G Q P E N N Y K T T P P V L D S D G

S F F L Y S R L T V D K S S W Q E G N V F S C S V

M H E A L H N H Y T Q K S L S L S L G K I E G R M

D R A Q G E A C V Q F Q A L K G Q E F A P S H Q Q

V Y A P L R A D G D K P R A H L T V V R Q T P T Q

H F K N Q F P A L H W E H E L G L A F T K N R M N

Y T N K F L L I P E S G D Y F I Y S Q V T F R G M

T S E C S E I R Q A G R P N K P D S I T V V I T K

V T D S Y P E P T Q L L M G T K S V C E V G S N W

F Q P I Y L G A M F S L Q E G D K L M V N V S D I

S L V D Y T K E D K T F F G A F L L Stop

There are many type I membrane proteins expressed by tumor cells that could be masked by a fusion protein encoding the extracellular domain of a cognate receptor. Additional examples would include a fusion protein encoding the extracellular domain of BTLA, linked through an Fc to OX40L. Such a construct could be encoded by the nucleic acid sequence:

(SEQ ID NO: 6)
ATGAAGACATTGCCTGCCATGCTTGGAACTGGGAAATTATTTTGGG

TCTTCTTCTTAATCCCATATCTGGACATCTGGAACATCCATGGAA

AGAATCATGTGATGTACAGCTTTATATAAAGAGACAATCTGAACACT

CCATCTTAGCAGGAGATCCCTTTGAACTAGAATGCCCTGTGAAATA

CTGTGCTAACAGGCCTCATGTGACTTGGTGCAAGCTCAATGGAAC

AACATGTGTAAAACTTGAAGATAGACAAACAAGTTGGAAGGAAGAG

AAGAACATTTCATTTTTCATTCTACATTTTGAACCAGTGCTTCCTAAT

GACAATGGGTCATACCGCTGTTCTGCAAATTTTCAGTCTAATCTCA

TTGAAAGCCACTCAACAACTCTTTATGTGACAGATGTAAAAAGTGC

CTCAGAACGACCCTCCAAGGACGAAATGGCAAGCTCTAAGTACGG

CCCTCCCTGCCCTAGCTGTCCCGCCCCTGAATTTCTGGGCGGACC

CTCCGTGTTTCTGTTCCCCCCAAAGCCCAAGGACACCCTGATGAT

CAGCCGGACCCCCGAAGTGACCTGTGTGGTGGTGGATGTGTCCC

AGGAAGATCCCGAGGTGCAGTTCAATTGGTACGTGGACGGGGTG

GAAGTGCACAACGCCAAGACCAAGCCCAGAGAGGAACAGTTCAAC

AGCACCTACCGGGTGGTGTCTGTGCTGACCGTGCTGCACCAGGAT

TGGCTGAGCGGCAAAGAGTACAAGTGCAAGGTGTCCAGCAAGGG

CCTGCCCAGCAGCATCGAAAAGACCATCAGCAACGCCACCGGCCA

GCCCAGGGAACCCCAGGTGTACACACTGCCCCCTAGCCAGGAAG

AGATGACCAAGAACCAGGTGTCCCTGACATGCCTCGTGAAGGGCT

TCTACCCCTCCGATATCGCCGTGGAATGGGAGAGCAACGGCCAGC

CAGAGAACAACTACAAGACCACCCCCCCAGTGCTGGACAGCGACG

GCTCATTCTTCCTGTACTCCCGGCTGACAGTGGACAAGAGCAGCT

GGCAGGAAGGCAACGTGTTCAGCTGCAGCGTGATGCACGAAGCC

CTGCACAACCACTACACCCAGAAGTCCCTGAGCCTGTCCCTGGGC

AAAATAGGGACGAATGGACCAGGTATCACATCGGTATCCTCGA

ATTCAAAGTATCAAAGTACAATTTACCGAATATAAGAAGGAGAAA

GGTTTCATCCTCACTTCCCAAAAGGAGGATGAAATCATGAAGGTG

CAGAACAACTCAGTCATCATCAACTGTGATGGGTTTTATCTCATC

TCCCTGAAGGGCTACTTCTCCCAGGAAGTCAACATTAGCCTTCAT

TACCAGAAGGATGAGGAGCCCCTCTTCCAACTGAAGAAGGTCAG

GTCTGTCAACTCCTTGATGGTGGCCTCTCTGACTTACAAAGACAA

AGTCTACTTGAATGTGACCACTGACAATACCTCCCTGGATGACTT

CCATGTGAATGGCGGAGAACTGATTCTTATCCATCAAAATCCTGG

TGAATTCTGTGTCCTTTGA

This nucleotide sequence encodes a protein with an amino acid sequence:

(SEQ ID NO: 7)
M K T L P A M L G T G K L F W V F F L I P Y L D I

W N I H G K E S C D V Q L Y I K R Q S E H S I L A

-continued
G D P F E L E C P V K Y C A N R P H V T W C K L N

G T T C V K L E D R Q T S W K E E K N I S F F I L

H F E P V L P N D N G S Y R C S A N F Q S N L I E

S H S T T L Y V T D V K S A S E R P S K D E M A S

S K Y G P P C P S C P A P E F L G G P S V F L F P

P K P K D T L M I S R T P E V T C V V V D V S Q E

D P E V Q F N W Y V D G V E V H N A K T K P R E E

Q F N S T Y R V V S V L T V L H Q D W L S G K E Y

K C K V S S K G L P S S I E K T I S N A T G Q P R

E P Q V Y T L P P S Q E E M T K N Q V S L T C L V

K G F Y P S D I A V E W E S N G Q P E N N Y K T T

P P V L D S D G S F F L Y S R L T V D K S S W Q E

G N V F S C S V M H E A L H N H Y T Q K S L S L S

L G K I E G R M D Q V S H R Y P R I Q S I K V Q F

T E Y K K E K G F I L T S Q K E D E I M K V Q N N

S V I I N C D G F Y L I S L K G Y F S Q E V N I S

L H Y Q K D E E P L F Q L K K V R S V N S L M V A

S L T Y K D K V Y L N V T T D N T S L D D F H V N

G G E L I L I H Q N P G E F C V L Stop

Another example would include a fusion protein incorporating the extracellular domain of TIGIT, linked via an Fc linker to OX40L:

(SEQ ID NO: 8)
ATGCGCTGGTGTCTCCTCCTGATCTGGGCCCAGGGGCTGAGGCA

GGCTCCCCTCGCCTCAGGAATGATGACAGGCACAATAGAAACAAC

GGGGAACATTTCTGCAGAGAAAGGTGGCTCTATCATCTTACAATGT

CACCTCTCCTCCACCACGGCACAAGTGACCCAGGTCAACTGGGAG

CAGCAGGACCAGCTTCTGGCCATTTGTAATGCTGACTTGGGGTGG

CACATCTCCCCATCCTTCAAGGATCGAGTGGCCCCAGGTCCCGGC

CTGGGCCTCACCCTCCAGTCGCTGACCGTGAACGATACAGGGGA

GTACTTCTGCATCTATCACACCTACCCTGATGGGACGTACACTGGG

AGAATCTTCCTGGAGGTCCTAGAAAGCTCAGTGGCTGAGCACGGT

GCCAGGTTCCAGATTCCATCTAAGTACGGCCCTCCCTGCCCTAGC

TGTCCCGCCCCTGAATTTCTGGGCGGACCCTCCGTGTTTCTGTTC

CCCCCAAAGCCCAAGGACACCCTGATGATCAGCCGGACCCCCGA

AGTGACCTGTGTGGTGGTGGATGTGTCCCAGGAAGATCCCGAGGT

GCAGTTCAATTGGTACGTGGACGGGGTGGAAGTGCACAACGCCAA

GACCAAGCCCAGAGAGGAACAGTTCAACAGCACCTACCGGGTGGT

GTCTGTGCTGACCGTGCTGCACCAGGATTGGCTGAGCGGCAAAGA

GTACAAGTGCAAGGTGTCCAGCAAGGGCCTGCCCAGCAGCATCG

AAAAGACCATCAGCAACGCCACCGGCCAGCCCAGGGAACCCCAG

-continued
```
GTGTACACACTGCCCCCTAGCCAGGAAGAGATGACCAAGAACCAG

GTGTCCCTGACATGCCTCGTGAAGGGCTTCTACCCCTCCGATATC

GCCGTGGAATGGGAGAGCAACGGCCAGCCAGAGAACAACTACAA

GACCACCCCCCAGTGCTGGACAGCGACGGCTCATTCTTCCTGTA

CTCCCGGCTGACAGTGGACAAGAGCAGCTGGCAGGAAGGCAACG

TGTTCAGCTGCAGCGTGATGCACGAAGCCCTGCACAACCACTACA

CCCAGAAGTCCCTGAGCCTGTCCCTGGGCAAAATAGAGGGACGAA

TGGACCAGGTATCACATCGGTATCCTCGAATTCAAAGTATCAAAG

TACAATTTACCGAATATAAGAAGGAGAAAGGTTTCATCCTCACTT

CCCAAAAGGAGGATGAAATCATGAAGGTGCAGAACAACTCAGTC

ATCATCAACTGTGATGGGTTTTATCTCATCTCCCTGAAGGGCTAC

TTCTCCCAGGAAGTCAACATTAGCCTTCATTACCAGAAGGATGAG

GAGCCCCTCTTCCAACTGAAGAAGGTCAGGTCTGTCAACTCCTTG

ATGGTGGCCTCTCTGACTTACAAAGACAAAGTCTACTTGAATGTG

ACCACTGACAATACCTCCCTGGATGACTTCCATGTGAATGGCGG

AGAACTGATTCTTATCCATCAAAATCCTGGTGAATTCTGTGTCCTT

TGA.
```

This sequence could be codon optimized to encode a protein with an amino acid sequence:

(SEQ ID NO: 9)
M R W C L L L I W A Q G L R Q A P L A S G M M T G
T I E T T G N I S A E K G G S I I L Q C H L S S T
T A Q V T Q V N W E Q Q D Q L L A I C N A D L G W
H I S P S F K D R V A P G P G L G L T L Q S L T V
N D T G E Y F C I Y H T Y P D G T Y T G R I F L E
V L E S S V A E H G A R F Q I P S K Y G P P C P S
C P A P E F L G G P S V F L F P P K P K D T L M I
S R T P E V T C V V V D V S Q E D P E V Q F N W Y
V D G V E V H N A K T K P R E E Q F N S T Y R V V
S V L T V L H Q D W L S G K E Y K C K V S S K G L
P S S I E K T I S N A T G Q P R E P Q V Y T L P P
S Q E E M T K N Q V S L T C L V K G F Y P S D I A
V E W E S N G Q P E N N Y K T T P P V L D S D G S
F F L Y S R L T V D K S S W Q E G N V F S C S V M
H E A L H N H Y T Q K S L S L S L G K I E G R M D
Q V S H R Y P R I Q S I K V Q F T E Y K K E K G F
I L T S Q K E D E I M K V Q N N S V I I N C D G F
Y L I S L K G Y F S Q E V N I S L H Y Q K D E E P
L F Q L K K V R S V N S L M V A S L T Y K D K V Y
L N V T T D N T S L D D F H V N G G E L I L I H Q
N P G E F C V L Stop.

Another example would include a fusion protein incorporating the extracellular domain of TIM3, linked through an Fc region to human OX40L:

(SEQ ID NO: 10)
```
ATGTTTTCACATCTTCCCTTTGACTGTGTCCTGCTGCTGCTGCTGC

TACTACTTACAAGGTCCTCAGAAGTGGAATACAGAGCGGAGGTCG

GTCAGAATGCCTATCTGCCCTGCTTCTACACCCCAGCCGCCCCAG

GGAACCTCGTGCCCGTCTGCTGGGCAAAGGAGCCTGTCCTGTG

TTTGAATGTGGCAACGTGGTGCTCAGGACTGATGAAAGGGATGTG

AATTATTGGACATCCAGATACTGGCTAAATGGGGATTTCCGCAAAG

GAGATGTGTCCCTGACCATAGAGAATGTGACTCTAGCAGACAGTG

GGATCTACTGCTGCCGGATCCAAATCCCAGGCATAATGAATGATG

AAAAATTTAACCTGAAGTTGGTCATCAAACCAGCCAAGGTCACCCC

TGCACCGACTCGGCAGAGAGACTTCACTGCAGCCTTTCCAAGGAT

GCTTACCACCAGGGGACATGGCCCAGCAGAGACACAGACACTGG

GGAGCCTCCCTGATATAAATCTAACACAAATATCCACATTGGCCAA

TGAGTTACGGGACTCTAGATTGGCCAATGACTTACGGGACTCTGG

AGCAACCATCAGAATAGGCTCTAAGTACGGCCCTCCCTGCCCTAG

CTGTCCCGCCCCTGAATTTCTGGGCGGACCCTCCGTGTTTCTGTT

CCCCCCAAAGCCCAAGGACACCCTGATGATCAGCCGGACCCCCG

AAGTGACCTGTGTGGTGGTGGATGTGTCCCAGGAAGATCCCGAGG

TGCAGTTCAATTGGTACGTGGACGGGGTGGAAGTGCACAACGCCA

AGACCAAGCCCAGAGAGGAACAGTTCAACAGCACCTACCGGGTG

GTGTCTGTGCTGACCGTGCTGCACCAGGATTGGCTGAGCGGCAAA

GAGTACAAGTGCAAGGTGTCCAGCAAGGGCCTGCCCAGCAGCAT

CGAAAAGACCATCAGCAACGCCACCGGCCAGCCCAGGGAACCCC

AGGTGTACACACTGCCCCCTAGCCAGGAAGAGATGACCAAGAACC

AGGTGTCCCTGACATGCCTCGTGAAGGGCTTCTACCCCTCCGATA

TCGCCGTGGAATGGGAGAGCAACGGCCAGCCAGAGAACAACTAC

AAGACCACCCCCCAGTGCTGGACAGCGACGGCTCATTCTTCCTG

TACTCCCGGCTGACAGTGGACAAGAGCAGCTGGCAGGAAGGCAA

CGTGTTCAGCTGCAGCGTGATGCACGAAGCCCTGCACAACCACTA

CACCCAGAAGTCCCTGAGCCTGTCCCTGGGCAAAATAGAGGGACG

AATGGACCAGGTATCACATCGGTATCCTCGAATTCAAAGTATCAA

AGTACAATTTACCGAATATAAGAAGGAGAAAGGTTTCATCCTCAC

TTCCCAAAAGGAGGATGAAATCATGAAGGTGCAGAACAACTCAG

TCATCATCAACTGTGATGGGTTTTATCTCATCTCCCTGAAGGGCT

ACTTCTCCCAGGAAGTCAACATTAGCCTTCATTACCAGAAGGATG

AGGAGCCCCTCTTCCAACTGAAGAAGGTCAGGTCTGTCAACTCC

TTGATGGTGGCCTCTCTGACTTACAAAGACAAAGTCTACTTGAAT

GTGACCACTGACAATACCTCCCTGGATGACTTCCATGTGAATGGC
```

GGAGAACTGATTCTTATCCATCAAAATCCTGGTGAATTCTGTGTC

CTTTGA.

Such a sequence could be codon optimized to encode a protein with an amino acid sequence:

(SEQ ID NO: 11)
M F S H L P F D C V L L L L L L L L T R S S E V E

Y R A E V G Q N A Y L P C F Y T P A A P G N L V P

V C W G K G A C P V F E C G N V V L R T D E R D V

N Y W T S R Y W L N G D F R K G D V S L T I E N V

T L A D S G I Y C C R I Q I P G I M N D E K F N L

K L V I K P A K V T P A P T R Q R D F T A A F P R

M L T T R G H G P A E T Q T L G S L P D I N L T Q

I S T L A N E L R D S R L A N D L R D S G A T I R

I G S K Y G P P C P S C P A P E F L G G P S V F L

F P P K P K D T L M I S R T P E V T C V V V D V S

Q E D P E V Q F N W Y V D G V E V H N A K T K P R

E E Q F N S T Y R V V S V L T V L H Q D W L S G K

E Y K C K V S S K G L P S S I E K T I S N A T G Q

P R E P Q V Y T L P P S Q E E M T K N Q V S L T C

L V K G F Y P S D I A V E W E S N G Q P E N N Y K

T T P P V L D S D G S F F L Y S R L T V D K S S W

Q E G N V F S C S V M H E A L H N H Y T Q K S L S

L S L G K I E G R M D Q V S H R Y P R I Q S I K V

Q F T E Y K K E K G F I L T S Q K E D E I M K V Q

N N S V I I N C D G F Y L I S L K G Y F S Q E V N

I S L H Y Q K D E E P L F Q L K K V R S V N S L M

V A S L T Y K D K V Y L N V T T D N T S L D D F H

V N G G E L I L I H Q N P G E F C V L Stop.

Another example could include the extracellular domain of CD172a adjoined with an Fc linker sequence to the extracellular domain of human OX40L:

(SEQ ID NO: 12)
ATGGAGCCCGCCGGCCCGGCCCCCGGCCGCCTCGGGCCGCTGC

TCTGCCTGCTGCTCGCCGCGTCCTGCGCCTGGTCAGGAGTGGCG

GGTGAGGAGGAGCTGCAGGTGATTCAGCCTGACAAGTCCGTGTTG

GTTGCAGCTGGAGAGACAGCCACTCTGCGCTGCACTGCGACCTCT

CTGATCCCTGTGGGCCCATCCAGTGGTTCAGAGGAGCTGGACCA

GGCCGGGAATTAATCTACAATCAAAAGAAGGCCACTTCCCCCGG

GTAACAACTGTTTCAGACCTCACAAAGAGAAACAACATGGACTTTT

CCATCCGCATCGGTAACATCACCCCAGCAGATGCCGGCACCTACT

ACTGTGTGAAGTTCCGGAAAGGGAGCCCCGATGACGTGGAGTTTA

AGTCTGGAGCAGGCACTGAGCTGTCTGTGCGCGCCAAACCCTCTG

CCCCCGTGGTATCGGGCCCTGCGGCGAGGGCCACACCTCAGCAC

ACAGTGAGCTTCACCTGCGAGTCCCACGGCTTCTCACCCAGAGAC

ATCACCCTGAAATGGTTCAAAAATGGGAATGAGCTCTCAGACTTCC

AGACCAACGTGGACCCCGTAGGAGAGAGCGTGTCCTACAGCATCC

ACAGCACAGCCAAGGTGGTGCTGACCCGCGAGGACGTTCACTCTC

AAGTCATCTGCGAGGTGGCCCACGTCACCTTGCAGGGGACCCT

CTTCGTGGGACTGCCAACTTGTCTGAGACCATCCGAGTTCCACCC

ACCTTGGAGGTTACTCAACAGCCCGTGAGGGCAGAGAACCAGGTG

AATGTCACCTGCCAGGTGAGGAAGTTCTACCCCCAGAGACTACAG

CTGACCTGGTTGGAGAATGGAAACGTGTCCCGGACAGAAACGGCC

TCAACCGTTACAGAGAACAAGGATGGTACCTACAACTGGATGAGC

TGGCTCCTGGTGAATGTATCTGCCCACAGGGATGATGTGAAGCTC

ACCTGCCAGGTGGAGCATGACGGGCAGCCAGCGGTCAGCAAAAG

CCATGACCTGAAGGTCTCAGCCCACCCGAAGGAGCAGGGCTCAAA

TACCGCCGCTGAGAACACTGGATCTAATGAACGGAACATCTATTCT

AAGTACGGCCCTCCCTGCCCTAGCTGTCCCGCCCCTGAATTTCTG

GGCGGACCCTCCGTGTTTCTGTTCCCCCCAAAGCCCAAGGACACC

CTGATGATCAGCCGGACCCCCGAAGTGACCTGTGTGGTGGTGGAT

GTGTCCCAGGAAGATCCCGAGGTGCAGTTCAATTGGTACGTGGAC

GGGGTGGAAGTGCACAACGCCAAGACCAAGCCCAGAGAGGAACA

GTTCAACAGCACCTACCGGGTGGTGTCTGTGCTGACCGTGCTGCA

CCAGGATTGGCTGAGCGGCAAAGAGTACAAGTGCAAGGTGTCCAG

CAAGGGCCTGCCCAGCAGCATCGAAAAGACCATCAGCAACGCCAC

CGGCCAGCCCAGGGAACCCCAGGTGTACACACTGCCCCCTAGCC

AGGAAGAGATGACCAAGAACCAGGTGTCCCTGACATGCCTCGTGA

AGGGCTTCTACCCCTCCGATATCGCCGTGGAATGGGAGAGCAACG

GCCAGCCAGAGAACAACTACAAGACCACCCCCCCAGTGCTGGACA

GCGACGGCTCATTCTTCCTGTACTCCCGGCTGACAGTGGACAAGA

GCAGCTGGCAGGAAGGCAACGTGTTCAGCTGCAGCGTGATGCAC

GAAGCCCTGCACAACCACTACACCCAGAAGTCCCTGAGCCTGTCC

CTGGGCAAAATAGAGGGACGAATGGACCAGGTATCACATCGGTAT

CCTCGAATTCAAAGTATCAAAGTACAATTTACCGAATATAAGAAG

GAGAAAGGTTTCATCCTCACTTCCCAAAAGGAGGATGAAATCAT

GAAGGTGCAGAACAACTCAGTCATCATCAACTGTGATGGGTTTTA

TCTCATCTCCCTGAAGGGCTACTTCTCCCAGGAAGTCAACATTAG

CCTTCATTACCAGAAGGATGAGGAGCCCCTCTTCCAACTGAAGA

AGGTCAGGTCTGTCAACTCCTTGATGGTGGCCTCTCTGACTTACA

AAGACAAAGTCTACTTGAATGTGACCACTGACAATACCTCCCTGG

```
ATGACTTCCATGTGAATGGCGGAGAACTGATTCTTATCCATCAAA
ATCCTGGTGAATTCTGTGTCCTTTGA.
```

Such a sequence could be codon optimized to encode a protein with an amino acid sequence:

(SEQ ID NO: 13)
```
M E P A G P A P G R L G P L L C L L L A A S C A W
S G V A G E E E L Q V I Q P D K S V L V A A G E T
A T L R C T A T S L I P V G P I Q W F R G A G P G
R E L I Y N Q K E G H F P R V T T V S D L T K R N
N M D F S I R I G N I T P A D A G T Y Y C V K F R
K G S P D D V E F K S G A G T E L S V R A K P S A
P V V S G P A A R A T P Q H T V S F T C E S H G F
S P R D I T L K W F K N G N E L S D F Q T N V D P
V G E S V S Y S I H S T A K V V L T R E D V H S Q
V I C E V A H V T L Q G D P L R G T A N L S E T I
R V P P T L E V T Q Q P V R A E N Q V N V T C Q V
R K F Y P Q R L Q L T W L E N G N V S R T E T A S
T V T E N K D G T Y N W M S W L L V N V S A H R D
D V K L T C Q V E H D G Q P A V S K S H D L K V S
A H P K E Q G S N T A A E N T G S N E R N I Y S K
Y G P P C P S C P A P E F L G G P S V F L F P P K
P K D T L M I S R T P E V T C V V V D V S Q E D P
E V Q F N W Y V D G V E V H N A K T K P R E E Q F
N S T Y R V V S V L T V L H Q D W L S G K E Y K C
K V S S K G L P S S I E K T I S N A T G Q P R E P
Q V Y T L P P S Q E E M T K N Q V S L T C L V K G
F Y P S D I A V E W E S N G Q P E N N Y K T T P P
V L D S D G S F F L Y S R L T V D K S S W Q E G N
V F S C S V M H E A L H N H Y T Q K S L S L S L G
K I E G R M D Q V S H R Y P R I Q S I K V Q F T E
Y K K E K G F I L T S Q K E D E I M K V Q N N S V
I I N C D G F Y L I S L K G Y F S Q E V N I S L H
Y Q K D E E P L F Q L K K V R S V N S L M V A S L
T Y K D K V Y L N V T T D N T S L D D F H V N G G
E L I L I H Q N P GE F C V L Stop.
```

Another example could include the extracellular domain of TMIGD2 adjoined with an Fc linker sequence to the extracellular domain of human OX40L:

(SEQ ID NO: 14)
```
ATGGGGTCCCCGGGCATGGTGCTGGGCCTCCTGGTGCAGATCTG
GGCCCTGCAAGAAGCCTCAAGCCTGAGCGTGCAGCAGGGGCCCA
ACTTGCTGCAGGTGAGGCAGGGCAGTCAGGCGACCCTGGTCTGC
CAGGTGGACCAGGCCACAGCCTGGGAACGGCTCCGTGTTAAGTG
GACAAAGGATGGGGCCATCCTGTGTCAACCGTACATCACCAACGG
CAGCCTCAGCCTGGGGGTCTGCGGGCCCCAGGGACGGCTCTCCT
GGCAGGCACCCAGCCATCTCACCCTGCAGCTGGACCCTGTGAGC
CTCAACCAGCGGGGCGTACGTGTGCTGGGCGGCCGTAGAGAT
TCCTGAGTTGGAGGAGGCTGAGGGCAACATAACAAGGCTCTTTGT
GGACCCAGATGACCCCACACAGAACAGAAACCGGATCGCAAGCTT
CCCAGGATCTAAGTACGGCCCTCCCTGCCCTAGCTGTCCCGCCCC
TGAATTTCTGGGCGGACCCTCCGTGTTTCTGTTCCCCCCAAAGCC
CAAGGACACCCTGATGATCAGCCGGACCCCCGAAGTGACCTGTGT
GGTGGTGGATGTGTCCCAGGAAGATCCCGAGGTGCAGTTCAATTG
GTACGTGGACGGGGTGGAAGTGCACAACGCCAAGACCAAGCCCA
GAGAGGAACAGTTCAACAGCACCTACCGGGTGGTGTCTGTGCTGA
CCGTGCTGCACCAGGATTGGCTGAGCGGCAAAGAGTACAAGTGCA
AGGTGTCCAGCAAGGGCCTGCCCAGCAGCATCGAAAAGACCATCA
GCAACGCCACCGGCCAGCCCAGGGAACCCCAGGTGTACACACTG
CCCCCTAGCCAGGAAGAGATGACCAAGAACCAGGTGTCCCTGACA
TGCCTCGTGAAGGGCTTCTACCCCTCCGATATCGCCGTGGAATGG
GAGAGCAACGGCCAGCCAGAGAACAACTACAAGACCACCCCCCC
AGTGCTGGACAGCGACGGCTCATTCTTCCTGTACTCCCGGCTGAC
AGTGGACAAGAGCAGCTGGCAGGAAGGCAACGTGTTCAGCTGCA
GCGTGATGCACGAAGCCCTGCACAACCACTACACCCAGAAGTCCC
TGAGCCTGTCCCTGGGCAAAATAGAGGGACGAATGGACCAGGTAT
CACATCGGTATCCTCGAATTCAAAGTATCAAAGTACAATTTACCG
AATATAAGAAGGAGAAAGGTTTCATCCTCACTTCCCAAAAGGAG
GATGAAATCATGAAGGTGCAGAACAACTCAGTCATCATCAACTGT
GATGGGTTTTATCTCATCTCCCTGAAGGGCTACTTCTCCCAGGAA
GTCAACATTAGCCTTCATTACCAGAAGGATGAGGAGCCCCTCTTC
CAACTGAAGAAGGTCAGGTCTGTCAACTCCTTGATGGTGGCCTCT
CTGACTTACAAAGACAAAGTCTACTTGAATGTGACCACTGACAAT
ACCTCCCTGGATGACTTCCATGTGAATGGCGGAGAACTGATTCTT
ATCCATCAAAATCCTGGTGAATTCTGTGTCCTTTGA.
```

Such a sequence could be codon optimized to encode a protein with an amino acid sequence:

(SEQ ID NO: 15)
```
M G S P G M V L G L L V Q I W A L Q E A S S L S V
Q Q G P N L L Q V R Q G S Q A T L V C Q V D Q A T
A W E R L R V K W T K D G A I L C Q P Y I T N G S
L S L G V C G P Q G R L S W Q A P S H L T L Q L D
```

-continued

```
P V S L N H S G A Y V C W A A V E I P E L E E A E

G N I T R L F V D P D D P T Q N R N R I A S F P G

S K Y G P P C P S C P A P E F L G G P S V F L F P

P K P K D T L M I S R T P E V T C V V V D V S Q E

D P E V Q F N W Y V D G V E V H N A K T K P R E E

Q F N S T Y R V V S V L T V L H Q D W L S G K E Y

K C K V S S K G L P S S I E K T I S N A T G Q P R

E P Q V Y T L P P S Q E E M T K N Q V S L T C L V

K G F Y P S D I A V E W E S N G Q P E N N Y K T T

P P V L D S D G S F F L Y S R L T V D K S S W Q E

G N V F S C S V M H E A L H N H Y T Q K S L S L S

L G K I E G R M D Q V S H R Y P R I Q S I K V Q F

T E Y K K E K G F I L T S Q K E D E I M K V Q N N

S V I I N C D G F Y L I S L K G Y F S Q E V N I S

L H Y Q K D E E P L F Q L K K V R S V N S L M V A

S L T Y K D K V Y L N V T T D N T S L D D F H V N

G G E L I L I H Q N P G E F C V L Stop
```

In various embodiments, the chimeric protein may comprise an amino acid sequence having one or more amino acid mutations relative to any of the protein sequences described herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the chimeric proteins by reference to the genetic code, including taking into account codon degeneracy.

In various embodiments, the chimeric protein comprises a linker. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et. al., (2000), Protein Eng. 13(5):309-312, the entire contents of which are hereby incorporated by reference.

In some embodiments, the linker is a synthetic linker such as PEG.

In other embodiments, the linker is a polypeptide. In some embodiments, the linker is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines).

In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In other embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites.

In various embodiments, the linker comprises an Fc domain of an antibody (e.g., of IgG, IgA, IgD, and IgE, inclusive of subclasses (e.g. IgG1, IgG2, IgG3, and IgG4, and IgA1 and IgA2)). In various embodiments, the linker comprises a hinge-CH2-CH3 Fc domain derived from a human IgG4 antibody. In various embodiments, the linker comprises a hinge-CH2-CH3 Fc domain derived from a human IgG1 antibody. In some embodiments, the Fc domain exhibits increased affinity for and enhanced binding to the neonatal Fc receptor (FcRn). In some embodiments, the Fc domain includes one or more mutations that increases the affinity and enhances binding to FcRn. Without wishing to be bound by theory, it is believed that increased affinity and enhanced binding to FcRn increases the in vivo half-life of the present chimeric proteins.

In some embodiments, the Fc domain linker contains one or more amino acid substitutions at amino acid residue 250, 252, 254, 256, 308, 309, 311, 428, 433 or 434 (in accordance with Kabat numbering), or equivalents thereof. In an embodiment, the amino acid substitution at amino acid residue 250 is a substitution with glutamine. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 308 is a substitution with threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 428 is a substitution with leucine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain linker (e.g., comprising an IgG constant region) comprises one or more mutations such as substitutions at amino acid residue 252, 254, 256, 433, 434, or 436 (in accordance with Kabat numbering). In an embodiment, the IgG constant region includes a triple M252Y/S254T/T256E mutation or YTE mutation. In another embodiment, the IgG constant region includes a triple H433K/N434F/Y436H mutation or KFH mutation. In a further embodiment, the IgG constant region includes an YTE and KFH mutation in combination.

In some embodiments, the modified humanized antibodies of the invention comprise an IgG constant region that contains one or more mutations at amino acid residues 250, 253, 307, 310, 380, 428, 433, 434, and 435. Illustrative mutations include T250Q, M428L, T307A, E380A, I253A, H310A, M428L, H433K, N434A, N434F, N434S, and H435A. In an embodiment, the IgG constant region comprises a M428L/N434S mutation or LS mutation. In another embodiment, the IgG constant region comprises a T250Q/M428L mutation or QL mutation. In another embodiment, the IgG constant region comprises an N434A mutation. In another embodiment, the IgG constant region comprises a T307A/E380A/N434A mutation or AAA mutation. In another embodiment, the IgG constant region comprises an I253A/H310A/H435A mutation or IHH mutation. In another embodiment, the IgG constant region comprises a H433K/N434F mutation. In another embodiment, the IgG constant region comprises a M252Y/S254T/T256E and a H433K/N434F mutation in combination.

Additional exemplary mutations in the IgG constant region are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al. Nature (2014) 514:642-645, Grevys et al. Journal of Immunology. (2015), 194(11):5497-508, and U.S. Pat. No. 7,083,784, the entire contents of which are hereby incorporated by reference.

In some embodiments, the linker has the amino acid sequence of SEQ ID NO: 70, or at least 90%, or 93%, or 95%, or 97%, or 98%, or 99% identity thereto. In various embodiments, mutations are made to SEQ ID No: 70 to increase stability and/or half-life. For instance, in some embodiments, the linker has the amino acid sequence of SEQ ID NO: 71 or 72, or at least 90%, or 93%, or 95%, or 97%, or 98%, or 99% identity thereto. An illustrative Fc stabilizing mutant is S228P. Illustrative Fc half-life extending mutants are T250Q, M428L, V308T, L309P, and Q311S and the present linkers may comprise 1, or 2, or 3, or 4, or 5 of these mutants.

Further, one or more joining linkers may be employed to connect the present IgG linkers (e.g. one or SEQ ID NOs: 70, 71, or 71, or at least 90%, or 93%, or 95%, or 97%, or 98%, or 99% identity thereto) and the extracellular domains. For example, any one of SEQ ID NO: 73, SEQ ID NO: 74, SEQ ID NO: 75, SEQ ID NO: 76, SEQ ID NO: 77, SEQ ID NO: 78, or variants thereof may connect an extracellular domain as described herein and a linker as described herein. Optionally, any one of SEQ ID NO: 73, SEQ ID NO: 74, SEQ ID NO: 75, SEQ ID NO: 76, SEQ ID NO: 77, SEQ ID NO: 78, or variants thereof are displaced between an extracellular domain as described herein and a linker as described herein.

Additional illustrative linkers include, but are not limited to, linkers having the sequence LE, GGGGS (SEQ ID NO: 23), (GGGGS)$_n$ (n=1-4), (Gly)$_8$, (Gly)$_6$, (EAAAK)$_n$ (n=1-3) (SEQ ID NO: 24), A(EAAAK)$_n$A (n=2-5) (SEQ ID NO: 25), AEAAAKEAAAKA (SEQ ID NO: 26), A(EAAAK)$_4$ALEA (EAAAK)$_4$A (SEQ ID NO: 27), PAPAP (SEQ ID NO: 28), KESGSVSSEQLAQFRSLD (SEQ ID NO: 29), EGKSSGSGSESKST (SEQ ID NO: 30), GSAGSAAGS-GEF (SEQ ID NO:31), and (XP)$_n$, with X designating any amino acid, e.g., Ala, Lys, or Glu.

In various embodiments, the linker may be functional. For example, without limitation, the linker may function to improve the folding and/or stability, improve the expression, improve the pharmacokinetics, and/or improve the bioactivity of the present chimeric protein. In another example, the linker may function to target the chimeric protein to a particular cell type or location.

In various embodiments, the present chimeric proteins are capable of, and can be used in methods comprising, promoting immune activation (e.g. against tumors). In various embodiments, the present chimeric proteins are capable of, and can be used in methods comprising, suppressing immune inhibition (e.g. that allows tumors to survive). In various embodiments, the present chimeric proteins provide improved immune activation and/or improved suppression of immune inhibition due to the proximity of signaling that is provided by the chimeric nature of the constructs.

In various embodiments, the present chimeric proteins are capable of, or can be used in methods comprising, modulating the amplitude of an immune response, e.g. modulating the level of effector output. In some embodiments, e.g. when used for the treatment of cancer, the present chimeric proteins alter the extent of immune stimulation as compared to immune inhibition to increase the amplitude of a T cell response, including, without limitation, stimulating increased levels of cytokine production, proliferation or target killing potential.

Figure 4:
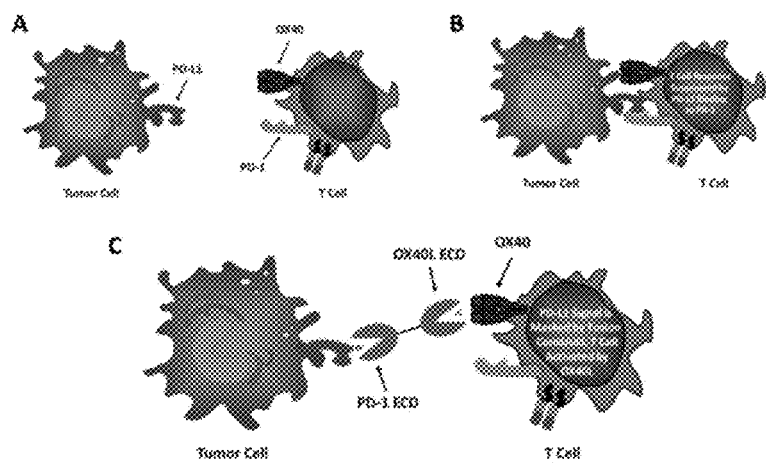
FIG. 4 shows that tumor cells may express PD-L1 on the cell surface (panel A), which can bind to PD-1 expressed by a T cell (panel B). This interaction suppresses activation of T cells. A fusion protein of the extracellular domain of PD-1, adjoined to the extracellular domain of OX40L may bind to PD-L1 on the surface of a tumor cell, preventing binding to PD-1 on the surface of a T cell (panel C). The fusion protein may then 'dangle' from the surface of the tumor cell, and the OX40L portion of the fusion protein may then bind to OX40 expressed on the surface of the T cell. This would result in replacement of an inhibitory PD-L1 signal with a co-stimulatory OX40L signal to enhance the anti-tumor activity of T cells.

In various embodiments the present chimeric proteins, in some embodiments are capable of, or find use in methods involving, masking an inhibitory ligand on the surface of a tumor cell and replacing that immune inhibitory ligand with an immune stimulatory ligand (see, e.g. FIG. 4). For example, a chimeric protein construct comprising (i) the extracellular domain of PD-1 and (ii) extracellular domain of OX40L, allows for the disruption of an inhibitory PD-L1 signal and replacing it with a stimulating OX40L. Accordingly, the present chimeric proteins, in some embodiments are capable of, or find use in methods involving, reducing or eliminating an inhibitory immune signal and/or increasing or activating an immune stimulatory signal. For example, a tumor cell bearing an inhibitory signal (and thus evading an immune response) may be substituted for a positive signal binding on a T cell that can then attack a tumor cell. Accordingly, in some embodiments, an inhibitory immune signal is masked by the present constructs and a stimulatory immune signal is activated. Such beneficial properties are enhanced by the single construct approach of the present chimeric proteins. For instance, the signal replacement can be effected nearly simultaneously and the signal replacement is tailored to be local at a site of clinical importance (e.g. the tumor microenvironment). Further embodiments apply the same principle to other chimeric protein constructs, such as, for example, (i) the extracellular domain of PD-1 and (ii) extracellular domain of GITRL; (i) the extracellular domain of BTLA and (ii) extracellular domain of OX40L; (i) the extracellular domain of TIGIT and (ii) extracellular domain of OX40L; (i) the extracellular domain of TIM3 and (ii) extracellular domain of OX40L; and (i) the extracellular domain of CD172a and (ii) extracellular domain of CD40L; and (i) the extracellular domain of CD115 and (ii) extracellular domain of CD40L; and (i) the extracellular domain of TIM3 and (ii) extracellular domain of OX40L; and (i) the extracellular domain of TIGIT and (ii) extracellular domain of OX40L; among others.

In various embodiments, the present chimeric proteins are capable of, or find use in methods comprising, stimulating or enhancing the binding of immune stimulatory receptor/ligand pairs. Illustrative T cell costimulatory receptors and their ligands include OX-40:OX40-L, CD27:CD70, CD30:CD30-L, CD40:CD40-L; CD137:CD137-L, HVEM:LIGHT, GITR:GITR-L, TNFRSF25:TL1A, DR5:TRAIL, and BTLA:HVEM. In various embodiments, the present chimeric proteins are capable of, or find use in methods comprising, inhibiting or reducing the binding of immune inhibitory receptor/ligand pairs. Illustrative T cell coinhibitory receptors and their ligands include, for example, CTLA-4:CD80/CD86, PD-1:PD-L1/PD-L2, BTLA:HVEM, TIM-3:galectin-9/phosphatidylserine, TIGIT/CD155 or CD112, VISTA/VSIG8, CD172a/CD47, B7H3R/B7H3, B7H4R/B7H4, CD244/CD48, TMIGD2/HHLA2, among others.

In various embodiments, the present chimeric protein blocks, reduces and/or inhibits PD-1 and PD-L1 or PD-L2 and/or the binding of PD-1 with PD-L1 or PD-L2. In various embodiments, the present chimeric protein blocks, reduces and/or inhibits the activity of CTLA-4 and/or the binding of CTLA-4 with one or more of AP2M1, CD80, CD86, SHP-2, and PPP2R5A. In various embodiments, the present chimeric protein increases and/or stimulates GITR and/or the binding of GITR with one or more of GITR ligand. In various embodiments, the present chimeric protein increases and/or stimulates OX40 and/or the binding of OX40 with one or more of OX40 ligand.

In other embodiments, the present chimeric proteins are capable of, or find use in methods involving, enhancing, restoring, promoting and/or stimulating immune modulation. In some embodiments, the present chimeric proteins described herein, restore, promote and/or stimulate the activity or activation of one or more immune cells against tumor cells including, but not limited to: T cells, cytotoxic T lymphocytes, T helper cells, natural killer (NK) cells, natural killer T (NKT) cells, anti-tumor macrophages (e.g. M1 macrophages), B cells, and dendritic cells. In some embodiments, the present chimeric proteins enhance, restore, promote and/or stimulate the activity and/or activation of T cells, including, by way of a non-limiting example, activating and/or stimulating one or more T-cell intrinsic signals, including a pro-survival signal; an autocrine or paracrine growth signal; a p38 MAPK-, ERK-, STAT-, JAK-, AKT- or PI3K-mediated signal; an anti-apoptotic signal; and/or a signal promoting and/or necessary for one or more of: proinflammatory cytokine production or T cell migration or T cell tumor infiltration.

In some embodiments, the present chimeric proteins are capable of, or find use in methods involving, causing an increase of one or more of T cells (including without limitation cytotoxic T lymphocytes, T helper cells, natural killer T (NKT) cells), B cells, natural killer (NK) cells, natural killer T (NKT) cells, dendritic cells, monocytes, and macrophages (e.g. one or more of M1 and M2) into a tumor or the tumor microenvironment. In some embodiments, the present chimeric proteins are capable of, or find use in methods involving, inhibiting and/or causing a decrease in recruitment of immunosuppressive cells (e.g. myeloid-derived suppressor cells (MDSCs), regulatory T cells (Tregs), tumor associated neutrophils (TANs), M2 macrophages, and tumor associated macrophages (TAMs)) to the tumor and/or tumor microenvironment (TME). In some embodiments, the present therapies may alter the ratio of M1 versus M2 macrophages in the tumor site and/or TME to favor M1 macrophages.

In various embodiments, the present chimeric proteins are capable of, and can be used in methods comprising, inhibiting and/or reducing T cell inactivation and/or immune tolerance to a tumor, comprising administering an effective amount of a chimeric protein described herein to a subject. In some embodiments, the present chimeric proteins are able to increase the serum levels of various cytokines including, but not limited to, one or more of IFNγ, TNFα, IL-2, IL-4, IL-5, IL-6, IL-9, IL-10, IL-13, IL-17A, IL-17F, and IL-22. In some embodiments, the present chimeric proteins are capable of enhancing IL-2, IL-4, IL-5, IL-10, IL-13, IL-17A, IL-22, TNFα or IFNγ in the serum of a treated subject (see, e.g. FIG. 11, panel J). Detection of such a cytokine response may provide a method to determine the optimal dosing regimen for the indicated chimeric fusion protein (see, e.g. FIG. 11, panel K).

In various embodiments, the present chimeric proteins inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion. Accordingly, a pro-tumor T cell refers to a state of T cell dysfunction that arises during many chronic infections and cancer. This dysfunction is defined by poor proliferative and/or effector functions, sustained expression of inhibitory receptors and a transcriptional state distinct from that of functional effector or memory T cells. Exhaustion prevents optimal control of infection and tumors. In addition, an anti-tumor CD8+ and/or CD4+ T cell refers to T cells that can mount an immune response to a tumor. Illustrative pro-tumor T cells include, but are not limited to, Tregs, CD4+ and/or CD8+ T cells expressing one or more checkpoint inhibitory receptors, Th2 cells and Th17 cells. Checkpoint inhibitory receptors refers to receptors (e.g. CTLA-4, B7-H3, B7-H4, TIM-3) expressed on immune cells that prevent or inhibit uncontrolled immune responses.

In various embodiments, the present chimeric proteins capable of, and can be used in methods comprising, increasing a ratio of effector T cells to regulatory T cells. Illustrative effector T cells include ICOS$^+$ effector T cells; cytotoxic T cells (e.g. αβ TCR, CD3$^+$, CD8$^+$, CD45RO$^+$); CD4$^+$ effector T cells (e.g. αβ TCR, CD3$^+$, CD4$^+$, CCR7$^+$, CD62Lhi, IL$^-$7R/CD127$^+$); CD8$^+$ effector T cells (e.g. αβ TCR, CD3$^+$, CD8$^+$, CCR7$^+$, CD62Lhi, IL$^-$7R/CD127$^+$); effector memory T cells (e.g. CD62Llow, CD44$^+$, TCR, CD3$^+$≤, IL$^-$7R/CD127$^+$, IL-15R$^+$, CCR7low); central memory T cells (e.g. CCR7$^+$, CD62L$^+$, CD27$^+$; or CCR7hi, CD44$^+$, CD62Lhi, TCR, CD3$^+$, IL-7R/CD127$^+$, IL-15R$^+$); CD62L$^+$ effector T cells; CD8$^+$ effector memory T cells (TEM) including early effector memory T cells (CD27$^+$ CD62L$^-$) and late effector memory T cells (CD27$^-$CD62L$^-$) (TemE and TemL, respectively); CD127($^+$)CD25(low/−) effector T cells; CD127($^-$) CD25($^-$) effector T cells; CD8$^+$ stem cell memory effector cells (TSCM) (e.g. CD44(low)CD62L(high)CD122(high) sca($^+$)); TH1 effector T-cells (e.g. CXCR3$^+$, CXCR6$^+$ and CCR5$^+$; or αβ TCR, CD3$^+$, CD4$^+$, IL-12R$^+$, IFNγR$^+$, CXCR3$^+$), TH2 effector T cells (e.g. CCR3$^+$, CCR4$^+$ and CCR8$^+$; or αβ TCR, CD3$^+$, CD4$^+$, IL-4R$^+$, IL-33R$^+$, CCR4$^+$, IL-17RB$^+$, CRTH2$^+$); TH9 effector T cells (e.g. αβ TCR, CD3$^+$, CD4$^+$); TH17 effector T cells (e.g. αβ TCR, CD3$^+$, CD4$^+$, IL-23R$^+$, CCR6$^+$, IL-1R$^+$); CD4$^+$CD45RO$^+$ CCR7$^+$ effector T cells, CD4$^+$CD45RO$^+$CCR7($^-$) effector T cells; and effector T cells secreting IL-2, IL-4 and/or IFN-γ. Illustrative regulatory T cells include ICOS$^+$ regulatory T cells, CD4$^+$CD25$^+$FOXP3$^+$ regulatory T cells, CD4$^+$CD25$^+$ regulatory T cells, CD4$^+$CD25$^-$ regulatory T cells, CD4$^+$ CD25high regulatory T cells, TIM-3$^+$PD-1$^+$ regulatory T cells, lymphocyte activation gene-3 (LAG-3)$^+$ regulatory T cells, CTLA-4/CD152$^+$ regulatory T cells, neuropilin-1 (Nrp-1)$^+$ regulatory T cells, CCR4$^+$CCR8$^+$ regulatory T cells, CD62L (L-selectin)$^+$ regulatory T cells, CD45RBlow regulatory T cells, CD127low regulatory T cells, LRRC32/ GARP$^+$ regulatory T cells, CD39$^+$ regulatory T cells, GITR$^+$ regulatory T cells, LAP$^+$ regulatory T cells, 1B11$^+$ regulatory T cells, BTLA$^+$ regulatory T cells, type 1 regulatory T cells (Tr1 cells), T helper type 3 (Th3) cells, regulatory cell of natural killer T cell phenotype (NKTregs), CD8$^+$ regulatory T cells, CD8$^+$CD28$^-$regulatory T cells and/or regulatory T-cells secreting IL-10, IL-35, TGF-β, TNF-α, Galectin-1, IFN-γ and/or MCP1.

In various embodiments, the present chimeric proteins are capable of, and can be used in methods comprising, transiently stimulating effector T cells for no longer than about 12 hours, about 24 hours, about 48 hours, about 72 hours or about 96 hours or about 1 week or about 2 weeks. In various embodiments, the present chimeric proteins are capable of, and can be used in methods comprising, transiently depleting or inhibiting regulatory T cells for no longer than about 12 hours, about 24 hours, about 48 hours, about 72 hours or about 96 hours or about 1 week or about 2 weeks. In various embodiments, the transient stimulation of effector T cells and/or transient depletion or inhibition of regulatory T cells occurs substantially in a patient's bloodstream or in a particular tissue/location including lymphoid tissues such as for example, the bone marrow, lymph-node, spleen, thymus, mucosa-associated lymphoid tissue (MALT), non-lymphoid tissues, or in the tumor microenvironment.

In various embodiments, the present chimeric proteins provide advantages including, without limitation, ease of use and ease of production. This is because two distinct immunotherapy agents are combined into a single product which allows for a single manufacturing process instead of two independent manufacturing processes. In addition, administration of a single agent instead of two separate agents allows for easier administration and greater patient compliance. Further, in contrast to, for example, monoclonal antibodies, which are large multimeric proteins containing numerous disulfide bonds and post-translational modifications such as glycosylation, the present chimeric proteins are easier and more cost effective to manufacture.

In various embodiments, the present chimeric protein is produceable in a mammalian host cell as a secretable and fully functional single polypeptide chain (see, e.g., FIG. 13, panel A, FIG. 17, panels E-H, FIG. 17, panels N-S).

In various embodiments, the present chimeric protein unexpectedly provides binding of the extracellular domain components to their respective binding partners with slow off rates (Kd or $K_{off}$). In some embodiments, this provides an unexpectedly long interaction of the receptor to ligand and vice versa. Such an effect allows for a sustained negative signal masking effect (see, e.g., FIG. 14, FIG. 17, panels I-M). Further, in some embodiments, this delivers a longer positive signal effect, e.g. to allow an effector cell to be adequately stimulated for an anti-tumor effect. For example, the present chimeric protein, e.g. via the long off rate binding allows sufficient signal transmission to provide T cell proliferation and allow for anti-tumor attack. By way of further example, the present chimeric protein, e.g. via the long off rate binding allows sufficient signal transmission to provide release of stimulatory signals, such as, for example, cytokines Also. The stable synapse of cells promoted by the present agents (e.g. a tumor cell bearing negative signals and a T cell which could attack the tumor) provides spatial orientation to favor tumor reduction—such as positioning the T cells to attack tumor cells and/or sterically preventing the tumor cell from delivering negative signals, including negative signals beyond those masked by the chimeric protein of the invention.

In some embodiments, this provides longer on-target (e.g. intra-tumoral) half-life ($t_{1/2}$) as compared to serum $t_{1/2}$ of the chimeric proteins. Such properties could have the combined advantage of reducing off-target toxicities associated with systemic distribution of the chimeric proteins (see, e.g., FIG. 14, panels M-O).

Further, in various embodiments, the present chimeric proteins provide synergistic therapeutic effects as it allows for improved site-specific interplay of two immunotherapy agents. In some embodiments, the present chimeric proteins provide the potential for reducing off-site and/or systemic toxicity.

Diseases; Methods of Treatment, and Patient Selections

In various embodiments, the present invention pertains to cancers and/or tumors; for example, the treatment or prevention of cancers and/or tumors. As described elsewhere herein, the treatment of cancer may involve in various embodiments, modulating the immune system with the present chimeric proteins to favor immune stimulation over immune inhibition.

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g. virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the chimeric protein is used to treat a subject that has a treatment-refractory cancer. In some embodiments, the chimeric protein is used to treat a subject that is refractory to one or more immune-modulating agents. For example, in some embodiments, the chimeric protein is used to treat a subject that presents no response to treatment, or even progress, after 12 weeks or so of treatment. For instance, in some embodiments, the subject is refractory to a PD-1 and/or PD-L1 and/or PD-L2 agent, including, for example, nivolumab (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), Ibrutinib (PHARMACYCLICS/ABBVIE), atezolizumab (TECENTRIQ, GENENTECH), and/or MPDL328OA (ROCHE)-refractory patients. For instance, in some embodiments, the subject is refractory to an anti-CTLA-4 agent, e.g. ipilimumab (YERVOY)-refractory patients (e.g. melanoma patients). Accordingly, in various embodiments the present invention provides methods of cancer treatment that rescue patients that are non-responsive to various therapies, including monotherapy of one or more immune-modulating agents.

In some embodiments, the present methods provide treatment with the chimeric protein in a patient who is refractory to an additional agent, such "additional agents" being described elsewhere herein, inclusive, without limitation, of the various chemotherapeutic agents described herein.

In some aspects, the present chimeric agents are used to eliminate intracellular pathogens. In some aspects, the present chimeric agents are used to treat one or more infections. In some embodiments, the present chimeric proteins are used in methods of treating viral infections (including, for example, HIV and HCV), parasitic infections (including, for example, malaria), and bacterial infections. In various embodiments, the infections induce immunosuppression. For example, HIV infections often result in immunosuppression in the infected subjects. Accordingly, as described elsewhere herein, the treatment of such infections may involve, in various embodiments, modulating the immune system with the present chimeric proteins to favor immune stimulation over immune inhibition. Alternatively, the present invention provides methods for treating infections that induce immunoactivation. For example, intestinal helminth infections have been associated with chronic immune activation. In these embodiments, the treatment of such infections may involve modulating the immune system with the present chimeric proteins to favor immune inhibition over immune stimulation.

In various embodiments, the present invention provides methods of treating viral infections including, without limitation, acute or chronic viral infections, for example, of the respiratory tract, of papilloma virus infections, of herpes simplex virus (HSV) infection, of human immunodeficiency virus (HIV) infection, and of viral infection of internal organs such as infection with hepatitis viruses. In some embodiments, the viral infection is caused by a virus of family Flaviviridae. In some embodiments, the virus of family Flaviviridae is selected from Yellow Fever Virus, West Nile virus, Dengue virus, Japanese Encephalitis Virus, St. Louis Encephalitis Virus, and Hepatitis C Virus. In other embodiments, the viral infection is caused by a virus of family Picornaviridae, e.g., poliovirus, rhinovirus, coxsackievirus. In other embodiments, the viral infection is caused by a member of Orthomyxoviridae, e.g., an influenza virus. In other embodiments, the viral infection is caused by a member of Retroviridae, e.g., a lentivirus. In other embodiments, the viral infection is caused by a member of Paramyxoviridae, e.g., respiratory syncytial virus, a human parainfluenza virus, rubulavirus (e.g., mumps virus), measles virus, and human metapneumovirus. In other embodiments, the viral infection is caused by a member of Bunyaviridae, e.g., hantavirus. In other embodiments, the viral infection is caused by a member of Reoviridae, e.g., a rotavirus.

In various embodiments, the present invention provides methods of treating parasitic infections such as protozoan or helminths infections. In some embodiments, the parasitic infection is by a protozoan parasite. In some embodiments, the oritiziab parasite is selected from intestinal protozoa, tissue protozoa, or blood protozoa. Illustrative protozoan parasites include, but are not limited to, *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis*, and *Histomonas meleagridis*. In some embodiments, the parasitic infection is by a helminthic parasite such as nematodes (e.g., Adenophorea). In some embodiments, the parasite is selected from Secementea (e.g., *Trichuris trichiura, Ascaris lumbricoides, Enterobius vermicularis, Ancylostoma duodenale, Necator americanus, Strongyloides stercoralis, Wuchereria bancrofti, Dracunculus medinensis*). In some embodiments, the parasite is selected from trematodes (e.g. blood flukes, liver flukes, intestinal flukes, and lung flukes). In some embodiments, the parasite is selected from: *Schistosoma mansoni, Schistosoma haematobium, Schistosoma japonicum, Fasciola hepatica, Fasciola gigantica, Heterophyes heterophyes, Paragonimus westermani*. In some embodiments, the parasite is selected from cestodes (e.g., *Taenia solium, Taenia saginata, Hymenolepis nana, Echinococcus granulosus*).

In various embodiments, the present invention provides methods of treating bacterial infections. In various embodiments, the bacterial infection is by a gram-positive bacteria, gram-negative bacteria, aerobic and/or anaerobic bacteria. In various embodiments, the bacteria is selected from, but not limited to, *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms. In some embodiments, the bacteria is selected from, but not limited to, *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyti-* cus, *Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus subsp. hyicus, Staphylococcus haemolyticus, Staphylococcus hominis,* or *Staphylococcus saccharolyticus.*

In some aspects, the present chimeric agents are used to treat one or more autoimmune diseases or disorders. In various embodiments, the treatment of an autoimmune disease or disorder may involve modulating the immune system with the present chimeric proteins to favor immune inhibition over immune stimulation. Illustrative autoimmune diseases or disorders treatable with the present chimeric proteins include those in which the body's own antigens become targets for an immune response, such as, for example, rheumatoid arthritis, systemic lupus erythematosus, diabetes mellitus, ankylosing spondylitis, Sjögren's syndrome, inflammatory bowel diseases (e.g. colitis ulcerosa, Crohn's disease), multiple sclerosis, sarcoidosis, psoriasis, Grave's disease, Hashimoto's thyroiditis, psoriasis, hypersensitivity reactions (e.g., allergies, hay fever, asthma, and acute edema cause type I hypersensitivity reactions), and vasculitis.

In still another other aspect, the present invention is directed toward methods of treating and preventing T cell-mediated diseases and disorders, such as, but not limited to diseases or disorders described elsewhere herein and inflammatory disease or disorder, graft-versus-host disease (GVHD), transplant rejection, and T cell proliferative disorder. Specific examples of type I ECD domains with utility in this method of use include but are not limited to: TNFRSF1b, BTNL2, PD-L1, PD-L2, CTLA-4, B7-H3, B7-H4, CD40, OX40, CD137, among others.

In some aspects, the present chimeric agents are used in methods of activating a T cell, e.g. via the extracellular domain having an immune stimulatory signal.

In some aspects, the present chimeric agents are used in methods of preventing the cellular transmission of an immunosuppressive signal.

Combination Therapies and Conjugation

In some embodiments, the invention provides for chimeric proteins and methods that further comprise administering an additional agent to a subject. In some embodiments, the invention pertains to co-administration and/or co-formulation. Any of the compositions described herein may be co-formulated and/or co-administered.

In some embodiments, any chimeric protein described herein acts synergistically when co-administered with another agent and is administered at doses that are lower than the doses commonly employed when such agents are used as monotherapy. In various embodiments, any agent referenced herein may be used in combination with any of the chimeric proteins described herein.

In some embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In various embodiments, inclusive of, without limitation, cancer applications, the present additional agent is one or more immune-modulating agents selected from an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), atezolizumab (TECENTRIQ, GENENTECH), MPDL328OA (ROCHE)), an agent that increases and/or stimulates CD137 (4-1BB) and/or the binding of CD137 (4-1BB) with one or more of 4-1BB ligand (by way of non-limiting example, urelumab (BMS-663513 and anti-4-1BB antibody), and an agent that blocks, reduces and/or inhibits the activity of CTLA-4 and/or the binding of CTLA-4 with one or more of AP2M1, CD80, CD86, SHP-2, and PPP2R5A and/or the binding of OX40 with OX40L (by way of non-limiting example GBR 830 (GLENMARK), MEDI6469 (MEDIMMUNE).

In some embodiments, inclusive of, without limitation, infectious disease applications, the present invention pertains to anti-infectives as additional agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmune applications, the additional agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin).

In some embodiments, the chimeric proteins (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids. In still other embodiments, the chimeric proteins (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The chimeric proteins (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Formulations

The chimeric proteins (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In some embodiments, the compositions described herein are in the form of a pharmaceutically acceptable salt.

Further, any chimeric protein (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In some embodiments, the compositions described herein are resuspended in a saline buffer (including, without limitation TBS, PBS, and the like).

In various embodiments, the chimeric proteins may by conjugated and/or fused with another agent to extend half-life or otherwise improve pharmacodynamic and pharmacokinetic properties. In some embodiments, the chimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In various embodiments, each of the individual chimeric proteins is fused to one or more of the agents described in BioDrugs (2015) 29:215-239, the entire contents of which are hereby incorporated by reference.

Administration, Dosing, and Treatment Regimens

The present invention includes the described chimeric protein (and/or additional agents) in various formulations.

Any chimeric protein (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the formulations comprising the chimeric protein (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the chimeric protein (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, any chimeric protein (and/or additional agents) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. In most instances, administration results in the release of any agent described herein into the bloodstream.

Any chimeric protein (and/or additional agents) described herein can be administered orally. Such chimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment. In one embodiment, for instance in the treatment of cancer, the chimeric protein (and/or additional agents) are administered in the tumor microenvironment (e.g. cells, molecules, extracellular matrix and/or blood vessels that surround and/or feed a tumor cell, inclusive of, for example, tumor vasculature; tumor-infiltrating lymphocytes; fibroblast reticular cells;

endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor or lymph node and/or targeted to the tumor microenvironment or lymph node. In various embodiments, for instance in the treatment of cancer, the chimeric protein (and/or additional agents) are administered intratumorally.

In the various embodiments, the present chimeric protein allows for a dual effect that provides less side effects than are seen in conventional immunotherapy (e.g. treatments with one or more of OPDIVO, KEYTRUDA, YERVOY, and TECENTRIQ). For example, the present chimeric proteins reduce or prevent commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease. Further, the present local administration, e.g. intratumorally, obviate adverse event seen with standard systemic administration, e.g. IV infusions, as are used with conventional immunotherapy (e.g. treatments with one or more of OPDIVO, KEYTRUDA, YERVOY, and TECENTRIQ).

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The dosage of any chimeric protein (and/or additional agents) described herein as well as the dosing schedule can depend on various parameters, including, but not limited to, the disease being treated, the subject's general health, and the administering physician's discretion. Any chimeric protein described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof. In various embodiments any chimeric protein and additional agent described herein are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart.

The dosage of any chimeric protein (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

For administration of any chimeric protein (and/or additional agents) described herein by parenteral injection, the dosage is normally 0.1 mg to 250 mg per day, 1 mg to 20 mg per day, or 3 mg to 5 mg per day. Injections may be given up to four times daily. Generally, when orally or parenterally administered, the dosage of any agent described herein is normally 0.1 mg to 1500 mg per day, or 0.5 mg to 10 mg per day, or 0.5 mg to 5 mg per day. A dosage of up to 3000 mg per day can be administered.

In another embodiment, delivery can be in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989).

Any chimeric protein (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any chimeric protein (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any chimeric protein (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any chimeric protein (and/or additional agents) described herein can be administered in a single daily dose, or the total daily dosage can be administered in divided doses of two, three or four times daily. Furthermore, any chimeric protein (and/or additional agents) described herein can be administered continuously rather than intermittently throughout the dosage regimen.

Cells and Nucleic Acids

In various embodiments, the present invention provides an expression vector, comprising a nucleic acid encoding the chimeric protein described herein. In various embodiments, the expression vector comprises DNA or RNA. In various embodiments, the expression vector is a mammalian expression vector.

Both prokaryotic and eukaryotic vectors can be used for expression of the chimeric protein. Prokaryotic vectors include constructs based on $E.\ coli$ sequences (see, e.g., Makrides, $Microbiol\ Rev$ 1996, 60:512-538). Non-limiting examples of regulatory regions that can be used for expression in $E.\ coli$ include lac, trp, Ipp, phoA, recA, tac, T3, T7 and $\lambda P_L$. Non-limiting examples of prokaryotic expression vectors may include the $\lambda$gt vector series such as $\lambda$gt11 (Huynh et al., in "DNA Cloning Techniques, Vol. I: A Practical Approach," 1984, (D. Glover, ed.), pp. 49-78, IRL Press, Oxford), and the pET vector series (Studier et al., $Methods\ Enzymol$ 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the chimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., $Cancer\ Res$ 1989, 49:2735-42; and Taylor et al., $Mol\ Cell\ Biol$ 1990, 10:165-75). Heat shock promoters or stress promoters also may be advantageous for driving expression of the fusion proteins in recombinant host cells.

In some embodiments, expression vectors of the invention comprise a nucleic acid encoding the chimeric proteins (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In an embodiment, the cell is a tumor cell. In another embodiment, the cell is a non-tumor cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In an embodiment, the present invention contemplates the use of inducible promoters capable of effecting high level of expression transiently in response to a cue. For example, when in the proximity of a tumor cell, a cell transformed with an expression vector for the chimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences encoding the chimeric fusion proteins including CRISPR/CAS9, zinc finger, TALEN, and meganuclease gene-editing technologies.

In one aspect, the invention provides expression vectors for the expression of the chimeric proteins (and/or additional agents) that are viral vectors. Many viral vectors useful for gene therapy are known (see, e.g., Lundstrom, Trends Biotechnol., 21: 1 17, 122, 2003. Illustrative viral vectors include those selected from Antiviruses (LV), retroviruses (RV), adenoviruses (AV), adeno-associated viruses (AAV), and α viruses, though other viral vectors may also be used. For in vivo uses, viral vectors that do not integrate into the host genome are suitable for use, such as α viruses and adenoviruses. Illustrative types of α viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In one embodiment, the invention provides methods of transducing a human cell in vivo, comprising contacting a solid tumor in vivo with a viral vector of the invention.

In various embodiments, the present invention provides a host cell, comprising the expression vector comprising the chimeric protein described herein.

Expression vectors can be introduced into host cells for producing the present chimeric proteins. Cells may be cultured in vitro or genetically engineered, for example. Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); DG44 CHO cells, CHO-K1 cells, mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the fusion proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC#2 and SCLC#7.

Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production of the present chimeric proteins in vitro, ex vivo, and/or in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, fetal liver, etc. The choice of cell type depends on the type of tumor or infectious disease being treated or prevented, and can be determined by one of skill in the art.

Subjects and/or Animals

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein. The invention will be further described in the following example, which does not limit the scope of the invention described in the claims.

EXAMPLES

Example 1. Construction and Characterization of Mouse PD-1-Fc-OX40L Construct

Figure 5:
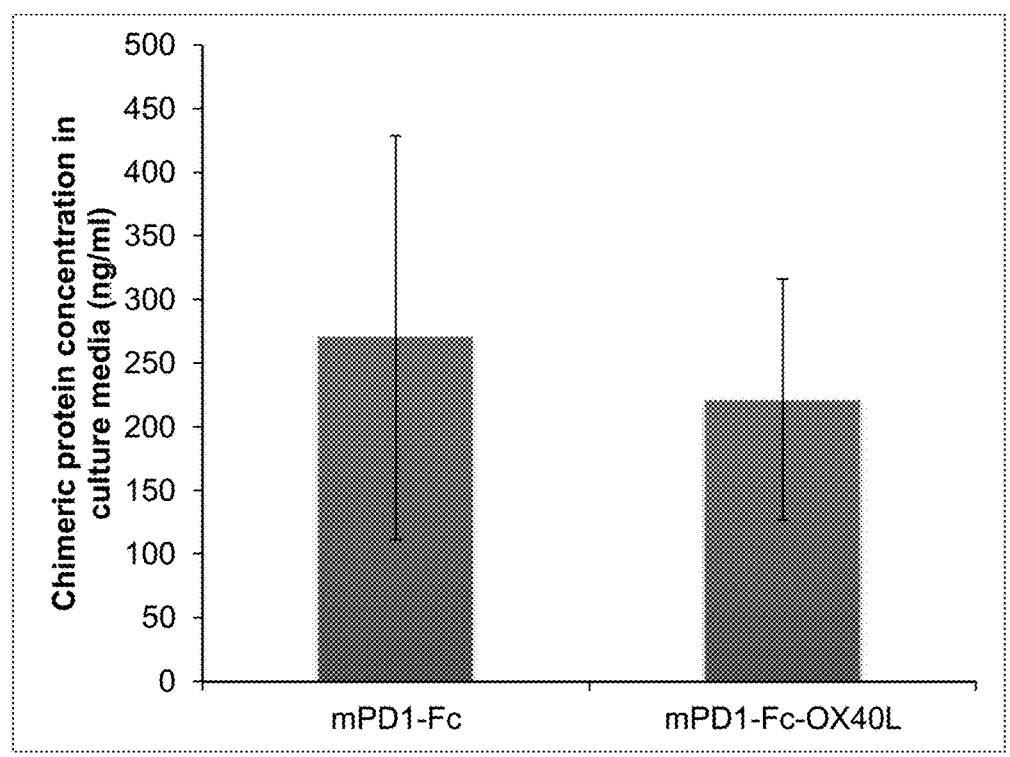
FIG. 5 shows the expression of chimeric mouse (m) PD-1-Fc and PD-1-Fc-OX40 ligand (L) from CHO-K1 cells detected using a mouse IgG capture and anti-mIgG detection ELISA assay.

A chimeric mouse PD-1-Fc-OX40L construct was generated and its expression in CHO-K1 cells was verified using a mouse IgG capture ELISA assay (here, the Fc is derived from IgG1). Specifically, CHO-K1 cells were stably nucleofected with pVITRO2-GS-hygro or pcDNA3.4 vectors expressing either the mouse extracellular domain (ECD) of PD-1 fused to Fc (mPD-1-Fc) or mPD-1-Fc fused to the ECD of OX40L (mPD-1-Fc-OX40L). Antibiotic-resistant single cell clones were isolated via limiting dilution. The concentration of each chimeric protein secreted into the culture media was determined by a mIgG capture ELISA as shown in FIG. 5.

Figure 6:
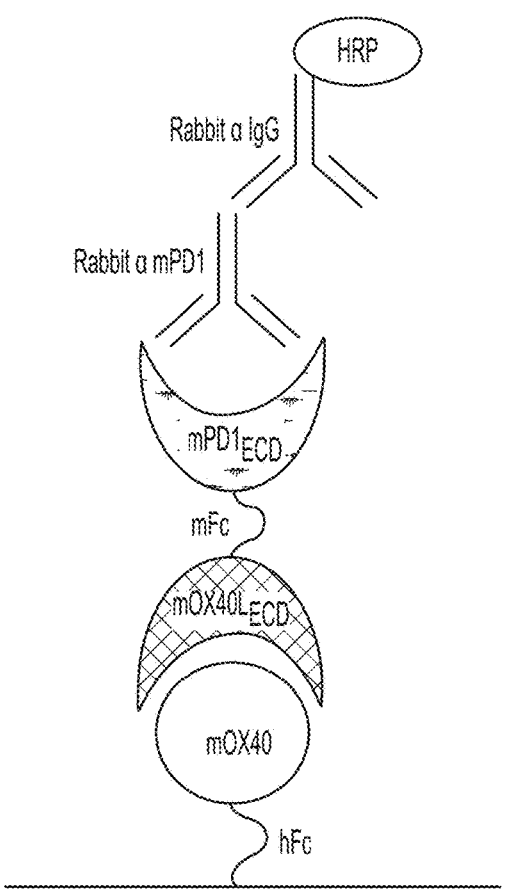
FIG. 6 shows results from an ELISA assay confirming the binding of mPD-1-Fc-OX40L to mOX40. Panel A shows a schematic representation of the ELISA method used to detect binding of mPD-1-Fc-OX40L to mOX40. Recombinant mOX40 fused to human Fc (mOX40-hFc) was used to capture mPD-1-Fc-OX40L in the culture media. A rabbit polyclonal antibody to mPD-1 was used to detect the mPD-1 domain in the chimeric protein and subsequently detected using a horseradish peroxidase (HRP)-conjugated polyclonal antibody to rabbit IgG (H+L). Panel B shows results in which two-fold serial dilutions of the CHO-K1 culture media containing mPD-1-Fc-OX40L protein was incubated with plate-bound mOX40-hFc and binding was measured by absorbance at 450 nm. mPD-1-Fc protein (which is not predicted to bind recombinant mouse OX40) containing culture media, as well as culture media alone, were used as negative controls.
Figure 6:
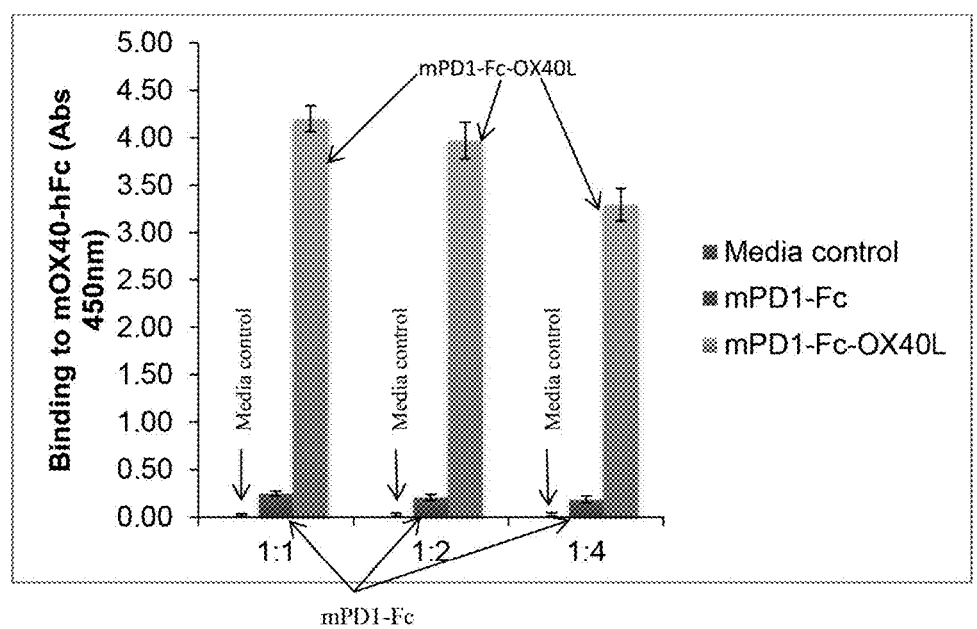
Figure 7:
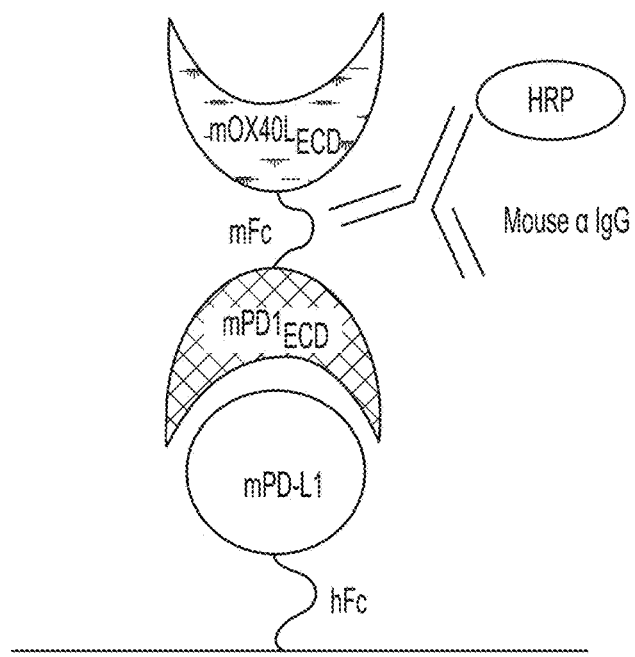
FIG. 7 shows results from an ELISA assay confirming binding of mPD-1-Fc-OX40L to mPD-L1. Panel A shows a schematic representation of the ELISA method used to detect binding of mPD-1-Fc-OX40L to mPD-L1. Recombinant mPD-L1 fused to human Fc (mPD-L1-hFc) was used to capture the mPD-1-Fc-OX40L chimeric protein in the culture media. A horseradish peroxidase (HRP)-conjugated polyclonal antibody to mouse IgG (H+L) was used for the detection of the bound proteins. Panel B shows results in which two-fold serial dilutions of CHO-K1 culture media containing mPD-1-Fc-OX40L protein was incubated with plate-bound mPD-L1-hFc and binding was measured by absorbance at 450 nm. mPD-1-Fc protein containing culture media was used as a positive control and media alone was used as a negative control.
Figure 7:
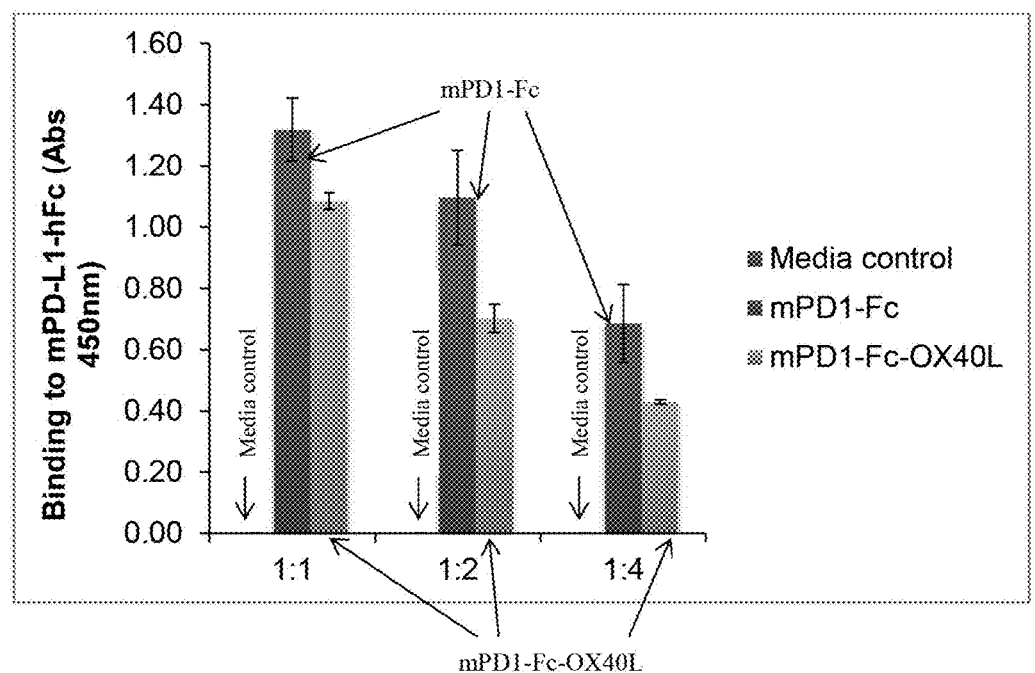

Binding assays were carried out to characterize the ability of mouse PD-1-Fc-OX40L to bind to mOX40 as well as to mPD-L1. FIG. 6, panel A, shows a schematic representation of the ELISA assay used to detect binding of mouse PD-1-Fc-OX40L to mOX40. Specifically, recombinant mOX40 fused to human Fc (mOX40-hFc) was used to capture mPD-1-Fc-OX40L in the culture media. A rabbit polyclonal antibody to mPD-1 was used to detect the mPD-1 domain in the chimeric protein and subsequently detected using a horseradish peroxidase (HRP)-conjugated polyclonal antibody to rabbit IgG (H+L). FIG. 6, panel B, shows that mouse PD-1-Fc-OX40L efficiently bound to OX40 compared to the mPD-1-Fc negative control. FIG. 7, panel A, shows a schematic representation of the ELISA assay used to detect binding of mouse PD-1-Fc-OX40L to mPD-L1. Specifically, recombinant mPD-L1 fused to human Fc (mPD-L1-hFc) was used to capture the mPD-1-Fc-OX40L chimeric protein in the culture media. A horseradish peroxidase (HRP)-conjugated polyclonal antibody to mouse IgG (H+L) was used for the detection of the bound proteins. FIG. 7, panel B, shows that mouse PD-1-Fc-OX40L efficiently bound to PD-L1 as compared to a negative media control and a positive control using recombinant mouse PD1-Fc.

Figure 8:
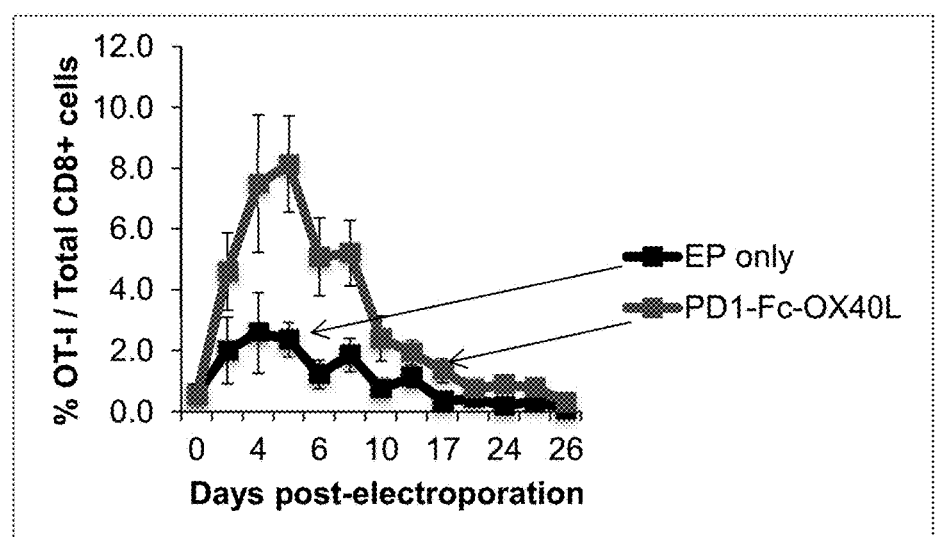
FIG. 8 shows that the in vivo intratumoral delivery of plasmid DNA encoding mouse (m) PD-1-Fc-OX40L led to an expansion of antigen-specific CD8+ T-cells. "EP only" is an electroporation negative control. In this experiment, C57BL/6 mice were adoptively transferred with ovalbumin-specific CD8+ T cells (OT-I) 2 days before tumor inoculation. B16-F10-ova tumors were then implanted on the hind flank of each mouse on day 0. 7-day established B16-F10-ova tumors were injected with the plasmid DNA encoding mPD1-Fc-OX40L and electroporated immediately thereafter on days 7 and 10, as compared to the EP only control. The frequency of OT-I cells was measured on the indicated days in the peripheral blood by flow cytometry.

Experiments were carried out to characterize the activity of mouse PD-1-Fc-OX40L in eliciting T-cell response and in treating tumors. Chicken ovalbumin antigen-specific OT-I/EGFP, CD8+ T cells ($5 \times 10^5$) were adoptively transferred to C57/BL6-albino mice via tail vein injections 2 days prior to inoculation with B16.F10-ova tumor cells ($5 \times 10^5$) into the right flank of the mice. Once tumors reached 3-5 mm in diameter, PD-1-Fc-OX40L expressing DNA (50 µg) was electroporated into the tumor using a defined electrical pulse (1500 V/cm) using 8 pulses at 100 µS. The percentage of CD8+ OT-I/EGFP cells in the peripheral blood was quantified by flow cytometry analysis over the assigned time course following electroporation. As shown in FIG. 8, in vivo intratumoral delivery of mouse (m) PD-1-Fc-OX40L led to an expansion of antigen-specific CD8+ T-cells.

Figure 9:
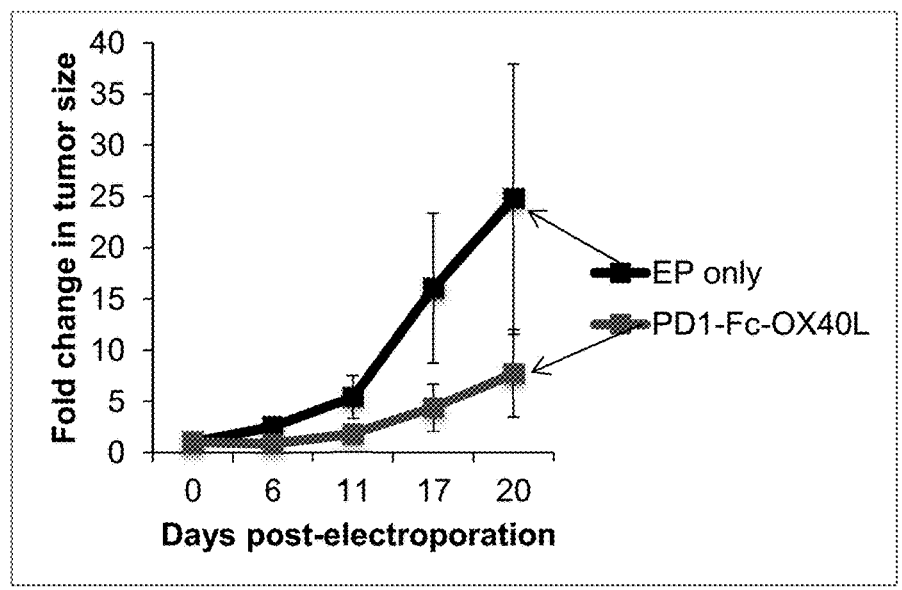
FIG. 9 shows that the in vivo intratumoral delivery of plasmid DNA encoding mPD-1-Fc-OX40L led to tumor regression in the B16.F10-ova melanoma tumor model. "EP only" is an electroporation negative control. Mice were treated as indicated in FIG. 9, and the tumor diameter was measured on the indicated days.

FIG. 9 shows that the in vivo intratumoral delivery of mPD-1-Fc-OX40L also led to tumor regression in the B16.F10-ova tumor model. B16.F10-ova tumors were generated in C57/Bl6-albino mice that were adoptively transferred with CD8+ OT-I/EGFP cells and electroporated once with mPD-1-Fc-OX40L expressing DNA (50 µg). Control mice did not receive DNA but were subjected to electroporation (EP only). Tumor diameters were measured using a digital caliper over the assigned time course following electroporation. FIG. 9 demonstrates that the administration of mPD-1-Fc-OX40L significantly reduced tumor size.

Example 2. Additional Characterization of Mouse PD-1-Fc-OX40L Construct

Figure 10:
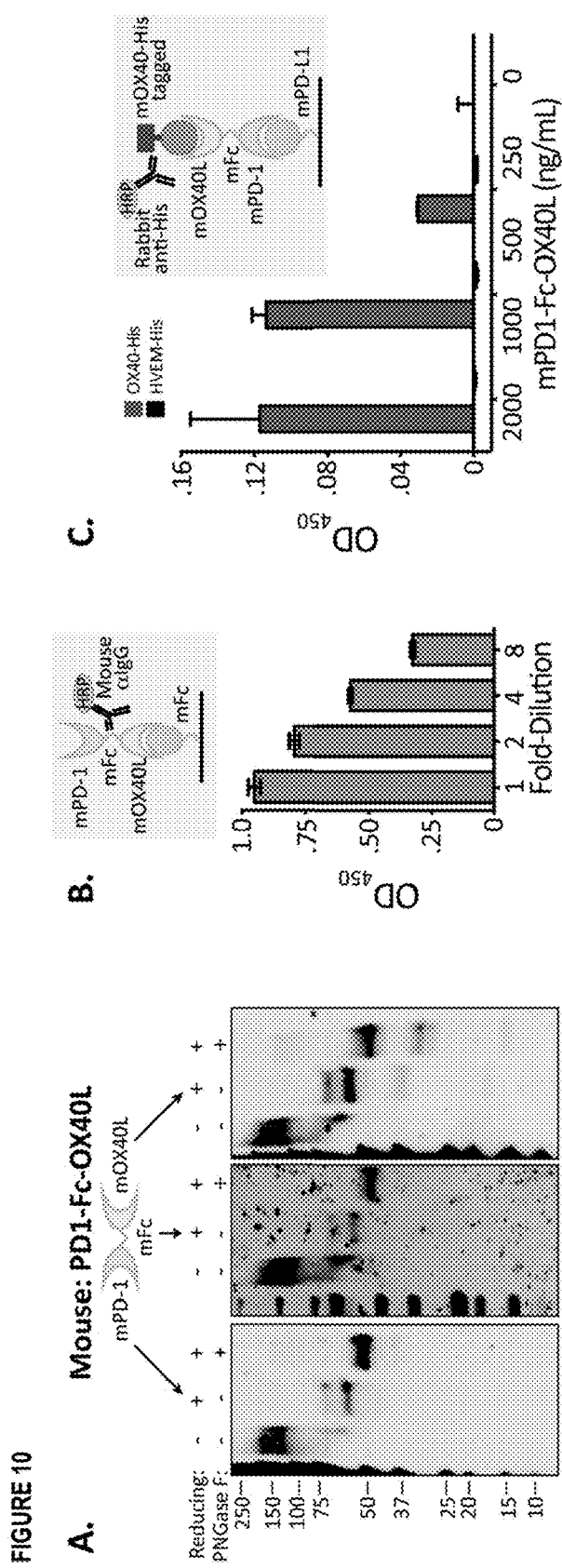
FIG. 10 shows results from additional characterization of mPD-1-Fc-OX40L. Panel A provides Western blot analysis probed with antibodies for mPD-1 (left gel), mFc (middle panel) and mOX40L (right panel), run in reducing or non-reducing condition and with or without the deglycosylase PNGase F (as indicated by the '+' or '−' marks above each blot). The murine protein has a predicted molecular weight of ~60 kDa as a monomeric protein. Panel B shows results from a functional ELISA assay demonstrating the binding of mPD-1-Fc-OX40L to mPD-L1 and mOX40. For each set of histograms, the bars represent, from left to right, a serial dilution of the purified mPD1-Fc-OX40L fusion protein. Panel C shows results from a functional ELISA assay demonstrating the binding of mPD-1-Fc-OX40L to mFc (for each concentration, OX40-His is the left bar and HVEM-His is the right bar). Panel D shows binding to mPD-1-Fc-OX40L to activated mouse splenocytes as detected on HLA I-A/I-E$^+$PD-L1$^+$ (APC$^+$PD-L1$^+$) and CD4$^+$OX40$^+$ cells (for each graph, the cell populations to the left represent APC$^-$PD-L1$^-$ or CD4$^-$OX40$^-$ cells and the cell populations to the right represent APC$^+$PD-L1$^+$ or CD4$^+$OX40$^+$ cells). Panel E shows identification of PD-L1$_{low}$ (4T1) and PD-L1$_{high}$ (B16.F10) cell lines. Panel F shows results from a splenocyte/tumor co-culture assay. IL2 ELISA was performed 5 days after initial harvest. The line graphs from left to right represent +4T1 cells (−FP), +4T1 cells (+500 ng FP), +4T1 cells (+5 ug FP), +B16 cells (−FP), +B16 cells (+500 ng FP), and +B16 cells (+5 ug FP).
Figure 10:
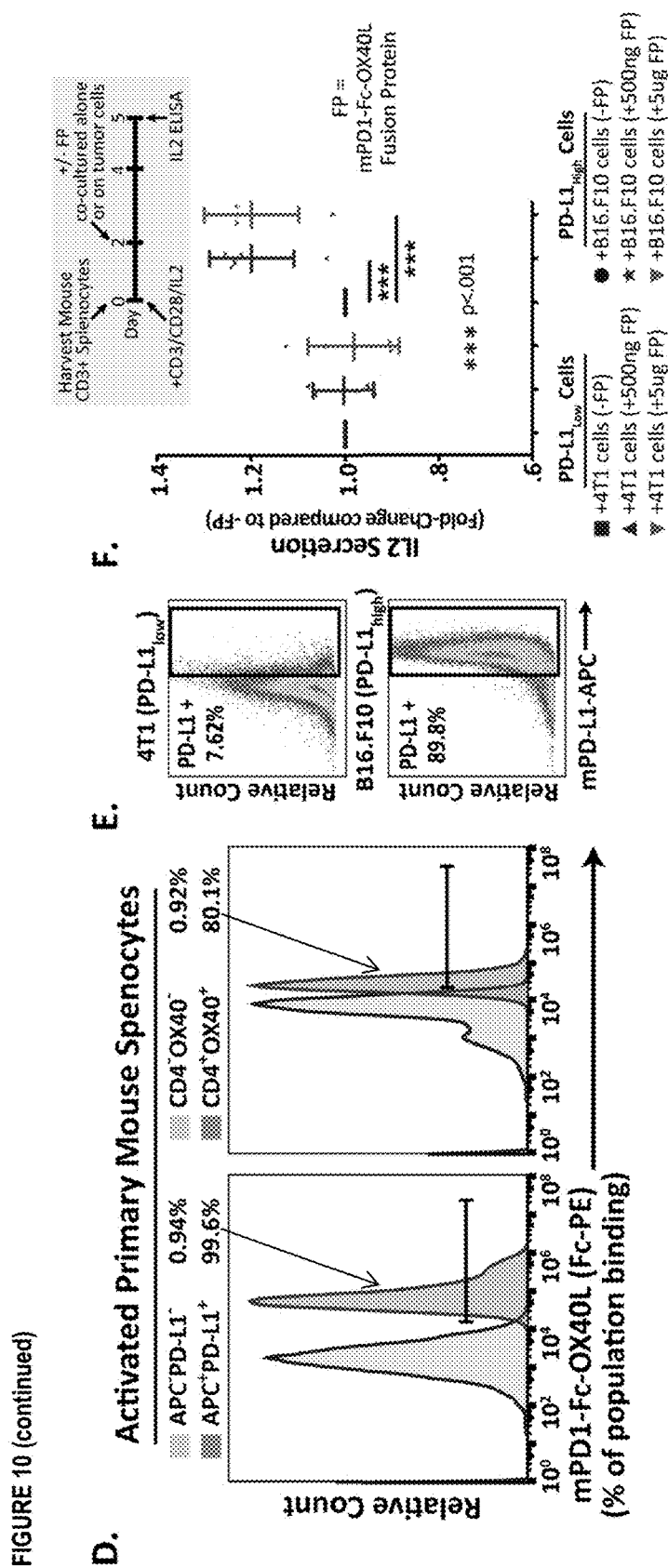

A mPD-1-Fc-OX40L construct was generated which included the mouse extracellular domain (ECD) of PD-1 fused to the ECD of OX40L via a hinge-CH2-CH3 Fc domain derived from IgG1 (mPD-1-Fc-OX40L). The mPD- 1-Fc-OX40L construct was transiently expressed in 293 cells and purified using protein A affinity chromatography. Western blot and functional ELISA analysis were performed to validate the detection and binding of all 3 components of mPD-1-Fc-OX40L (FIG. 10, panel A). Quanitation of mPD1-Fc-OX40L can be assessed using a murine IgG capture and detection ELISA (FIG. 10, panel B). The binding of mPD-1 and mOX40L to their partners mPD-L1 and mOX40, respectively, was demonstrated simultaneously by capturing mPD-1-Fc-OX40L with mPD-L1-Fc and detecting it with mOX40-His, followed by His-HRP for chemiluminescence quantitation (FIG. 8, panel C). It was also noted that there were monomeric and dimeric conformations of mPD-1-Fc-OX40L.

To assess the ex vivo cellular binding of mPD-1-Fc-OX40L, primary mouse splenocytes were isolated and activated for 2 days with PMA/PHA/Ionomycin, in order to up-regulate OX40 and PD-L1 expression. Activated splenocytes were then treated with 500 ng/mL of mPD-1-Fc-OX40L and analyzed by flow cytometry for binding (Fc-PE) (FIG. 8, panel D). To isolate PD-L1 expressing cells, splenocytes were co-stained with an antibody targeting MHC II on antigen presenting cells (I-A/I-E). To isolate OX40 expressing cells, splenocytes were co-stained with CD4. mPD-1-Fc-OX40L bound significantly to both PD-L1+ and OX40+ populations of splenocytes, indicating that mPD-1-Fc-OX40L had been generated and purified competently to bind its targets on primary derived cells. The binding activity of mPD1-Fc-OX40L to primary mouse tumor cell lines expressing PD-L1 was also assessed. The murine 4T1 tumor cell line was identified as expressing low amounts of PD-L1 and the B16.F10 tumor cell line expressed comparatively high amounts of PD-L1. mPD1-Fc-OX40L was shown to bind the PD-L1 positive B16.F10 tumor cell line to a greater extent than the PD-L1 low 4T1 tumor cell line (FIG. 10, panel E).

Additional functional activities of mPD-1-Fc-OX40L were characterized using a T cell activation/tumor co-culture assay. First, murine (4T1) and PD-L1$_{high}$ (B16.F10) cells were identified by flow cytometry (FIG. 8, panel E). Next, mouse splenocytes were activated for 2 days with CD3/CD28 beads and a sub-saturating concentration of IL2. After 2 days, activated splenocytes were co-cultured with either irradiated 4T1 or B16.F10 cells in the presence or absence of mPD-1-Fc-OX40L. Five days after the initial isolation of splenocytes, culture medium was collected and analyzed for the cytokine IL2 by ELISA (FIG. 8, panel F). It was observed that mPD-1-Fc-OX40L was capable of significant induction of IL2 secretion, especially in co-cultures containing PD-L1$_{high}$ tumor cells. Without wishing to be bound by theory, it is believed that mPD-1-Fc-OX40L was concomitantly blocking the suppressive effects of PD-L1 while also activating T cells via OX40/OX40L signaling, thereby inducing IL2 secretion. Altogether, these findings suggest that mPD-1-Fc-OX40L may provide significant anti-tumor immunity in pre-clinical models.

Figure 11:
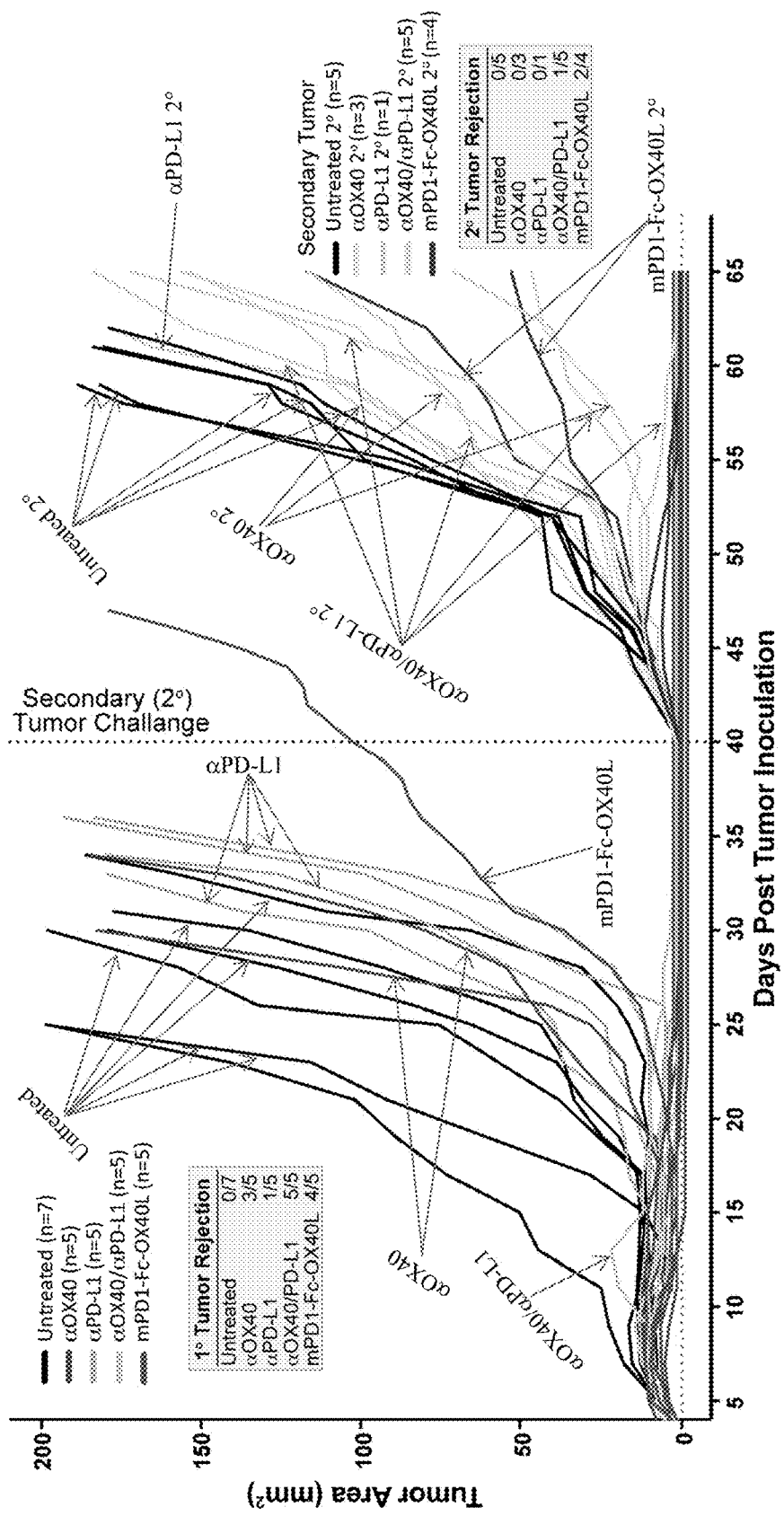
FIG. 11 shows the anti-tumor efficacy of mPD-1-Fc-OX40L. Panel A shows MC38 tumor growth kinetics following treatment with the indicated regimens. Balb.c mice were inoculated in the hind flank with 2.5×10$^5$ MC38-ova tumor cells. On days 5 and 8, mice were treated with the indicated treatment group. Anti-OX40 treated animals received 100 μg of OX86 mAb on each of two days, anti-PD-L1 treated animals received 100 μg of 10F.9G2 mAb on each of two days, anti-OX40 and anti-PD-L1 combination treated animals received 100 μg each of OX86 and 10F.9G2 on each of two days and mPD1-Fc-OX40L treated mice received 100 μg total of mPD1-Fc-OX40L on each of two days. Tumor area was calculated on the indicated days by taking perpendicular tumor diameter measurements using electronic calipers. On day 40, mice which had completely rejected the prior tumor (no visible or palpable tumor remained), were challenged with 2.5×10$^5$ MC38 parental (not expressing ova) tumor cells, without any additional treatment, and tumor area was calculated as stated above. Panel B shows the overall survival for each treatment group over the course of the experiment as determined by overall tumor size exceeding 150 mm$^2$ according to IACUC protocols (at day 65, the curves are, top to bottom, αOX40/αPD-L1, mPD1-Fc-OX40L, αOX40, αPD-L1, and untreated). Panel C shows peripheral blood analysis of CD4/CD8 ratio (top) and the percentage of FOXP3+ Treg cells (bottom) for each indicated treatment group (in both graphs, the treatment groups are, left to right, untreated, αOX40, αPD-L1, αOX40/αPD-L1, and mPD1-Fc-OX40L). Panel D shows serum cytokine analysis of IFNγ, TNFα, IL4, and IL6. For each set of data, the line graphs from left to right represent untreated, α-OX40, α-PD-L1, α-OX40/α-PD-L1, and mPD-1-Fc-OX40L (in the four graphs, the treatment groups are, left to right, untreated, αOX40, αPD-L1, αOX40/αPD-L1, and mPD1-Fc-OX40L). Panel E shows the mean tumor size for each treatment group on day 13 of the experiment (for each graph, the samples are, left to right: untreated, mPD1-Fc-OX40L, mPD1-Fc-GITRL, mCD172a-Fc-CD40L, αOX40, αPD-L1, and α GITR). Panel F shows the percentage of KSP Tetramer specific CD8+ T cells isolated from the tumor (TIL) for each treatment group on day 13 of the experiment (for each graph, the samples are, left to right: untreated, mPD1-Fc-OX40L, mPD1-Fc-GITRL, mCD172a-Fc-CD40L, αOX40, αPD-L1, and a GITR). Panel G shows the phenotype of CD8+ splenocytes according to well characterized 'immune memory' markers on day 13 of the experiment for each treatment group (for each graph, the samples are, left to right: untreated, mPD1-Fc-OX40L, mPD1-Fc-GITRL, mCD172a-Fc-CD40L, αOX40, αPD-L1, and a GITR). Panel H shows the ratio of CD4 to CD8 cells in the peripheral blood (left panel), spleen (middle panel) and tumor (right panel) for each treatment group on day 13 of the experiment (for each graph, the samples are, left to right: untreated, mPD1-Fc-OX40L, mPD1-Fc-GITRL, mCD172a-
Figure 11:
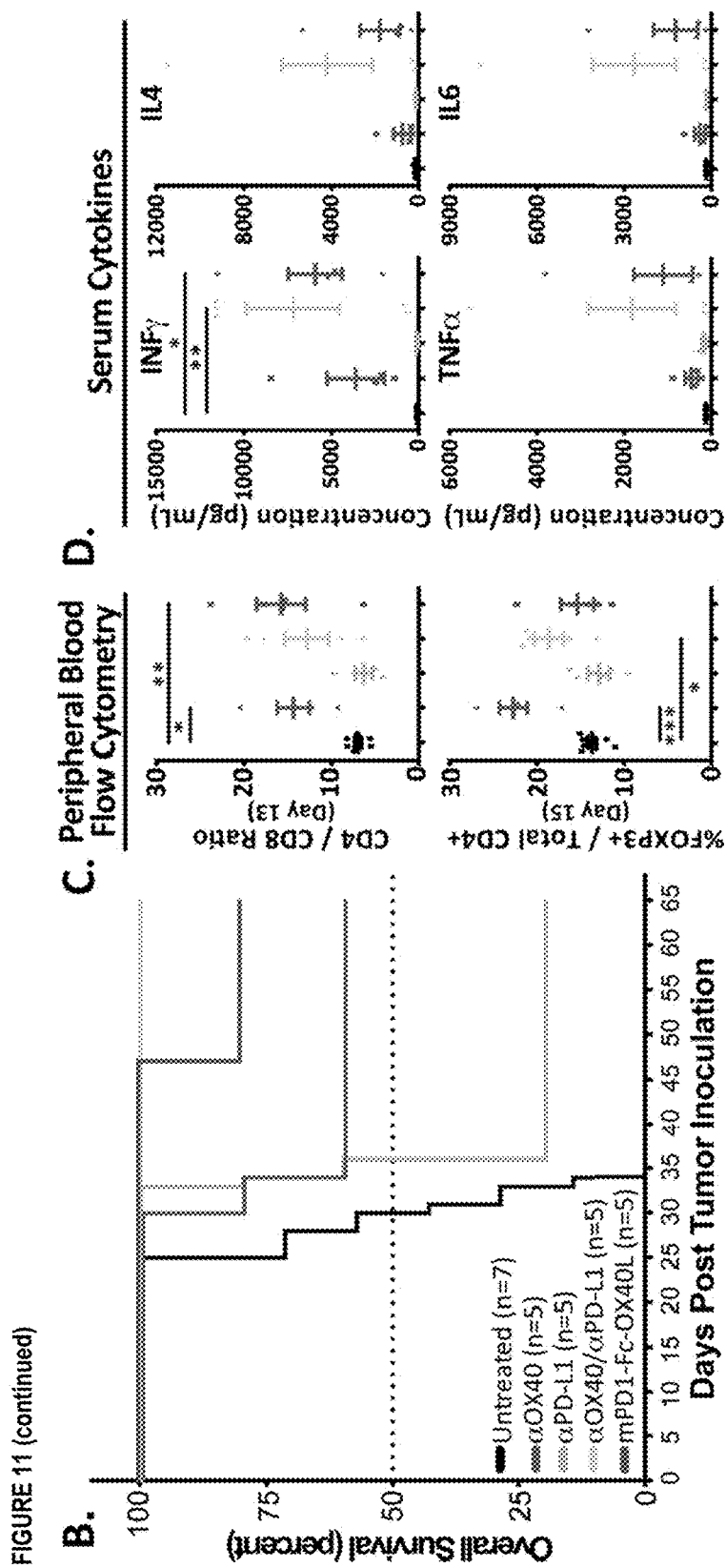
Figure 11:
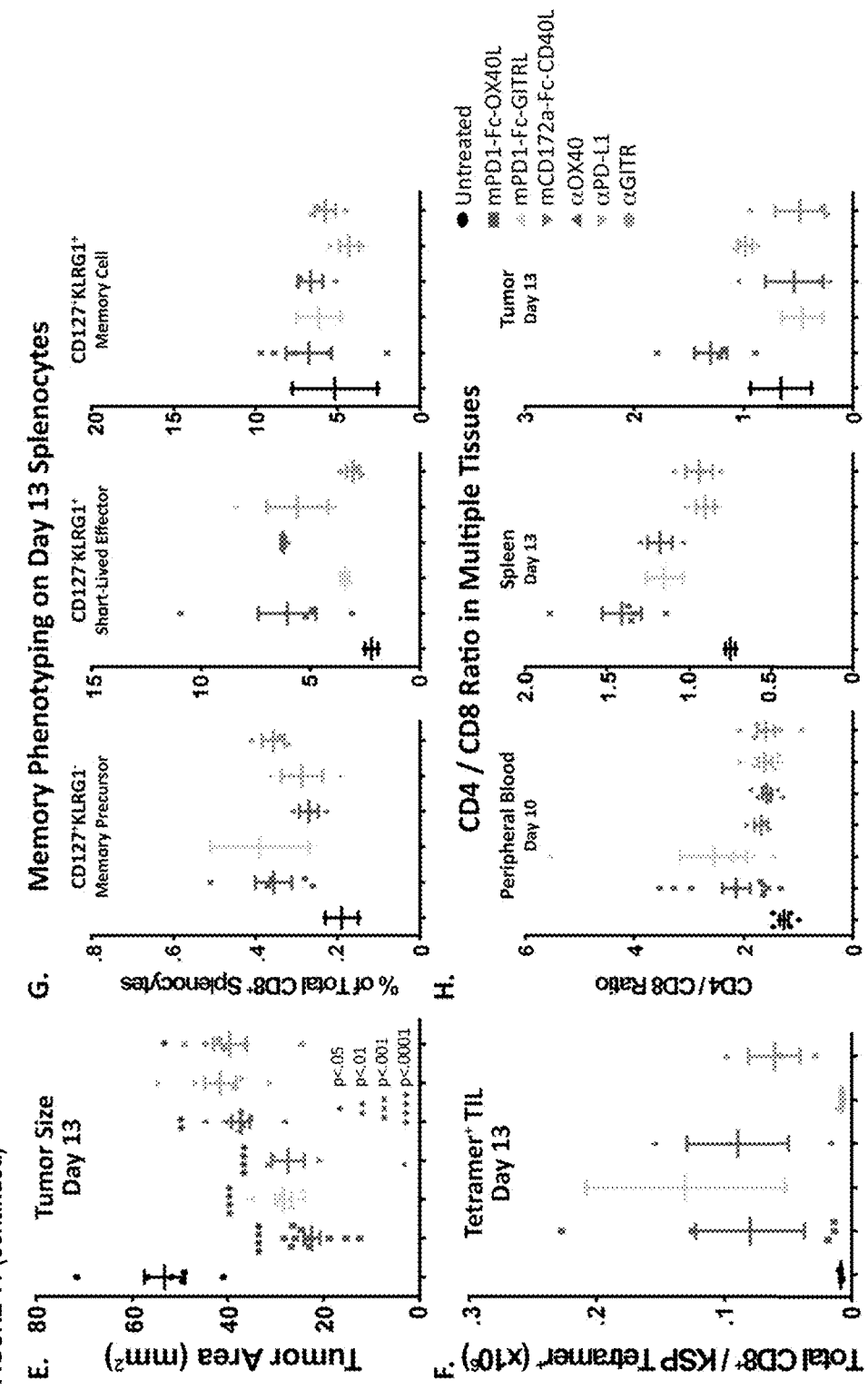
Figure 11:
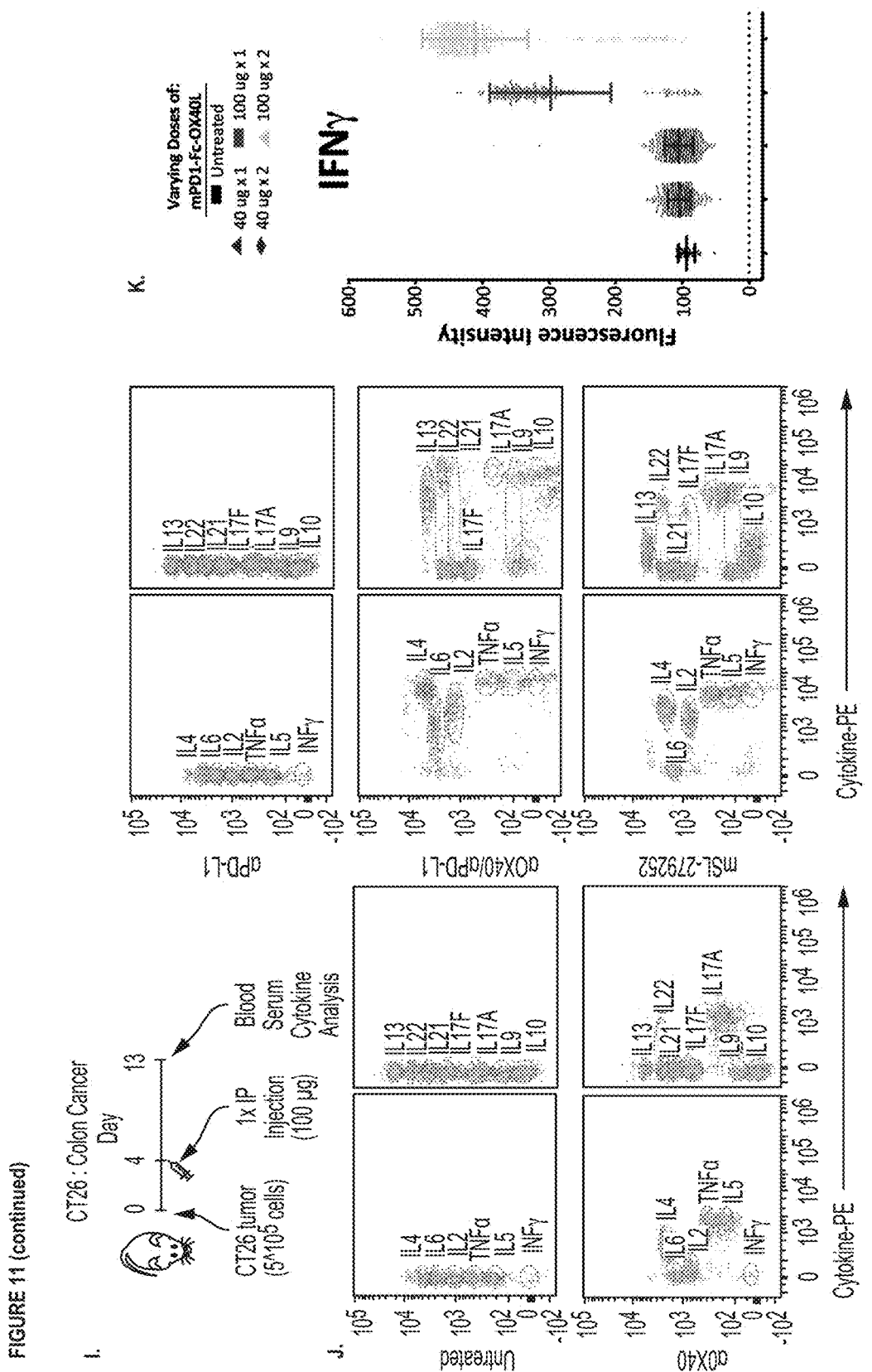
Figure 11:
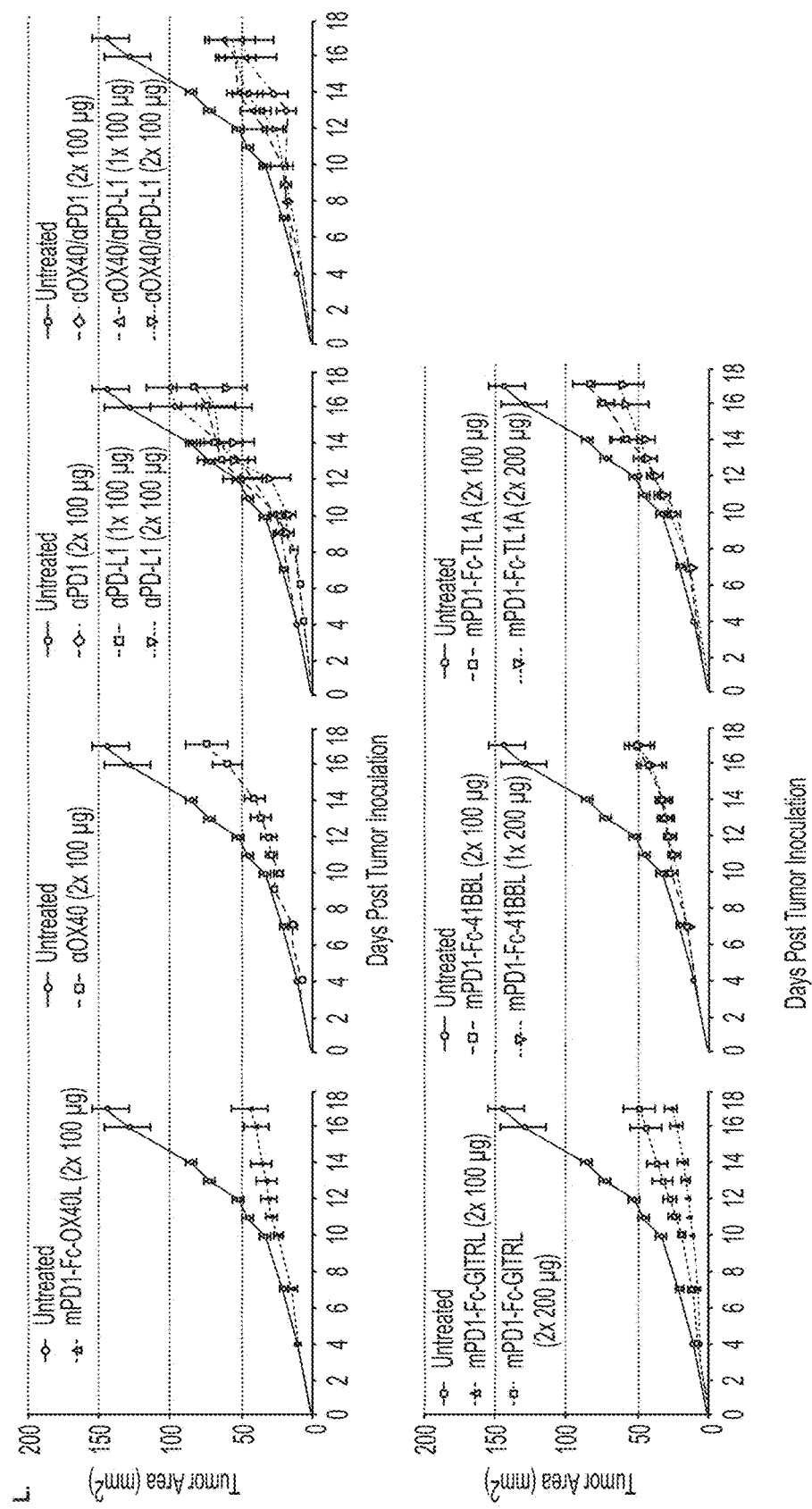

The anti-tumor potency of mPD-1-Fc-OX40L was tested using several preclinical tumor model systems. Specifically murine models of colorectal cancer (CT26 and MC38) were used to assess the effects of mPD-1-Fc-OX40L on tumor growth, overall survival, and the induction of a serum cytokine response following therapy. These experiments were performed head-to-head with extensively characterized OX40 agonist (OX86) and PD-L1 blocking (10F.9G2) antibodies given as monotherapy or in combination, at an equivalent active dose to mPD-1-Fc-OX40L via intraperitoneal injection (2 doses of 100 ug each). As shown in FIG. 11, panel A, mPD-1-Fc-OX40L significantly reduced tumor size in the MC38 model. More particularly, administration of mPD-1-Fc-OX40L resulted in greater tumor regression than the OX40 agonist and PD-L1 blocking antibodies administered individually or in combination. Importantly, repeat challenge of mice that rejected the primary tumor with the parental MC38 tumor cell line was performed for each group. These data demonstrated that, in the absence of repeat treatment, mice treated with mPD1-Fc-OX40L were able to reject a re-challenge with the parental tumor to a greater degree than any of the other treatment groups (FIG. 11, panels A and B). Further, other fusion constructs including mPD1-Fc-GITRL and mPD1-Fc-41BBL were produced and used in tumor bearing mice as described above for mPD1-Fc-OX40L. Both the GITRL and 41BBL containing constructs led to reduced tumor size in treated animals.

In addition to measuring tumor size, a pharmacodynamic biomarker for mPD-1-Fc-OX40L signaling in vivo was also determined. Specifically, a serum cytokine analysis for mice treated with anti-PD-L1 and anti-OX40 antibodies as well as with PD-1-Fc-OX40L was performed. As shown in FIG. 11, panels B and C, there was a dose-dependent cytokine signature following treatment with mPD-1-Fc-OX40L that was remarkably similar to the cytokine signature observed following combined administration of anti-PD-L1 and anti-OX40 antibodies, comprising of increased IFNγ, TNFα, IL-2, IL-4, IL-5, IL-6, IL-10, IL-17A and IL-22 (FIG. 11, panels C, D & J). Importantly, detection of a serum cytokine response following treatment with mPD1-Fc-OX40L was shown to be dose dependent. Specifically, treatment with one or two injections of 40 µg did not lead to a detectable serum cytokine response, while treatment with 100 µg once led to an intermediate cytokine response and treatment with 100 µg two times led to a higher cytokine response (FIG. 11, panel K). Treatment of mice with mPD1-Fc-GITRL was also shown to stimulated a specific serum cytokine response.

In some experiments, mice bearing MC38 tumors were sacrificed on day 13 of the experiment to evaluate the cellular immune response in the tumor, peripheral blood and spleen. On day 13 of the experiment, mPD1-Fc-OX40L, mPD1-Fc-GITRL and mCD172a-Fc-CD40L were all shown to cause reduced tumor growth as compared to untreated animals or animals treated with OX40 agonist antibodies, GITR agonist antibodies or PD-L1 blocking antibodies (FIG. 11, panel E). In accordance with these data, mice treated with mPD1-Fc-OX40L or mPD1-Fc-GITRL were shown to have increased numbers of tumor antigen specific tumor infiltrating lymphocytes (TIL) on day 13 of the experiment (FIG. 11, panel F). Analysis of the memory phenotype in the spleen of CD8+ T cells was performed (FIG. 11, panel G) and the CD4/CD8 T cell ratio was also compared across multiple treatments (FIG. 11, panel H).

The pharmacodynamic biomarkers for PD-1-Fc-OX40L signaling in vivo was also determined using the CT26 model. Specifically, a serum cytokine analysis for mice treated with anti-PD-L1 and anti-OX40 antibodies, individually or in combination, as well as with PD-1-Fc-OX40L was performed. As shown in FIG. 11, panel D, the cytokine signature following treatment with mPD-1-Fc-OX40L was remarkably similar to the cytokine signature observed following the combined administration of anti-PD-L1 and anti-OX40 antibodies. Specifically, the cytokine signature comprised of increased IFNγ, TNFα, IL-2, IL-4, IL-5, IL-6, IL-9, IL-10, IL-13, IL-17A, IL-17F, and IL-22 (FIG. 11, panels J and K).

Consistent with the results derived from the MC38 model, administration of mPD-1-Fc-OX40L also significantly reduced tumor size in the CT26 colorectal cancer model. Particularly, use of mPD-1-Fc-OX40L resulted in greater tumor regression than the OX40 agonist and PD-L1 blocking antibodies (FIG. 11, panel L). Further, mice administered with mPD-1-Fc-OX40L exhibited longer survival time than mice administered with the OX40 agonist and PD-L1 blocking antibodies (FIG. 11, panel L). In addition, other chimeric fusion protein constructs including PD1-Fc-GITRL, PD1-Fc-41BBL and PD1-Fc-TL1A were all shown to exhibit delayed tumor growth an regression in the CT26 model (FIG. 11, panel L).

Altogether, these data clearly demonstrate, inter alia, the functional activity of mPD-1-Fc-OX40L in vivo.

Example 3. Construction and Characterization of Human PD-1-Fc-OX40L

A human PD-1-Fc-OX40L comprising human PD-1 linked to OX40L via a hinge-CH2-CH3 Fc domain derived from the human immunoglobulin 4 (IgG4) antibody was constructed. This construct was referred to as SL-279252.

The mRNA sequence of human OX40L was as follows (bold text—CDS of OX40L; bold & underlined text—extracellular domain of OX40L):

(SEQ ID NO: 16)

```
   1  TCAATCGCCTTTTATCTCTGGCCCTGGGACCTTTGCCTATTTTCTGATTGATAGGCTTTG
  61  TTTTGTCTTTACCTCCTTCTTTCTGGGGAAAACTTCAGTTTTATCGCACGTTCCCCTTTT
 121  CCATATCTTCATCTTCCCTCTACCCAGATTGTGAAGATGGAAAGGGTCCAACCCCTGGAA
 181  GAGAATGTGGGAAATGCAGCCAGGCCAAGATTCGAGAGGAACAAGCTATTGCTGGTGGCC
 241  TCTGTAATTCAGGGACTGGGGCTGCTCCTGTGCTTCACCTACATCTGCCTGCACTTCTCT
 301  GCTCTTCAGGTATCACATCGGTATCCTCGAATTCAAAGTATCAAAGTACAATTTACCGAA
 361  TATAAGAAGGAGAAAGGTTTCATCCTCACTTCCCAAAAGGAGGATGAAATCATGAAGGTG
 421  CAGAACAACTCAGTCATCATCAACTGTGATGGGTTTTATCTCATCTCCCTGAAGGGCTAC
 481  TTCTCCCAGGAAGTCAACATTAGCCTTCATTACCAGAAGGATGAGGAGCCCCTCTTCCAA
 541  CTGAAGAAGGTCAGGTCTGTCAACTCCTTGATGGTGGCCTCTCTGACTTACAAAGACAAA
 601  GTCTACTTGAATGTGACCACTGACAATACCTCCCTGGATGACTTCCATGTGAATGGCGGA
 661  GAACTGATTCTTATCCATCAAAATCCTGGTGAATTCTGTGTCCTTTGAGGGGCTGATGGC
 721  AATATCTAAAACCAGGCACCAGCATGAACACCAAGCTGGGGGTGGACAGGGCATGGATTC
 781  TTCATTGCAAGTGAAGGAGCCTCCCAGCTCAGCCACGTGGGATGTGACAAGAAGCAGATC
 841  CTGGCCCTCCCGCCCCACCCCTCAGGGATATTTAAAACTTATTTTATATACCAGTTAAT
 901  CTTATTTATCCTTATATTTTCTAAATTGCCTAGCCGTCACACCCCAAGATTGCCTTGAGC
 961  CTACTAGGCACCTTTGTGAGAAAGAAAAAATAGATGCCTCTTCTTCAAGATGCATTGTTT
1021  CTATTGGTCAGGCAATTGTCATAATAAACTTATGTCATTGAAAACGGTACCTGACTACCA
1081  TTTGCTGGAAATTTGACATGTGTGTGGCATTATCAAAATGAAGAGGAGCAAGGAGTGAAG
1141  GAGTGGGGTTATGAATCTGCCAAAGGTGGTATGAACCAACCCCTGGAAGCCAAAGCGGCC
1201  TCTCCAAGGTTAAATTGATTGCAGTTTGCATATTGCCTAAATTTAAACTTTCTCATTTGG
1261  TGGGGGTTCAAAAGAAGAATCAGCTTGTGAAAAATCAGGACTTGAAGAGAGCCGTCTAAG
1321  AAATACCACGTGCTTTTTTTCTTTACCATTTTGCTTTCCCAGCCTCCAAACATAGTTAAT
1381  AGAAATTTCCCTTCAAAGAACTGTCTGGGGATGTGATGCTTTGAAAAATCTAATCAGTGA
1441  CTTAAGAGAGATTTTCTTGTATACAGGGAGAGTGAGATAACTTATTGTGAAGGGTTAGCT
1501  TTACTGTACAGGATAGCAGGGAACTGGACATCTCAGGGTAAAAGTCAGTACGGATTTTAA
1561  TAGCCTGGGGAGGAAAACACATTCTTTGCCACAGACAGGCAAAGCAACACATGCTCATCC
1621  TCCTGCCTATGCTGAGATACGCACTCAGCTCCATGTCTTGTACACACAGAAACATTGCTG
1681  GTTTCAAGAAATGAGGTGATCCTATTATCAAATTCAATCTGATGTCAAATAGCACTAAGA
1741  AGTTATTGTGCCTTATGAAAAATAATGATCTCTGTCTAGAAATACCATAGACCATATATA
1801  GTCTCACATTGATAATTGAAACTAGAAGGGTCTATAATCAGCCTATGCCAGGGCTTCAAT
1861  GGAATAGTATCCCCTTATGTTTAGTTGAAATGTCCCCTTAACTTGATATAATGTGTTATG
```

-continued

```
1921  CTTATGGCGCTGTGGACAATCTGATTTTTCATGTCAACTTTCCAGATGATTTGTAACTTC
1981  TCTGTGCCAAACCTTTTATAAACATAAATTTTTGAGATATGTATTTTAAAATTGTAGCAC
2041  ATGTTTCCCTGACATTTTCAATAGAGGATACAACATCACAGAATCTTTCTGGATGATTCT
2101  GTGTTATCAAGGAATTGTACTGTGCTACAATTATCTCTAGAATCTCCAGAAAGGTGGAGG
2161  GCTGTTCGCCCTTACACTAAATGGTCTCAGTTGGATTTTTTTTCCTGTTTTCTATTTCC
2221  TCTTAAGTACACCTTCAACTATATTCCCATCCCTCTATTTTAATCTGTTATGAAGGAAGG
2281  TAAATAAAAATGCTAAATAGAAGAAATTGTAGGTAAGGTAAGAGGAATCAAGTTCTGAGT
2341  GGCTGCCAAGGCACTCACAGAATCATAATCATGGCTAAATATTTATGGAGGGCCTACTGT
2401  GGACCAGGCACTGGGCTAAATACTTACATTTACAAGAATCATTCTGAGACAGATATTCAA
2461  TGATATCTGGCTTCACTACTCAGAAGATTGTGTGTGTTTGTGTGTGTGTGTGTGTG
2521  TATTTCACTTTTTGTTATTGACCATGTTCTGCAAAATTGCAGTTACTCAGTGAGTGATAT
2581  CCGAAAAAGTAAACGTTTATGACTATAGGTAATATTTAAGAAAATGCATGGTTCATTTTT
2641  AAGTTTGGAATTTTTATCTATATTTCTCACAGATGTGCAGTGCACATGCAGGCCTAAGTA
2701  TATGTTGTGTGTGTTGTTTGTCTTTGATGTCATGGTCCCCTCTCTTAGGTGCTCACTCGC
2761  TTTGGGTGCACCTGGCCTGCTCTTCCCATGTTGGCCTCTGCAACCACACAGGGATATTTC
2821  TGCTATGCACCAGCCTCACTCCACCTTCCTTCCATCAAAAATATGTGTGTGTCTCAGT
2881  CCCTGTAAGTCATGTCCTTCACAGGGAGAATTAACCCTTCGATATACATGGCAGAGTTTT
2941  GTGGGAAAAGAATTGAATGAAAAGTCAGGAGATCAGAATTTTAAATTTGACTTAGCCACT
3001  AACTAGCCATGTAACCTTGGGAAAGTCATTTCCCATTTCTGGGTCTTGCTTTTCTTTCTG
3061  TTAAATGAGGAATGTTAAATATCTAACAGTTTAGAATCTTATGCTTACAGTGTTATCT
3121  GTGAATGCACATATTAAATGTCTATGTTCTTGTTGCTATGAGTCAAGGAGTGTAACCTTC
3181  TCCTTTACTATGTTAATGTATTTTTTTCTGGACAAGCTTACATCTTCCTCAGCCATCTT
3241  TGTGAGTCCTTCAAGAGCAGTTATCAATTGTTAGTTAGATATTTTCTATTTAGAGAATGC
3301  TTAAGGGATTCCAATCCCGATCCAAATCATAATTTGTTCTTAAGTATACTGGGCAGGTCC
3361  CCTATTTTAAGTCATAATTTTGTATTTAGTGCTTTCCTGGCTCTCAGAGAGTATTAATAT
3421  TGATATTAATAATATAGTTAATAGTAATATTGCTATTTACATGGAAACAAATAAAGATC
3481  TCAGAATTCACTA
```

The amino acid sequence of human OX40L was as follows (bolded—extracellular domain):

(SEQ ID NO: 17)
MERVQPLEENVGNAARPRFERNKLLLVASVIQGLGLLLCFTYICLHFSAL

QVSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKVY

LNVTTDNTSLDDFHVNGGELILIHQNPGEFCVL

The nucleic acid sequence of the hinge-CH2-CH3 Sequence from human IgG4 was as follows:

(SEQ ID NO: 18)
TCTAAGTACGGCCCTCCCTGCCCTAGCTGTCCCGCCCCTGAATTTCTGGG

CGGACCCTCCGTGTTTCTGTTCCCCCCAAAGCCCAAGGACACCCTGATGA

TCAGCCGGACCCCCGAAGTGACCTGTGTGGTGGTGGATGTGTCCCAGGAA

GATCCCGAGGTGCAGTTCAATTGGTACGTGGACGGGGTGGAAGTGCACAA

CGCCAAGACCAAGCCCAGAGAGGAACAGTTCAACAGCACCTACCGGGTGG

TGTCTGTGCTGACCGTGCTGCACCAGGATTGGCTGAGCGGAAAGAGTAC

AAGTGCAAGGTGTCCAGCAAGGGCCTGCCCAGCAGCATCGAAAAGACCAT

CAGCAACGCCACCGGCCAGCCCAGGGAACCCCAGGTGTACACACTGCCCC

CTAGCCAGGAAGAGATGACCAAGAACCAGGTGTCCCTGACATGCCTCGTG

AAGGGCTTCTACCCCTCCGATATCGCCGTGGAATGGGAGAGCAACGGCCA

GCCAGAGAACAACTACAAGACCACCCCCCCAGTGCTGGACAGCGACGGCT

CATTCTTCCTGTACTCCCGGCTGACAGTGGACAAGAGCAGCTGGCAGGAA

GGCAACGTGTTCAGCTGCAGCGTGATGCACGAAGCCCTGCACAACCACTA

CACCCAGAAGTCCCTGAGCCTGTCCCTGGGCAAA

The cDNA sequence of human PD-1 was as follows:

(SEQ ID NO: 19)
ATGCAGATCCCACAGGCGCCCTGGCCAGTCGTCTGGGCGGTGCTACAACT
GGGCTGGCGGCCAGGATGGTTCTTAGACTCCCCAGACAGGCCCTGGAACC
CCCCCACCTTCTCCCCAGCCCTGCTCGTGGTGACCGAAGGGGACAACGCC
ACCTTCACCTGCAGCTTCTCCAACACATCGGAGAGCTTCGTGCTAAACTG
GTACCGCATGAGCCCCAGCAACCAGACGGACAAGCTGGCCGCCTTCCCCG
AGGACCGCAGCCAGCCCGGCCAGGACTGCCGCTTCCGTGTCACACAACTG
CCCAACGGGCGTGACTTCCACATGAGCGTGGTCAGGGCCCGGCGCAATGA
CAGCGGCACCTACCTCTGTGGGGCCATCTCCCTGGCCCCCAAGGCGCAGA
TCAAAGAGAGCCTGCGGGCAGAGCTCAGGGTGACAGAGAGAAGGGCAGAA
GTGCCCACAGCCCACCCCAGCCCCTCACCCAGGCCAGCCGGCCAGTTCCA
AACCCTGGTGGTTGGTGTCGTGGGCGGCCTGCTGGGCAGCCTGGTGCTGC
TAGTCTGGGTCCTGGCCGTCATCTGCTCCCGGGCCGCACGAGGGACAATA
GGAGCCAGGCGCACCGGCCAGCCCCTGAAGGAGGACCCCTCAGCCGTGCC
TGTGTTCTCTGTGGACTATGGGGAGCTGGATTTCCAGTGGCGAGAGAAGA
CCCCGGAGCCCCCCGTGCCCTGTGTCCCTGAGCAGACGGAGTATGCCACC
ATTGTCTTTCCTAGCGGAATGGGCACCTCATCCCCCGCCCGCAGGGCTC
AGCTGACGGCCCTCGGAGTGCCCAGCCACTGAGGCCTGAGGATGGACACT
GCTCTTGGCCCCTCTGA

The nucleic acid sequence of human PD-1-Fc-OX40L was as follows:

(SEQ ID NO: 20)
GTCGACGCCACCATGCAGATCCCACAGGCGCCCTGGCCAGTCGTCTGGGC
GGTGCTACAACTGGGCTGGCGGCCAGGATGGTTCTTAGACTCCCCAGACA
GGCCCTGGAACCCCCCACCTTCTCCCCAGCCCTGCTCGTGGTGACCGAA
GGGGACAACGCCACCTTCACCTGCAGCTTCTCCAACACATCGGAGAGCTT
CGTGCTAAACTGGTACCGCATGAGCCCCAGCAACCAGACGGACAAGCTGG
CCGCCTTCCCCGAGGACCGCAGCCAGCCCGGCCAGGACTGCCGCTTCCGT
GTCACACAACTGCCCAACGGGCGTGACTTCCACATGAGCGTGGTCAGGGC
CCGGCGCAATGACAGCGGCACCTACCTCTGTGGGGCCATCTCCCTGGCCC
CCAAGGCGCAGATCAAAGAGAGCCTGCGGGCAGAGCTCAGGGTGACAGAG
AGAAGGGCAGAAGTGCCCACAGCCCACCCCAGCCCCTCACCCAGGCCAGC
CGGCCAGTTCCA<u>ATCTAAGTACGGCCCTCCCTGCCCTAGCTGTCCCGCCC
CTGAATTTCTGGGCGGACCCTCCGTGTTTCTGTTCCCCCCAAAGCCCAAG
GACACCCTGATGATCAGCCGGACCCCCGAAGTGACCTGTGTGGTGGTGGA
TGTGTCCCAGGAAGATCCCGAGGTGCAGTTCAATTGGTACGTGGACGGGG
TGGAAGTGCACAACGCCAAGACCAAGCCCAGAGAGGAACAGTTCAACAGC
ACCTACCGGGTGGTGTCTGTGCTGACCGTGCTGCACCAGGATTGGCTGAG
CGGCAAAGAGTACAAGTGCAAGGTGTCCAGCAAGGGCCTGCCCAGCAGCA
TCGAAAAGACCATCAGCAACGCCACCGGCCAGCCCAGGGAACCCCAGGTG
TACACACTGCCCCCTAGCCAGGAAGAGATGACCAAGAACCAGGTGTCCCT
GACATGCCTCGTGAAGGGCTTCTACCCCTCCGATATCGCCGTGGAATGGG
AGAGCAACGGCCAGCCAGAGAACAACTACAAGACCACCCCCCCAGTGCTG
GACAGCGACGGCTCATTCTTCCTGTACTCCCGGCTGACAGTGGACAAGAG
CAGCTGGCAGGAAGGCAACGTGTTCAGCTGCAGCGTGATGCACGAAGCCC
TGCACAACCACTACACCCAGAAGTCCCTGAGCCTGTCCCTGGGCAAAATA
GAGGGACGAATGGAC</u>caggtatcacatcggtatcctcgaattcaaagtat
caaagtacaatttaccgaatataagaaggagaaaggtttcatcctcactt
cccaaaaggaggatgaaatcatgaaggtgcagaacaactcagtcatcatc
aactgtgatgggttttatctcatctccctgaagggctacttctcccagga
agtcaacattagccttcattaccagaaggatgaggagcccctcttccaac
tgaagaaggtcaggtctgtcaactccttgatggtggcctctctgacttac
aaagacaaagtctacttgaatgtgaccactgacaatacctccctggatga
cttccatgtgaatggcggagaactgattcttatccatcaaaatcctggtg
aattctgtgtcctt<u>TGAGTCGAC</u>

The sequence was codon optimized for expression by Chinese Hamster (CHO) cells as follows:

(SEQ ID NO: 21)
CACCGGCGAGATCTGCCACCATGCAGATCCCTCAGGCCCCCTGGCCTGTC
GTGTGGGCTGTGCTGCAGCTGGGATGGCGGCCTGGCTGGTTCCTGGACTC
TCCTGACAGACCCTGGAACCCCCCCACCTTTAGCCCTGCTCTGCTGGTCG
TGACCGAGGGCGACAACGCCACCTTCACCTGTTCCTTCAGCAACACCTCC
GAGTCCTTCGTGCTGAACTGGTACAGAATGTCCCCCAGCAACCAGACCGA
CAAGCTGGCCGCCTTCCCCGAGGATAGATCCCAGCCTGGACAGGACTGCC
GGTTCAGAGTGACCCAGCTGCCCAACGGCCGGGACTTCCACATGTCTGTC
GTGCGGGCCAGACGGAACGACTCCGGCACATATCTGTGCGGCGCCATCTC
CCTGGCCCCCAAGGCTCAGATCAAAGAGTCTCTGCGGGCCGAGCTGAGAG
TGACCGAGAGAAGGGCTGAGGTGCCAACCGCCCACCCTAGCCCATCTCCA
AGACCTGCCGGCCAGTTCCAGTCTAAGTACGGCCCTCCTTGCCCTAGCTG
CCCTGCCCCTGAATTTCTGGGCGGACCCTCCGTGTTCCTGTTCCCCCCAA
AGCCCAAGGACACCCTGATGATCTCCCGGACCCCCGAAGTGACCTGCGTG
GTGGTGGATGTGTCCCAGGAAGATCCCGAGGTGCAGTTCAATTGGTACGT
GGACGGCGTGGAAGTGCACAACGCCAAGACCAAGCCCAGAGAGGAACAGT
TCAACTCCACCTACCGGGTGGTGTCCGTGCTGACCGTGCTGCACCAGGAT
TGGCTGTCCGGCAAAGAGTACAAGTGCAAGGTGTCCTCCAAGGGCCTGCC
CTCCAGCATCGAAAAGACCATCTCTAACGCCACCGGCCAGCCCCGGGAAC
CCCAGGTGTACACACTGCCTCCAAGCCAGGAAGAGATGACCAAGAACCAG
GTGTCCCTGACCTGTCTCGTGAAGGGCTTCTACCCCTCCGATATCGCCGT
GGAATGGGAGTCCAACGGCCAGCCTGAGAACAACTACAAGACCACCCCCC
CTGTGCTGGACTCCGACGGCTCCTTCTTCCTGTACTCCCGCCTGACCGTG
GACAAGTCCTCCTGGCAGGAAGGCAACGTGTTCTCCTGCTCCGTGATGCA

-continued

```
CGAGGCCCTGCACAACCACTACACCCAGAAGTCCCTGTCCCTGTCTCTGG

GCAAGATCGAGGGCCGGATGGATCAGGTGTCACACAGATACCCCCGGATC

CAGTCCATCAAAGTGCAGTTTACCGAGTACAAGAAAGAGAAGGGATTCAT

CCTGACCTCCCAGAAAGAGGACGAGATCATGAAGGTGCAGAACAACTCCG

TGATCATCAACTGCGACGGGTTCTACCTGATCTCCCTGAAGGGCTACTTC

AGTCAGGAAGTGAACATCAGCCTGCACTACCAGAAGGACGAGGAACCCCT

GTTCCAGCTGAAGAAAGTGCGGAGCGTGAACTCCCTGATGGTGGCCTCTC

TGACCTACAAGGACAAGGTGTACCTGAACGTGACCACCGACAATACCTCC

CTGGACGACTTCCACGTGAACGGCGGCGAGCTGATCCTGATCCACCAGAA

CCCTGGCGAGTTCTGCGTGCTGTGACTCGAGGCTAGC
```

Accordingly, the amino acid sequence of SL-279252 was as follows:

(SEQ ID NO: 22)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQSKYGPPCPSCPAPEFLGGPSVFLFPPKPKDTLM

ISRTPEVTCVVVDVSQEDPEVQFNWYVDGVEVHNAKTKPREEQFNSTYRV

VSVLTVLHQDWLSGKEYKCKVSSKGLPSSIEKTISNATGQPREPQVYTLP

PSQEEMTKNQVSLTCLVKGFYPSDIAVEWESNGQPENNYKTTPPVLDSDG

SFFLYSRLTVDKSSWQEGNVFSCSVMHEALHNHYTQKSLSLSLGKIEGRM

DQVSHRYPRIQSIKVQFTEYKKEKGFILTSQKEDEIMKVQNNSVIINCDG

FYLISLKGYFSQEVNISLHYQKDEEPLFQLKKVRSVNSLMVASLTYKDKV

YLNVTTDNTSLDDFHVNGGELILIHQNPGEFCVL

Alternatively, SL-279252 may include other signaling peptides such as those derived from human collagen V or human IgG heavy chain. Alternatively, SL-279252 may include one or more mutations in the Fc domain to increase stability or to increase binding affinity to FcRn, such as those previously described. The human PD-1-Fc-OX40L construct was imported into the protein tertiary prediction software RaptorX, to ensure proper folding of the three major domains (see FIG. 12, panel A). The tertiary structures of each component (i.e., PD-1, Fc, and OX40L) adopted their native conformations within the larger macromolecule, suggesting that PD-1-Fc-OX40L would retain binding capability and molecular function of all domains. Next, the immunogenic probability of PD-1-Fc-OX40L was assessed using an in silico molecular modeling algorithm, cross-referenced to a T cell epitope database (ABZENA/ANTITOPE, FIG. 12, panel B). Although all coding sequences were human, there was minimal potential for lead and linker sequences to elicit an immune response following treatment. Further analysis was performed using the iTope antigen prediction technology in silico (ANTITOPE). Based on this analysis, SL-279252 was predicted to have a 'low-risk' of immunogenicity because no identifiable T cell epitopes were detected. Accordingly, SL-279252 was expected to have low immunogenicity.

The codon-optimized DNA sequence of SL-279252 was then synthesized and directionally cloned into pcDNA3.4-hygro-mcs (THERMO FISHER) and pVITRO2-hygro-mcs (INVIVOGEN) expression vectors. Vectors were then either transiently or stably transfected into CHO-K1 and 293T cells, and culture supernatants were purified using standard protein A agarose affinity chromatography. Human Fc/IgG ELISAs on eluted fractions (from stable transfection experiments) of purified protein show definitive peaks that align with the first major peak detected from a large-scale purification obtained from transient transfection experiments (FIG. 13, panel A), indicating that successful production of SL-279252 can be achieved using routine protein purification techniques such as protein A.

To confirm that all three domains of SL-279252 are intact and recognizable by a protein detection assay, Western blot analysis was performed on purified fusion protein probing for human anti-PD-1, anti-Fc, and anti-OX40L (FIG. 13, panel B). SL-279252 was detected by all three antibodies and when the protein was run under reducing conditions, migrated at approximately 75 kDa. Approximately 50% of the non-reduced protein ran as a dimer, which was a potential advantage, given the in vivo oligomerization associated with OX40/L signaling and function. The predicted molecular weight for SL-279252 was 60.3 kDa. The reduced fraction of SL-279252 was detected at a higher molecular weight, which, without wishing to be bound by theory, may be due to glycosylation. This was verified by treating SL-279252 with a protein deglycosylase, PNGase F (FIG. 13, panel B). Following deglycosylation, the reduced fraction of SL-279252 migrated exactly at the predicted molecular weight of 60.3 kDa. This provided evidence that SL-279252 was co/post-translationally modified through glycosylation, which played essential roles in the proper folding and stability of proteins, and cell-to-cell adhesion (Dalziel M, Dwek R A. Science 2014, Maverakis E, Lebrilla C B. J Autoimmun. 2015).

Next, analysis was performed to determine whether SL-279252 was able to bind to its receptor/ligand targets using plate-immobilized recombinant proteins in functional ELISA assays. SL-279252 was successfully captured with recombinant human OX40 (FIG. 13, panel C), and detected with anti-human OX40L/anti-goat HRP. In this regard, the capture of SL-279252 with human OX40, followed by detection with a two-step incubation with goat-anti-OX40L followed by anti-goat-HRP led to efficient detection. To establish whether both ends of SL-279252 could bind their respective receptor/ligand simultaneously, another ELISA assay was developed which captures SL-279252 using plate absorbed human PD-L1 and detects SL-279252 using recombinant OX40-his (FIG. 13, panel D). This assay demonstrates that SL-279252 can simultaneously bind human PD-L1 and human OX40.

Next, surface plasmon resonance (SPR) analysis was performed to determine the affinity by which SL-279252 bound to hPD-L1, hPD-L1, hOX40 and various human Fc receptors (FIG. 14). Specifically, polyhistidine-tagged versions of recombinant human PD-L1, PD-L2 and human OX40 was bound to ProteOn HTG tris-NTA chips (BIO-RAD). SL-279252 was then flowed over the bound ligands over a time course and a relative index of 'on-rate' (Ka) and 'off-rate' (Kd) was generated to calculate binding affinity ($K_D$) of SL-279252 to each partner. Recombinant human PD-1-Fc and OX40L-Fc were used as positive controls for binding. These controls have a relatively fast 'on-rate' and an equally fast 'off-rate', resulting in low nanomolar binding affinities. Consistent with these results, the 'on-rate' of SL-279252 to human PD-L1 was rapid, however the 'off-rate' was much lower, in fact ~20-fold slower than the 'off-rate' of recombinant PD-1-Fc, indicating that SL-279252 bound quickly and stably, with long on-target residence time (FIG. 14, panel A). The $K_D$ of SL-279252 binding to human PD-L1 was calculated to be 2.08 nM, nearly identical to the observed $K_D$ of BMS's OPDIVO (~4 nM). The $K_D$ of SL-279252 binding to human PD-L2 was calculated to be 1.24 nM (FIG. 14, panel B). SL-279252 bound with high affinity to human OX40 (246 pM), again with a fast 'on-rate' and slow 'off-rate' (FIG. 14, panel C).

To further define the molecular characteristics of SL-279252, SPR was performed, analyzing the binding affinities of SL-279252 to chip-bound, Fcγ receptors FcγR1A and to the neonatal receptor, FcRn. The human immunoglobulin IgG1 was shown to bind with the highest affinities to FcγR1A, followed by FcRn, in addition to low-level binding to FcγR2b (FIG. 14, panel C and D). SL-279252 did not bind to FcγR1A or FcγR2B, but did bind to FcRn at 73 nM affinity (FIG. 14, panel D and E). Without wishing to be bound by theory, this binding characteristic may be important to the fusion protein because FcRn is involved in IgG recycling to the surface of a cell, thereby avoiding lysosomal degradation, and potentially extending the in vivo half-life of SL-279252. Summary data for SL-279252 binding affinities are including (FIG. 14, panel F).

Next, surface plasmon resonance (SPR) analysis was performed to determine the affinity by which a mutated SL-279252 construct containing a collagen V leader peptide and Fc region mutations to increase binding to FcRn (named colPD1-FcRnOX40L) was examined for binding to hPD-L1, hPD-L1, hOX40 and various human Fc receptors (FIG. 14). Specifically, polyhistidine-tagged versions of recombinant human PD-L1, PD-L2 and human OX40 was bound to ProteOn HTG tris-NTA chips (BIORAD). colPD1-FcRnOX40L was then flowed over the bound ligands over a time course and a relative index of 'on-rate' (Ka) and 'off-rate' (Kd) was generated to calculate binding affinity ($K_D$) of colPD1-FcRnOX40L to each partner. Recombinant human PD-1-Fc and OX40L-Fc were used as positive controls for binding. These controls have a relatively fast 'on-rate' and an equally fast 'off-rate', resulting in low nanomolar binding affinities. Consistent with these results, the 'on-rate' of colPD1-FcRnOX40L to human PD-L1 was rapid, however the 'off-rate' was much lower, in fact ~10-fold slower than the 'off-rate' of recombinant PD-1-Fc, indicating that colPD1-FcRnOX40L bound quickly and stably, with long on-target residence time (FIG. 14, panel G). The $K_D$ of colPD1-FcRnOX40L binding to human PD-L1 was calculated to be 6.35 nM, nearly identical to the observed $K_D$ of BMS's OPDIVO (~4 nM). The $K_D$ of colPD1-FcRnOX40L binding to human PD-L2 was calculated to be 7.93 nM (FIG. 14, panel H). colPD1-FcRnOX40L bound with high affinity to human OX40 (9.61 nM), again with a fast 'on-rate' and slow 'off-rate' (FIG. 14, panel I).

To further define the molecular characteristics of colPD1-FcRnOX40L, SPR was performed, analyzing the binding affinities of colPD1-FcRnOX40L to chip-bound, Fcγ receptors FcγR1A and to the neonatal receptor, FcRn. The human immunoglobulin IgG1 was shown to bind with the highest affinities to FcγR1A, followed by FcRn, in addition to low-level binding to FcγR2b (FIG. 14, panel J and K). colPD1-FcRnOX40L did not bind to FcγR1A or FcγR2B, but did bind to FcRn at 2.51 nM affinity (FIG. 14, panel K). Without wishing to be bound by theory, this binding characteristic may be important to the fusion protein because FcRn is involved in IgG recycling to the surface of a cell, thereby avoiding lysosomal degradation, and potentially extending the in vivo half-life of colPD1-FcRnOX40L. Summary data for colPD1-FcRnOX40L binding affinities are including (FIG. 14, panel L).

Additionally, the in vivo half-life of the purified SL-279252 was tested in C57BL/6 mice by injecting 200 μg of the protein by intra-peritoneal injection. Blood was then collected from treated animals by cardiac puncture at 10 minutes, 30 minutes, 1 hour, 3, 6, 12 and 24 hours and allowed to clot for 2 hours at room temperature. The serum was then assayed using a human IgG or OX40L specific ELISA as outlined above. As shown in FIG. 14, panel M, the serum half-life of SL-279252 in mice following a single injection of 200 μg of protein was determined to be between 7-15 hours. It is anticipated that constructs containing mutations to increase binding affinity to FcRn will lead to longer half-life in vivo.

The slow off-rates detected by SPR suggested that SL-279252 may have a longer on-target (i.e. intratumoral) half-life than serum half life. To investigate this question, immunocompromised NSG mice were implanted with a PD-L1 negative HeLa (human cervical cancer) tumor on one flank, and with a PD-L1 expressing HeLa tumor on the opposite flank. Mice were treated with single injections of 200 μg of SL-279252 and individual mice were sacrificed at defined time points. At the time of sacrifice, both HeLa tumors were excised and bisected. Half of the tumor was dissociated and analyzed for SL-279252 binding by flow cytometry. This analysis demonstrated that SL-279252 accumulated specifically in PD-L1 positive, but not PD-L1 negative tumors. The concentration of SL-279252 was observed to increase in the tumor up to 48 hours post treatment (FIG. 14, panel N). Further, immunohistochemical analysis of the other half of each tumor demonstrated that significant staining for human OX40L was present 5 days post treatment, suggesting that SL-279252 was detectable in PD-L1 positive human tumors at least 5 days following a single treatment (FIG. 14, panel O).

Example 4. Additional Functional Characterization of Human PD-1-Fc-OX40L

The previous data indicated that SL-279252 binds to immobilized targets at low nanomolar affinities and was detectable by multiple protein assays. Additional analysis was carried out to determine whether SL-279252 could bind its targets on the surface of living cells in vitro. To assess SL-279252 binding to the human OX40 receptor, the human AML T cell line Jurkat was engineered to overexpress OX40, creating Jurkat/hOX40 cells (verified by flow cytometry; FIG. 15, panel A). To assess binding to PD-L1, the Chinese hamster ovary cell line, CHO-K1, which does not express human PD-L1, was transfected to stably express human PD-L1 (FIG. 15, panel B). To assess binding to human CD47, CHO-K1 cells were transfected to stably express human CD47 (FIG. 15, panel C).

CHO-K1 or CHO-K1-PD-L1 cells were then treated with increasing amounts of SL-279252 and analyzed by flow cytometry for the detection of the human OX40L domain using anti-human OX40L-APC antibodies. SL-279252 did not bind to parental CHO-K1 cells since they expressed no detectable human PD-L1. However, nearly the entire population of CHO-K1-PD-L1 cells shifted significantly, indicating that the human PD1 component of SL-279252 was capable of binding its receptor on living cells (FIG. 15, panel D). Jurkat or Jurkat/OX40 cells were then treated with increasing amounts of SL-279252 and analyzed by flow cytometry for detection of the human OX40L domain using anti-human OX40L-APC antibodies. SL-279252 did not bind parental Jurkat cells with high efficiency, since they express low amounts of human OX40. However, nearly the entire population of Jurkat/OX40 cells shifted significantly, indicating that the human OX40L component of SL-279252 was capable of binding its receptor on living cells (FIG. 15, panel E).

To investigate binding of another chimeric fusion protein, human CD172a-Fc-OX40L, CHO-K1 or CHO-K1-CD47 cells were then treated with increasing amounts of CD172a-Fc-OX40L and analyzed by flow cytometry for the detection of the human OX40L domain using anti-human OX40L-APC antibodies. CD172a-Fc-OX40L did not bind to parental CHO-K1 cells since they expressed no detectable human CD47. However, nearly the entire population of CHO-K1-PD-L1 cells shifted significantly, indicating that the human CD172a component of CD172a-Fc-OX40L was capable of binding its receptor on living cells (FIG. 15, panel F). Jurkat or Jurkat/OX40 cells were then treated with increasing amounts of CD172a-Fc-OX40L and analyzed by flow cytometry for detection of the human OX40L domain using anti-human OX40L-APC antibodies. CD172a-Fc-OX40L did not bind parental Jurkat cells with high efficiency, since they express low amounts of human OX40. However, nearly the entire population of Jurkat/OX40 cells shifted significantly, indicating that the human OX40L component of CD172a-Fc-OX40L was capable of binding its receptor on living cells (FIG. 15, panel G).

Additionally, a number of human tumor cell lines were screened for differing levels of endogenous human PD-L1 expression by flow cytometry. A prostate cancer cell line (PC3) as PD-L1$_{low}$ and a lung adenocarcinoma cell line (HCC827) as PD-L1$_{high}$ were identified (FIG. 15, panel H). The PC3 and HCC827 cells were incubated with increasing amounts of SL-279252, and binding was detected using flow cytometry. SL-279252 did not bind to PC3 cells (PD-L1$_{low}$) efficiently (FIG. 15, panel I). However, SL-279252 bound significantly to HCC827 cells (PD-L1$_{high}$) in a concentration dependent manner (FIG. 15, panel J). This clearly indicated that SL-279252 could bind both human OX40 and PD-L1 expressed on the cell surface, which provided compelling evidence for its dual binding functionality.

To expand upon these results, experiments were performed SL-279252 binding to primary T cells isolated from peripheral blood mononuclear cells (PBMCs), induced for 2 days ex vivo with a chemical combination known to stimulate OX40 expression (phorbol 12-myristate 13-acetate; PMA, phytohemagglutinin; PHA, and Ionomycin). As expected, a large increase in OX40 expression on CD4+ and CD8+ T cells was observed following PMA/PHA/Ion treatment (FIG. 16, panel A). Binding of SL-279252 to CD4+ and CD8+ cells was confirmed using the methods described above (FIG. 16, panel B). It was noted that SL-279252 bound efficiently to human T cells (both CD4+ and CD8+).

A T cell activation/IL2 release assay was utilized to assess the extent that PD-L1 expression on tumor cells inhibited T cell secretion of the anti-tumorigenic cytokine IL2 when the cells were co-cultured (FIG. 16, panel C). After 2 days, activated T cells were plated on irradiated PD-L1$_{low}$ (PC3) and PD-L1$_{high}$ (HCC827) expressing cancer cell lines in the presence or absence of SL-279252. Various readouts of T cell activation were assessed for up to 1 week following initial T cell isolation, including IL2 secretion (FIG. 16 panel D), proliferation and cytokine expression (FIG. 16, panel E). Baseline levels of IL2 secretion (in the absence of SL-279252) were significantly higher in PD-L1$_{low}$ PC3 co-cultures than with PD-L1$_{high}$ HCC827 cells 6 days after T cell isolation, suggesting that tumor PD-L1 expression either directly or indirectly suppressed the further activation of T cells, as determined by IL2 secretion (FIG. 16, panel D). The addition of SL-279252 to both PC3 and HCC827 co-cultures increased the IL2 secretion in a concentration dependent manner. Specifically, the observed increase in IL-2 from HCC827 co-cultures (PD-L1$_{high}$) from baseline (no SL-279252) to 5 ug/mL of SL-279252 was 1.92-fold, compared to 1.27-fold when co-cultured with PC3 cells (PD-L1low).

Furthermore, additional characteristics of T cell activation were analyzed, including expression of the proliferation marker Ki67 (FIG. 16, panel E; top). Co-culture of activated T cells with PD-L1$_{high}$ HCC827 cells inhibited proliferation as compared to the level observed in the absence of HCC827 cells (black line). The addition of SL-279252 to the co-culture increased Ki67 staining in both CD4+ and CD8+ T cells. Moreover, activated T cells expressed higher levels of the cytokines IFNγ and TNFα when co-cultured on HCC827 cells than when T cells were cultured alone, possibly due to the secretion of other stimulatory factors by the tumor cells (FIG. 16, panel E; bottom). The expression of these cytokines increased significantly following treatment with SL-279252.

Altogether these data demonstrate, inter alia, that SL-279252 bound tightly to its partners PD-L1 and OX40 and was able to reverse PD-L1 mediated T cell inhibition by PD-L1 positive human tumor cells in vitro.

Example 5. Construction and Characterization of Additional Chimeric Proteins

Additional constructs were generated which include: additional human PD-1-Fc-OX40L constructs as well as human hCD172a-Fc-OX40L, hPD1-Fc-TL1A, hBTLA-Fc-OX40L, hTMIGD2-Fc-OX40L, hTIM3-Fc-OX40L, mPD1-Fc-GITRL, mPD1-Fc-41BBL, mPD1-Fc-TL1A, mCD172a-Fc-CD40L, hTIGIT-Fc-OX40L and canine PD-1-Fc-OX40L. Each of these constructs was codon optimized for expression in Chinese Hamster Ovary (CHO) cells, transfected into CHO cells and individual clones were selected for high expression. High expressing clones were then used for small-scale manufacturing in stirred bioreactors in serum-free media and the relevant chimeric fusion proteins were purified with Protein A binding resin columns. FIG. 17, panel A shows a Western blot characterization of various chimeric proteins including hCD172a-Fc-OX40L, hPD1-Fc-TL1A, hBTLA-Fc-OX40L, hTMIGD2-Fc-OX40L, hTIM3-Fc-OX40L, mPD1-Fc-GITRL, mPD1-Fc-41BBL, mPD1-Fc-TL1A, mCD172a-Fc-CD40L, hTIGIT-Fc-OX40L.

Binding assays were carried out to characterize the ability of the various human ECD-Fc-OX40L constructs to bind to hOX40. With respect to hX$_{ECD}$-Fc-OX40L, X refers to the ECD of each protein listed in the bracket on the left (with reference to FIG. 17, panel B). Panel B of FIG. 17 shows a schematic representation of the ELISA method used to detect binding of hX$_{ECD}$-Fc-OX40L to hOX40. Recombinant hOX40 fused to human Fc (hOX40-hFc) was used to capture hX$_{ECD}$-Fc-OX40L in the culture media. Because the hOX40 fusion protein used to capture the target fusion proteins also contains a hIgG region, blocking was performed using a non-HRP conjugated anti-hIgG prior to incubation with the culture supernatants containing the target fusion proteins. A rabbit polyclonal antibody to hIgG was used to detect the hIgG domain in the chimeric protein and subsequently detected using a horseradish peroxidase (HRP)-conjugated polyclonal antibody to rabbit IgG (H+L).

The binding of SL-279252 to cell surface expressed OX40 on Jurkat cells by flow cytometry was compared to two negative control proteins which are not expected to bind human OX40. These data demonstrate that SL-279252 efficiently binds human OX40 (left panel), while neither human PD1-Fc-TL1A or canine PD1-Fc-OX40L were observed to bind human OX40 (FIG. 17, panel C).

The human CD172a-Fc-OX40L construct was imported into the protein tertiary prediction software RaptorX to determine the tertiary structure. The predicted tertiary structure is shown in FIG. 17, panel D.

The codon-optimized DNA sequence of several chimeric fusion proteins were synthesized and directionally cloned into pVITRO2, pcDNA3.4 and other expression vectors. Vectors were then either transiently or stably transfected into CHO or 293 cells and individual clones were selected for high expression. For example, SL-279252 was produced from a transient transfection from 293 cells, purified by affinity chromatography to Protein A columns and evaluated by Coomassie staining, Western blot and quantitated as compared to a BCG standard (FIG. 17, panel E).

In another example, CD172a-Fc-OX40L was produced from a transient transfection from 293 cells, purified by affinity chromatography to Protein A columns and evaluated by Coomassie staining, Western blot and quantitated as compared to a BCG standard (FIG. 17, panel F). In another example, CD172a-Fc-CD40L was produced from a transient transfection from 293 cells, purified by affinity chromatography to Protein A columns and evaluated by the Perkin Elmer LabChip system and quantitated as compared to a BCG standard (FIG. 17, panel G). In another example, human TIGIT-Fc-OX40L was produced from a transient transfection from 293 cells, purified by affinity chromatography to Protein A columns and evaluated by Coomassie staining, Western blot and quantitated as compared to a BCG standard (FIG. 17, panel H).

The binding affinity of human CD172a-Fc-OX40L was evaluated by surface plasmon resonance (SPR) analysis to hCD47, hOX40 and various human Fc receptors (FIG. 17, panels I-M). Specifically, polyhistidine-tagged versions of recombinant human CD47 and human OX40 was bound to ProteOn HTG tris-NTA chips (BIORAD). CD172a-Fc-OX40L was then flowed over the bound ligands over a time course and a relative index of 'on-rate' (Ka) and 'off-rate' (Kd) was generated to calculate binding affinity ($K_D$) of CD172a-Fc-OX40L to each partner. Recombinant human CD47-Fc and OX40L-Fc were used as positive controls for binding. These controls have a relatively fast 'on-rate' and an equally fast 'off-rate', resulting in low nanomolar binding affinities. Consistent with these results, the 'on-rate' of CD172a-Fc-OX40L to human CD47 was rapid, however the 'off-rate' was much lower, in fact ~40-fold slower than the 'off-rate' of recombinant CD47-Fc, indicating that CD172a-Fc-OX40L bound quickly and stably, with long on-target residence time (FIG. 17, panel I). The $K_D$ of CD172a-Fc-OX40L binding to human CD47 was calculated to be 3.59 nM. CD172a-Fc-OX40L bound with high affinity to human OX40 (869 pM), again with a fast 'on-rate' and slow 'off-rate' (FIG. 17, panel J).

To further define the molecular characteristics of CD172a-Fc-OX40L, SPR was performed, analyzing the binding affinities of CD172a-Fc-OX40L to chip-bound, Fcγ receptors FcγR1A and to the neonatal receptor, FcRn. The human immunoglobulin IgG1 was shown to bind with the highest affinities to FcγR1A, followed by FcRn, in addition to low-level binding to FcγR2b (FIG. 17, panel K and L). CD172a-Fc-OX40L did not bind to FcγR1A or FcγR2B, but did bind to FcRn at 790 nM affinity (FIG. 17, panel L). Without wishing to be bound by theory, this binding characteristic may be important to the fusion protein because FcRn is involved in IgG recycling to the surface of a cell, thereby avoiding lysosomal degradation, and potentially extending the in vivo half-life of CD172a-Fc-OX40L. Summary data for CD172a-Fc-OX40L binding affinities are including (FIG. 17, panel M).

The codon-optimized DNA sequence of several additional chimeric fusion proteins were synthesized and directionally cloned into pVITRO2, pcDNA3.4 and other expression vectors. Vectors were then either transiently or stably transfected into CHO or 293 cells and individual clones were selected for high expression. For example, canine PD1-Fc-OX40L was produced from a transient transfection from 293 cells, purified by affinity chromatography to Protein A columns and evaluated by Coomassie staining, Western blot and quantitated as compared to a BCG standard (FIG. 17, panel N). In another example, mouse PD1-Fc-OX40L was produced from a transient transfection from 293 cells, purified by affinity chromatography to Protein A columns and evaluated by Coomassie staining, Western blot and quantitated as compared to a BCG standard (FIG. 17, panel O). In another example, mouse PD1-Fc-GITRL was produced from a transient transfection from 293 cells, purified by affinity chromatography to Protein A columns and evaluated by Coomassie staining, Western blot and quantitated as compared to a BCG standard (FIG. 17, panel P). In another example, mouse PD1-Fc-41BBL was produced from a transient transfection from 293 cells, purified by affinity chromatography to Protein A columns and evaluated by Coomassie staining, Western blot and quantitated as compared to a BCG standard (FIG. 17, panel Q). In another example, mouse PD1-Fc-TL1A was produced from a transient transfection from 293 cells, purified by affinity chromatography to Protein A columns and evaluated by Coomassie staining, Western blot and quantitated as compared to a BCG standard (FIG. 17, panel R). In yet another example, CD115-Fc-CD40L was produced from a transient transfection from 293 cells, purified by affinity chromatography to Protein A columns and evaluated by Coomassie staining, Western blot and quantitated as compared to a BCG standard (FIG. 17, panel S). Each purified protein is characterized by ELISA assays to bind to the marker, e.g. the intended inhibitory ligand as well as the intended costimulatory receptor. For example, to test the binding of purified human PD-1-Fc-OX40L, recombinant PD-L1-Fc is adsorbed to microtiter plates and used to capture PD-1-Fc-OX40L. Any bound PD-1-Fc-OX40L is then detected by using recombinant human OX40-Fc linked to biotin, which is then detected in a chromogenic assay through binding with streptravidin-HRP.

In addition, each purified protein has been characterized by flow cytometry to bind the intended inhibitory ligand as well as the intended costimulatory receptor. For example, human tumor cell lines are characterized for endogenous expression of PD-L1, which was found to be particularly abundant on several human melanoma tumor cell lines. These same tumor cell lines were shown to be negative for human OX40L. Following incubation with PD-1-Fc-OX40L, any bound chimeric fusion protein is detected with human OX40L specific antibodies. Similarly, human Jurkat cells were transfected with human OX40 and shown to be negative for human PD-L1. Following incubation with the chimeric PD-1-Fc-OX40L constructs, any bound complex is detected using anti-human PD-L1 specific antibodies. A series of screening cell lines were generated in order to detect specific cell surface binding of each chimeric fusion protein to its respective receptor/ligand, these included: CHO-K1-CD47, CHO-K1-PD-L1, CHO-K1-HVEM, CHO-K1-HHLA2, CHO-K1-VISTA, CHO-K1-Gal9, HeLa-PD-L1, HeLa-CD47, HeLa-HVEM, HeLa-HHLA2, HeLa-VISTA, HeLa-Gal9.

To determine the functional activity of each receptor, in vitro T cell proliferation assays are performed in the presence of inhibitory ligand positive human tumor cells. For example, human melanoma tumor cells expressing PD-L1 are pulsed with peptides specific for hen egg lysozyme (HEL) and incubated with human HEL specific T cells expressing OX40 receptor. The proliferation of these cells is monitored in the presence and absence of the PD-1-Fc-OX40L construct and found to be functionally responsive to the presence of the chimeric constructs. In a similar system, human tumors expressing HVEM, CD47, galectin-9, TIGIT receptors or TMIGD2 receptors are used.

In some experiments, mouse PD-1-Fc-OX40L or mouse PD-1-Fc-TL1A are used to treat murine tumors known to be positive for murine PD-L1 (including B16-F10 melanoma, MC38 colon carcinoma and CT26 colon carcinoma). In these systems, established tumors are treated with purified chimeric fusion proteins as compared to PD-1-Fc fusion proteins, anti-PD-1 or anti-PD-L1 monoclonal antibodies or anti-OX40 or anti-GITR monoclonal antibodies. In these experiments, the activity of the chimeric constructs is observed to lead to enhanced antigen-specific T cell responses and increased rates of tumor rejection as compared to the individual therapeutics. In some experiments, nucleic acid constructs encoding PD-1-Fc-OX40L or PD-1-Fc-TL1A are directly electroporated into established tumors. In these experiments, the chimeric constructs are shown to lead to increased rates of tumor rejection as well as increased tumor antigen specific CD8+ T cell proliferation detected both in the peripheral blood and within established tumors.

To determine the binding of purified chimeric fusion proteins to human tumor explants, fresh frozen human tumor samples are obtained and incubated with each chimeric fusion protein. Any bound fusion protein is detected with anti-human OX40L and controlled against background staining by separate staining with anti-human OX40L.

To determine the molecular characteristics of each fusion protein, purified chimeric fusion proteins are characterized by size exclusion chromatography. This analysis is important because, for example, the OX40L ECD is known to form a homo-trimer, while the Fc region is known to form a homo-dimer, while the inhibitory ligand binding receptor may either be monomeric (e.g. PD-1) or form homo-multimers (e.g. TIM3). Thus, there are several possibilities for the individual species that may be formed by these chimeric constructs. Further molecular characterization by mass spec, thermal stability, pH stability, physical stability, charge profile, hydrophobicity, physical stability, buffer compatibility and solubility up to 100 mg/mL are also performed.

TABLE 1

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P04439 | 1A03_HUMAN | HLA class I histocompatibility antigen, A-3 alpha chain (MHC class I antigen A*3) | HLA-A HLAA | 365 |
| P30456 | 1A43_HUMAN | HLA class I histocompatibility antigen, A-43 alpha chain (Aw-43) (MHC class I antigen A*43) | HLA-A HLAA | 365 |
| P10316 | 1A69_HUMAN | HLA class I histocompatibility antigen, A-69 alpha chain (Aw-69) (HLA class I histocompatibility antigen, A-28 alpha chain) (MHC class I antigen A*69) | HLA-A HLAA | 365 |
| P30460 | 1B08_HUMAN | HLA class I histocompatibility antigen, B-8 alpha chain (MHC class I antigen B*8) | HLA-B HLAB | 362 |
| Q95365 | 1B38_HUMAN | HLA class I histocompatibility antigen, B-38 alpha chain (Bw-4) (MHC class I antigen B*38) | HLA-B HLAB | 362 |
| P18464 | 1B51_HUMAN | HLA class I histocompatibility antigen, B-51 alpha chain (MHC class I antigen B*51) | HLA-B HLAB | 362 |
| P30495 | 1B56_HUMAN | HLA class I histocompatibility antigen, B-56 alpha chain (Bw-22) (Bw-56) (MHC class I antigen B*56) | HLA-B HLAB | 362 |
| P10319 | 1B58_HUMAN | HLA class I histocompatibility antigen, B-58 alpha chain (Bw-58) (MHC class I antigen B*58) | HLA-B HLAB | 362 |
| P30501 | 1C02_HUMAN | HLA class I histocompatibility antigen, Cw-2 alpha chain (MHC class I antigen Cw*2) | HLA-C HLAC | 366 |
| P04222 | 1C03_HUMAN | HLA class I histocompatibility antigen, Cw-3 alpha chain (MHC class I antigen Cw*3) | HLA-C HLAC | 366 |
| Q9TNN7 | 1C05_HUMAN | HLA class I histocompatibility antigen, Cw-5 alpha chain (MHC class I antigen Cw*5) | HLA-C HLAC | 366 |
| P10321 | 1C07_HUMAN | HLA class I histocompatibility antigen, Cw-7 alpha chain (MHC class I antigen Cw*7) | HLA-C HLAC | 366 |
| Q07000 | 1C15_HUMAN | HLA class I histocompatibility antigen, Cw-15 alpha chain (MHC class I antigen Cw*15) | HLA-C HLAC | 366 |
| Q95604 | 1C17_HUMAN | HLA class I histocompatibility antigen, Cw-17 alpha chain (MHC class I antigen Cw*17) | HLA-C D6S204 HLA-JY3 HLAC | 372 |
| P13760 | 2B14_HUMAN | HLA class II histocompatibility antigen, DRB1-4 beta chain (MHC class II antigen DRB1*4) (DR-4) (DR4) | HLA-DRB1 | 266 |
| Q9TQE0 | 2B19_HUMAN | HLA class II histocompatibility antigen, DRB1-9 beta chain (MHC class II antigen DRB1*9) (DR-9) (DR9) | HLA-DRB1 | 266 |
| Q30167 | 2B1A_HUMAN | HLA class II histocompatibility antigen, DRB1-10 beta chain (DRw10) (MHC class II antigen DRB1*10) | HLA-DRB1 | 266 |
| Q29974 | 2B1G_HUMAN | HLA class II histocompatibility antigen, DRB1-16 beta chain (MHC class II antigen DRB1*16) (DR-16) (DR16) | HLA-DRB1 | 266 |
| P01889 | 1B07_HUMAN | HLA class I histocompatibility antigen, B-7 alpha chain (MHC class I antigen B*7) | HLA-B HLAB | 362 |
| P30462 | 1B14_HUMAN | HLA class I histocompatibility antigen, B-14 alpha chain (MHC class I antigen B*14) | HLA-B HLAB | 362 |
| P30464 | 1B15_HUMAN | HLA class I histocompatibility antigen, B-15 alpha chain (MHC class I antigen B*15) | HLA-B HLAB | 362 |
| P03989 | 1B27_HUMAN | HLA class I histocompatibility antigen, B-27 alpha chain (MHC class I antigen B*27) | HLA-B HLAB | 362 |
| P18463 | 1B37_HUMAN | HLA class I histocompatibility antigen, B-37 alpha chain (MHC class I antigen B*37) | HLA-B HLAB | 362 |
| P30479 | 1B41_HUMAN | HLA class I histocompatibility antigen, B-41 alpha chain (Bw-41) (MHC class I antigen B*41) | HLA-B HLAB | 362 |
| P30483 | 1B45_HUMAN | HLA class I histocompatibility antigen, B-45 alpha chain (Bw-45) (MHC class I antigen B*45) | HLA-B HLAB | 362 |
| P30485 | 1B47_HUMAN | HLA class I histocompatibility antigen, B-47 alpha chain (Bw-47) (MHC class I antigen B*47) | HLA-B HLAB | 362 |
| P30487 | 1B49_HUMAN | HLA class I histocompatibility antigen, B-49 alpha chain (HLA class I histocompatibility antigen, B-21 alpha chain) (MHC class I antigen B*49) | HLA-B HLAB | 362 |
| P30491 | 1B53_HUMAN | HLA class I histocompatibility antigen, B-53 alpha chain (Bw-53) (MHC class I antigen B*53) | HLA-B HLAB | 362 |
| Q29940 | 1B59_HUMAN | HLA class I histocompatibility antigen, B-59 alpha chain (MHC class I antigen B*59) | HLA-B HLAB | 362 |
| P30498 | 1B78_HUMAN | HLA class I histocompatibility antigen, B-78 alpha chain (MHC class I antigen B*78) | HLA-B HLAB | 362 |
| P30499 | 1C01_HUMAN | HLA class I histocompatibility antigen, Cw-1 alpha chain (MHC class I antigen Cw*1) | HLA-C HLAC | 366 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P30505 | 1C08_HUMAN | HLA class I histocompatibility antigen, Cw-8 alpha chain (MHC class I antigen Cw*8) | HLA-C HLAC | 366 |
| P30508 | 1C12_HUMAN | HLA class I histocompatibility antigen, Cw-12 alpha chain (MHC class I antigen Cw*12) | HLA-C HLAC | 366 |
| P01912 | 2B13_HUMAN | HLA class II histocompatibility antigen, DRB1-3 chain (Clone P2-beta-3) (MHC class II antigen DRB1*3) | HLA-DRB1 | 266 |
| Q30134 | 2B18_HUMAN | HLA class II histocompatibility antigen, DRB1-8 beta chain (MHC class II antigen DRB1*8) (DR-8) (DRw8) | HLA-DRB1 | 266 |
| Q95IE3 | 2B1C_HUMAN | HLA class II histocompatibility antigen, DRB1-12 beta chain (MHC class II antigen DRB1*12) (DR-12) (DR12) | HLA-DRB1 | 266 |
| Q9BYF1 | ACE2_HUMAN | Angiotensin-converting enzyme 2 (EC 3.4.17.23) (ACE-related carboxypeptidase) (Angiotensin-converting enzyme homolog) (ACEH) (Metalloprotease MPROT15) [Cleaved into: Processed angiotensin-converting enzyme 2] | ACE2 UNQ868/PRO1885 | 805 |
| P16188 | 1A30_HUMAN | HLA class I histocompatibility antigen, A-30 alpha chain (MHC class I antigen A*30) | HLA-A HLAA | 365 |
| P16190 | 1A33_HUMAN | HLA class I histocompatibility antigen, A-33 alpha chain (Aw-19) (Aw-33) (MHC class I antigen A*33) | HLA-A HLAA | 365 |
| P01891 | 1A68_HUMAN | HLA class I histocompatibility antigen, A-68 alpha chain (Aw-68) (HLA class I histocompatibility antigen, A-28 alpha chain) (MHC class I antigen A*68) | HLA-A HLAA | 365 |
| Q29836 | 1B67_HUMAN | HLA class I histocompatibility antigen, B-67 alpha chain (MHC class I antigen B*67) | HLA-B HLAB | 362 |
| P13761 | 2B17_HUMAN | HLA class II histocompatibility antigen, DRB1-7 beta chain (MHC class II antigen DRB1*7) (DR-7) (DR7) | HLA-DRB1 | 266 |
| Q5Y7A7 | 2B1D_HUMAN | HLA class II histocompatibility antigen, DRB1-13 beta chain (MHC class II antigen DRB1*13) (DR-13) (DR13) | HLA-DRB1 | 266 |
| P13746 | 1A11_HUMAN | HLA class I histocompatibility antigen, A-11 alpha chain (MHC class I antigen A*11) | HLA-A HLAA | 365 |
| P05534 | 1A24_HUMAN | HLA class I histocompatibility antigen, A-24 alpha chain (Aw-24) (HLA class I histocompatibility antigen, A-9 alpha chain) (MHC class I antigen A*24) | HLA-A HLAA | 365 |
| P30512 | 1A29_HUMAN | HLA class I histocompatibility antigen, A-29 alpha chain (Aw-19) (MHC class I antigen A*29) | HLA-A HLAA | 365 |
| P16189 | 1A31_HUMAN | HLA class I histocompatibility antigen, A-31 alpha chain (MHC class I antigen A*31) | HLA-A HLAA | 365 |
| P10314 | 1A32_HUMAN | HLA class I histocompatibility antigen, A-32 alpha chain (MHC class I antigen A*32) | HLA-A HLAA | 365 |
| Q04826 | 1B40_HUMAN | HLA class I histocompatibility antigen, B-40 alpha chain (Bw-60) (MHC class I antigen B*40) | HLA-B HLAB | 362 |
| P30484 | 1B46_HUMAN | HLA class I histocompatibility antigen, B-46 alpha chain (Bw-46) (MHC class I antigen B*46) | HLA-B HLAB | 362 |
| P30486 | 1B48_HUMAN | HLA class I histocompatibility antigen, B-48 alpha chain (Bw-48) (MHC class I antigen B*48) | HLA-B HLAB | 362 |
| P30490 | 1B52_HUMAN | HLA class I histocompatibility antigen, B-52 alpha chain (Bw-52) (HLA class I histocompatibility antigen, B-5 alpha chain) (MHC class I antigen B*52) | HLA-B HLAB | 362 |
| Q31612 | 1B73_HUMAN | HLA class I histocompatibility antigen, B-73 alpha chain (MHC class I antigen B*73) | HLA-B HLAB | 363 |
| Q31610 | 1B81_HUMAN | HLA class I histocompatibility antigen, B-81 alpha chain (BDT) (MHC class I antigen B*81) | HLA-B HLAB | 362 |
| Q29960 | 1C16_HUMAN | HLA class I histocompatibility antigen, Cw-16 alpha chain (MHC class I antigen Cw*16) | HLA-C HLAC | 366 |
| Q29865 | 1C18_HUMAN | HLA class I histocompatibility antigen, Cw-18 alpha chain (MHC class I antigen Cw*18) | HLA-C HLAC | 366 |
| Q9GIY3 | 2B1E_HUMAN | HLA class II histocompatibility antigen, DRB1-14 beta chain (MHC class II antigen DRB1*14) (DR-14) (DR14) | HLA-DRB1 | 266 |
| P30443 | 1A01_HUMAN | HLA class I histocompatibility antigen, A-1 alpha chain (MHC class I antigen A*1) | HLA-A HLAA | 365 |
| P01892 | 1A02_HUMAN | HLA class I histocompatibility antigen, A-2 alpha chain (MHC class I antigen A*2) | HLA-A HLAA | 365 |
| P30447 | 1A23_HUMAN | HLA class I histocompatibility antigen, A-23 alpha chain (HLA class I histocompatibility antigen, A-9 alpha chain) (MHC class I antigen A*23) | HLA-A HLAA | 365 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P18462 | 1A25_HUMAN | HLA class I histocompatibility antigen, A-25 alpha chain (HLA class I histocompatibility antigen, A-10 alpha chain) (MHC class I antigen A*25) | HLA-A HLAA | 365 |
| P30450 | 1A26_HUMAN | HLA class I histocompatibility antigen, A-26 alpha chain (MHC class I antigen A*26) | HLA-A HLAA | 365 |
| P30453 | 1A34_HUMAN | HLA class I histocompatibility antigen, A-34 alpha chain (Aw-34) (HLA class I histocompatibility antigen, A-10 alpha chain) (MHC class I antigen A*34) | HLA-A HLAA | 365 |
| P30457 | 1A66_HUMAN | HLA class I histocompatibility antigen, A-66 alpha chain (Aw-66) (HLA class I histocompatibility antigen, A-10 alpha chain) (MHC class I antigen A*66) | HLA-A HLAA | 365 |
| Q09160 | 1A80_HUMAN | HLA class I histocompatibility antigen, A-80 alpha chain (Aw-80) (HLA class I histocompatibility antigen, A-1 alpha chain) (MHC class I antigen A*80) | HLA-A HLAA | 365 |
| P30461 | 1B13_HUMAN | HLA class I histocompatibility antigen, B-13 alpha chain (MHC class I antigen B*13) | HLA-B HLAB | 362 |
| P30466 | 1B18_HUMAN | HLA class I histocompatibility antigen, B-18 alpha chain (MHC class I antigen B*18) | HLA-B HLAB | 362 |
| P30685 | 1B35_HUMAN | HLA class I histocompatibility antigen, B-35 alpha chain (MHC class I antigen B*35) | HLA-B HLAB | 362 |
| P30475 | 1B39_HUMAN | HLA class I histocompatibility antigen, B-39 alpha chain (MHC class I antigen B*39) | HLA-B HLAB | 362 |
| P30480 | 1B42_HUMAN | HLA class I histocompatibility antigen, B-42 alpha chain (MHC class I antigen B*42) | HLA-B HLAB | 362 |
| P30481 | 1B44_HUMAN | HLA class I histocompatibility antigen, B-44 alpha chain (Bw-44) (MHC class I antigen B*44) | HLA-B HLAB | 362 |
| P30488 | 1B50_HUMAN | HLA class I histocompatibility antigen, B-50 alpha chain (Bw-50) (HLA class I histocompatibility antigen, B-21 alpha chain) (MHC class I antigen B*50) | HLA-B HLAB | 362 |
| P30492 | 1B54_HUMAN | HLA class I histocompatibility antigen, B-54 alpha chain (Bw-22) (Bw-54) (MHC class I antigen B*54) | HLA-B HLAB | 362 |
| P18465 | 1B57_HUMAN | HLA class I histocompatibility antigen, B-57 alpha chain (Bw-57) (MHC class I antigen B*57) | HLA-B HLAB | 362 |
| Q29718 | 1B82_HUMAN | HLA class I histocompatibility antigen, B-82 alpha chain (MHC class I antigen B*82) | HLA-B HLAB | 362 |
| P30504 | 1C04_HUMAN | HLA class I histocompatibility antigen, Cw-4 alpha chain (MHC class I antigen Cw*4) | HLA-C HLAC | 366 |
| Q29963 | 1C06_HUMAN | HLA class I histocompatibility antigen, Cw-6 alpha chain (MHC class I antigen Cw*6) | HLA-C HLAC | 366 |
| P30510 | 1C14_HUMAN | HLA class I histocompatibility antigen, Cw-14 alpha chain (MHC class I antigen Cw*14) | HLA-C HLAC | 366 |
| P04229 | 2B11_HUMAN | HLA class II histocompatibility antigen, DRB1-1 beta chain (MHC class II antigen DRB1*1) (DR-1) (DR1) | HLA-DRB1 | 266 |
| P20039 | 2B1B_HUMAN | HLA class II histocompatibility antigen, DRB1-11 beta chain (DR-5) (DRw11) (MHC class II antigen DRB1*11) | HLA-DRB1 | 266 |
| P01911 | 2B1F_HUMAN | HLA class II histocompatibility antigen, DRB1-15 beta chain (DW2.2/DR2.2) (MHC class II antigen DRB1*15) | HLA-DRB1 HLA-DRB2 | 266 |
| O14672 | ADA10_HUMAN | Disintegrin and metalloproteinase domain-containing protein 10 (ADAM 10) (EC 3.4.24.81) (CDw156) (Kuzbanian protein homolog) (Mammalian disintegrin-metalloprotease) (CD antigen CD156c) | ADAM10 KUZ MADM | 748 |
| Q13444 | ADA15_HUMAN | Disintegrin and metalloproteinase domain-containing protein 15 (ADAM 15) (EC 3.4.24.—) (Metalloprotease RGD disintegrin protein) (Metalloproteinase-like, disintegrin-like, and cysteine-rich protein 15) (MDC-15) (Metargidin) | ADAM15 MDC15 | 863 |
| O75077 | ADA23_HUMAN | Disintegrin and metalloproteinase domain-containing protein 23 (ADAM 23) (Metalloproteinase-like, disintegrin-like, and cysteine-rich protein 3) (MDC-3) | ADAM23 MDC3 | 832 |
| P30455 | 1A36_HUMAN | HLA class I histocompatibility antigen, A-36 alpha chain (Aw-36) (MHC class I antigen A*36) | HLA-A HLAA | 365 |
| P30459 | 1A74_HUMAN | HLA class I histocompatibility antigen, A-74 alpha chain (Aw-19) (Aw-74) (MHC class I antigen A*74) | HLA-A HLAA | 365 |
| P30493 | 1B55_HUMAN | HLA class I histocompatibility antigen, B-55 alpha chain (Bw-55) (HLA class I histocompatibility antigen, B-12 alpha chain) (MHC class I antigen B*55) | HLA-B HLAB CDABP0067 | 362 |
| O43184 | ADA12_HUMAN | Disintegrin and metalloproteinase domain-containing protein 12 (ADAM 12) (EC 3.4.24.—) (Meltrin-alpha) | ADAM12 MLTN UNQ346/PRO545 | 909 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9Y3Q7 | ADA18_HUMAN | Disintegrin and metalloproteinase domain-containing protein 18 (ADAM 18) (Transmembrane metalloproteinase-like, disintegrin-like, and cysteine-rich protein III) (tMDC III) | ADAM18 TMDC3 UNQ858/PRO1867 | 739 |
| Q9H013 | ADA19_HUMAN | Disintegrin and metalloproteinase domain-containing protein 19 (ADAM 19) (EC 3.4.24.—) (Meltrin-beta) (Metalloprotease and disintegrin dendritic antigen marker) (MADDAM) | ADAM19 MLTNB FKSG34 | 955 |
| Q9UKF5 | ADA29_HUMAN | Disintegrin and metalloproteinase domain-containing protein 29 (ADAM 29) (Cancer/testis antigen 73) (CT73) | ADAM29 | 820 |
| Q8TC27 | ADA32_HUMAN | Disintegrin and metalloproteinase domain-containing protein 32 (ADAM 32) | ADAM32 UNQ5982/PRO21340 | 787 |
| Q9BZ11 | ADA33_HUMAN | Disintegrin and metalloproteinase domain-containing protein 33 (ADAM 33) (EC 3.4.24.—) | ADAM33 C20orf153 UNQ873/PRO1891 | 813 |
| P05067 | A4_HUMAN | Amyloid beta A4 protein (ABPP) (APP) (Alzheimer disease amyloid protein) (Amyloid precursor protein) (Beta-amyloid precursor protein) (Cerebral vascular amyloid peptide) (CVAP) (PreA4) (Protease nexin-II) (PN-II) [Cleaved into: N-APP; Soluble APP-alpha (S-APP-alpha); Soluble APP-beta (S-APP-beta); C99; Beta-amyloid protein 42 (Beta-APP42); Beta-amyloid protein 40 (Beta-APP40); C83; P3(42); P3(40); C80; Gamma-secretase C-terminal fragment 59 (Amyloid intracellular domain 59) (AICD-59) (AID(59)) (Gamma-CTF(59)); Gamma-secretase C-terminal fragment 57 (Amyloid intracellular domain 57) (AICD-57) (AID(57)) (Gamma-CTF(57)); Gamma-secretase C-terminal fragment 50 (Amyloid intracellular domain 50) (AICD-50) (AID(50)) (Gamma-CTF(50)); C31] | APP A4 AD1 | 770 |
| P12821 | ACE_HUMAN | Angiotensin-converting enzyme (ACE) (EC 3.2.1.—) (EC 3.4.15.1) (Dipeptidyl carboxypeptidase I) (Kininase II) (CD antigen CD143) [Cleaved into: Angiotensin-converting enzyme, soluble form] | ACE DCP DCP1 | 1306 |
| Q04771 | ACVR1_HUMAN | Activin receptor type-1 (EC 2.7.11.30) (Activin receptor type I) (ACTR-I) (Activin receptor-like kinase 2) (ALK-2) (Serine/threonine-protein kinase receptor R1) (SKR1) (TGF-B superfamily receptor type I) (TSR-I) | ACVR1 ACVRLK2 | 509 |
| Q8NER5 | ACV1C_HUMAN | Activin receptor type-1C (EC 2.7.11.30) (Activin receptor type 1C) (ACTR-IC) (Activin receptor-like kinase 7) (ALK-7) | ACVR1C ALK7 | 493 |
| Q9H2U9 | ADAM7_HUMAN | Disintegrin and metalloproteinase domain-containing protein 7 (ADAM 7) (Sperm maturation-related glycoprotein GP-83) | ADAM7 GP83 | 754 |
| P36896 | ACV1B_HUMAN | Activin receptor type-1B (EC 2.7.11.30) (Activin receptor type IB) (ACTR-IB) (Activin receptor-like kinase 4) (ALK-4) (Serine/threonine-protein kinase receptor R2) (SKR2) | ACVR1B ACVRLK4 ALK4 | 505 |
| O75078 | ADA11_HUMAN | Disintegrin and metalloproteinase domain-containing protein 11 (ADAM 11) (Metalloproteinase-like, disintegrin-like, and cysteine-rich protein) (MDC) | ADAM11 MDC | 769 |
| P78536 | ADA17_HUMAN | Disintegrin and metalloproteinase domain-containing protein 17 (ADAM 17) (EC 3.4.24.86) (Snake venom-like protease) (TNF-alpha convertase) (TNF-alpha-converting enzyme) (CD antigen CD156b) | ADAM17 CSVP TACE | 824 |
| Q9P0K1 | ADA22_HUMAN | Disintegrin and metalloproteinase domain-containing protein 22 (ADAM 22) (Metalloproteinase-disintegrin ADAM22-3) (Metalloproteinase-like, disintegrin-like, and cysteine-rich protein 2) | ADAM22 MDC2 | 906 |
| Q9UKQ2 | ADA28_HUMAN | Disintegrin and metalloproteinase domain-containing protein 28 (ADAM 28) (EC 3.4.24.—) (Epididymal metalloproteinase-like, disintegrin-like, and cysteine-rich protein II) (eMDC II) (Metalloproteinase-like, disintegrin-like, and cysteine-rich protein L) (MDC-L) | ADAM28 ADAM23 MDCL | 775 |
| Q9UKF2 | ADA30_HUMAN | Disintegrin and metalloproteinase domain-containing protein 30 (ADAM 30) (EC 3.4.24.—) | ADAM30 UNQ2509/PRO5997 | 790 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P19021 | AMD_HUMAN | Peptidyl-glycine alpha-amidating monooxygenase (PAM) [Includes: Peptidylglycine alpha-hydroxylating monooxygenase (PHM) (EC 1.14.17.3); Peptidyl-alpha-hydroxyglycine alpha-amidating lyase (EC 4.3.2.5) (Peptidylamidoglycolate lyase) (PAL)] | PAM | 973 |
| Q86SJ2 | AMIGO2_HUMAN | Amphoterin-induced protein 2 (AMIGO-2) (Alivin-1) (Differentially expressed in gastric adenocarcinomas) (DEGA) | AMIGO2 ALI1 | 522 |
| Q16671 | AMHR2_HUMAN | Anti-Muellerian hormone type-2 receptor (EC 2.7.11.30) (Anti-Muellerian hormone type II receptor) (AMH type II receptor) (MIS type II receptor) (MISRII) (MRII) | AMHR2 AMHR MISR2 | 573 |
| P37023 | ACVL1_HUMAN | Serine/threonine-protein kinase receptor R3 (SKR3) (EC 2.7.11.30) (Activin receptor-like kinase 1) (ALK-1) (TGF-B superfamily receptor type I) (TSR-I) | ACVRL1 ACVRLK1 ALK1 | 503 |
| Q13443 | ADAM9_HUMAN | Disintegrin and metalloproteinase domain-containing protein 9 (ADAM 9) (EC 3.4.24.—) (Cellular disintegrin-related protein) (Meltrin-gamma) (Metalloprotease/disintegrin/cysteine-rich protein 9) (Myeloma cell metalloproteinase) | ADAM9 KIAA0021 MCMP MDC9 MLTNG | 819 |
| O43506 | ADA20_HUMAN | Disintegrin and metalloproteinase domain-containing protein 20 (ADAM 20) (EC 3.4.24.—) | ADAM20 | 726 |
| Q9UKJ8 | ADA21_HUMAN | Disintegrin and metalloproteinase domain-containing protein 21 (ADAM 21) (EC 3.4.24.—) | ADAM21 | 722 |
| Q99965 | ADAM2_HUMAN | Disintegrin and metalloproteinase domain-containing protein 2 (ADAM 2) (Cancer/testis antigen 15) (CT15) (Fertilin subunit beta) (PH-30) (PH30-beta) | ADAM2 FTNB | 735 |
| P78325 | ADAM8_HUMAN | Disintegrin and metalloproteinase domain-containing protein 8 (ADAM 8) (EC 3.4.24.—) (Cell surface antigen MS2) (CD antigen CD156a) | ADAM8 MS2 | 824 |
| Q9H6X2 | ANTR1_HUMAN | Anthrax toxin receptor 1 (Tumor endothelial marker 8) | ANTXR1 ATR TEM8 | 564 |
| P58335 | ANTR2_HUMAN | Anthrax toxin receptor 2 (Capillary morphogenesis gene 2 protein) (CMG-2) | ANTXR2 CMG2 | 489 |
| Q86WK6 | AMGO1_HUMAN | Amphoterin-induced protein 1 (AMIGO-1) (Alivin-2) | AMIGO1 ALI2 AMIGO KIAA1163 | 493 |
| P16066 | ANPRA_HUMAN | Atrial natriuretic peptide receptor 1 (EC 4.6.1.2) (Atrial natriuretic peptide receptor type A) (ANP-A) (ANPR-A) (NPR-A) (Guanylate cyclase A) (GC-A) | NPR1 ANPRA | 1061 |
| Q6UXC1 | AEGP_HUMAN | Apical endosomal glycoprotein (MAM domain-containing protein 4) | MAMDC4 AEGP UNQ3001/PRO9742 | 1216 |
| Q9BXJ7 | AMNLS_HUMAN | Protein amnionless | AMN UNQ513/PRO1028 | 453 |
| P20594 | ANPRB_HUMAN | Atrial natriuretic peptide receptor 2 (EC 4.6.1.2) (Atrial natriuretic peptide receptor type B) (ANP-B) (ANPR-B) (NPR-B) (Guanylate cyclase B) (GC-B) | NPR2 ANPRB | 1047 |
| Q8IU25 | APCD1_HUMAN | Protein APCDD1 (Adenomatosis polyposis coli down-regulated 1 protein) | APCDD1 DRAPC1 FP7019 | 514 |
| P51693 | APLP1_HUMAN | Amyloid-like protein 1 (APLP) (APLP-1) [Cleaved into: C30] | APLP1 | 650 |
| Q9UM73 | ALK_HUMAN | ALK tyrosine kinase receptor (EC 2.7.10.1) (Anaplastic lymphoma kinase) (CD antigen CD246) | ALK | 1620 |
| A6NF34 | ANTRL_HUMAN | Anthrax toxin receptor-like | ANTXRL | 631 |
| Q86WK7 | AMGO3_HUMAN | Amphoterin-induced protein 3 (AMIGO-3) (Alivin-3) | AMIGO3 ALI3 KIAA1851 UNQ6084/PRO20089 | 504 |
| P17342 | ANPRC_HUMAN | Atrial natriuretic peptide receptor 3 (Atrial natriuretic peptide clearance receptor) (Atrial natriuretic peptide receptor type C) (ANP-C) (ANPR-C) (NPR-C) | NPR3 ANPRC C5orf23 NPRC | 541 |
| Q06481 | APLP2_HUMAN | Amyloid-like protein 2 (APLP-2) (APPH) (Amyloid protein homolog) (CDEI box-binding protein) (CDEBP) | APLP2 APPL2 | 763 |
| Q13705 | AVR2B_HUMAN | Activin receptor type-2B (EC 2.7.11.30) (Activin receptor type IIB) (ACTR-IIB) | ACVR2B | 512 |
| P35613 | BASI_HUMAN | Basigin (5F7) (Collagenase stimulatory factor) (Extracellular matrix metalloproteinase inducer) (EMMPRIN) (Leukocyte activation antigen M6) (OK blood group antigen) (Tumor cell-derived collagenase stimulatory factor) (TCSF) (CD antigen CD147) | BSG UNQ6505/PRO21383 | 385 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P50895 | BCAM_HUMAN | Basal cell adhesion molecule (Auberger B antigen) (B-CAM cell surface glycoprotein) (F8/G253 antigen) (Lutheran antigen) (Lutheran blood group glycoprotein) (CD antigen CD239) | BCAM LU MSK19 | 628 |
| O75882 | ATRN_HUMAN | Attractin (DPPT-L) (Mahogany homolog) | ATRN KIAA0548 MGCA | 1429 |
| Q9Y5Z0 | BACE2_HUMAN | Beta-secretase 2 (EC 3.4.23.45) (Aspartic-like protease 56 kDa) (Aspartyl protease 1) (ASP1) (Asp 1) (Beta-site amyloid precursor protein cleaving enzyme 2) (Beta-site APP cleaving enzyme 2) (Down region aspartic protease) (DRAP) (Memapsin-1) (Membrane-associated aspartic protease 1) (Theta-secretase) | BACE2 AEPLC ALP56 ASP21 CDA13 UNQ418/PRO852 | 518 |
| Q13145 | BAMBI_HUMAN | BMP and activin membrane-bound inhibitor homolog (Non-metastatic gene A protein) (Putative transmembrane protein NMA) | BAMBI NMA | 260 |
| P36894 | BMR1A_HUMAN | Bone morphogenetic protein receptor type-1A (BMP type-1A receptor) (BMPR-1A) (EC 2.7.11.30) (Activin receptor-like kinase 3) (ALK-3) (Serine/threonine-protein kinase receptor R5) (SKR5) (CD antigen CD292) | BMPR1A ACVRLK3 ALK3 | 532 |
| P56817 | BACE1_HUMAN | Beta-secretase 1 (EC 3.4.23.46) (Aspartyl protease 2) (ASP2) (Asp 2) (Beta-site amyloid precursor protein cleaving enzyme 1) (Beta-site APP cleaving enzyme 1) (Memapsin-2) (Membrane-associated aspartic protease 2) | BACE1 BACE KIAA1149 | 501 |
| Q5VV63 | ATRNL1_HUMAN | Attractin-like protein 1 | ATRNL1 KIAA0534 | 1379 |
| P27037 | AVR2A_HUMAN | Activin receptor type-2A (EC 2.7.11.30) (Activin receptor type IIA) (ACTR-IIA) (ACTRIIA) | ACVR2A ACVR2 | 513 |
| Q9BWV1 | BOC_HUMAN | Brother of CDO (Protein BOC) | BOC UNQ604/PRO1190 | 1114 |
| O00238 | BMR1B_HUMAN | Bone morphogenetic protein receptor type-1B (BMP type-1B receptor) (BMPR-1B) (EC 2.7.11.30) (CD antigen CDw293) | BMPR1B | 502 |
| O00481 | BT3A1_HUMAN | Butyrophilin subfamily 3 member A1 (CD antigen CD277) | BTN3A1 BTF5 | 513 |
| Q7Z6A9 | BTLA_HUMAN | B- and T-lymphocyte attenuator (B- and T-lymphocyte-associated protein) (CD antigen CD272) | BTLA | 289 |
| Q96KV6 | BT2A3_HUMAN | Putative butyrophilin subfamily 2 member A3 | BTN2A3P BTN2A3 | 586 |
| P78410 | BT3A2_HUMAN | Butyrophilin subfamily 3 member A2 | BTN3A2 BT3.2 BTF3 BTF4 | 334 |
| Q6UXE8 | BTNL3_HUMAN | Butyrophilin-like protein 3 (Butyrophilin-like receptor) | BTNL3 BTNLR COLF4100 UNQ744/PRO1472 | 466 |
| Q6UXG8 | BTNL9_HUMAN | Butyrophilin-like protein 9 | BTNL9 UNQ1900/PRO4346 | 535 |
| Q5SY80 | CA101_HUMAN | Uncharacterized protein C1orf101 | C1orf101 | 951 |
| F2Z333 | CA233_HUMAN | Fibronectin type-III domain-containing transmembrane protein C1orf233 | C1orf233 | 226 |
| Q13410 | BT1A1_HUMAN | Butyrophilin subfamily 1 member A1 (BT) | BTN1A1 BTN | 526 |
| Q8WVV5 | BT2A2_HUMAN | Butyrophilin subfamily 2 member A2 | BTN2A2 BT2.2 BTF2 | 523 |
| O00478 | BT3A3_HUMAN | Butyrophilin subfamily 3 member A3 | BTN3A3 BTF3 | 584 |
| Q6UX41 | BTNL8_HUMAN | Butyrophilin-like protein 8 | BTNL8 UNQ702/PRO1347 | 500 |
| Q6UWJ8 | C16L2_HUMAN | CD164 sialomucin-like 2 protein | CD164L2 | 174 |
| P55289 | CAD12_HUMAN | Cadherin-12 (Brain cadherin) (BR-cadherin) (Neural type cadherin 2) (N-cadherin 2) | CDH12 | 794 |
| Q9UJ99 | CAD22_HUMAN | Cadherin-22 (Pituitary and brain cadherin) (PB-cadherin) | CDH22 C20orf25 UNQ6122/PRO20044 | 828 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9H251 | CAD23_HUMAN | Cadherin-23 (Otocadherin) | CDH23 KIAA1774 KIAA1812 UNQ1894/PRO4340 | 3354 |
| Q8IXH8 | CAD26_HUMAN | Cadherin-like protein 26 (Cadherin-like protein VR20) | CDH26 | 852 |
| P19022 | CADH2_HUMAN | Cadherin-2 (CDw325) (Neural cadherin) (N-cadherin) (CD antigen CD325) | CDH2 CDHN NCAD | 906 |
| P55285 | CADH6_HUMAN | Cadherin-6 (Kidney cadherin) (K-cadherin) | CDH6 | 790 |
| Q9ULB5 | CADH7_HUMAN | Cadherin-7 | CDH7 CDH7L1 | 785 |
| P55286 | CADH8_HUMAN | Cadherin-8 | CDH8 | 799 |
| Q9ULX7 | CAH14_HUMAN | Carbonic anhydrase 14 (EC 4.2.1.1) (Carbonate dehydratase XIV) (Carbonic anhydrase XIV) (CA-XIV) | CA14 | 337 |
| Q5VU97 | CAHD1_HUMAN | VWFA and cache domain-containing protein 1 (Cache domain-containing protein 1) | CACHD1 KIAA1573 VWCD1 | 1274 |
| P27824 | CALX_HUMAN | Calnexin (IP90) (Major histocompatibility complex class I antigen-binding protein p88) (p90) | CANX | 592 |
| Q13873 | BMPR2_HUMAN | Bone morphogenetic protein receptor type-2 (BMP type-2 receptor) (BMPR-2) (EC 2.7.11.30) (Bone morphogenetic protein receptor type II) (BMP type II receptor) (BMPR-II) | BMPR2 PPH1 | 1038 |
| Q7KYR7 | BT2A1_HUMAN | Butyrophilin subfamily 2 member A1 | BTN2A1 BT2.1 BTF1 | 527 |
| P35070 | BTC_HUMAN | Probetacellulin [Cleaved into: Betacellulin (BTC)] | BTC | 178 |
| Q86VB7 | C163A_HUMAN | Scavenger receptor cysteine-rich type 1 protein M130 (Hemoglobin scavenger receptor) (CD antigen CD163) [Cleaved into: Soluble CD163 (sCD163)] | CD163 M130 | 1156 |
| Q8TCZ2 | C99L2_HUMAN | CD99 antigen-like protein 2 (MIC2-like protein 1) (CD antigen CD99) | CD99L2 MIC2L1 UNQ1964/PRO4486 | 262 |
| Q8IZS8 | CA2D3_HUMAN | Voltage-dependent calcium channel subunit alpha-2/delta-3 (Voltage-gated calcium channel subunit alpha-2/delta-3) [Cleaved into: Voltage-dependent calcium channel subunit alpha-2-3; Voltage-dependent calcium channel subunit delta-3] | CACNA2D3 | 1091 |
| Q7Z3S7 | CA2D4_HUMAN | Voltage-dependent calcium channel subunit alpha-2/delta-4 (Voltage-gated calcium channel subunit alpha-2/delta-4) [Cleaved into: Voltage-dependent calcium channel subunit alpha-2-4; Voltage-dependent calcium channel subunit delta-4] | CACNA2D4 | 1137 |
| Q9Y6N8 | CAD10_HUMAN | Cadherin-10 (T2-cadherin) | CDH10 | 788 |
| Q12864 | CAD17_HUMAN | Cadherin-17 (Intestinal peptide-associated transporter HPT-1) (Liver-intestine cadherin) (LI-cadherin) | CDH17 | 832 |
| P55283 | CADH4_HUMAN | Cadherin-4 (Retinal cadherin) (R-CAD) (R-cadherin) | CDH4 | 916 |
| P33151 | CADH5_HUMAN | Cadherin-5 (7B4 antigen) (Vascular endothelial cadherin) (VE-cadherin) (CD antigen CD144) | CDH5 | 784 |
| Q8NFZ8 | CADM4_HUMAN | Cell adhesion molecule 4 (Immunoglobulin superfamily member 4C) (IgSF4C) (Nectin-like protein 4) (NECL-4) (TSLC1-like protein 2) | CADM4 IGSF4C NECL4 TSLL2 | 388 |
| Q9NPY3 | C1QR1_HUMAN | Complement component C1q receptor (C1q/MBL/SPA receptor) (C1qR(p)) (C1qRp) (CDw93) (Complement component 1 q subcomponent receptor 1) (Matrix-remodeling-associated protein 4) (CD antigen CD93) | CD93 C1QR1 MXRA4 | 652 |
| Q9NY47 | CA2D2_HUMAN | Voltage-dependent calcium channel subunit alpha-2/delta-2 (Voltage-gated calcium channel subunit alpha-2/delta-2) [Cleaved into: Voltage-dependent calcium channel subunit alpha-2-2; Voltage-dependent calcium channel subunit delta-2] | CACNA2D2 KIAA0558 | 1150 |
| Q8N3J6 | CADM2_HUMAN | Cell adhesion molecule 2 (Immunoglobulin superfamily member 4D) (IgSF4D) (Nectin-like protein 3) (NECL-3) (Synaptic cell adhesion molecule 2) (SynCAM 2) | CADM2 IGSF4D NECL3 | 435 |
| Q13634 | CAD18_HUMAN | Cadherin-18 (Cadherin-14) | CDH18 CDH14 | 790 |
| A8MVZ5 | BTNLA_HUMAN | Butyrophilin-like protein 10 | BTNL10 | 291 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9NR16 | C163B_HUMAN | Scavenger receptor cysteine-rich type 1 protein M160 (CD163 antigen-like 1) (CD antigen CD163b) | CD163L1 CD163B M160 UNQ6434/PRO23202 | 1453 |
| P54289 | CA2D1_HUMAN | Voltage-dependent calcium channel subunit alpha-2/delta-1 (Voltage-gated calcium channel subunit alpha-2/delta-1) [Cleaved into: Voltage-dependent calcium channel subunit alpha-2-1; Voltage-dependent calcium channel subunit delta-1] | CACNA2D1 CACNL2A CCHL2A MHS3 | 1103 |
| Q86UP0 | CAD24_HUMAN | Cadherin-24 | CDH24 CDH11L UNQ2834/PRO34009 | 819 |
| Q9BY67 | CADM1_HUMAN | Cell adhesion molecule 1 (Immunoglobulin superfamily member 4) (IgSF4) (Nectin-like protein 2) (NECL-2) (Spermatogenic immunoglobulin superfamily) (SgIgSF) (Synaptic cell adhesion molecule) (SynCAM) (Tumor suppressor in lung cancer 1) (TSLC-1) | CADM1 IGSF4 IGSF4A NECL2 SYNCAM TSLC1 | 442 |
| Q9HBT6 | CAD20_HUMAN | Cadherin-20 | CDH20 CDH7L3 | 801 |
| Q16790 | CAH9_HUMAN | Carbonic anhydrase 9 (EC 4.2.1.1) (Carbonate dehydratase IX) (Carbonic anhydrase IX) (CA-IX) (CAIX) (Membrane antigen MN) (P54/58N) (Renal cell carcinoma-associated antigen G250) (RCC-associated antigen G250) (pMW1) | CA9 G250 MN | 459 |
| O75976 | CBPD_HUMAN | Carboxypeptidase D (EC 3.4.17.22) (Metallocarboxypeptidase D) (gp180) | CPD | 1380 |
| P55287 | CAD11_HUMAN | Cadherin-11 (OSF-4) (Osteoblast cadherin) (OB-cadherin) | CDH11 | 796 |
| P55291 | CAD15_HUMAN | Cadherin-15 (Cadherin-14) (Muscle cadherin) (M-cadherin) | CDH15 CDH14 CDH3 | 814 |
| O75309 | CAD16_HUMAN | Cadherin-16 (Kidney-specific cadherin) (Ksp-cadherin) | CDH16 UNQ695/PRO1340 | 829 |
| Q9H159 | CAD19_HUMAN | Cadherin-19 | CDH19 CDH7L2 UNQ478/PRO941 | 772 |
| P12830 | CADH1_HUMAN | Cadherin-1 (CAM 120/80) (Epithelial cadherin) (E-cadherin) (Uvomorulin) (CD antigen CD324) [Cleaved into: E-Cad/CTF1; E-Cad/CTF2; E-Cad/CTF3] | CDH1 CDHE UVO | 882 |
| P22223 | CADH3_HUMAN | Cadherin-3 (Placental cadherin) (P-cadherin) | CDH3 CDHP | 829 |
| Q9ULB4 | CADH9_HUMAN | Cadherin-9 | CDH9 | 789 |
| Q8N126 | CADM3_HUMAN | Cell adhesion molecule 3 (Brain immunoglobulin receptor) (Immunoglobulin superfamily member 4B) (IgSF4B) (Nectin-like protein 1) (NECL-1) (Synaptic cell adhesion molecule 3) (SynCAM3) (TSLC1-like protein 1) (TSLL1) | CADM3 IGSF4B NECL1 SYNCAM3 TSLL1 UNQ225/PRO258 | 398 |
| O43570 | CAH12_HUMAN | Carbonic anhydrase 12 (EC 4.2.1.1) (Carbonate dehydratase XII) (Carbonic anhydrase XII) (CA-XII) (Tumor antigen HOM-RCC-3.1.3) | CA12 | 354 |
| P15813 | CD1D_HUMAN | Antigen-presenting glycoprotein CD1d (R3G1) (CD antigen CD1d) | CD1D | 335 |
| Q9BZW8 | CD244_HUMAN | Natural killer cell receptor 2B4 (NK cell activation-inducing ligand) (NAIL) (NK cell type I receptor protein 2B4) (NKR2B4) (h2B4) (SLAM family member 4) (SLAMF4) (Signaling lymphocytic activation molecule 4) (CD antigen CD244) | CD244 2B4 | 370 |
| Q5ZPR3 | CD276_HUMAN | CD276 antigen (4Ig-B7-H3) (B7 homolog 3) (B7-H3) (Costimulatory molecule) (CD antigen CD276) | CD276 B7H3 PSEC0249 UNQ309/PRO352 | 534 |
| P34810 | CD68_HUMAN | Macrosialin (Gp110) (CD antigen CD68) | CD68 | 354 |
| P40259 | CD79B_HUMAN | B-cell antigen receptor complex-associated protein beta chain (B-cell-specific glycoprotein B29) (Ig-beta) (Immunoglobulin-associated B29 protein) (CD antigen CD79b) | CD79B B29 IGB | 229 |
| P01732 | CD8A_HUMAN | T-cell surface glycoprotein CD8 alpha chain (T-lymphocyte differentiation antigen T8/Leu-2) (CD antigen CD8a) | CD8A MAL | 235 |
| P06126 | CD1A_HUMAN | T-cell surface glycoprotein CD1a (T-cell surface antigen T6/Leu-6) (hTa1 thymocyte antigen) (CD antigen CD1a) | CD1A | 327 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P20273 | CD22_HUMAN | B-cell receptor CD22 (B-lymphocyte cell adhesion molecule) (BL-CAM) (Sialic acid-binding Ig-like lectin 2) (Siglec-2) (T-cell surface antigen Leu-14) (CD antigen CD22) | CD22 SIGLEC2 | 847 |
| P06127 | CD5_HUMAN | T-cell surface glycoprotein CD5 (Lymphocyte antigen T1/Leu-1) (CD antigen CD5) | CD5 LEU1 | 495 |
| P10966 | CD8B_HUMAN | T-cell surface glycoprotein CD8 beta chain (CD antigen CD8b) | CD8B CD8B1 | 210 |
| P14209 | CD99_HUMAN | CD99 antigen (12E7) (E2 antigen) (Protein MIC2) (T-cell surface glycoprotein E2) (CD antigen CD99) | CD99 MIC2 MIC2X MIC2Y | 185 |
| P29017 | CD1C_HUMAN | T-cell surface glycoprotein CD1c (CD antigen CD1c) | CD1C | 333 |
| P10747 | CD28_HUMAN | T-cell-specific surface glycoprotein CD28 (TP44) (CD antigen CD28) | CD28 | 220 |
| A6NJW9 | CD8BL_HUMAN | Putative T-cell surface glycoprotein CD8 beta-2 chain (CD8b pseudogene) | CD8BP CD8B2 | 211 |
| Q9BYE9 | CDHR2_HUMAN | Cadherin-related family member 2 (Protocadherin LKC) (PC-LKC) (Protocadherin-24) | CDHR2 PCDH24 PCLKC | 1310 |
| Q9HBB8 | CDHR5_HUMAN | Cadherin-related family member 5 (Mu-protocadherin) (Mucin and cadherin-like protein) (Mucin-like protocadherin) (MLPCDH) | CDHR5 MUCDHL MUPCDH UNQ2781/PRO7168 | 845 |
| Q6UY09 | CEA20_HUMAN | Carcinoembryonic antigen-related cell adhesion molecule 20 | CEACAM20 UNQ9366/PRO34155 | 585 |
| Q3KPI0 | CEA21_HUMAN | Carcinoembryonic antigen-related cell adhesion molecule 21 | CEACAM21 UNQ3098/PRO10075 | 293 |
| P15391 | CD19_HUMAN | B-lymphocyte antigen CD19 (B-lymphocyte surface antigen B4) (Differentiation antigen CD19) (T-cell surface antigen Leu-12) (CD antigen CD19) | CD19 | 556 |
| P15812 | CD1E_HUMAN | T-cell surface glycoprotein CD1e, membrane-associated (hCD1e) (R2G1) (CD antigen CD1e) [Cleaved into: T-cell surface glycoprotein CD1e, soluble (sCD1e)] | CD1E | 388 |
| Q15762 | CD226_HUMAN | CD226 antigen (DNAX accessory molecule 1) (DNAM-1) (CD antigen CD226) | CD226 DNAM1 | 336 |
| P26842 | CD27_HUMAN | CD27 antigen (CD27L receptor) (T-cell activation antigen CD27) (T14) (Tumor necrosis factor receptor superfamily member 7) (CD antigen CD27) | CD27 TNFRSF7 | 260 |
| P06729 | CD2_HUMAN | T-cell surface antigen CD2 (Erythrocyte receptor) (LFA-2) (LFA-3 receptor) (Rosette receptor) (T-cell surface antigen T11/Leu-5) (CD antigen CD2) | CD2 SRBC | 351 |
| Q9NPF0 | CD320_HUMAN | CD320 antigen (8D6 antigen) (FDC-signaling molecule 8D6) (FDC-SM-8D6) (Transcobalamin receptor) (TCblR) (CD antigen CD320) | CD320 8D6A UNQ198/PRO224 | 282 |
| P04234 | CD3D_HUMAN | T-cell surface glycoprotein CD3 delta chain (T-cell receptor T3 delta chain) (CD antigen CD3d) | CD3D T3D | 171 |
| P16070 | CD44_HUMAN | CD44 antigen (CDw44) (Epican) (Extracellular matrix receptor III) (ECMR-III) (GP90 lymphocyte homing/adhesion receptor) (HUTCH-I) (Heparan sulfate proteoglycan) (Hermes antigen) (Hyaluronate receptor) (Phagocytic glycoprotein 1) (PGP-1) (Phagocytic glycoprotein I) (PGP-I) (CD antigen CD44) | CD44 LHR MDU2 MDU3 MIC4 | 742 |
| P30203 | CD6_HUMAN | T-cell differentiation antigen CD6 (T12) (TP120) (CD antigen CD6) [Cleaved into: Soluble CD6] | CD6 | 668 |
| P33681 | CD80_HUMAN | T-lymphocyte activation antigen CD80 (Activation B7-1 antigen) (BB1) (CTLA-4 counter-receptor B7.1) (B7) (CD antigen CD80) | CD80 CD28LG CD28LG1 LAB7 | 288 |
| P13688 | CEAM1_HUMAN | Carcinoembryonic antigen-related cell adhesion molecule 1 (Biliary glycoprotein 1) (BGP-1) (CD antigen CD66a) | CEACAM1 BGP BGP1 | 526 |
| P29016 | CD1B_HUMAN | T-cell surface glycoprotein CD1b (CD antigen CD1b) | CD1B | 333 |
| Q9HCU0 | CD248_HUMAN | Endosialin (Tumor endothelial marker 1) (CD antigen CD248) | CD248 CD164L1 TEM1 | 757 |
| P28906 | CD34_HUMAN | Hematopoietic progenitor cell antigen CD34 (CD antigen CD34) | CD34 | 385 |
| P07766 | CD3E_HUMAN | T-cell surface glycoprotein CD3 epsilon chain (T-cell surface antigen T3/Leu-4 epsilon chain) (CD antigen CD3e) | CD3E T3E | 207 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P09693 | CD3G_HUMAN | T-cell surface glycoprotein CD3 gamma chain (T-cell receptor T3 gamma chain) (CD antigen CD3g) | CD3G T3G | 182 |
| Q6ZTQ4 | CDHR3_HUMAN | Cadherin-related family member 3 (Cadherin-like protein 28) | CDHR3 CDH28 | 885 |
| P20963 | CD3Z_HUMAN | T-cell surface glycoprotein CD3 zeta chain (T-cell receptor T3 zeta chain) (CD antigen CD247) | CD247 CD3Z T3Z TCRZ | 164 |
| P11912 | CD79A_HUMAN | B-cell antigen receptor complex-associated protein alpha chain (Ig-alpha) (MB-1 membrane glycoprotein) (Membrane-bound immunoglobulin-associated protein) (Surface IgM-associated protein) (CD antigen CD79a) | CD79A IGA MB1 | 226 |
| O75871 | CEAM4_HUMAN | Carcinoembryonic antigen-related cell adhesion molecule 4 (Carcinoembryonic antigen CGM7) (Non-specific cross-reacting antigen W236) | CEACAM4 CGM7 | 244 |
| Q13740 | CD166_HUMAN | CD166 antigen (Activated leukocyte cell adhesion molecule) (CD antigen CD166) | ALCAM MEMD | 583 |
| Q99467 | CD180_HUMAN | CD180 antigen (Lymphocyte antigen 64) (Radioprotective 105 kDa protein) (CD antigen CD180) | CD180 LY64 RP105 | 661 |
| Q8IX05 | CD302_HUMAN | CD302 antigen (C-type lectin BIMLEC) (C-type lectin domain family 13 member A) (DEC205-associated C-type lectin 1) (Type I transmembrane C-type lectin receptor DCL-1) (CD antigen CD302) | CD302 CLEC13A DCL1KIAA0022 | 232 |
| P20138 | CD33_HUMAN | Myeloid cell surface antigen CD33 (Sialic acid-binding Ig-like lectin 3) (Siglec-3) (gp67) (CD antigen CD33) | CD33 SIGLEC3 | 364 |
| P01730 | CD4_HUMAN | T-cell surface glycoprotein CD4 (T-cell surface antigen T4/Leu-3) (CD antigen CD4) | CD4 | 458 |
| P09564 | CD7_HUMAN | T-cell antigen CD7 (GP40) (T-cell leukemia antigen) (T-cell surface antigen Leu-9) (TP41) (CD antigen CD7) | CD7 | 240 |
| Q01151 | CD83_HUMAN | CD83 antigen (hCD83) (B-cell activation protein) (Cell surface protein HB15) (CD antigen CD83) | CD83 | 205 |
| P42081 | CD86_HUMAN | T-lymphocyte activation antigen CD86 (Activation B7-2 antigen) (B70) (BU63) (CTLA-4 counter-receptor B7.2) (FUN-1) (CD antigen CD86) | CD86 CD28LG2 | 329 |
| A6H8M9 | CDHR4_HUMAN | Cadherin-related family member 4 (Cadherin-like protein 29) | CDHR4 CDH29 UNQ9392/PRO34300 | 788 |
| Q7Z692 | CEA19_HUMAN | Carcinoembryonic antigen-related cell adhesion molecule 19 (Carcinoembryonic antigen-like 1) | CEACAM19 CEAL1 UNQ2973/PRO7436 | 300 |
| P40198 | CEAM3_HUMAN | Carcinoembryonic antigen-related cell adhesion molecule 3 (Carcinoembryonic antigen CGM1) (CD antigen CD66d) | CEACAM3 CD66D CGM1 | 252 |
| Q9H9P2 | CHODL_HUMAN | Chondrolectin (Transmembrane protein MT75) | CHODL C21orf68 PRED12 UNQ872/PRO1890 | 273 |
| Q08708 | CLM6_HUMAN | CMRF35-like molecule 6 (CLM-6) (CD300 antigen-like family member C) (CMRF35-A1) (CMRF-35) (Immunoglobulin superfamily member 16) (IgSF16) (CD antigen CD300c) | CD300C CMRF35 CMRF35A CMRF35A1 IGSF16 | 224 |
| O14967 | CLGN_HUMAN | Calmegin | CLGN | 610 |
| Q496F6 | CLM2_HUMAN | CMRF35-like molecule 2 (CLM-2) (CD300 antigen-like family member E) (CMRF35-A5) (Immune receptor expressed on myeloid cells 2) (IREM-2) (Polymeric immunoglobulin receptor 2) (PIgR-2) (PIgR2) (Poly-Ig receptor 2) (CD antigen CD300e) | CD300E CD300LE CLM2 CMRF35A5 IREM2 | 205 |
| Q6UXG3 | CLM9_HUMAN | CMRF35-like molecule 9 (CLM-9) (CD300 antigen-like family member G) (Triggering receptor expressed on myeloid cells 4) (TREM-4) (CD antigen CD300g) | CD300LG CLM9 TREM4 UNQ422/PRO846 | 332 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9UQC9 | CLCA2_HUMAN | Calcium-activated chloride channel regulator 2 (EC 3.4.—.—.—) (Calcium-activated chloride channel family member 2) (hCLCA2) (Calcium-activated chloride channel protein 3) (CaCC-3) (hCaCC-3) [Cleaved into: Calcium-activated chloride channel regulator 2, 109 kDa form; Calcium-activated chloride channel regulator 2, 35 kDa form] | CLCA2 CACC3 | 943 |
| Q9H6B4 | CLMP_HUMAN | CXADR-like membrane protein (Adipocyte adhesion molecule) (Coxsackie- and adenovirus receptor-like membrane protein) (CAR-like membrane protein) | CLMP ACAM ASAM UNQ318/PRO363 | 373 |
| Q96F05 | CK024_HUMAN | Uncharacterized protein C11orf24 (Protein DM4E3) | C11orf24 FP2568 UNQ1872/PRO4315 | 449 |
| Q6NUJ2 | CK087_HUMAN | Uncharacterized protein C11orf87 | C11orf87 | 197 |
| A8K4G0 | CLM7_HUMAN | CMRF35-like molecule 7 (CLM-7) (CD300 antigen-like family member B) (CMRF35-A2) (Immune receptor expressed on myeloid cells 3) (IREM-3) (Leukocyte mono-Ig-like receptor 5) (Triggering receptor expressed on myeloid cells 5) (TREM-5) (CD antigen CD300b) | CD300LB CD300B CLM7 CMRF35A2 IREM3 LMIR5 TREM5 | 201 |
| Q9UGN4 | CLM8_HUMAN | CMRF35-like molecule 8 (CLM-8) (CD300 antigen-like family member A) (CMRF-35-H9) (CMRF35-H9) (CMRF35-H) (IRC1/IRC2) (Immunoglobulin superfamily member 12) (IgSF12) (Inhibitory receptor protein 60) (IRp60) (NK inhibitory receptor) (CD antigen CD300a) | CD300A CMRF35H IGSF12 HSPC083 UNQ2530/PRO6029 | 299 |
| Q96NU0 | CNT3B_HUMAN | Contactin-associated protein-like 3B (Cell recognition molecule Caspr3b) | CNTNAP3B CASPR3B | 1288 |
| P78357 | CNTP1_HUMAN | Contactin-associated protein 1 (Caspr) (Caspr1) (Neurexin IV) (Neurexin-4) (p190) | CNTNAP1 CASPR NRXN4 | 1384 |
| Q9UHC6 | CNTP2_HUMAN | Contactin-associated protein-like 2 (Cell recognition molecule Caspr2) | CNTNAP2 CASPR2 KIAA0868 | 1331 |
| Q9C0A0 | CNTP4_HUMAN | Contactin-associated protein-like 4 (Cell recognition molecule Caspr4) | CNTNAP4 CASPR4 KIAA1763 | 1308 |
| Q8WYK1 | CNTP5_HUMAN | Contactin-associated protein-like 5 (Cell recognition molecule Caspr5) | CNTNAP5 CASPR5 | 1306 |
| Q8TDQ1 | CLM1_HUMAN | CMRF35-like molecule 1 (CLM-1) (CD300 antigen-like family member F) (Immune receptor expressed on myeloid cells 1) (IREM-1) (Immunoglobulin superfamily member 13) (IgSF13) (NK inhibitory receptor) (CD antigen CD300f) | CD300LF CD300F CLM1 IGSF13 IREM1 NKIR UNQ3105/PRO10111 | 290 |
| Q5T292 | CJ128_HUMAN | Putative uncharacterized protein C10orf128 | C10orf128 | 105 |
| Q86T13 | CLC14_HUMAN | C-type lectin domain family 14 member A (Epidermal growth factor receptor 5) (EGFR-5) | CLEC14A C14orf27 EGFR5 UNQ236/PRO269 | 490 |
| Q6UXZ3 | CLM4_HUMAN | CMRF35-like molecule 4 (CLM-4) (CD300 antigen-like family member D) (CMRF35-A4) (CD antigen CD300d) | CD300LD CD300D CMRF35A4 UNQ9218/PRO28686 | 194 |
| Q9BZ76 | CNTP3_HUMAN | Contactin-associated protein-like 3 (Cell recognition molecule Caspr3) | CNTNAP3 CASPR3 KIAA1714 | 1288 |
| Q86TY3 | CN037_HUMAN | Uncharacterized protein C14orf37 | C14orf37 | 774 |
| Q9HC73 | CRLF2_HUMAN | Cytokine receptor-like factor 2 (Cytokine receptor-like factor 2) (IL-XR) (Thymic stromal lymphopoietin protein receptor) (TSLP receptor) | CRLF2 CRL2 ILXR TSLPR | 371 |
| Q9BVV8 | CS024_HUMAN | Uncharacterized membrane protein C19orf24 | C19orf24 | 132 |
| P09603 | CSF1_HUMAN | Macrophage colony-stimulating factor 1 (CSF-1) (M-CSF) (MCSF) (Lanimostim) [Cleaved into: Processed macrophage colony-stimulating factor 1] | CSF1 | 554 |
| Q5I48 | CRUM2_HUMAN | Protein crumbs homolog 2 (Crumbs-like protein 2) | CRB2 | 1285 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q96PZ7 | CSMD1_HUMAN | CUB and sushi domain-containing protein 1 (CUB and sushi multiple domains protein 1) | CSMD1 KIAA1890 UNQ5952/PRO19863 | 3565 |
| O95196 | CSPG5_HUMAN | Chondroitin sulfate proteoglycan 5 (Acidic leucine-rich EGF-like domain-containing brain protein) (Neuroglycan C) | CSPG5 CALEB NGC | 566 |
| Q9BUF7 | CRUM3_HUMAN | Protein crumbs homolog 3 | CRB3 UNQ588/PRO1158 | 120 |
| O94985 | CSTN1_HUMAN | Calsyntenin-1 (Alcadein-alpha) (Alc-alpha) (Alzheimer-related cadherin-like protein) (Non-classical cadherin XB31alpha) [Cleaved into: Soluble Alc-alpha (SAlc-alpha); CTF1-alpha (C-terminal fragment 1-alpha)] | CLSTN1 CS1 KIAA0911 | 981 |
| Q6ZRH7 | CTSRG_HUMAN | Cation channel sperm-associated protein subunit gamma | CATSPERG C19orf15 | 1159 |
| Q86UP6 | CUZD1_HUMAN | CUB and zona pellucida-like domain-containing protein 1 (CUB and ZP domain-containing protein 1) (Transmembrane protein UO-44) | CUZD1 UNQ224/PRO257 | 607 |
| Q5JRM2 | CX066_HUMAN | Uncharacterized protein CXorf66 | CXorf66 | 361 |
| Q8NEA5 | CS018_HUMAN | Uncharacterized protein C19orf18 | C19orf18 | 215 |
| P17927 | CR1_HUMAN | Complement receptor type 1 (C3b/C4b receptor) (CD antigen CD35) | CR1 C3BR | 2039 |
| P20023 | CR2_HUMAN | Complement receptor type 2 (Cr2) (Complement C3d receptor) (Epstein-Barr virus receptor) (EBV receptor) (CD antigen CD21) | CR2 C3DR | 1033 |
| P15509 | CSF2R_HUMAN | Granulocyte-macrophage colony-stimulating factor receptor subunit alpha (GM-CSF-R-alpha) (GMCSFR-alpha) (GMR-alpha) (CDw116) (CD antigen CD116) | CSF2RA CSF2R CSF2RY | 400 |
| Q99062 | CSF3R_HUMAN | Granulocyte colony-stimulating factor receptor (G-CSF receptor) (G-CSF-R) (CD antigen CD114) | CSF3R GCSFR | 836 |
| Q9BQT9 | CSTN3_HUMAN | Calsyntenin-3 (Alcadein-beta) (Alc-beta) | CLSTN3 CS3 KIAA0726 | 956 |
| Q9NZV1 | CRIM1_HUMAN | Cysteine-rich motor neuron 1 protein (CRIM-1) (Cysteine-rich repeat-containing protein S52) [Cleaved into: Processed cysteine-rich motor neuron 1 protein] | CRIM1 S52 UNQ1886/PRO4330 | 1036 |
| P82279 | CRUM1_HUMAN | Protein crumbs homolog 1 | CRB1 | 1406 |
| Q6UVK1 | CSPG4_HUMAN | Chondroitin sulfate proteoglycan 4 (Chondroitin sulfate proteoglycan NG2) (Melanoma chondroitin sulfate proteoglycan) (Melanoma-associated Chondroitin sulfate proteoglycan) | CSPG4 MCSP | 2322 |
| P16410 | CTLA4_HUMAN | Cytotoxic T-lymphocyte protein 4 (Cytotoxic T-lymphocyte-associated antigen 4) (CTLA-4) (CD antigen CD152) | CTLA4 CD152 | 223 |
| Q86XM0 | CTSRD_HUMAN | Cation channel sperm-associated protein subunit delta (CatSper-delta) (CatSperdelta) (Transmembrane protein 146) | CATSPERD TMEM146 | 798 |
| P78310 | CXAR_HUMAN | Coxsackievirus and adenovirus receptor (CAR) (hCAR) (CVB3-binding protein) (Coxsackievirus B-adenovirus receptor) (HCVADR) | CXADR CAR | 365 |
| O95727 | CRTAM_HUMAN | Cytotoxic and regulatory T-cell molecule (Class-I MHC-restricted T-cell-associated molecule) (CD antigen CD355) | CRTAM | 393 |
| P07333 | CSF1R_HUMAN | Macrophage colony-stimulating factor 1 receptor (CSF-1 receptor) (CSF-1R) (CSF-1R) (M-CSF-R) (EC 2.7.10.1) (Proto-oncogene c-Fms) (CD antigen CD115) | CSF1R FMS | 972 |
| Q4G0I0 | CSMT1_HUMAN | Protein CCSMST1 | CCSMST1 C16orf91 | 132 |
| Q9H4D0 | CSTN2_HUMAN | Calsyntenin-2 (Alcadein-gamma) (Alc-gamma) | CLSTN2 CS2 | 955 |
| Q9H2A7 | CXL16_HUMAN | C-X-C motif chemokine 16 (Scavenger receptor for phosphatidylserine and oxidized low density lipoprotein) (SR-PSOX) (Small-inducible cytokine B16) (Transmembrane chemokine CXCL16) | CXCL16 SCYB16 SRPSOX UNQ2759/PRO6714 | 254 |
| P08174 | DAF_HUMAN | Complement decay-accelerating factor (CD antigen CD55) | CD55 CR DAF | 381 |
| Q14118 | DAG1_HUMAN | Dystroglycan (Dystrophin-associated glycoprotein 1) [Cleaved into: Alpha-dystroglycan (Alpha-DG); Beta-dystroglycan (Beta-DG)] | DAG1 | 895 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q96J86 | CYYR1_HUMAN | Cysteine and tyrosine-rich protein 1 (Proline-rich domain-containing protein) | CYYR1 C21orf95 | 154 |
| P43146 | DCC_HUMAN | Netrin receptor DCC (Colorectal cancer suppressor) (Immunoglobulin superfamily DCC subclass member 1) (Tumor suppressor protein DCC) | DCC IGDCC1 | 1447 |
| Q08345 | DDR1_HUMAN | Epithelial discoidin domain-containing receptor 1 (Epithelial discoidin domain receptor 1) (EC 2.7.10.1) (CD167 antigen-like family member A) (Cell adhesion kinase) (Discoidin receptor tyrosine kinase) (HGK2) (Mammary carcinoma kinase 10) (MCK-10) (Protein-tyrosine kinase 3A) (Protein-tyrosine kinase RTK-6) (TRK E) (Tyrosine kinase DDR) (Tyrosine-protein kinase CAK) (CD antigen CD167a) | DDR1 CAK EDDR1 NEP NTRK4 PTK3A RTK6 TRKE | 913 |
| Q16832 | DDR2_HUMAN | Discoidin domain-containing receptor 2 (Discoidin domain receptor 2) (EC 2.7.10.1) (CD167 antigen-like family member B) (Discoidin domain-containing receptor tyrosine kinase 2) (Neurotrophic tyrosine kinase, receptor-related 3) (Receptor protein-tyrosine kinase TKT) (Tyrosine-protein kinase TYRO10) (CD antigen CD167b) | DDR2 NTRKR3 TKT TYRO10 | 855 |
| Q8N6Z6 | DCBD1_HUMAN | Discoidin, CUB and LCCL domain-containing protein 1 | DCBLD1 | 715 |
| Q96PD2 | DCBD2_HUMAN | Discoidin, CUB and LCCL domain-containing protein 2 (CUB, LCCL and coagulation factor V/VIII-homology domains protein 1) (Endothelial and smooth muscle cell-derived neuropilin-like protein) | DCBLD2 CLCP1 ESDN | 775 |
| P28068 | DMB_HUMAN | HLA class II histocompatibility antigen, DM beta chain (MHC class II antigen DMB) (Really interesting new gene 7 protein) | HLA-DMB DMB RING7 | 263 |
| P80370 | DLK1_HUMAN | Protein delta homolog 1 (DLK-1) (pG2) [Cleaved into: Fetal antigen 1 (FA1)] | DLK1 DLK | 383 |
| Q9NYJ7 | DLL3_HUMAN | Delta-like protein 3 (Drosophila Delta homolog 3) (Delta3) | DLL3 | 618 |
| P28067 | DMA_HUMAN | HLA class II histocompatibility antigen, DM alpha chain (MHC class II antigen DMA) (Really interesting new gene 6 protein) | HLA-DMA DMA RING6 | 261 |
| P06340 | DOA_HUMAN | HLA class II histocompatibility antigen, DO alpha chain (MHC DN-alpha) (MHC DZ alpha) (MHC class II antigen DOA) | HLA-DOA HLA-DNA HLA-DZA | 250 |
| Q6UY11 | DLK2_HUMAN | Protein delta homolog 2 (DLK-2) (Epidermal growth factor-like protein 9) (EGF-like protein 9) | DLK2 EGFL9 UNQ2903/PRO28633 | 383 |
| Q8NFT8 | DNER_HUMAN | Delta and Notch-like epidermal growth factor-related receptor | DNER BET UNQ262/PRO299 | 737 |
| P20036 | DPA1_HUMAN | HLA class II histocompatibility antigen, DP alpha 1 chain (DP(W3)) (DP(W4)) (HLA-SB alpha chain) (MHC class II DP3-alpha) (MHC class II DPA1) | HLA-DPA1 HLA-DP1A HLASB | 260 |
| P79483 | DRB3_HUMAN | HLA class II histocompatibility antigen, DR beta 3 chain (MHC class II antigen DRB3) | HLA-DRB3 | 266 |
| Q96KC8 | DNJC1_HUMAN | DnaJ homolog subfamily C member 1 (DnaJ protein homolog MTJ1) | DNAJC1 HTJ1 | 554 |
| Q8TD84 | DSCL1_HUMAN | Down syndrome cell adhesion molecule-like protein 1 (Down syndrome cell adhesion molecule 2) | DSCAML1 DSCAM2 KIAA1132 | 2053 |
| O00548 | DLL1_HUMAN | Delta-like protein 1 (Drosophila Delta homolog 1) (Delta1) (H-Delta-1) | DLL1 UNQ146/PRO172 | 723 |
| Q02487 | DSC2_HUMAN | Desmocollin-2 (Cadherin family member 2) (Desmocollin-3) (Desmosomal glycoprotein II) (Desmosomal glycoprotein III) | DSC2 CDHF2 DSC3 | 901 |
| O60469 | DSCAM_HUMAN | Down syndrome cell adhesion molecule (CHD2) | DSCAM | 2012 |
| Q9NR61 | DLL4_HUMAN | Delta-like protein 4 (Drosophila Delta homolog 4) (Delta4) | DLL4 UNQ1895/PRO4341 | 685 |
| P13765 | DOB_HUMAN | HLA class II histocompatibility antigen, DO beta chain (MHC class II antigen DOB) | HLA-DOB | 273 |
| P01906 | DQA2_HUMAN | HLA class II histocompatibility antigen, DQ alpha 2 chain (DX alpha chain) (HLA class II histocompatibility antigen, DQ(6) alpha chain) (HLA-DQA1) (MHC class II DQA2) | HLA-DQA2 HLA-DXA | 255 |
| P01920 | DQB1_HUMAN | HLA class II histocompatibility antigen, DQ beta 1 chain (MHC class II DQB1) | HLA-DQB1 HLA-DQB | 261 |
| Q30154 | DRB5_HUMAN | HLA class II histocompatibility antigen, DR beta 5 chain (DR2-beta-5) (Dw2) (MHC class II antigen DRB5) | HLA-DRB5 | 266 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q14574 | DSC3_HUMAN | Desmocollin-3 (Cadherin family member 3) (Desmocollin-4) (HT-CP) | DSC3 CDHF3 DSC4 | 896 |
| P01909 | DQA1_HUMAN | HLA class II histocompatibility antigen, DQ alpha 1 chain (DC-1 alpha chain) (DC-alpha) (HLA-DCA) (MHC class II DQA1) | HLA-DQA1 | 254 |
| P32926 | DSG3_HUMAN | Desmoglein-3 (130 kDa pemphigus vulgaris antigen) (PVA) (Cadherin family member 6) | DSG3 CDHF6 | 999 |
| Q9NZJ5 | E2AK3_HUMAN | Eukaryotic translation initiation factor 2-alpha kinase 3 (EC 2.7.11.1) (PRKR-like endoplasmic reticulum kinase) (Pancreatic eIF2-alpha kinase) (HsPEK) | EIF2AK3 PEK PERK | 1116 |
| P04440 | DPB1_HUMAN | HLA class II histocompatibility antigen, DP beta 1 chain (HLA class II histocompatibility antigen, DP(W4) beta chain) (MHC class II antigen DPB1) | HLA-DPB1 HLA-DP1B | 258 |
| P13762 | DRB4_HUMAN | HLA class II histocompatibility antigen, DR beta 4 chain (MHC class II antigen DRB4) | HLA-DRB4 | 266 |
| Q86SJ6 | DSG4_HUMAN | Desmoglein-4 (Cadherin family member 13) | DSG4 CDHF13 | 1040 |
| Q3MIW9 | DPCR1_HUMAN | Diffuse panbronchiolitis critical region protein 1 | DPCR1 C6orf37 PBLT | 517 |
| P01903 | DRA_HUMAN | HLA class II histocompatibility antigen, DR alpha chain (MHC class II antigen DRA) | HLA-DRA HLA-DRA1 | 254 |
| Q08554 | DSC1_HUMAN | Desmocollin-1 (Cadherin family member 1) (Desmosomal glycoprotein 2/3) (DG2/DG3) | DSC1 CDHF1 | 894 |
| Q02413 | DSG1_HUMAN | Desmoglein-1 (Cadherin family member 4) (Desmosomal glycoprotein 1) (DG1) (DGI) (Pemphigus foliaceus antigen) | DSG1 CDHF4 | 1049 |
| P05538 | DQB2_HUMAN | HLA class II histocompatibility antigen, DQ beta 2 chain (HLA class II histocompatibility antigen, DX beta chain) (MHC class II antigen DQB2) | HLA-DQB2 HLA-DXB | 268 |
| Q14126 | DSG2_HUMAN | Desmoglein-2 (Cadherin family member 5) (HDGC) | DSG2 CDHF5 | 1118 |
| P01133 | EGF_HUMAN | Pro-epidermal growth factor (EGF) [Cleaved into: Epidermal growth factor (Urogastrone)] | EGF | 1207 |
| Q19T08 | ECSCR_HUMAN | Endothelial cell-specific chemotaxis regulator (Apoptosis regulator through modulating IAP expression) (ARIA) (Endothelial cell-specific molecule 2) | ECSCR ECSM2 | 205 |
| Q9UNE0 | EDAR_HUMAN | Tumor necrosis factor receptor superfamily member EDAR (Anhidrotic ectodysplasin receptor 1) (Downless homolog) (EDA-A1 receptor) (Ectodermal dysplasia receptor) (Ectodysplasin-A receptor) | EDAR DL | 448 |
| P98172 | EFNB1_HUMAN | Ephrin-B1 (EFL-3) (ELK ligand) (ELK-L) (EPH-related receptor tyrosine kinase ligand 2) (LERK-2) | EFNB1 EFL3 EPLG2 LERK2 | 346 |
| Q15768 | EFNB3_HUMAN | Ephrin-B3 (EPH-related receptor transmembrane ligand ELK-L3) (EPH-related receptor tyrosine kinase ligand 8) (LERK-8) | EFNB3 EPLG8 LERK8 | 340 |
| Q9NPA0 | EMC7_HUMAN | ER membrane protein complex subunit 7 | EMC7 C11orf3 C15orf24 HT022 UNQ905/PRO1926 | 242 |
| Q902F9 | EN113_HUMAN | Endogenous retrovirus group K member 113 Env polyprotein (EnvK5 protein) (Envelope polyprotein) (HERV-K113 envelope protein) (HERV-K_19p13.11 provirus ancestral Env polyprotein) [Cleaved into: Surface protein (SU); Transmembrane protein (TM)] | HERVK_113 | 699 |
| Q6UWV6 | ENPP7_HUMAN | Ectonucleotide pyrophosphatase/phosphodiesterase family member 7 (E-NPP 7) (NPP-7) (EC 3.1.4.12) (Alkaline sphingomyelin phosphodiesterase) (Intestinal alkaline sphingomyelinase) (Alk-SMase) | ENPP7 UNQ3077/PRO9912 | 458 |
| P61566 | ENK24_HUMAN | Endogenous retrovirus group K member 24 Env polyprotein (Envelope polyprotein) (HERV-K101 envelope protein) (HERV-K_22q11.21 provirus ancestral Env polyprotein) [Cleaved into: Surface protein (SU); Transmembrane protein (TM)] | ERVK-24 | 588 |
| Q902F8 | ENK8_HUMAN | Endogenous retrovirus group K member 8 Env polyprotein (EnvK6 protein) (Envelope polyprotein) (HERV-K115 envelope protein) (HERV-K_8p23.1 provirus ancestral Env polyprotein) [Cleaved into: Surface protein (SU); Transmembrane protein (TM)] | ERVK-8 | 699 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P29320 | EPHA3_HUMAN | Ephrin type-A receptor 3 (EC 2.7.10.1) (EPH-like kinase 4) (EK4) (hEK4) (HEK) (Human embryo kinase) (Tyrosine-protein kinase TYRO4) (Tyrosine-protein kinase receptor ETK1) (Eph-like tyrosine kinase 1) | EPHA3 ETK ETK1 HEK TYRO4 | 983 |
| P54764 | EPHA4_HUMAN | Ephrin type-A receptor 4 (EC 2.7.10.1) (EPH-like kinase 8) (EK8) (hEK8) (Tyrosine-protein kinase TYRO1) (Tyrosine-protein kinase receptor SEK) | EPHA4 HEK8 SEK TYRO1 | 986 |
| Q9UF33 | EPHA6_HUMAN | Ephrin type-A receptor 6 (EC 2.7.10.1) (EPH homology kinase 2) (EHK-2) (EPH-like kinase 12) (EK12) | EPHA6 EHK2 HEK12 | 1036 |
| Q5JZY3 | EPHAA_HUMAN | Ephrin type-A receptor 10 (EC 2.7.10.1) | EPHA10 | 1008 |
| P19235 | EPOR_HUMAN | Erythropoietin receptor (EPO-R) | EPOR | 508 |
| P04626 | ERBB2_HUMAN | Receptor tyrosine-protein kinase erbB-2 (EC 2.7.10.1) (Metastatic lymph node gene 19 protein) (MLN 19) (Proto-oncogene Neu) (Proto-oncogene c-ErbB-2) (Tyrosine-kinase-type cell surface receptor HER2) (p185erbB2) (CD antigen CD340) | ERBB2 HER2 MLN19 NEU NGL | 1255 |
| P52799 | EFNB2_HUMAN | Ephrin-B2 (EPH-related receptor tyrosine kinase ligand 5) (LERK-5) (HTK ligand) (HTK-L) | EFNB2 EPLG5 HTKL LERK5 | 333 |
| P17813 | EGLN_HUMAN | Endoglin (CD antigen CD105) | ENG END | 658 |
| Q5UCC4 | EMC10_HUMAN | ER membrane protein complex subunit 10 (Hematopoietic signal peptide-containing membrane domain-containing protein 1) | EMC10 C19orf63 HSM1 INM02 UNQ764/PRO1556 | 262 |
| Q69384 | ENK6_HUMAN | Endogenous retrovirus group K member 6 Env polyprotein (EnvK2 protein) (Envelope polyprotein) (HERV-K(C7) envelope protein) (HERV-K(HML-2.HOM) envelope protein) (HERV-K108 envelope protein) (HERV-K_7p22.1 provirus ancestral Env polyprotein) [Cleaved into: Surface protein (SU); Transmembrane protein (TM)] | ERVK-6 ERVK6 | 699 |
| Q9UKH3 | ENK9_HUMAN | Endogenous retrovirus group K member 9 Env polyprotein (EnvK4 protein) (Envelope polyprotein) (HERV-K(C6) envelope protein) (HERV-K109 envelope protein) (HERV-K_6q14.1 provirus ancestral Env polyprotein) [Cleaved into: Surface protein (SU); Transmembrane protein (TM)] | ERVK-9 | 698 |
| Q6UW88 | EPGN_HUMAN | Epigen (Epithelial mitogen) (EPG) | EPGN UNQ3072/PRO9904 | 154 |
| P29317 | EPHA2_HUMAN | Ephrin type-A receptor 2 (EC 2.7.10.1) (Epithelial cell kinase) (Tyrosine-protein kinase receptor ECK) | EPHA2 ECK | 976 |
| P54753 | EPHB3_HUMAN | Ephrin type-B receptor 3 (EC 2.7.10.1) (EPH-like tyrosine kinase 2) (EPH-like kinase 2) (Embryonic kinase 2) (EK2) (hEK2) (Tyrosine-protein kinase TYRO6) | EPHB3 ETK2 HEK2 TYRO6 | 998 |
| O15197 | EPHB6_HUMAN | Ephrin type-B receptor 6 (HEP) (Tyrosine-protein kinase-defective receptor EPH-6) | EPHB6 | 1021 |
| O14944 | EREG_HUMAN | Proepiregulin [Cleaved into: Epiregulin (EPR)] | EREG | 169 |
| B6SEH8 | ERVV1_HUMAN | Endogenous retrovirus group V member 1 Env polyprotein (HERV-V_19q13.41 provirus ancestral Env polyprotein) | ERVV-1 ENVV1 | 477 |
| P00533 | EGFR_HUMAN | Epidermal growth factor receptor (EC 2.7.10.1) (Proto-oncogene c-ErbB-1) (Receptor tyrosine-protein kinase erbB-1) | EGFR ERBB ERBB1 HER1 | 1210 |
| Q8N766 | EMC1_HUMAN | ER membrane protein complex subunit 1 | EMC1 KIAA0090 PSEC0263 | 993 |
| O42043 | ENK18_HUMAN | Endogenous retrovirus group K member 18 Env polyprotein (Envelope polyprotein) (HERV-K(C1a) envelope protein) (HERV-K110 envelope protein) (HERV-K18 envelope protein) (HERV-K_1q23.3 provirus ancestral Env polyprotein) (IDDMK1,2 22 envelope protein) (IDDMK1, 2 22 superantigen) [Cleaved into: Surface protein (SU); Transmembrane protein (TM)] | ERVK-18 | 560 |
| O71037 | ENK19_HUMAN | Endogenous retrovirus group K member 19 Env polyprotein (EnvK3 protein) (Envelope polyprotein) (HERV-K(C19) envelope protein) (HERV-K_19q11 provirus ancestral Env polyprotein) [Cleaved into: Surface protein (SU); Transmembrane protein (TM)] | ERVK-19 | 699 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q15375 | EPHA7_HUMAN | Ephrin type-A receptor 7 (EC 2.7.10.1) (EPH homology kinase 3) (EHK-3) (EPH-like kinase 11) (EK11) (hEK11) | EPHA7 EHK3 HEK11 | 998 |
| Q9NQ60 | EQTN_HUMAN | Equatorin (Acrosome formation-associated factor) | EQTN AFAF C9orf11 | 294 |
| P61565 | ENK21_HUMAN | Endogenous retrovirus group K member 21 Env polyprotein (EnvK1 protein) (Envelope polyprotein) (HERV-K_12q14.1 provirus ancestral Env polyprotein) [Cleaved into: Surface protein (SU); Transmembrane protein (TM)] | ERVK-21 | 698 |
| Q9UNN8 | EPCR_HUMAN | Endothelial protein C receptor (Activated protein C receptor) (APC receptor) (Endothelial cell protein C receptor) (CD antigen CD201) | PROCR EPCR | 238 |
| P54762 | EPHB1_HUMAN | Ephrin type-B receptor 1 (EC 2.7.10.1) (ELK) (EPH tyrosine kinase 2) (EPH-like kinase 6) (EK6) (hEK6) (Neuronally-expressed EPH-related tyrosine kinase) (NET) (Tyrosine-protein kinase receptor EPH-2) | EPHB1 ELK EPHT2 HEK6 NET | 984 |
| P54760 | EPHB4_HUMAN | Ephrin type-B receptor 4 (EC 2.7.10.1) (Hepatoma transmembrane kinase) (Tyrosine-protein kinase TYRO11) | EPHB4 HTK MYK1 TYRO11 | 987 |
| P21860 | ERBB3_HUMAN | Receptor tyrosine-protein kinase erbB-3 (EC 2.7.10.1) (Proto-oncogene-like protein c-ErbB-3) (Tyrosine kinase-type cell surface receptor HER3) | ERBB3 HER3 | 1342 |
| A8MVW0 | F1712_HUMAN | Protein FAM171A2 | FAM171A2 | 826 |
| Q5JX69 | F209B_HUMAN | Protein FAM209B | FAM209B C20orf107 | 171 |
| P0C7U0 | ELFN1_HUMAN | Protein ELFN1 (Extracellular leucine-rich repeat and fibronectin type-III domain-containing protein 1) (Protein phosphatase 1 regulatory subunit 28) | ELFN1 PPP1R28 | 828 |
| Q6PCB8 | EMB_HUMAN | Embigin | EMB | 327 |
| Q9Y6X5 | ENPP4_HUMAN | Bis(5'-adenosyl)-triphosphatase ENPP4 (EC 3.6.1.29) (AP3A hydrolase) (AP3Aase) (Ectonucleotide pyrophosphatase/phosphodiesterase family member 4) (E-NPP 4) (NPP-4) | ENPP4 KIAA0879 NPP4 | 453 |
| P21709 | EPHA1_HUMAN | Ephrin type-A receptor 1 (hEpha1) (EC 2.7.10.1) (EPH tyrosine kinase) (EPH tyrosine kinase 1) (Erythropoietin-producing hepatoma receptor) (Tyrosine-protein kinase receptor EPH) | EPHA1 EPH EPHT EPHT1 | 976 |
| P54756 | EPHA5_HUMAN | Ephrin type-A receptor 5 (EC 2.7.10.1) (Brain-specific kinase) (EPH homology kinase 1) (EHK-1) (EPH-like kinase 7) (EK7) (hEK7) | EPHA5 BSK EHK1 HEK7 TYRO4 | 1037 |
| P29322 | EPHA8_HUMAN | Ephrin type-A receptor 8 (EC 2.7.10.1) (EPH- and ELK-related kinase) (EPH-like kinase 3) (EK3) (hEK3) (Tyrosine-protein kinase receptor EEK) | EPHA8 EEK HEK3 KIAA1459 | 1005 |
| P29323 | EPHB2_HUMAN | Ephrin type-B receptor 2 (EC 2.7.10.1) (Developmentally-regulated Eph-related tyrosine kinase) (ELK-related tyrosine kinase) (EPH tyrosine kinase 3) (EPH-like kinase 5) (EK5) (hEK5) (Renal carcinoma antigen NY-REN-47) (Tyrosine-protein kinase TYRO5) (Tyrosine-protein kinase receptor EPH-3) | EPHB2 DRT EPHT3 EPTH3 ERK HEK5 TYRO5 | 1055 |
| P03372 | ESR1_HUMAN | Estrogen receptor (ER) (ER-alpha) (Estradiol receptor) (Nuclear receptor subfamily 3 group A member 1) | ESR1 ESR NR3A1 | 595 |
| Q15884 | F1892_HUMAN | Protein FAM189A2 (Protein X123) | FAM189A2 C9orf61 X123 | 450 |
| P16422 | EPCAM_HUMAN | Epithelial cell adhesion molecule (Ep-CAM) (Adenocarcinoma-associated antigen) (Cell surface glycoprotein Trop-1) (Epithelial cell surface antigen) (Epithelial glycoprotein) (EGP) (Epithelial glycoprotein 314) (EGP314) (hEGP314) (KS 1/4 antigen) (KSA) (Major gastrointestinal tumor-associated protein GA733-2) (Tumor-associated calcium signal transducer 1) (CD antigen CD326) | EPCAM GA733-2 MIS2 M4S1 MIC18 TACSTD1 TROP1 | 314 |
| Q15303 | ERBB4_HUMAN | Receptor tyrosine-protein kinase erbB-4 (EC 2.7.10.1) (Proto-oncogene-like protein c-ErbB-4) (Tyrosine kinase-type cell surface receptor HER4) (p180erbB4) [Cleaved into: ERBB4 intracellular domain (4ICD) (E4ICD) (s80HER4)] | ERBB4 HER4 | 1308 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| O75460 | ERN1_HUMAN | Serine/threonine-protein kinase/endoribonuclease IRE1 (Endoplasmic reticulum-to-nucleus signaling 1) (Inositol-requiring protein 1) (hIRE1p) (Ire1-alpha) (IRE1a) [Includes: Serine/threonine-protein kinase (EC 2.7.11.1); Endoribonuclease (EC 3.1.26.—)] | ERN1 IRE1 | 977 |
| P58658 | EVA1C_HUMAN | Protein eva-1 homolog C (Protein FAM176C) (SUE21) | EVA1C C21orf63 C21orf64 FAM176C PRED34 UNQ2504/PRO5993 | 441 |
| P22794 | EVI2A_HUMAN | Protein EVI2A (Ecotropic viral integration site 2A protein homolog) (EVI-2A) | EVI2A EVDA EVI2 | 236 |
| Q5VUB5 | FI711_HUMAN | Protein FAM171A1 (Astroprincin) | FAM171A1 C10orf38 | 890 |
| Q6VOI7 | FAT4_HUMAN | Protocadherin Fat 4 (hFat4) (Cadherin family member 14) (FAT tumor suppressor homolog 4) (Fat-like cadherin protein FAT-J) | FAT4 CDHF14 FAT-J Nbla00548 | 4981 |
| Q96PL5 | ERMAP_HUMAN | Erythroid membrane-associated protein (hERMAP) (Radin blood group antigen) (Scianna blood group antigen) | ERMAP RD SC | 475 |
| Q76MJ5 | ERN2_HUMAN | Serine/threonine-protein kinase/endoribonuclease IRE2 (Endoplasmic reticulum-to-nucleus signaling 2) (Inositol-requiring protein 2) (hIRE2p) (Ire1-beta) (IRE1b) [Includes: Serine/threonine-protein kinase (EC 2.7.11.1); Endoribonuclease (EC 3.1.26.—)] | ERN2 IRE2 | 926 |
| Q96AP7 | ESAM_HUMAN | Endothelial cell-selective adhesion molecule | ESAM UNQ220/PRO246 | 390 |
| P34910 | EVI2B_HUMAN | Protein EVI2B (Ecotropic viral integration site 2B protein homolog) (EVI-2B) (CD antigen CD361) | EVI2B EVDB | 448 |
| Q3ZCQ3 | F174B_HUMAN | Membrane protein FAM174B | FAM174B | 159 |
| Q8WWV6 | FCAMR_HUMAN | High affinity immunoglobulin alpha and immunoglobulin mu Fc receptor (Fc alpha/mu receptor) (CD antigen CD351) | FCAMR FKSG87 | 532 |
| P30273 | FCERG_HUMAN | High affinity immunoglobulin epsilon receptor subunit gamma (Fc receptor gamma-chain) (FcRgamma) (Fc-epsilon RI-gamma) (IgE Fc receptor subunit gamma) (FceRI gamma) | FCER1G | 86 |
| Q8TBP5 | F174A_HUMAN | Membrane protein FAM174A (Hepatitis C virus NS5A-transactivated protein 6) (HCV NS5A-transactivated protein 6) (Transmembrane protein 157) | FAM174A NS5ATP6 TMEM157 UNQ1912/PRO4371 | 190 |
| P31995 | FCG2C_HUMAN | Low affinity immunoglobulin gamma Fc region receptor II-c (IgG Fc receptor II-c) (CDw32) (Fc-gamma RII-c) (Fc-gamma-RIIc) (FcRII-c) (CD antigen CD32) | FCGR2C CD32 FCG2 IGFR2 | 323 |
| P55899 | FCGRN_HUMAN | IgG receptor FcRn large subunit p51 (FcRn) (IgG Fc fragment receptor transporter alpha chain) (Neonatal Fc receptor) | FCGRT FCRN | 365 |
| Q96LA5 | FCRL2_HUMAN | Fc receptor-like protein 2 (FcR-like protein 2) (FcRL2) (Fc receptor homolog 2) (FcRH2) (IFGP family protein 4) (Immunoglobulin receptor translocation-associated protein 4) (SH2 domain-containing phosphatase anchor protein 1) (CD antigen CD307b) | FCRL2 FCRH2 IFGP4 IRTA4 SPAP1 UNQ9236/PRO31998 | 508 |
| Q96RD9 | FCRL5_HUMAN | Fc receptor-like protein 5 (FcR-like protein 5) (FcRL5) (BXMAS1) (Fc receptor homolog 5) (FcRH5) (Immune receptor translocation-associated protein 2) (CD antigen CD307e) | FCRL5 FCRH5 IRTA2 UNQ503/PRO820 | 977 |
| P31994 | FCG2B_HUMAN | Low affinity immunoglobulin gamma Fc region receptor II-b (IgG Fc receptor II-b) (CDw32) (Fc-gamma RII-b) (Fc-gamma-RIIb) (FcRII-b) (CD antigen CD32) | FCGR2B CD32 FCG2 IGFR2 | 310 |
| Q96PJ5 | FCRL4_HUMAN | Fc receptor-like protein 4 (FcR-like protein 4) (FcRL4) (Fc receptor homolog 4) (FcRH4) (IFGP family protein 2) (hIFGP2) (Immune receptor translocation-associated protein 1) (CD antigen CD307d) | FCRL4 FCRH4 IFGP2 IRTA1 | 515 |
| P22607 | FGFR3_HUMAN | Fibroblast growth factor receptor 3 (FGFR-3) (EC 2.7.10.1) (CD antigen CD333) | FGFR3 JTK4 | 806 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q6P995 | F171B_HUMAN | Protein FAM171B | FAM171B KIAA1946 NPD019 | 826 |
| A6NFU0 | F187A_HUMAN | Ig-like V-type domain-containing protein FAM187A | FAM187A | 413 |
| Q17R55 | F187B_HUMAN | Protein FAM187B (Transmembrane protein 162) | FAM187B TMEM162 | 369 |
| Q5JX71 | F209A_HUMAN | Protein FAM209A | FAM209A C20orf106 | 171 |
| Q14517 | FAT1_HUMAN | Protocadherin Fat 1 (Cadherin family member 7) (Cadherin-related tumor suppressor homolog) (Protein fat homolog) [Cleaved into: Protocadherin Fat 1, nuclear form] | FAT1 CDHF7 FAT | 4588 |
| Q9NYQ8 | FAT2_HUMAN | Protocadherin Fat 2 (hFat2) (Cadherin family member 8) (Multiple epidermal growth factor-like domains protein 1) (Multiple EGF-like domains protein 1) | FAT2 CDHF8 KIAA0811 MEGF1 | 4349 |
| Q8TDW7 | FAT3_HUMAN | Protocadherin Fat 3 (hFat3) (Cadherin family member 15) (FAT tumor suppressor homolog 3) | FAT3 CDHF15 KIAA1989 | 4589 |
| P24071 | FCAR_HUMAN | Immunoglobulin alpha Fc receptor (IgA Fc receptor) (CD antigen CD89) | FCAR CD89 | 287 |
| P12314 | FCGR1_HUMAN | High affinity immunoglobulin gamma Fc receptor I (IgG Fc receptor I) (Fc-gamma RI) (FcRI) (Fc-gamma RIA) (FcgammaRIa) | FCGR1A FCG1 FCGR1 IGFR1 | 374 |
| Q96LA6 | FCRL1_HUMAN | Fc receptor-like protein 1 (FcR-like protein 1) (FcRL1) (Fc receptor homolog 1) (FcRH1) (IFGP family protein 1) (hIFGP1) (Immune receptor translocation-associated protein 5) (CD antigen CD307a) | FCRL1 FCRH1 IFGP1 IRTA5 | 429 |
| Q96P31 | FCRL3_HUMAN | Fc receptor-like protein 3 (FcR-like protein 3) (FcRL3) (Fc receptor homolog 3) (FcRH3) (IFGP family protein 3) (hIFGP3) (Immune receptor translocation-associated protein 3) (SH2 domain-containing phosphatase anchor protein 2) (CD antigen CD307c) | FCRL3 FCRH3 IFGP3 IRTA3 SPAP2 | 734 |
| P12318 | FCG2A_HUMAN | Low affinity immunoglobulin gamma Fc region receptor II-a (IgG Fc receptor II-a) (CDw32) (Fc-gamma RII-a) (Fc-gamma-RIIa) (FcRII-a) (FcR(II-a)) (CD antigen CD32) | FCGR2A CD32 FCG2 FCGR2A1 IGFR2 | 317 |
| P08637 | FCG3A_HUMAN | Low affinity immunoglobulin gamma Fc region receptor III-A (CD16a antigen) (Fc-gamma RIII-alpha) (Fc-gamma RIII) (Fc-gamma RIIIa) (FcRIII) (FcRIIIa) (FcR-10) (IgG Fc receptor III-2) (CD antigen CD16a) | FCGR3A CD16A FCG3 FCGR3 IGFR3 | 254 |
| Q92637 | FCGRB_HUMAN | High affinity immunoglobulin gamma Fc receptor IB (IgG Fc receptor IB) (Fc-gamma RIB) (FcRIB) (hFcgammaRIB) | FCGR1B IGFRB | 280 |
| Q8N441 | FGRL1_HUMAN | Fibroblast growth factor receptor-like 1 (FGF receptor-like protein 1) (FGF homologous factor receptor) (FGFR-like protein) (Fibroblast growth factor receptor 5) (FGFR-5) | FGFRL1 FGFR5 FHFR UNQ480/PRO943 | 504 |
| P12319 | FCERA_HUMAN | High affinity immunoglobulin epsilon receptor subunit alpha (Fc-epsilon RI-alpha) (FcERI) (IgE Fc receptor subunit alpha) | FCER1A FCE1A | 257 |
| Q6DN72 | FCRL6_HUMAN | Fc receptor-like protein 6 (FcR-like protein 6) (FcRL6) (Fc receptor homolog 6) (FcRH6) (IFGP6) | FCRL6 FCRH6 | 434 |
| P11362 | FGFR1_HUMAN | Fibroblast growth factor receptor 1 (FGFR-1) (EC 2.7.10.1) (Basic fibroblast growth factor receptor 1) (BFGFR) (bFGF-R-1) (Fms-like tyrosine kinase 2) (FLT-2) (N-sam) (Proto-oncogene c-Fgr) (CD antigen CD331) | FGFR1 BFGFR CEK FGFBR FLG FLT2 HBGFR | 822 |
| P21802 | FGFR2_HUMAN | Fibroblast growth factor receptor 2 (FGFR-2) (EC 2.7.10.1) (K-sam) (KGFR) (Keratinocyte growth factor receptor) (CD antigen CD332) | FGFR2 BEK KGFR KSAM | 821 |
| A6NKC4 | FCGRC_HUMAN | Putative high affinity immunoglobulin gamma Fc receptor IC (IgG Fc receptor IC) (Fc-gamma RIC) (FcRIC) (hFcgammaRIC) | FCGR1C IGFRC | 280 |
| Q9H6D8 | FNDC4_HUMAN | Fibronectin type III domain-containing protein 4 (Fibronectin type III repeat-containing protein 1) | FNDC4 FRCP1 UNQ6389/PRO21134 | 234 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9P2B2 | FPRP_HUMAN | Prostaglandin F2 receptor negative regulator (CD9 partner 1) (CD9P-1) (Glu-Trp-Ile EWI motif-containing protein F) (EWI-F) (Prostaglandin F2-alpha receptor regulatory protein) (Prostaglandin F2-alpha receptor-associated protein) (CD antigen CD315) | PTGFRN CD9P1 EWIF FPRP KIAA1436 | 879 |
| Q5SZK8 | FREM2_HUMAN | FRAS1-related extracellular matrix protein 2 | FREM2 | 3169 |
| P22455 | FGFR4_HUMAN | Fibroblast growth factor receptor 4 (FGFR-4) (EC 2.7.10.1) (CD antigen CD334) | FGFR4 JTK2 TKF | 802 |
| O95866 | G6B_HUMAN | Protein G6b | G6B C6orf25 | 241 |
| P49771 | FLT3L_HUMAN | Fms-related tyrosine kinase 3 ligand (Flt3 ligand) (SL cytokine) | FLT3LG | 235 |
| P59646 | FXYD4_HUMAN | FXYD domain-containing ion transport regulator 4 | FXYD4 UNQ526/PRO1069 | 89 |
| P36888 | FLT3_HUMAN | Receptor-type tyrosine-protein kinase FLT3 (EC 2.7.10.1) (FL cytokine receptor) (Fetal liver kinase-2) (FLK-2) (Fms-like tyrosine kinase 3) (FLT-3) (Stem cell tyrosine kinase 1) (STK-1) (CD antigen CD135) | FLT3 CD135 FLK2 STK1 | 993 |
| Q8NAU1 | FNDC5_HUMAN | Fibronectin type III domain-containing protein 5 (Fibronectin type III repeat-containing protein 2) [Cleaved into: Irisin] | FNDC5 FRCP2 | 212 |
| Q86XX4 | FRAS1_HUMAN | Extracellular matrix protein FRAS1 | FRAS1 KIAA1500 | 4008 |
| P09958 | FURIN_HUMAN | Furin (EC 3.4.21.75) (Dibasic-processing enzyme) (Paired basic amino acid residue-cleaving enzyme) (PACE) | FURIN FUR PACE PCSK3 | 794 |
| Q14802 | FXYD3_HUMAN | FXYD domain-containing ion transport regulator 3 (Chloride conductance inducer protein Mat-8) (Mammary tumor 8 kDa protein) (Phospholemman-like) | FXYD3 MAT8 PLML | 87 |
| Q9H0Q3 | FXYD6_HUMAN | FXYD domain-containing ion transport regulator 6 (Phosphohippolin) | FXYD6 UNQ521/PRO1056 | 95 |
| Q96DB9 | FXYD5_HUMAN | FXYD domain-containing ion transport regulator 5 (Dysadherin) | FXYD5 DYSAD IWU1 HSPC113 UNQ2561/PRO6241 | 178 |
| P58550 | FXYD8_HUMAN | Putative FXYD domain-containing ion transport regulator 8 | FXYD6P3 FXYD8 | 94 |
| I3L273 | GFY_HUMAN | Golgi-associated olfactory signaling regulator (Protein Goofy) | GFY | 518 |
| P06028 | GLPB_HUMAN | Glycophorin-B (PAS-3) (SS-active sialoglycoprotein) (Sialoglycoprotein delta) (CD antigen CD235b) | GYPB GPB | 91 |
| P10912 | GHR_HUMAN | Growth hormone receptor (GH receptor) (Somatotropin receptor) [Cleaved into: Growth hormone-binding protein (GH-binding protein) (GHBP) (Serum-binding protein)] | GHR | 638 |
| P15421 | GLPE_HUMAN | Glycophorin-E | GYPE GPE | 78 |
| P13224 | GP1BB_HUMAN | Platelet glycoprotein Ib beta chain (GP-Ib beta) (GPIb-beta) (Antigen CD42b-beta) (CD antigen CD42c) | GP1BB | 206 |
| Q9NU53 | GINM1_HUMAN | Glycoprotein integral membrane protein 1 | GINM1 C6orf72 UNQ710/PRO1361 | 330 |
| P02724 | GLPA_HUMAN | Glycophorin-A (MN sialoglycoprotein) (PAS-2) (Sialoglycoprotein alpha) (CD antigen CD235a) | GYPA GPA | 150 |
| Q3T906 | GNPTA_HUMAN | N-acetylglucosamine-1-phosphotransferase subunits alpha/beta (EC 2.7.8.17) (GlcNAc-1-phosphotransferase subunits alpha/beta) (Stealth protein GNPTAB) (UDP-N-acetylglucosamine-1-phosphotransferase subunits alpha/beta) [Cleaved into: N-acetylglucosamine-1-phosphotransferase subunit alpha; N-acetylglucosamine-1-phosphotransferase subunit beta] | GNPTAB GNPTA KIAA1208 | 1256 |
| Q8WWB7 | GLMP_HUMAN | Glycosylated lysosomal membrane protein (Lysosomal protein NCU-G1) | GLMP C1orf85 PSEC0030 UNQ2553/PRO6182 | 406 |
| P07359 | GP1BA_HUMAN | Platelet glycoprotein Ib alpha chain (GP-Ib alpha) (GPIb-alpha) (Glycoprotein Ibalpha) (Antigen CD42b-alpha) (CD antigen CD42b) [Cleaved into: Glycocalicin] | GP1BA | 652 |
| P40197 | GPV_HUMAN | Platelet glycoprotein V (GPV) (Glycoprotein 5) (CD antigen CD42d) | GP5 | 560 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q99795 | GPA33_HUMAN | Cell surface A33 antigen (Glycoprotein A33) | GPA33 | 319 |
| P14770 | GPIX_HUMAN | Platelet glycoprotein IX (GP-IX) (GPIX) (Glycoprotein 9) (CD antigen CD42a) | GP9 | 177 |
| Q86XS8 | GOLI_HUMAN | E3 ubiquitin-protein ligase RNF130 (EC 6.3.2.—) (Goliath homolog) (H-Goliath) (RING finger protein 130) | RNF130 | 419 |
| P25092 | GUC2C_HUMAN | Heat-stable enterotoxin receptor (STA receptor) (hSTAR) (EC 4.6.1.2) (Guanylyl cyclase C) (GC-C) (Intestinal guanylate cyclase) | GUCY2C GUC2C STAR | 1073 |
| Q14789 | GOGB1_HUMAN | Golgin subfamily B member 1 (372 kDa Golgi complex-associated protein) (GCP372) (Giantin) (Macrogolgin) | GOLGB1 | 3259 |
| Q14956 | GPNMB_HUMAN | Transmembrane glycoprotein NMB (Transmembrane glycoprotein HGFIN) | GPNMB HGFIN NMB UNQ1725/PRO9925 | 572 |
| P51841 | GUC2F_HUMAN | Retinal guanylyl cyclase 2 (RETGC-2) (EC 4.6.1.2) (Guanylate cyclase 2F, retinal) (Guanylate cyclase F) (GC-F) (Rod outer segment membrane guanylate cyclase 2) (ROS-GC2) | GUCY2F GUC2F RETGC2 | 1108 |
| Q92643 | GPI8_HUMAN | GPI-anchor transamidase (GPI transamidase) (EC 3.—.—.—) (GPI8 homolog) (hGPI8) (Phosphatidylinositol-glycan biosynthesis class K protein) (PIG-K) | PIGK GPI8 | 395 |
| Q02846 | GUC2D_HUMAN | Retinal guanylyl cyclase 1 (RETGC-1) (EC 4.6.1.2) (Guanylate cyclase 2D, retinal) (Rod outer segment membrane guanylate cyclase) (ROS-GC) | GUCY2D CORD6 GUC1A4 GUC2D RETGC RETGC1 | 1103 |
| Q9UBK5 | HCST_HUMAN | Hematopoietic cell signal transducer (DNAX-activation protein 10) (Membrane protein DAP10) (Transmembrane adapter protein KAP10) | HCST DAP10 KAP10 PIK3AP UNQ587/PRO1157 | 93 |
| Q14CZ8 | HECAM_HUMAN | Hepatocyte cell adhesion molecule (Protein hepaCAM) | HEPACAM | 416 |
| A8MVW5 | HECA2_HUMAN | HEPACAM family member 2 (Mitotic kinetics regulator) | HEPACAM2 MIKI UNQ305/PRO346 | 462 |
| Q9ULI3 | HEG1_HUMAN | Protein HEG homolog 1 | HEG1 KIAA1237 | 1381 |
| Q92896 | GSLG1_HUMAN | Golgi apparatus protein 1 (CFR-1) (Cysteine-rich fibroblast growth factor receptor) (E-selectin ligand 1) (ESL-1) (Golgi sialoglycoprotein MG-160) | GLG1 CFR1 ESL1 MG160 | 1179 |
| Q99075 | HBEGF_HUMAN | Proheparin-binding EGF-like growth factor [Cleaved into: Heparin-binding EGF-like growth factor (HB-EGF) (HBEGF) (Diphtheria toxin receptor) (DT-R)] | HBEGF DTR DTS HEGFL | 208 |
| Q96D42 | HAVR1_HUMAN | Hepatitis A virus cellular receptor 1 (HAVcr-1) (Kidney injury molecule 1) (KIM-1) (T-cell immunoglobulin and mucin domain-containing protein 1) (TIMD-1) (T-cell immunoglobulin mucin receptor 1) (TIM) (TIM-1) (T-cell membrane protein 1) | HAVCR1 KIM1 TIM1 TIMD1 | 359 |
| Q8TDQ0 | HAVR2_HUMAN | Hepatitis A virus cellular receptor 2 (HAVcr-2) (T-cell immunoglobulin and mucin domain-containing protein 3) (TIMD-3) (T-cell immunoglobulin mucin receptor 3) (TIM-3) (T-cell membrane protein 3) | HAVCR2 TIM3 TIMD3 | 301 |
| Q30201 | HFE_HUMAN | Hereditary hemochromatosis protein (HLA-H) | HFE HLAH | 348 |
| P30511 | HLAF_HUMAN | HLA class I histocompatibility antigen, alpha chain F (CDA12) (HLA F antigen) (Leukocyte antigen F) (MHC class I antigen F) | HLA-F HLA-5.4 HLAF | 346 |
| A8MVS5 | HIDE1_HUMAN | Protein HIDE1 | HIDE1 C19orf38 | 230 |
| P13747 | HLAE_HUMAN | HLA class I histocompatibility antigen, alpha chain E (MHC class I antigen E) | HLA-E HLA-6.2 HLAE | 358 |
| Q9BQS7 | HEPH_HUMAN | Hephaestin (EC 1.—.—.—) | HEPH KIAA0698 UNQ2562/PRO6242 | 1158 |
| Q95460 | HMR1_HUMAN | Major histocompatibility complex class I-related gene protein (MHC class I-related gene protein) (Class I histocompatibility antigen-like protein) | MR1 | 341 |
| Q6MZM0 | HPHL1_HUMAN | Hephaestin-like protein 1 (EC 1.—.—.—) | HEPHL1 | 1159 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9UM44 | HHLA2_HUMAN | HERV-H LTR-associating protein 2 (Human endogenous retrovirus-H long terminal repeat-associating protein 2) | HHLA2 | 414 |
| P17693 | HLAG_HUMAN | HLA class I histocompatibility antigen, alpha chain G (HLA G antigen) (MHC class I antigen G) | HLA-G HLA-6.0 HLAG | 338 |
| Q08334 | I10R2_HUMAN | Interleukin-10 receptor subunit beta (IL-10 receptor subunit beta) (IL-10RB) (Cytokine receptor class-II member 4) (Cytokine receptor family 2 member 4) (CRF2-4) (Interleukin-10 receptor subunit 2) (IL-10R subunit 2) (IL-10R2) (CD antigen CDw210b) | IL10RB CRFB4 D21S58 D21S66 | 325 |
| Q96F46 | I17RA_HUMAN | Interleukin-17 receptor A (IL-17 receptor A) (IL-17RA) (CDw217) (CD antigen CD217) | IL17RA IL17R | 866 |
| Q99665 | I12R2_HUMAN | Interleukin-12 receptor subunit beta-2 (IL-12 receptor subunit beta-2) (IL-12R subunit beta-2) (IL-12R-beta-2) (IL-12RB2) | IL12RB2 | 862 |
| Q14627 | I13R2_HUMAN | Interleukin-13 receptor subunit alpha-2 (IL-13 receptor subunit alpha-2) (IL-13R subunit alpha-2) (IL-13R-alpha-2) (IL-13RA2) (Interleukin-13-binding protein) (CD antigen CD213a2) | IL13RA2 IL13R | 380 |
| Q9NRM6 | I17RB_HUMAN | Interleukin-17 receptor B (IL-17 receptor B) (IL-17RB) (Cytokine receptor-like 4) (IL-17 receptor homolog 1) (IL-17RM) (IL17Rh1) (Interleukin-17B receptor) (IL-17B receptor) | IL17RB CRL4 EVI27 IL17BR UNQ2501/PRO19612 | 502 |
| Q8NFM7 | I17RD_HUMAN | Interleukin-17 receptor D (IL-17 receptor D) (IL-17RD) (IL17Rhom) (Interleukin-17 receptor-like protein) (Set homolog) (hSef) | IL17RD IL17RLM SEF UNQ6115/PRO20026 | 739 |
| Q8N6P7 | I22R1_HUMAN | Interleukin-22 receptor subunit alpha-1 (IL-22 receptor subunit alpha-1) (IL-22R-alpha-1) (IL-22RA1) (Cytokine receptor class-II member 9) (Cytokine receptor family 2 member 9) (CRF2-9) (ZcytoR11) | Il22RA1 IL22R | 574 |
| Q9UMF0 | ICAM5_HUMAN | Intercellular adhesion molecule 5 (ICAM-5) (Telencephalin) | ICAM5 TLCN TLN | 924 |
| P42701 | I12R1_HUMAN | Interleukin-12 receptor subunit beta-1 (IL-12 receptor subunit beta-1) (IL-12R subunit beta-1) (IL-12R-beta-1) (IL-12RB1) (IL-12 receptor beta component) (CD antigen CD212) | IL12RB1 IL12R | 662 |
| P78552 | I13R1_HUMAN | Interleukin-13 receptor subunit alpha-1 (IL-13 receptor subunit alpha-1) (IL-13R subunit alpha-1) (IL-13R-alpha-1) (IL-13RA1) (Cancer/testis antigen 19) (CT19) (CD antigen CD213a1) | IL13RA1 IL13R IL13RA | 427 |
| Q8NFR9 | I17RE_HUMAN | Interleukin-17 receptor E (IL-17 receptor E) (IL-17RE) | IL17RE UNQ3056/PRO9877 | 667 |
| O95256 | I18RA_HUMAN | Interleukin-18 receptor accessory protein (IL-18 receptor accessory protein) (IL-18RAcP) (Accessory protein-like) (AcPL) (CD218 antigen-like family member B) (CDw218b) (IL-1R accessory protein-like) (IL-1RAcPL) (Interleukin-1 receptor 7) (IL-1R-7) (IL-1R7) (Interleukin-18 receptor accessory protein-like) (Interleukin-18 receptor beta) (IL-18R-beta) (IL-18Rbeta) (CD antigen CD218b) | IL18RAP IL1R7 | 599 |
| Q6UXL0 | I20RB_HUMAN | Interleukin-20 receptor subunit beta (IL-20 receptor subunit beta) (IL-20R-beta) (IL-20RB) (Fibronectin type III domain containing 6) (FNDC6) (IL-20R2) | IL20RB DIRS1 UNQ557/PRO1114 | 311 |
| P32942 | ICAM3_HUMAN | Intercellular adhesion molecule 3 (ICAM-3) (CDw50) (ICAM-R) (CD antigen CD50) | ICAM3 | 547 |
| Q13261 | I15RA_HUMAN | Interleukin-15 receptor subunit alpha (IL-15 receptor subunit alpha) (IL-15R-alpha) (IL-15RA) (CD antigen CD215) [Cleaved into: Soluble interleukin-15 receptor subunit alpha (sIL-15 receptor subunit alpha) (sIL-15R-alpha) (sIL-15RA)] | IL15RA | 267 |
| Q9H2X8 | I27L2_HUMAN | Interferon alpha-inducible protein 27-like protein 2 (Interferon-stimulated gene 12b protein) (ISG12(b)) (Protein TLH29) (pIFI27-like protein) | IFI27L2 FAM14A TLH29 | 130 |
| Q9Y6W8 | ICOS_HUMAN | Inducible T-cell costimulator (Activation-inducible lymphocyte immunomediatory molecule) (CD antigen CD278) | ICOS AILIM | 199 |
| P13598 | ICAM2_HUMAN | Intercellular adhesion molecule 2 (ICAM-2) (CD antigen CD102) | ICAM2 | 275 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P98153 | IDD_HUMAN | Integral membrane protein DGCR2/IDD | DGCR2 IDD KIAA0163 | 550 |
| O75054 | IGSF3_HUMAN | Immunoglobulin superfamily member 3 (IgSF3) (Glu-Trp-Ile EWI motif-containing protein 3) (EWI-3) | IGSF3 EWI3 KIAA0466 | 1194 |
| P01589 | IL2RA_HUMAN | Interleukin-2 receptor subunit alpha (IL-2 receptor subunit alpha) (IL-2-RA) (IL-2R subunit alpha) (IL2-RA) (TAC antigen) (p55) (CD antigen CD25) | IL2RA | 272 |
| P26951 | IL3RA_HUMAN | Interleukin-3 receptor subunit alpha (IL-3 receptor subunit alpha) (IL-3R subunit alpha) (IL-3R-alpha) (IL-3RA) (CD antigen CD123) | IL3RA IL3R | 378 |
| P24394 | IL4RA_HUMAN | Interleukin-4 receptor subunit alpha (IL-4 receptor subunit alpha) (IL-4R subunit alpha) (IL-4R-alpha) (IL-4RA) (CD antigen CD124) [Cleaved into: Soluble interleukin-4 receptor subunit alpha (Soluble IL-4 receptor subunit alpha) (Soluble IL-4R-alpha) (sIL4Ralpha/prot) (IL-4-binding protein) (IL4-BP)] | IL4R IL4RA 582J2.1 | 825 |
| Q8NAC3 | I17RC_HUMAN | Interleukin-17 receptor C (IL-17 receptor C) (IL-17RC) (Interleukin-17 receptor homolog) (IL17Rhom) (Interleukin-17 receptor-like protein) (IL-17RL) (ZcytoR14) | IL17RC UNQ6118/PRO20040/PRO38901 | 791 |
| Q9UHF4 | I20RA_HUMAN | Interleukin-20 receptor subunit alpha (IL-20 receptor subunit alpha) (IL-20R-alpha) (IL-20RA) (Cytokine receptor class-II member 8) (Cytokine receptor family 2 member 8) (CRF2-8) (IL-20R1) (ZcytoR7) | IL20RA UNQ681/PRO1315 | 553 |
| Q6UWB1 | I27RA_HUMAN | Interleukin-27 receptor subunit alpha (IL-27 receptor subunit alpha) (IL-27R subunit alpha) (IL-27R-alpha) (IL-27RA) (Cytokine receptor WSX-1) (Cytokine receptor-like 1) (Type I T-cell cytokine receptor) (TCCR) (ZcytoR1) | IL27RA CRL1 TCCR WSX1 UNQ296/PRO336 | 636 |
| Q9H665 | IGFR1_HUMAN | IGF-like family receptor 1 (Transmembrane protein 149) (U2 small nuclear RNA auxiliary factor 1-like 4) | IGFLR1 TMEM149 U2AF1L4 | 355 |
| P01880 | IGHD_HUMAN | Ig delta chain C region | IGHD | 384 |
| Q5DX21 | IGS11_HUMAN | Immunoglobulin superfamily member 11 (IgSF11) (Brain and testis-specific immunoglobulin superfamily protein) (Bt-IGSF) (V-set and immunoglobulin domain-containing protein 3) | IGSF11 BTIGSF CXADRL1 VSIG3 | 431 |
| Q93033 | IGSF2_HUMAN | Immunoglobulin superfamily member 2 (IgSF2) (Cell surface glycoprotein V7) (Glu-Trp-Ile EWI motif-containing protein 101) (EWI-101) (CD antigen CD101) | CD101 EWI101 IGSF2 V7 | 1021 |
| Q9HBE5 | IL21R_HUMAN | Interleukin-21 receptor (IL-21 receptor) (IL-21R) (Novel interleukin receptor) (CD antigen CD360) | IL21R NILR UNQ3121/PRO10273 | 538 |
| Q71H61 | ILDR2_HUMAN | Immunoglobulin-like domain-containing receptor 2 | ILDR2 C1orf32 | 639 |
| O75144 | ICOSL_HUMAN | ICOS ligand (B7 homolog 2) (B7-H2) (B7-like protein Gl50) (B7-related protein 1) (B7RP-1) (CD antigen CD275) | ICOSLG B7H2 B7RP1 ICOSL KIAA0653 | 302 |
| Q8TDY8 | IGDC4_HUMAN | Immunoglobulin superfamily DCC subclass member 4 (Neighbor of punc e11) (Protein DDM36) (hDDM36) | IGDCC4 DDM36 KIAA1628 NOPE | 1250 |
| P01871 | IGHM_HUMAN | Ig mu chain C region | IGHM | 452 |
| O95976 | IGSF6_HUMAN | Immunoglobulin superfamily member 6 (IgSF6) (Protein DORA) | IGSF6 DORA | 241 |
| Q9NPH3 | IL1AP_HUMAN | Interleukin-1 receptor accessory protein (IL-1 receptor accessory protein) (IL-1RAcP) (Interleukin-1 receptor 3) (IL-1R-3) (IL-1R3) | IL1RAP C3orf13 IL1R3 | 570 |
| P31785 | IL2RG_HUMAN | Cytokine receptor common subunit gamma (Interleukin-2 receptor subunit gamma (IL-2 receptor subunit gamma) (IL-2R subunit gamma) (IL-2RG) (gammaC) (CD antigen CD132) | IL2RG | 369 |
| P32927 | IL3RB_HUMAN | Cytokine receptor common subunit beta (CDw131) (GM-CSF/IL-3/IL-5 receptor common beta subunit) (CD antigen CD131) | CSF2RB IL3RB IL5RB | 897 |
| Q01113 | IL9R_HUMAN | Interleukin-9 receptor (IL-9 receptor) (IL-9R) (CD antigen CD129) | IL9R | 521 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9HB29 | ILRL2_HUMAN | Interleukin-1 receptor-like 2 (IL-36 receptor) (IL-36R) (Interleukin-1 receptor-related protein 2) (IL-1Rrp2) | IL1RL2 IL1RRP2 | 575 |
| P15260 | INGR1_HUMAN | Interferon gamma receptor 1 (IFN-gamma receptor 1) (IFN-gamma-R1) (CDw119) (CD antigen CD119) | IFNGR1 | 489 |
| Q13651 | I10R1_HUMAN | Interleukin-10 receptor subunit alpha (IL-10 receptor subunit alpha) (IL-10R subunit alpha) (IL-10RA) (CDw210a) (Interleukin-10 receptor subunit 1) (IL-10R subunit 1) (IL-10R1) (CD antigen CD210) | IL10RA IL10R | 578 |
| Q14626 | I11RA_HUMAN | Interleukin-11 receptor subunit alpha (IL-11 receptor subunit alpha) (IL-11R subunit alpha) (IL-11R-alpha) (IL-11RA) | IL11RA | 422 |
| P05362 | ICAM1_HUMAN | Intercellular adhesion molecule 1 (ICAM-1) (Major group rhinovirus receptor) (CD antigen CD54) | ICAM1 | 532 |
| Q14773 | ICAM4_HUMAN | Intercellular adhesion molecule 4 (ICAM-4) (Landsteiner-Wiener blood group glycoprotein) (LW blood group protein) (CD antigen CD242) | ICAM4 LW | 271 |
| Q9NSI5 | IGSF5_HUMAN | Immunoglobulin superfamily member 5 (IgSF5) (Junctional adhesion molecule 4) (JAM-4) | IGSF5 JAM4 | 407 |
| P14778 | IL1R1_HUMAN | Interleukin-1 receptor type 1 (IL-1R-1) (IL-1RT-1) (CD121 antigen-like family member A) (Interleukin-1 receptor alpha) (IL-1R-alpha) (Interleukin-1 receptor type I) (p80) (CD antigen CD121a) [Cleaved into: Interleukin-1 receptor type 1, membrane form (mIL-1R1) (mIL-1RI); Interleukin-1 receptor type 1, soluble form (sIL-1R1) (sIL-1RI] | IL1R1 IL1R IL1RA IL1RT1 | 569 |
| Q8NI17 | IL31R_HUMAN | Interleukin-31 receptor subunit alpha (IL-31 receptor subunit alpha) (IL-31R subunit alpha) (IL-31R-alpha) (IL-31RA) (Cytokine receptor-like 3) (GLM-R) (hGLM-R) (Gp130-like monocyte receptor) (Gp130-like receptor) (ZcytoR17) | IL31RA CRL3 GPL UNQ6368/PRO21073/PRO21384 | 732 |
| Q01344 | IL5RA_HUMAN | Interleukin-5 receptor subunit alpha (IL-5 receptor subunit alpha) (IL-5R subunit alpha) (IL-5R-alpha) (IL-5RA) (CDw125) (CD antigen CD125) | IL5RA IL5R | 420 |
| P16871 | IL7RA_HUMAN | Interleukin-7 receptor subunit alpha (IL-7 receptor subunit alpha) (IL-7R subunit alpha) (IL-7R-alpha) (IL-7RA) (CDw127) (CD antigen CD127) | IL7R | 459 |
| P08887 | IL6RA_HUMAN | Interleukin-6 receptor subunit alpha (IL-6 receptor subunit alpha) (IL-6R subunit alpha) (IL-6R-alpha) (IL-6RA) (IL-6R 1) (Membrane glycoprotein 80) (gp80) (CD antigen CD126) | IL6R | 468 |
| Q01638 | ILRL1_HUMAN | Interleukin-1 receptor-like 1 (Protein ST2) | IL1RL1 DER4 ST2 T1 | 556 |
| P06213 | INSR_HUMAN | Insulin receptor (IR) (EC 2.7.10.1) (CD antigen CD220) [Cleaved into: Insulin receptor subunit alpha; Insulin receptor beta] | INSR | 1382 |
| P08069 | IGF1R_HUMAN | Insulin-like growth factor 1 receptor (EC 2.7.10.1) (Insulin-like growth factor I receptor) (IGF-I receptor) (CD antigen CD221) [Cleaved into: Insulin-like growth factor 1 receptor alpha chain; Insulin-like growth factor 1 receptor beta chain] | IGF1R | 1367 |
| P14784 | IL2RB_HUMAN | Interleukin-2 receptor subunit beta (IL-2 receptor subunit beta) (IL-2R subunit beta) (IL-2RB) (High affinity IL-2 receptor subunit beta) (p70-75) (p75) (CD antigen CD122) | IL2RB | 551 |
| Q86SU0 | ILDR1_HUMAN | Immunoglobulin-like domain-containing receptor 1 | ILDR1 | 546 |
| P14616 | INSRR_HUMAN | Insulin receptor-related protein (IRR) (EC 2.7.10.1) (IR-related receptor) [Cleaved into: Insulin receptor-related protein alpha chain; Insulin receptor-related protein beta chain] | INSRR IRR | 1297 |
| Q13478 | IL18R_HUMAN | Interleukin-18 receptor 1 (IL-18R-1) (IL-18R1) (CD218 antigen-like family member A) (CDw218a) (IL1 receptor-related protein) (IL-1Rrp) (CD antigen CD218a) | IL18R1 IL1RRP | 541 |
| Q5VWK5 | IL23R_HUMAN | Interleukin-23 receptor (IL-23 receptor) (IL-23R) | IL23R | 629 |
| Q9BZV3 | IMPG2_HUMAN | Interphotoreceptor matrix proteoglycan 2 (Interphotoreceptor matrix proteoglycan of 200 kDa) (IPM 200) (Sialoprotein associated with cones and rods proteoglycan) (Spacrcan) | IMPG2 IPM200 | 1241 |
| Q8IU57 | INLR1_HUMAN | Interferon lambda receptor 1 (IFN-lambda receptor 1) (IFN-lambda-R1) (Cytokine receptor class-11 member 12) (Cytokine receptor family 2 member 12) (CRF2-12) (Interleukin-28 receptor subunit alpha) (IL-28 receptor subunit alpha) (IL-28R-alpha) (IL-28RA) (Likely interleukin or cytokine receptor 2) (LICR2) | IFNLR1 IL28RA LICR2 | 520 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q6GPH6 | IPIL1_HUMAN | Inositol 1,4,5-trisphosphate receptor-interacting protein-like 1 | ITPRIPL1 KIAA1754L | 555 |
| Q9NP60 | IRPL2_HUMAN | X-linked interleukin-1 receptor accessory protein-like 2 (IL-1 receptor accessory protein-like 2) (IL-1-RAPL-2) (IL1RAPL-2) (IL1RAPL-2-related protein) (Interleukin-1 receptor 9) (IL-1R-9) (IL-1R9) (Three immunoglobulin domain-containing IL-1 receptor-related 1) (TIGIRR-1) | IL1RAPL2 IL1R9 | 686 |
| Q8IVU1 | IGDC3_HUMAN | Immunoglobulin superfamily DCC subclass member 3 (Putative neuronal cell adhesion molecule) | IGDCC3 PUNC | 814 |
| P17181 | INAR1_HUMAN | Interferon alpha/beta receptor 1 (IFN-R-1) (IFN-alpha/beta receptor 1) (Cytokine receptor class-II member 1) (Cytokine receptor family 2 member 1) (CRF2-1) (Type I interferon receptor 1) | IFNAR1 IFNAR | 557 |
| Q13683 | ITA7_HUMAN | Integrin alpha-7 [Cleaved into: Integrin alpha-7 heavy chain; Integrin alpha-7 light chain; Integrin alpha-7 70 kDa form] | ITGA7 UNQ406/PRO768 | 1181 |
| P53708 | ITA8_HUMAN | Integrin alpha-8 [Cleaved into: Integrin alpha-8 heavy chain; Integrin alpha-8 light chain] | ITGA8 | 1063 |
| Q13349 | ITAD_HUMAN | Integrin alpha-D (ADB2) (CD11 antigen-like family member D) (Leukointegrin alpha D) (CD antigen CD11d) | ITGAD | 1161 |
| P06756 | ITAV_HUMAN | Integrin alpha-V (Vitronectin receptor subunit alpha) (CD antigen CD51) [Cleaved into: Integrin alpha-V heavy chain; Integrin alpha-V light chain] | ITGAV MSK8 VNRA | 1048 |
| Q6UXV1 | IZUM2_HUMAN | Izumo sperm-egg fusion protein 2 | IZUMO2 C19orf41 SCRL UNQ6978/PRO21961 | 221 |
| P27930 | IL1R2_HUMAN | Interleukin-1 receptor type 2 (IL-1R-2) (IL-1RT-2) (IL-1RT2) (CD121 antigen-like family member B) (CDw121b) (IL-1 type II receptor) (Interleukin-1 receptor beta) (IL-1R-beta) (Interleukin-1 receptor type II) (CD antigen CD121b) [Cleaved into: Interleukin-1 receptor type 2, membrane form (mIL-1R2) (mIL-1RII); Interleukin-1 receptor type 2, soluble form (sIL-1R2) (sIL-1RII)] | IL1R2 IL1RB | 398 |
| P40189 | IL6RB_HUMAN | Interleukin-6 receptor subunit beta (IL-6 receptor subunit beta) (IL-6R subunit beta) (IL-6R-beta) (IL-6RB) (CDw130) (Interleukin-6 signal transducer) (Membrane glycoprotein 130) (gp130) (Oncostatin-M receptor subunit alpha) (CD antigen CD130) | IL6ST | 918 |
| P17301 | ITA2_HUMAN | Integrin alpha-2 (CD49 antigen-like family member B) (Collagen receptor) (Platelet membrane glycoprotein Ia) (GPIa) (VLA-2 subunit alpha) (CD antigen CD49b) | ITGA2 CD49B | 1181 |
| P26006 | ITA3_HUMAN | Integrin alpha-3 (CD49 antigen-like family member C) (FRP-2) (Galactoprotein B3) (GAPB3) (VLA-3 subunit alpha) (CD antigen CD49c) [Cleaved into: Integrin alpha-3 heavy chain; Integrin alpha-3 light chain] | ITGA3 MSK18 | 1051 |
| P11215 | ITAM_HUMAN | Integrin alpha-M (CD11 antigen-like family member B) (CR-3 alpha chain) (Cell surface glycoprotein MAC-1 subunit alpha) (Leukocyte adhesion receptor MO1) (Neutrophil adherence receptor) (CD antigen CD11b) | ITGAM CD11B CR3A | 1152 |
| P16144 | ITB4_HUMAN | Integrin beta-4 (GP150) (CD antigen CD104) | ITGB4 | 1822 |
| O75578 | ITA10_HUMAN | Integrin alpha-10 | ITGA10 UNQ468/PRO827 | 1167 |
| P56199 | ITA1_HUMAN | Integrin alpha-1 (CD49 antigen-like family member A) (Laminin and collagen receptor) (VLA-1) (CD antigen CD49a) | ITGA1 | 1179 |
| P08514 | ITA2B_HUMAN | Integrin alpha-IIb (GPalpha IIb) (GPIIb) (Platelet membrane glycoprotein IIb) (CD antigen CD41) [Cleaved into: Integrin alpha-IIb heavy chain; Integrin alpha-IIb light chain, form 1; Integrin alpha-IIb light chain, form 2] | ITGA2B GP2B ITGAB | 1039 |
| P08648 | ITA5_HUMAN | Integrin alpha-5 (CD49 antigen-like family member E) (Fibronectin receptor subunit alpha) (Integrin alpha-F) (VLA-5) (CD antigen CD49e) [Cleaved into: Integrin alpha-5 heavy chain; Integrin alpha-5 light chain] | ITGA5 FNRA | 1049 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P38570 | ITAE_HUMAN | Integrin alpha-E (HML-1 antigen) (Integrin alpha-IEL) (Mucosal lymphocyte 1 antigen) (CD antigen CD103) [Cleaved into: Integrin alpha-E light chain; Integrin alpha-E heavy chain] | ITGAE | 1179 |
| P20702 | ITAX_HUMAN | Integrin alpha-X (CD11 antigen-like family member C) (Leu M5) (Leukocyte adhesion glycoprotein p150, 95 alpha chain) (Leukocyte adhesion receptor p150, 95) (CD antigen CD11c) | ITGAX CD11C | 1163 |
| P05106 | ITB3_HUMAN | Integrin beta-3 (Platelet membrane glycoprotein IIIa) (GPIIIa) (CD antigen CD61) | ITGB3 GP3A | 788 |
| Q5VZ72 | IZUM3_HUMAN | Izumo sperm-egg fusion protein 3 | IZUMO3 C9orf134 | 239 |
| P78504 | JAG1_HUMAN | Protein jagged-1 (Jagged1) (hJ1) (CD antigen CD339) | JAG1 JAGL1 | 1218 |
| A8MWY0 | K132L_HUMAN | UPF0577 protein KIAA1324-like (Estrogen-induced gene 121-like protein) (hEIG121L) | KIAA1324L EIG121L | 1029 |
| P48551 | INAR2_HUMAN | Interferon alpha/beta receptor 2 (IFN-R-2) (IFN-alpha binding protein) (IFN-alpha/beta receptor 2) (Interferon alpha binding protein) (Type I interferon receptor 2) | IFNAR2 IFNABR IFNARB | 515 |
| P38484 | INGR2_HUMAN | Interferon gamma receptor 2 (IFN-gamma receptor 2) (Interferon gamma receptor accessory factor 1) (AF-1) (Interferon gamma transducer 1) | IFNGR2 IFNGT1 | 337 |
| Q3MIP1 | IPIL2_HUMAN | Inositol 1,4,5-trisphosphate receptor-interacting protein-like 2 | ITPRIPL2 | 535 |
| Q6UXG2 | K1324_HUMAN | UPF0577 protein KIAA1324 (Estrogen-induced gene 121 protein) | KIAA1324 EIG121 UNQ2426/PRO4985 | 1013 |
| Q3SXP7 | K1644_HUMAN | Uncharacterized protein KIAA1644 | KIAA1644 | 199 |
| Q9NZN1 | IRPL1_HUMAN | Interleukin-1 receptor accessory protein-like 1 (IL-1-RAPL-1) (IL-1RAPL-1) (IL1RAPL-1) (Oligophrenin-4) (Three immunoglobulin domain-containing IL-1 receptor-related 2) (TIGIRR-2) (X-linked interleukin-1 receptor accessory protein-like 1) | IL1RAPL1 OPHN4 | 696 |
| Q9UKX5 | ITA11_HUMAN | Integrin alpha-11 | ITGA11 MSTP018 | 1188 |
| P05556 | ITB1_HUMAN | Integrin beta-1 (Fibronectin receptor subunit beta) (Glycoprotein IIa) (GPIIA) (VLA-4 subunit beta) (CD antigen CD29) | ITGB1 FNRB MDF2 MSK12 | 798 |
| P05107 | ITB2_HUMAN | Integrin beta-2 (Cell surface adhesion glycoproteins LFA-1/CR3/p150, 95 subunit beta) (Complement receptor C3 subunit beta) (CD antigen CD18) | ITGB2 CD18 MFI7 | 769 |
| P18564 | ITB6_HUMAN | Integrin beta-6 | ITGB6 | 788 |
| P26010 | ITB7_HUMAN | Integrin beta-7 (Gut homing receptor beta subunit) | ITGB7 | 798 |
| P26012 | ITB8_HUMAN | Integrin beta-8 | ITGB8 | 769 |
| Q9Y624 | JAM1_HUMAN | Junctional adhesion molecule A (JAM-A) (Junctional adhesion molecule 1) (JAM-1) (Platelet F11 receptor) (Platelet adhesion molecule 1) (PAM-1) (CD antigen CD321) | F11R JAM1 JCAM UNQ264/PRO301 | 299 |
| Q9BX67 | JAM3_HUMAN | Junctional adhesion molecule C (JAM-C) (JAM-2) (Junctional adhesion molecule 3) (JAM-3) | JAM3 UNQ859/PRO1868 | 310 |
| Q8IYV9 | IZUM1_HUMAN | Izumo sperm-egg fusion protein 1 (Oocyte binding/fusion factor) (OBF) (Sperm-specific protein izumo) | IZUMO1 | 350 |
| Q9UJ90 | KCNE5_HUMAN | Potassium voltage-gated channel subfamily E regulatory beta subunit 5 (AMME syndrome candidate gene 2 protein) (Potassium channel subunit beta MiRP4) (Potassium voltage-gated channel subfamily E member 1-like protein) | KCNE5 AMMECR2 KCNE1L | 142 |
| P13612 | ITA4_HUMAN | Integrin alpha-4 (CD49 antigen-like family member D) (Integrin alpha-IV) (VLA-4 subunit alpha) (CD antigen CD49d) | ITGA4 CD49D | 1032 |
| P23229 | ITA6_HUMAN | Integrin alpha-6 (CD49 antigen-like family member F) (VLA-6) (CD antigen CD49f) [Cleaved into: Integrin alpha-6 heavy chain; Integrin alpha-6 light chain; Processed integrin alpha-6 (Alpha6p)] | ITGA6 | 1130 |
| Q13797 | ITA9_HUMAN | Integrin alpha-9 (Integrin alpha-RLC) | ITGA9 | 1035 |
| P20701 | ITAL_HUMAN | Integrin alpha-L (CD11 antigen-like family member A) (Leukocyte adhesion glycoprotein LFA-1 alpha chain) (LFA-1A) (Leukocyte function-associated molecule 1 alpha chain) (CD antigen CD11a) | ITGAL CD11A | 1170 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P18084 | ITB5_HUMAN | Integrin beta-5 | ITGB5 | 799 |
| Q9Y219 | JAG2_HUMAN | Protein jagged-2 (Jagged2) (hJ2) | JAG2 | 1238 |
| Q5VV43 | K0319_HUMAN | Dyslexia-associated protein KIAA0319 | KIAA0319 | 1072 |
| Q8IYS2 | K2013_HUMAN | Uncharacterized protein KIAA2013 | KIAA2013 | 634 |
| P57087 | JAM2_HUMAN | Junctional adhesion molecule B (JAM-B) (Junctional adhesion molecule 2) (JAM-2) (Vascular endothelial junction-associated molecule) (VE-JAM) (CD antigen CD322) | JAM2 C21orf43 VEJAM UNQ219/PRO245 | 298 |
| Q86YT9 | JAML_HUMAN | Junctional adhesion molecule-like (Adhesion molecule interacting with CXADR antigen 1) (Dendritic cell-specific protein CREA7-1) | JAML AMICA1 UNQ722/PRO1387 | 394 |
| A0A087 WTH5 | KCE1B_HUMAN | Potassium voltage-gated channel subfamily E member 1B | KCNE1B | 132 |
| Q8NC54 | KCT2_HUMAN | Keratinocyte-associated transmembrane protein 2 | KCT2 C5orf15 HTGN29 | 265 |
| Q6UWL6 | KIRR2_HUMAN | Kin of IRRE-like protein 2 (Kin of irregular chiasm-like protein 2) (Nephrin-like protein 3) | KIRREL2 NEPH3 UNQ5827/PRO19646 | 708 |
| O76095 | JTB_HUMAN | Protein JTB (Jumping translocation breakpoint protein) (Prostate androgen-regulated protein) (PAR protein) | JTB HSPC222 | 146 |
| Q9Y6I6 | KCNE2_HUMAN | Potassium voltage-gated channel subfamily E member 2 (MinK-related peptide 1) (Minimum potassium ion channel-related peptide 1) (Potassium channel subunit beta MiRP1) | KCNE2 | 123 |
| Q9Y6H6 | KCNE3_HUMAN | Potassium voltage-gated channel subfamily E member 3 (MinK-related peptide 2) (Minimum potassium ion channel-related peptide 2) (Potassium channel subunit beta MiRP2) | KCNE3 | 103 |
| Q8NHK3 | KI2LB_HUMAN | Killer cell immunoglobulin-like receptor 2DL5B (CD158 antigen-like family member F2) (Killer cell immunoglobulin-like receptor 2DLX) (CD antigen CD158f2) | KIR2DL5B CD158F CD158F2 KIR2DL5 KIR2DLX | 375 |
| Q14952 | KI2S3_HUMAN | Killer cell immunoglobulin-like receptor 2DS3 (MHC class I NK cell receptor) (Natural killer-associated transcript 7) (NKAT-7) | KIR2DS3 NKAT7 | 304 |
| Q14943 | KI3S1_HUMAN | Killer cell immunoglobulin-like receptor 3DS1 (MHC class I NK cell receptor) (Natural killer-associated transcript 10) (NKAT-10) | KIR3DS1 NKAT10 | 387 |
| Q9NRX6 | KISHB_HUMAN | Protein kish-B (Transmembrane protein 167B) | TMEM167B C1orf119 AD-020 | 74 |
| P15382 | KCNE1_HUMAN | Potassium voltage-gated channel subfamily E member 1 (Delayed rectifier potassium channel subunit IsK) (IKs producing slow voltage-gated potassium channel subunit beta Mink) (Minimal potassium channel) | KCNE1 | 129 |
| P43626 | KI2L1_HUMAN | Killer cell immunoglobulin-like receptor 2DL1 (CD158 antigen-like family member A) (MHC class I NK cell receptor) (Natural killer-associated transcript 1) (NKAT-1) (p58 natural killer cell receptor clones CL-42/47.11) (p58 NK receptor CL-42/47.11) (p58.1 MHC class-I-specific NK receptor) (CD antigen CD158a) | KIR2DL1 CD158A NKAT1 | 348 |
| Q99706 | KI2L4_HUMAN | Killer cell immunoglobulin-like receptor 2DL4 (CD158 antigen-like family member D) (G9P) (Killer cell inhibitory receptor 103AS) (KIR-103AS) (MHC class I NK cell receptor KIR103AS) (CD antigen CD158d) | KIR2DL4 CD158D KIR103AS | 377 |
| P43632 | KI2S4_HUMAN | Killer cell immunoglobulin-like receptor 2DS4 (CD158 antigen-like family member I) (MHC class I NK cell receptor) (Natural killer-associated transcript 8) (NKAT-8) (P58 natural killer cell receptor clones CL-39/CL-17) (p58 NK receptor CL-39/CL-17) (CD antigen CD158i) | KIR2DS4 CD158I KKA3 NKAT8 | 304 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q8IZU9 | KIRR3_HUMAN | Kin of IRRE-like protein 3 (Kin of irregular chiasm-like protein 3) (Nephrin-like protein 2) [Cleaved into: Processed kin of IRRE-like protein 3] | KIRREL3 KIAA1867 NEPH2 UNQ5923/PRO4502/PRO19814 | 778 |
| P32004 | L1CAM_HUMAN | Neural cell adhesion molecule L1 (N-CAM-L1) (NCAM-L1) (CD antigen CD171) | L1CAM CAML1 MIC5 | 1257 |
| Q6GTX8 | LAIR1_HUMAN | Leukocyte-associated immunoglobulin-like receptor 1 (LAIR-1) (hLAIR1) (CD antigen CD305) | LAIR1 CD305 | 287 |
| P43628 | KI2L3_HUMAN | Killer cell immunoglobulin-like receptor 2DL3 (CD158 antigen-like family member B2) (KIR-023GB) (Killer inhibitory receptor cl 2-3) (MHC class I NK cell receptor) (NKAT2a) (NKAT2b) (Natural killer-associated transcript 2) (NKAT-2) (p58 natural killer cell receptor clone CL-6) (p58 NK receptor CL-6) (p58.2 MHC class-I-specific NK receptor) (CD antigen CD158b2) | KIR2DL3 CD158B2 KIRCL23 NKAT2 | 341 |
| Q14954 | KI2S1_HUMAN | Killer cell immunoglobulin-like receptor 2DS1 (CD158 antigen-like family member H) (MHC class I NK cell receptor Eb6 Act1) (CD antigen CD158h) | KIR2DS1 CD158H | 304 |
| Q14953 | KI2S5_HUMAN | Killer cell immunoglobulin-like receptor 2DS5 (CD158 antigen-like family member G) (MHC class I NK cell receptor) (Natural killer-associated transcript 9) (NKAT-9) (CD antigen CD158g) | KIR2DS5 CD158G NKAT9 | 304 |
| P43629 | KI3L1_HUMAN | Killer cell immunoglobulin-like receptor 3DL1 (CD158 antigen-like family member E) (HLA-BW4-specific inhibitory NK cell receptor) (MHC class I NK cell receptor) (Natural killer-associated transcript 3) (NKAT-3) (p70 natural killer cell receptor clones CL-2/CL-11) (p70 NK receptor CL-2/CL-11) (CD antigen CD158e) | KIR3DL1 CD158E NKAT3 NKB1 | 444 |
| Q8N743 | KI3L3_HUMAN | Killer cell immunoglobulin-like receptor 3DL3 (CD158 antigen-like family member Z) (Killer cell inhibitory receptor 1) (CD antigen CD158z) | KIR3DL3 CD158Z KIR3DL7 KIRC1 | 410 |
| Q96184 | KIRR1_HUMAN | Kin of IRRE-like protein 1 (Kin of irregular chiasm-like protein 1) (Nephrin-like protein 1) | KIRREL KIRREL1 NEPH1 | 757 |
| P10721 | KIT_HUMAN | Mast/stem cell growth factor receptor Kit (SCFR) (Tyrosine-protein kinase Kit) (p145 c-kit Hardy-Zuckerman 4 feline sarcoma viral oncogene homolog) (CD antigen CD117) (PBT) (Proto-oncogene c-Kit) (EC 2.7.10.1) (Piebald trait protein) | KIT SCFR | 976 |
| Q86UK5 | LBN_HUMAN | Limbin (Ellis-van Creveld syndrome protein 2) (EVC2) | EVC2 LBN | 1308 |
| P43627 | KI2L2_HUMAN | Killer cell immunoglobulin-like receptor 2DL2 (CD158 antigen-like family member B1) (MHC class I NK cell receptor) (Natural killer-associated transcript 6) (NKAT-6) (p58 natural killer cell receptor clone CL-43) (p58 NK receptor CL-43) (CD antigen CD158b1) | KIR2DL2 CD158B1 NKAT6 | 348 |
| Q8N109 | KI2LA_HUMAN | Killer cell immunoglobulin-like receptor 2DL5A (CD antigen CD158f1) | KIR2DL5A CD158F CD158F1 KIR2DL5 | 375 |
| P43631 | KI2S2_HUMAN | Killer cell immunoglobulin-like receptor 2DS2 (CD158 antigen-like family member J) (MHC class I NK cell receptor) (NK receptor 183 Act1) (Natural killer-associated transcript 5) (NKAT-5) (p58 natural killer cell receptor clone CL-49) (p58 NK receptor CL-49) (CD antigen CD158j) | KIR2DS2 CD158J NKAT5 | 304 |
| P43630 | KI3L2_HUMAN | Killer cell immunoglobulin-like receptor 3DL2 (CD158 antigen-like family member K) (MHC class I NK cell receptor) (Natural killer-associated transcript 4) (NKAT-4) (p70 natural killer cell receptor clone CL-5) (p70 NK receptor CL-5) (CD antigen CD158k) | KIR3DL2 CD158K NKAT4 | 455 |
| Q8TBQ9 | KISHA_HUMAN | Protein kish-A (Transmembrane protein 167) (Transmembrane protein 167A) | TMEM167A TMEM167 | 72 |
| Q96MU8 | KREM1_HUMAN | Kremen protein 1 (Dickkopf receptor) (Kringle domain-containing transmembrane protein 1) (Kringle-containing protein marking the eye and the nose) | KREMEN1 KREMEN KRM1 | 473 |
| P11279 | LAMP1_HUMAN | Lysosome-associated membrane glycoprotein 1 (LAMP-1) (Lysosome-associated membrane protein 1) (CD107 antigen-like family member A) (CD antigen CD107a) | LAMP1 | 417 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P13473 | LAMP2_HUMAN | Lysosome-associated membrane glycoprotein 2 (LAMP-2) (Lysosome-associated membrane protein 2) (CD107 antigen-like family member B) (CD antigen CD107b) | LAMP2 | 410 |
| P01130 | LDLR_HUMAN | Low-density lipoprotein receptor (LDL receptor) | LDLR | 860 |
| Q9UEF7 | KLOT_HUMAN | Klotho (EC 3.2.1.31) [Cleaved into: Klotho peptide] | KL | 1012 |
| A6NM11 | L37A2_HUMAN | Leucine-rich repeat-containing protein 37A2 | LRRC37A2 | 1700 |
| Q9UJQ1 | LAMP5_HUMAN | Lysosome-associated membrane glycoprotein 5 (Brain and dendritic cell-associated LAMP) (Brain-associated LAMP-like protein) (BAD-LAMP) (Lysosome-associated membrane protein 5) (LAMP-5) | LAMP5 C20orf103 | 280 |
| P19256 | LFA3_HUMAN | Lymphocyte function-associated antigen 3 (Ag3) (Surface glycoprotein LFA-3) (CD antigen CD58) | CD58 LFA3 | 250 |
| Q8NCW0 | KREM2_HUMAN | Kremen protein 2 (Dickkopf receptor 2) (Kringle domain-containing transmembrane protein 2) (Kringle-containing protein marking the eye and the nose) | KREMEN2 KRM2 | 462 |
| A6NMS7 | L37A1_HUMAN | Leucine-rich repeat-containing protein 37A | LRRC37A LRRC37A1 | 1700 |
| O60309 | L37A3_HUMAN | Leucine-rich repeat-containing protein 37A3 | LRRC37A3 KIAA0563 | 1634 |
| P18627 | LAG3_HUMAN | Lymphocyte activation gene 3 protein (LAG-3) (Protein FDC) (CD antigen CD223) | LAG3 FDC | 525 |
| Q6UX15 | LAYN_HUMAN | Layilin | LAYN UNQ208/PRO234 | 382 |
| P48357 | LEPR_HUMAN | Leptin receptor (LEP-R) (HuB219) (OB receptor) (OB-R) (CD antigen CD295) | LEPR DB OBR | 1165 |
| Q8N149 | LIRA2_HUMAN | Leukocyte immunoglobulin-like receptor subfamily A member 2 (CD85 antigen-like family member H) (Immunoglobulin-like transcript 1) (ILT-1) (Leukocyte immunoglobulin-like receptor 7) (LIR-7) (CD antigen CD85h) | LILRA2 ILT1 LIR7 | 483 |
| A6NI73 | LIRA5_HUMAN | Leukocyte immunoglobulin-like receptor subfamily A member 5 (CD85 antigen-like family member F) (Immunoglobulin-like transcript 11) (ILT-11) (Leukocyte immunoglobulin-like receptor 9) (LIR-9) (CD antigen CD85f) | LILRA5 ILT11 LILRB7 LIR9 | 299 |
| Q8N423 | LIRB2_HUMAN | Leukocyte immunoglobulin-like receptor subfamily B member 2 (LIR-2) (Leukocyte immunoglobulin-like receptor 2) (CD85 antigen-like family member D) (Immunoglobulin-like transcript 4) (ILT-4) (Monocyte/macrophage immunoglobulin-like receptor 10) (MIR-10) (CD antigen CD85d) | LILRB2 ILT4 LIR2 MIR10 | 598 |
| P42702 | LIFR_HUMAN | Leukemia inhibitory factor receptor (LIF receptor) (LIF-R) (CD antigen CD118) | LIFR | 1097 |
| Q6UY18 | LIGO4_HUMAN | Leucine-rich repeat and immunoglobulin-like domain-containing nogo receptor-interacting protein 4 (Leucine-rich repeat neuronal protein 6D) | LINGO4 LRRN6D UNQ9248/PRO34002 | 593 |
| Q6PI73 | LIRA6_HUMAN | Leukocyte immunoglobulin-like receptor subfamily A member 6 (Immunoglobulin-like transcript 8) (ILT-8) (Leukocyte Ig-like receptor) | LILRA6 ILT8 | 481 |
| O75022 | LIRB3_HUMAN | Leukocyte immunoglobulin-like receptor subfamily B member 3 (LIR-3) (Leukocyte immunoglobulin-like receptor 3) (CD85 antigen-like family member A) (Immunoglobulin-like transcript 5) (ILT-5) (Monocyte inhibitory receptor HL9) (CD antigen CD85a) | LILRB3 ILT5 LIR3 | 631 |
| P49257 | LMAN1_HUMAN | Protein ERGIC-53 (ER-Golgi intermediate compartment 53 kDa protein) (Gp58) (Intracellular mannose-specific lectin MR60) (Lectin mannose-binding 1) | LMAN1 ERGIC53 F5F8D | 510 |
| Q9UQV4 | LAMP3_HUMAN | Lysosome-associated membrane glycoprotein 3 (LAMP-3) (Lysosomal-associated membrane protein 3) (DC-lysosome-associated membrane glycoprotein) (DC LAMP) (Protein TSC403) (CD antigen CD208) | LAMP3 DCLAMP TSC403 | 416 |
| Q7L985 | LIGO2_HUMAN | Leucine-rich repeat and immunoglobulin-like domain-containing nogo receptor-interacting protein 2 (Leucine-rich repeat neuronal protein 3) (Leucine-rich repeat neuronal protein 6C) | LINGO2 LERN3 LRRN6C UNQ9234/PRO31993 | 606 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9H0V9 | LMA2L_HUMAN | VIP36-like protein (Lectin mannose-binding 2-like) (LMAN2-like protein) | LMAN2L VIPL PSEC0028 UNQ368/PRO704 | 348 |
| P09848 | LPH_HUMAN | Lactase-phlorizin hydrolase (Lactase-glycosylceramidase) [Includes: Lactase (EC 3.2.1.108); Phlorizin hydrolase (EC 3.2.1.62)] | LCT LPH | 1927 |
| Q96FE5 | LIGO1_HUMAN | Leucine-rich repeat and immunoglobulin-like domain-containing nogo receptor-interacting protein 1 (Leucine-rich repeat and immunoglobulin domain-containing protein 1) (Leucine-rich repeat neuronal protein 1) (Leucine-rich repeat neuronal protein 6A) | LINGO1 LERN1 LRRN6A UNQ201/PRO227 | 620 |
| Q12907 | LMAN2_HUMAN | Vesicular integral-membrane protein VIP36 (Glycoprotein GP36b) (Lectin mannose-binding 2) (Vesicular integral-membrane protein 36) (VIP36) | LMAN2 C5orf8 | 356 |
| Q9H756 | LRC19_HUMAN | Leucine-rich repeat-containing protein 19 | LRRC19 | 370 |
| Q5VT99 | LRC38_HUMAN | Leucine-rich repeat-containing protein 38 (BK channel auxiliary gamma subunit LRRC38) | LRRC38 | 294 |
| A6NDA9 | LRIT2_HUMAN | Leucine-rich repeat, immunoglobulin-like domain and transmembrane domain-containing protein 2 (Leucine-rich repeat-containing protein 22) | LRIT2 LRRC22 | 550 |
| P16150 | LEUK_HUMAN | Leukosialin (Galactoglycoprotein) (GALGP) (Leukocyte sialoglycoprotein) (Sialophorin) (CD antigen CD43) | SPN CD43 | 400 |
| P0C6S8 | LIGO3_HUMAN | Leucine-rich repeat and immunoglobulin-like domain-containing nogo receptor-interacting protein 3 (Leucine-rich repeat neuronal protein 2) (Leucine-rich repeat neuronal protein 6B) | LINGO3 LERN2 LRRN6B | 592 |
| O75023 | LIRB5_HUMAN | Leukocyte immunoglobulin-like receptor subfamily B member 5 (CD85 antigen-like family member C) (Leukocyte immunoglobulin-like receptor 8) (LIR-8) (CD antigen CD85c) | LILRB5 LIR8 | 590 |
| Q9HAT1 | LMA1L_HUMAN | Protein ERGIC-53-like (ERGIC53-like protein) (Lectin mannose-binding 1-like) (LMAN1-like protein) | LMAN1L ERGL UNQ2784/PRO7174 | 526 |
| O75197 | LRP5_HUMAN | Low-density lipoprotein receptor-related protein 5 (LRP-5) | LRP5 LR3 LRP7 | 1615 |
| O75581 | LRP6_HUMAN | Low-density lipoprotein receptor-related protein 6 (LRP-6) | LRP6 | 1613 |
| Q9H3W5 | LRRN3_HUMAN | Leucine-rich repeat neuronal protein 3 (Neuronal leucine-rich repeat protein 3) (NLRR-3) | LRRN3 Nbla10363 UNQ194/PRO220 | 708 |
| P59901 | LIRA4_HUMAN | Leukocyte immunoglobulin-like receptor subfamily A member 4 (CD85 antigen-like family member G) (Immunoglobulin-like transcript 7) (ILT-7) (CD antigen CD83g) | LILRA4 ILT7 | 499 |
| Q8NHL6 | LIRB1_HUMAN | Leukocyte immunoglobulin-like receptor subfamily B member 1 (LIR-1) (Leukocyte immunoglobulin-like receptor 1) (CD85 antigen-like family member J) (Immunoglobulin-like transcript 2) (ILT-2) (Monocyte/macrophage immunoglobulin-like receptor 7) (MIR-7) (CD antigen CD85j) | LILRB1 ILT2 LIR1 MIR7 | 650 |
| Q96QE4 | LR37B_HUMAN | Leucine-rich repeat-containing protein 37B (C66 SLIT-like testicular protein) | LRRC37B | 947 |
| Q9HC12 | LRC4C_HUMAN | Leucine-rich repeat-containing protein 4C (Netrin-G1 ligand) (NGL-1) | LRRC4C KIAA1580 NGL1 UNQ292/PRO331 | 640 |
| Q9P2V4 | LRIT1_HUMAN | Leucine-rich repeat, immunoglobulin-like domain and transmembrane domain-containing protein 1 (Leucine-rich repeat-containing protein 21) (Photoreceptor-associated LRR superfamily protein) (Retina-specific protein PAL) | LRIT1 LRRC21 PAL | 623 |
| P29376 | LTK_HUMAN | Leukocyte tyrosine kinase receptor (EC 2.7.10.1) (Protein tyrosine kinase 1) | LTK TYK1 | 864 |
| Q9HBG7 | LY9_HUMAN | T-lymphocyte surface antigen Ly-9 (Cell surface molecule Ly-9) (Lymphocyte antigen 9) (SLAM family member 3) (SLAMF3) (Signaling lymphocytic activation molecule 3) (CD antigen CD229) | LY9 CDABP0070 | 655 |
| P14151 | LYAM1_HUMAN | L-selectin (CD62 antigen-like family member L) (Leukocyte adhesion molecule 1) (LAM-1) (Leukocyte surface antigen Leu-8) (Leukocyte-endothelial cell adhesion molecule 1) (LECAM1) (Lymph node homing receptor) (TQ1) (gp90-MEL) (CD antigen CD62L) | SELL LNHR LYAM1 | 372 |
| Q5SZI1 | LRAD2_HUMAN | Low-density lipoprotein receptor class A domain-containing protein 2 | LDLRAD2 | 272 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q8TF66 | LRC15_HUMAN | Leucine-rich repeat-containing protein 15 (Leucine-rich repeat protein induced by beta-amyloid homolog) (hLib) | LRRC15 LIB | 581 |
| Q2I0M4 | LRC26_HUMAN | Leucine-rich repeat-containing protein 26 (BK channel auxiliary gamma subunit LRRC26) (Cytokeratin-associated protein in cancer) | LRRC26 CAPC | 334 |
| Q9P244 | LRFN1_HUMAN | Leucine-rich repeat and fibronectin type III domain-containing protein 1 (Synaptic adhesion-like molecule 2) | LRFN1 KIAA1484 SALM2 | 771 |
| Q9ULH4 | LRFN2_HUMAN | Leucine-rich repeat and fibronectin type-III domain-containing protein 2 (Synaptic adhesion-like molecule 1) | LRFN2 KIAA1246 SALM1 | 789 |
| Q9BTN0 | LRFN3_HUMAN | Leucine-rich repeat and fibronectin type-III domain-containing protein 3 (Synaptic adhesion-like molecule 4) | LRFN3 SALM4 UNQ5865/PRO34192 | 628 |
| Q6PIG9 | LRFN4_HUMAN | Leucine-rich repeat and fibronectin type-III domain-containing protein 4 | LRFN4 SALM3 | 635 |
| Q96NI6 | LRFN5_HUMAN | Leucine-rich repeat and fibronectin type-III domain-containing protein 5 | LRFN5 C14orf146 SALM5 | 719 |
| Q96JA1 | LRIG1_HUMAN | Leucine-rich repeats and immunoglobulin-like domains protein 1 (LIG-1) | LRIG1 LIG1 | 1093 |
| O94898 | LRIG2_HUMAN | Leucine-rich repeats and immunoglobulin-like domains protein 2 (LIG-2) | LRIG2 KIAA0806 LIG2 | 1065 |
| Q6UXM1 | LRIG3_HUMAN | Leucine-rich repeats and immunoglobulin-like domains protein 3 (LIG-3) | LRIG3 UNQ287/PRO326/PRO335 | 1119 |
| Q9HBW1 | LRRC4_HUMAN | Leucine-rich repeat-containing protein 4 (Brain tumor-associated protein BAG) (Nasopharyngeal carcinoma-associated gene 14 protein) (Netrin-G2 ligand) (NGL-2) | LRRC4 BAG NAG14 UNQ554/PRO1111 | 653 |
| Q6UXK5 | LRRN1_HUMAN | Leucine-rich repeat neuronal protein 1 (Neuronal leucine-rich repeat protein 1) (NLRR-1) | LRRN1 KIAA1497 Nbla10449 | 716 |
| Q86VH5 | LRRT3_HUMAN | Leucine-rich repeat transmembrane neuronal protein 3 | LRRTM3 UNQ803/PRO1693 | 581 |
| P16581 | LYAM2_HUMAN | E-selectin (CD62 antigen-like family member E) (Endothelial leukocyte adhesion molecule 1) (ELAM-1) (Leukocyte-endothelial cell adhesion molecule 2) (LECAM2) (CD antigen CD62E) | SELE ELAM1 | 610 |
| P16109 | LYAM3_HUMAN | P-selectin (CD62 antigen-like family member P) (Granule membrane protein 140) (GMP-140) (Leukocyte-endothelial cell adhesion molecule 3) (LECAM3) (Platelet activation dependent granule-external membrane protein) (PADGEM) (CD antigen CD62P) | SELP GMRP GRMP | 830 |
| O75019 | LIRA1_HUMAN | Leukocyte immunoglobulin-like receptor subfamily A member 1 (CD85 antigen-like family member I) (Leukocyte immunoglobulin-like receptor 6) (LIR-6) (CD antigen CD85i) | LILRA1 LIR6 | 489 |
| Q8NHJ6 | LIRB4_HUMAN | Leukocyte immunoglobulin-like receptor subfamily B member 4 (CD85 antigen-like family member K) (Immunoglobulin-like transcript 3) (ILT-3) (Leukocyte immunoglobulin-like receptor 5) (LIR-5) (Monocyte inhibitory receptor HM18) (CD antigen CD83k) | LILRB4 ILT3 LIR5 | 448 |
| Q6ZMQ8 | LMTK1_HUMAN | Serine/threonine-protein kinase LMTK1 (EC 2.7.11.1) (Apoptosis-associated tyrosine kinase) (AATYK) (Brain apoptosis-associated tyrosine kinase) (CDK5-binding protein) (Lemur tyrosine kinase 1) (p35-binding protein) (p35BP) | AATK AATYK KIAA0641 LMR1 LMTK1 | 1374 |
| Q8N386 | LRC25_HUMAN | Leucine-rich repeat-containing protein 25 (Monocyte and plasmacytoid-activated protein) | LRRC25 MAPA UNQ6169/PRO20174 | 305 |
| Q8ND94 | LRN4L_HUMAN | LRRN4 C-terminal-like protein | LRRN4CL UNQ728/PRO1410 | 238 |
| Q86VZ4 | LRP11_HUMAN | Low-density lipoprotein receptor-related protein 11 (LRP-11) | LRP11 | 500 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q07954 | LRP1_HUMAN | Prolow-density lipoprotein receptor-related protein 1 (LRP-1) (Alpha-2-macroglobulin receptor) (A2MR) (Apolipoprotein E receptor) (APOER) (CD antigen CD91) [Cleaved into: Low-density lipoprotein receptor-related protein 1 85 kDa subunit (LRP-85); Low-density lipoprotein receptor-related protein 1 515 kDa subunit (LRP-515); Low-density lipoprotein receptor-related protein 1 intracellular domain (LRPICD)] | LRP1 A2MR APR | 4544 |
| O75074 | LRP3_HUMAN | Low-density lipoprotein receptor-related protein 3 (LRP-3) (105 kDa low-density lipoprotein receptor-related protein) (hLRp105) | LRP3 | 770 |
| O75096 | LRP4_HUMAN | Low-density lipoprotein receptor-related protein 4 (LRP-4) (Multiple epidermal growth factor-like domains 7) | LRP4 KIAA0816 LRP10 MEGF7 | 1905 |
| Q14114 | LRP8_HUMAN | Low-density lipoprotein receptor-related protein 8 (LRP-8) (Apolipoprotein E receptor 2) | LRP8 APOER2 | 963 |
| O43300 | LRRT2_HUMAN | Leucine-rich repeat transmembrane neuronal protein 2 (Leucine-rich repeat neuronal 2 protein) | LRRTM2 KIAA0416 LRRN2 | 516 |
| Q9HBL6 | LRTM1_HUMAN | Leucine-rich repeat and transmembrane domain-containing protein 1 | LRTM1 HT017 | 345 |
| Q7Z4F1 | LRP10_HUMAN | Low-density lipoprotein receptor-related protein 10 (LRP-10) | LRP10 MSTP087 SP220 UNQ389/PRO724 | 713 |
| Q8N967 | LRTM2_HUMAN | Leucine-rich repeat and transmembrane domain-containing protein 2 | LRTM2 | 370 |
| Q9Y561 | LRP12_HUMAN | Low-density lipoprotein receptor-related protein 12 (LRP-12) (Suppressor of tumorigenicity 7 protein) | LRP12 ST7 | 859 |
| P98164 | LRP2_HUMAN | Low-density lipoprotein receptor-related protein 2 (LRP-2) (Glycoprotein 330) (gp330) (Megalin) | LRP2 | 4655 |
| Q9H8J5 | MANS1_HUMAN | MANSC domain-containing protein 1 (Loss of heterozygosity 12 chromosomal region 3 protein) | MANSC1 LOH12CR3 UNQ316/PRO361 | 431 |
| Q86YD5 | LRAD3_HUMAN | Low-density lipoprotein receptor class A domain-containing protein 3 | LDLRAD3 | 345 |
| Q14392 | LRC32_HUMAN | Leucine-rich repeat-containing protein 32 (Garpin) (Glycoprotein A repetitions predominant) (GARP) | LRRC32 D11S833E GARP | 662 |
| Q9NZR2 | LRP1B_HUMAN | Low-density lipoprotein receptor-related protein 1B (LRP-1B) (Low-density lipoprotein receptor-related protein-deleted in tumor) (LRP-DIT) | LRP1B LRPDIT | 4599 |
| O75325 | LRRN2_HUMAN | Leucine-rich repeat neuronal protein 2 (Glioma amplified on chromosome 1 protein) (Leucine-rich repeat neuronal protein 5) | LRRN2 GAC1 LRRN5 UNQ256/PRO293 | 713 |
| Q8WUT4 | LRRN4_HUMAN | Leucine-rich repeat neuronal protein 4 (Neuronal leucine-rich repeat protein 4) (NLRR-4) | LRRN4 C20orf75 | 740 |
| Q86UE6 | LRRT1_HUMAN | Leucine-rich repeat transmembrane neuronal protein 1 | LRRTM1 UNQ675/PRO1309 | 522 |
| A6NHS7 | MANS4_HUMAN | MANSC domain-containing protein 4 | MANSC4 | 340 |
| P15529 | MCP_HUMAN | Membrane cofactor protein (TLX) (Trophoblast leukocyte common antigen) (CD antigen CD46) | CD46 MCP MIC10 | 392 |
| Q86VH4 | LRRT4_HUMAN | Leucine-rich repeat transmembrane neuronal protein 4 | LRRTM4 UNQ3075/PRO9907 | 590 |
| Q13477 | MADCA_HUMAN | Mucosal addressin cell adhesion molecule 1 (MAdCAM-1) (hMAdCAM-1) | MADCAM1 | 382 |
| Q5SQ64 | LY66F_HUMAN | Lymphocyte antigen 6 complex locus protein G6f | LY6G6F C6orf21 G6F LY6G6D NG32 | 297 |
| O60449 | LY75_HUMAN | Lymphocyte antigen 75 (Ly-75) (C-type lectin domain family 13 member B) (DEC-205) (gp200-MR6) (CD antigen CD205) | LY75 CD205 CLEC13B | 1722 |
| Q9Y5Y7 | LYVE1_HUMAN | Lymphatic vessel endothelial hyaluronic acid receptor 1 (LYVE-1) (Cell surface retention sequence-binding protein 1) (CRSBP-1) (Extracellular link domain-containing protein 1) (Hyaluronic acid receptor) | LYVE1 CRSBP1 HAR XLKD1 UNQ230/PRO263 | 322 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P20916 | MAG_HUMAN | Myelin-associated glycoprotein (Siglec-4a) | MAG GMA | 626 |
| Q16820 | MEP1B_HUMAN | Meprin A subunit beta (EC 3.4.24.63) (Endopeptidase-2) (Meprin B) (N-benzoyl-L-tyrosyl-P-amino-benzoic acid hydrolase subunit beta) (PABA peptide hydrolase) (PPH beta) | MEP1B | 701 |
| Q9H9K5 | MER34_HUMAN | Endogenous retrovirus group MER34 member 1 Env polyprotein (HERV-MER_4q12 provirus ancestral Env polyprotein) | ERVMER34-1 LP9056 | 563 |
| Q14703 | MBTP1_HUMAN | Membrane-bound transcription factor site-1 protease (EC 3.4.21.112) (Endopeptidase S1P) (Subtilisin/kexin-isozyme 1) (SKI-1) | MBTPS1 KIAA0091 S1P SKI1 | 1052 |
| Q12866 | MERTK_HUMAN | Tyrosine-protein kinase Mer (EC 2.7.10.1) (Proto-oncogene c-Mer) (Receptor tyrosine kinase MerTK) | MERTK MER | 999 |
| Q7Z7M0 | MEGF8_HUMAN | Multiple epidermal growth factor-like domains protein 8 (Multiple EGF-like domains protein 8) (Epidermal growth factor-like protein 4) (EGF-like protein 4) | MEGF8 C19orf49 EGFL4 KIAA0817 | 2845 |
| P55082 | MFAP3_HUMAN | Microfibril-associated glycoprotein 3 | MFAP3 | 362 |
| Q96KG7 | MEG10_HUMAN | Multiple epidermal growth factor-like domains protein 10 (Multiple EGF-like domains protein 10) | MEGF10 KIAA1780 | 1140 |
| A6BM72 | MEG11_HUMAN | Multiple epidermal growth factor-like domains protein 11 (Multiple EGF-like domains protein 11) | MEGF11 KIAA1781 UNQ1949/PRO4432 | 1044 |
| Q16819 | MEP1A_HUMAN | Meprin A subunit alpha (EC 3.4.24.18) (Endopeptidase-2) (N-benzoyl-L-tyrosyl-P-amino-benzoic acid hydrolase subunit alpha) (PABA peptide hydrolase) (PPH alpha) | MEP1A | 746 |
| P51512 | MMP16_HUMAN | Matrix metalloproteinase-16 (MMP-16) (EC 3.4.24.—) (MMP-X2) (Membrane-type matrix metalloproteinase 3) (MT-MMP 3) (MTMMP3) (Membrane-type-3 matrix metalloproteinase) (MT3-MMP) (MT3MMP) | MMP16 MMPX2 | 607 |
| Q9H1U4 | MEGF9_HUMAN | Multiple epidermal growth factor-like domains protein 9 (Multiple EGF-like domains protein 9) (Epidermal growth factor-like protein 5) (EGF-like protein 5) | MEGF9 EGFL5 KIAA0818 UNQ671/PRO1305 | 602 |
| Q5JRA6 | MIA3_HUMAN | Melanoma inhibitory activity protein 3 (C219-reactive peptide) (D320) (Transport and Golgi organization protein 1) | MIA3 KIAA0268 TANGO TANGO1 UNQ6077/PRO20088 | 1907 |
| P51511 | MMP15_HUMAN | Matrix metalloproteinase-15 (MMP-15) (EC 3.4.24.—) (Membrane-type matrix metalloproteinase 2) (MT-MMP 2) (MTMMP2) (Membrane-type-2 matrix metalloproteinase) (MT2-MMP) (MT2MMP) (SMCP-2) | MMP15 | 669 |
| O75121 | MFA3L_HUMAN | Microfibrillar-associated protein 3-like (Testis development protein NYD-SP9) | MFAP3L KIAA0626 HSD-39 HSD39 | 409 |
| P08581 | MET_HUMAN | Hepatocyte growth factor receptor (HGF receptor) (EC 2.7.10.1) (HGF/SF receptor) (Proto-oncogene c-Met) (Scatter factor receptor) (SF receptor) (Tyrosine-protein kinase Met) | MET | 1390 |
| Q29983 | MICA_HUMAN | MHC class I polypeptide-related sequence A (MIC-A) | MICA PERB11.1 | 383 |
| Q8TD46 | MO2R1_HUMAN | Cell surface glycoprotein CD200 receptor 1 (CD200 cell surface glycoprotein receptor) (Cell surface glycoprotein OX2 receptor 1) | CD200R1 CD200R CRTR2 MOX2R OX2R UNQ2522/PRO6015 | 325 |
| Q29980 | MICB_HUMAN | MHC class I polypeptide-related sequence B (MIC-B) | MICB PERB11.2 | 383 |
| P50281 | MMP14_HUMAN | Matrix metalloproteinase-14 (MMP-14) (EC 3.4.24.80) (MMP-X1) (Membrane-type matrix metalloproteinase 1) (MT-MMP 1) (MTMMP1) (Membrane-type-1 matrix metalloproteinase) (MT1-MMP) (MT1MMP) | MMP14 | 582 |
| Q2M385 | MPEG1_HUMAN | Macrophage-expressed gene 1 protein (Macrophage gene 1 protein) (Mpg-1) | MPEG1 | 716 |
| Q7Z6M3 | MILR1_HUMAN | Allergin-1 (Allergy inhibitory receptor 1) (Mast cell antigen 32) (MCA-32) (Mast cell immunoglobulin-like receptor 1) | MILR1 C17orf60 MCA32 | 343 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P20645 | MPRD_HUMAN | Cation-dependent mannose-6-phosphate receptor (CD Man-6-P receptor) (CD-MPR) (46 kDa mannose 6-phosphate receptor) (MPR 46) | M6PR MPR46 MPRD | 277 |
| P11717 | MPRI_HUMAN | Cation-independent mannose-6-phosphate receptor (CI Man-6-P receptor) (CI-MPR) (M6PR) (300 kDa mannose 6-phosphate receptor) (MPR 300) (Insulin-like growth factor 2 receptor) (Insulin-like growth factor II receptor) (IGF-II receptor) (M6P/IGF2 receptor) (M6P/IGF2R) (CD antigen CD222) | IGF2R MPRI | 2491 |
| Q14165 | MLEC_HUMAN | Malectin | MLEC KIAA0152 | 292 |
| Q9Y5R2 | MMP24_HUMAN | Matrix metalloproteinase-24 (MMP-24) (EC 3.4.24.—) (Membrane-type matrix metalloproteinase 5) (MT-MMP 5) (MTMMP5) (Membrane-type-5 matrix metalloproteinase) (MT5-MMP) (MT5MMP) [Cleaved into: Processed matrix metalloproteinase-24] | MMP24 MT5MMP | 645 |
| Q16653 | MOG_HUMAN | Myelin-oligodendrocyte glycoprotein | MOG | 247 |
| Q6UWV2 | MPZL3_HUMAN | Myelin protein zero-like protein 3 | MPZL3 UNQ2966/PRO7425 | 235 |
| Q6UVY6 | MOXD1_HUMAN | DBH-like monooxygenase protein 1 (EC 1.14.17.—) (Monooxygenase X) | MOXD1 MOX UNQ2493/PRO5780 | 613 |
| Q6Q8B3 | MO2R2_HUMAN | Cell surface glycoprotein CD200 receptor 2 (CD200 cell surface glycoprotein receptor-like 2) (CD200 receptor-like 2) (HuCD200R2) (CD200 cell surface glycoprotein receptor-like a) (CD200RLa) (Cell surface glycoprotein CD200 receptor 1-like) (Cell surface glycoprotein OX2 receptor 2) | CD200R1L CD200R2 | 271 |
| O60487 | MPZL2_HUMAN | Myelin protein zero-like protein 2 (Epithelial V-like antigen 1) | MPZL2 EVA EVA1 UNQ606/PRO1192 | 215 |
| Q96KJ4 | MSLNL_HUMAN | Mesothelin-like protein (Pre-pro-megakaryocyte-potentiating-factor-like) | MSLNL C16orf37 MPFL | 702 |
| P43121 | MUC18_HUMAN | Cell surface glycoprotein MUC18 (Cell surface glycoprotein P1H12) (Melanoma cell adhesion molecule) (Melanoma-associated antigen A32) (Melanoma-associated antigen MUC18) (S-endo 1 endothelial-associated antigen) (CD antigen CD146) | MCAM MUC18 | 646 |
| P15941 | MUC1_HUMAN | Mucin-1 (MUC-1) (Breast carcinoma-associated antigen DF3) (Cancer antigen 15-3) (CA 15-3) (Carcinoma-associated mucin) (Episialin) (H23AG) (Krebs von den Lungen-6) (KL-6) (PEMT) (Peanut-reactive urinary mucin) (PUM) (Polymorphic epithelial mucin) (PEM) (Tumor-associated epithelial membrane antigen) (EMA) (Tumor-associated mucin) (CD antigen CD227) [Cleaved into: Mucin-1 subunit alpha (MUC1-NT) (MUC1-alpha); Mucin-1 subunit beta (MUC1-beta) (MUC1-CT)] | MUC1 PUM | 1255 |
| O95297 | MPZL1_HUMAN | Myelin protein zero-like protein 1 (Protein zero-related) | MPZL1 PZR UNQ849/PRO1787 | 269 |
| P22897 | MRC1_HUMAN | Macrophage mannose receptor 1 (MMR) (C-type lectin domain family 13 member D) (C-type lectin domain family 13 member D-like) (Human mannose receptor) (hMR) (Macrophage mannose receptor 1-like protein 1) (CD antigen CD206) | MRC1 CLEC13D CLEC13DL MRC1L1 | 1456 |
| Q9UBG0 | MRC2_HUMAN | C-type mannose receptor 2 (C-type lectin domain family 13 member E) (Endocytic receptor 180) (Macrophage mannose receptor 2) (Urokinase-type plasminogen activator receptor-associated protein) (UPAR-associated protein) (Urokinase receptor-associated protein) (CD antigen CD280) | MRC2 CLEC13E ENDO180 KIAA0709 UPARAP | 1479 |
| Q9UKN1 | MUC12_HUMAN | Mucin-12 (MUC-12) (Mucin-11) (MUC-11) | MUC12 MUC11 | 5478 |
| Q8N387 | MUC15_HUMAN | Mucin-15 (MUC-15) | MUC15 UNQ750/PRO1481 | 334 |
| Q8WXI7 | MUC16_HUMAN | Mucin-16 (MUC-16) (Ovarian cancer-related tumor marker CA125) (CA-125) (Ovarian carcinoma antigen CA125) | MUC16 CA125 | 14507 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q5SSG8 | MUC21_HUMAN | Mucin-21 (MUC-21) (Epiglycanin) | MUC21 C6orf205 UNQ697/PRO1342 | 566 |
| Q9H3R2 | MUC13_HUMAN | Mucin-13 (MUC-13) (Down-regulated in colon cancer 1) | MUC13 DRCC1 RECC UNQ6194/PRO20221 | 512 |
| O15146 | MUSK_HUMAN | Muscle, skeletal receptor tyrosine-protein kinase (EC 2.7.10.1) (Muscle-specific tyrosine-protein kinase receptor) (MuSK) (Muscle-specific kinase receptor) | MUSK | 869 |
| Q13505 | MTX1_HUMAN | Metaxin-1 (Mitochondrial outer membrane import complex protein 1) | MTX1 MTX MTXN | 466 |
| Q9ULC0 | MUCEN_HUMAN | Endomucin (Endomucin-2) (Gastric cancer antigen Ga34) (Mucin-14) (MUC-14) | EMCN EMCN2 MUC14 | 261 |
| Q04900 | MUC24_HUMAN | Sialomucin core protein 24 (MUC-24) (Endolyn) (Multi-glycosylated core protein 24) (MGC-24) (MGC-24v) (CD antigen CD164) | CD164 | 197 |
| P25189 | MYP0_HUMAN | Myelin protein P0 (Myelin peripheral protein) (MPP) (Myelin protein zero) | MPZ | 248 |
| Q9BRK3 | MXRA8_HUMAN | Matrix-remodeling-associated protein 8 (Limitrin) | MXRA8 | 442 |
| Q9UK23 | NAGPA_HUMAN | N-acetylglucosamine-1-phosphodiester alpha-N-acetylglucosaminidase (EC 3.1.4.45) (Mannose 6-phosphate-uncovering enzyme) (Phosphodiester alpha-GlcNAcase) | NAGPA | 515 |
| O15394 | NCAM2_HUMAN | Neural cell adhesion molecule 2 (N-CAM-2) (NCAM-2) | NCAM2 NCAM21 | 837 |
| O76036 | NCTR1_HUMAN | Natural cytotoxicity triggering receptor 1 (Lymphocyte antigen 94 homolog) (NK cell-activating receptor) (Natural killer cell p46-related protein) (NK-p46) (NKp46) (hNKp46) (CD antigen CD335) | NCR1 LY94 | 304 |
| Q8NC67 | NETO2_HUMAN | Neuropilin and tolloid-like protein 2 (Brain-specific transmembrane protein containing 2 CUB and 1 LDL-receptor class A domains protein 2) | NETO2 BTCL2 UNQ1926/PRO4401 | 525 |
| Q8TD07 | N2DL4_HUMAN | NKG2D ligand 4 (N2DL-4) (NKG2DL4) (Lymphocyte effector toxicity activation ligand) (RAE-1-like transcript 4) (RL-4) (Retinoic acid early transcript 1E) | RAET1E LETAL N2DL4 ULBP4 UNQ1867/PRO4303 | 263 |
| O14931 | NCTR3_HUMAN | Natural cytotoxicity triggering receptor 3 (Activating natural killer receptor p30) (Natural killer cell p30-related protein) (NK-p30) (NKp30) (CD antigen CD337) | NCR3 1C7 LY117 | 201 |
| Q8TDF5 | NETO1_HUMAN | Neuropilin and tolloid-like protein 1 (Brain-specific transmembrane protein containing 2 CUB and 1 LDL-receptor class A domains protein 1) | NETO1 BTCL1 | 533 |
| Q92542 | NICA_HUMAN | Nicastrin | NCSTN KIAA0253 UNQ1874/PRO4317 | 709 |
| P13591 | NCAM1_HUMAN | Neural cell adhesion molecule 1 (N-CAM-1) (NCAM-1) (CD antigen CD56) | NCAM1 NCAM | 858 |
| Q5T1S8 | NCMAP_HUMAN | Noncompact myelin-associated protein (Myelin protein of 11 kDa) (MP11) | NCMAP C1orf130 | 102 |
| O95944 | NCTR2_HUMAN | Natural cytotoxicity triggering receptor 2 (Lymphocyte antigen 95 homolog) (NK cell-activating receptor) (Natural killer cell p44-related protein) (NK-p44) (NKp44) (CD antigen CD336) | NCR2 LY95 | 276 |
| Q15223 | NECT1_HUMAN | Nectin-1 (Herpes virus entry mediator C) (Herpesvirus entry mediator C) (HveC) (Herpesvirus Ig-like receptor) (HIgR) (Nectin cell adhesion molecule 1) (Poliovirus receptor-related protein 1) (CD antigen CD111) | NECTIN1 HVEC PRR1 PVRL1 | 517 |
| Q92859 | NEO1_HUMAN | Neogenin (Immunoglobulin superfamily DCC subclass member 2) | NEO1 IGDCC2 NGN | 1461 |
| O00533 | NCHL1_HUMAN | Neural cell adhesion molecule L1-like protein (Close homolog of L1) [Cleaved into: Processed neural cell adhesion molecule L1-like protein] | CHL1 CALL | 1208 |
| Q8N2Q7 | NLGN1_HUMAN | Neuroligin-1 | NLGN1 KIAA1070 | 840 |
| Q8N0W4 | NLGNX_HUMAN | Neuroligin-4, X-linked (Neuroligin X) (HNLX) | NLGN4X KIAA1260 NLGN4 | 816 |
| O60500 | NPHN_HUMAN | Nephrin (Renal glomerulus-specific cell adhesion receptor) | UNQ365/PRO701 NPHS1 NPHN | 1241 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q96NY8 | NECT4_HUMAN | Nectin-4 (Ig superfamily receptor LNIR) (Nectin cell adhesion molecule 4) (Poliovirus receptor-related protein 4) [Cleaved into: Processed poliovirus receptor-related protein 4] | NECTIN4 LNIR PRR4 PVRL4 | 510 |
| Q8NET5 | NFAM1_HUMAN | NFAT activation molecule 1 (Calcineurin/NFAT-activating ITAM-containing protein) (NFAT-activating protein with ITAM motif 1) | NFAM1 CNAIP | 270 |
| O94856 | NFASC_HUMAN | Neurofascin | NFASC KIAA0756 | 1347 |
| Q9UM47 | NOTC3_HUMAN | Neurogenic locus notch homolog protein 3 (Notch 3) [Cleaved into: Notch 3 extracellular truncation; Notch 3 intracellular domain] | NOTCH3 | 2321 |
| O14511 | NRG2_HUMAN | Pro-neuregulin-2, membrane-bound isoform (Pro-NRG2) [Cleaved into: Neuregulin-2 (NRG-2) (Divergent of neuregulin-1) (DON-1) (Neural- and thymus-derived activator for ERBB kinases) (NTAK)] | NRG2 NTAK | 850 |
| Q02297 | NRG1_HUMAN | Pro-neuregulin-1, membrane-bound isoform (Pro-NRG1) [Cleaved into: Neuregulin-1 (Acetylcholine receptor-inducing activity) (ARIA) (Breast cancer cell differentiation factor p45) (Glial growth factor) (Heregulin) (HRG) (Neu differentiation factor) (Sensory and motor neuron-derived factor)] | NRG1 GGF HGL HRGA NDF SMDF | 640 |
| Q9Y4C0 | NRX3A_HUMAN | Neurexin-3 (Neurexin III-alpha) (Neurexin-3-alpha) | NRXN3 C14orf60 KIAA0743 | 1643 |
| Q92692 | NECT2_HUMAN | Nectin-2 (Herpes virus entry mediator B) (Herpesvirus entry mediator B) (HveB) (Nectin cell adhesion molecule 2) (Poliovirus receptor-related protein 2) (CD antigen CD112) | NECTIN2 HVEB PRR2 PVRL2 | 538 |
| Q8NFZ4 | NLGN2_HUMAN | Neuroligin-2 | NLGN2 KIAA1366 | 835 |
| Q8NFZ3 | NLGNY_HUMAN | Neuroligin-4, Y-linked (Neuroligin Y) | NLGN4Y KIAA0951 | 816 |
| Q15155 | NOMO1_HUMAN | Nodal modulator 1 (pM5 protein) | NOMO1 PM5 | 1222 |
| P69849 | NOMO3_HUMAN | Nodal modulator 3 (pM5 protein 3) | NOMO3 | 1222 |
| Q9NZ94 | NLGN3_HUMAN | Neuroligin-3 (Gliotactin homolog) | NLGN3 KIAA1480 NL3 | 848 |
| P46531 | NOTC1_HUMAN | Neurogenic locus notch homolog protein 1 (Notch 1) (hN1) (Translocation-associated notch protein TAN-1) [Cleaved into: Notch 1 extracellular truncation (NEXT); Notch 1 intracellular domain (NICD)] | NOTCH1 TAN1 | 2555 |
| Q04721 | NOTC2_HUMAN | Neurogenic locus notch homolog protein 2 (Notch 2) (hN2) [Cleaved into: Notch 2 extracellular truncation (N2ECD); Notch 2 intracellular domain (N2ICD)] | NOTCH2 | 2471 |
| Q92823 | NRCAM_HUMAN | Neuronal cell adhesion molecule (Nr-CAM) (Neuronal surface protein Bravo) (hBravo) (NgCAM-related cell adhesion molecule) (Ng-CAM-related) | NRCAM KIAA0343 | 1304 |
| O60462 | NRP2_HUMAN | Neuropilin-2 (Vascular endothelial cell growth factor 165 receptor 2) | NRP2 VEGF165R2 | 931 |
| Q9Y639 | NPTN_HUMAN | Neuroplastin (Stromal cell-derived receptor 1) (SDR-1) | NPTN SDFR1 SDR1 | 398 |
| Q68D85 | NR3L1_HUMAN | Natural cytotoxicity triggering receptor 3 ligand 1 (B7 homolog 6) (B7-H6) | NCR3LG1 B7H6 | 454 |
| O14786 | NRP1_HUMAN | Neuropilin-1 (Vascular endothelial cell growth factor 165 receptor) (CD antigen CD304) | NRP1 NRP VEGF165R | 923 |
| P56975 | NRG3_HUMAN | Pro-neuregulin-3, membrane-bound isoform (Pro-NRG3) [Cleaved into: Neuregulin-3 (NRG-3)] | NRG3 | 720 |
| Q86YC3 | NRROS_HUMAN | Negative regulator of reactive oxygen species (Leucine-rich repeat-containing protein 33) | NRROS LRRC33 UNQ3030/PRO9833 | 692 |
| P58400 | NRX1B_HUMAN | Neurexin-1-beta (Neurexin 1-beta) | NRXN1 | 442 |
| Q9HDB5 | NRX3B_HUMAN | Neurexin-3-beta (Neurexin III-beta) [Cleaved into: Neurexin-3-beta, soluble form; Neurexin-3-beta, C-terminal fragment (NRXN3-CTF)] | NRXN3 KIAA0743 | 637 |
| Q16620 | NTRK2_HUMAN | BDNF/NT-3 growth factors receptor (EC 2.7.10.1) (GP145-TrkB) (Trk-B) (Neurotrophic tyrosine kinase receptor type 2) (TrkB tyrosine kinase) (Tropomyosin-related kinase B) | NTRK2 TRKB | 822 |
| Q16288 | NTRK3_HUMAN | NT-3 growth factor receptor (EC 2.7.10.1) (GP145-TrkC) (Trk-C) (Neurotrophic tyrosine kinase receptor type 3) (TrkC tyrosine kinase) | NTRK3 TRKC | 839 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q99466 | NOTC4_HUMAN | Neurogenic locus notch homolog protein 4 (Notch 4) (hNotch4) [Cleaved into: Notch 4 extracellular truncation; Notch 4 intracellular domain] | NOTCH4 INT3 | 2003 |
| Q8WWG1 | NRG4_HUMAN | Pro-neuregulin-4, membrane-bound isoform (Pro-NRG4) [Cleaved into: Neuregulin-4 (NRG-4)] | NRG4 | 115 |
| Q9P2S2 | NRX2A_HUMAN | Neurexin-2 (Neurexin II-alpha) (Neurexin-2-alpha) | NRXN2 KIAA0921 | 1712 |
| Q9ULB1 | NRX1A_HUMAN | Neurexin-1 (Neurexin I-alpha) (Neurexin-1-alpha) | NRXN1 KIAA0578 | 1477 |
| P58401 | NRX2B_HUMAN | Neurexin-2-beta (Neurexin II-beta) | NRXN2 | 666 |
| P04629 | NTRK1_HUMAN | High affinity nerve growth factor receptor (EC 2.7.10.1) (Neurotrophic tyrosine kinase receptor type 1) (TRK1-transforming tyrosine kinase protein) (Tropomyosin-related kinase A) (Tyrosine kinase receptor) (Tyrosine kinase receptor A) (Trk-A) (gp140trk) (p140-TrkA) | NTRK1 MTC TRK TRKA | 796 |
| Q96PE5 | OPALI_HUMAN | Opalin (Oligodendrocytic myelin paranodal and inner loop protein) (Transmembrane protein 10) | OPALIN HTMP10 TMEM10 | 141 |
| P41217 | OX2G_HUMAN | OX-2 membrane glycoprotein (CD antigen CD200) | CD200 MOX1 MOX2 My033 | 278 |
| Q8NBR0 | P5I13_HUMAN | Tumor protein p53-inducible protein 13 (Damage-stimulated cytoplasmic protein 1) | TP53I13 DSCP1 | 393 |
| Q99650 | OSMR_HUMAN | Oncostatin-M-specific receptor subunit beta (Interleukin-31 receptor subunit beta) (IL-31 receptor subunit beta) (IL-31R subunit beta) (IL-31R-beta) (IL-31RB) | OSMR OSMRB | 979 |
| Q8TYS5 | OSCAR_HUMAN | Osteoclast-associated immunoglobulin-like receptor (Osteoclast-associated receptor) (hOSCAR) (Polymeric immunoglobulin receptor 3) (PIgR-3) (PIgR3) (Poly-Ig receptor 3) | OSCAR | 282 |
| P39656 | OST48_HUMAN | Dolichyl-diphosphooligosaccharide--protein glycosyltransferase 48 kDa subunit (DDOST 48 kDa subunit) (Oligosaccharyl transferase 48 kDa subunit) (EC 2.4.99.18) | DDOST KIAA0115 OST48 OK/SW-cl.45 | 456 |
| Q86WC4 | OSTM1_HUMAN | Osteopetrosis-associated transmembrane protein 1 (Chloride channel 7 beta subunit) | OSTM1 GL HSPC019 UNQ6098/PRO21201 | 334 |
| Q9BZA7 | PC11X_HUMAN | Protocadherin-11 X-linked (Protocadherin-11) (Protocadherin on the X chromosome) (PCDH-X) (Protocadherin-S) | PCDH11X KIAA1326 PCDH11 PCDHX | 1347 |
| Q9P2E7 | PCD10_HUMAN | Protocadherin-10 | PCDH10 KIAA1400 | 1040 |
| Q96QU1 | PCD15_HUMAN | Protocadherin-15 | PCDH15 USH1F | 1955 |
| Q8N6Y1 | PCD20_HUMAN | Protocadherin-20 (Protocadherin-13) | PCDH20 PCDH13 | 951 |
| Q9UN67 | PCDBA_HUMAN | Protocadherin beta-10 (PCDH-beta-10) | PCDHB10 UNQ1906/PRO4352 | 800 |
| Q9Y5E8 | PCDBF_HUMAN | Protocadherin beta-15 (PCDH-beta-15) | PCDHB15 | 787 |
| Q9Y5I4 | PCDC2_HUMAN | Protocadherin alpha-C2 (PCDH-alpha-C2) | PCDHAC2 | 1007 |
| Q9Y5H0 | PCDG3_HUMAN | Protocadherin gamma-A3 (PCDH-gamma-A3) | PCDHGA3 | 932 |
| Q9Y5G8 | PCDG5_HUMAN | Protocadherin gamma-A5 (PCDH-gamma-A5) | PCDHGA5 | 931 |
| Q9Y5G6 | PCDG7_HUMAN | Protocadherin gamma-A7 (PCDH-gamma-A7) | PCDHGA7 | 932 |
| Q9Y5G1 | PCDGF_HUMAN | Protocadherin gamma-B3 (PCDH-gamma-B3) | PCDHGB3 | 929 |
| Q96FE7 | P3IP1_HUMAN | Phosphoinositide-3-kinase-interacting protein 1 (Kringle domain-containing protein HGFL) | PIK3IP1 HGFL | 263 |
| Q9HCL0 | PCD18_HUMAN | Protocadherin-18 | PCDH18 KIAA1562 | 1135 |
| Q9Y5H7 | PCDA5_HUMAN | Protocadherin alpha-5 (PCDH-alpha-5) | PCDHA5 CNRS6 | 936 |
| Q9Y5I1 | PCDAB_HUMAN | Protocadherin alpha-11 (PCDH-alpha-11) | PCDHA11 CNRS7 | 949 |
| Q9Y5E7 | PCDB2_HUMAN | Protocadherin beta-2 (PCDH-beta-2) | PCDHB2 | 798 |
| Q9Y5E5 | PCDB4_HUMAN | Protocadherin beta-4 (PCDH-beta-4) | PCDHB4 | 795 |
| Q9HC56 | PCDH9_HUMAN | Protocadherin-9 | PCDH9 | 1237 |
| Q92824 | PCSK5_HUMAN | Proprotein convertase subtilisin/kexin type 5 (EC 3.4.21.—) (Proprotein convertase 5) (PC5) (Proprotein convertase 6) (PC6) (hPC6) (Subtilisin/kexin-like protease PC5) | PCSK5 PC5 PC6 | 1860 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q96IQ0 | PCD16_HUMAN | Protocadherin-16 (Cadherin-19) (Cadherin-25) (Fibroblast cadherin-1) (Protein dachsous homolog 1) | DCHS1 CDH19 CDH25 FIB1 KIAA1773 PCDH16 | 3298 |
| Q9Y5I0 | PCDAD_HUMAN | Protocadherin alpha-13 (PCDH-alpha-13) | PCDHA13 CNRS5 | 950 |
| Q9Y5E6 | PCDB3_HUMAN | Protocadherin beta-3 (PCDH-beta-3) | PCDHB3 | 796 |
| Q9Y5E3 | PCDB6_HUMAN | Protocadherin beta-6 (PCDH-beta-6) | PCDHB6 | 794 |
| Q9Y5F1 | PCDBC_HUMAN | Protocadherin beta-12 (PCDH-beta-12) | PCDHB12 | 795 |
| Q9Y5G7 | PCDG6_HUMAN | Protocadherin gamma-A6 (PCDH-gamma-A6) | PCDHGA6 | 932 |
| Q9Y5G5 | PCDG8_HUMAN | Protocadherin gamma-A8 (PCDH-gamma-A8) | PCDHGA8 KIAA0327 | 932 |
| Q9Y5H3 | PCDGA_HUMAN | Protocadherin gamma-A10 (PCDH-gamma-A10) | PCDHGA10 | 936 |
| Q9Y5H2 | PCDGB_HUMAN | Protocadherin gamma-A11 (PCDH-gamma-A11) | PCDHGA11 | 935 |
| Q9Y5F6 | PCDGM_HUMAN | Protocadherin gamma-C5 (PCDH-gamma-C5) | PCDHGC5 | 944 |
| Q08174 | PCDH1_HUMAN | Protocadherin-1 (Cadherin-like protein 1) (Protocadherin-42) (PC42) | PCDH1 | 1060 |
| O95206 | PCDH8_HUMAN | Protocadherin-8 (Arcadlin) | PCDH8 | 1070 |
| Q9NZQ7 | PD1L1_HUMAN | Programmed cell death 1 ligand 1 (PD-L1) (PDCD1 ligand 1) (Programmed death ligand 1) (B7 homolog 1) (B7-H1) (CD antigen CD274) | CD274 B7H1 PDCD1L1 PDCD1LG1 PDL1 | 290 |
| Q6UWI2 | PARM1_HUMAN | Prostate androgen-regulated mucin-like protein 1 (PARM-1) | PARM1 UNQ1879/PRO4322 | 310 |
| Q9Y5I3 | PCDA1_HUMAN | Protocadherin alpha-1 (PCDH-alpha-1) | PCDHA1 | 950 |
| Q9Y5H8 | PCDA3_HUMAN | Protocadherin alpha-3 (PCDH-alpha-3) | PCDHA3 | 950 |
| Q9UN74 | PCDA4_HUMAN | Protocadherin alpha-4 (PCDH-alpha-4) | PCDHA4 | 947 |
| Q86YL7 | PDPN_HUMAN | Podoplanin (Aggrus) (Glycoprotein 36) (Gp36) (PA2.26 antigen) (T1-alpha) (T1A) | PDPN GP36 PSEC0003 PSEC0025 | 162 |
| P07202 | PERT_HUMAN | Thyroid peroxidase (TPO) (EC 1.11.1.8) | TPO | 933 |
| Q9BZA8 | PC11Y_HUMAN | Protocadherin-11 Y-linked (Protocadherin-11) (Protocadherin on the Y chromosome) (PCDH-Y) (Protocadherin prostate cancer) (Protocadherin-PC) (Protocadherin-22) | PCDH11Y PCDHY PCDH22 PCDHY | 1340 |
| O14917 | PCD17_HUMAN | Protocadherin-17 (Protocadherin-68) | PCDH17 PCDH68 PCH68 | 1159 |
| Q8TAB3 | PCD19_HUMAN | Protocadherin-19 | PCDH19 KIAA1313 | 1148 |
| Q9UN73 | PCDA6_HUMAN | Protocadherin alpha-6 (PCDH-alpha-6) | PCDHA6 CNRS2 | 950 |
| Q9Y5I2 | PCDAA_HUMAN | Protocadherin alpha-10 (PCDH-alpha-10) | PCDHA10 CNRS8 | 948 |
| Q9UN75 | PCDAC_HUMAN | Protocadherin alpha-12 (PCDH-alpha-12) | PCDHA12 | 941 |
| Q9Y5F3 | PCDB1_HUMAN | Protocadherin beta-1 (PCDH-beta-1) | PCDHB1 | 818 |
| Q9Y5E4 | PCDB5_HUMAN | Protocadherin beta-5 (PCDH-beta-5) | PCDHB5 | 795 |
| Q9UN66 | PCDB8_HUMAN | Protocadherin beta-8 (PCDH-beta-8) (Protocadherin-3I) | PCDHB8 PCDH3I | 801 |
| Q9Y5F2 | PCDBB_HUMAN | Protocadherin beta-11 (PCDH-beta-11) | PCDHB11 | 797 |
| Q9Y5F0 | PCDBD_HUMAN | Protocadherin beta-13 (PCDH-beta-13) | PCDHB13 UNQ332/PRO531 | 798 |
| Q9Y5H1 | PCDG2_HUMAN | Protocadherin gamma-A2 (PCDH-gamma-A2) | PCDHGA2 | 932 |
| Q9Y5G4 | PCDG9_HUMAN | Protocadherin gamma-A9 (PCDH-gamma-A9) | PCDHGA9 | 932 |
| O60330 | PCDGC_HUMAN | Protocadherin gamma-A12 (PCDH-gamma-A12) (Cadherin-21) (Fibroblast cadherin-3) | PCDHGA12 CDH21 FIB3 KIAA0588 UNQ371/PRO707 | 932 |
| Q9Y5G2 | PCDGE_HUMAN | Protocadherin gamma-B2 (PCDH-gamma-B2) | PCDHGB2 | 931 |
| Q9Y5F9 | PCDGI_HUMAN | Protocadherin gamma-B6 (PCDH-gamma-B6) | PCDHGB6 | 930 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9UN70 | PCDGK_HUMAN | Protocadherin gamma-C3 (PCDH-gamma-C3) (Protocadherin-2) (Protocadherin-43) (PC-43) | PCDHGC3 PCDH2 | 934 |
| O60245 | PCDH7_HUMAN | Protocadherin-7 (Brain-heart protocadherin) (BH-Pcdh) | PCDH7 BHPCDH | 1069 |
| Q16549 | PCSK7_HUMAN | Proprotein convertase subtilisin/kexin type 7 (EC 3.4.21.—) (Lymphoma proprotein convertase) (Prohormone convertase 7) (Proprotein convertase 7) (PC7) (Proprotein convertase 8) (PC8) (hPC8) (Subtilisin/kexin-like protease PC7) | PCSK7 LPC PC7 PC8 SPC7 | 785 |
| Q9BQ51 | PD1L2_HUMAN | Programmed cell death 1 ligand 2 (PD-1 ligand 2) (PDCD1 ligand 2) (Programmed death ligand 2) (Butyrophilin B7-DC) (B7-DC) (CD antigen CD273) | PDCD1LG2 B7DC CD273 PDCD1L2 PDL2 | 273 |
| P16284 | PECA1_HUMAN | Platelet endothelial cell adhesion molecule (PECAM-1) (EndoCAM) (GPIIA') (PECA1) (CD antigen CD31) | PECAM1 | 738 |
| Q9NPG4 | PCD12_HUMAN | Protocadherin-12 (Vascular cadherin-2) (Vascular endothelial cadherin-2) (VE-cad-2) (VE-cadherin-2) | PCDH12 UNQ395/PRO731 | 1184 |
| Q9Y5H9 | PCDA2_HUMAN | Protocadherin alpha-2 (PCDH-alpha-2) | PCDHA2 | 948 |
| Q9UN72 | PCDA7_HUMAN | Protocadherin alpha-7 (PCDH-alpha-7) | PCDHA7 CNRS4 | 937 |
| Q9Y5H6 | PCDA8_HUMAN | Protocadherin alpha-8 (PCDH-alpha-8) | PCDHA8 | 950 |
| Q9Y5H5 | PCDA9_HUMAN | Protocadherin alpha-9 (PCDH-alpha-9) | PCDHA9 KIAA0345 | 950 |
| Q9Y5E2 | PCDB7_HUMAN | Protocadherin beta-7 (PCDH-beta-7) | PCDHB7 | 793 |
| Q9Y5E1 | PCDB9_HUMAN | Protocadherin beta-9 (PCDH-beta-9) (Protocadherin-3H) | PCDHB9 PCDH3H | 797 |
| Q9Y5E9 | PCDBE_HUMAN | Protocadherin beta-14 (PCDH-beta-14) | PCDHB14 | 798 |
| Q9NRJ7 | PCDBG_HUMAN | Protocadherin beta-16 (PCDH-beta-16) (Protocadherin-3X) | PCDHB16 KIAA1621 PCDH3X | 776 |
| Q9H158 | PCDC1_HUMAN | Protocadherin alpha-C1 (PCDH-alpha-C1) | PCDHAC1 | 963 |
| Q9Y5H4 | PCDG1_HUMAN | Protocadherin gamma-A1 (PCDH-gamma-A1) | PCDHGA1 | 931 |
| Q9Y5G9 | PCDG4_HUMAN | Protocadherin gamma-A4 (PCDH-gamma-A4) | PCDHGA4 | 931 |
| Q9Y5G3 | PCDGD_HUMAN | Protocadherin gamma-B1 (PCDH-gamma-B1) | PCDHGB1 | 927 |
| Q9UN71 | PCDGG_HUMAN | Protocadherin gamma-B4 (PCDH-gamma-B4) (Cadherin-20) (Fibroblast cadherin-2) | PCDHGB4 CDH20 FIB2 | 923 |
| Q9Y5G0 | PCDGH_HUMAN | Protocadherin gamma-B5 (PCDH-gamma-B5) | PCDHGB5 | 923 |
| Q9Y5F8 | PCDGJ_HUMAN | Protocadherin gamma-B7 (PCDH-gamma-B7) | PCDHGB7 | 929 |
| Q9Y5F7 | PCDGL_HUMAN | Protocadherin gamma-C4 (PCDH-gamma-C4) | PCDHGC4 | 938 |
| P09619 | PGFRB_HUMAN | Platelet-derived growth factor receptor beta (PDGF-R-beta) (PDGFR-beta) (EC 2.7.10.1) (Beta platelet-derived growth factor receptor) (Beta-type platelet-derived growth factor receptor) (CD140 antigen-like family member B) (Platelet-derived growth factor receptor 1) (PDGFR-1) (CD antigen CD140b) | PDGFRB PDGFR PDGFR1 | 1106 |
| Q15116 | PDCD1_HUMAN | Programmed cell death protein 1 (Protein PD-1) (hPD-1) (CD antigen CD279) | PDCD1 PD1 | 288 |
| P16234 | PGFRA_HUMAN | Platelet-derived growth factor receptor alpha (PDGF-R-alpha) (PDGFR-alpha) (EC 2.7.10.1) (Alpha platelet-derived growth factor receptor) (Alpha-type platelet-derived growth factor receptor) (CD140 antigen-like family member A) (CD140a antigen) (Platelet-derived growth factor alpha receptor) (Platelet-derived growth factor receptor 2) (PDGFR-2) (CD antigen CD140a) | PDGFRA PDGFR2 RHEPDGFRA | 1089 |
| Q9NZ53 | PDXL2_HUMAN | Podocalyxin-like protein 2 (Endoglycan) | PODXL2 UNQ1861/PRO3742 | 605 |
| Q6UXB8 | PI16_HUMAN | Peptidase inhibitor 16 (PI-16) (Cysteine-rich secretory protein 9) (CRISP-9) (PSP94-binding protein) | PI16 CRISP9 PSPBP PSEC0164 UNQ289/PRO328 | 463 |
| Q9UKJ0 | PILRB_HUMAN | Paired immunoglobulin-like type 2 receptor beta (Activating receptor PILR-beta) (Cell surface receptor FDFACT) | PILRB FDFACT PP1551 | 227 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q8IY10 | PIANP_HUMAN | PILR alpha-associated neural protein (PILR-associating neural protein) (Paired immunoglobulin-like type 2 receptor-associating neural protein) | PIANP C12orf53 PANP UNQ828/PRO1755 | 282 |
| P01833 | PIGR_HUMAN | Polymeric immunoglobulin receptor (PIgR) (Poly-Ig receptor) (Hepatocellular carcinoma-associated protein TB6) [Cleaved into: Secretory component] | PIGR | 764 |
| Q9UKJ1 | PILRA_HUMAN | Paired immunoglobulin-like type 2 receptor alpha (Cell surface receptor FDF03) (Inhibitory receptor PILR-alpha) | PILRA | 303 |
| Q13018 | PLA2R_HUMAN | Secretory phospholipase A2 receptor (PLA2-R) (PLA2R) (180 kDa secretory phospholipase A2 receptor) (C-type lectin domain family 13 member C) (M-type receptor) [Cleaved into: Soluble secretory phospholipase A2 receptor (Soluble PLA2-R) (Soluble PLA2R)] | PLA2R1 CLEC13C | 1463 |
| Q8TUK5 | PLDX1_HUMAN | Plexin domain-containing protein 1 (Tumor endothelial marker 3) (Tumor endothelial marker 7) | PLXDC1 TEM3 TEM7 | 500 |
| O43157 | PLXB1_HUMAN | Plexin-B1 (Semaphorin receptor SEP) | PLXNB1 KIAA0407 PLXN5 SEP | 2135 |
| O60486 | PLXC1_HUMAN | Plexin-C1 (Virus-encoded semaphorin protein receptor) (CD antigen CD232) | PLXNC1 VESPR | 1568 |
| Q969N2 | PIGT_HUMAN | GPI transamidase component PIG-T (Phosphatidylinositol-glycan biosynthesis class T protein) | PIGT CGI-06 PSEC0163 UNQ716/PRO1379 | 578 |
| P08F94 | PKHD1_HUMAN | Fibrocystin (Polycystic kidney and hepatic disease 1 protein) (Polyductin) (Tigmin) | PKHD1 FCYT TIGM1 | 4074 |
| Q6P1J6 | PLB1_HUMAN | Phospholipase B1, membrane-associated (Phospholipase B) (hPLB) (Phospholipase B/lipase) (PLB/LIP) [Includes: Phospholipase A2 (EC 3.1.1.4); Lysophospholipase (EC 3.1.1.5)] | PLB1 PLB | 1458 |
| Q8TEM1 | PO210_HUMAN | Nuclear pore membrane glycoprotein 210 (Nuclear pore protein gp210) (Nuclear envelope pore membrane protein POM 210) (POM210) (Nucleoporin Nup210) (Pore membrane protein of 210 kDa) | NUP210 KIAA0906 PSEC0245 | 1887 |
| O00168 | PLM_HUMAN | Phospholemman (FXYD domain-containing ion transport regulator 1) | FXYD1 PLM | 92 |
| P51805 | PLXA3_HUMAN | Plexin-A3 (Plexin-4) (Semaphorin receptor SEX) | PLXNA3 PLXN4 SEX | 1871 |
| Q9UIW2 | PLXA1_HUMAN | Plexin-A1 (Semaphorin receptor NOV) | PLXNA1 NOV PLXN1 | 1896 |
| O75051 | PLXA2_HUMAN | Plexin-A2 (Semaphorin receptor OCT) | PLXNA2 KIAA0463 OCT PLXN2 UNQ209/PRO235 | 1894 |
| Q8TBF5 | PIGX_HUMAN | Phosphatidylinositol-glycan biosynthesis class X protein (PIG-X) | PIGX | 258 |
| P40967 | PMEL_HUMAN | Melanocyte protein PMEL (ME20-M) (ME20M) (Melanocyte protein Pmel 17) (Melanocytes lineage-specific antigen GP100) (Melanoma-associated ME20 antigen) (P1) (P100) (Premelanosome protein) (Silver locus protein homolog) [Cleaved into: M-alpha (95 kDa melanocyte-specific secreted glycoprotein) (P26) (Secreted melanoma-associated ME20 antigen) (ME20S); M-beta] | PMEL D12S53E PMEL17 SILV | 661 |
| Q8IY17 | PLPL6_HUMAN | Neuropathy target esterase (EC 3.1.1.5) (Patatin-like phospholipase domain-containing protein 6) | PNPLA6 NTE | 1366 |
| Q9BZG2 | PPAT_HUMAN | Testicular acid phosphatase (EC 3.1.3.2) | ACPT | 426 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q86XR5 | PRIMA_HUMAN | Praline-rich membrane anchor 1 (PRiMA) | PRIMA1 | 153 |
| Q9HCM2 | PLXA4_HUMAN | Plexin-A4 | PLXNA4 KIAA1550 PLXNA4A PLXNA4B UNQ2820/PRO34003 | 1894 |
| O15031 | PLXB2_HUMAN | Plexin-B2 (MM1) | PLXNB2 KIAA0315 | 1838 |
| Q9ULL4 | PLXB3_HUMAN | Plexin-B3 | PLXNB3 KIAA1206 PLXN6 | 1909 |
| O00592 | PODXL_HUMAN | Podocalyxin (GCTM-2 antigen) (Gp200) (Podocalyxin-like protein 1) (PC) (PCLP-1) | PODXL PCLP PCLP1 | 558 |
| Q8N131 | PORIM_HUMAN | Porimin (Keratinocytes-associated transmembrane protein 3) (KCT-3) (Pro-oncosis receptor inducing membrane injury) (Transmembrane protein 123) | TMEM123 KCT3 PSEC0111 UNQ641/PRO1271 | 208 |
| P15309 | PPAP_HUMAN | Prostatic acid phosphatase (PAP) (EC 3.1.3.2) (5'-nucleotidase) (5'-NT) (EC 3.1.3.5) (Ecto-5'-nucleotidase) (Thiamine monophosphatase) (TMPase) [Cleaved into: PAP39] | ACPP | 386 |
| Q5SGD2 | PPM1L_HUMAN | Protein phosphatase 1L (EC 3.1.3.16) (Protein phosphatase 1-like) (Protein phosphatase 2C isoform epsilon) (PP2C-epsilon) | PPM1L PP2CE | 360 |
| P16471 | PRLR_HUMAN | Prolactin receptor (PRL-R) | PRLR | 622 |
| Q6UWB4 | PRS55_HUMAN | Serine protease 55 (EC 3.4.21.—) (Testis serine protease 1) (T-SP1) | PRSS55 TSP1 UNQ9391/PRO34284 | 352 |
| P10586 | PTPRF_HUMAN | Receptor-type tyrosine-protein phosphatase F (EC 3.1.3.48) (Leukocyte common antigen related) (LAR) | PTPRF LAR | 1907 |
| P28827 | PTPRM_HUMAN | Receptor-type tyrosine-protein phosphatase mu (Protein-tyrosine phosphatase mu) (R-PTP-mu) (EC 3.1.3.48) | PTPRM PTPRL1 | 1452 |
| Q16849 | PTPRN_HUMAN | Receptor-type tyrosine-protein phosphatase-like N (R-PTP-N) (Islet cell antigen 512) (ICA 512) (Islet cell autoantigen 3) (PTP IA-2) | PTPRN ICA3 ICA512 | 979 |
| Q13332 | PTPRS_HUMAN | Receptor-type tyrosine-protein phosphatase S (R-PTP-S) (EC 3.1.3.48) (Receptor-type tyrosine-protein phosphatase sigma) (R-PTP-sigma) | PTPRS | 1948 |
| Q6ISU1 | PTCRA_HUMAN | Pre T-cell antigen receptor alpha (pT-alpha) (pTa) (pT-alpha-TCR) | PTCRA | 281 |
| P53801 | PTTG_HUMAN | Pituitary tumor-transforming gene 1 protein-interacting protein (Pituitary tumor-transforming gene protein-binding factor) (PBF) (PTTG-binding factor) | PTTG1IP C21orf1 C21orf3 | 180 |
| Q13308 | PTK7_HUMAN | Inactive tyrosine-protein kinase 7 (Colon carcinoma kinase 4) (CCK-4) (Protein-tyrosine kinase 7) (Pseudo tyrosine kinase receptor 7) (Tyrosine-protein kinase-like 7) | PTK7 CCK4 | 1070 |
| P23468 | PTPRD_HUMAN | Receptor-type tyrosine-protein phosphatase delta (Protein-tyrosine phosphatase delta) (R-PTP-delta) (EC 3.1.3.48) | PTPRD | 1912 |
| Q15262 | PTPRK_HUMAN | Receptor-type tyrosine-protein phosphatase kappa (Protein-tyrosine phosphatase kappa) (R-PTP-kappa) (EC 3.1.3.48) | PTPRK PTPK | 1439 |
| Q9UMZ3 | PTPRQ_HUMAN | Phosphatidylinositol phosphatase PTPRQ (EC 3.1.3.—) (Receptor-type tyrosine-protein phosphatase Q) (PTP-RQ) (R-PTP-Q) (EC 3.1.3.48) | PTPRQ | 2332 |
| P23467 | PTPRB_HUMAN | Receptor-type tyrosine-protein phosphatase beta (Protein-tyrosine phosphatase beta) (R-PTP-beta) (EC 3.1.3.48) (Vascular endothelial protein tyrosine phosphatase) (VE-PTP) | PTPRB PTPB | 1997 |
| Q9HD43 | PTPRH_HUMAN | Receptor-type tyrosine-protein phosphatase H (R-PTP-H) (EC 3.1.3.48) (Stomach cancer-associated protein tyrosine phosphatase 1) (SAP-1) (Transmembrane-type protein-tyrosine phosphatase type H) | PTPRH SAP1 | 1115 |
| Q16827 | PTPRO_HUMAN | Receptor-type tyrosine-protein phosphatase O (R-PTP-O) (EC 3.1.3.48) (Glomerular epithelial protein 1) (Protein tyrosine phosphatase U2) (PTP-U2) (PTPase U2) | PTPRO GLEPP1 PTPU2 | 1216 |
| Q15256 | PTPRR_HUMAN | Receptor-type tyrosine-protein phosphatase R (R-PTP-R) (EC 3.1.3.48) (Ch-1PTPase) (NC-PTPCOM1) (Protein-tyrosine phosphatase PCPTP1) | PTPRR ECPTP PTPRQ | 657 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P15151 | PVR_HUMAN | Poliovirus receptor (Nectin-like protein 5) (NECL-5) (CD antigen CD155) | PVR PVS | 417 |
| P18433 | PTPRA_HUMAN | Receptor-type tyrosine-protein phosphatase alpha (Protein-tyrosine phosphatase alpha) (R-PTP-alpha) (EC 3.1.3.48) | PTPRA PTPA PTPRL2 | 802 |
| P08575 | PTPRC_HUMAN | Receptor-type tyrosine-protein phosphatase C (EC 3.1.3.48) (Leukocyte common antigen) (L-CA) (T200) (CD antigen CD45) | PTPRC CD45 | 1304 |
| O14522 | PTPRT_HUMAN | Receptor-type tyrosine-protein phosphatase T (R-PTP-T) (EC 3.1.3.48) (Receptor-type tyrosine-protein phosphatase rho) (RPTP-rho) | PTPRT KIAA0283 | 1441 |
| Q92729 | PTPRU_HUMAN | Receptor-type tyrosine-protein phosphatase U (R-PTP-U) (EC 3.1.3.48) (Pancreatic carcinoma phosphatase 2) (PCP-2) (Protein-tyrosine phosphatase J) (PTP-J) (hPTP-J) (Protein-tyrosine phosphatase pi) (PTP pi) (Protein-tyrosine phosphatase receptor omicron) (PTP-RO) (Receptor-type protein-tyrosine phosphatase psi) (R-PTP-psi) | PTPRU FMI PCP2 PTPRO | 1446 |
| P23471 | PTPRZ_HUMAN | Receptor-type tyrosine-protein phosphatase zeta (R-PTP-zeta) (EC 3.1.3.48) (Protein-tyrosine phosphatase receptor type Z polypeptide 1) (Protein-tyrosine phosphatase receptor type Z polypeptide 2) (R-PTP-zeta-2) | PTPRZ1 HTPZP2 PTPRZ PTPRZ2 PTPZ | 2315 |
| Q9NXS2 | QPCTL_HUMAN | Glutaminyl-peptide cyclotransferase-like protein (EC 2.3.2.5) (Golgi-resident glutaminyl-peptide cyclotransferase) (isoQC) (gQC) | QPCTL | 382 |
| Q92932 | PTPR2_HUMAN | Receptor-type tyrosine-protein phosphatase N2 (R-PTP-N2) (EC 3.1.3.48) (Islet cell autoantigen-related protein) (IAR) (ICAAR) (Phogrin) | PTPRN2 KIAA0387 | 1015 |
| P23469 | PTPRE_HUMAN | Receptor-type tyrosine-protein phosphatase epsilon (Protein-tyrosine phosphatase epsilon) (R-PTP-epsilon) (EC 3.1.3.48) | PTPRE | 700 |
| P23470 | PTPRG_HUMAN | Receptor-type tyrosine-protein phosphatase gamma (Protein-tyrosine phosphatase gamma) (R-PTP-gamma) (EC 3.1.3.48) | PTPRG PTPG | 1445 |
| Q12913 | PTPRJ_HUMAN | Receptor-type tyrosine-protein phosphatase eta (Protein-tyrosine phosphatase eta) (R-PTP-eta) (EC 3.1.3.48) (Density-enhanced phosphatase 1) (DEP-1) (HPTP eta) (Protein-tyrosine phosphatase receptor type J) (R-PTP-J) (CD antigen CD148) | PTPRJ DEP1 | 1337 |
| Q15109 | RAGE_HUMAN | Advanced glycosylation end product-specific receptor (Receptor for advanced glycosylation end products) | AGER RAGE | 404 |
| Q6UX71 | PXDC2_HUMAN | Plexin domain-containing protein 2 (Tumor endothelial marker 7-related protein) | PLXDC2 TEM7R UNQ2514/PRO6003 | 529 |
| O60894 | RAMP1_HUMAN | Receptor activity-modifying protein 1 (Calcitonin-receptor-like receptor activity-modifying protein 1) (CRLR activity-modifying protein 1) | RAMP1 | 148 |
| O60895 | RAMP2_HUMAN | Receptor activity-modifying protein 2 (Calcitonin-receptor-like receptor activity-modifying protein 2) (CRLR activity-modifying protein 2) | RAMP2 | 175 |
| O60896 | RAMP3_HUMAN | Receptor activity-modifying protein 3 (Calcitonin-receptor-like receptor activity-modifying protein 3) (CRLR activity-modifying protein 3) | RAMP3 | 148 |
| Q8IUW5 | RELL1_HUMAN | RELT-like protein 1 | RELL1 PSEC0162 | 271 |
| O75787 | RENR_HUMAN | Renin receptor (ATPase H(+)-transporting lysosomal accessory protein 2) (ATPase H(+)-transporting lysosomal-interacting protein 2) (ER-localized type I transmembrane adaptor) (Embryonic liver differentiation factor 10) (N14F) (Renin/prorenin receptor) (Vacuolar ATP synthase membrane sector-associated protein M8-9) (ATP6M8-9) (V-ATPase M8.9 subunit) | ATP6AP2 ATP6IP2 CAPER ELDF10 HT028 MSTP009 PSEC0072 | 350 |
| Q6H3X3 | RET1G_HUMAN | Retinoic acid early transcript 1G protein (UL-16 binding protein 5) (ULBP5) | RAET1G | 334 |
| P07949 | RET_HUMAN | Proto-oncogene tyrosine-protein kinase receptor Ret (EC 2.7.10.1) (Cadherin family member 12) (Proto-oncogene c-Ret) [Cleaved into: Soluble RET kinase fragment; Extracellular cell-membrane anchored RET cadherin 120 kDa fragment] | RET CDHF12 CDHR16 PTC RET51 | 1114 |
| Q9ULK6 | RN150_HUMAN | RING finger protein 150 | RNF150 KIAA1214 | 438 |
| Q9Y6N7 | ROBO1_HUMAN | Roundabout homolog 1 (Deleted in U twenty twenty) (H-Robo-1) | ROBO1 DUTT1 | 1651 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q01974 | ROR2_HUMAN | Tyrosine-protein kinase transmembrane receptor ROR2 (EC 2.7.10.1) (Neurotrophic tyrosine kinase, receptor-related 2) | ROR2 NTRKR2 | 943 |
| P04843 | RPN1_HUMAN | Dolichyl-diphosphooligosaccharide--protein glycosyltransferase subunit 1 (EC 2.4.99.18) (Dolichyl-diphosphooligosaccharide--protein glycosyltransferase 67 kDa subunit) (Ribophorin I) (RPN-I) (Ribophorin-1) | RPN1 | 607 |
| Q68DV7 | RNF43_HUMAN | E3 ubiquitin-protein ligase RNF43 (EC 6.3.2.—) (RING finger protein 43) | RNF43 | 783 |
| Q04912 | RON_HUMAN | Macrophage-stimulating protein receptor (MSP receptor) (EC 2.7.10.1) (CDw136) (Protein-tyrosine kinase 8) (p185-Ron) (CD antigen CD136) [Cleaved into: Macrophage-stimulating protein receptor alpha chain; Macrophage-stimulating protein receptor beta chain] | MST1R PTK8 RON | 1400 |
| Q96MS0 | ROBO3_HUMAN | Roundabout homolog 3 (Roundabout-like protein 3) | ROBO3 | 1386 |
| Q01973 | ROR1_HUMAN | Inactive tyrosine-protein kinase transmembrane receptor ROR1 (Neurotrophic tyrosine kinase, receptor-related 1) | ROR1 NTRKR1 | 937 |
| P08922 | ROS1_HUMAN | Proto-oncogene tyrosine-protein kinase ROS (EC 2.7.10.1) (Proto-oncogene c-Ros) (Proto-oncogene c-Ros-1) (Receptor tyrosine kinase c-ros oncogene 1) (c-Ros receptor tyrosine kinase) | ROS1 MCF3 ROS | 2347 |
| Q9HCK4 | ROBO2_HUMAN | Roundabout homolog 2 | ROBO2 KIAA1568 | 1378 |
| P34925 | RYK_HUMAN | Tyrosine-protein kinase RYK (EC 2.7.10.1) | RYK JTK5A | 604 |
| Q9HBV2 | SACA1_HUMAN | Sperm acrosome membrane-associated protein 1 (Sperm acrosomal membrane-associated protein 32) | SPACA1 SAMP32 | 294 |
| P31431 | SDC4_HUMAN | Syndecan-4 (SYND4) (Amphiglycan) (Ryudocan core protein) | SDC4 | 198 |
| P21583 | SCF_HUMAN | Kit ligand (Mast cell growth factor) (MGF) (Stem cell factor) (SCF) (c-Kit ligand) [Cleaved into: Soluble KIT ligand (sKITLG)] | KITLG MGF SCF | 273 |
| O60939 | SCN2B_HUMAN | Sodium channel subunit beta-2 | SCN2B UNQ326/PRO386 | 215 |
| Q8IWT1 | SCN4B_HUMAN | Sodium channel subunit beta-4 | SCN4B | 228 |
| P18827 | SDC1_HUMAN | Syndecan-1 (SYND1) (CD antigen CD138) | SDC1 SDC | 310 |
| O75056 | SDC3_HUMAN | Syndecan-3 (SYND3) | SDC3 KIAA0468 | 442 |
| Q9NTN9 | SEM4G_HUMAN | Semaphorin-4G | SEMA4G KIAA1619 | 838 |
| W5XKT8 | SACA6_HUMAN | Sperm acrosome membrane-associated protein 6 (BACHELOR-like protein) | SPACA6 SPACA6P UNQ2487/PRO5774 | 324 |
| Q96BY9 | SARAF_HUMAN | Store-operated calcium entry-associated regulatory factor (SARAF) (SOCE-associated regulatory factor) (HBV X-transactivated gene 3 protein) (HBV XAg-transactivated protein 3) (Protein FOAP-7) (Transmembrane protein 66) | SARAF TMEM66 XTP3 HSPC035 NPD003 PSEC0019 UNQ1967/PRO4499 | 339 |
| Q13591 | SEM5A_HUMAN | Semaphorin-5A (Semaphorin-F) (Sema F) | SEMA5A SEMAF | 1074 |
| Q53EL9 | SEZ6_HUMAN | Seizure protein 6 homolog (SEZ-6) (hSEZ-6) | SEZ6 | 994 |
| Q9NY72 | SCN3B_HUMAN | Sodium channel subunit beta-3 | SCN3B KIAA1158 | 215 |
| Q8WVN6 | SCTM1_HUMAN | Secreted and transmembrane protein 1 (Protein K-12) | SECTM1 K12 | 248 |
| Q9UBV2 | SE1L1_HUMAN | Protein sel-1 homolog 1 (Suppressor of lin-12-like protein 1) (Sel-1L) | SEL1L TSA305 UNQ128/PRO1063 | 794 |
| Q9NPR2 | SEM4B_HUMAN | Semaphorin-4B | SEMA4B KIAA1745 SEMAC UNQ749/PRO1480 | 832 |
| O95754 | SEM4F_HUMAN | Semaphorin-4F (Semaphorin-M) (Sema M) (Semaphorin-W) (Sema W) | SEMA4F SEMAM SEMAW | 770 |
| Q96RL6 | SIG11_HUMAN | Sialic acid-binding Ig-like lectin 11 (Sialic acid-binding lectin 11) (Siglec-11) | SIGLEC11 UNQ9222/PRO28718 | 698 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q07699 | SCN1B_HUMAN | Sodium channel subunit beta-1 | SCN1B | 218 |
| P34741 | SDC2_HUMAN | Syndecan-2 (SYND2) (Fibroglycan) (Heparan sulfate proteoglycan core protein) (HSPG) (CD antigen CD362) | SDC2 HSPG1 | 201 |
| Q7Z5N4 | SDK1_HUMAN | Protein sidekick-1 | SDK1 | 2213 |
| Q58EX2 | SDK2_HUMAN | Protein sidekick-2 | SDK2 KIAA1514 | 2172 |
| Q5TEA6 | SEL1L2_HUMAN | Protein sel-1 homolog 2 (Suppressor of lin-12-like protein 2) (Sel-1L2) | SEL1L2 C20orf50 | 688 |
| Q9BYH1 | SE6L1_HUMAN | Seizure 6-like protein | SEZ6L KIAA0927 UNQ2542/PRO6094 | 1024 |
| Q14242 | SELPL_HUMAN | P-selectin glycoprotein ligand 1 (PSGL-1) (Selectin P ligand) (CD antigen CD162) | SELPLG | 412 |
| Q9H3T2 | SEM6C_HUMAN | Semaphorin-6C (Semaphorin-Y) (Sema Y) | SEMA6C KIAA1869 SEMAY | 930 |
| Q96DD7 | SHSA4_HUMAN | Protein shisa-4 (Transmembrane protein 58) | SHISA4 C1orf40 TMEM58 | 197 |
| Q9P0V8 | SLAF8_HUMAN | SLAM family member 8 (B-lymphocyte activator macrophage expressed) (BCM-like membrane protein) (CD antigen CD353) | UNQ583/PRO1153 SLAMF8 BLAME | 285 |
| Q9H3T3 | SEM6B_HUMAN | Semaphorin-6B (Semaphorin-Z) (Sema Z) | SEMA6B SEMAN SEMAZ UNQ1907/PRO4353 | 888 |
| Q8NFY4 | SEM6D_HUMAN | Semaphorin-6D | SEMA6D KIAA1479 | 1073 |
| O94933 | SLIK3_HUMAN | SLIT and NTRK-like protein 3 | SLITRK3 KIAA0848 | 977 |
| Q6UXD5 | SE6L2_HUMAN | Seizure 6-like protein 2 | SEZ6L2 PSK UNQ1903/PRO4349 | 910 |
| Q9C0C4 | SEM4C_HUMAN | Semaphorin-4C | SEMA4C KIAA1739 SEMAI | 833 |
| Q92854 | SEM4D_HUMAN | Semaphorin-4D (A8) (BB18) (GR3) (CD antigen CD100) | SEMA4D C9orf164 CD100 SEMAJ UNQ5855/PRO34487 | 862 |
| P78324 | SHPS1_HUMAN | Tyrosine-protein phosphatase non-receptor type substrate 1 (SHP substrate 1) (SHPS-1) (Brain Ig-like molecule with tyrosine-based activation motifs) (Bit) (CD172 antigen-like family member A) (Inhibitory receptor SHPS-1) (Macrophage fusion receptor) (MyD-1 antigen) (Signal-regulatory protein alpha-1) (Sirp-alpha-1) (Signal-regulatory protein alpha-2) (Sirp-alpha-2) (Signal-regulatory protein alpha-3) (Sirp-alpha-3) (p84) (CD antigen CD172a) | SIRPA BIT MFR MYD1 PTPNS1 SHPS1 SIRP | 504 |
| Q8N114 | SHSA5_HUMAN | Protein shisa-5 (Putative NF-kappa-B-activating protein 120) (Scotin) | SHISA5 SCOTIN PSEC0133 | 240 |
| B8ZZ34 | SHSA8_HUMAN | Putative protein shisa-8 | SHISA8 C22orf17 | 492 |
| Q96PQ1 | SIG12_HUMAN | Sialic acid-binding Ig-like lectin 12 (Siglec-12) (Sialic acid-binding Ig-like lectin-like 1) (Siglec-L1) | SIGLEC12 SIGLECL1 SLG UNQ9215/PRO34042 | 595 |
| Q5JXA9 | SIRB2_HUMAN | Signal-regulatory protein beta-2 (SIRP-beta-2) (Protein tyrosine phosphatase non-receptor type substrate 1-like 3) (Protein tyrosine phosphatase non-receptor type substrate protein) | SIRPB2 PTPN1L PTPNS1L3 | 342 |
| Q9P1W8 | SIRPG_HUMAN | Signal-regulatory protein gamma (SIRP-gamma) (CD172 antigen-like family member B) (Signal-regulatory protein beta-2) (SIRP-b2) (CD antigen CD172g) | SIRPG SIRPB2 | 387 |
| Q9BQ49 | SMIM7_HUMAN | Small integral membrane protein 7 | SMIM7 C19orf42 | 75 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9H3S1 | SEM4A_HUMAN | Semaphorin-4A (Semaphorin-B) (Sema B) | SEMA4A SEMAB SEMB UNQ783/PRO1317 | 761 |
| Q9H2E6 | SEM6A_HUMAN | Semaphorin-6A (Semaphorin VIA) (Sema VIA) (Semaphorin-6A-1) (SEMA6A-1) | SEMA6A KIAA1368 SEMAQ | 1030 |
| B4DS77 | SHSA9_HUMAN | Protein shisa-9 | SHISA9 | 424 |
| A6NMB1 | SIG16_HUMAN | Sialic acid-binding Ig-like lectin 16 (Siglec-16) (Siglec-P16) | SIGLEC16 SIGLECP16 | 481 |
| Q9NYZ4 | SIGL8_HUMAN | Sialic acid-binding Ig-like lectin 8 (Siglec-8) (Sialoadhesin family member 2) (SAF-2) | SIGLEC8 SAF2 | 499 |
| Q9UIB8 | SLAF5_HUMAN | SLAM family member 5 (Cell surface antigen MAX.3) (Hly9-beta) (Leukocyte differentiation antigen CD84) (Signaling lymphocytic activation molecule 5) (CD antigen CD84) | CD84 SLAMF5 | 345 |
| Q16586 | SGCA_HUMAN | Alpha-sarcoglycan (Alpha-SG) (50 kDa dystrophin-associated glycoprotein) (50DAG) (Adhalin) (Dystroglycan-2) | SGCA ADL DAG2 | 387 |
| A0PJX4 | SHSA3_HUMAN | Protein shisa-3 homolog | SHISA3 | 238 |
| Q96LC7 | SIG10_HUMAN | Sialic acid-binding Ig-like lectin 10 (Siglec-like protein 2) | SIGLEC10 SLG2 UNQ477/PRO940 | 697 |
| O15389 | SIGL5_HUMAN | Sialic acid-binding Ig-like lectin 5 (Siglec-5) (CD33 antigen-like 2) (Obesity-binding protein 2) (OB-BP2) (OB-binding protein 2) (CD antigen CD170) | SIGLEC5 CD33L2 OBBP2 | 551 |
| O43699 | SIGL6_HUMAN | Sialic acid-binding Ig-like lectin 6 (Siglec-6) (CD33 antigen-like 1) (CDw327) (Obesity-binding protein 1) (OB-BP1) (CD antigen CD327) | SIGLEC6 CD33L CD33L1 OBBP1 | 453 |
| Q9Y336 | SIGL9_HUMAN | Sialic acid-binding Ig-like lectin 9 (Siglec-9) (CDw329) (Protein FOAP-9) (CD antigen CD329) | SIGLEC9 UNQ668/PRO1302 | 463 |
| O00241 | SIRB1_HUMAN | Signal-regulatory protein beta-1 (SIRP-beta-1) (CD172 antigen-like family member B) (CD antigen CD172b) | SIRPB1 | 398 |
| Q13291 | SLAF1_HUMAN | Signaling lymphocytic activation molecule (CDw150) (IPO-3) (SLAM family member 1) (CD antigen CD150) | SLAMF1 SLAM | 335 |
| Q96DU3 | SLAF6_HUMAN | SLAM family member 6 (Activating NK receptor) (NK-T-B-antigen) (NTB-A) (CD antigen CD352) | SLAMF6 KALI UNQ6123/PRO20080 | 332 |
| O94991 | SLIK5_HUMAN | SLIT and NTRK-like protein 5 (Leucine-rich repeat-containing protein 11) | SLITRK5 KIAA0918 LRRC11 | 958 |
| Q96PQ0 | SORC2_HUMAN | VPS10 domain-containing receptor SorCS2 | SORCS2 KIAA1329 | 1159 |
| Q6UWI4 | SHSA2_HUMAN | Protein shisa-2 homolog (Transmembrane protein 46) | SHISA2 C13orf13 TMEM46 UNQ9166/PRO28631 | 295 |
| Q6ZMC9 | SIG15_HUMAN | Sialic acid-binding Ig-like lectin 15 (Siglec-15) (CD33 antigen-like 3) | SIGLEC15 CD33L3 | 328 |
| Q9Y286 | SIGL7_HUMAN | Sialic acid-binding Ig-like lectin 7 (Siglec-7) (Adhesion inhibitory receptor molecule 1) (AIRM-1) (CDw328) (D-siglec) (QA79 membrane protein) (p75) (CD antigen CD328) | SIGLEC7 AIRM1 | 467 |
| Q96A28 | SLAF9_HUMAN | SLAM family member 9 (CD2 family member 10) (CD2F-10) (CD84 homolog 1) (CD84-H1) | SLAMF9 CD2F10 UNQ1938/PRO4421 | 289 |
| Q9H156 | SLIK2_HUMAN | SLIT and NTRK-like protein 2 | SLITRK2 CXorf2 KIAA1854 SLITL1 UNQ9197/PRO34756 | 845 |
| Q8IW52 | SLIK4_HUMAN | SLIT and NTRK-like protein 4 | SLITRK4 | 837 |
| A6NGZ8 | SMIM9_HUMAN | Small integral membrane protein 9 | SMIM9 CXorf68 | 99 |
| Q8WY21 | SORC1_HUMAN | VPS10 domain-containing receptor SorCS1 (hSorCS) | SORCS1 SORCS | 1168 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q92673 | SORL_HUMAN | Sortilin-related receptor (Low-density lipoprotein receptor relative with 11 ligand-binding repeats) (LDLR relative with 11 ligand-binding repeats) (LR11) (SorLA-1) (Sorting protein-related receptor containing LDLR class A repeats) (SorLA) | SORL1 C11orf32 | 2214 |
| Q99523 | SORT_HUMAN | Sortilin (100 kDa NT receptor) (Glycoprotein 95) (Gp95) (Neurotensin receptor 3) (NT3) | SORT1 | 831 |
| Q9Y3P8 | SIT1_HUMAN | Signaling threshold-regulating transmembrane adapter 1 (SHP2-interacting transmembrane adapter protein) (Suppression-inducing transmembrane adapter 1) (gp30/40) | SIT1 SIT | 196 |
| Q9NQ25 | SLAF7_HUMAN | SLAM family member 7 (CD2 subset 1) (CD2-like receptor-activating cytotoxic cells) (CRACC) (Membrane protein FOAP-12) (Novel Ly9) (Protein 19A) (CD antigen CD319) | SLAMF7 CS1 UNQ576/PRO1138 | 335 |
| Q96PX8 | SLIK1_HUMAN | SLIT and NTRK-like protein 1 (Leucine-rich repeat-containing protein 12) | SLITRK1 KIAA1910 LRRC12 | 696 |
| Q9H5Y7 | SLIK6_HUMAN | SLIT and NTRK-like protein 6 | SLITRK6 UNQ233/PRO266 | 841 |
| Q6ZSJ9 | SHSA6_HUMAN | Protein shisa-6 homolog | SHISA6 | 500 |
| Q08ET2 | SIG14_HUMAN | Sialic acid-binding Ig-like lectin 14 (Siglec-14) | SIGLEC14 | 396 |
| Q5TFQ8 | SIRBL_HUMAN | Signal-regulatory protein beta-1 isoform 3 (SIRP-beta-1 isoform 3) | SIRPB1 | 398 |
| Q9UPU3 | SORC3_HUMAN | VPS10 domain-containing receptor SorCS3 | SORCS3 KIAA1059 | 1222 |
| O43291 | SPIT2_HUMAN | Kunitz-type protease inhibitor 2 (Hepatocyte growth factor activator inhibitor type 2) (HAI-2) (Placental bikunin) | SPINT2 HAI2 KOP UNQ294/PRO333 | 252 |
| Q9BZZ2 | SN_HUMAN | Sialoadhesin (Sialic acid-binding Ig-like lectin 1) (Siglec-1) (CD antigen CD169) | SIGLEC1 SN | 1709 |
| Q9P246 | STIM2_HUMAN | Stromal interaction molecule 2 | STIM2 KIAA1482 | 746 |
| Q9UBS9 | SUCO_HUMAN | SUN domain-containing ossification factor (Membrane protein CH1) (Protein osteopotentia homolog) (SUN-like protein 1) | SUCO C1orf9 CH1 OPT SLP1 | 1254 |
| Q96GP6 | SREC2_HUMAN | Scavenger receptor class F member 2 (SRECRP-1) (Scavenger receptor expressed by endothelial cells 2 protein) (SREC-II) | SCARF2 SREC2 SREPCR | 870 |
| P43307 | SSRA_HUMAN | Translocon-associated protein subunit alpha (TRAP-alpha) (Signal sequence receptor subunit alpha) (SSR-alpha) | SSR1 TRAPA PSEC0262 | 286 |
| Q5VX71 | SUSD4_HUMAN | Sushi domain-containing protein 4 | SUSD4 UNQ196/PRO222 | 490 |
| P43308 | SSRB_HUMAN | Translocon-associated protein subunit beta (TRAP-beta) (Signal sequence receptor subunit beta) (SSR-beta) | SSR2 TRAPB HSD25 | 183 |
| P51571 | SSRD_HUMAN | Translocon-associated protein subunit delta (TRAP-delta) (Signal sequence receptor subunit delta) (SSR-delta) | SSR4 TRAPD | 173 |
| Q13586 | STIM1_HUMAN | Stromal interaction molecule 1 | STIM1 GOK | 685 |
| Q14162 | SREC_HUMAN | Scavenger receptor class F member 1 (Acetyl LDL receptor) (Scavenger receptor expressed by endothelial cells 1) (SREC-I) | SCARF1 KIAA0149 SREC | 830 |
| Q92537 | SUSD6_HUMAN | Sushi domain-containing protein 6 (Drug-activated gene overexpressed protein) | SUSD6 DRAGO KIAA0247 | 303 |
| Q9NY15 | STAB1_HUMAN | Stabilin-1 (Fasciclin, EGF-like, laminin-type EGF-like and link domain-containing scavenger receptor 1) (FEEL-1) (MS-1 antigen) | STAB1 FEEL1 KIAA0246 | 2570 |
| Q8WWQ8 | STAB2_HUMAN | Stabilin-2 (FAS1 EGF-like and X-link domain-containing adhesion molecule 2) (Fasciclin, EGF-like, laminin-type EGF-like and link domain-containing scavenger receptor 2) (FEEL-2) (Hyaluronan receptor for endocytosis) [Cleaved into: 190 kDa form stabilin-2 (190 kDa hyaluronan receptor for endocytosis)] | STAB2 FEEL2 FELL FEX2 HARE | 2551 |
| O60279 | SUSD5_HUMAN | Sushi domain-containing protein 5 | SUSD5 KIAA0527 | 629 |
| Q9UGT4 | SUSD2_HUMAN | Sushi domain-containing protein 2 | SUSD2 | 822 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9UQF0 | SYCY1_HUMAN | Syncytin-1 (Endogenous retrovirus group W member 1) (Env-W) (Envelope polyprotein gPr73) (Enverin) (HERV-7q Envelope protein) (HERV-W envelope protein) (HERV-W_7q21.2 provirus ancestral Env polyprotein) (Syncytin) [Cleaved into: Surface protein (SU) (gp50); Transmembrane protein (TM) (gp24)] | ERVW-1 ERVWE1 | 538 |
| Q6UWL2 | SUSD1_HUMAN | Sushi domain-containing protein 1 | SUSD1 UNQ2438/PRO4999 | 747 |
| Q8N3T6 | T132C_HUMAN | Transmembrane protein 132C | TMEM132C KIAA0922 | 1108 |
| A2VDJ0 | T131L_HUMAN | Transmembrane protein 131-like | TMEM131L | 1609 |
| Q6IEE7 | T132E_HUMAN | Transmembrane protein 132E | TMEM132E KIAA1786 | 984 |
| Q14DG7 | T132B_HUMAN | Transmembrane protein 132B | TMEM132B KIAA1906 | 1078 |
| P09758 | TACD2_HUMAN | Tumor-associated calcium signal transducer 2 (Cell surface glycoprotein Trop-2) (Membrane component chromosome 1 surface marker 1) (Pancreatic carcinoma marker protein GA733-1) | TACSTD2 GA733-1 M1S1 TROP2 | 323 |
| Q14C87 | T132D_HUMAN | Transmembrane protein 132D (Mature oligodendrocytes transmembrane protein) (Mature OL transmembrane protein) | TMEM132D HBE120 KIAA1944 MOLT | 1099 |
| Q96GX1 | TECT2_HUMAN | Tectonic-2 | TCTN2 C12orf38 TECT2 | 697 |
| Q24IP5 | T132A_HUMAN | Transmembrane protein 132A (HSPA5-binding protein 1) | TMEM132A HSPA5BP1 KIAA1583 | 1023 |
| B6A8C7 | TARM1_HUMAN | T-cell-interacting, activating receptor on myeloid cells protein 1 (OSCAR-like transcript-2 protein) (OLT-2) | TARM1 | 271 |
| P40200 | TACT_HUMAN | T-cell surface protein tactile (Cell surface antigen CD96) (T cell-activated increased late expression protein) (CD antigen CD96) | CD96 | 585 |
| Q9UIK5 | TEFF2_HUMAN | Tomoregulin-2 (TR-2) (Hyperplastic polyposis protein 1) (Transmembrane protein with EGF-like and two follistatin-like domains) | TMEFF2 HPP1 TENB2 TPEF UNQ178/PRO204 | 374 |
| P36897 | TGFR1_HUMAN | TGF-beta receptor type-1 (TGFR-1) (EC 2.7.11.30) (Activin A receptor type II-like protein kinase of 53 kD) (Activin receptor-like kinase 5) (ALK-5) (ALK5) (Serine/threonine-protein kinase receptor R4) (SKR4) (TGF-beta type I receptor) (Transforming growth factor-beta receptor type I) (TGF-beta receptor type I) (TbetaR-I) | TGFBR1 ALK5 SKR4 | 503 |
| Q9NS62 | THSD1_HUMAN | Thrombospondin type-1 domain-containing protein 1 (Transmembrane molecule with thrombospondin module) | THSD1 TMTSP UNQ3010/PRO9769 | 852 |
| Q02763 | TIE2_HUMAN | Angiopoietin-1 receptor (EC 2.7.10.1) (Endothelial tyrosine kinase) (Tunica interna endothelial cell kinase) (Tyrosine kinase with Ig and EGF homology domains-2) (Tyrosine-protein kinase receptor TEK) (Tyrosine-protein kinase receptor TIE-2) (hTIE2) (p140 TEK) (CD antigen CD202b) | TEK TIE2 VMCM VMCM1 | 1124 |
| P13726 | TF_HUMAN | Tissue factor (TF) (Coagulation factor III) (Thromboplastin) (CD antigen CD142) | F3 | 295 |
| Q495A1 | TIGIT_HUMAN | T-cell immunoreceptor with Ig and ITIM domains (V-set and immunoglobulin domain-containing protein 9) (V-set and transmembrane domain-containing protein 3) | TIGIT VSIG9 VSTM3 | 244 |
| Q03167 | TGBR3_HUMAN | Transforming growth factor beta receptor type 3 (TGF-beta receptor type 3) (TGFR-3) (Betaglycan) (Transforming growth factor beta receptor III) (TGF-beta receptor type III) | TGFBR3 | 851 |
| O43493 | TGON2_HUMAN | Trans-Golgi network integral membrane protein 2 (TGN38 homolog) (TGN46) (TGN48) (Trans-Golgi network protein TGN51) | TGOLN2 TGN46 TGN51 | 480 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q9BXR5 | TLR10_HUMAN | Toll-like receptor 10 (CD antigen CD290) | TLR10 UNQ315/PRO358 | 811 |
| Q8IYR6 | TEFF1_HUMAN | Tomoregulin-1 (TR-1) (H7365) (Transmembrane protein with EGF-like and one follistatin-like domain) | TMEFF1 C9orf2 | 380 |
| Q8N3G9 | TM130_HUMAN | Transmembrane protein 130 | TMEM130 UNQ719/PRO1383 | 435 |
| Q4KMG9 | TM52B_HUMAN | Transmembrane protein 52B | TMEM52B C12orf59 UNQ5927/PRO19821 | 183 |
| Q9BZD6 | TMG4_HUMAN | Transmembrane gamma-carboxyglutamic acid protein 4 (Proline-rich gamma-carboxyglutamic acid protein 4) (Proline-rich Gla protein 4) | PRRG4 PRGP4 TMG4 | 226 |
| Q8NEW7 | TMIE_HUMAN | Transmembrane inner ear expressed protein | TMIE | 156 |
| Q9HB18 | TMM27_HUMAN | Collectrin (Transmembrane protein 27) | TMEM27 UNQ679/PRO1312 | 222 |
| Q6UXU6 | TMM92_HUMAN | Transmembrane protein 92 | TMEM92 UNQ5801/PRO19608 | 159 |
| Q6NUS6 | TECT3_HUMAN | Tectonic-3 | TCTN3 C10orf61 TECT3 PSEC0041 UNQ1881/PRO4324 | 607 |
| P35590 | TIE1_HUMAN | Tyrosine-protein kinase receptor Tie-1 (EC 2.7.10.1) | TIE1 TIE | 1138 |
| Q15363 | TMED2_HUMAN | Transmembrane emp24 domain-containing protein 2 (Membrane protein p24A) (p24 family protein beta-1) (p24beta1) | TMED2 RNP24 | 201 |
| Q7Z7H5 | TMED4_HUMAN | Transmembrane emp24 domain-containing protein 4 (Endoplasmic reticulum stress-response protein 25) (ERS25) (GMP25iso) (Putative NF-kappa-B-activating protein 156) (p24 family protein alpha-3) (p24alpha3) | TMED4 ERS25 | 227 |
| Q9Y3B3 | TMED7_HUMAN | Transmembrane emp24 domain-containing protein 7 (p24 family protein gamma-3) (p24gamma3) (p27) | TMED7 CGI-109 | 224 |
| Q07011 | TNR9_HUMAN | Tumor necrosis factor receptor superfamily member 9 (4-1BB ligand receptor) (CDw137) (T-cell antigen 4-1BB homolog) (T-cell antigen ILA) (CD antigen CD137) | TNFRSF9 CD137 ILA | 255 |
| P01135 | TGFA_HUMAN | Protransforming growth factor alpha [Cleaved into: Transforming growth factor alpha (TGF-alpha) (EGF-like TGF) (ETGF) (TGF type 1)] | TGFA | 160 |
| P37173 | TGFR2_HUMAN | TGF-beta receptor type-2 (TGFR-2) (EC 2.7.11.30) (TGF-beta type II receptor) (Transforming growth factor-beta receptor type II) (TGF-beta receptor type II) (TbetaR-II) | TGFBR2 | 567 |
| Q9UPZ6 | THS7A_HUMAN | Thrombospondin type-1 domain-containing protein 7A | THSD7A KIAA0960 | 1657 |
| Q9C0I4 | THS7B_HUMAN | Thrombospondin type-1 domain-containing protein 7B | THSD7B KIAA1679 | 1608 |
| Q96H15 | TMD4_HUMAN | T-cell immunoglobulin and mucin domain-containing protein 4 (TIMD-4) (T-cell immunoglobulin mucin receptor 4) (TIM-4) (T-cell membrane protein 4) | TIMD4 TIM4 | 378 |
| Q15399 | TLR1_HUMAN | Toll-like receptor 1 (Toll/interleukin-1 receptor-like protein) (TIL) (CD antigen CD281) | TLR1 KIAA0012 | 786 |
| O15455 | TLR3_HUMAN | Toll-like receptor 3 (CD antigen CD283) | TLR3 | 904 |
| O60602 | TLR5_HUMAN | Toll-like receptor 5 (Toll/interleukin-1 receptor-like protein 3) | TLR5 TIL3 | 858 |
| Q4V9L6 | TM119_HUMAN | Transmembrane protein 119 (Osteoblast induction factor) (OBIF) | TMEM119 PSEC0199 UNQ731/PRO1415 | 283 |
| Q13445 | TMED1_HUMAN | Transmembrane emp24 domain-containing protein 1 (Interleukin-1 receptor-like 1 ligand) (Putative T1/ST2 receptor-binding protein) (p24 family protein gamma-1) (Tp24) (p24gamma1) | TMED1 IL1RL1L IL1RL1LG | 227 |
| Q9Y3A6 | TMED5_HUMAN | Transmembrane emp24 domain-containing protein 5 (p24 family protein gamma-2) (p24gamma2) (p28) | TMED5 CGI-100 UNQ397/PRO733 | 229 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P49755 | TMEDA_HUMAN | Transmembrane emp24 domain-containing protein 10 (21 kDa transmembrane-trafficking protein) (S31III125) (S31I125) (Tmp-21-I) (Transmembrane protein Tmp21) (p23) (p24 family protein delta-1) (p24delta1) (p24delta) | TMED10 TMP21 | 219 |
| Q86V40 | TIKI1_HUMAN | Metalloprotease TIKI1 (EC 3.4.—.—) (TRAB domain-containing protein 2A) | TRABD2A C2orf89 TIKI1 | 505 |
| Q9Y2C9 | TLR6_HUMAN | Toll-like receptor 6 (CD antigen CD286) | TLR6 | 796 |
| Q9NR97 | TLR8_HUMAN | Toll-like receptor 8 (CD antigen CD288) | TLR8 UNQ249/PRO286 | 1041 |
| Q8WZ59 | TM190_HUMAN | Transmembrane protein 190 | TMEM190 MDAC1 | 177 |
| Q6UWW9 | TM207_HUMAN | Transmembrane protein 207 | TMEM207 UNQ846/PRO1784 | 146 |
| Q9UK28 | TM59L_HUMAN | Transmembrane protein 59-like (Brain-specific membrane-anchored protein) | TMEM59L BSMAP C19orf4 | 342 |
| Q8WW62 | TMED6_HUMAN | Transmembrane emp24 domain-containing protein 6 (p24 family protein gamma-5) (p24gamma5) | TMED6 UNQ9146/PRO34237 | 240 |
| Q9BVK6 | TMED9_HUMAN | Transmembrane emp24 domain-containing protein 9 (GMP25) (Glycoprotein 25L2) (p24 family protein alpha-2) (p24alpha2) (p25) | TMED9 GP25L2 | 235 |
| O14668 | TMG1_HUMAN | Transmembrane gamma-carboxyglutamic acid protein 1 (Proline-rich gamma-carboxyglutamic acid protein 1) (Proline-rich Gla protein 1) | PRRG1 PRGP1 TMG1 | 218 |
| Q96BF3 | TMIG2_HUMAN | Transmembrane and immunoglobulin domain-containing protein 2 (CD28 homolog) (Immunoglobulin and proline-rich receptor 1) (IGPR-1) | TMIGD2 CD28H IGPR1 UNQ3059/PRO9879 | 282 |
| P43489 | TNR4_HUMAN | Tumor necrosis factor receptor superfamily member 4 (ACT35 antigen) (OX40L receptor) (TAX transcriptionally-activated glycoprotein 1 receptor) (CD antigen CD134) | TNFRSF4 TXGP1L | 111 |
| P25942 | TNR5_HUMAN | Tumor necrosis factor receptor superfamily member 5 (B-cell surface antigen CD40) (Bp50) (CD40L receptor) (CDw40) (CD antigen CD40) | CD40 TNFRSF5 | 277 |
| P25445 | TNR6_HUMAN | Tumor necrosis factor receptor superfamily member 6 (Apo-1 antigen) (Apoptosis-mediating surface antigen FAS) (FASLG receptor) (CD antigen CD95) | FAS APT1 FAS1 TNFRSF6 | 335 |
| O14763 | TR10B_HUMAN | Tumor necrosis factor receptor superfamily member 10B (Death receptor 5) (TNF-related apoptosis-inducing ligand receptor 2) (TRAIL receptor 2) (TRAIL-R2) (CD antigen CD262) | TNFRSF10B DR5 KILLER TRAILR2 TRICK2 ZTNFR9 UNQ160/PRO186 | 440 |
| Q8TB96 | TIP_HUMAN | T-cell immunomodulatory protein (Protein TIP) (Integrin-alpha FG-GAP repeat-containing protein 1) (Linkin) | ITFG1 LNKN-1 TIP CDA08 | 612 |
| O00206 | TLR4_HUMAN | Toll-like receptor 4 (hToll) (CD antigen CD284) | TLR4 | 839 |
| Q6P9G4 | TM154_HUMAN | Transmembrane protein 154 | TMEM154 | 183 |
| Q9BXS4 | TMM59_HUMAN | Transmembrane protein 59 (Liver membrane-bound protein) | TMEM59 C1orf8 HSPC001 | 323 |
| Q9NP84 | TNR12_HUMAN | Tumor necrosis factor receptor superfamily member 12A (Fibroblast growth factor-inducible immediate-early response protein 14) (FGF-inducible 14) (Tweak-receptor) (TweakR) (CD antigen CD266) | TNFRSF12A FN14 UNQ169/PRO195 | 129 |
| Q9Y5U5 | TNR18_HUMAN | Tumor necrosis factor receptor superfamily member 18 (Activation-inducible TNFR family receptor) (Glucocorticoid-induced TNFR-related protein) (CD antigen CD357) | TNFRSF18 AITR GITR UNQ319/PRO364 | 241 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| P20333 | TNR1B_HUMAN | Tumor necrosis factor receptor superfamily member 1B (Tumor necrosis factor receptor 2) (TNF-R2) (Tumor necrosis factor receptor type II) (TNF-RII) (TNFR-II) (p75) (p80 TNF-alpha receptor) (CD antigen CD120b) (Etanercept) [Cleaved into: Tumor necrosis factor receptor superfamily member 1b, membrane form; Tumor necrosis factor-binding protein 2 (TBP-2) (TBPII)] | TNFRSF1B TNFBR TNFR2 | 461 |
| Q9UBN6 | TR10D_HUMAN | Tumor necrosis factor receptor superfamily member 10D (Decoy receptor 2) (DcR2) (TNF-related apoptosis-inducing ligand receptor 4) (TRAIL receptor 4) (TRAIL-R4) (TRAIL receptor with a truncated death domain) (CD antigen CD264) | TNFRSF10D DCR2 TRAILR4 TRUNDD UNQ251/PRO288 | 386 |
| Q9NZC2 | TREM2_HUMAN | Triggering receptor expressed on myeloid cells 2 (TREM-2) (Triggering receptor expressed on monocytes 2) | TREM2 | 230 |
| A6NFA1 | TIKI2_HUMAN | Metalloprotease TIKI2 (EC 3.4.—.—) (Heart, kidney and adipose-enriched transmembrane protein homolog) (TRAB domain-containing protein 2B) | TRABD2B HKAT TIKI2 | 517 |
| Q9NYK1 | TLR7_HUMAN | Toll-like receptor 7 | TLR7 UNQ248/PRO285 | 1049 |
| Q9NR96 | TLR9_HUMAN | Toll-like receptor 9 (CD antigen CD289) | TLR9 UNQ5798/PRO19605 | 1032 |
| A2RRL7 | TM213_HUMAN | Transmembrane protein 213 | TMEM213 | 107 |
| Q9P0T7 | TMEM9_HUMAN | Transmembrane protein 9 (Dermal papilla-derived protein 4) | TMEM9 DERP4 | 183 |
| A2RUT3 | TMM89_HUMAN | Transmembrane protein 89 | TMEM89 | 159 |
| Q9H3N1 | TMX1_HUMAN | Thioredoxin-related transmembrane protein 1 (Thioredoxin domain-containing protein 1) (Transmembrane Trx-related protein) | TMX1 TMX TXNDC TXNDC1 PSEC0085 | 280 |
| Q92956 | TNR14_HUMAN | Tumor necrosis factor receptor superfamily member 14 (Herpes virus entry mediator A) (Herpesvirus entry mediator A) (HveA) (Tumor necrosis factor receptor-like 2) (TR2) (CD antigen CD270) | TNFRSF14 HVEA HVEM UNQ235/PRO268 | 283 |
| Q9NS68 | TNR19_HUMAN | Tumor necrosis factor receptor superfamily member 19 (TRADE) (Toxicity and JNK inducer) | TNFRSF19 TAJ TROY UNQ329/PRO509 | 423 |
| P19438 | TNR1A_HUMAN | Tumor necrosis factor receptor superfamily member 1A (Tumor necrosis factor receptor 1) (TNF-R1) (Tumor necrosis factor receptor type I) (TNF-RI) (TNFR-I) (p55) (p60) (CD antigen CD120a) [Cleaved into: Tumor necrosis factor receptor superfamily member 1A, membrane form; Tumor necrosis factor-binding protein 1 (TBPI)] | TNFRSF1A TNFAR TNFR1 UNQ1888/PRO4333 | 455 |
| Q93038 | TNR25_HUMAN | Tumor necrosis factor receptor superfamily member 25 (Apo-3) (Apoptosis-inducing receptor AIR) (Apoptosis-mediating receptor DR3) (Apoptosis-mediating receptor TRAMP) (Death receptor 3) (Lymphocyte-associated receptor of death) (LARD) (Protein WSL) (Protein WSL-1) | TNFRSF25 APO3 DDR3 DR3 TNFRSF12 WSL WSL1 UNQ455/PRO779 | 417 |
| P0DKB5 | TPBGL_HUMAN | Trophoblast glycoprotein-like | TPBGL | 382 |
| Q9BX59 | TPSNR_HUMAN | Tapasin-related protein (TAPASIN-R) (TAP-binding protein-like) (TAP-binding protein-related protein) (TAPBP-R) (Tapasin-like) | TAPBPL | 468 |
| O60603 | TLR2_HUMAN | Toll-like receptor 2 (Toll/interleukin-1 receptor-like protein 4) (CD antigen CD282) | TLR2 TIL4 | 784 |
| Q6UXF1 | TM108_HUMAN | Transmembrane protein 108 | TMEM108 KIAA1690 UNQ1875/PRO4318 | 575 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q8IV31 | TM139_HUMAN | Transmembrane protein 139 | TMEM139 UNQ1932/PRO4407 | 216 |
| A6NLX4 | TM210_HUMAN | Transmembrane protein 210 | TMEM210 | 147 |
| Q9Y3Q3 | TMED3_HUMAN | Transmembrane emp24 domain-containing protein 3 (Membrane protein p24B) (p24 family protein gamma-4) (p24gamma4) (p26) | TMED3 C15orf22 UNQ5357/PRO1078 | 217 |
| O14669 | TMG2_HUMAN | Transmembrane gamma-carboxyglutamic acid protein 2 (Praline-rich gamma-carboxyglutamic acid protein 2) (Proline-rich Gla protein 2) | PRRG2 PRGP2 TMG2 | 202 |
| Q9BZD7 | TMG3_HUMAN | Transmembrane gamma-carboxyglutamic acid protein 3 (Proline-rich gamma-carboxyglutamic acid protein 3) (Proline-rich Gla protein 3) | PRRG3 PRGP3 TMG3 | 231 |
| Q9Y320 | TMX2_HUMAN | Thioredoxin-related transmembrane protein 2 (Cell proliferation-inducing gene 26 protein) (Thioredoxin domain-containing protein 14) | TMX2 TXNDC14 CGI-31 My009 PIG26 PSEC0045 UNQ237/PRO270 | 296 |
| P36941 | TNR3_HUMAN | Tumor necrosis factor receptor superfamily member 3 (Lymphotoxin-beta receptor) (Tumor necrosis factor C receptor) (Tumor necrosis factor receptor 2-related protein) (Tumor necrosis factor receptor type III) (TNF-RIII) (TNFR-III) | LTBR D12S370 TNFCR TNFR3 TNFRSF3 | 435 |
| Q13641 | TPBG_HUMAN | Trophoblast glycoprotein (5T4 oncofetal antigen) (5T4 oncofetal trophoblast glycoprotein) (5T4 oncotrophoblast glycoprotein) (M6P1) (Wnt-activated inhibitory factor 1) (WAIF1) | TPBG 5T4 | 420 |
| P40238 | TPOR_HUMAN | Thrombopoietin receptor (TPO-R) (Myeloproliferative leukemia protein) (Proto-oncogene c-MpI) (CD antigen CD110) | MPL TPOR | 635 |
| P07204 | TRBM_HUMAN | Thrombomodulin (TM) (Fetomodulin) (CD antigen CD141) | THBD THRM | 575 |
| Q5T2D2 | TRML2_HUMAN | Trem-like transcript 2 protein (TLT-2) (Triggering receptor expressed on myeloid cells-like protein 2) | TREML2 C6orf76 TLT2 | 321 |
| Q6UXZ0 | TMIG1_HUMAN | Transmembrane and immunoglobulin domain-containing protein 1 | UNQ6268/PRO20473 TMIGD1 TMIGD UNQ9372/PRO34164 | 262 |
| Q86YD3 | TMM25_HUMAN | Transmembrane protein 25 | TMEM25 UNQ2531/PRO6030 | 366 |
| Q6P7N7 | TMM81_HUMAN | Transmembrane protein 81 | TMEM81 UNQ2788/PRO7178 | 255 |
| Q3KNT9 | TMM95_HUMAN | Transmembrane protein 95 | TMEM95 UNQ9390/PRO34281 | 176 |
| Q9H1E5 | TMX4_HUMAN | Thioredoxin-related transmembrane protein 4 (Thioredoxin domain-containing protein 13) | TMX4 KIAA1162 TXNDC13 PSEC0095 UNQ475/PRO938 | 349 |
| Q9Y6Q6 | TNR11_HUMAN | Tumor necrosis factor receptor superfamily member 11A (Osteoclast differentiation factor receptor) (ODFR) (Receptor activator of NF-KB) (CD antigen CD265) | TNFRSF11A RANK | 616 |
| Q86YW5 | TRML1_HUMAN | Trem-like transcript 1 protein (TLT-1) (Triggering receptor expressed on myeloid cells-like protein 1) | TREML1 TLT1 UNQ1825/PRO3438 | 311 |
| P08138 | TNR16_HUMAN | Tumor necrosis factor receptor superfamily member 16 (Gp80-LNGFR) (Low affinity neurotrophin receptor p75NTR) (Low-affinity nerve growth factor receptor) (NGF receptor) (p75ICD) (CD antigen CD271) | NGFR TNFRSF16 | 427 |
| O75509 | TNR21_HUMAN | Tumor necrosis factor receptor superfamily member 21 (Death receptor 6) (CD antigen CD358) | TNFRSF21 DR6 UNQ437/PRO868 | 655 |
| P28908 | TNR8_HUMAN | Tumor necrosis factor receptor superfamily member 8 (CD30L receptor) (Ki-1 antigen) (Lymphocyte activation antigen CD30) (CD antigen CD30) | TNFRSF8 CD30 D1S166E | 595 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| O00220 | TR10A_HUMAN | Tumor necrosis factor receptor superfamily member 10A (Death receptor 4) (TNF-related apoptosis-inducing ligand receptor 1) (TRAIL receptor 1) (TRAIL-R1) (CD antigen CD261) | TNFRSF10A APO2 DR4 TRAILR1 | 468 |
| Q9NP99 | TREM1_HUMAN | Triggering receptor expressed on myeloid cells 1 (TREM-1) (Triggering receptor expressed on monocytes 1) (CD antigen CD354) | TREM1 | 234 |
| O15533 | TPSN_HUMAN | Tapasin (TPN) (TPSN) (NGS-17) (TAP-associated protein) (TAP-binding protein) | TAPBP NGS17 TAPA | 448 |
| Q96Z4 | TR19L_HUMAN | Tumor necrosis factor receptor superfamily member 19L (Receptor expressed in lymphoid tissues) | RELT TNFRSF19L | 430 |
| Q7L0X0 | TRIL_HUMAN | TLR4 interactor with leucine rich repeats (Leucine-rich repeat-containing protein KIAA0644) | TRIL KIAA0644 | 811 |
| Q5BVD1 | TTMP_HUMAN | TPA-induced transmembrane protein | TTMP C3orf52 | 217 |
| Q96142 | TXD15_HUMAN | Thioredoxin domain-containing protein 15 | TXNDC15 C5orf14 UNQ335/PRO534 | 360 |
| Q9P212 | TUTLA_HUMAN | Protein turtle homolog A (Immunoglobulin superfamily member 9A) (IgSF9A) | IGSF9 IGSF9A KIAA1355 NRT1 | 1179 |
| Q9UPX0 | TUTLB_HUMAN | Protein turtle homolog B (Immunoglobulin superfamily member 9B) (IgSF9B) | IGSF9B KIAA1030 | 1349 |
| Q3SY77 | UD3A2_HUMAN | UDP-glucuronosyltransferase 3A2 (UDPGT 3A2) (EC 2.4.1.17) | UGT3A2 PSEC0073 UNQ842/PRO1780 | 523 |
| P14679 | TYRO_HUMAN | Tyrosinase (EC 1.14.18.1) (LB24-AB) (Monophenol monooxygenase) (SK29-AB) (Tumor rejection antigen AB) | TYR | 529 |
| P40126 | TYRP2_HUMAN | L-dopachrome tautomerase (DCT) (DT) (EC 5.3.3.12) (L-dopachrome Delta-isomerase) (Tyrosinase-related protein 2) (TRP-2) (TRP2) | DCT TYRP2 | 519 |
| O95185 | UNC5C_HUMAN | Netrin receptor UNC5C (Protein unc-5 homolog 3) (Protein unc-5 homolog C) | UNC5C UNC5H3 | 931 |
| Q06418 | TYRO3_HUMAN | Tyrosine-protein kinase receptor TYRO3 (EC 2.7.10.1) (Tyrosine-protein kinase BYK) (Tyrosine-protein kinase DTK) (Tyrosine-protein kinase RSE) (Tyrosine-protein kinase SKY) (Tyrosine-protein kinase TIF) | TYRO3 BYK DTK RSE SKY TIF | 890 |
| Q9Y4X1 | UD2A1_HUMAN | UDP-glucuronosyltransferase 2A1 (UDPGT 2A1) (EC 2.4.1.17) | UGT2A1 UGT2A2 | 527 |
| Q9BT76 | UPK3B_HUMAN | Uroplakin-3b (UP3b) (Uroplakin IIIb) (UPIIIb) (p35) | UPK3B | 320 |
| O43914 | TYOBP_HUMAN | TYRO protein tyrosine kinase-binding protein (DNAX-activation protein 12) (Killer-activating receptor-associated protein) (KAR-associated protein) | TYROBP DAP12 KARAP | 113 |
| Q6NUS8 | UD3A1_HUMAN | UDP-glucuronosyltransferase 3A1 (UDPGT 3A1) (EC 2.4.1.17) | UGT3A1 | 523 |
| O00526 | UPK2_HUMAN | Uroplakin-2 (UP2) (Uroplakin II) (UPII) | UPK2 | 184 |
| B0FP48 | UPK3L_HUMAN | Uroplakin-3b-like protein | UPK3BL UPLP | 263 |
| P17643 | TYRP1_HUMAN | 5,6-dihydroxyindole-2-carboxylic acid oxidase (DHICA oxidase) (EC 1.14.18.—) (Catalase B) (Glycoprotein 75) (Melanoma antigen gp75) (Tyrosinase-related protein 1) (TRP) (TRP-1) (TRP1) | TYRP1 CAS2 TYRP TYRRP | 537 |
| O75631 | UPK3A_HUMAN | Uroplakin-3a (UP3a) (Uroplakin III) (UPIII) | UPK3A UPK3 | 287 |
| O75445 | USH2A_HUMAN | Usherin (Usher syndrome type IIa protein) (Usher syndrome type-2A protein) | USH2A | 5202 |
| P30530 | UFO_HUMAN | Tyrosine-protein kinase receptor UFO (EC 2.7.10.1) (AXL oncogene) | AXL UFO | 894 |
| Q8IZJ1 | UNC5B_HUMAN | Netrin receptor UNC5B (Protein unc-5 homolog 2) (Protein unc-5 homolog B) (p53-regulated receptor for death and life protein 1) (p53RDL1) | UNC5B P53RDL1 UNC5H2 UNQ1883/PRO4326 | 945 |
| Q6UWM9 | UD2A3_HUMAN | UDP-glucuronosyltransferase 2A3 (UDPGT 2A3) (EC 2.4.1.17) | UGT2A3 UNQ2559/PRO6239 | 527 |
| Q5DID0 | UROL1_HUMAN | Uromodulin-like 1 (Olfactorin) | UMODL1 | 1318 |
| Q6ZN44 | UNC5A_HUMAN | Netrin receptor UNC5A (Protein unc-5 homolog 1) (Protein unc-5 homolog A) | UNC5A KIAA1976 UNC5H1 | 842 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q6UXZ4 | UNC5D_HUMAN | Netrin receptor UNC5D (Protein unc-5 homolog 4) (Protein unc-5 homolog D) | UNC5D KIAA1777 UNC5H4 UNQ6012/PRO34692 | 953 |
| P19320 | VCAM1_HUMAN | Vascular cell adhesion protein 1 (V-CAM 1) (VCAM-1) (INCAM-100) (CD antigen CD106) | VCAM1 L1CAM | 739 |
| P35916 | VGFR3_HUMAN | Vascular endothelial growth factor receptor 3 (VEGFR-3) (EC 2.7.10.1) (Fms-like tyrosine kinase 4) (FLT-4) (Tyrosine-protein kinase receptor FLT4) | FLT4 VEGFR3 | 1363 |
| Q7Z7D3 | VTCN1_HUMAN | V-set domain-containing T-cell activation inhibitor 1 (B7 homolog 4) (B7-H4) (B7h.5) (Immune costimulatory protein B7-H4) (Protein B7S1) (T-cell costimulatory molecule B7x) | VTCN1 B7H4 UNQ659/PRO1291 | 282 |
| Q6EMK4 | VASN_HUMAN | Vasorin (Protein slit-like 2) | VASN SLITL2 UNQ314/PRO357/PRO1282 | 673 |
| Q96AW1 | VOPP1_HUMAN | Vesicular, overexpressed in cancer, prosurvival protein 1 (EGFR-coamplified and overexpressed protein) (ECop) (Glioblastoma-amplified secreted protein) (Putative NF-kappa-B-activating protein 055N) | VOPP1 ECOP GASP | 172 |
| P17948 | VGFR1_HUMAN | Vascular endothelial growth factor receptor 1 (VEGFR-1) (EC 2.7.10.1) (Fms-like tyrosine kinase 1) (FLT-1) (Tyrosine-protein kinase FRT) (Tyrosine-protein kinase receptor FLT) (FLT) (Vascular permeability factor receptor) | FLT1 FLT FRT VEGFR1 | 1338 |
| Q9H7M9 | VISTA_HUMAN | V-type immunoglobulin domain-containing suppressor of T-cell activation (Platelet receptor Gi24) (Stress-induced secreted protein-1) (Sisp-1) (V-set domain-containing immunoregulatory receptor) | C10orf54 SISP1 VISTA PP2135 UNQ730/PRO1412 | 311 |
| Q86VR7 | VS10L_HUMAN | V-set and immunoglobulin domain-containing protein 10-like | VSIG10L | 867 |
| Q96Q7 | VSIG2_HUMAN | V-set and immunoglobulin domain-containing protein 2 (Cortical thymocyte-like protein) (CT-like protein) | VSIG2 CTH CTXL UNQ2770/PRO7154 | 327 |
| Q5VU13 | VSIG8_HUMAN | V-set and immunoglobulin domain-containing protein 8 | VSIG8 C1orf204 | 414 |
| P78423 | X3CL1_HUMAN | Fractalkine (C-X3-C motif chemokine 1) (CX3C membrane-anchored chemokine) (Neurotactin) (Small-inducible cytokine D1) [Cleaved into: Processed fractalkine] | CX3CL1 FKN NTT SCYD1 A-152E5.2 | 397 |
| P35968 | VGFR2_HUMAN | Vascular endothelial growth factor receptor 2 (VEGFR-2) (EC 2.7.10.1) (Fetal liver kinase 1) (FLK-1) (Kinase insert domain receptor) (KDR) (Protein-tyrosine kinase receptor flk-1) (CD antigen CD309) | KDR FLK1 VEGFR2 | 1356 |
| Q8N0Z9 | VSI10_HUMAN | V-set and immunoglobulin domain-containing protein 10 | VSIG10 | 540 |
| Q8IW00 | VSTM4_HUMAN | V-set and transmembrane domain-containing protein 4 [Cleaved into: Peptide Lv] | VSTM4 C10orf72 | 320 |
| P55808 | XG_HUMAN | Glycoprotein Xg (Protein PBDX) | XG PBDX | 180 |
| P98155 | VLDLR_HUMAN | Very low-density lipoprotein receptor (VLDL receptor) (VLDL-R) | VLDLR | 873 |
| Q86XK7 | VSIG1_HUMAN | V-set and immunoglobulin domain-containing protein 1 (Cell surface A33 antigen) (Glycoprotein A34) | VSIG1 GPA34 | 387 |
| Q9Y279 | VSIG4_HUMAN | V-set and immunoglobulin domain-containing protein 4 (Protein Z39Ig) | VSIG4 CRIg Z39IG UNQ317/PRO362 | 399 |
| A6NLU5 | VTM2B_HUMAN | V-set and transmembrane domain-containing protein 2B | VSTM2B | 285 |
| A8MXK1 | VSTM5_HUMAN | V-set and transmembrane domain-containing protein 5 | VSTM5 C11orf90 | 200 |
| Q8N1Y9 | YI025_HUMAN | Putative uncharacterized protein FLJ37218 | | 231 |
| P60852 | ZP1_HUMAN | Zona pellucida sperm-binding protein 1 (Zona pellucida glycoprotein 1) (Zp-1) [Cleaved into: Processed zona pellucida sperm-binding protein 1] | ZP1 | 638 |
| Q05996 | ZP2_HUMAN | Zona pellucida sperm-binding protein 2 (Zona pellucida glycoprotein 2) (Zp-2) (Zona pellucida protein A) [Cleaved into: Processed zona pellucida sperm-binding protein 2] | ZP2 ZPA | 745 |
| Q9Y493 | ZAN_HUMAN | Zonadhesin | ZAN | 2812 |
| Q9ULT6 | ZNRF3_HUMAN | E3 ubiquitin-protein ligase ZNRF3 (EC 6.3.2.—) (RING finger protein 203) (Zinc/RING finger protein 3) | ZNRF3 KIAA1133 RNF203 | 936 |
| Q8TCW7 | ZPLD1_HUMAN | Zona pellucida-like domain-containing protein 1 (ZP domain-containing protein 1) | ZPLD1 | 415 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q8WWF5 | ZNRF4_HUMAN | E3 ubiquitin-protein ligase ZNRF4 (EC 6.3.2.—) (Nixin) (RING finger protein 204) (Zinc/RING finger protein 4) | ZNRF4 RNF204 | 429 |
| P21754 | ZP3_HUMAN | Zona pellucida sperm-binding protein 3 (Sperm receptor) (ZP3A/ZP3B) (Zona pellucida glycoprotein 3) (Zp-3) (Zona pellucida protein C) [Cleaved into: Processed zona pellucida sperm-binding protein 3] | ZP3 ZP3A ZP3B ZPC | 424 |
| Q12836 | ZP4_HUMAN | Zona pellucida sperm-binding protein 4 (Zona pellucida glycoprotein 4) (Zp-4) (Zona pellucida protein B) [Cleaved into: Processed zona pellucida sperm-binding protein 4] | ZP4 ZPB | 540 |
| K9MUJ5 | K9MUJ5_HUMAN | Toll-like receptor 4 (Fragment) | TLR4 | 138 |
| K9MUQ3 | K9MUQ3_HUMAN | Toll-like receptor 4 (Fragment) | TLR4 | 138 |
| D3DNA1 | D3DNA1_HUMAN | Integrin beta | ITGB5 hCG_17803 | 691 |
| K9MTL8 | K9MTL8_HUMAN | Toll-like receptor 4 (Fragment) | TLR4 | 138 |
| K9MSZ3 | K9MSZ3_HUMAN | Toll-like receptor 4 (Fragment) | TLR4 | 138 |
| K9MT91 | K9MT91_HUMAN | Toll-like receptor 4 (Fragment) | TLR4 | 138 |
| D3DSM0 | D3DSM0_HUMAN | Integrin beta | ITGB2 hCG_401305 | 712 |
| K9MT22 | K9MT22_HUMAN | Toll-like receptor 4 (Fragment) | TLR4 | 138 |
| K9MUK7 | K9MUK7_HUMAN | Toll-like receptor 4 (Fragment) | TLR4 | 138 |
| D0EWT7 | D0EWT7_HUMAN | Toll-like receptor 4 (Fragment) | TLR4-4 TLR4 | 169 |
| G3V119 | G3V119_HUMAN | Transmembrane emp24 domain-containing protein 3 (Transmembrane emp24 protein transport domain containing 3, isoform CRA_b) | TMED3 hCG_24828 | 146 |
| L7RT22 | L7RT22_HUMAN | Integrin beta | ITGB5 | 799 |
| G3V1W8 | G3V1W8_HUMAN | Serine/threonine-protein kinase receptor (EC 2.7.11.30) | ACVRL1 hCG_37967 | 517 |
| A3QNQ0 | A3QNQ0_HUMAN | TGF-beta receptor type-2 (TGFR-2) (EC 2.7.11.30) (TGF-beta receptor type II) (Transforming growth factor-beta receptor type II) | TGFBR2 hCG_1997782 | 567 |
| B4EIS6 | B4EIS6_HUMAN | Syndecan | SDC4 hCG_38363 | 126 |
| A0A024R8T0 | A0A024R8T0_HUMAN | Integrin beta | ITGB4 hCG_27538 | 1822 |
| D3DPA4 | D3DPA4_HUMAN | Serine/threonine-protein kinase receptor (EC 2.7.11.30) | ACVR1 hCG_1811747 | 509 |
| A0A024R6I3 | A0A024R6I3_HUMAN | Testicular tissue protein Li 206 (Transmembrane emp24-like trafficking protein 10 (Yeast), isoform CRA_a) | TMED10 hCG_22348 | 219 |
| A0A024RB01 | A0A024RB01_HUMAN | Integrin, alpha 5 (Fibronectin receptor, alpha polypeptide), isoform CRA_b | ITGA5 hCG_21939 | 1098 |
| A0A024R7M0 | A0A024R7M0_HUMAN | Transmembrane emp24 protein transport domain containing 9, isoform CRA_a | TMED9 hCG_41592 | 235 |
| B7Z4L4 | B7Z4L4_HUMAN | Dolichyl-diphosphooligosaccharide--protein glycosyltransferase subunit 1 (EC 2.4.99.18) | RPN1 | 435 |
| A0A024DBF0 | A0A024DBF0_HUMAN | Integrin beta (Fragment) | ITGB2 | 80 |
| A0A024RDA0 | A0A024RDA0_HUMAN | V-kit Hardy-Zuckerman 4 feline sarcoma viral oncogene homolog, isoform CRA_a | KIT hCG_22160 | 976 |
| Q9BUG9 | Q9BUG9_HUMAN | Integrin beta | ITGB8 hCG_37311 | 439 |
| D3DPN2 | D3DPN2_HUMAN | Syndecan | SDC3 hCG_15913 | 384 |
| A0A024RC30 | A0A024RC30_HUMAN | Desmoglein 3 (Pemphigus vulgaris antigen), isoform CRA_a | DSG3 hCG_25473 | 999 |
| E9PBI9 | E9PBI9_HUMAN | Syndecan | SDC2 | 172 |
| A0A024RC29 | A0A024RC29_HUMAN | Desmocollin 3, isoform CRA_b | DSC3 hCG_2022649 | 896 |
| X5D8X5 | X5D8X5_HUMAN | Cadherin 10 type 2 isoform A (Cadherin 10, type 2 (T2-cadherin)) (Fragment) | CDH10 hCG_36812 | 788 |
| B2R627 | B2R627_HUMAN | cDNA, FLJ92752, highly similar to Homo sapiens integrin, alpha 5 (fibronectin receptor, alphapolypeptide) (ITGA5), mRNA | | 1049 |
| Q6FHT8 | Q6FHT8_HUMAN | RNP24 protein (Transmembrane emp24 domain trafficking protein 2, isoform CRA_a) (cDNA, FLJ93436, Homo sapiens coated vesicle membrane protein (RNP24), mRNA) | RNP24 TMED2 hCG_1743563 | 201 |
| B4DTY8 | B4DTY8_HUMAN | cDNA FLJ61587, highly similar to Integrin alpha-1 (Fragment) | | 1173 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| Q96C29 | Q96C29_HUMAN | Cadherin 11, type 2, OB-cadherin (Osteoblast) (Cadherin 11, type 2, OB-cadherin (Osteoblast), isoform CRA_c) | CDH11 hCG_26636 | 796 |
| A0A024RD88 | A0A024RD88_HUMAN | Kinase insert domain receptor (A type III receptor tyrosine kinase), isoform CRA_a | KDR hCG_31572 | 1356 |
| A0A024R8N2 | A0A024R8N2_HUMAN | Integrin beta | ITGB4 hCG_27538 | 1875 |
| A0A024R2B2 | A0A024R2B2_HUMAN | Cadherin 7, type 2, isoform CRA_a | CDH7 hCG_32903 | 785 |
| E7EQW5 | E7EQW5_HUMAN | Integrin beta (Fragment) | ITGB1 | 163 |
| Q59F03 | Q59F03_HUMAN | Integrin alpha 3 isoform b, variant (Fragment) | | 749 |
| A0A0G2JRA4 | A0A0G2JRA4_HUMAN | Cadherin-4 (Fragment) | CDH4 | 566 |
| U3KQ84 | U3KQ84_HUMAN | Dolichyl-diphosphooligosaccharide--protein glycosyltransferase 48 kDa subunit (Oligosaccharyl transferase 48 kDa subunit) (EC 2.4.99.18) (Fragment) | DDOST | 155 |
| B4E2C1 | B4E2C1_HUMAN | cDNA FLJ57776, highly similar to Transmembrane emp24 domain-containing protein 7 | | 136 |
| J3KRI5 | J3KRI5_HUMAN | Cadherin-8 | CDH8 | 744 |
| E9PD35 | E9PD35_HUMAN | Vascular endothelial growth factor receptor 3 | FLT4 | 1306 |
| E7EQ72 | E7EQ72_HUMAN | Transmembrane emp24 domain-containing protein 2 (Fragment) | TMED2 | 166 |
| D2JYI3 | D2JYI3_HUMAN | Toll-like receptor 4 (Fragment) | TLR4 | 121 |
| J3KT08 | J3KT08_HUMAN | Uncharacterized protein (Fragment) | | 172 |
| A8K0L1 | A8K0L1_HUMAN | cDNA FLJ77485, highly similar to Homo sapiens cadherin-like 24 (CDH24), transcript variant 2, mRNA | | 781 |
| D2JYI2 | D2JYI2_HUMAN | Toll-like receptor 4 (Fragment) | TLR4 | 122 |
| E7EP60 | E7EP60_HUMAN | Integrin alpha-4 (Fragment) | ITGA4 | 614 |
| Q59H01 | Q59H01_HUMAN | Protocadherin gamma subfamily A, 7 isoform 1 variant (Fragment) | | 895 |
| D2JYI5 | D2JYI5_HUMAN | Toll-like receptor 4 (Fragment) | TLR4 | 124 |
| J3KNV4 | J3KNV4_HUMAN | Integrin alpha-7 | ITGA7 | 1131 |
| H3BM21 | H3BM21_HUMAN | Integrin beta (Fragment) | | 787 |
| B4DN28 | B4DN28_HUMAN | cDNA FLJ54639, highly similar to Integrin alpha-8 (Fragment) | | 1048 |
| A0A0S2Z4U3 | A0A0S2Z4U3_HUMAN | Syndecan (Fragment) | SDC3 | 370 |
| B4DL99 | B4DL99_HUMAN | Dolichyl-diphosphooligosaccharide--protein glycosyltransferase subunit 1 (EC 2.4.99.18) | | 581 |
| B4DLF0 | B4DLF0_HUMAN | cDNA FLJ50795, highly similar to Cadherin-3 | | 774 |
| Q6P4R2 | Q6P4R2_HUMAN | Protocadherin alpha subfamily C, 2 | PCDHAC2 | 1007 |
| V9GYZ1 | V9GYZ1_HUMAN | Integrin beta (Fragment) | ITGB5 | 139 |
| D1CSS5 | D1CSS5_HUMAN | Toll-like receptor 4 | TLR4 | 839 |
| D0EWT8 | D0EWT8_HUMAN | Toll-like receptor 4 (Fragment) | TLR4 TLR4 | 169 |
| A8K2C5 | A8K2C5_HUMAN | cDNA FLJ78159, highly similar to Homo sapiens cadherin 20, type 2 (CDH20), mRNA | | 801 |
| Q59GD1 | Q59GD1_HUMAN | Protocadherin gamma subfamily A, 6 isoform 1 variant (Fragment) | | 950 |
| L7RSL3 | L7RSL3_HUMAN | Fms-related tyrosine kinase 1 (Vascular endothelial growth factor/vascular permeability factor receptor) | FLT1 | 1338 |
| A8K8T0 | A8K8T0_HUMAN | cDNA FLJ78760, highly similar to Homo sapiens integrin, alpha 11 (ITGA11), transcript variant 1, mRNA | | 1188 |
| Q4VAU9 | Q4VAU9_HUMAN | Serine/threonine-protein kinase receptor (EC 2.7.11.30) | ACVR2B | 303 |
| Q5T3E5 | Q5T3E5_HUMAN | Integrin beta (Fragment) | ITGB1 | 89 |
| E5RK25 | E5RK25_HUMAN | Integrin beta (Fragment) | ITGB2 | 160 |
| A8KAM8 | A8KAM8_HUMAN | Platelet-derived growth factor receptor beta (PDGF-R-beta) (PDGFR-beta) (EC 2.7.10.1) (Beta platelet-derived growth factor receptor) (Beta-type platelet-derived growth factor receptor) | | 1106 |
| E9PQJ2 | E9PQJ2_HUMAN | Integrin beta (Fragment) | ITGB1 | 104 |
| B4E2S6 | B4E2S6_HUMAN | Serine/threonine-protein kinase receptor (EC 2.7.11.30) | | 397 |
| A0A087WXP3 | A0A087WXP3_HUMAN | Integrin beta | ITGB6 | 693 |
| A8K0L9 | A8K0L9_HUMAN | cDNA FLJ76999, highly similar to Homo sapiens cadherin-like 22 (CDH22), mRNA | | 828 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| D2JY11 | D2JY11_HUMAN | TGF-beta receptor type-2 (TGFR-2) (EC 2.7.11.30) (TGF-beta type II receptor) (Transforming growth factor-beta receptor type II) | TGFBR2 | 592 |
| B7ZLD8 | B7ZLD8_HUMAN | Integrin beta | ITGB4 | 1752 |
| L7UW06 | L7UW06_HUMAN | Integrin beta | ITGB3 | 470 |
| B4E3M0 | B4E3M0_HUMAN | cDNA FLJ58807, highly similar to Integrin alpha-11 | | 650 |
| B4DNJ5 | B4DNJ5_HUMAN | Dolichyl-diphosphooligosaccharide--protein glycosyltransferase subunit 1 (EC 2.4.99.18) | | 378 |
| Q96HX3 | Q96HX3_HUMAN | Dolichyl-diphosphooligosaccharide--protein glycosyltransferase subunit 1 (EC 2.4.99.18) (Fragment) | | 568 |
| X5DNG6 | X5DNG6_HUMAN | Cadherin 10 type 2 isoform B (Fragment) | CDH10 | 786 |
| B7Z5H2 | B7Z5H2_HUMAN | Syndecan | | 172 |
| F8VNX4 | F8VNX4_HUMAN | Integrin beta (Fragment) | ITGB7 | 158 |
| B4DP4 | B4DPP4_HUMAN | cDNA FLJ56646, highly similar to Transmembrane emp24 domain-containing protein 9 | | 121 |
| B2RCN5 | B2RCN5_HUMAN | cDNA, FLJ96176, highly similar to Homo sapiens cadherin 4, type 1, R-cadherin (retinal) (CDH4), mRNA | | 916 |
| G3V2K7 | G3V2K7_HUMAN | Transmembrane emp24 domain-containing protein 10 | TMED10 | 153 |
| A8K6T3 | A8K6T3_HUMAN | cDNA FLJ78674, highly similar to Homo sapiens desmocollin type 4 | | 896 |
| E9PLR6 | E9PLR6_HUMAN | Integrin beta (Fragment) | ITGB1 | 143 |
| D3XNU5 | D3XNU5_HUMAN | E-cadherin 1 | CDH1 | 882 |
| B4E2A1 | B4E2A1_HUMAN | cDNA FLJ54402, highly similar to Integrin alpha-10 | | 1095 |
| C9JPK5 | C9JPK5_HUMAN | Integrin beta (Fragment) | ITGB1 | 98 |
| B2R8A2 | B2R8A2_HUMAN | cDNA, FLJ93804, highly similar to Homo sapiens gp25L2 protein (HSGP25L2G), mRNA | | 214 |
| L7UUZ7 | L7UUZ7_HUMAN | Integrin beta | ITGB3 | 788 |
| Q53EP4 | Q53EP4_HUMAN | Dolichyl-diphosphooligosaccharide--protein glycosyltransferase subunit 1 (EC 2.4.99.18) (Fragment) | | 607 |
| Q59H32 | Q59H32_HUMAN | Protocadherin gamma subfamily A, 3 isoform 1 variant (Fragment) | | 961 |
| K9MUK4 | K9MUK4_HUMAN | Toll-like receptor 4 (Fragment) | TLR4 | 138 |
| B3KMS6 | B3KMS6_HUMAN | cDNA FLJ12486 fis, clone NT2RM2000566, highly similar to Integrin alpha-7 | | 973 |
| B4E045 | B4E045_HUMAN | cDNA FLJ59131, highly similar to Integrin alpha-4 | | 174 |
| B7ZLD5 | B7ZLD5_HUMAN | Integrin beta | ITGB4 | 1752 |
| Q59EA3 | Q59EA3_HUMAN | Cadherin 5, type 2 preproprotein variant (Fragment) | | 807 |
| E7ESK6 | E7ESK6_HUMAN | Syndecan | SDC2 | 165 |
| B4DTP0 | B4DTP0_HUMAN | cDNA FLJ51087, highly similar to Cadherin-5 | | 525 |
| B4E3N0 | B4E3N0_HUMAN | Integrin beta | | 628 |
| A7U833 | A7U833_HUMAN | Integrin beta (Fragment) | ITGB3 | 65 |
| A0A024R8K7 | A0A024R8K7_HUMAN | Integrin beta | ITGB4 hCG_27538 | 1752 |
| H7C580 | H7C580_HUMAN | Integrin beta (Fragment) | ITGB5 | 79 |
| H0YA32 | H0YA32_HUMAN | Integrin alpha-3 (Fragment) | ITGA3 | 84 |
| Q59H14 | Q59H14_HUMAN | PREDICTED: integrin, alpha D variant (Fragment) | | 1177 |
| E9PDS3 | E9PDS3_HUMAN | Integrin alpha-9 | ITGA9 | 632 |
| B2R6U9 | B2R6U9_HUMAN | Delta-like protein | | 1218 |
| B4E0R1 | B4E0R1_HUMAN | Integrin beta | | 700 |
| A5YM53 | A5YM53_HUMAN | ITGAV protein | ITGAV | 1048 |
| Q6IBR0 | Q6IBR0_HUMAN | Dolichyl-diphosphooligosaccharide--protein glycosyltransferase subunit 1 (EC 2.4.99.18) | RPN1 | 607 |
| B4DP27 | B4DP27_HUMAN | cDNA FLJ52153, highly similar to Transmembrane emp24 domain-containing protein 2 | | 169 |
| A0A0U2ZQU7 | A0A0U2ZQU7_HUMAN | E-cadherin 1 | CDH1 | 882 |
| B4DYQ7 | B4DYQ7_HUMAN | cDNA FLJ57822, highly similar to Integrin alpha-V | | 482 |
| B2RAL6 | B2RAL6_HUMAN | cDNA, FLJ94991, highly similar to Homo sapiens integrin, alpha L (antigen CD11A (p180), lymphocyte function-associated antigen 1; alpha polypeptide) (ITGAL), mRNA | | 1170 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| E7ERX5 | E7ERX5_HUMAN | Integrin beta (Fragment) | ITGB1 | 125 |
| F8WF32 | F8WF32_HUMAN | Dolichyl-diphosphooligosaccharide--protein glycosyltransferase subunit 1 (EC 2.4.99.18) | RPN1 | 121 |
| B4E0Q2 | B4E0Q2_HUMAN | cDNA FLJ60208, highly similar to Integrin alpha-4 | | 366 |
| B4DDT0 | B4DDT0_HUMAN | cDNA FLJ59664, highly similar to Integrin alpha-3 | | 294 |
| B7Z769 | B7Z769_HUMAN | Integrin beta | | 228 |
| E9PEE8 | E9PEE8_HUMAN | Integrin beta | ITGB6 | 746 |
| H7C4W1 | H7C4W1_HUMAN | Integrin beta (Fragment) | ITGB5 | 263 |
| E9PB77 | E9PB77_HUMAN | Integrin alpha-2 | ITGA2 | 641 |
| B7Z8B0 | B7Z8B0_HUMAN | cDNA FLJ50317, highly similar to Integrin alpha-IIb | | 219 |
| D6RA20 | D6RA20_HUMAN | Protocadherin alpha-4 | PCDHA4 | 901 |
| Q5T3E6 | Q5T3E6_HUMAN | Integrin beta (Fragment) | ITGB1 | 136 |
| B4DQ56 | B4DQ56_HUMAN | Syndecan | | 192 |
| C9JA99 | C9JA99_HUMAN | Protocadherin alpha-13 | PCDHA13 | 904 |
| Q9UII7 | Q9UII7_HUMAN | E-cadherin | | 901 |
| B3KRT0 | B3KRT0_HUMAN | cDNA FLJ34857 fis, clone NT2NE2012533, highly similar to Cadherin-12 | | 404 |
| Q8N6H6 | Q8N6H6_HUMAN | ITGA9 protein | | 632 |
| A0A0B5HR54 | A0A0B5HR54_HUMAN | Serine/threonine-protein kinase receptor (EC 2.7.11.30) | | 509 |
| C9JXX7 | C9JXX7_HUMAN | Integrin alpha-6 (Fragment) | ITGA6 | 231 |
| B4DLJ5 | B4DLJ5_HUMAN | cDNA FLJ55716, highly similar to Desmocollin-2 | | 912 |
| V9GZ57 | V9GZ57_HUMAN | Integrin beta (Fragment) | ITGB5 | 324 |
| Q4LE35 | Q4LE35_HUMAN | ITGA7 variant protein (Fragment) | ITGA7 variant protein | 1200 |
| B4DIN4 | B4DIN4_HUMAN | Syndecan | | 346 |
| J3KNI6 | J3KNI6_HUMAN | Integrin beta (Fragment) | | 322 |
| A8K2P8 | A8K2P8_HUMAN | cDNA FLJ76245, highly similar to Homo sapiens desmocollin 2 (DSC2), transcript variant Dsc2a, mRNA | ITGB2 | 901 |
| B4DLU2 | B4DLU2_HUMAN | cDNA FLJ56496, highly similar to Integrin alpha-IIb | | 521 |
| F5H4M7 | F5H4M7_HUMAN | Transmembrane emp24 domain-containing protein 3 | TMED3 | 155 |
| D0EWT9 | D0EWT9_HUMAN | Toll-like receptor 4 (Fragment) | TLR-4 TLR4 | 169 |
| Q6PIE7 | Q6PIE7_HUMAN | ITGA4 protein (Fragment) | ITGA4 | 617 |
| E7ESP4 | E7ESP4_HUMAN | Integrin alpha-2 | ITGA2 | 942 |
| B4E277 | B4E277_HUMAN | cDNA FLJ58873, highly similar to Transmembrane emp24 domain-containing protein 3 | | 155 |
| B4DU18 | B4DU18_HUMAN | cDNA FLJ51093, highly similar to Cadherin-5 | | 750 |
| B2R918 | B2R918_HUMAN | cDNA, FLJ94427, highly similar to Homo sapiens cadherin 20, type 2 (CDH20), mRNA | | 801 |
| B4E282 | B4E282_HUMAN | cDNA FLJ52401, highly similar to Integrin alpha-10 | | 1036 |
| F5H6T4 | F5H6T4_HUMAN | Integrin beta | ITGB7 | 471 |
| G3V2Y2 | G3V2Y2_HUMAN | Transmembrane emp24 domain-containing protein 7 (Fragment) | TMED7 | 82 |
| B4DDR7 | B4DDR7_HUMAN | cDNA FLJ54845, highly similar to Transmembrane emp24 domain-containing protein 5 | | 178 |
| A0A087WT05 | A0A087WT05_HUMAN | Protocadherin gamma-A4 | PCDHGA4 | 962 |
| B4DMA7 | B4DMA7_HUMAN | cDNA FLJ58514, highly similar to Cadherin-11 | | 779 |
| A0A0U2N547 | A0A0U2N547_HUMAN | Mast/stem cell growth factor receptor Kit isoform 3 (EC 2.7.10.1) | KIT | 971 |
| B2R9L8 | B2R9L8_HUMAN | Delta-like protein | | 685 |
| E7EVZ9 | E7EVZ9_HUMAN | Integrin beta (Fragment) | ITGB2 | 166 |
| B4E2B8 | B4E2B8_HUMAN | Integrin beta | | 746 |
| F5GX39 | F5GX39_HUMAN | Transmembrane emp24 domain-containing protein 2 | TMED2 | 116 |
| Q2VP98 | Q2VP98_HUMAN | Integrin beta (Fragment) | ITGB4 | 644 |
| A0A0S2Z310 | A0A0S2Z310_HUMAN | Serine/threonine-protein kinase receptor (EC 2.7.11.30) (Fragment) | ACVRL1 | 503 |
| H3BRM2 | H3BRM2_HUMAN | Integrin beta (Fragment) | ITGB7 | 93 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| A9X9L0 | A9X9L0_HUMAN | Desmocollin 2 | DSC2 | 901 |
| B7Z6U6 | B7Z6U6_HUMAN | Integrin beta | | 471 |
| B4DT61 | B4DT61_HUMAN | Syndecan | | 81 |
| D2JY14 | D2JY14_HUMAN | Toll-like receptor 4 (Fragment) | TLR4 | 124 |
| E5RIG7 | E5RIG7_HUMAN | Integrin beta (Fragment) | ITGB2 | 120 |
| E5RFI0 | E5RFI0_HUMAN | Integrin beta (Fragment) | ITGB2 | 70 |
| B7Z506 | B7Z506_HUMAN | Integrin beta | | 626 |
| B4DTY9 | B4DTY9_HUMAN | Integrin beta | | 751 |
| G3V2C6 | G3V2C6_HUMAN | Integrin alpha-7 (Fragment) | ITGA7 | 153 |
| Q6P175 | Q6P175_HUMAN | Integrin beta (Fragment) | ITGB2 | 758 |
| B4DDX0 | B4DDX0_HUMAN | cDNA FLJ59843, highly similar to Integrin alpha-X | | 264 |
| A9X9K9 | A9X9K9_HUMAN | Desmocollin 2 | DSC2 | 901 |
| H3BN02 | H3BN02_HUMAN | Integrin alpha-X | ITGAX | 1169 |
| A0A024RAD5 | A0A024RAD5_HUMAN | Dolichyl-diphosphooligosaccharide--protein glycosyltransferase 48 kDa subunit (Oligosaccharyl transferase 48 kDa subunit) (EC 2.4.99.18) | DDOST hCG_38871 | 456 |
| A0A0C4DGS1 | A0A0C4DGS1_HUMAN | Dolichyl-diphosphooligosaccharide--protein glycosyltransferase 48 kDa subunit (Oligosaccharyl transferase 48 kDa subunit) (EC 2.4.99.18) | DDOST | 439 |
| B4DFP0 | B4DFP0_HUMAN | cDNA FLJ57804, highly similar to Cadherin-9 | | 382 |
| Q53GF9 | Q53GF9_HUMAN | Full-length cDNA 5-PRIME end of clone CSODF013YM24 of Fetal brain of Homo sapiens (Human) variant (Fragment) | | 225 |
| A8K2N5 | A8K2N5_HUMAN | Integrin beta | | 788 |
| E7EUI6 | E7EUI6_HUMAN | Integrin beta (Fragment) | ITGB1 | 152 |
| Q4KMR2 | Q4KMR2_HUMAN | Delta-like protein | JAG1 | 1218 |
| Q59FA8 | Q59FA8_HUMAN | Integrin alpha-IIb variant (Fragment) | | 551 |
| J3QQL2 | J3QQL2_HUMAN | Integrin beta (Fragment) | ITGB4 | 114 |
| L7RXH0 | L7RXH0_HUMAN | Integrin, alpha V | ITGAV | 1048 |
| A0A0A6YYA0 | A0A0A6YYA0_HUMAN | Protein TMED7-TICAM2 | TMED7-TICAM2 | 188 |
| B4DL12 | B4DL12_HUMAN | cDNA FLJ53754, highly similar to Transmembrane emp24 domain-containing protein 10 | | 177 |
| B1AKT3 | B1AKT3_HUMAN | Transmembrane emp24 domain-containing protein 5 | TMED5 | 162 |
| H7C5U2 | H7C5U2_HUMAN | Integrin beta (Fragment) | ITGB5 | 401 |
| F8W7F7 | F8W7F7_HUMAN | Transmembrane emp24 domain-containing protein 4 | TMED4 | 178 |
| Q59H50 | Q59H50_HUMAN | Integrin beta (Fragment) | | 475 |
| H3BUU9 | H3BUU9_HUMAN | Cadherin-11 | CDH11 | 670 |
| B4E0H8 | B4E0H8_HUMAN | cDNA FLJ60385, highly similar to Integrin alpha-3 | | 1037 |
| A8K6A5 | A8K6A5_HUMAN | cDNA FLJ77742, highly similar to Homo sapiens integrin, alpha 5 (fibronectin receptor, alpha polypeptide), mRNA | | 1049 |
| O60574 | O60574 | Cadherin-7 (Fragment) | CDH7 | 317 |
| Q53HR4 | Q53HR4_HUMAN | Chromosome 15 open reading frame 22 variant (Fragment) | | 217 |
| Q59H35 | Q59H35_HUMAN | Protocadherin alpha 13 isoform 1 variant (Fragment) | | 921 |
| A0A024DAS2 | A0A024DAS2_HUMAN | Integrin beta (Fragment) | ITGB2 | 80 |
| A0A024RC42 | A0A024RC42_HUMAN | Cadherin 2, type 1, N-cadherin (Neuronal), isoform CRA_b | CDH2 hCG_22518 | 906 |
| E7EMF1 | E7EMF1_HUMAN | Integrin alpha-2 | ITGA2 | 815 |
| A0A024R9D1 | A0A024R9D1_HUMAN | Syndecan | SDC2 hCG_15745 | 201 |
| Q1PBM2 | Q1PBM2_HUMAN | Integrin beta (Fragment) | ITGB3 | 65 |
| Q8NB64 | Q8NB64_HUMAN | cDNA FLJ34177 fis, clone FCBBF3016451, highly similar to RETINAL-CADHERIN | | 824 |
| Q59EB0 | Q59EB0_HUMAN | Kinase insert domain receptor (A type III receptor tyrosine kinase) variant (Fragment) | | 1451 |
| Q2YFE1 | Q2YFE1_HUMAN | Integrin beta | | 443 |
| Q3B7W7 | Q3B7W7_HUMAN | TMED7 protein (Fragment) | TMED7 | 134 |

TABLE 1-continued

Illustrative human Type I proteins which may be incorporated into the present compositions and methods include (as used herein "Entry" refers to the human Type I protein entry in the Uniprot database and "Entry name" refers to the human Type I protein entry in the Uniprot database).

| Entry | Entry name | Protein names | Gene names | Length |
|---|---|---|---|---|
| K7EQ63 | K7EQ63_HUMAN | Transmembrane emp24 domain-containing protein 1 (Fragment) | TMED1 | 191 |
| A0A087WTR7 | A0A087WTR7_HUMAN | Cadherin-24 | CDH24 | 314 |
| K7EMU3 | K7EMU3_HUMAN | Integrin alpha-3 (Fragment) | ITGA3 | 117 |
| Q49AG2 | Q49AG2_HUMAN | TMED5 protein | TMED5 | 172 |
| A0A087WX36 | A0A087WX36_HUMAN | Integrin beta | ITGB2 | 378 |
| Q9HAX1 | Q9HAX1_HUMAN | Desmocollin 3 (Fragment) | DSC3 | 316 |
| A0A087WXI5 | A0A087WXI5_HUMAN | Cadherin-1 | CDH1 | 903 |
| M0R072 | M0R072_HUMAN | Transmembrane emp24 domain-containing protein 5 | TMED5 | 120 |
| Q8N9I3 | Q8N9I3_HUMAN | cDNA FLJ37047 fis, clone BRACE2012232, highly similar to *Homo sapiens* cadherin 20 (CDH20) mRNA | | 335 |
| Q8WWJ8 | Q8WWJ8_HUMAN | Integrin beta | | 378 |
| Q59H34 | Q59H34_HUMAN | Protocadherin alpha 4 isoform 1 variant (Fragment) | | 921 |
| A0A024DAE5 | A0A024DAE5_HUMAN | Integrin beta (Fragment) | ITGB2 | 80 |
| Q59H46 | Q59H46_HUMAN | Integrin beta (Fragment) | | 1515 |
| Q4VAI4 | Q4VAI4_HUMAN | CDH5 protein | CDH5 | 662 |
| Q59FL1 | Q59FL1_HUMAN | Serine/threonine-protein kinase receptor (EC 2.7.11.30) (Fragment) | | 514 |
| Q2TAL1 | Q2TAL1_HUMAN | CDH24 protein | CDH24 | 314 |
| Q59H74 | Q59H74_HUMAN | Integrin alpha 4 variant (Fragment) | | 854 |
| A0A087WX99 | A0A087WX99_HUMAN | Cadherin-4 | CDH4 | 822 |
| Q59FN1 | Q59FN1_HUMAN | Integrin beta (Fragment) | | 166 |
| X6R3Y6 | X6R3Y6_HUMAN | Cadherin-8 | CDH8 | 745 |
| Q59EQ1 | Q59EQ1_HUMAN | Cadherin 11, type 2 isoform 1 preproprotein variant (Fragment) | | 798 |
| X5DQT8 | X5DQT8_HUMAN | Cadherin 10 type 2 isoform C (Fragment) | CDH10 | 243 |
| Q8N2D9 | Q8N2D9_HUMAN | cDNA PSEC0228 fis, clone HEMBA1006099, weakly similar to COP-COATED VESICLE MEMBRANE PROTEIN P24 | | 146 |
| Q63HM4 | Q63HM4_HUMAN | Putative uncharacterized protein DKFZp686P18250 | DKFZp686P18250 | 758 |
| A0A0E3XJU3 | A0A0E3XJU3_HUMAN | E-cadherin 1 | CDH1 | 882 |
| Q68DY8 | Q68DY8_HUMAN | Putative uncharacterized protein DKFZp686I11137 | DKFZp686I11137 | 667 |

TABLE 2

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9BUJ0 | ABHEA_HUMAN | Protein ABHD14A (EC 3.-.-.-) (Alpha/beta hydrolase domain-containing protein 14A) (Abhydrolase domain-containing protein 14A) | ABHD14A UNQ1913/PRO4373 | 271 |
| P08195 | 4F2_HUMAN | 4F2 cell-surface antigen heavy chain (4F2hc) (4F2 heavy chain antigen) (Lymphocyte activation antigen 4F2 large subunit) (Solute carrier family 3 member 2) (CD antigen CD98) | SLC3A2 MDU1 | 630 |
| Q9NPC4 | A4GAT_HUMAN | Lactosylceramide 4-alpha-galactosyltransferase (EC 2.4.1.228) (Alpha-1,4-N-acetylglucosaminyltransferase) (Alpha-1,4-galactosyltransferase) (Alpha4Gal-T1) (CD77 synthase) (Globotriaosylceramide synthase) (Gb3 synthase) (P1/Pk synthase) (UDP-galactose: beta-D-galactosyl-beta1-R 4-alpha-D-galactosyltransferase) | A4GALT A14GALT A4GALT1 | 353 |
| Q9UNA3 | A4GCT_HUMAN | Alpha-1,4-N-acetylglucosaminyltransferase (Alpha4GnT) (EC 2.4.1.-) | A4GNT | 340 |
| Q96SE0 | ABHD1_HUMAN | Protein ABHD1 (EC 3.1.1.-) (Alpha/beta hydrolase domain-containing protein 1) (Abhydrolase domain-containing protein 1) (Lung alpha/beta hydrolase 1) | ABHD1 LABH1 | 405 |
| P08910 | ABHD2_HUMAN | Monoacylglycerol lipase ABHD2 (EC 3.1.1.23) (2-arachidonoylglycerol hydrolase) (Abhydrolase domain-containing protein 2) (Lung alpha/beta hydrolase 2) (Protein PHPS1-2) | ABHD2 LABH2 | 425 |
| Q9BV23 | ABHD6_HUMAN | Monoacylglycerol lipase ABHD6 (EC 3.1.1.23) (2-arachidonoylglycerol hydrolase) (Abhydrolase domain-containing protein 6) | ABHD6 | 337 |
| Q7L211 | ABHDD_HUMAN | Protein ABHD13 (EC 3.-.-.-) (Alpha/beta hydrolase domain-containing protein 13) (Abhydrolase domain-containing protein 13) | ABHD13 C13orf6 | 337 |
| P22760 | AAAD_HUMAN | Arylacetamide deacetylase (EC 3.1.1.3) | AADAC DAC | 399 |
| Q5VUY2 | ADCL4_HUMAN | Arylacetamide deacetylase-like 4 (EC 3.1.1.-) | AADACL4 | 407 |
| Q8WU67 | ABHD3_HUMAN | Phospholipase ABHD3 (EC 3.1.1.32) (EC 3.1.1.4) (Abhydrolase domain-containing protein 3) | ABHD3 | 409 |
| O00468 | AGRIN_HUMAN | Agrin [Cleaved into: Agrin N-terminal 110 kDa subunit; Agrin C-terminal 110 kDa subunit; Agrin C-terminal 90 kDa fragment (C90); Agrin C-terminal 22 kDa fragment (C22)] | AGRN AGRIN | 2067 |
| Q9Y673 | ALG5_HUMAN | Dolichyl-phosphate beta-glucosyltransferase (DolP-glucosyltransferase) (EC 2.4.1.117) (Asparagine-linked glycosylation protein 5 homolog) | ALG5 HSPC149 | 324 |
| P15144 | AMPN_HUMAN | Aminopeptidase N (AP-N) (hAPN) (EC 3.4.11.2) (Alanyl aminopeptidase) (Aminopeptidase M) (AP-M) (Microsomal aminopeptidase) (Myeloid plasma membrane glycoprotein CD13) (gp150) (CD antigen CD13) | ANPEP APN CD13 PEPN | 967 |
| Q6Q4G3 | AMPQ_HUMAN | Aminopeptidase Q (AP-Q) (APQ) (EC 3.4.11.-) (CHL2 antigen) (Laeverin) | LVRN AQPEP | 990 |
| Q16853 | AOC3_HUMAN | Membrane primary amine oxidase (EC 1.4.3.21) (Copper amine oxidase) (HPAO) (Semicarbazide-sensitive amine oxidase) (SSAO) (Vascular adhesion protein 1) (VAP-1) | AOC3 VAP1 | 763 |
| Q9BT22 | ALG1_HUMAN | Chitobiosyldiphosphodolichol beta-mannosyltransferase (EC 2.4.1.142) (Asparagine-linked glycosylation protein 1 homolog) (Beta-1,4-mannosyltransferase) (GDP-Man: GlcNAc2-PP-dolichol mannosyltransferase) (GDP-mannose-dolichol diphosphochitobiose mannosyltransferase) (Mannosyltransferase-1) (hMat-1) | ALG1 HMAT1 HMT1 PSEC0061 UNQ861/PRO1870 | 464 |
| Q07075 | AMPE_HUMAN | Glutamyl aminopeptidase (EAP) (EC 3.4.11.7) (Aminopeptidase A) (AP-A) (Differentiation antigen gp160) (CD antigen CD249) | ENPEP | 957 |
| Q9HDC9 | APMAP_HUMAN | Adipocyte plasma membrane-associated protein (Protein BSCv) | APMAP C20orf3 UNQ1869/PRO4305 | 416 |
| P07306 | ASGR1_HUMAN | Asialoglycoprotein receptor 1 (ASGP-R 1) (ASGPR 1) (C-type lectin domain family 4 member H1) (Hepatic lectin H1) (HL-1) | ASGR1 CLEC4H1 | 291 |
| Q9NR71 | ASAH2_HUMAN | Neutral ceramidase (N-CDase) (NCDase) (EC 3.5.1.23) (Acylsphingosine deacylase 2) (BCDase) (LCDase) (hCD) (N-acylsphingosine amidohydrolase 2) (Non-lysosomal ceramidase) [Cleaved into: Neutral ceramidase soluble form] | ASAH2 HNAC1 | 780 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q5U4P2 | ASPH1_HUMAN | Aspartate beta-hydroxylase domain-containing protein 1 (EC 1.14.11.—) | ASPHD1 | 390 |
| Q9UN42 | AT1B4_HUMAN | Protein ATP1B4 (X,K-ATPase subunit beta-m) (X/potassium-transporting ATPase subunit beta-m) | ATP1B4 | 357 |
| Q99941 | ATF6B_HUMAN | Cyclic AMP-dependent transcription factor ATF-6 beta (cAMP-dependent transcription factor ATF-6 beta) (Activating transcription factor 6 beta) (ATF6-beta) (Protein G13) (cAMP response element-binding protein-related protein) (Creb-rp) (cAMP-responsive element-binding protein-like 1) [Cleaved into: Processed cyclic AMP-dependent transcription factor ATF-6 beta] | ATF6B CREBL1 G13 | 703 |
| Q6ICH7 | ASPH2_HUMAN | Aspartate beta-hydroxylase domain-containing protein 2 (EC 1.14.11.—) | ASPHD2 | 369 |
| P51164 | ATP4B_HUMAN | Potassium-transporting ATPase subunit beta (Gastric H(+)/K(+) ATPase subunit beta) (Proton pump beta chain) | ATP4B | 291 |
| Q12797 | ASPH_HUMAN | Aspartyl/asparaginyl beta-hydroxylase (EC 1.14.11.16) (Aspartate beta-hydroxylase) (ASP beta-hydroxylase) (Peptide-aspartate beta-dioxygenase) | ASPH BAH | 758 |
| P07307 | ASGR2_HUMAN | Asialoglycoprotein receptor 2 (ASGP-R 2) (ASGPR 2) (C-type lectin domain family 4 member H2) (Hepatic lectin H2) (HL-2) | ASGR2 CLEC4H2 | 311 |
| P05026 | AT1B1_HUMAN | Sodium/potassium-transporting ATPase subunit beta-1 (Sodium/potassium-dependent ATPase subunit beta-1) | ATP1B1 ATP1B | 303 |
| P14415 | AT1B2_HUMAN | Sodium/potassium-transporting ATPase subunit beta-2 (Adhesion molecule in glia) (AMOG) (Sodium/potassium-dependent ATPase subunit beta-2) | ATP1B2 | 290 |
| P54709 | AT1B3_HUMAN | Sodium/potassium-transporting ATPase subunit beta-3 (Sodium/potassium-dependent ATPase subunit beta-3) (ATPB-3) (CD antigen CD298) | ATP1B3 | 279 |
| P18850 | ATF6A_HUMAN | Cyclic AMP-dependent transcription factor ATF-6 alpha (cAMP-dependent transcription factor ATF-6 alpha) (Activating transcription factor 6 alpha) (ATF6-alpha) [Cleaved into: Processed cyclic AMP-dependent transcription factor ATF-6 alpha] | ATF6 | 670 |
| Q9P2W7 | B3GA1_HUMAN | Galactosylgalactosylxylosylprotein 3-beta-glucuronosyltransferase 1 (EC 2.4.1.135) (Beta-1,3-glucuronyltransferase 1) (Glucuronosyltransferase P) (GlcAT-P) (UDP-GlcUA: glycoprotein beta-1,3-glucuronyltransferase) (GlcUAT-P) | B3GAT1 GLCATP | 334 |
| Q9NPZ5 | B3GA2_HUMAN | Galactosylgalactosylxylosylprotein 3-beta-glucuronosyltransferase 2 (EC 2.4.1.135) (Beta-1,3-glucuronyltransferase 2) (GlcAT-D) (UDP-glucuronosyltransferase S) (GlcAT-S) (Glucuronosyltransferase S) | B3GAT2 GLCATS KIAA1963 | 323 |
| O94766 | B3GA3_HUMAN | Galactosylgalactosylxylosylprotein 3-beta-glucuronosyltransferase 3 (EC 2.4.1.135) (Beta-1,3-glucuronyltransferase 3) (Glucuronosyltransferase I) (GlcAT-I) (UDP-GlcUA: Gal beta-1,3-Gal-R glucuronyltransferase) (GlcUAT-I) | B3GAT3 | 335 |
| Q9Y2A9 | B3GN3_HUMAN | N-acetyllactosaminide beta-1,3-N-acetylglucosaminyltransferase 3 (EC 2.4.1.149) (Beta-1,3-galactosyl-O-glycosyl-glycoprotein beta-1,3-N-acetylglucosaminyltransferase) (EC 2.4.1.146) (Beta-1,3-galactosyltransferase 8) (Beta-1,3-GalTase 8) (Beta3Gal-T8) (Beta3GalT8) (b3Gal-T8) (Beta-3-Gx-T8) (Core 1 extending beta-1,3-N-acetylglucosaminyltransferase) (Core1-beta3GlcNAcT) (Transmembrane protein 3) (UDP-Gal: beta-GlcNAc beta-1,3-galactosyltransferase 8) (UDP-GlcNAc: betaGal beta-1,3-N-acetylglucosaminyltransferase 3) (BGnT-3) (Beta-1,3-Gn-T3) (Beta-1,3-N-acetylglucosamine beta-1,3-galactosyltransferase 8) | B3GNT3 B3GALT8 TMEM3 UNQ637/PRO1266 | 372 |
| Q96L58 | B3GT6_HUMAN | Beta-1,3-galactosyltransferase 6 (Beta-1,3-GalTase 6) (Beta3Gal-T6) (Beta3GalT6) (EC 2.4.1.134) (GAG GalTII) (Galactosyltransferase II) (Galactosylxylosylprotein 3-beta-galactosyltransferase) (UDP-Gal: betaGal beta 1,3-galactosyltransferase polypeptide 6) | B3GALT6 | 329 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| O43505 | B4GA1_HUMAN | Beta-1,4-glucuronyltransferase 1 (EC 2.4.1.—) (I-beta-1,3-N-acetylglucosaminyltransferase) (iGnT) (N-acetyllactosaminide beta-1,3-N-acetylglucosaminyltransferase) (Poly-N-acetyllactosamine extension enzyme) (UDP-GlcNAc: betaGal beta-1,3-N-acetylglucosaminyltransferase 1) | B4GAT1 B3GNT1 B3GNT6 | 415 |
| O75752 | B3GL1_HUMAN | UDP-GalNAc: beta-1,3-N-acetylgalactosaminyltransferase 1 (Beta-1,3-GalNAc-T1) (EC 2.4.1.79) (Beta-1,3-galactosyltransferase 3) (Beta-1,3-GalTase 3) (Beta3Gal-T3) (Beta3GalT3) (b3Gal-T3) (Beta-3-Gx-T3) (Galactosylgalactosylglucosylceramide beta-D-acetyl-galactosaminyltransferase) (Globoside synthase) (UDP-N-acetylgalactosamine: globotriaosylceramide beta-1,3-N-acetylgalactosaminyltransferase) | B3GALNT1 B3GALT3 UNQ531/PRO1074 | 331 |
| Q7Z7M8 | B3GN8_HUMAN | UDP-GlcNAc: betaGal beta-1,3-N-acetylglucosaminyltransferase 8 (BGnT-8) (Beta-1,3-Gn-T8) (Beta-1,3-N-acetylglucosaminyltransferase 8) (Beta3Gn-T8) (EC 2.4.1.—) | B3GNT8 B3GALT7 BGALT15 | 397 |
| Q9Y2C3 | B3GT5_HUMAN | Beta-1,3-galactosyltransferase 5 (Beta-1,3-GalTase 5) (Beta3Gal-T5) (Beta3GalT5) (b3Gal-T5) (EC 2.4.1.—) (Beta-3-Gx-T5) (UDP-Gal: beta-GlcNAc beta-1,3-galactosyltransferase 5) (UDP-galactose: beta-N-acetylglucosamine beta-1,3-galactosyltransferase 5) | B3GALT5 | 310 |
| Q8NFL0 | B3GN7_HUMAN | UDP-GlcNAc: betaGal beta-1,3-N-acetylglucosaminyltransferase 7 (BGnT-7) (Beta-1,3-Gn-T7) (Beta-1,3-N-acetylglucosaminyltransferase 7) (Beta3Gn-T7) (EC 2.4.1.—) | B3GNT7 | 401 |
| O43825 | B3GT2_HUMAN | Beta-1,3-galactosyltransferase 2 (Beta-1,3-GalTase 2) (Beta3Gal-T2) (Beta3GalT2) (EC 2.4.1.—) (UDP-galactose: 2-acetamido-2-deoxy-D-glucose 3beta-galactosyltransferase 2) | B3GALT2 | 422 |
| Q00973 | B4GN1_HUMAN | Beta-1,4 N-acetylgalactosaminyltransferase 1 (EC 2.4.1.92) (N-acetylneuraminyl)-galactosylglucosylceramide) (GM2/GD2 synthase) (GalNAc-T) | B4GALNT1 GALGT SIAT2 | 533 |
| P15291 | B4GT1_HUMAN | Beta-1,4-galactosyltransferase 1 (Beta-1,4-GalTase 1) (Beta4Gal-T1) (b4Gal-T1) (EC 2.4.1.—) (UDP-Gal: beta-GlcNAc beta-1,4-galactosyltransferase 1) [Cleaved into: Processed beta-1,4-galactosyltransferase 1] [Includes: Lactose synthase A protein (EC 2.4.1.22); N-acetyllactosamine synthase (EC 2.4.1.90) (Nal synthase); Beta-N-acetylglucosaminylglycopeptide beta-1,4-galactosyltransferase (EC 2.4.1.38); Beta-N-acetylglucosaminyl-glycolipid beta-1,4-galactosyltransferase (EC 2.4.1.—)] | B4GALT1 GGTB2 | 398 |
| O60513 | B4GT4_HUMAN | Beta-1,4-galactosyltransferase 4 (Beta-1,4-GalTase 4) (Beta4Gal-T4) (b4Gal-T4) (EC 2.4.1.—) (UDP-Gal: beta-GlcNAc beta-1,4-galactosyltransferase 4) (UDP-galactose: beta-N-acetylglucosamine beta-1,4-galactosyltransferase 4) [Includes: N-acetyllactosamine synthase (EC 2.4.1.90) (Nal synthase); Lactotriaosylceramide beta-1,4-galactosyltransferase (EC 2.4.1.275) (Beta-N-acetylglucosaminyl-glycolipid beta-1,4-galactosyltransferase)] | B4GALT4 UNQ552/PRO1109 | 344 |
| O43286 | B4GT5_HUMAN | Beta-1,4-galactosyltransferase 5 (Beta-1,4-GalTase 5) (Beta4Gal-T5) (b4Gal-T5) (EC 2.4.1.—) (Beta-1,4-GalT II) (UDP-Gal: beta-GlcNAc beta-1,4-galactosyltransferase 5) (UDP-galactose: beta-N-acetylglucosamine beta-1,4-galactosyltransferase 5) | B4GALT5 | 388 |
| Q9NY97 | B3GN2_HUMAN | N-acetyllactosaminide beta-1,3-N-acetylglucosaminyltransferase 2 (EC 2.4.1.149) (Beta-1,3-N-acetylglucosaminyltransferase 1) (BGnT-1) (Beta-1,3-Gn-T1) (Beta-1,3-galactosyltransferase 7) (Beta-1,3-GalTase 7) (Beta3Gal-T7) (Beta3GalT7) (b3Gal-T7) (Beta-3-Gx-T7) (UDP-Gal: beta-GlcNAc beta-1,3-galactosyltransferase 7) (UDP-GlcNAc: betaGal beta-1,3-N-acetylglucosaminyltransferase 2) (BGnT-2) (Beta-1,3-Gn-T2) (Beta-1,3-N-acetylglucosaminyltransferase 2) (Beta3Gn-T2) (UDP-galactose: beta-N-acetylglucosamine beta-1,3-galactosyltransferase 7) | B3GNT2 B3GALT7 B3GNT1 | 397 |
| O60512 | B4GT3_HUMAN | Beta-1,4-galactosyltransferase 3 (Beta-1,4-GalTase 3) (Beta4Gal-T3) (b4Gal-T3) (EC 2.4.1.—) (UDP-Gal: beta-GlcNAc beta-1,4-galactosyltransferase 3) (UDP-galactose: beta-N-acetylglucosamine beta-1,4-galactosyltransferase 3) [Includes: N-acetyllactosamine synthase (EC 2.4.1.90) (Nal synthase); Beta-N-acetylglucosaminylglycopeptide beta-1,4- | B4GALT3 | 393 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9Y5Z6 | B3GT1_HUMAN | galactosyltransferase (EC 2.4.1.38; Beta-N-acetylglucosaminyl-glycolipid beta-1,4-galactosyltransferase (EC 2.4.1.—)] | B3GALT1 | 326 |
| O96024 | B3GT4_HUMAN | Beta-1,3-galactosyltransferase 1 (Beta-1,3-GalTase 1) (Beta3Gal-T1) (Beta3GalT1) (EC 2.4.1.—) (UDP-galactose: beta-N-acetyl-glucosamine-beta-1,3-galactosyltransferase 1) | B3GALT4 GALT4 | 378 |
| Q76KP1 | B4GN4_HUMAN | Beta-1,3-galactosyltransferase 4 (Beta-1,3-GalTase 4) (Beta3Gal-T4) (Beta3GalT4) (GalT4) (b5Gal-T4) (EC 2.4.1.62) (Gal-T2) (Ganglioside galactosyltransferase) (UDP-galactose: beta-N-acetyl-galactosamine-beta-1,3-galactosyltransferase) | B4GALNT4 | 1039 |
| O60909 | B4GT2_HUMAN | N-acetyl-beta-glucosaminyl-glycoprotein 4-beta-N-acetylgalactosaminyltransferase 1 (NGalNAc-T1) (EC 2.4.1.244) (Beta-1,4-N-acetylgalactosaminyltransferase IV) (Beta4GalNAc-T4) (Beta4GalNAcT4) | B4GALT2 | 372 |
| Q9UBX8 | B4GT6_HUMAN | Beta-1,4-galactosyltransferase 2 (Beta-1,4-GalTase 2) (Beta4Gal-T2) (b4Gal-T2) (EC 2.4.1.—) (UDP-Gal: beta-GlcNAc beta-1,4-galactosyltransferase 2) (UDP-galactose: beta-N-acetylglucosamine beta-1,4-galactosyltransferase 2) [Includes: Lactose synthase A protein (EC 2.4.1.22); N-acetyllactosamine synthase (EC 2.4.1.90) (Nal synthase); Beta-N-acetylglucosaminylglycopeptide beta-1,4-galactosyltransferase (EC 2.4.1.38; Beta-N-acetylglucosaminyl-glycolipid beta-1,4-galactosyltransferase (EC 2.4.1.—)] | B4GALT6 | 382 |
| Q9UBV7 | B4GT7_HUMAN | Beta-1,4-galactosyltransferase 6 (Beta-1,4-GalTase 6) (Beta4Gal-T6) (b4Gal-T6) (UDP-Gal: beta-GlcNAc beta-1,4-galactosyltransferase 6) (UDP-galactose: beta-N-acetylglucosamine beta-1,4-galactosyltransferase 6) [Includes: Glucosylceramide beta-1,4-galactosyltransferase (EC 2.4.1.274) (Lactosylceramide synthase) (LacCer synthase) (UDP-Gal: glucosylceramide beta-1,4-galactosyltransferase)] | B4GALT7 XGALT1 UNQ748/PRO1478 | 327 |
| Q8NCR0 | B3GL2_HUMAN | Beta-1,4-galactosyltransferase 7 (Beta-1,4-GalTase 7) (Beta4Gal-T7) (b4Gal-T7) (EC 2.4.1.—) (UDP-Gal: beta-GlcNAc beta-1,4-galactosyltransferase 7) (UDP-galactose: beta-N-acetylglucosamine beta-1,4-galactosyltransferase 7) [Includes: Xylosylprotein 4-beta-galactosyltransferase (EC 2.4.1.133) (Proteoglycan UDP-galactose: beta-xylose beta1,4-galactosyltransferase I) (UDP-galactose: beta-xylose beta-1,4-galactosyltransferase) (XGPT) (XGalT-1) (Xylosylprotein beta-1,4-galactosyltransferase)] | B3GALNT2 | 500 |
| Q9C0I1 | B3GN4_HUMAN | UDP-GalNAc: beta-1,3-N-acetylgalactosaminyltransferase 2 (Beta-1,3-GalNAc-T2) (EC 2.4.1.—) (Beta-1,3-N-acetylgalactosaminyltransferase II) | B3GNT4 UNQ1898/PRO4344 | 378 |
| Q6ZMB0 | B3GN6_HUMAN | N-acetyllactosaminide beta-1,3-N-acetylglucosaminyltransferase 4 (EC 2.4.1.149) (UDP-GlcNAc: betaGal beta-1,3-N-acetylglucosaminyltransferase 4) (BGnT-4) (Beta-1,3-Gn-T4) (Beta-1,3-N-acetylglucosaminyltransferase 4) (Beta3Gn-T4) | B3GNT6 | 384 |
| Q9BYG0 | B3GN5_HUMAN | Acetylgalactosaminyl-O-glycosyl-glycoprotein beta-1,3-N-acetylglucosaminyltransferase (EC 2.4.1.147) (Core 3 synthase) (UDP-GlcNAc: betaGal beta-1,3-N-acetylglucosaminyltransferase 6) (BGnT-6) (Beta-1,3-Gn-T6) (Beta-1,3-N-acetylglucosaminyltransferase 6) (Beta3Gn-T6) | B3GNT5 | 378 |
| Q6UX72 | B3GN9_HUMAN | Lactosylceramide 1,3-N-acetyl-beta-D-glucosaminyltransferase (EC 2.4.1.206) (Lactotriaosylceramide synthase) (Lc(3)Cer synthase) (Lc3 synthase) (UDP-GlcNAc: beta-Gal beta-1,3-N-acetylglucosaminyltransferase 5) (BGnT-5) (Beta-1,3-Gn-T5) (Beta-1,3-N-acetylglucosaminyltransferase 5) (Beta3Gn-T5) | B3GNT9 UNQ1922/PRO4397 | 402 |
| Q6L9W6 | B4GN3_HUMAN | UDP-GlcNAc: betaGal beta-1,3-N-acetylglucosaminyltransferase 9 (BGnT-9) (Beta-1,3-Gn-T9) (Beta-1,3-N-acetylglucosaminyltransferase 9) (Beta3Gn-T9) (EC 2.4.1.—) | B4GALNT3 | 998 |
| Q6Y288 | B3GLT_HUMAN | Beta-1,4-N-acetylgalactosaminyltransferase 3 (B4GalNAcT3) (Beta4GalNAc-T3) (Beta4GalNAcT3) (EC 2.4.1.244) (Beta-1,4-N-acetylgalactosaminyltransferase III) (N-acetyl-beta-glucosaminyl-glycoprotein 4-beta-N-acetylgalactosaminyltransferase 2) (NGalNAc-T2) | B3GLCT B3GALTL B3GTL | 498 |
| | | Beta-1,3-glucosyltransferase (Beta3Glc-T) (EC 2.4.1.—) (Beta 3-glucosyltransferase) (Beta-3-glycosyltransferase-like) | | |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q8NHY0 | B4GN2_HUMAN | Beta-1,4 N-acetylgalactosaminyltransferase 2 (EC 2.4.1.—) (Sd(a) beta-1,4-GalNAc transferase) (UDP-GalNAc: NeuSAca2-3Galb-R b1,4-N-acetylgalactosaminyltransferase) | B4GALNT2 GALGT2 | 566 |
| P0DN25 | C1C1L_HUMAN | C1GALT1-specific chaperone 1-like protein | C1GALT1C1L | 315 |
| P16442 | BGAT_HUMAN | Histo-blood group ABO system transferase (Fucosylglycoprotein 3-alpha-galactosyltransferase) (Fucosylglycoprotein alpha-N-acetylgalactosaminyltransferase) (Glycoprotein-fucosylgalactoside alpha-N-acetylgalactosaminyltransferase) (EC 2.4.1.40) (Glycoprotein-fucosylgalactoside alpha-galactosyltransferase) (EC 2.4.1.37) (Histo-blood group A transferase) (A transferase) (Histo-blood group B transferase) (B transferase) (NAGAT) [Cleaved into: Fucosylglycoprotein alpha-N-acetylgalactosaminyltransferase soluble form] | ABO | 354 |
| Q9NS00 | C1GLT_HUMAN | Glycoprotein-N-acetylgalactosamine 3-beta-galactosyltransferase 1 (EC 2.4.1.122) (B3Gal-T8) (Core 1 O-glycan T-synthase) (Core 1 UDP-galactose: N-acetylgalactosamine-alpha-R beta 1,3-galactosyltransferase 1) (Beta-1,3-galactosyltransferase) (Core 1 beta1,3-galactosyltransferase 1) (C1GalT1) (Core 1 beta3-Gal-T1) | C1GALT1 | 363 |
| Q10589 | BST2_HUMAN | Bone marrow stromal antigen 2 (BST-2) (HM1.24 antigen) (Tetherin) (CD antigen CD317) | BST2 | 180 |
| Q96EU7 | C1GLC_HUMAN | C1GALT1-specific chaperone 1 (C38H2-like protein 1) (C38H2-L1) (Core 1 beta1,3-galactosyltransferase 2) (C1Gal-T2) (C1GalT2) (Core 1 beta3-Gal-T2) (Core 1 beta3-galactosyltransferase-specific molecular chaperone) | C1GALT1C1 COSMC HSPC067 MSTP143 UNQ273/PRO310 | 318 |
| Q9UIR0 | BTNL2_HUMAN | Butyrophilin-like protein 2 (BTL-II) | BTNL2 | 455 |
| Q6P4E1 | CASC4_HUMAN | Protein CASC4 (Cancer susceptibility candidate gene 4 protein) | CASC4 | 433 |
| Q9NNX6 | CD209_HUMAN | CD209 antigen (C-type lectin domain family 4 member L) (Dendritic cell-specific ICAM-3-grabbing non-integrin 1) (DC-SIGN) (DC-SIGN1) (CD antigen CD209) | CD209 CLEC4L | 404 |
| Q8WVQ1 | CANT1_HUMAN | Soluble calcium-activated nucleotidase 1 (SCAN-1) (EC 3.6.1.6) (Apyrase homolog) (Putative MAPK-activating protein PM09) (Putative NF-kappa-B-activating protein 107) | CANT1 SHAPY | 401 |
| P29965 | CD40L_HUMAN | CD40 ligand (CD40-L) (T-cell antigen Gp39) (TNF-related activation protein) (TRAP) (Tumor necrosis factor ligand superfamily member 5) (CD antigen CD154) [Cleaved into: CD40 ligand, membrane form; CD40 ligand, soluble form] | CD40LG CD40L TNFSF5 TRAP | 261 |
| P21854 | CD72_HUMAN | B-cell differentiation antigen CD72 (Lyb-2) (CD antigen CD72) | CD72 | 359 |
| Q07108 | CD69_HUMAN | Early activation antigen CD69 (Activation inducer molecule) (AIM) (BL-AC/P26) (C-type lectin domain family 2 member C) (EA1) (Early T-cell activation antigen p60) (GP32/28) (Leukocyte surface antigen Leu-23) (MLR-3) (CD antigen CD69) | CD69 CLEC2C | 199 |
| Q9ULG6 | CCPG1_HUMAN | Cell cycle progression protein 1 (Cell cycle progression restoration protein 8) | CCPG1 CCP8 CPR8 KIAA1254 | 757 |
| Q8TDX6 | CGAT1_HUMAN | Chondroitin sulfate N-acetylgalactosaminyltransferase 1 (CsGalNAcT-1) (EC 2.4.1.174) (Chondroitin beta-1,4-N-acetylgalactosaminyltransferase 1) (Beta4GalNAcT-1) | CSGALNACT1 CHGN GALNACT1 UNQ656/PRO1287 | 532 |
| P32970 | CD70_HUMAN | CD70 antigen (CD27 ligand) (CD27-L) (Tumor necrosis factor ligand superfamily member 7) (CD antigen CD70) | CD70 CD27L CD27LG TNFSF7 | 193 |
| Q8IZ52 | CHSS2_HUMAN | Chondroitin sulfate synthase 2 (EC 2.4.1.226) (Chondroitin glucuronyltransferase 2) (Chondroitin-polymerizing factor) (ChPF) (Glucuronosyl-N-acetylgalactosaminyl-proteoglycan 4-beta-N-acetylgalactosaminyltransferase II) (N-acetylgalactosaminyl-proteoglycan 3-beta-glucuronosyltransferase II) (N-acetylgalactosaminyltransferase 2) | CHPF CSS2 UNQ651/PRO1281 | 775 |
| Q9GZX3 | CHST6_HUMAN | Carbohydrate sulfotransferase 6 (EC 2.8.2.—) (Corneal N-acetylglucosamine-6-O-sulfotransferase) (C-GlcNAc6ST) (hCGn6ST) (Galactose/N-acetylglucosamine/N- | CHST6 | 395 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9NRB3 | CHSTC_HUMAN | acetylglucosamine 6-O-sulfotransferase 4-beta) (GST4-beta) (N-acetylglucosamine 6-O-sulfotransferase 5) (GlcNAc6ST-5) (Gn6st-5) | CHST12 | 414 |
| P28907 | CD38_HUMAN | Carbohydrate sulfotransferase 12 (EC 2.8.2.5) (Chondroitin 4-O-sulfotransferase 2) (Chondroitin 4-sulfotransferase 2) (C4ST2) (Sulfotransferase Hlo) | UNQ500/PRO1017 | 300 |
| | | ADP-ribosyl cyclase/cyclic ADP-ribose hydrolase 1 (EC 3.2.2.6) (2'-phospho-ADP-ribosyl cyclase) (2'-phospho-ADP-ribosyl cyclase/2'-phospho-cyclic-ADP-ribose transferase) (EC 2.4.99.20) (2'-phospho-cyclic-ADP-ribose transferase) (ADP-ribosyl cyclase 1) (ADPRC 1) (Cyclic ADP-ribose hydrolase 1) (cADPr hydrolase 1) (T10) (CD antigen CD38) | CD38 | |
| Q8N6G5 | CGAT2_HUMAN | Chondroitin sulfate N-acetylgalactosaminyltransferase 2 (EC 2.4.1.174) (Chondroitin beta-1,4-N-acetylgalactosaminyltransferase 2) (Beta4GalNAcT-2) (GalNAcT-2) | CSGALNACT2 CHGN2 GALNACT2 PRO0082 | 542 |
| Q5QGZ9 | CL12A_HUMAN | C-type lectin domain family 12 member A (C-type lectin-like molecule 1) (CLL-1) (Dendritic cell-associated lectin 2) (DCAL-2) (Myeloid inhibitory C-type lectin-like receptor) (MICL) | CLEC12A CLL1 DCAL2 MICL | 265 |
| Q9P2E5 | CHPF2_HUMAN | Chondroitin sulfate glucuronyltransferase (EC 2.4.1.226) (CSGlcA-T) (Chondroitin glucuronyltransferase) (Chondroitin polymerizing factor 2) (ChPF-2) (Chondroitin synthase 3) (ChSy-3) (N-acetylgalactosaminyl-proteoglycan 3-beta-glucuronosyltransferase) | CHPF2 CHSY3 CSGLCAT KIAA1402 UNQ299/PRO339 | 772 |
| Q7OI A7 | CHSS3_HUMAN | Chondroitin sulfate synthase 3 (EC 2.4.1.175) (EC 2.4.1.226) (Carbohydrate synthase 2) (Chondroitin glucuronyltransferase 3) (Chondroitin synthase 2) (ChSy-2) (Glucuronosyl-N-acetylgalactosaminyl-proteoglycan 4-beta-N-acetylgalactosaminyltransferase II) (N-acetylgalactosaminyl-proteoglycan 3-beta-glucuronosyltransferase 3) (N-acetylgalactosaminyltransferase 3) | CHSY3 CHSY2 CSS3 | 882 |
| Q9Y4C5 | CHST2_HUMAN | Carbohydrate sulfotransferase 2 (EC 2.8.2.—) (Galactose/N-acetylglucosamine/N-acetylglucosamine 6-O-sulfotransferase 2) (GST-2) (N-acetylglucosamine 6-O-sulfotransferase 1) (GlcNAc6ST-1) (Gn6ST-1) | CHST2 GN6ST | 530 |
| Q8NCG5 | CHST4_HUMAN | Carbohydrate sulfotransferase 4 (EC 2.8.2.—) (Galactose/N-acetylglucosamine/N-acetylglucosamine 6-O-sulfotransferase 3) (GST-3) (High endothelial cells N-acetylglucosamine 6-O-sulfotransferase) (HEC-GlcNAc6ST) (L-selectin ligand sulfotransferase) (LSST) (N-acetylglucosamine 6-O-sulfotransferase 2) (GlcNAc6ST-2) (Gn6st-2) | CHST4 | 386 |
| O43529 | CHSTA_HUMAN | Carbohydrate sulfotransferase 10 (EC 2.8.2.—) (HNK-1 sulfotransferase) (HNK-1ST) (HNK1ST) (HuHNK-1ST) | CHST10 | 356 |
| Q92478 | CLC2B_HUMAN | C-type lectin domain family 2 member B (Activation-induced C-type lectin) (C-type lectin superfamily member 2) (IFN-alpha-2b-inducing-related protein 1) | CLEC2B AICL CLECSF2 IFNRG1 | 149 |
| Q6UXN8 | CLC9A_HUMAN | C-type lectin domain family 9 member A | CLEC9A UNQ9341/PRO34046 | 241 |
| Q6UWU4 | CF089_HUMAN | Bombesin receptor-activated protein C6orf89 (Amfion) | C6orf89 BRAP UNQ177/PRO203 | 347 |
| Q86X52 | CHSS1_HUMAN | Chondroitin sulfate synthase 1 (EC 2.4.1.175) (EC 2.4.1.226) (Chondroitin glucuronyltransferase 1) (Chondroitin synthase 1) (ChSy-1) (Glucuronosyl-N-acetylgalactosaminyl-proteoglycan 4-beta-N-acetylgalactosaminyltransferase 1) (N-acetylgalactosaminyl-proteoglycan 3-beta-glucuronosyltransferase 1) (N-acetylgalactosaminyltransferase 1) | CHSY1 CHSY CSS1 KIAA0990 UNQ756/PRO1487 | 802 |
| Q8NET6 | CHSTD_HUMAN | Carbohydrate sulfotransferase 13 (EC 2.8.2.5) (Chondroitin 4-O-sulfotransferase 3) (Chondroitin 4-sulfotransferase 3) (C4ST3) | CHST13 | 341 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q7LFX5 | CHSTF_HUMAN | Carbohydrate sulfotransferase 15 (EC 2.8.2.33) (B-cell RAG-associated gene protein) (hBRAG) (N-acetylgalactosamine 4-sulfate 6-O-sulfotransferase) (GalNAc4S-6ST) | CHST15 BRAG GALNAC4S6ST KIAA0598 | 561 |
| Q9P126 | CLC1B_HUMAN | C-type lectin domain family 1 member B (C-type lectin-like receptor 2) (CLEC-2) | CLEC1B CLEC2 UNQ721/PRO1384 | 229 |
| Q8IZS7 | CLCL1_HUMAN | C-type lectin-like domain family 1 (Dendritic cell-associated lectin 1) (DC-associated lectin-1) (DCAL-1) | CLECL1 DCAL1 | 167 |
| O43916 | CHST1_HUMAN | Carbohydrate sulfotransferase 1 (EC 2.8.2.21) (Galactose/N-acetylglucosamine/N-acetylglucosamine 6-O-sulfotransferase 1) (GST-1) (Keratan sulfate Gal-6 sulfotransferase) (KS6ST) (KSGal6ST) (KSST) | CHST1 | 411 |
| Q7LGC8 | CHST3_HUMAN | Carbohydrate sulfotransferase 3 (EC 2.8.2.17) (Chondroitin 6-O-sulfotransferase 1) (C6ST-1) (Chondroitin 6-sulfotransferase) (Galactose/N-acetylglucosamine/N-acetylglucosamine 6-O-sulfotransferase 0) (GST-0) | CHST3 | 479 |
| Q9GZS9 | CHST5_HUMAN | Carbohydrate sulfotransferase 5 (EC 2.8.2.—) (Galactose/N-acetylglucosamine/N-acetylglucosamine 6-O-sulfotransferase 4-alpha) (GST4-alpha) (Intestinal N-acetylglucosamine-6-O-sulfotransferase) (I-GlcNAc6ST) (Intestinal GlcNAc-6-sulfotransferase) (hIGn6ST) (N-acetylglucosamine 6-O-sulfotransferase 3) (GlcNAc6ST-3) (Gn6st-3) | CHST5 | 411 |
| Q9NPF2 | CHSTB_HUMAN | Carbohydrate sulfotransferase 11 (EC 2.8.2.5) (Chondroitin 4-O-sulfotransferase 1) (Chondroitin 4-sulfotransferase 1) (C4ST-1) (C4ST1) | CHST11 | 352 |
| Q9UMR7 | CLC4A_HUMAN | C-type lectin domain family 4 member A (C-type lectin DDB27) (C-type lectin superfamily member 6) (Dendritic cell immunoreceptor) (Lectin-like immunoreceptor) | CLEC4A CLECSF6 DCIR LLIR HDCGC13P | 237 |
| Q8WXI8 | CLC4D_HUMAN | C-type lectin domain family 4 member D (C-type lectin superfamily member 8) (C-type lectin-like receptor 6) (CLEC-6) | CLEC4D CLECSF8 MCL | 215 |
| Q8N1N0 | CLC4F_HUMAN | C-type lectin domain family 4 member F (C-type lectin superfamily member 13) (C-type lectin 13) | CLEC4F CLECSF13 | 589 |
| Q6UXB4 | CLC4G_HUMAN | C-type lectin domain family 4 member G (Liver and lymph node sinusoidal endothelial cell C-type lectin) (LSECtin) | CLEC4G UNQ431/PR0792 | 293 |
| Q9BXN2 | CLC7A_HUMAN | C-type lectin domain family 7 member A (Beta-glucan receptor) (C-type lectin 1) (DC-associated C-type lectin 1) (Dendritic cell-associated C-type lectin 1) (Dectin-1) | CLEC7A BGR CLECSF12 DECTIN1 UNQ539/PRO1082 | 247 |
| Q86VU5 | CMTD1_HUMAN | Catechol O-methyltransferase domain-containing protein 1 (EC 2.1.1.—) | COMTD1 UNQ766/PRO1558 | 262 |
| Q9NS84 | CHST7_HUMAN | Carbohydrate sulfotransferase 7 (EC 2.8.2.17) (Chondroitin 6-sulfotransferase 2) (C6ST-2) (Galactose/N-acetylglucosamine/N-acetylglucosamine 6-O-sulfotransferase 5) (GST-5) (N-acetylglucosamine 6-O-sulfotransferase 4) (GlcNAc6ST-4) (Gn6st-4) | CHST7 | 486 |
| Q8NCH0 | CHSTE_HUMAN | Carbohydrate sulfotransferase 14 (EC 2.8.2.35) (Dermatan 4-sulfotransferase 1) (D4ST-1) (hD4ST1) | CHST14 D4ST1 UNQ1925/PRO4400 | 376 |
| Q6UVW9 | CLC2A_HUMAN | C-type lectin domain family 2 member A (Keratinocyte-associated C-type lectin) (KACL) (Proliferation-induced lymphocyte-associated receptor) (PILAR) | CLEC2A KACL UNQ5792/PRO19597 | 174 |
| Q8WTT0 | CLC4C_HUMAN | C-type lectin domain family 4 member C (Blood dendritic cell antigen 2) (BDCA-2) (C-type lectin superfamily member 7) (Dendritic lectin) (CD antigen CD303) | CLEC4C BDCA2 CLECSF11 CLECSF7 DLEC HECL UNQ9361/PRO34150 | 213 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9ULY5 | CLC4E_HUMAN | C-type lectin domain family 4 member E (C-type lectin superfamily member 9) (Macrophage-inducible C-type lectin) | CLEC4E CLECSF9 MINCLE UNQ218/PRO244 | 219 |
| Q9H2A9 | CHST8_HUMAN | Carbohydrate sulfotransferase 8 (EC 2.8.2.—) (GalNAc-4-O-sulfotransferase 1) (GalNAc-4-ST1) (GalNAc4ST-1) (N-acetylgalactosamine-4-O-sulfotransferase 1) | CHST8 | 424 |
| Q8IUN9 | CLC10_HUMAN | C-type lectin domain family 10 member A (C-type lectin superfamily member 14) (Macrophage lectin 2) (CD antigen CD301) | CLEC10A CLECSF13 CLECSF14 HML | 316 |
| Q8NC01 | CLC1A_HUMAN | C-type lectin domain family 1 member A (C-type lectin-like receptor 1) (CLEC-1) | CLEC1A CLEC1 UNQ569/PRO1131 | 280 |
| Q9UJ71 | CLC4K_HUMAN | C-type lectin domain family 4 member K (Langerin) (CD antigen CD207) | CD207 CLEC4K | 328 |
| Q7L1S5 | CHST9_HUMAN | Carbohydrate sulfotransferase 9 (EC 2.8.2.—) (GalNAc-4-O-sulfotransferase 2) (GalNAc-4-ST2) (GalNAc4ST-2) (N-acetylgalactosamine-4-O-sulfotransferase 2) | CHST9 UNQ2549/PRO6175 | 443 |
| Q07065 | CKAP4_HUMAN | Cytoskeleton-associated protein 4 (63-kDa cytoskeleton-linking membrane protein) (Climp-63) (p63) | CKAP4 | 602 |
| Q2HXU8 | CLI2B_HUMAN | C-type lectin domain family 12 member B (Macrophage antigen H) | CLEC12B UNQ5782/PRO16089 | 276 |
| Q6ZS10 | CL17A_HUMAN | C-type lectin domain family 17, member A (Prolectin) | CLEC17A | 378 |
| Q9NY25 | CLC5A_HUMAN | C-type lectin domain family 5 member A (C-type lectin superfamily member 5) (Myeloid DAP12-associating lectin 1) (MDL-1) | CLEC5A CLECSF5 MDL1 | 188 |
| Q6EIG7 | CLC6A_HUMAN | C-type lectin domain family 6 member A (C-type lectin superfamily member 10) (Dendritic cell-associated C-type lectin 2) (DC-associated C-type lectin 2) (Dectin-2) | CLEC6A CLECSF10 DECTIN2 | 209 |
| P21964 | COMT_HUMAN | Catechol O-methyltransferase (EC 2.1.1.6) | COMT | 271 |
| Q9UHP7 | CLC2D_HUMAN | C-type lectin domain family 2 member D (Lectin-like NK cell receptor) (Lectin-like transcript 1) (LLT-1) (Osteoclast inhibitory lectin) | CLEC2D CLAX LIT1 OCIL | 191 |
| Q9H2X3 | CLC4M_HUMAN | C-type lectin domain family 4 member M (CD209 antigen-like protein 1) (DC-SIGN-related protein) (DC-SIGNR) (Dendritic cell-specific ICAM-3-grabbing non-integrin 2) (DC-SIGN2) (Liver/lymph node-specific ICAM-3-grabbing non-integrin) (L-SIGN) (CD antigen CD299) | CLEC4M CD209L CD209L1 CD299 | 399 |
| Q5KU26 | COL12_HUMAN | Collectin-12 (Collectin placenta protein 1) (CL-P1) (hCL-P1) (Nurse cell scavenger receptor 2) (Scavenger receptor class A member 4) (Scavenger receptor with C-type lectin) | COLEC12 CLP1 NSR2 SCARA4 SRCL | 742 |
| Q5TAT6 | CODA1_HUMAN | Collagen alpha-1(XIII) chain (COLXIIIA1) | COL13A1 | 717 |
| Q96BA8 | CR3L1_HUMAN | Cyclic AMP-responsive element-binding protein 3-like protein 1 (cAMP-responsive element-binding protein 3-like protein 1) (Old astrocyte specifically-induced substance) (OASIS) [Cleaved into: Processed cyclic AMP-responsive element-binding protein 3-like protein 1] | CREB3L1 OASIS PSEC0238 | 519 |
| Q86Y22 | CONA1_HUMAN | Collagen alpha-1(XXIII) chain | COL23A1 | 540 |
| Q70SY1 | CR3L2_HUMAN | Cyclic AMP-responsive element-binding protein 3-like protein 2 (cAMP-responsive element-binding protein 3-like protein 2) (BBF2 human homolog on chromosome 7) [Cleaved into: Processed cyclic AMP-responsive element-binding protein 3-like protein 2] | CREB3L2 BBF2H7 | 520 |
| Q9UMD9 | COHA1_HUMAN | Collagen alpha-1(XVII) chain (180 kDa bullous pemphigoid antigen 2) (Bullous pemphigoid antigen 2) [Cleaved into: 120 kDa linear IgA disease antigen (120 kDa linear IgA dermatosis antigen) (Linear IgA disease antigen 1) (LAD-1); 97 kDa linear IgA disease antigen (97 kDa linear IgA bullous dermatosis antigen) (97 kDa LAD antigen) (97-LAD) (Linear IgA bullous disease antigen of 97 kDa) (LABD97)] | COL17A1 BP180 BPAG2 | 1497 |
| Q8N1L4 | CP4Z2_HUMAN | Putative inactive cytochrome P450 family member 4Z2 | CYP4Z2P | 340 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9BXS0 | COPA1_HUMAN | Collagen alpha-1(XXV) chain (Alzheimer disease amyloid-associated protein) (AMY) (CLAC-P) [Cleaved into: Collagen-like Alzheimer amyloid plaque component (CLAC)] | COL25A1 | 654 |
| Q9Y5Q5 | CORIN_HUMAN | Atrial natriuretic peptide-converting enzyme (EC 3.4.21.—) (Corin) (Heart-specific serine proteinase ATC2) (Pro-ANP-converting enzyme) (Transmembrane protease serine 10) [Cleaved into: Atrial natriuretic peptide-converting enzyme, N-terminal propeptide; Atrial natriuretic peptide-converting enzyme, activated protease fragment; Atrial natriuretic peptide-converting enzyme, 180 kDa soluble fragment; Atrial natriuretic peptide-converting enzyme, 160 kDa soluble fragment; Atrial natriuretic peptide-converting enzyme, 100 kDa soluble fragment] | CORIN CRN TMPRSS10 | 1042 |
| Q86W10 | CP4Z1_HUMAN | Cytochrome P450 4Z1 (EC 1.14.14.1) (CYPIVZ1) | CYP4Z1 UNQ3060/PRO9882 | 505 |
| O43889 | CREB3_HUMAN | Cyclic AMP-responsive element-binding protein 3 (CREB-3) (cAMP-responsive element-binding protein 3) (Leucine zipper protein) (Luman) (Transcription factor LZIP-alpha) [Cleaved into: Processed cyclic AMP-responsive element-binding protein 3 (N-terminal Luman) (Transcriptionally active form)] | CREB3 LZIP | 395 |
| Q8TEY5 | CR3L4_HUMAN | Cyclic AMP-responsive element-binding protein 3-like protein 4 (cAMP-responsive element-binding protein 3-like protein 4) (Androgen-induced basic leucine zipper protein) (AIbZIP) (Attaching to CRE-like 1) (ATCE1) (Cyclic AMP-responsive element-binding protein 4) (CREB-4) (cAMP-responsive element-binding protein 4) (Transcript induced in spermiogenesis protein 40) (Tisp40) (hJAL) [Cleaved into: Processed cyclic AMP-responsive element-binding protein 3-like protein 4] | CREB3L4 AIBZIP CREB4 JAL | 395 |
| Q68CJ9 | CR3L3_HUMAN | Cyclic AMP-responsive element-binding protein 3-like protein 3 (cAMP-responsive element-binding protein 3-like protein 3) (Transcription factor CREB-H) [Cleaved into: Processed cyclic AMP-responsive element-binding protein 3-like protein 3] | CREB3L3 CREBH HYST1481 | 461 |
| P37059 | DHB2_HUMAN | Estradiol 17-beta-dehydrogenase 2 (EC 1.1.1.62) (17-beta-hydroxysteroid dehydrogenase type 2) (17-beta-HSD 2) (20 alpha-hydroxysteroid dehydrogenase) (20-alpha-HSD) (E2DH) (Microsomal 17-beta-hydroxysteroid dehydrogenase) (Short chain dehydrogenase/reductase family 9C member 2) (Testosterone 17-beta-dehydrogenase) (EC 1.1.1.239) | HSD17B2 EDH17B2 SDR9C2 | 387 |
| P27487 | DPP4_HUMAN | Dipeptidyl peptidase 4 (EC 3.4.14.5) (Adenosine deaminase complexing protein 2) (ADCP-2) (Dipeptidyl peptidase IV) (DPP IV) (T-cell activation antigen CD26) (TP103) (CD antigen CD26) [Cleaved into: Dipeptidyl peptidase 4 membrane form (Dipeptidyl peptidase IV membrane form); Dipeptidyl peptidase 4 soluble form (Dipeptidyl peptidase IV soluble form)] | DPP4 ADCP2 CD26 | 766 |
| P28845 | DHI1_HUMAN | Corticosteroid 11-beta-dehydrogenase isozyme 1 (EC 1.1.1.146) (11-beta-hydroxysteroid dehydrogenase 1) (11-DH) (11-beta-HSD1) (Short chain dehydrogenase/reductase family 26C member 1) | HSD11B1 HSD11 HSD11L SDR26C1 | 292 |
| P09172 | DOPO_HUMAN | Dopamine beta-hydroxylase (EC 1.14.17.1) (Dopamine beta-monooxygenase) [Cleaved into: Soluble dopamine beta-hydroxylase] | DBH | 617 |
| Q8N608 | DPP10_HUMAN | Inactive dipeptidyl peptidase 10 (Dipeptidyl peptidase IV-related protein 3) (DPRP-3) (Dipeptidyl peptidase X) (DPP X) (Dipeptidyl peptidase-like protein 2) (DPL2) | DPP10 DPRP3 KIAA1492 | 796 |
| P42658 | DPP6_HUMAN | Dipeptidyl aminopeptidase-like protein 6 (DPPX) (Dipeptidyl aminopeptidase-related protein) (Dipeptidyl peptidase 6) (Dipeptidyl peptidase IV-like protein) (Dipeptidyl peptidase VI) (DPP VI) | DPP6 | 865 |
| Q6IAN0 | DRS7B_HUMAN | Dehydrogenase/reductase SDR family member 7B (EC 1.1.—.—) (Short-chain dehydrogenase/reductase family 32C member 1) | DHRS7B SDR32C1 CGI-93 UNQ212/PRO238 | 325 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| O60344 | ECE2_HUMAN | Endothelin-converting enzyme 2 (ECE-2) [Includes: Methyltransferase-like region (EC 2.1.1.—); Endothelin-converting enzyme 2 region (EC 3.4.24.71)] | ECE2 KIAA0604 UNQ403/PRO740 | 883 |
| O75923 | DYSF_HUMAN | Dysferlin (Dystrophy-associated fer-1-like protein) (Fer-1-like protein 1) | DYSF FER1L1 | 2080 |
| O95672 | ECEL1_HUMAN | Endothelin-converting enzyme-like 1 (EC 3.4.24.—) (Xce protein) | ECEL1 XCE UNQ2431/PRO4991 | 775 |
| Q92838 | EDA_HUMAN | Ectodysplasin-A (Ectodermal dysplasia protein) (EDA protein) [Cleaved into: Ectodysplasin-A, membrane form; Ectodysplasin-A, secreted form] | EDA EDI EDA2 | 391 |
| P42892 | ECE1_HUMAN | Endothelin-converting enzyme 1 (ECE-1) (EC 3.4.24.71) | ECE1 | 770 |
| Q92611 | EDEM1_HUMAN | ER degradation-enhancing alpha-mannosidase-like protein 1 | EDEM1 EDEM KIAA0212 | 657 |
| O75354 | ENTP6_HUMAN | Ectonucleoside triphosphate diphosphohydrolase 6 (NTPDase 6) (EC 3.6.1.6) (CD39 antigen-like 2) | ENTPD6 CD39L2 IL6ST2 | 484 |
| P98073 | ENTK_HUMAN | Enteropeptidase (EC 3.4.21.9) (Enterokinase) (Serine protease 7) (Transmembrane protease serine 15) [Cleaved into: Enteropeptidase non-catalytic heavy chain; Enteropeptidase catalytic light chain] | TMPRSS15 ENTK PRSS7 | 1019 |
| P22413 | ENPP1_HUMAN | Ectonucleotide pyrophosphatase/phosphodiesterase family member 1 (E-NPP 1) (Membrane component chromosome 6 surface marker 1) (Phosphodiesterase I/nucleotide pyrophosphatase 1) (Plasma-cell membrane glycoprotein PC-1) [Includes: Alkaline phosphodiesterase I (EC 3.1.4.1); Nucleotide pyrophosphatase (NPPase) (EC 3.6.1.9)] | ENPP1 M6S1 NPPS PC1 PDNP1 | 925 |
| O14638 | ENPP3_HUMAN | Ectonucleotide pyrophosphatase/phosphodiesterase family member 3 (E-NPP 3) (Phosphodiesterase I beta) (PD-Ibeta) (Phosphodiesterase I/nucleotide pyrophosphatase 3) (CD antigen CD203c) [Includes: Alkaline phosphodiesterase I (EC 3.1.4.1); Nucleotide pyrophosphatase (NPPase) (EC 3.6.1.9)] | ENPP3 PDNP3 | 875 |
| O43909 | EXTL3_HUMAN | Exostosin-like 3 (EC 2.4.1.223) (EXT-related protein 1) (Glucuronyl-galactosyl-proteoglycan 4-alpha-N-acetylglucosaminyltransferase) (Hereditary multiple exostoses gene isolog) (Multiple exostosis-like protein 3) (Putative tumor suppressor protein EXTL3) | EXTL3 EXTL1L EXTR1 KIAA0519 | 919 |
| Q6UWH4 | F198B_HUMAN | Protein FAM198B (Expressed in nerve and epithelium during development) | FAM198B C4orf18 ENED AD021 UNQ2512/PRO6001 | 519 |
| Q9H0X4 | F234A_HUMAN | Protein FAM234A (Protein ITFG3) | FAM234A C16orf9 ITFG3 | 552 |
| Q5VUD6 | FA69B_HUMAN | Protein FAM69B | FAM69B C9orf136 PP6977 | 431 |
| Q8IUS5 | EPHX4_HUMAN | Epoxide hydrolase 4 (EC 3.3.—.—) (Abhydrolase domain-containing protein 7) (Epoxide hydrolase-related protein) | EPHX4 ABHD7 EPHXRP | 362 |
| O94905 | ERLN2_HUMAN | Erlin-2 (Endoplasmic reticulum lipid raft-associated protein 2) (Stomatin-prohibitin-flotillin-HflC/K domain-containing protein 2) (SPFH domain-containing protein 2) | ERLIN2 C8orf2 SPFH2 UNQ2441/PRO5003/PRO9924 | 339 |
| Q93063 | EXT2_HUMAN | Exostosin-2 (EC 2.4.1.224) (EC 2.4.1.225) (Glucuronosyl-N-acetylglucosaminyl-proteoglycan/N-acetylglucosaminyl-proteoglycan 4-alpha-N-acetylglucosaminyltransferase) (Multiple exostoses protein 2) (Putative tumor suppressor protein EXT2) | EXT2 | 718 |
| Q9NZ08 | ERAP1_HUMAN | Endoplasmic reticulum aminopeptidase 1 (EC 3.4.11.—) (ARTS-1) (Adipocyte-derived leucine aminopeptidase) (A-LAP) (Aminopeptidase PILS) (Puromycin-insensitive leucyl-specific aminopeptidase) (PILS-AP) (Type 1 tumor necrosis factor receptor shedding aminopeptidase regulator) | ERAP1 APPILS ARTS1 KIAA0525 UNQ584/PRO1154 | 941 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q6P179 | ERAP2_HUMAN | Endoplasmic reticulum aminopeptidase 2 (EC 3.4.11.—) (Leukocyte-derived arginine aminopeptidase) (L-RAP) | ERAP2 LRAP | 960 |
| O75477 | ERLN1_HUMAN | Erlin-1 (Endoplasmic reticulum lipid raft-associated protein 1) (Protein KE04) (Stomatin-prohibitin-flotillin-HflC/K domain-containing protein 1) (SPFH domain-containing protein 1) | ERLIN1 C10orf69 KE04 KEO4 SPFH1 | 346 |
| Q92935 | EXTL1_HUMAN | Exostosin-like 1 (EC 2.4.1.224) (Exostosin-L) (Glucuronosyl-N-acetylglucosaminyl-proteoglycan 4-alpha-N-acetylglucosaminyltransferase) (Multiple exostosis-like protein) | EXTL1 EXTL | 676 |
| Q16394 | EXT1_HUMAN | Exostosin-1 (EC 2.4.1.224) (EC 2.4.1.225) (Glucuronosyl-N-acetylglucosaminyl-proteoglycan/N-acetylglucosaminyl-proteoglycan 4-alpha-N-acetylglucosaminyltransferase) (Multiple exostoses protein 1) (Putative tumor suppressor protein EXT1) | EXT1 | 746 |
| Q9UBQ6 | EXTL2_HUMAN | Exostosin-like 2 (EC 2.4.1.223) (Alpha-1,4-N-acetylhexosaminyltransferase EXTL2) (Alpha-GalNAcT EXTL2) (EXT-related protein 2) (Glucuronyl-galactosyl-proteoglycan 4-alpha-N-acetylglucosaminyltransferase) [Cleaved into: Processed exostosin-like 2] | EXTL2 EXTR2 | 330 |
| Q0P6D2 | FA69C_HUMAN | Protein FAM69C | FAM69C C18orf51 | 419 |
| Q5T7M9 | FA69A_HUMAN | Protein FAM69A | FAM69A | 428 |
| Q9H9S5 | FKRP_HUMAN | Fukutin-related protein (EC 2.—.—.—) | FKRP | 495 |
| Q8N539 | FBCD1_HUMAN | Fibrinogen C domain-containing protein 1 | FIBCD1 UNQ701/PRO1346 | 461 |
| P06734 | FCER2_HUMAN | Low affinity immunoglobulin epsilon Fc receptor (BLAST-2) (C-type lectin domain family 4 member J) (Fc-epsilon-RII) (Immunoglobulin E-binding factor) (Lymphocyte IgE receptor) (CD antigen CD23) [Cleaved into: Low affinity immunoglobulin epsilon Fc receptor membrane-bound form; Low affinity immunoglobulin epsilon Fc receptor soluble form] | FCER2 CD23A CLEC4J FCE2 IGEBF | 321 |
| O75072 | FKTN_HUMAN | Fukutin (EC 2.—.—.—) (Fukuyama-type congenital muscular dystrophy protein) | FKTN FCMD | 461 |
| Q04609 | FOLH1_HUMAN | Glutamate carboxypeptidase 2 (EC 3.4.17.21) (Cell growth-inhibiting gene 27 protein) (Folate hydrolase 1) (Folylpoly-gamma-glutamate carboxypeptidase) (FGCP) (Glutamate carboxypeptidase II) (GCPII) (Membrane glutamate carboxypeptidase) (mGCP) (N-acetylated-alpha-linked acidic dipeptidase I) (NAALADase I) (Prostate-specific membrane antigen) (PSM) (PSMA) (Pteroylpoly-gamma-glutamate carboxypeptidase) | FOLH1 FOLH NAALAD1 PSM PSMA GIG27 | 750 |
| Q9BYC5 | FUT8_HUMAN | Alpha-(1,6)-fucosyltransferase (Alpha1,6-FucT) (EC 2.4.1.68) (Fucosyltransferase 8) (GDP-L-Fuc: N-acetyl-beta-D-glucosaminide alpha1,6-fucosyltransferase) (GDP-fucose--glycoprotein fucosyltransferase) (Glycoprotein 6-alpha-L-fucosyltransferase) | FUT8 | 575 |
| P19526 | FUT1_HUMAN | Galactoside 2-alpha-L-fucosyltransferase 1 (EC 2.4.1.69) (Alpha(1,2)FT 1) (Blood group H alpha 2-fucosyltransferase) (Fucosyltransferase 1) (GDP-L-fucose: beta-D-galactoside 2-alpha-L-fucosyltransferase 1) | FUT1 H HSC | 365 |
| P51993 | FUT6_HUMAN | Alpha-(1,3)-fucosyltransferase 6 (EC 2.4.1.65) (Fucosyltransferase 6) (Fucosyltransferase VI) (Fuc-TVI) (FucT-VI) (Galactoside 3-L-fucosyltransferase) | FUT6 FCT3A | 359 |
| Q9H3Q3 | G3ST2_HUMAN | Galactose-3-O-sulfotransferase 2 (Gal3ST-2) (EC 2.8.—.—) (Beta-galactose-3-O-sulfotransferase 2) (Gal-beta-1,3-GalNAc 3′-sulfotransferase 2) (Glycoprotein beta-Gal 3′-sulfotransferase 2) | GAL3ST2 GP3ST | 398 |
| Q10981 | FUT2_HUMAN | Galactoside 2-alpha-L-fucosyltransferase 2 (EC 2.4.1.69) (Alpha(1,2)FT 2) (Fucosyltransferase 2) (GDP-L-fucose: beta-D-galactoside 2-alpha-L-fucosyltransferase 2) (SE2) (Secretor blood group alpha-2-fucosyltransferase) (Secretor factor) (Se) | FUT2 SEC2 | 343 |
| P22083 | FUT4_HUMAN | Alpha-(1,3)-fucosyltransferase 4 (EC 2.4.1.—) (ELAM-1 ligand fucosyltransferase) (Fucosyltransferase 4) (Fucosyltransferase IV) (Fuc-TIV) (FucT-IV) (Galactoside 3-L-fucosyltransferase) | FUT4 ELFT FCT3A | 530 |
| Q96A11 | G3ST3_HUMAN | Galactose-3-O-sulfotransferase 3 (Gal3ST-3) (EC 2.8.2.—) (Beta-galactose-3-O-sulfotransferase 3) (Gal3ST3) (Gal-beta-1,3-GalNAc 3′-sulfotransferase 3) | GAL3ST3 | 431 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q10472 | GALT1_HUMAN | Polypeptide N-acetylgalactosaminyltransferase 1 (EC 2.4.1.41) (Polypeptide GalNAc transferase 1) (GalNAc-T1) (pp-GaNTase 1) (Protein-UDP acetylgalactosaminyltransferase 1) (UDP-GalNAc: polypeptide N-acetylgalactosaminyltransferase 1) [Cleaved into: Polypeptide N-acetylgalactosaminyltransferase 1 soluble form] | GALNT1 | 559 |
| Q10471 | GALT2_HUMAN | Polypeptide N-acetylgalactosaminyltransferase 2 (EC 2.4.1.41) (Polypeptide GalNAc transferase 2) (GalNAc-T2) (pp-GaNTase 2) (Protein-UDP acetylgalactosaminyltransferase 2) (UDP-GalNAc: polypeptide N-acetylgalactosaminyltransferase 2) [Cleaved into: Polypeptide N-acetylgalactosaminyltransferase 2 soluble form] | GALNT2 | 571 |
| Q14435 | GALT3_HUMAN | Polypeptide N-acetylgalactosaminyltransferase 3 (EC 2.4.1.41) (Polypeptide GalNAc transferase 3) (GalNAc-T3) (pp-GaNTase 3) (Protein-UDP acetylgalactosaminyltransferase 3) (UDP-GalNAc: polypeptide N-acetylgalactosaminyltransferase 3) | GALNT3 | 633 |
| Q8NCL4 | GALT6_HUMAN | Polypeptide N-acetylgalactosaminyltransferase 6 (EC 2.4.1.41) (Polypeptide GalNAc transferase 6) (GalNAc-T6) (pp-GaNTase 6) (Protein-UDP acetylgalactosaminyltransferase 6) (UDP-GalNAc: polypeptide N-acetylgalactosaminyltransferase 6) | GALNT6 | 622 |
| Q6P4F1 | FUT10_HUMAN | Alpha-(1,3)-fucosyltransferase 10 (EC 2.4.1.—) (Fucosyltransferase X) (Fuc-TX) (FucT-X) (Galactoside 3-L-fucosyltransferase 10) (Fucosyltransferase 10) | FUT10 | 479 |
| Q99999 | G3ST1_HUMAN | Galactosylceramide sulfotransferase (GalCer sulfotransferase) (EC 2.8.2.11) (3'-phosphoadenosine-5'-phosphosulfate: GalCer sulfotransferase) (3'-phosphoadenylylsulfate: galactosylceramide 3'-sulfotransferase) (Cerebroside sulfotransferase) | GAL3ST1 CST | 423 |
| Q96RP7 | G3ST4_HUMAN | Galactose-3-O-sulfotransferase 4 (Gal3ST-4) (EC 2.8.2.—) (Beta-galactose-3-O-sulfotransferase 4) (Gal-beta-1,3-GalNAc 3'-sulfotransferase) | GAL3ST4 PP6968 | 486 |
| Q9NY28 | GALT8_HUMAN | Probable polypeptide N-acetylgalactosaminyltransferase 8 (EC 2.4.1.41) (Polypeptide GalNAc transferase 8) (GalNAc-T8) (pp-GaNTase 8) (Protein-UDP acetylgalactosaminyltransferase 8) (UDP-GalNAc: polypeptide N-acetylgalactosaminyltransferase 8) | GALNT8 | 637 |
| Q9HCQ5 | GALT9_HUMAN | Polypeptide N-acetylgalactosaminyltransferase 9 (EC 2.4.1.41) (Polypeptide GalNAc transferase 9) (GalNAc-T9) (pp-GaNTase 9) (Protein-UDP acetylgalactosaminyltransferase 9) (UDP-GalNAc: polypeptide N-acetylgalactosaminyltransferase 9) | GALNT9 | 603 |
| Q495W5 | FUT11_HUMAN | Alpha-(1,3)-fucosyltransferase 11 (EC 2.4.1.—) (Fucosyltransferase XI) (Fuc-TXI) (FucT-XI) (Galactoside 3-L-fucosyltransferase 11) (Fucosyltransferase 11) | FUT11 | 492 |
| P21217 | FUT3_HUMAN | Galactoside 3(4)-L-fucosyltransferase (EC 2.4.1.65) (Blood group Lewis alpha-4-fucosyltransferase) (Lewis FT) (Fucosyltransferase 3) (Fucosyltransferase III) (FucT-III) | FUT3 FT3B LE | 361 |
| Q9Y231 | FUT9_HUMAN | Alpha-(1,3)-fucosyltransferase 9 (EC 2.4.1.—) (Fucosyltransferase 9) (Fucosyltransferase IX) (Fuc-TIX) (FucT-IX) (Galactoside 3-L-fucosyltransferase) | FUT9 | 359 |
| Q7Z7M9 | GALT5_HUMAN | Polypeptide N-acetylgalactosaminyltransferase 5 (EC 2.4.1.41) (Polypeptide GalNAc transferase 5) (GalNAc-T5) (pp-GaNTase 5) (Protein-UDP acetylgalactosaminyltransferase 5) (UDP-GalNAc: polypeptide N-acetylgalactosaminyltransferase 5) | GALNT5 | 940 |
| Q9P109 | GCNT4_HUMAN | Beta-1,3-galactosyl-O-glycosyl-glycoprotein beta-1,6-N-acetylglucosaminyltransferase 4 (EC 2.4.1.102) (Core 2-branching enzyme 3) (Core2-GlcNAc-transferase 3) (C2GnT3) | GCNT4 | 453 |
| Q6ZNI0 | GCNT7_HUMAN | Beta-1,3-galactosyl-O-glycosyl-glycoprotein beta-1,6-N-acetylglucosaminyltransferase 7 (EC 2.4.1.—) | GCNT7 C20orf105 | 430 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q11128 | FUT5_HUMAN | Alpha-(1,3)-fucosyltransferase 5 (EC 2.4.1.65) (Fucosyltransferase 5) (Fucosyltransferase V) (Fuc-TV) (Galactoside 3-L-fucosyltransferase) | FUT5 | 374 |
| Q11130 | FUT7_HUMAN | Alpha-(1,3)-fucosyltransferase 7 (EC 2.4.1.—) (Fucosyltransferase 7) (Fucosyltransferase VII) (Fuc-TVII) (FucT-VII) (Galactoside 3-L-fucosyltransferase) (Selectin ligand synthase) | FUT7 | 342 |
| Q02742 | GCNT1_HUMAN | Beta-1,3-galactosyl-O-glycosyl-glycoprotein beta-1,6-N-acetylglucosaminyltransferase (EC 2.4.1.102) (Core 2-branching enzyme) (Core2-GlcNAc-transferase) (C2GNT) (Core 2 GNT) | GCNT1 NACGT2 | 428 |
| Q8N5D6 | GBGT1_HUMAN | Globoside alpha-1,3-N-acetylgalactosaminyltransferase 1 (EC 2.4.1.—) (Forssman glycolipid synthase-like protein) | GBGT1 UNQ2513/PRO6002 | 347 |
| Q5T4I0 | GCNT6_HUMAN | Beta-1,3-galactosyl-O-glycosyl-glycoprotein beta-1,6-N-acetylglucosaminyltransferase 6 (EC 2.4.1.—) | GCNT6 | 391 |
| Q4G0N0 | GGTA1_HUMAN | Inactive N-acetyllactosamine alpha-1,3-galactosyltransferase (Glycoprotein alpha-galactosyltransferase 1 pseudogene) | GGTA1P GGTA1 | 100 |
| Q68CQ7 | GL8D1_HUMAN | Glycosyltransferase 8 domain-containing protein 1 (EC 2.4.1.—) | GLT8D1 GALA4A AD-017 MSTP137 UNQ572/PRO1134 | 371 |
| Q8N4A0 | GALT4_HUMAN | Polypeptide N-acetylgalactosaminyltransferase 4 (EC 2.4.1.41) (Polypeptide GalNAc transferase 4) (GalNAc-T4) (pp-GaNTase 4) (Protein-UDP acetylgalactosaminyltransferase 4) (UDP-GalNAc: polypeptide N-acetylgalactosaminyltransferase 4) | GALNT4 | 578 |
| Q86SF2 | GALT7_HUMAN | N-acetylgalactosaminyltransferase 7 (EC 2.4.1.—) (Polypeptide GalNAc transferase 7) (GalNAc-T7) (pp-GaNTase 7) (Protein-UDP acetylgalactosaminyltransferase 7) (UDP-GalNAc: polypeptide N-acetylgalactosaminyltransferase 7) | GALNT7 | 657 |
| O95395 | GCNT3_HUMAN | Beta-1,3-galactosyl-O-glycosyl-glycoprotein beta-1,6-N-acetylglucosaminyltransferase 3 (EC 2.4.1.102) (EC 2.4.1.150) (C2GnT-mucin type) (C2GnT-M) (hC2GnT) (Core 2/core 4 beta-1,6-N-acetylglucosaminyltransferase) (C2/4GnT) | GCNT3 | 438 |
| P19440 | GGT1_HUMAN | Gamma-glutamyltranspeptidase 1 (GGT 1) (EC 2.3.2.2) (Gamma-glutamyltransferase 1) (Glutathione hydrolase 1) (EC 3.4.19.13) (Leukotriene-C4 hydrolase) (EC 3.4.19.14) (CD antigen CD224) [Cleaved into: Gamma-glutamyltranspeptidase 1 heavy chain; Gamma-glutamyltranspeptidase 1 light chain] | GGT1 GGT | 569 |
| Q7Z4J2 | GL6D1_HUMAN | Glycosyltransferase 6 domain-containing protein 1 (EC 2.4.1.—) (Galactosyltransferase family 6 domain-containing 1) | GLT6D1 GLTDC1 GT6M7 | 308 |
| O94923 | GLCE_HUMAN | D-glucuronyl C5-epimerase (EC 5.1.3.17) (Heparan sulfate C5-epimerase) (Hsepi) (Heparin/heparan sulfate: glucuronic acid C5-epimerase) (Heparosan-N-sulfate-glucuronate 5-epimerase) | GLCE KIAA0836 | 617 |
| Q86SR1 | GLT10_HUMAN | Polypeptide N-acetylgalactosaminyltransferase 10 (EC 2.4.1.41) (Polypeptide GalNAc transferase 10) (GalNAc-T10) (pp-GaNTase 10) (Protein-UDP acetylgalactosaminyltransferase 10) (UDP-GalNAc: polypeptide N-acetylgalactosaminyltransferase 10) | GALNT10 | 603 |
| Q8IXK2 | GLT12_HUMAN | Polypeptide N-acetylgalactosaminyltransferase 12 (EC 2.4.1.41) (Polypeptide GalNAc transferase 12) (GalNAc-T12) (pp-GaNTase 12) (Protein-UDP acetylgalactosaminyltransferase 12) (UDP-GalNAc: polypeptide N-acetylgalactosaminyltransferase 12) | GALNT12 | 581 |
| Q96FL9 | GLT14_HUMAN | Polypeptide N-acetylgalactosaminyltransferase 14 (EC 2.4.1.41) (Polypeptide GalNAc transferase 14) (GalNAc-T14) (pp-GaNTase 14) (Protein-UDP acetylgalactosaminyltransferase 14) (UDP-GalNAc: polypeptide N-acetylgalactosaminyltransferase 14) | GALNT14 UNQ2434/PRO4994 | 552 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q8N428 | GLT16_HUMAN | Polypeptide N-acetylgalactosaminyltransferase 16 (EC 2.4.1.41) (Polypeptide GalNAc transferase 16) (GalNAc-T16) (Polypeptide GalNAc transferase-like protein 1) (GalNAc-T-like protein 1) (pp-GaNTase-like protein 1) (Polypeptide N-acetylgalactosaminyltransferase-like protein 1) (Protein-UDP acetylgalactosaminyltransferase-like protein 1) (UDP-GalNAc: polypeptide N-acetylgalactosaminyltransferase-like protein 1) | GALNT16 GALNTL1 KIAA1130 | 558 |
| P36269 | GGT5_HUMAN | Gamma-glutamyltransferase 5 (GGT 5) (EC 2.3.2.2) (Gamma-glutamyl transpeptidase-related enzyme) (GGT-rel) (Gamma-glutamyltransferase-like activity 1) (Gamma-glutamyltranspeptidase 5) (Glutathione hydrolase 5) (EC 3.4.19.13) (Leukotriene-C4 hydrolase) (EC 3.4.19.14) [Cleaved into: Gamma-glutamyltransferase 5 heavy chain; Gamma-glutamyltransferase 5 light chain] | GGT5 GGTLA1 | 586 |
| Q6P531 | GGT6_HUMAN | Gamma-glutamyltransferase 6 (GGT 6) (EC 2.3.2.2) (Gamma-glutamyltranspeptidase 6) (Glutathione hydrolase 6) (EC 3.4.19.13) [Cleaved into: Gamma-glutamyltransferase 6 heavy chain; Gamma-glutamyltransferase 6 light chain] | GGT6 | 493 |
| Q9UJ14 | GGT7_HUMAN | Gamma-glutamyltransferase 7 (GGT 7) (EC 2.3.2.2) (Gamma-glutamyltransferase-like 3) (Gamma-glutamyltransferase-like 5) (Gamma-glutamyltranspeptidase 7) (Glutathione hydrolase 7) (EC 3.4.19.13) [Cleaved into: Gamma-glutamyltransferase 7 heavy chain; Gamma-glutamyltransferase 7 light chain] | GGT7 GGTL3 GGTL5 | 662 |
| Q6ZMI3 | GLDN_HUMAN | Gliomedin [Cleaved into: Gliomedin shedded ectodomain] | GLDN COLM UNQ9339/PRO34011 | 551 |
| Q8IUC8 | GLT13_HUMAN | Polypeptide N-acetylgalactosaminyltransferase 13 (EC 2.4.1.41) (Polypeptide GalNAc transferase 13) (GalNAc-T13) (pp-GaNTase 13) (Protein-UDP acetylgalactosaminyltransferase 13) (UDP-GalNAc: polypeptide N-acetylgalactosaminyltransferase 13) | GALNT13 KIAA1918 | 556 |
| Q6P9A2 | GLT18_HUMAN | Polypeptide N-acetylgalactosaminyltransferase 18 (EC 2.4.1.41) (Polypeptide GalNAc transferase 18) (GalNAc-T18) (Polypeptide GalNAc transferase-like protein 4) (GalNAc-T-like protein 4) (pp-GaNTase-like protein 4) (Polypeptide N-acetylgalactosaminyltransferase-like protein 4) (Protein-UDP acetylgalactosaminyltransferase-like protein 4) (UDP-GalNAc: polypeptide N-acetylgalactosaminyltransferase-like protein 4) | GALNT18 GALNTL4 | 607 |
| Q49A17 | GLTL6_HUMAN | Polypeptide N-acetylgalactosaminyltransferase-like 6 (EC 2.4.1.41) (Polypeptide GalNAc transferase 17) (GalNAc-T17) (pp-GaNTase 17) (Putative polypeptide N-acetylgalactosaminyltransferase 17) (UDP-GalNAc: polypeptide N-acetylgalactosaminyltransferase 17) | GALNTL6 GALNT17 | 601 |
| Q3T906 | GNPTA_HUMAN | N-acetylglucosamine-1-phosphotransferase subunits alpha/beta (EC 2.7.8.17) (GlcNAc-1-phosphotransferase subunits alpha/beta) (Stealth protein GNPTAB) (UDP-N-acetylglucosamine-1-phosphotransferase subunits alpha/beta) [Cleaved into: N-acetylglucosamine-1-phosphotransferase subunit alpha; N-acetylglucosamine-1-phosphotransferase subunit beta] | GNPTAB GNPTA KIAA1208 | 1256 |
| A6NGU5 | GGT3_HUMAN | Putative gamma-glutamyltranspeptidase 3 (GGT 3) (EC 2.3.2.2) (Gamma-glutamyltransferase 3) (Glutathione hydrolase 3) (EC 3.4.19.13) [Cleaved into: Putative gamma-glutamyltranspeptidase 3 heavy chain; Putative gamma-glutamyltranspeptidase 3 light chain] | GGT3P GGT3 | 568 |
| Q9H1C3 | GL8D2_HUMAN | Glycosyltransferase 8 domain-containing protein 2 (EC 2.4.1.—) | GLT8D2 GALA4A UNQ1901/PRO4347 | 349 |
| Q8N3T1 | GLT15_HUMAN | Polypeptide N-acetylgalactosaminyltransferase 15 (EC 2.4.1.41) (Polypeptide GalNAc transferase-like protein 2) (GalNAc-T-like protein 2) (pp-GaNTase-like protein 2) | GALNT15 GALNTL2 UNQ770/PRO1564 | 639 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q6IS24 | GLTL3_HUMAN | (Polypeptide N-acetylgalactosaminyltransferase-like protein 2) (Protein-UDP acetylgalactosaminyltransferase-like protein 2) (UDP-GalNAc: polypeptide N-acetylgalactosaminyltransferase-like protein 2) Putative polypeptide N-acetylgalactosaminyltransferase-like protein 3 (EC 2.4.1.41) (Polypeptide GalNAc transferase-like protein 3) (GalNAc-T-like protein 3) (pp-GaNTase-like protein 3) (Protein-UDP acetylgalactosaminyltransferase-like protein 3) (UDP-GalNAc: polypeptide N-acetylgalactosaminyltransferase-like protein 3) (Williams-Beuren syndrome chromosomal region 17 protein) | WBSCR17 GALNTL3 | 598 |
| Q8NCW6 | GLT11_HUMAN | Polypeptide N-acetylgalactosaminyltransferase 11 (EC 2.4.1.41) (Polypeptide GalNAc transferase 11) (GalNAc-T11) (pp-GaNTase 11) (Protein-UDP acetylgalactosaminyltransferase 11) (UDP-GalNAc: polypeptide N-acetylgalactosaminyltransferase 11) | GALNT11 | 608 |
| Q7Z4T8 | GLTL5_HUMAN | Inactive polypeptide N-acetylgalactosaminyltransferase-like protein 5 (Polypeptide GalNAc transferase 15) (GalNAc-T15) (pp-GaNTase 15) (Protein-UDP acetylgalactosaminyltransferase 15) (UDP-GalNAc: polypeptide N-acetylgalactosaminyltransferase 15) | GALNTL5 GALNT15 | 443 |
| Q8N0V5 | GNT2A_HUMAN | N-acetyllactosamide beta-1,6-N-acetylglucosaminyl-transferase (N-acetylglucosaminyltransferase) (EC 2.4.1.150) (I-branching enzyme) (IGNT) | GCNT2 GCNT5 II NACGT1 | 402 |
| O00461 | GOL4_HUMAN | Golgi integral membrane protein 4 (Golgi integral membrane protein, cis) (GIMPc) (Golgi phosphoprotein 4) (Golgi-localized phosphoprotein of 130 kDa) (Golgi phosphoprotein of 130 kDa) | GOLIM4 GIMPC GOLPH4 GPP130 | 696 |
| Q8NBJ4 | GOLM1_HUMAN | Golgi membrane protein 1 (Golgi membrane protein GP73) (Golgi phosphoprotein 2) | GOLM1 C9orf155 GOLPH2 PSEC0242 UNQ686/PRO1326 | 401 |
| A0PJZ3 | GXLT2_HUMAN | Glucoside xylosyltransferase 2 (EC 2.4.2.n2) (Glycosyltransferase 8 domain-containing protein 4) | GXYLT2 GLT8D4 | 443 |
| Q4G148 | GXLT1_HUMAN | Glucoside xylosyltransferase 1 (EC 2.4.2.n2) (Glycosyltransferase 8 domain-containing protein 3) | GXYLT1 GLT8D3 | 440 |
| Q96MM7 | H6ST2_HUMAN | Heparan-sulfate 6-O-sulfotransferase 2 (HS6ST-2) (EC 2.8.2.—) | HS6ST2 PSEC0092 | 605 |
| O60243 | H6ST1_HUMAN | Heparan-sulfate 6-O-sulfotransferase 1 (HS6ST-1) (EC 2.8.2.—) | HS6ST1 HS6ST | 411 |
| Q8IZP7 | H6ST3_HUMAN | Heparan-sulfate 6-O-sulfotransferase 3 (HS6ST-3) (EC 2.8.2.—) | HS6ST3 | 471 |
| P04233 | HG2A_HUMAN | HLA class II histocompatibility antigen gamma chain (HLA-DR antigens-associated invariant chain) (Ia antigen-associated invariant chain) (Ii) (p33) (CD antigen CD74) | CD74 DHLAG | 296 |
| Q7LGA3 | HS2ST_HUMAN | Heparan sulfate 2-O-sulfotransferase 1 (2-O-sulfotransferase) (2OST) (EC 2.8.2.—) | HS2ST1 HS2ST KIAA0448 | 356 |
| Q8IZT8 | HS3S5_HUMAN | Heparan sulfate glucosamine 3-O-sulfotransferase 5 (EC 2.8.2.23) (Heparan sulfate D-glucosaminyl 3-O-sulfotransferase 5) (3-OST-5) (Heparan sulfate 3-O-sulfotransferase 5) (h3-OST-5) | HS3ST5 3OST5 HS3OST5 | 346 |
| P05981 | HEPS_HUMAN | Serine protease hepsin (EC 3.4.21.106) [Transmembrane protease serine 1) [Cleaved into: Serine protease hepsin non-catalytic chain; Serine protease hepsin catalytic chain] | HPN TMPRSS1 | 417 |
| Q9Y663 | HS3SA_HUMAN | Heparan sulfate glucosamine 3-O-sulfotransferase 3A1 (EC 2.8.2.30) (Heparan sulfate D-glucosaminyl 3-O-sulfotransferase 3A1) (3-OST-3A) (Heparan sulfate 3-O-sulfotransferase 3A1) (h3-OST-3A) | HS3ST3A1 3OSTA1 HS3ST3A UNQ2551/PRO6180 | 406 |
| Q9Y278 | HS3S2_HUMAN | Heparan sulfate glucosaminyl 3-O-sulfotransferase 2 (3-OST-2) (Heparan sulfate D-glucosaminyl 3-O-sulfotransferase 2) (EC 2.8.2.29) (Heparan sulfate 3-O-sulfotransferase 2) (h3-OST-2) | HS3ST2 3OST2 UNQ2442/PRO5004 | 367 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9Y661 | HS3S4_HUMAN | Heparan sulfate glucosamine 3-O-sulfotransferase 4 (EC 2.8.2.23) (Heparan sulfate D-glucosaminyl 3-O-sulfotransferase 4) (3-OST-4) (Heparan sulfate 3-O-sulfotransferase 4) (h3-OST-4) | HS3ST4 3OST4 | 456 |
| Q96QI5 | HS3S6_HUMAN | Heparan sulfate glucosamine 3-O-sulfotransferase 6 (EC 2.8.2.23) (Heparan sulfate D-glucosaminyl 3-O-sulfotransferase 6) (3-OST-6) (Heparan sulfate 3-O-sulfotransferase 6) (h3-OST-6) | HS3ST6 HS3ST5 | 342 |
| Q9Y662 | HS3SB_HUMAN | Heparan sulfate glucosamine 3-O-sulfotransferase 3B1 (EC 2.8.2.30) (Heparan sulfate D-glucosaminyl 3-O-sulfotransferase 3B1) (3-OST-3B) (Heparan sulfate 3-O-sulfotransferase 3B1) (h3-OST-3B) | HS3ST3B1 3OST3B1 HS3ST3B | 390 |
| P07099 | HYEP_HUMAN | Epoxide hydrolase 1 (EC 3.3.2.9) (Epoxide hydratase) (Microsomal epoxide hydrolase) | EPHX1 EPHX EPOX | 455 |
| P46695 | IEX1_HUMAN | Radiation-inducible immediate-early gene IEX-1 (Differentiation-dependent gene 2 protein) (Protein DIF-2) (Immediate early protein GLY96) (Immediate early response 3 protein) (PACAP-responsive gene 1 protein) (Protein PRG1) | IER3 DIF2 IEX1 PRG1 | 156 |
| P55073 | IOD3_HUMAN | Thyroxine 5-deiodinase (EC 1.21.99.3) (5DIII) (DIOIII) (Type 3 DI) (Type III iodothyronine deiodinase) | DIO3 ITDI3 TXDI3 | 304 |
| Q9NX62 | IMPA3_HUMAN | Inositol monophosphatase 3 (IMP 3) (IMPase 3) (EC 3.1.3.25) (EC 3.1.3.7) (Golgi 3-prime phosphoadenosine 5-prime phosphate 3-prime phosphatase) (Golgi-resident PAP phosphatase) (gPAPP) (Inositol monophosphatase domain-containing protein 1) (Inositol 1(or 4)-monophosphatase 3) (Myo-inositol monophosphatase A3) | IMPAD1 IMPA3 | 359 |
| Q01628 | IFM3_HUMAN | Interferon-induced transmembrane protein 3 (Dispanin subfamily A member 2b) (DSPA2b) (Interferon-inducible protein 1-8U) | IFITM3 | 133 |
| Q9NQX7 | ITM2C_HUMAN | Integral membrane protein 2C (Cerebral protein 14) (Transmembrane protein BRI3) [Cleaved into: CT-BRI3] | ITM2C BRI3 hucep-14 NPD018 PSEC0047 | 267 |
| O43736 | ITM2A_HUMAN | Integral membrane protein 2A (Protein E25) | ITM2A UNQ603/PRO1189 | 263 |
| Q6NSI0 | K1161_HUMAN | Uncharacterized family 31 glucosidase KIAA1161 (EC 3.2.1.—) | KIAA1161 | 714 |
| Q9Y287 | ITM2B_HUMAN | Integral membrane protein 2B (Immature BRI2) (imBRI2) (Protein E25B) (Transmembrane protein BRI) (Bri) [Cleaved into: BRI2, membrane form (Mature BRI2) (mBRI2); BRI2 intracellular domain (BRI2 ICD); BRI2C, soluble form; Bri23 peptide (Bri2-23) (ABri23) (C-terminal peptide) (P23 peptide)] | ITM2B BRI BRI2 | 266 |
| Q9NZS2 | KLRF1_HUMAN | Killer cell lectin-like receptor subfamily F member 1 (Lectin-like receptor F1) (Activating coreceptor NKp80) (C-type lectin domain family 5 member C) | KLRF1 CLEC5C ML | 232 |
| P23276 | KELL_HUMAN | Kell blood group glycoprotein (EC 3.4.24.—) (CD antigen CD238) | KEL | 732 |
| Q5H943 | KKLC1_HUMAN | Kita-kyushu lung cancer antigen 1 (KK-LC-1) (Cancer/testis antigen 83) | CT83 CXorf61 KKLC1 | 113 |
| Q13241 | KLRD1_HUMAN | Natural killer cells antigen CD94 (KP43) (Killer cell lectin-like receptor subfamily D member 1) (NK cell receptor) (CD antigen CD94) | KLRD1 CD94 | 179 |
| Q8N3Y3 | LARG2_HUMAN | Glycosyltransferase-like protein LARGE2 (EC 2.4.—.—) (Glycosyltransferase-like 1B) [Includes: Xylosyltransferase LARGE2 (EC 2.4.2.—); Beta-1,3-glucuronyltransferase LARGE2 (EC 2.4.1.—)] | GYLTL1B LARGE2 PP5656 | 721 |
| Q12918 | KLRB1_HUMAN | Killer cell lectin-like receptor subfamily B member 1 (C-type lectin domain family 5 member B) (HNKR-P1a) (NKR-P1a) (Natural killer cell surface protein P1A) (CD antigen CD161) | KLRB1 CLEC5B NKRP1A | 225 |
| Q96E93 | KLRG1_HUMAN | Killer cell lectin-like receptor subfamily G member 1 (C-type lectin domain family 15 member A) (ITIM-containing receptor MAFA-L) (MAFA-like receptor) (Mast cell function-associated antigen) | KLRG1 CLEC15A MAFA MAFAL | 195 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9UIQ6 | LCAP_HUMAN | Leucyl-cystinyl aminopeptidase (Cystinyl aminopeptidase) (EC 3.4.11.3) (Insulin-regulated membrane aminopeptidase) (Insulin-responsive aminopeptidase) (IRAP) (Oxytocinase) (OTase) (Placental leucine aminopeptidase) (P-LAP) [Cleaved into: Leucyl-cystinyl aminopeptidase, pregnancy serum form] | LNPEP OTASE | 1025 |
| O95461 | LARGE_HUMAN | Glycosyltransferase-like protein LARGE1 (EC 2.4.—.—) (Acetylglucosaminyltransferase-like 1A) [Includes: Xylosyltransferase LARGE (EC 2.4.2.—); Beta-1,3-glucuronyltransferase LARGE (EC 2.4.1.—)] | LARGE KIAA0609 LARGE1 | 756 |
| D3W0D1 | KLRF2_HUMAN | Killer cell lectin-like receptor subfamily F member 2 (Lectin-like receptor F2) (Activating coreceptor NKp65) | KLRF2 | 207 |
| Q86UP2 | KTN1_HUMAN | Kinectin (CG-1 antigen) (Kinesin receptor) | KTN1 CG1 KIAA0004 | 1357 |
| P42167 | LAP2B_HUMAN | Lamina-associated polypeptide 2, isoforms beta/gamma (Thymopoietin, isoforms beta/gamma) (TP beta/gamma) (Thymopoietin-related peptide isoforms beta/gamma) (TPRP isoforms beta/gamma) [Cleaved into: Thymopoietin (TP) (Splenin); Thymopentin (TP5)] | TMPO LAP2 | 454 |
| Q8NES3 | LFNG_HUMAN | Beta-1,3-N-acetylglucosaminyltransferase lunatic fringe (EC 2.4.1.222) (O-fucosylpeptide 3-beta-N-acetylglucosaminyltransferase) | LFNG | 379 |
| Q96AG4 | LRC59_HUMAN | Leucine-rich repeat-containing protein 59 (Ribosome-binding protein p34) (p34) | LRRC59 PRO1855 | 307 |
| Q5SRI9 | MANEA_HUMAN | Glycoprotein endo-alpha-1,2-mannosidase (Endo-alpha mannosidase) (Endomannosidase) (hEndo) (EC 3.2.1.130) (Mandaselin) | MANEA | 462 |
| Q5VSG8 | MANEL_HUMAN | Glycoprotein endo-alpha-1,2-mannosidase-like protein (EC 3.2.1.—) | MANEAL | 457 |
| Q5VT66 | MARC1_HUMAN | Mitochondrial amidoxime-reducing component 1 (mARC1) (EC 1.—.—.—) (Molybdenum cofactor sulfurase C-terminal domain-containing protein 1) (MOSC domain-containing protein 1) (Moco sulfurase C-terminal domain-containing protein 1) | MARC1 MOSC1 | 337 |
| Q9UKM7 | MA1B1_HUMAN | Endoplasmic reticulum mannosyl-oligosaccharide 1,2-alpha-mannosidase (EC 3.2.1.113) (ER alpha-1,2-mannosidase) (ER mannosidase 1) (ERMan1) (Man9GlcNAc2-specific-processing alpha-mannosidase) (Mannosidase alpha class 1B member 1) | MAN1B1 UNQ747/PRO1477 | 699 |
| Q16706 | MA2A1_HUMAN | Alpha-mannosidase 2 (EC 3.2.1.114) (Golgi alpha-mannosidase II) (AMan II) (Man II) (Mannosidase alpha class 2A member 1) (Mannosyl-oligosaccharide 1,3-1,6-alpha-mannosidase) | MAN2A1 MANA2 | 1144 |
| P49641 | MA2A2_HUMAN | Alpha-mannosidase 2x (EC 3.2.1.114) (Alpha-mannosidase IIx) (Man IIx) (Mannosidase alpha class 2A member 2) (Mannosyl-oligosaccharide 1,3-1,6-alpha-mannosidase) | MAN2A2 MANA2X | 1150 |
| P33908 | MA1A1_HUMAN | Mannosyl-oligosaccharide 1,2-alpha-mannosidase IA (EC 3.2.1.113) (Man(9)-alpha-mannosidase) (Man9-mannosidase) (Mannosidase alpha class 1A member 1) (Processing alpha-1,2-mannosidase IA) (Alpha-1,2-mannosidase IA) | MAN1A1 | 653 |
| O60476 | MA1A2_HUMAN | Mannosyl-oligosaccharide 1,2-alpha-mannosidase IB (EC 3.2.1.113) (Mannosidase alpha class 1A member 2) (Processing alpha-1,2-mannosidase IB) (Alpha-1,2-mannosidase IB) | MAN1A2 MAN1B | 641 |
| Q9NR34 | MA1C1_HUMAN | Mannosyl-oligosaccharide 1,2-alpha-mannosidase IC (EC 3.2.1.113) (HMIC) (Mannosidase alpha class 1C member 1) (Processing alpha-1,2-mannosidase IC) (Alpha-1,2-mannosidase IC) | MAN1C1 MAN1A3 MAN1C | 630 |
| Q9UEW3 | MARCO_HUMAN | Macrophage receptor MARCO (Macrophage receptor with collagenous structure) (Scavenger receptor class A member 2) | MARCO SCARA2 | 520 |
| O00587 | MFNG_HUMAN | Beta-1,3-N-acetylglucosaminyltransferase manic fringe (EC 2.4.1.222) (O-fucosylpeptide 3-beta-N-acetylglucosaminyltransferase) | MFNG | 321 |
| Q09327 | MGAT3_HUMAN | Beta-1,4-mannosyl-glycoprotein 4-beta-N-acetylglucosaminyltransferase (EC 2.4.1.144) (N-glycosyl-oligosaccharide-glycoprotein N-acetylglucosaminyltransferase III) (GNT-III) (GlcNAc-T III) (N-acetylglucosaminyltransferase III) | MGAT3 GGNT3 | 533 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q3V5L5 | MGT5B_HUMAN | Alpha-1,6-mannosylglycoprotein 6-beta-N-acetylglucosaminyltransferase B (EC 2.4.1.—) (EC 2.4.1.155) (Alpha-mannoside beta-1,6-N-acetylglucosaminyltransferase B) (GlcNAc-T Vb) (GNT-Vb) (hGnTVb) (Mannoside acetylglucosaminyltransferase 5B) (N-acetylglucosaminyl-transferase Vb) (N-acetylglucosaminyltransferase IX) (GNT-IX) | MGAT5B KIAA2008 | 792 |
| Q8IX19 | MCEM1_HUMAN | Mast cell-expressed membrane protein 1 | MCEMP1 C19orf59 | 187 |
| O43451 | MGA_HUMAN | Maltase-glucoamylase, intestinal [Includes: Maltase (EC 3.2.1.20) (Alpha-glucosidase); Glucoamylase (EC 3.2.1.3) (Glucan 1,4-alpha-glucosidase)] | MGAM MGA MGAML | 1857 |
| Q9UBM8 | MGT4C_HUMAN | Alpha-1,3-mannosyl-glycoprotein 4-beta-N-acetylglucosaminyltransferase C (EC 2.4.1.145) (N-acetylglucosaminyltransferase IV homolog) (hGnT-IV-H) (N-glycosyl-oligosaccharide-glycoprotein N-acetylglucosaminyltransferase IVc) (GlcNAc-T IVc) (GnT-IVc) (N-acetylglucosaminyltransferase IVc) (UDP-N-acetylglucosamine: alpha-1,3-D-mannoside beta-1,4-N-acetylglucosaminyltransferase IVc) | MGAT4C | 478 |
| Q10469 | MGAT2_HUMAN | Alpha-1,6-mannosyl-glycoprotein 2-beta-N-acetylglucosaminyltransferase (EC 2.4.1.143) (Beta-1,2-N-acetylglucosaminyltransferase II) (GlcNAc-T II) (GNT-II) (Mannoside acetylglucosaminyltransferase 2) (N-glycosyl-oligosaccharide-glycoprotein N-acetylglucosaminyltransferase II) | MGAT2 | 447 |
| P26572 | MGAT1_HUMAN | Alpha-1,3-mannosyl-glycoprotein 2-beta-N-acetylglucosaminyltransferase (EC 2.4.1.101) (N-glycosyl-oligosaccharide-glycoprotein N-acetylglucosaminyltransferase I) (GNT-I) (GlcNAc-T I) | MGAT1 GGNT1 GLCT1 GLYT1 MGAT | 445 |
| Q9UM21 | MGT4A_HUMAN | Alpha-1,3-mannosyl-glycoprotein 4-beta-N-acetylglucosaminyltransferase A (EC 2.4.1.145) (N-glycosyl-oligosaccharide-glycoprotein N-acetylglucosaminyltransferase IVa) (GlcNAc-T IVa) (GnT-IVa) (N-acetylglucosaminyltransferase IVa) (UDP-N-acetylglucosamine: alpha-1,3-D-mannoside beta-1,4-N-acetylglucosaminyltransferase IVa) [Cleaved into: Alpha-1,3-mannosyl-glycoprotein 4-beta-N-acetylglucosaminyltransferase A soluble form] | MGAT4A | 535 |
| Q9UQ53 | MGT4B_HUMAN | Alpha-1,3-mannosyl-glycoprotein 4-beta-N-acetylglucosaminyltransferase B (EC 2.4.1.145) (N-glycosyl-oligosaccharide-glycoprotein N-acetylglucosaminyltransferase IVb) (GlcNAc-T IVb) (GnT-IVb) (N-acetylglucosaminyltransferase IVb) (UDP-N-acetylglucosamine: alpha-1,3-D-mannoside beta-1,4-N-acetylglucosaminyltransferase IVb) | MGAT4B UNQ906/PRO1927 | 548 |
| Q9BY79 | MFRP_HUMAN | Membrane frizzled-related protein (Membrane-type frizzled-related protein) | MFRP | 579 |
| Q495T6 | MMEL1_HUMAN | Membrane metallo-endopeptidase-like 1 (EC 3.4.24.11) (Membrane metallo-endopeptidase-like 2) (NEP2(m)) (Neprilysin II) (NEPII) (Neprilysin-2) (NEP2) (NL2) [Cleaved into: Membrane metallo-endopeptidase-like 1, soluble form (Neprilysin-2 secreted) (NEP2(s))] | MMEL1 MELL1 MMEL2 NEP2 | 779 |
| O75900 | MMP23_HUMAN | Matrix metalloproteinase-23 (MMP-23) (EC 3.4.24.—) (Femalysin) (MIFR-1) (Matrix metalloproteinase-21) (MMP-21) (Matrix metalloproteinase-22) (MMP-22) [Cleaved into: Matrix metalloproteinase-23, soluble form] | MMP23A MMP21; MMP23B MMP21 MMP22 | 390 |
| Q00328 | MGT5A_HUMAN | Alpha-1,6-mannosylglycoprotein 6-beta-N-acetylglucosaminyltransferase A (EC 2.4.1.155) (Alpha-mannoside beta-1,6-N-acetylglucosaminyltransferase) (GlcNAc-T V) (GNT-V) (Mannoside acetylglucosaminyltransferase 5) (N-acetylglucosaminyl-transferase V) | MGAT5 GGNT5 | 741 |
| Q13724 | MOGS_HUMAN | Mannosyl-oligosaccharide glucosidase (EC 3.2.1.106) (Processing A-glucosidase I) | MOGS GCS1 | 837 |
| P21757 | MSRE_HUMAN | Macrophage scavenger receptor types I and II (Macrophage acetylated LDL receptor I and II) (Scavenger receptor class A member 1) (CD antigen CD204) | MSR1 SCARA1 | 451 |
| Q9NZM1 | MYOF_HUMAN | Myoferlin (Fer-1-like protein 3) | MYOF FER1L3 KIAA1207 | 2061 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q58DX5 | NADL2_HUMAN | Inactive N-acetylated-alpha-linked acidic dipeptidase-like protein 2 (NAALADase L2) | NAALADL2 | 795 |
| Q9Y3Q0 | NALD2_HUMAN | N-acetylated-alpha-linked acidic dipeptidase 2 (EC 3.4.17.21) (Glutamate carboxypeptidase III) (GCPIII) (N-acetylated-alpha-linked acidic dipeptidase II) (NAALADase II) | NAALAD2 | 740 |
| O95803 | NDST3_HUMAN | Bifunctional heparan sulfate N-deacetylase/N-sulfotransferase 3 (EC 2.8.2.8) (Glucosaminyl N-deacetylase/N-sulfotransferase 3) (NDST-3) (hNDST-3) (N-heparan sulfate sulfotransferase 3) (N-HSST 3) [Includes: Heparan sulfate N-deacetylase 3 (EC 3.-.-.-); Heparan sulfate N-sulfotransferase 3 (EC 2.8.2.-)] | NDST3 HSST3 UNQ2544/PRO4998 | 873 |
| Q9UQQ1 | NALDL_HUMAN | N-acetylated-alpha-linked acidic dipeptidase-like protein (NAALADase L) (EC 3.4.17.21) (100 kDa ileum brush border membrane protein) (I100) (Ileal dipeptidylpeptidase) | NAALADL1 NAALADASEL NAALADL | 740 |
| Q9UHE5 | NAT8_HUMAN | N-acetyltransferase 8 (EC 2.3.1.—) (Acetyltransferase 2) (Camello-like protein 1) (Cysteinyl-conjugate N-acetyltransferase) (CCNAT) (EC 2.3.1.80) | NAT8 CML1 GLA TSC501 | 227 |
| Q6PIU2 | NCEH1_HUMAN | Neutral cholesterol ester hydrolase 1 (NCEH) (EC 3.1.1.—) (Arylacetamide deacetylase-like 1) | NCEH1 AADACL1 KIAA1363 | 408 |
| P52848 | NDST1_HUMAN | Bifunctional heparan sulfate N-deacetylase/N-sulfotransferase 1 (EC 2.8.2.8) (Glucosaminyl N-deacetylase/N-sulfotransferase 1) (NDST-1) (N-heparan sulfate sulfotransferase 1) (N-HSST 1) ([Heparan sulfate]-glucosamine N-sulfotransferase 1) (HSNST 1) [Includes: Heparan sulfate N-deacetylase 1 (EC 3.-.-.-); Heparan sulfate N-sulfotransferase 1 (EC 2.8.2.—)] | NDST1 HSST HSST1 | 882 |
| P52849 | NDST2_HUMAN | Bifunctional heparan sulfate N-deacetylase/N-sulfotransferase 2 (EC 2.8.2.8) (Glucosaminyl N-deacetylase/N-sulfotransferase 2) (NDST-2) (N-heparan sulfate sulfotransferase 2) (N-HSST 2) [Includes: Heparan sulfate N-deacetylase 2 (EC 3.-.-.-); Heparan sulfate N-sulfotransferase 2 (EC 2.8.2.—)] | NDST2 HSST2 | 883 |
| Q9H3R1 | NDST4_HUMAN | Bifunctional heparan sulfate N-deacetylase/N-sulfotransferase 4 (EC 2.8.2.8) (Glucosaminyl N-deacetylase/N-sulfotransferase 4) (NDST-4) (N-heparan sulfate sulfotransferase 4) (N-HSST 4) [Includes: Heparan sulfate N-deacetylase 4 (EC 3.-.-.-); Heparan sulfate N-sulfotransferase 4 (EC 2.8.2.—)] | NDST4 HSST4 | 872 |
| P26717 | NKG2C_HUMAN | NKG2-C type II integral membrane protein (CD159 antigen-like family member C) (NK cell receptor C) (NKG2-C-activating NK receptor) (CD antigen CD159c) | KLRC2 NKG2C | 231 |
| P26718 | NKG2D_HUMAN | NKG2-D type II integral membrane protein (Killer cell lectin-like receptor subfamily K member 1) (NK cell receptor D) (NKG2-D-activating NK receptor) (CD antigen CD314) | KLRK1 D12S2489E NKG2D | 216 |
| Q9UHF3 | NAT8B_HUMAN | Putative N-acetyltransferase 8B (EC 2.3.1.—) (Acetyltransferase 1) (Camello-like protein 2) | NAT8B CML2 | 227 |
| P08473 | NEP_HUMAN | Neprilysin (EC 3.4.24.11) (Atriopeptidase) (Common acute lymphocytic leukemia antigen) (CALLA) (Enkephalinase) (Neutral endopeptidase 24.11) (NEP) (Neutral endopeptidase) (Skin fibroblast elastase) (SFE) (CD antigen CD10) | MME EPN | 750 |
| P26715 | NKG2A_HUMAN | NKG2-A/NKG2-B type II integral membrane protein (CD159 antigen-like family member A) (NK cell receptor A) (NKG2-A/B-activating NK receptor) (CD antigen CD159a) | KLRC1 NKG2A | 233 |
| Q14494 | NF2L1_HUMAN | Nuclear factor erythroid 2-related factor 1 (NF-E2-related factor 1) (NFE2-related factor 1) (Locus control region-factor 1) (Nuclear factor, erythroid derived 2, like 1) (Transcription factor 11) (TCF-11) (Transcription factor HBZ17) (Transcription factor LCR-F1) | NFE2L1 HBZ17 NRF1 TCF11 | 772 |
| O43908 | NKG2F_HUMAN | NKG2F type II integral membrane protein (NK cell receptor F) (NKG2-F-activating NK receptor) | KLRC4 NKG2F | 158 |
| P42857 | NSG1_HUMAN | Neuron-specific protein family member 1 (Brain neuron cytoplasmic protein 1) | NSG1 D4S234 | 185 |
| Q07444 | NKG2E_HUMAN | NKG2-E type II integral membrane protein (NK cell receptor E) (NKG2-E-activating NK receptor) | KLRC3 NKG2E | 240 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9Y328 | NSG2_HUMAN | Neuron-specific protein family member 2 (Protein p19) (Hmp19) | NSG2 | 171 |
| O95502 | NPTXR_HUMAN | Neuronal pentraxin receptor | NPTXR | 500 |
| Q6PK18 | OGFD3_HUMAN | 2-oxoglutarate and iron-dependent oxygenase domain-containing protein 3 (EC 1.14.11.—) | OGFOD3 C17orf101 | 319 |
| Q9NXG6 | P4HTM_HUMAN | Transmembrane prolyl 4-hydroxylase (P4H-TM) (EC 1.14.11.—) (Hypoxia-inducible factor prolyl hydroxylase 4) (HIF-PH4) (HIF-prolyl hydroxylase 4) (HPH-4) | P4HTM PH4 | 502 |
| Q9HC10 | OTOF_HUMAN | Otoferlin (Fer-1-like protein 2) | OTOF FER1L2 | 1997 |
| P78380 | OLR1_HUMAN | Oxidized low-density lipoprotein receptor 1 (Ox-LDL receptor 1) (C-type lectin domain family 8 member A) (Lectin-like oxidized LDL receptor 1) (LOX-1) (Lectin-like oxLDL receptor 1) (hLOX-1) (Lectin-type oxidized LDL receptor 1) [Cleaved into: Oxidized low-density lipoprotein receptor 1, soluble form] | OLR1 CLEC8A LOX1 | 273 |
| Q8NF37 | PCAT1_HUMAN | Lysophosphatidylcholine acyltransferase 1 (LPC acyltransferase 1) (LPCAT-1) (LysoPC acyltransferase 1) (EC 2.3.1.23) (1-acylglycerophosphocholine O-acyltransferase) (1-alkylglycerophosphocholine O-acetyltransferase) (EC 2.3.1.67) (Acetyl-CoA: lyso-platelet-activating factor acetyltransferase) (Acetyl-CoA: lyso-PAF acetyltransferase) (Lyso-PAF acetyltransferase) (LysoPAFAT) (Acyltransferase-like 2) (Phosphonoformate immuno-associated protein 3) | LPCAT1 AYTL2 PFAAP3 | 534 |
| Q7L5N7 | PCAT2_HUMAN | Lysophosphatidylcholine acyltransferase 2 (LPC acyltransferase 2) (LPCAT-2) (LysoPC acyltransferase 2) (EC 2.3.1.23) (1-acylglycerol-3-phosphate O-acyltransferase 11) (1-AGP acyltransferase 11) (1-AGPAT 11) (EC 2.3.1.51) (1-acylglycerophosphocholine O-acyltransferase) (1-alkylglycerophosphocholine O-acetyltransferase) (EC 2.3.1.67) (Acetyl-CoA: lyso-platelet-activating factor acetyltransferase) (Acetyl-CoA: lyso-PAF acetyltransferase) (Lyso-PAF acetyltransferase) (LysoPAFAT) (Acyltransferase-like 1) (Lysophosphatidic acid acyltransferase alpha) (LPAAT-alpha) | LPCAT2 AGPAT11 AYTL1 | 544 |
| Q7Z412 | PEX26_HUMAN | Peroxisome assembly protein 26 (Peroxin-26) | PEX26 | 305 |
| Q9NST1 | PLPL3_HUMAN | Patatin-like phospholipase domain-containing protein 3 (EC 3.1.1.3) (Acylglycerol O-acyltransferase) (EC 2.3.1.—) (Adiponutrin) (Calcium-independent phospholipase A2-epsilon) (iPLA2-epsilon) | PNPLA3 ADPN C22orf20 | 481 |
| Q9NRQ2 | PLS4_HUMAN | Phospholipid scramblase 4 (PL scramblase 4) (Ca(2+)-dependent phospholipid scramblase 4) (Cell growth-inhibiting gene 43 protein) (TRA1) | PLSCR4 GIG43 | 329 |
| P78562 | PHEX_HUMAN | Phosphate-regulating neutral endopeptidase (EC 3.4.24.—) (Metalloendopeptidase homolog PEX) (Vitamin D-resistant hypophosphatemic rickets protein) (X-linked hypophosphatemia protein) (HYP) | PHEX PEX | 749 |
| O15162 | PLS1_HUMAN | Phospholipid scramblase 1 (PL scramblase 1) (Ca(2+)-dependent phospholipid scramblase 1) (Erythrocyte phospholipid scramblase) (MmTRA1b) | PLSCR1 | 318 |
| Q8NAT1 | PMGT2_HUMAN | Protein O-linked-mannose beta-1,4-N-acetylglucosaminyltransferase 2 (POMGnT2) (EC 2.4.1.—) (Extracellular O-linked N-acetylglucosamine transferase-like) (Glycosyltransferase-like domain-containing protein 2) | POMGNT2 AGO61 C3orf39 EOGTL GTDC2 | 580 |
| Q8IV08 | PLD3_HUMAN | Phospholipase D3 (PLD 3) (EC 3.1.4.4) (Choline phosphatase 3) (HindIII K4L homolog) (Hu-K4) (Phosphatidylcholine-hydrolyzing phospholipase D3) | PLD3 | 490 |
| Q9NRY6 | PLS3_HUMAN | Phospholipid scramblase 3 (PL scramblase 3) (Ca(2+)-dependent phospholipid scramblase 3) | PLSCR3 | 295 |
| Q9NRY7 | PLS2_HUMAN | Phospholipid scramblase 2 (PL scramblase 2) (Ca(2+)-dependent phospholipid scramblase 2) | PLSCR2 | 297 |
| Q96AD5 | PLPL2_HUMAN | Patatin-like phospholipase domain-containing protein 2 (EC 3.1.1.3) (Adipose triglyceride lipase) (Calcium-independent phospholipase A2) (Desnutrin) (Pigment epithelium-derived factor) (TTS2.2) (Transport-secretion protein 2) (TTS2) | PNPLA2 ATGL FP17548 | 504 |
| Q9BX97 | PLVAP_HUMAN | Plasmalemma vesicle-associated protein (Fenestrated endothelial-linked structure protein) (Plasmalemma vesicle protein 1) (PV-1) | PLVAP FELS PV1 | 442 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q8WZA1 | PMGT1_HUMAN | Protein O-linked-mannose beta-1,2-N-acetylglucosaminyltransferase 1 (POMGnT1) (EC 2.4.1.—) (UDP-GlcNAc: alpha-D-mannoside beta-1,2-N-acetylglucosaminyltransferase I.2) (GnT I.2) | POMGNT1 MGAT1.2 | 660 |
| Q8TE99 | PXYP1_HUMAN | 2-phosphoxylose phosphatase 1 (EC 3.1.3.—) (Acid phosphatase-like protein 2) (Xylosyl phosphatase) (epididymis luminal protein 124) | UNQ746/PRO1475 PXYLP1 ACPL2 HEL124 XYLP UNQ370/PRO706 | 480 |
| Q8TC12 | RDH11_HUMAN | Retinol dehydrogenase 11 (EC 1.1.1.300) (Androgen-regulated short-chain dehydrogenase/reductase 1) (HCV core-binding protein HCBP12) (Prostate short-chain dehydrogenase/reductase 1) (Retinal reductase 1) (RalR1) (Short chain dehydrogenase/reductase family 7C member 1) | RDH11 ARSDR1 PSDR1 SDR7C1 CGI-82 | 318 |
| Q9Y644 | RFNG_HUMAN | Beta-1,3-N-acetylglucosaminyltransferase radical fringe (EC 2.4.1.222) (O-fucosylpeptide 3-beta-N-acetylglucosaminyltransferase) | RFNG | 331 |
| Q6AZY7 | SCAR3_HUMAN | Scavenger receptor class A member 3 (Cellular stress response gene protein) | SCARA3 CSR | 606 |
| Q6ZMJ2 | SCAR5_HUMAN | Scavenger receptor class A member 5 (Scavenger receptor hfg) | SCARA5 UNQ2938/PRO28700 | 495 |
| P67812 | SC11A_HUMAN | Signal peptidase complex catalytic subunit SEC11A (EC 3.4.21.89) (Endopeptidase SP18) (Microsomal signal peptidase 18 kDa subunit) (SPase 18 kDa subunit) (SEC11 homolog A) (SEC11-like protein 1) (SPC18) | SEC11A SEC11L1 SPC18 SPCS4A | 179 |
| Q9BY50 | SC11C_HUMAN | Signal peptidase complex catalytic subunit SEC11C (EC 3.4.21.89) (Microsomal signal peptidase 21 kDa subunit) (SPase 21 kDa subunit) (SEC11 homolog C) (SEC11-like protein 3) (SPC21) | SEC11C SEC11L3 SPC21 SPCS4C | 192 |
| Q8IXA5 | SACA3_HUMAN | Sperm acrosome membrane-associated protein 3 (Cancer/testis antigen 54) (CT54) (Lysozyme-like acrosomal sperm-specific secretory protein ALLP-17) (Lysozyme-like protein 3) (Sperm lysozyme-like protein 1) (Sperm protein reactive with antisperm antibodies) (Sperm protein reactive with ASA) [Cleaved into: Sperm acrosome membrane-associated protein 3, membrane form; Sperm acrosome membrane-associated protein 3, processed form] | SPACA3 LYZC3 LYZL3 SLLP1 SPRASA UNQ424/PRO862 | 215 |
| P0CV7V | SC11B_HUMAN | Putative signal peptidase complex catalytic subunit SEC11B (EC 3.4.21.89) (SEC11 homolog B) (SEC11-like protein 2) | SEC11B SEC11L2 SPCS4B | 166 |
| Q9NSC7 | SIA7A_HUMAN | Alpha-N-acetylgalactosaminide alpha-2,6-sialyltransferase 1 (EC 2.4.99.3) (GalNAc alpha-2,6-sialyltransferase I) (ST6GalNAc I) (ST6GalNAcI) (Sialyltransferase 7A) (SIAT7-A) | ST6GALNAC1 SIAT7A UNQ543/PRO848 | 600 |
| Q9H4F1 | SIA7D_HUMAN | Alpha-N-acetyl-neuraminyl-2,3-beta-galactosyl-1,3-N-acetyl-galactosaminide alpha-2,6-sialyltransferase (EC 2.4.99.7) (NeuAc-alpha-2,3-Gal-beta-1,3-GalNAc-alpha-2,6-sialyltransferase) (ST6GalNAc IV) (ST6GalNAcIV) (Sialyltransferase 3C) (SIAT3-C) (Sialyltransferase 7D) (SIAT7-D) | ST6GALNAC4 SIAT3C SIAT7D | 302 |
| Q92186 | SIA8B_HUMAN | Alpha-2,8-sialyltransferase 8B (EC 2.4.99.—) (Sialyltransferase 8B) (SIAT8-B) (Sialyltransferase St8Sia II) (ST8SiaII) (Sialyltransferase X) (STX) | ST8SIA2 SIAT8B STX | 375 |
| P15907 | SIAT1_HUMAN | Beta-galactoside alpha-2,6-sialyltransferase 1 (Alpha 2,6-ST 1) (EC 2.4.99.1) (B-cell antigen CD75) (CMP-N-acetylneuraminate-beta-galactoside-alpha-2,6-sialyltransferase 1) (ST6Gal I) (ST6GalI) (Sialyltransferase 1) | ST6GAL1 SIAT1 | 406 |
| Q16585 | SGCB_HUMAN | Beta-sarcoglycan (Beta-SG) (43 kDa dystrophin-associated glycoprotein) (43DAG) (A3b) | SGCB | 318 |
| Q13326 | SGCG_HUMAN | Gamma-sarcoglycan (Gamma-SG) (35 kDa dystrophin-associated glycoprotein) (35DAG) | SGCG | 291 |
| Q96LD1 | SGCZ_HUMAN | Zeta-sarcoglycan (Zeta-SG) (ZSG1) | SGCZ | 299 |
| Q92185 | SIA8A_HUMAN | Alpha-N-acetylneuraminide alpha-2,8-sialyltransferase (EC 2.4.99.8) (Alpha-2,8-sialyltransferase 8A) (Ganglioside GD3 synthase) (Ganglioside GT3 synthase) (Sialyltransferase 8A) (SIAT8-A) (Sialyltransferase St8Sia 1) (ST8SiaI) | ST8SIA1 SIAT8 SIAT8A | 356 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q92187 | SIA8D_HUMAN | CMP-N-acetylneuraminate-poly-alpha-2,8-sialyltransferase (EC 2.4.99.—) (Alpha-2,8-sialyltransferase 8D) (Polysialyltransferase-1) (Sialyltransferase 8D) (SIAT8-D) (Sialyltransferase St8Sia IV) (ST8SiaIV) | ST8SIA4 PST PST1 SIAT8D | 359 |
| P61647 | SIA8F_HUMAN | Alpha-2,8-sialyltransferase 8F (EC 2.4.99.—) (Sialyltransferase 8F) (SIAT8-F) (Sialyltransferase St8Sia VI) (ST8SiaVI) | ST8SIA6 SIAT8F | 398 |
| Q96IF0 | SIAT2_HUMAN | Beta-galactoside alpha-2,6-sialyltransferase 2 (Alpha 2,6-ST 2) (EC 2.4.99.1) (CMP-N-acetylneuraminate-beta-galactosamide-alpha-2,6-sialyltransferase 2) (ST6Gal II) (ST6GalII) (hST6Gal II) (Sialyltransferase 2) | ST6GAL2 KIAA1877 SIAT2 | 529 |
| A6NLE4 Q07837 | SIM23_HUMAN SLC31_HUMAN | Small integral membrane protein 23<br>Neutral and basic amino acid transport protein rBAT (NBAT) (D2h) (Solute carrier family 3 member 1) (b(0,+)-type amino acid transport protein) | SMIM23 C5orf50<br>SLC3A1 RBAT | 156<br>685 |
| O43173 | SIA8C_HUMAN | Sia-alpha-2,3-Gal-beta-1,4-GlcNAc-R: alpha 2,8-sialyltransferase (EC 2.4.99.—) (Alpha-2,8-sialyltransferase 8C) (Alpha-2,8-sialyltransferase III) (ST8 alpha-N-acetyl-neuraminide alpha-2,8-sialyltransferase 3) (Sialyltransferase 8C) (SIAT8-C) (Sialyltransferase St8Sia III) (ST8SiaIII) | ST8SIA3 SIAT8C | 380 |
| Q11201 | SIA4A_HUMAN | CMP-N-acetylneuraminate-beta-galactosamide-alpha-2,3-sialyltransferase 1 (Alpha 2,3-ST 1) (Beta-galactoside alpha-2,3-sialyltransferase 1) (EC 2.4.99.4) (Gal-NAc6S) (Gal-beta-1,3-GalNAc-alpha-2,3-sialyltransferase) (SIATFL) (ST3Gal I) (ST3GalI) (ST3GalA.1) (ST3O) (Sialyltransferase 4A) (SIAT4-A) | ST3GAL1 SIAT4 SIAT4A | 340 |
| Q969X2 | SIA7F_HUMAN | Alpha-N-acetylgalactosaminide alpha-2,6-sialyltransferase 6 (EC 2.4.99.—) (GalNAc alpha-2,6-sialyltransferase VI) (ST6GalNAc VI) (ST6GalNAcVI) (hST6GalNAc VI) (Sialyltransferase 7F) (SIAT7-F) | ST6GALNAC6 SIAT7F UNQ708/PRO1359 | 333 |
| Q9UNP4 | SIAT9_HUMAN | Lactosylceramide alpha-2,3-sialyltransferase (EC 2.4.99.9) (CMP-NeuAc: lactosylceramide alpha-2,3-sialyltransferase) (Ganglioside GM3 synthase) (STSGal V) (ST5GalV) (Sialyltransferase 9) | ST3GAL5 SIAT9 UNQ2510/PRO5998 | 418 |
| Q9H5K3 | SG196_HUMAN | Protein O-mannose kinase (POMK) (EC 2.7.1.183) (Protein kinase-like protein SgK196) (Sugen kinase 196) | POMK SGK196 | 350 |
| Q9Y274 | SIA10_HUMAN | Type 2 lactosamine alpha-2,3-sialyltransferase (EC 2.4.99.—) (CMP-NeuAc: beta-galactoside alpha-2,3-sialyltransferase VI) (ST3Gal VI) (ST3GalVI) (Sialyltransferase 10) | ST3GAL6 SIAT10 | 331 |
| Q16842 | SIA4B_HUMAN | CMP-N-acetylneuraminate-beta-galactosamide-alpha-2,3-sialyltransferase 2 (Alpha 2,3-ST 2) (Beta-galactoside alpha-2,3-sialyltransferase 2) (EC 2.4.99.4) (Gal-NAc6S) (Gal-beta-1,3-GalNAc-alpha-2,3-sialyltransferase) (ST3Gal II) (ST3GalII) (ST3GalA.2) (Sialyltransferase 4B) (SIAT4-B) | ST3GAL2 SIAT4B | 350 |
| Q11206 | SIA4C_HUMAN | CMP-N-acetylneuraminate-beta-galactosamide-alpha-2,3-sialyltransferase 4 (Alpha 2,3-ST 4) (Beta-galactoside alpha-2,3-sialyltransferase 4) (EC 2.4.99.—) (Alpha 2,3-sialyltransferase IV) (Gal-NAc6S) (Gal-beta-1,4-GalNAc-alpha-2,3-sialyltransferase) (SAT-3) (ST-4) (ST3Gal IV) (ST3GalIV) (ST3GalA.2) (STZ) (Sialyltransferase 4C) (SIAT4-C) | ST3GAL4 CGS23 NANTA3 SIAT4C STZ | 333 |
| Q9UJ37 | SIA7B_HUMAN | Alpha-N-acetylgalactosaminide alpha-2,6-sialyltransferase II (ST6GalNAc II) (ST6GalNAcII) (SThM) (Sialyltransferase 7B) (SIAT7-B) | ST6GALNAC2 SIAT7B SIATL1 STHM | 374 |
| Q9BVH7 | SIA7E_HUMAN | Alpha-N-acetylgalactosaminide alpha-2,6-sialyltransferase 5 (EC 2.4.99.—) (GD1 alpha synthase) (GalNAc alpha-2,6-sialyltransferase V) (ST6GalNAc V) (ST6GalNAcV) (Sialyltransferase 7E) (SIAT7-E) | ST6GALNAC5 SIAT7E | 336 |
| Q11203 | SIAT6_HUMAN | CMP-N-acetylneuraminate-beta-1,4-galactoside alpha-2,3-sialyltransferase (EC 2.4.99.6) (Beta-galactoside alpha-2,3-sialyltransferase 3) (Alpha 2,3-ST 3) (Gal beta-1,3(4) GlcNAc alpha-2,3 Sialyltransferase) (N-acetyllactosaminide alpha-2,3-sialyltransferase) (ST3Gal III) (STSGalIII) (ST3N) (Sialyltransferase 6) | ST3GAL3 SIAT6 | 375 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q12884 | SEPR_HUMAN | Prolyl endopeptidase FAP (EC 3.4.21.26) (170 kDa melanoma membrane-bound gelatinase) (Dipeptidyl peptidase FAP) (EC 3.4.14.5) (Fibroblast activation protein alpha) (FAPalpha) (Gelatine degradation protease FAP) (EC 3.4.21.—) (Integral membrane serine protease) (Post-proline cleaving enzyme) (Serine integral membrane protease) (SIMP) (Surface-expressed protease) (Seprase) [Cleaved into: Antiplasmin-cleaving enzyme FAP, soluble form (APCe) (EC 3.4.14.5) (EC 3.4.21.—) (EC 3.4.21.26] | FAP | 760 |
| Q8NDV1 | SIA7C_HUMAN | Alpha-N-acetylgalactosaminide alpha-2,6-sialyltransferase 3 (EC 2.4.99.—) (GalNAc alpha-2,6-sialyltransferase III) (ST6GalNAc III) (ST6GalNAcIII) (STY) (Sialyltransferase 7C) (SIAT7-C) | ST6GALNAC3 SIAT7C UNQ2787/PRO7177 | 305 |
| O15466 | SIA8E_HUMAN | Alpha-2,8-sialyltransferase 8E (EC 2.4.99.—) (Sialyltransferase 8E) (SIAT8-E) (Sialyltransferase St8Sia V) (ST8SiaV) | ST8SIA5 SIAT8E | 376 |
| Q92629 | SGCD_HUMAN | Delta-sarcoglycan (Delta-SG) (35 kDa dystrophin-associated glycoprotein) (35DAG) | SGCD | 289 |
| Q86WD7 | SPA9_HUMAN | Serpin A9 (Centerin) (Germinal center B-cell-expressed transcript 1 protein) | SERPINA9 GCET1 SERPINA11 UNQ692/PRO1337 | 417 |
| P61009 | SPCS3_HUMAN | Signal peptidase complex subunit 3 (EC 3.4.—.—) (Microsomal signal peptidase 22/23 kDa subunit) (SPC22/23) (SPase 22/23 kDa subunit) | SPCS3 SPC22 UNQ1841/PRO3567 | 180 |
| Q9UH99 | SUN2_HUMAN | SUN domain-containing protein 2 (Protein unc-84 homolog B) (Rab5-interacting protein) (Rab5IP) (Sad1/unc-84 protein-like 2) | SUN2 FRIGG KIAA0668 RAB5IP UNC84B | 717 |
| Q9Y5Y6 | ST14_HUMAN | Suppressor of tumorigenicity 14 protein (EC 3.4.21.109) (Matriptase) (Membrane-type serine protease 1) (MT-SP1) (Prostamin) (Serine protease 14) (Serine protease TADG-15) (Tumor-associated differentially-expressed gene 15 protein) | ST14 PRSS14 SNC19 TADG15 | 855 |
| P14410 | SUIS_HUMAN | Sucrase-isomaltase, intestinal [Cleaved into: Sucrase (EC 3.2.1.48; Isomaltase (EC 3.2.1.10)] | SI | 1827 |
| O94901 | SUN1_HUMAN | SUN domain-containing protein 1 (Protein unc-84 homolog A) (Sad1/unc-84 protein-like 1) | SUN1 KIAA0810 UNC84A | 812 |
| Q9NUM4 | T106B_HUMAN | Transmembrane protein 106B | TMEM106B | 274 |
| Q9H7V2 | SYNG1_HUMAN | Synapse differentiation-inducing gene protein 1 (SynDIG1) (Dispanin subfamily C member 2) (DSPC2) (Transmembrane protein 90B) | SYNDIG1 C20orf39 TMEM90B | 258 |
| P02786 | TFR1_HUMAN | Transferrin receptor protein 1 (TR) (TfR) (TfR1) (Trfr) (T9) (p90) (CD antigen CD71) [Cleaved into: Transferrin receptor protein 1, serum form (sTfR)] | TFRC | 760 |
| Q9UP52 | TFR2_HUMAN | Transferrin receptor protein 2 (TfR2) | TFR2 | 801 |
| Q9NRS4 | TMPS4_HUMAN | Transmembrane protease serine 4 (EC 3.4.21.—) (Channel-activating protease 2) (CAPH2) (Membrane-type serine protease 2) (MT-SP2) | TMPRSS4 TMPRSS3 UNQ776/PRO1570 | 437 |
| P50591 | TNF10_HUMAN | Tumor necrosis factor ligand superfamily member 10 (Apo-2 ligand) (Apo-2L) (TNF-related apoptosis-inducing ligand) (Protein TRAIL) (CD antigen CD253) | TNFSF10 APO2L TRAIL | 281 |
| O43508 | TNF12_HUMAN | Tumor necrosis factor ligand superfamily member 12 (APO3 ligand) (TNF-related weak inducer of apoptosis) (TWEAK) [Cleaved into: Tumor necrosis factor ligand superfamily member 12, membrane form; Tumor necrosis factor ligand superfamily member 12, secreted form] | TNFSF12 APO3L DR3LG UNQ181/PRO207 | 249 |
| Q06643 | TNFC_HUMAN | Lymphotoxin-beta (LT-beta) (Tumor necrosis factor C) (TNF-C) (Tumor necrosis factor ligand superfamily member 3) | LTB TNFC TNFSF3 | 244 |
| P41273 | TNF9_HUMAN | Tumor necrosis factor ligand superfamily member 9 (4-1BB ligand) (4-1BBL) | TNFSF9 | 254 |
| Q6ZMR5 | TM11A_HUMAN | Transmembrane protease serine 11A (EC 3.4.21.—) (Airway trypsin-like protease 1) (Epidermal type-II transmembrane serine protease) (Esophageal cancer-susceptibility gene 1 protein) | TMPRSS11A ECRG1 HAT1L HESP | 421 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q6ZWK6 | TM11F_HUMAN | Transmembrane protease serine 11F (EC 3.4.21.—) (Airway trypsin-like protease 4) | TMPRSS11F HATL4 | 438 |
| P23510 | TNFL4_HUMAN | Tumor necrosis factor ligand superfamily member 4 (Glycoprotein Gp34) (OX40 ligand) (OX40L) (TAX transcriptionally-activated glycoprotein 1) (CD antigen CD252) | TNFSF4 TXGP1 | 183 |
| P01375 | TNFA_HUMAN | Tumor necrosis factor (Cachectin) (TNF-alpha) (Tumor necrosis factor ligand superfamily member 2) (TNF-a) [Cleaved into: Tumor necrosis factor, membrane form (N-terminal fragment) (NTF); Intracellular domain 1 (ICD1); Intracellular domain 2 (ICD2); C-domain 1; C-domain 2; Tumor necrosis factor, soluble form] | TNF TNFA TNFSF2 | 233 |
| O15393 | TMPS2_HUMAN | Transmembrane protease serine 2 (EC 3.4.21.—) (Serine protease 10) [Cleaved into: Transmembrane protease serine 2 non-catalytic chain; Transmembrane protease serine 2 catalytic chain] | TMPRSS2 PRSS10 | 492 |
| Q9H3S3 | TMPS5_HUMAN | Transmembrane protease serine 5 (EC 3.4.21.—) (Spinesin) | TMPRSS5 | 457 |
| Q7RTY8 | TMPS7_HUMAN | Transmembrane protease serine 7 (EC 3.4.21.—) (Matriptase-3) | TMPRSS7 | 843 |
| O43557 | TNF14_HUMAN | Tumor necrosis factor ligand superfamily member 14 (Herpes virus entry mediator ligand) (HVEM-L) (Herpesvirus entry mediator ligand) (CD antigen CD258) [Cleaved into: Tumor necrosis factor ligand superfamily member 14, membrane form; Tumor necrosis factor ligand superfamily member 14, soluble form] | TNFSF14 HVEML LIGHT UNQ391/PRO726 | 240 |
| P48023 | TNFL6_HUMAN | Tumor necrosis factor ligand superfamily member 6 (Apoptosis antigen ligand) (APTL) (CD95 ligand) (CD95-L) (Fas antigen ligand) (Fas ligand) (FasL) (CD antigen CD178) [Cleaved into: Tumor necrosis factor ligand superfamily member 6, soluble form (Receptor-binding FasL ectodomain) (Soluble Fas ligand) (sFasL); ADAM10-processed FasL form (APL); FasL intracellular domain (FasL ICD) (SPPL2A-processed FasL form) (SPA)] | FASLG APT1LG1 CD95L FASL TNFSF6 | 281 |
| Q86T26 | TM11B_HUMAN | Transmembrane protease serine 11B (EC 3.4.21.—) (Airway trypsin-like protease 5) | TMPRSS11B HATL5 | 416 |
| O95150 | TNF15_HUMAN | Tumor necrosis factor ligand superfamily member 15 (TNF ligand-related molecule 1) (Vascular endothelial cell growth inhibitor) [Cleaved into: Tumor necrosis factor ligand superfamily member 15, membrane form; Tumor necrosis factor ligand superfamily member 15, secreted form] | TNFSF15 TL1 VEGI | 251 |
| Q9UL52 | TM11E_HUMAN | Transmembrane protease serine 11E (EC 3.4.21.—) (Serine protease DESC1) (Transmembrane protease serine 11E2) [Cleaved into: Transmembrane protease serine 11E non-catalytic chain; Transmembrane protease serine 11E catalytic chain] | TMPRSS11E DESC1 TMPRSS11E2 UNQ742/PRO1461 | 423 |
| Q8IU80 | TMPS6_HUMAN | Transmembrane protease serine 6 (EC 3.4.21.—) (Matriptase-2) | TMPRSS6 UNQ354/PRO618 | 811 |
| Q7Z410 | TMPS9_HUMAN | Transmembrane protease serine 9 (EC 3.4.21.—) (Polyserase-I) (Polyserine protease 1) (Polyserase-1) [Cleaved into: Serase-1; Serase-2; Serase-3] | TMPRSS9 | 1059 |
| Q9BYE2 | TMPSD_HUMAN | Transmembrane protease serine 13 (EC 3.4.21.—) (Membrane-type mosaic serine protease) (Mosaic serine protease) | TMPRSS13 MSP TMPRSS11 | 586 |
| O14788 | TNF11_HUMAN | Tumor necrosis factor ligand superfamily member 11 (Osteoclast differentiation factor) (ODF) (Osteoprotegerin ligand) (OPGL) (Receptor activator of nuclear factor kappa-B ligand) (RANKL) (TNF-related activation-induced cytokine) (TRANCE) (CD antigen CD254) [Cleaved into: Tumor necrosis factor ligand superfamily member 11, membrane form; Tumor necrosis factor ligand superfamily member 11, soluble form] | TNFSF11 OPGL RANKL TRANCE | 317 |
| O60507 | TPST1_HUMAN | Protein-tyrosine sulfotransferase 1 (EC 2.8.2.20) (Tyrosylprotein sulfotransferase 1) (TPST-1) | TPST1 | 370 |
| O60235 | TM11D_HUMAN | Transmembrane protease serine 11D (EC 3.4.21.—) (Airway trypsin-like protease) [Cleaved into: Transmembrane protease serine 11D non-catalytic chain; Transmembrane protease serine 11D catalytic chain] | TMPRSS11D HAT | 418 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| Q9Y2B1 | TMEM5_HUMAN | Transmembrane protein 5 | TMEM5 | 443 |
| P57727 | TMPS3_HUMAN | Transmembrane protease serine 3 (EC 3.4.21.—) (Serine protease TADG-12) (Tumor-associated differentially-expressed gene 12 protein) | TMPRSS3 ECHOS1 TADG12 UNQ323/PRO382 | 454 |
| Q9Y275 | TN13B_HUMAN | Tumor necrosis factor ligand superfamily member 13B (B lymphocyte stimulator) (BLyS) (B-cell-activating factor) (BAFF) (Dendritic cell-derived TNF-like molecule) (TNF- and APOL-related leukocyte expressed ligand 1) (TALL-1) (CD antigen CD257) [Cleaved into: Tumor necrosis factor ligand superfamily member 13b, membrane form; Tumor necrosis factor ligand superfamily member 13b, soluble form] | TNFSF13B BAFF BLYS TALL1 TNFSF20 ZTNF4 UNQ401/PRO738 | 285 |
| P32971 | TNFL8_HUMAN | Tumor necrosis factor ligand superfamily member 8 (CD30 ligand) (CD30-L) (CD antigen CD153) | TNFSF8 CD30L CD30LG | 234 |
| Q13061 | TRDN_HUMAN | Triadin | TRDN | 729 |
| Q9UNG2 | TNF18_HUMAN | Tumor necrosis factor ligand superfamily member 18 (Activation-inducible TNF-related ligand) (AITRL) (Glucocorticoid-induced TNF-related ligand) (hGITRL) | TNFSF18 AITRL GITRL TL6 UNQ149/PRO175 | 199 |
| Q9H2S6 | TNMD_HUMAN | Tenomodulin (TeM) (hTeM) (Chondromodulin-1-like protein) (ChM1L) (hChM1L) (Chondromodulin-I-like protein) (Myodulin) (Tendin) | TNMD CHM1L UNQ771/PRO1565 | 317 |
| O60704 | TPST2_HUMAN | Protein-tyrosine sulfotransferase 2 (EC 2.8.2.20) (Tyrosylprotein sulfotransferase 2) (TPST-2) | TPST2 | 377 |
| Q9UKU6 | TRHDE_HUMAN | Thyrotropin-releasing hormone-degrading ectoenzyme (TRH-DE) (TRH-degrading ectoenzyme) (EC 3.4.19.6) (Pyroglutamyl-peptidase II) (PAP-II) (TRH-specific aminopeptidase) (Thyroliberinase) | TRHDE UNQ2507/PRO5995 | 1024 |
| Q9Y2C2 | UST_HUMAN | Uronyl 2-sulfotransferase (EC 2.8.2.—) | UST DS2ST | 406 |
| Q8NBZ7 | UXS1_HUMAN | UDP-glucuronic acid decarboxylase 1 (EC 4.1.1.35) (UDP-glucuronate decarboxylase 1) (UGD) (UXS-1) | UXS1 UNQ2538/PRO6079 | 420 |
| Q86Y38 | XYLT1_HUMAN | Xylosyltransferase 1 (EC 2.4.2.26) (Peptide O-xylosyltransferase 1) (Xylosyltransferase I) (XT-I) (XyIT-I) | XYLT1 XT1 | 959 |
| P17861 | XBP1_HUMAN | X-box-binding protein 1 (XBP-1) (Tax-responsive element-binding protein 5) (TREB-5) [Cleaved into: X-box-binding protein 1, cytoplasmic form; X-box-binding protein 1, luminal form] | XBP1 TREB5 XBP2 | 261 |
| O75063 | XYLK_HUMAN | Glycosaminoglycan xylosylkinase (EC 2.7.1.—) (Xylose kinase) | FAM20B KIAA0475 | 409 |
| Q8NBI6 | XXLT1_HUMAN | Xyloside xylosyltransferase 1 (EC 2.4.2.n3) (UDP-xylose: alpha-xyloside alpha-1,3-xylosyltransferase) | XXYLT1 C3orf21 PSEC0251 | 393 |
| Q9H1B5 | XYLT2_HUMAN | Xylosyltransferase 2 (EC 2.4.2.26) (Peptide O-xylosyltransferase 1) (Xylosyltransferase II) (XT-II) (XyIT-II) | XYLT2 XT2 UNQ3058/PRO9878 | 865 |
| A8MXE2 | YI036_HUMAN | Putative UDP-GlcNAc: betaGal beta-1,3-N-acetylglucosaminyltransferase LOC100288842 (EC 2.4.1.—) (Putative UDP-GlcNAc: betaGal beta-1,3-N-acetylglucosaminyltransferase LOC402377) (UDP-GlcNAc: betaGal beta-1,3-N-acetylglucosaminyltransferase 5 pseudogene) | | 369 |
| Q5ST17 | Q5ST17_HUMAN | Hexosyltransferase (EC 2.4.1.—) | B3GALT4 hCG_17511 | 378 |
| A0A090N7X6 | A0A090N7X6_HUMAN | Polypeptide N-acetylgalactosaminyltransferase (EC 2.4.1.—) (Protein-UDP acetylgalactosaminyltransferase) | GALNT11 hCG_1990637 tcag7.1057 | 608 |
| Q5Q0U2 | Q5Q0U2_HUMAN | Fucosyltransferase 9 (EC 2.4.1.152) (Fucosyltransferase 9 (Alpha (1,3) fucosyltransferase), isoform CRA_a) (cDNA, FLJ95882, Homo sapiens fucosyltransferase 9 (alpha (1,3) fucosyltransferase) (FUT9), mRNA) | FUT9 hCG_16703 | 359 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| A8K9Q8 | A8K9Q8_HUMAN | Hexosyltransferase (EC 2.4.1.—) | hCG_2018639 | 384 |
| A8K737 | A8K737_HUMAN | Fucosyltransferase (Fucosyltransferase 3 (Galactoside 3(4)-L-fucosyltransferase, Lewis blood group)) (cDNA FLJ78078, highly similar to Human alpha (1,3/1,4) fucosyltransferase (FUT3)) | FUT3 hCG_1645372 | 361 |
| G3V1S6 | G3V1S6_HUMAN | Polypeptide N-acetylgalactosaminyltransferase (EC 2.4.1.—) (Protein-UDP acetylgalactosaminyltransferase) | GALNT2 hCG_15927 | 533 |
| Q58A54 | Q58A54_HUMAN | Polypeptide N-acetylgalactosaminyltransferase (EC 2.4.1.—) (Protein-UDP acetylgalactosaminyltransferase) | GalNAc-T18 GALNT18 GALNTL4 hCG_1991780 | 607 |
| A0A087WY64 | A0A087WY64_HUMAN | Hexosyltransferase (EC 2.4.1.—) | B3GALNT2 | 92 |
| A3KLL5 | A3KLL5_HUMAN | Sodium/potassium-transporting ATPase subunit beta | ATP1B1 hCG_37798 | 303 |
| Q2L4S5 | Q2L4S5_HUMAN | Polypeptide N-acetylgalactosaminyltransferase (EC 2.4.1.—) (Protein-UDP acetylgalactosaminyltransferase) | GALNT19 WBSCR17 hCG_19354 tcag7.519 | 598 |
| B7ZKW0 | B7ZKW0_HUMAN | Sodium/potassium-transporting ATPase subunit beta | ATP1B4 | 314 |
| Q9P1W6 | Q9P1W6_HUMAN | Alpha-(1,3/1,4)-fucosyltransferase (cDNA, FLJ94139, highly similar to Homo sapiens fucosyltransferase 3 (galactoside 3(4)-L-fucosyltransferase, Lewis blood group included) (FUT3), mRNA) | FUT3 | 361 |
| A0A024RC48 | A0A024RC48_HUMAN | Polypeptide N-acetylgalactosaminyltransferase (EC 2.4.1.—) (Protein-UDP acetylgalactosaminyltransferase) | GALNT1 hCG_2042960 | 559 |
| D3DNF9 | D3DNF9_HUMAN | Sodium/potassium-transporting ATPase subunit beta | ATP1B3 hCG_19938 | 265 |
| A0A024RBT1 | A0A024RBT1_HUMAN | Polypeptide N-acetylgalactosaminyltransferase (EC 2.4.1.—) (Protein-UDP acetylgalactosaminyltransferase) | GALNT1 hCG_2016450 | 378 |
| D3DQI7 | D3DQI7_HUMAN | Polypeptide N-acetylgalactosaminyltransferase (EC 2.4.1.—) (Protein-UDP acetylgalactosaminyltransferase) | GALNT10 hCG_36809 | 506 |
| B7Z5G5 | B7Z5G5_HUMAN | Polypeptide N-acetylgalactosaminyltransferase (EC 2.4.1.—) (Protein-UDP acetylgalactosaminyltransferase) | | 527 |
| B5B9M4 | B5B9M4_HUMAN | Fucosyltransferase | FUT3 | 361 |
| Q68V18 | Q68V18_HUMAN | Polypeptide N-acetylgalactosaminyltransferase (EC 2.4.1.—) (Protein-UDP acetylgalactosaminyltransferase) | GALNT16 GALNTL1 hCG_21969 | 558 |
| E7EVF0 | E7EVF0_HUMAN | Hexosyltransferase (EC 2.4.1.—) | B3GALNT1 | 91 |
| B2R8J0 | B2R8J0_HUMAN | Polypeptide N-acetylgalactosaminyltransferase (EC 2.4.1.—) (Protein-UDP acetylgalactosaminyltransferase) | | 633 |
| C9J368 | C9J368_HUMAN | Hexosyltransferase (EC 2.4.1.—) (Fragment) | B3GNT5 | 50 |
| B2RC53 | B2RC53_HUMAN | cDNA, FLJ95856, highly similar to Homo sapiens fucosyltransferase 11 (alpha (1,3) fucosyltransferase) (FUT11), mRNA | | 492 |
| A8KAJ7 | A8KAJ7_HUMAN | Polypeptide N-acetylgalactosaminyltransferase (EC 2.4.1.—) (Protein-UDP acetylgalactosaminyltransferase) | | 559 |
| Q8NHI0 | Q8NHI0_HUMAN | Hexosyltransferase (EC 2.4.1.—) | | 67 |
| B4DIF4 | B4DIF4_HUMAN | Hexosyltransferase (EC 2.4.1.—) | | 91 |
| B3KT16 | B3KT16_HUMAN | Polypeptide N-acetylgalactosaminyltransferase (EC 2.4.1.—) (Protein-UDP acetylgalactosaminyltransferase) | | 372 |
| B7ZKV9 | B7ZKV9_HUMAN | Sodium/potassium-transporting ATPase subunit beta | ATP1B4 | 322 |
| Q6RC02 | Q6RC02_HUMAN | Hexosyltransferase (EC 2.4.1.—) | | 102 |
| A0A087WV18 | A0A087WV18_HUMAN | Polypeptide N-acetylgalactosaminyltransferase (EC 2.4.1.—) (Protein-UDP acetylgalactosaminyltransferase) | WBSCR17 | 519 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| R4X5Z0 | R4X5Z0_HUMAN | Hexosyltransferase (EC 2.4.1.—) | B3GALNT1 | 83 |
| C9JGI4 | C9JGI4_HUMAN | Polypeptide N-acetylgalactosaminyltransferase (EC 2.4.1.—) (Protein-UDP acetylgalactosaminyltransferase) | GALNT15 | 617 |
| Q24JS2 | Q24JS2_HUMAN | Polypeptide N-acetylgalactosaminyltransferase (EC 2.4.1.—) (Protein-UDP acetylgalactosaminyltransferase) | GALNT6 | 622 |
| B7ZKV8 | B7ZKV8_HUMAN | Sodium/potassium-transporting ATPase subunit beta | ATP1B4 | 357 |
| I3L1V9 | I3L1V9_HUMAN | Sodium/potassium-transporting ATPase subunit beta (Fragment) | ATP1B2 | 167 |
| B4DLS4 | B4DLS4_HUMAN | cDNA FLJ55721, highly similar to Homo sapiens fucosyltransferase 10 (alpha (1,3) fucosyltransferase) (FUT10), mRNA | | 521 |
| Q05BM8 | Q05BM8_HUMAN | Polypeptide N-acetylgalactosaminyltransferase (EC 2.4.1.—) (Protein-UDP acetylgalactosaminyltransferase) | GALNT1 | 499 |
| A0A087X115 | A0A087X115_HUMAN | Polypeptide N-acetylgalactosaminyltransferase (EC 2.4.1.—) (Protein-UDP acetylgalactosaminyltransferase) | GALNTL6 | 417 |
| J3KNN1 | J3KNN1_HUMAN | Polypeptide N-acetylgalactosaminyltransferase (EC 2.4.1.—) (Protein-UDP acetylgalactosaminyltransferase) | GALNT9 | 603 |
| B3KTQ4 | B3KTQ4_HUMAN | Hexosyltransferase (EC 2.4.1.—) | | 331 |
| B3KY85 | B3KY85_HUMAN | Polypeptide N-acetylgalactosaminyltransferase (EC 2.4.1.—) (Protein-UDP acetylgalactosaminyltransferase) | | 556 |
| E7EVS2 | E7EVS2_HUMAN | Hexosyltransferase (EC 2.4.1.—) (Fragment) | B3GALNT1 | 111 |
| B7ZQS8 | B7ZQS8_HUMAN | Sodium/potassium-transporting ATPase subunit beta | | 247 |
| B3W6H0 | B3W6H0_HUMAN | Fucosyltransferase | FUT3 | 361 |
| B3GVC1 | B3GVC1_HUMAN | Fucosyltransferase | FUT3 | 361 |
| Q8TDY1 | Q8TDY1_HUMAN | Hexosyltransferase (EC 2.4.1.—) | | 204 |
| Q6P7E6 | Q6P7E6_HUMAN | Fucosyltransferase 6 (Alpha (1,3) fucosyltransferase) | FUT6 | 359 |
| F8VU3 | F8VU3_HUMAN | Polypeptide N-acetylgalactosaminyltransferase (EC 2.4.1.—) (Protein-UDP acetylgalactosaminyltransferase) | POC1B-GALNT4 | 575 |
| B3KNV8 | B3KNV8_HUMAN | Polypeptide N-acetylgalactosaminyltransferase (EC 2.4.1.—) (Protein-UDP acetylgalactosaminyltransferase) | | 607 |
| Q7L9G8 | Q7L9G8_HUMAN | Hexosyltransferase (EC 2.4.1.—) | | 331 |
| Q6RC00 | Q6RC00_HUMAN | Hexosyltransferase (EC 2.4.1.—) | | 331 |
| M0QX58 | M0QX58_HUMAN | Hexosyltransferase (EC 2.4.1.—) (Fragment) | | 127 |
| B4E056 | B4E056_HUMAN | cDNA FLJ56031, highly similar to Homo sapiens fucosyltransferase 10 (alpha (1,3) fucosyltransferase) (FUT10), mRNA | | 529 |
| Q58A70 | Q58A70_HUMAN | Polypeptide N-acetylgalactosaminyltransferase (EC 2.4.1.—) (Protein-UDP acetylgalactosaminyltransferase) | GalNAc-T10 | 581 |
| B3KQP5 | B3KQP5_HUMAN | Hexosyltransferase (EC 2.4.1.—) | | 378 |
| B3KRF8 | B3KRF8_HUMAN | Hexosyltransferase (EC 2.4.1.—) | | 378 |
| Q6RBZ9 | Q6RBZ9_HUMAN | Hexosyltransferase (EC 2.4.1.—) | B3GNT3 | 319 |
| I3L3J8 | I3L3J8_HUMAN | Sodium/potassium-transporting ATPase subunit beta (Fragment) | ATP1B2 | 172 |
| D7UNW5 | D7UNW5_HUMAN | Polypeptide N-acetylgalactosaminyltransferase (EC 2.4.1.—) (Protein-UDP acetylgalactosaminyltransferase) | GALNT6 | 622 |
| Q49AT3 | Q49AT3_HUMAN | Hexosyltransferase (EC 2.4.1.—) | B3GALNT1 | 331 |
| B4DL56 | B4DL56_HUMAN | Polypeptide N-acetylgalactosaminyltransferase (EC 2.4.1.—) (Protein-UDP acetylgalactosaminyltransferase) | | 603 |
| Q6RC01 | Q6RC01_HUMAN | Hexosyltransferase (EC 2.4.1.—) | | 144 |
| B3KP58 | B3KP58_HUMAN | Polypeptide N-acetylgalactosaminyltransferase (EC 2.4.1.—) (Protein-UDP acetylgalactosaminyltransferase) | | 460 |
| E9PJ79 | E9PJ79_HUMAN | Hexosyltransferase (EC 2.4.1.—) (Fragment) | B3GNT6 | 121 |

TABLE 2-continued

Illustrative human Type II proteins which may be incorporated into the present compositions and methods include (as used herein "Entry" refers to the human Type II protein entry in the UniProt database and "Entry name" refers to the human Type II protein entry in the UniProt database):

| Entry | Entry name | Protein names | Gene names | Length |
|---|---|---|---|---|
| B2R7V3 | B2R7V3_HUMAN | cDNA, FLJ93618, highly similar to Homo sapiens fucosyltransferase 6 (alpha (1,3) fucosyltransferase) (FUT6), mRNA | | 359 |
| C9JOF8 | C9JOF8_HUMAN | Hexosyltransferase (EC 2.4.1.—) (Fragment) | B3GALNT1 | 65 |
| E5D8G0 | E5D8G0_HUMAN | Polypeptide N-acetylgalactosaminyltransferase (EC 2.4.1.—) (Protein-UDP acetylgalactosaminyltransferase) | | 601 |
| B3KQT5 | B3KQT5_HUMAN | Hexosyltransferase (EC 2.4.1.—) | | 372 |
| C9J5K2 | C9J5K2_HUMAN | Hexosyltransferase (EC 2.4.1.—) (Fragment) | B3GNT5 | 81 |
| C9J8U7 | C9J8U7_HUMAN | Hexosyltransferase (EC 2.4.1.—) (Fragment) | B3GALNT1 | 54 |
| H0YAH3 | H0YAH3_HUMAN | Polypeptide N-acetylgalactosaminyltransferase (EC 2.4.1.—) (Protein-UDP acetylgalactosaminyltransferase) (Fragment) | GALNT7 | 454 |
| C9JD16 | C9JD16_HUMAN | Hexosyltransferase (EC 2.4.1.—) (Fragment) | B3GALNT1 | 58 |
| B7Z6K2 | B7Z6K2_HUMAN | Polypeptide N-acetylgalactosaminyltransferase (EC 2.4.1.—) (Protein-UDP acetylgalactosaminyltransferase) | | 533 |
| B7Z5C5 | B7Z5C5_HUMAN | Polypeptide N-acetylgalactosaminyltransferase (EC 2.4.1.—) (Protein-UDP acetylgalactosaminyltransferase) | | 517 |
| Q58A53 | Q58A53_HUMAN | Polypeptide N-acetylgalactosaminyltransferase (EC 2.4.1.—) (Protein-UDP acetylgalactosaminyltransferase) | GalNAc-T17 | 598 |
| C9IYY0 | C9IYY0_HUMAN | Hexosyltransferase (EC 2.4.1.—) (Fragment) | B3GNT5 | 62 |
| A6NGH2 | A6NGH2_HUMAN | Sodium/potassium-transporting ATPase subunit beta | | 295 |
| V9GYR2 | V9GYR2_HUMAN | Sodium/potassium-transporting ATPase subunit beta (Fragment) | ATP1B1 | 130 |
| K7ENC0 | K7ENC0_HUMAN | Alpha-(1,3)-fucosyltransferase 5 | FUT5 | 374 |
| R4X604 | R4X604_HUMAN | Hexosyltransferase (EC 2.4.1.—) | B3GALNT1 | 151 |
| Q8NFN0 | Q8NFN0_HUMAN | Hexosyltransferase (EC 2.4.1.—) | | 181 |
| Q58I18 | Q58I18_HUMAN | Sodium/potassium-transporting ATPase subunit beta (Fragment) | ATP1B3 | 137 |
| R4X601 | R4X601_HUMAN | Hexosyltransferase (EC 2.4.1.—) | B3GALNT1 | 208 |
| Q499Z2 | Q499Z2_HUMAN | Hexosyltransferase (EC 2.4.1.—) (Fragment) | B3GALT6 | 304 |
| Q6LEU2 | Q6LEU2_HUMAN | Sodium/potassium-transporting ATPase subunit beta (Fragment) | ATP1B1 | 303 |
| A0A0A0MS93 | A0A0A0MS93_HUMAN | Hexosyltransferase (EC 2.4.1.—) | B3GALT5 | 314 |
| R4X524 | R4X524_HUMAN | Hexosyltransferase (EC 2.4.1.—) | B3GALNT1 | 331 |
| Q53F50 | Q53F50_HUMAN | Hexosyltransferase (EC 2.4.1.—) (Fragment) | | 331 |
| M0R199 | M0R199_HUMAN | Hexosyltransferase (EC 2.4.1.—) (Fragment) | B3GNT3 | 250 |

Table of Sequences in Appended Sequence Listing

| SEQ ID NO: | Illustrative Description |
|---|---|
| 1 | DNA sequence of chimeric protein - comprising the extracellular domain of PD-1, followed by the hinge-CH2—CH3 domain of human IgG4 and short linker, followed by the extracellular domain of OX40L. |
| 2 | Amino acid sequence of chimeric protein - comprising the extracellular domain of PD-1, followed by the hinge-CH2—CH3 domain of human IgG4 and short linker, followed by the extracellular domain of OX40L. |
| 3 | Codon-optimized nucleic acid sequence, which is optimized for expression by Chinese Hamster (CHO) cells |
| 4 | DNA sequence encoding the extracellular domain of PD-1-Fc-the extracellular domain of TL1A |
| 5 | Amino acid sequence encoded by a codon optimized nucleotide sequence of SEQ ID NO: 4 |
| 6 | Nucleotide sequence of construct (ex: A fusion protein encoding the extracellular domain of BTLA, linked through an Fc to OX40L) |
| 7 | Amino acid sequence encoded by nucleotide sequence of SEQ ID NO: 6 |
| 8 | DNA sequence of a fusion protein incorporating the extracellular domain of TIGIT, linked via an Fc linker to OX40L |
| 9 | Amino acid sequence encoded by a codon optimized nucleotide sequence of SEQ ID NO: 8 |
| 10 | DNA sequence of a fusion protein incorporating the extracellular domain of TIM3, linked through an Fc region to human OX40L |
| 11 | Amino acid sequence encoded by a codon optimized nucleotide sequence of SEQ ID NO: 10 |
| 12 | Nucleotide sequence of the extracellular domain of CD172a adjoined with an Fc linker sequence to the extracellular domain of human OX40L |
| 13 | Amino acid sequence encoded by a codon optimized nucleotide sequence of SEQ ID NO: 12 |
| 14 | Nucleotide sequence of the extracellular domain of TMIGD2 adjoined with an Fc linker sequence to the extracellular domain of human OX40L |
| 15 | Amino acid sequence encoded by a codon optimized nucleotide sequence of SEQ ID NO: 14 |
| 16 | mRNA sequence of human OX40L |
| 17 | Amino acid sequence of human OX40L |
| 18 | Nucleic acid sequence of the hinge-CH2—CH3 Sequence from human IgG1 |
| 19 | cDNA sequence of human PD-1 |
| 20 | Nucleic acid sequence of human PD-1-Fc-OX40L codon optimized for expression by Chinese Hamster (CHO) cells |
| 21 | Nucleic acid sequence of human PD-1-Fc-OX40L |
| 22 | Amino acid sequence of SL-279252 |
| 23 | Amino acid sequence of Linker |
| 24 | Amino acid sequence of Linker |
| 25 | Amino acid sequence of Linker |
| 26 | Amino acid sequence of Linker |
| 27 | Amino acid sequence of Linker |
| 28 | Amino acid sequence of Linker |
| 29 | Amino acid sequence of Linker |
| 30 | Amino acid sequence of Linker |
| 31 | Amino acid sequence of Linker |
| 32 | Amino acid sequence of CD279 |
| 33 | Amino acid sequence of CD172a |
| 34 | Amino acid sequence of BTLA |
| 35 | Amino acid sequence of TIGIT |
| 36 | Amino acid sequence of TIM3 |
| 37 | Amino acid sequence of CD200 |
| 38 | Amino acid sequence of TMIGD2 |
| 39 | Amino acid sequence of VISTA |
| 40 | Amino acid sequence of VSIG8 |
| 41 | Amino acid sequence of BTNL2 |
| 42 | Amino acid sequence of TNFRSF1b |
| 43 | Amino acid sequence of CD276 |
| 44 | Amino acid sequence of CD244 |
| 45 | Amino acid sequence of LAG3 |
| 46 | Amino acid sequence of CSF1R |
| 47 | Amino acid sequence of TGFBR1 |
| 48 | Amino acid sequence of IL-10R |
| 49 | Amino acid sequence of CD40 |
| 50 | Amino acid sequence of OX40 |
| 51 | Amino acid sequence of 41BB |
| 52 | Amino acid sequence of CTLA4 |
| 53 | Amino acid sequence of PD-L1 |
| 54 | Amino acid sequence of PD-L2 |
| 55 | Amino acid sequence of B7-H4 |
| 56 | Amino acid sequence of OX40L |
| 57 | Amino acid sequence of GITRL |
| 58 | Amino acid sequence of 41BBL |
| 59 | Amino acid sequence of TL1A |
| 60 | Amino acid sequence of CD40L |
| 61 | Amino acid sequence of CD30L |
| 62 | Amino acid sequence of TRAIL |
| 63 | Amino acid sequence of CD70 |
| 64 | blank |
| 65 | blank |

Table of Sequences in Appended Sequence Listing

| SEQ ID NO: | Illustrative Description |
|---|---|
| 66 | blank |
| 67 | blank |
| 68 | blank |
| 69 | blank |
| 70 | Amino acid sequence of Linker - IgG4 hinge-CH2—CH3 |
| 71 | Amino acid sequence of Linker - IgG4 hinge-CH2—CH3 S228P |
| 72 | Amino acid sequence of Linker - IgG4 hinge-CH2-CD3 S228P FcRn |
| 73 | Amino acid sequence of Joining Linker |
| 74 | Amino acid sequence of Joining Linker |
| 75 | Amino acid sequence of Joining Linker |
| 76 | Amino acid sequence of Joining Linker |
| 77 | Amino acid sequence of Joining Linker |
| 78 | Amino acid sequence of Joining Linker |

In some embodiments, the present chimeric protein comprises: (i) the amino acid sequence of SEQ ID NO: 32, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 33, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 34, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 35, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 36, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 37, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 38, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 39, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 40, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 41, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 42, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 43, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 44, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 45, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 46, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 47, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 48, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 49, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 50, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 51, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 52, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 53, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 54, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises: (i) the amino acid sequence of SEQ ID NO: 55, or at least 90%, or 93%, or 95%, or 97%, or 98%, or 99% identity thereto, and (ii) one of the amino acid sequences of SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, and SEQ ID NO: 69, or at least 90%, or 93%, or 95%, or 97%, or 98%, or 99% identity thereto, and, optionally (iii) an Ig linker selected from the amino acid sequences of SEQ ID NO: 70, SEQ ID NO: 71, and SEQ ID NO: 72, or at least 90%, or 93%, or 95%, or 97%, or 98%, or 99% identity thereto, where, also optionally, one or more of (i) and (ii) are connected to (iii) via (iv) a joining linker of SEQ ID NO: 73, SEQ ID NO: 74, SEQ ID NO: 75, SEQ ID NO: 76, SEQ ID NO: 77, SEQ ID NO: 78, or variants thereof. In various embodiments, the linkers (iii) or (iv) can be substituted for the amino acid sequence of SEQ ID NOs: 23-31, or at least 90%, or 93%, or 95%, or 97%, or 98%, or 99% identity thereto.

In some embodiments, the present chimeric protein comprises the amino acid sequence of SEQ ID NO: 2, or at least 90%, or 93%, or 95%, or 97%, or 98%, or 99% identity thereto.

In some embodiments, the present chimeric protein comprises the amino acid sequence of SEQ ID NO: 5, or at least 90%, or 93%, or 95%, or 97%, or 98%, or 99% identity thereto.

In some embodiments, the present chimeric protein comprises the amino acid sequence of SEQ ID NO: 7, or at least 90%, or 93%, or 95%, or 97%, or 98%, or 99% identity thereto.

In some embodiments, the present chimeric protein comprises the amino acid sequence of SEQ ID NO: 9, or at least 90%, or 93%, or 95%, or 97%, or 98%, or 99% identity thereto.

In some embodiments, the present chimeric protein comprises the amino acid sequence of SEQ ID NO: 11, or at least 90%, or 93%, or 95%, or 97%, or 98%, or 99% identity thereto.

In some embodiments, the present chimeric protein comprises the amino acid sequence of SEQ ID NO: 13, or at least 90%, or 93%, or 95%, or 97%, or 98%, or 99% identity thereto.

In some embodiments, the present chimeric protein comprises the amino acid sequence of SEQ ID NO: 15, or at least 90%, or 93%, or 95%, or 97%, or 98%, or 99% identity thereto.

In some embodiments, the present chimeric protein comprises the amino acid sequence of SEQ ID NO: 22, or at least 90%, or 93%, or 95%, or 97%, or 98%, or 99% identity thereto.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A heterologous chimeric protein comprising:
   (a) a first domain comprising a portion of PD-1 that is capable of binding a PD-1 ligand,
   (b) a second domain comprising a portion of OX-40 ligand (OX40L) that is capable of binding an OX-40L receptor, and
   (c) a linker linking the first domain and the second domain and comprising a hinge-CH2-CH3 Fc domain.

2. The heterologous chimeric protein of claim 1, wherein the first domain comprises substantially all of the extracellular domain of PD-1 and the second domain comprises substantially all of the extracellular domain of OX40L.

3. The heterologous chimeric protein of claim 1, wherein the heterologous chimeric protein is capable of inhibiting an immunosuppressive signal.

4. The heterologous chimeric protein of claim 1, wherein the heterologous chimeric protein is capable of:
   (a) reducing or eliminating an immune inhibitory signal when the portion of PD-1 is bound to its ligand and/or
   (b) increasing or activating an immune stimulatory signal when the portion of OX40L is bound to its receptor.

5. The heterologous chimeric protein of claim 1, wherein the PD-1 ligand is PD-L1.

6. The heterologous chimeric protein of claim 1, wherein the OX-40L receptor is OX40.

7. The heterologous chimeric protein of claim 1, wherein the heterologous chimeric protein is capable of simultaneously binding the PD-1 ligand and the OX-40L receptor, wherein the PD-1 ligand is PD-L1 and the OX-40L receptor is OX40.

8. The heterologous chimeric protein of claim 1, wherein the heterologous chimeric protein is capable of increasing or preventing a decrease in a sub-population of CD4+ and/or CD8+ T cells.

9. The heterologous chimeric protein of claim 1, wherein the heterologous chimeric protein is capable of enhancing tumor killing activity by T cells.

10. The heterologous chimeric protein of claim 1, wherein the heterologous chimeric protein is capable of providing a sustained immunomodulatory effect.

11. The heterologous chimeric protein of claim 1, wherein the linker comprises hinge-CH2-CH3 Fc domain derived from IgG4.

12. The heterologous chimeric protein of claim 11, wherein the hinge-CH2-CH3 Fc domain is derived from human IgG4.

13. The heterologous chimeric protein of claim 1, wherein the chimeric protein is expressed by a mammalian host cell as a secretable and functional single polypeptide chain.

14. The heterologous chimeric protein of claim 1, wherein the portion of PD-1 comprises the amino acid sequence of SEQ ID NO: 32.

15. The heterologous chimeric protein of claim 1, wherein the portion of OX40L comprises the amino acid sequence of SEQ ID NO: 56.

16. The heterologous chimeric protein of claim 1, wherein the linker comprises an amino acid sequence that is at least 95% identical to the amino acid sequence of SEQ ID NO: 71 or SEQ ID NO: 72.

17. The heterologous chimeric protein of claim 1, wherein
   (a) the first domain comprises the amino acid sequence of SEQ ID NO: 32,
   (b) the second domain comprises the amino acid sequence of SEQ ID NO: 56, and
   (c) the linker comprises an amino acid sequence that is at least 95% identical to SEQ ID NO: 72.

18. An expression vector, comprising a nucleic acid encoding the heterologous chimeric protein of claim 1.

19. A host cell, comprising the expression vector of claim 18.

20. A pharmaceutical composition, comprising a therapeutically effective amount of the heterologous chimeric protein of claim 1.

21. A recombinant fusion protein comprising:
   (a) a first domain comprising a portion of PD-1 comprising the amino acid sequence of SEQ ID NO: 32 and is capable of binding a PD-1 ligand,
   (b) a second domain comprising a portion of OX-40 ligand (OX40L) comprising the amino acid sequence of SEQ ID NO: 56 and is capable of binding an OX-40L receptor, and
   (c) a linker linking the first domain and the second domain and comprising a hinge-CH2-CH3 Fc domain.

22. The recombinant fusion protein of claim 21, wherein the linker comprises an amino acid sequence that is at least 95% identical to SEQ ID NO: 72.

23. The recombinant fusion protein of claim 21, wherein the heterologous fusion protein is capable of simultaneously binding the PD-1 ligand and the OX-40L receptor, wherein the PD-1 ligand is PD-L1 and the OX-40L receptor is OX40.

* * * * *